(12) United States Patent
Zhang et al.

(10) Patent No.: US 11,008,588 B2
(45) Date of Patent: May 18, 2021

(54) DELIVERY, ENGINEERING AND OPTIMIZATION OF TANDEM GUIDE SYSTEMS, METHODS AND COMPOSITIONS FOR SEQUENCE MANIPULATION

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Feng Zhang, Cambridge, MA (US); Chie-yu Lin, Boston, MA (US); Fei Ran, Boston, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/972,927

(22) Filed: Dec. 17, 2015

(65) Prior Publication Data

US 2016/0186213 A1    Jun. 30, 2016

Related U.S. Application Data

(63) Continuation-in-part of application No. PCT/US2014/041800, filed on Jun. 10, 2014.
(Continued)

(51) Int. Cl.
*C12N 15/90* (2006.01)
*C12N 15/10* (2006.01)
(Continued)

(52) U.S. Cl.
CPC ............ *C12N 15/907* (2013.01); *C12N 9/22* (2013.01); *C12N 15/102* (2013.01);
(Continued)

(58) Field of Classification Search
None
See application file for complete search history.

(56) References Cited

U.S. PATENT DOCUMENTS

| 5,622,856 A | 4/1997 | Natsoulis |
| 6,251,677 B1 | 6/2001 | Wilson et al. |

(Continued)

FOREIGN PATENT DOCUMENTS

| BR | 112015013784 | 7/2017 |
| CN | 101228176 | 7/2008 |

(Continued)

OTHER PUBLICATIONS

Brouns et al., Small CRISPR RNAs Guide Antiviral Defense in Prokaryotes. Science, 2008, 321:960-964.*
(Continued)

*Primary Examiner* — Arthur S Leonard
(74) *Attorney, Agent, or Firm* — Foley & Lardner LLP

(57) ABSTRACT

The invention provides for delivery, engineering and optimization of systems, methods, and compositions for manipulation of sequences and/or activities of target sequences. Provided are vectors and vector systems, some of which encode one or more components of a CRISPR complex, as well as methods for the design and use of such vectors. Also provided are methods of directing CRISPR complex formation in prokaryotic and eukaryotic cells to ensure enhanced specificity for target recognition and avoidance of toxicity.

46 Claims, 80 Drawing Sheets

Specification includes a Sequence Listing.

Related U.S. Application Data

(60) Provisional application No. 61/836,123, filed on Jun. 17, 2013, provisional application No. 61/862,355, filed on Aug. 5, 2013, provisional application No. 61/871,301, filed on Aug. 28, 2013, provisional application No. 61/847,537, filed on Jul. 17, 2013, provisional application No. 61/915,407, filed on Dec. 12, 2013, provisional application No. 61/862,468, filed on Aug. 5, 2013, provisional application No. 61/979,942, filed on Apr. 15, 2014.

(51) Int. Cl.
  *C12N 9/22* (2006.01)
  *C12N 15/63* (2006.01)

(52) U.S. Cl.
  CPC ......... *C12N 15/1082* (2013.01); *C12N 15/63* (2013.01); *C12N 2800/80* (2013.01)

(56) References Cited

U.S. PATENT DOCUMENTS

| | | | |
|---|---|---|---|
| 7,601,492 B2 | 10/2009 | Fu et al. | |
| 7,691,995 B2 | 4/2010 | Zamore et al. | |
| 8,697,359 B1 | 4/2014 | Zhang | |
| 8,771,945 B1 | 7/2014 | Zhang | |
| 8,865,406 B2 | 10/2014 | Zhang et al. | |
| 8,871,445 B2 | 10/2014 | Cong et al. | |
| 8,889,418 B2 | 11/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 9,512,446 B1 | 12/2016 | Joung et al. | |
| 9,549,901 B2 | 1/2017 | Shi et al. | |
| 9,597,357 B2 | 3/2017 | Gregory et al. | |
| 9,623,071 B2 | 4/2017 | Guo et al. | |
| 9,834,791 B2 | 12/2017 | Zhang et al. | |
| 9,873,894 B2 | 1/2018 | Conway et al. | |
| 10,301,651 B2 | 5/2019 | Doudna et al. | |
| 2003/0186238 A1 | 10/2003 | Allawi et al. | |
| 2004/0111221 A1 | 6/2004 | Beattie et al. | |
| 2005/0196851 A1 | 9/2005 | Uckun | |
| 2005/0220796 A1 | 10/2005 | Dynan et al. | |
| 2006/0178297 A1 | 8/2006 | Troy et al. | |
| 2006/0234247 A1 | 10/2006 | Puttaraju et al. | |
| 2007/0016012 A1 | 1/2007 | Hartlep et al. | |
| 2007/0244031 A1 | 10/2007 | Lu et al. | |
| 2008/0293655 A1* | 11/2008 | Aygun | C12N 15/111 514/44 A |
| 2010/0055798 A1 | 3/2010 | Battersby | |
| 2010/0076057 A1 | 3/2010 | Sontheimer et al. | |
| 2010/0081707 A1 | 4/2010 | Ali et al. | |
| 2010/0093617 A1 | 4/2010 | Barrangou et al. | |
| 2010/0233084 A1 | 9/2010 | Narasimhaswamy et al. | |
| 2011/0016540 A1 | 1/2011 | Weinstein et al. | |
| 2011/0059502 A1 | 3/2011 | Chalasani | |
| 2011/0189776 A1 | 8/2011 | Terns et al. | |
| 2011/0223638 A1 | 9/2011 | Wiedenheft et al. | |
| 2011/0239315 A1 | 9/2011 | Bonas et al. | |
| 2012/0029891 A1 | 2/2012 | Behlke et al. | |
| 2013/0096182 A1 | 4/2013 | Chatterjee et al. | |
| 2013/0130248 A1 | 5/2013 | Haurwitz et al. | |
| 2013/0315831 A1 | 11/2013 | Shi et al. | |
| 2014/0068797 A1* | 3/2014 | Doudna | C12N 15/102 800/18 |
| 2014/0294771 A1 | 10/2014 | Schaffer et al. | |
| 2014/0295557 A1 | 10/2014 | Joung et al. | |
| 2014/0315985 A1 | 10/2014 | May et al. | |
| 2014/0342456 A1 | 11/2014 | Mali et al. | |
| 2014/0356956 A1 | 12/2014 | Church et al. | |
| 2014/0357530 A1 | 12/2014 | Zhang et al. | |
| 2015/0045546 A1* | 2/2015 | Siksnys | C12N 9/22 536/23.1 |
| 2015/0071899 A1 | 3/2015 | Liu et al. | |
| 2015/0071903 A1 | 3/2015 | Liu et al. | |
| 2015/0071906 A1 | 3/2015 | Liu et al. | |
| 2015/0232881 A1 | 8/2015 | Glucksmann et al. | |
| 2015/0247150 A1 | 9/2015 | Zhang et al. | |
| 2015/0291965 A1 | 10/2015 | Zhang et al. | |
| 2015/0322457 A1 | 11/2015 | Kim et al. | |
| 2015/0353905 A1 | 12/2015 | Weiss et al. | |
| 2016/0017366 A1 | 1/2016 | Chen et al. | |
| 2016/0024510 A1 | 1/2016 | Bikard et al. | |
| 2016/0024524 A1 | 1/2016 | Joung et al. | |
| 2016/0130609 A1 | 5/2016 | Doudna et al. | |
| 2016/0237456 A1 | 8/2016 | Church et al. | |
| 2016/0251648 A1 | 9/2016 | Wang et al. | |
| 2016/0281072 A1 | 9/2016 | Zhang | |
| 2016/0298135 A1 | 10/2016 | Chen et al. | |
| 2016/0298137 A1 | 10/2016 | Chen et al. | |
| 2016/0324938 A1 | 11/2016 | Bikard et al. | |
| 2016/0340662 A1 | 11/2016 | Zhang et al. | |
| 2017/0175144 A1 | 6/2017 | Zhang et al. | |
| 2018/0127783 A1 | 5/2018 | Zhang et al. | |
| 2018/0230495 A1 | 8/2018 | Doudna et al. | |
| 2019/0010471 A1 | 1/2019 | Zhang et al. | |

FOREIGN PATENT DOCUMENTS

| | | |
|---|---|---|
| CN | 103388006 | 11/2013 |
| CN | 103668472 | 3/2014 |
| CN | 104854241 A | 8/2015 |
| EP | 2 591 770 A2 | 5/2013 |
| EP | 2 784 162 | 1/2014 |
| EP | 2 764 103 | 8/2014 |
| EP | 2 771 468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-522547 A | 7/2010 |
| JP | 2012-508235 | 4/2012 |
| JP | 2012-510812 A | 5/2012 |
| JP | 2012-511332 A | 5/2012 |
| JP | 2012-529287 A | 11/2012 |
| JP | 2013-500045 A | 1/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 | 1/2016 |
| JP | 2016-501531 | 1/2016 |
| JP | 2016-501532 A | 1/2016 |
| JP | 2016-025710 A | 2/2016 |
| JP | 2016-502840 A | 2/2016 |
| JP | 2016-504026 A | 2/2016 |
| JP | 2016-505256 A | 2/2016 |
| JP | 2016-093196 | 5/2016 |
| JP | 2016-516169 A | 6/2016 |
| JP | 2016-517954 A | 6/2016 |
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-521995 | 7/2016 |
| JP | 2016-523082 A | 8/2016 |
| JP | 2016-524472 | 8/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |

(56) References Cited

FOREIGN PATENT DOCUMENTS

| WO | WO-03/104414 | A2 | 12/2003 | | |
|---|---|---|---|---|---|
| WO | WO-2004/029219 | A2 | 4/2004 | | |
| WO | WO-2004/046321 | A2 | 6/2004 | | |
| WO | WO-2004/062618 | A2 | 7/2004 | | |
| WO | WO-2005/014791 | | 2/2005 | | |
| WO | WO-2005/049642 | A2 | 6/2005 | | |
| WO | WO-2007/014275 | A2 | 2/2007 | | |
| WO | WO-2007/134161 | A2 | 11/2007 | | |
| WO | WO-2008/093152 | A1 | 8/2008 | | |
| WO | WO-2008/108989 | | 9/2008 | | |
| WO | WO-2008/116860 | A2 | 10/2008 | | |
| WO | WO-2010/054108 | | 5/2010 | | |
| WO | WO-2010/065123 | A1 | 6/2010 | | |
| WO | WO-2010/068816 | A1 | 6/2010 | | |
| WO | WO-2010/075424 | A2 | 7/2010 | | |
| WO | WO-2010/079430 | A1 | 7/2010 | | |
| WO | WO-2010/143917 | | 12/2010 | | |
| WO | WO-2011/011767 | A1 | 1/2011 | | |
| WO | WO-2011/016840 | A2 | 2/2011 | | |
| WO | WO-2011/036510 | A1 | 3/2011 | | |
| WO | WO-2011/064736 | A1 | 6/2011 | | |
| WO | WO-2011/076873 | A1 | 6/2011 | | |
| WO | WO-2011/100058 | | 8/2011 | | |
| WO | WO-2011/146121 | A1 | 11/2011 | | |
| WO | WO-2012/012738 | A1 | 1/2012 | | |
| WO | WO-2012/031205 | | 3/2012 | | |
| WO | WO-2012/051343 | A1 | 4/2012 | | |
| WO | WO-2012/149470 | A1 | 11/2012 | | |
| WO | WO-2012/164565 | A1 | 12/2012 | | |
| WO | WO-2013/044008 | A2 | 3/2013 | | |
| WO | WO-2013/052681 | | 4/2013 | | |
| WO | WO-2013/071440 | A1 | 5/2013 | | |
| WO | WO-2013/078400 | A1 | 5/2013 | | |
| WO | WO-2013/082519 | A2 | 6/2013 | | |
| WO | WO-2013/098244 | | 7/2013 | | |
| WO | WO-2013/130824 | A1 | 9/2013 | | |
| WO | WO-2013/141680 | A1 | 9/2013 | | |
| WO | WO-2013/142578 | A1 | 9/2013 | | |
| WO | WO-2013/155572 | | 10/2013 | | |
| WO | WO-2013/176772 | A1 | 11/2013 | | |
| WO | WO-2014/165349 | A1 | 3/2014 | | |
| WO | WO-2014/065596 | A1 | 5/2014 | | |
| WO | WO 2014/089290 | | * | 6/2014 | A61K 45/00 |
| WO | WO-2014/089290 | A1 | 6/2014 | | |
| WO | WO-2014/093479 | | 6/2014 | | |
| WO | WO-2014/093595 | | 6/2014 | | |
| WO | WO-2014/093622 | A2 | 6/2014 | | |
| WO | WO-2014/093635 | A1 | 6/2014 | | |
| WO | WO-2014/093655 | | 6/2014 | | |
| WO | WO-2014/093661 | | 6/2014 | | |
| WO | WO-2014/093694 | | 6/2014 | | |
| WO | WO-2014/093701 | A1 | 6/2014 | | |
| WO | WO-2014/093709 | | 6/2014 | | |
| WO | WO-2014/093712 | A1 | 6/2014 | | |
| WO | WO-2014/093718 | | 6/2014 | | |
| WO | WO-2014/099744 | | 6/2014 | | |
| WO | WO-2014/099750 | A2 | 6/2014 | | |
| WO | WO-2015/031775 | | 8/2014 | | |
| WO | WO-2014/144761 | | 9/2014 | | |
| WO | WO-2014/186585 | A2 | 11/2014 | | |
| WO | WO-2014/191518 | A1 | 12/2014 | | |
| WO | WO-2014/197568 | A2 | 12/2014 | | |
| WO | WO-2014/197748 | | 12/2014 | | |
| WO | WO-2014/204724 | | 12/2014 | | |
| WO | WO-2014/204725 | | 12/2014 | | |
| WO | WO-2014/204726 | | 12/2014 | | |
| WO | WO-2014/204727 | A1 | 12/2014 | | |
| WO | WO-2014/204728 | | 12/2014 | | |
| WO | WO-2014/204729 | | 12/2014 | | |
| WO | WO-2015/006747 | A2 | 1/2015 | | |
| WO | WO-2015/035136 | A2 | 3/2015 | | |
| WO | WO-2015/048577 | | 4/2015 | | |
| WO | WO-2015/065964 | A1 | 5/2015 | | |
| WO | WO-2015/070083 | A1 | 5/2015 | | |
| WO | WO-2015/071474 | | 5/2015 | | |
| WO | WO-2015/089351 | A1 | 6/2015 | | |
| WO | WO-2015/089364 | | 6/2015 | | |
| WO | WO-2015/089419 | | 6/2015 | | |
| WO | WO-2015/089427 | A1 | 6/2015 | | |
| WO | WO-2015/113063 | A1 | 7/2015 | | |
| WO | WO-2016/022866 | A1 | 2/2016 | | |
| WO | WO-2016/141224 | A1 | 9/2016 | | |

OTHER PUBLICATIONS

Deltcheva et al., CRISPR RNA maturation by trans-encoded small RNA and host factor RNase III. Nature, 2011, 471:602-607. (Year: 2011).*
International Search Report dated Oct. 7, 2014, which issued during prosecution of International Application No. PCT/US2014/041800.
Cong et al. "Multiplex Genome Engineering Using CRISPR/Cas Systems" Science 339(6121):819-823, Feb. 2013.
Cong et al. "Supplementary Material for: Multiplex Genome Engineering Using CRISPR/Cas Systems" Science 339(6121):819-823, Jan. 2013.
Gaj, et al. "ZFN, TALEN and CRISPR/Cas-based methods for genome engineering" Trends in Biotechnology 31 (7):397-405, Jul. 2013.
Gilbert, et al. "CRISPR-Mediated Modular RNA-Guided Regulation of Transcription in Eukaryotes" Cell 154 (2):442-451, Jul. 2013.
Hsu, et al. "Development and Applications of CRISPR-Cas9 for Genome Engineering", Cell 157(6):1262-1278, Jun. 2014.
Jinek, et al. "A Programmable Dual-RNA-Guided DNA Endonuclease in Adaptive Bacterial Immunity" Science 337 (6096):816-821, Aug. 2012.
Krzysztof Chylinski et al. "The tracrRNA and Cas9 families of type II CRISPR-Cas immunity systems", RNA Biology, 10(5):726-737, May 2013.
G. Gasiunas et al. "Cas9-crRNA ribonucleoprotein complex mediates specific DNA cleavage for adaptive immunity in bacteria" Proceedings of the National Academy of Sciences, 109(39:E2579-E2586), Sep. 2012.
Wang, et al. "One-Step Generation of Mice Carrying Mutations in Multiple Genes by CRISPR/Cas-Mediated Genome Engineering" Cell 153(4):910-918, May 2013.
Woong, et al. "Efficient genome editing in zebrafish using a CRISPR-CAS system" Nature BioTechnology, 31(3):227-229, Jan. 2013.
Jiang Wenyan et al. "RNA-guided editing of bacterial genomes using CRISPR-Cas systems", Nature Biotechnology, 31(3):233-239, Mar. 2013.
Wiedenheft et al. "RNA-guided genetic silencing systems in bacteria and archaea", Nature 482(7385):331-338, Feb. 2012.
Elitza Deltcheva et al. "CRISPR RNA maturation by trans-encoded small RNA and host factor RNase III", Nature 471(7340):602-607, Mar. 31, 2011.
Terns et al. "CRISPR-based adaptive immune systems", Current Opinion in Microbiology, 14(3):321-327, Jun. 2011.
Brouns et al. "A Swiss Army Knife of Immunity" Science, 337(6096):808-809, Aug. 2012.
"Crispr genome engineering" XP055167591, Oct. 5, 2013, https://web.archive.org/web/2013100500 [retrieved on Feb. 5, 2015].
"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].
"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).
Abudayyeh, et al., "C2c2 is a single-component programmable RNA-guided RNA-targeting CRISPR effector," Science, vol. 10, dated 2016.
Addgene Materials May 2015.
Addgene Materials Oct. 2014 including Addgene News 2013.
Addgene Reagent distribution list for Zhang Lab.
Addgene, "gRNA_Cloning Vector", retrieved on Jan. 30, 2019, <https://www/addgenen.org/41824/>, 2 pages.

(56) References Cited

OTHER PUBLICATIONS

Al-Attar, et al., "Clustered regularly interspaced short palindromic repeats (CRISPRs): the hallmark of an ingenious antiviral defense mechanism in prokaryotes" Biol Chem., 2011, 392(4):277-289.
Alberts, et al., Molecular Biology of THE CELL, fourth edition, 2002, 671-676.
Andreas, et al. "Enhanced efficiency through nuclear localization signal fusion on phage C31-integrase: activity comparison with Cre and FLPe recombinase in mammalian cells", Nucleic Acids Research, 2002, 30(11):2299-2306.
*Arbitron, Inc. v. Kiefl*, No. 09-CV-04013 PAC, 2010 WL 3239414, at *1 (S.D.N.Y. Aug. 13, 2010).
Asuri, P., et al., "Directed Evolution of Adeno-Associated Virus for Enhanced Gene Delivery and Gene Targeting in Human Pluripotent Stem Cells," Molecular Therapy, vol. 30, No. 2, pp. 329-338, dated Feb. 2012, 10 pages.
Au, et al. "Characterization of a baculovirus nuclear localization signal domain in the late express factor 3 protein", Virology, 2009, 385:209-217.
Ausubel, et al. "Compendium of Methods from Current Protocols in Molecular Biology", Short Protocols in Molecular Biology, Fourth Edition, 1999, 9: 9-3-9-4.
Autofluorescence MIT Flow Cytometry Core Facility (2018), 6 pages.
Baena-Lopez, L., et al., "Accelerated homologous recombination and subsequent genome modification in *Drosophila*," Development, vol. 140, No. 23, pp. 4818-4825, dated Dec. 2013, 18 pages, including Supplementary Material.
Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, 78(3):1181-1194.
Baker, M., "Gene editing at CRISPR Speed," Nature Biotechnology, vol. 32, No. 4, pp. 309-312, dated Apr. 2014, 4 pages.
Balboa et al., "Conditionally Stabilized dCas9 Activator for Controlling Gene Expression in Human Cell Reprogramming and Differentiation. (plus Supplemental Information)", Stem Cell Reports, vol. 5, No. 3, Sep. 8, 2015, pp. 448-459 16PP.
Banaszewska, A., et al. "Proprotein Convertase Subtilisin/Kexin Type 9: A New Target Molecule for Gene Therapy," Cellular & Molecular Biology Letters, vol. 17, pp. 228-239, dated Feb. 7, 2012, 12 pages.
Barrangou and Van Der Oost (Eds.), "CRISPR-Cas Systems," Springer Heidelberg (2013; written in 2012 before the publication of Cong et al.).
Barrangou, R. et al.: "CRISPR provides acquired resistance against viruses in prokaryotes," Science, vol. 315, pp. 1709-1712, dated Mar. 23, 2007, 5 pages.
Barrangou, R., "RNA-mediated programmable DNA cleavage," Nature Biotechnology, vol. 30, No. 9, pp. 836-388, dated Sep. 2012, 3 pages.
Bassett, et al. "Highly Efficient Targeted Mutagenesis of *Drosophila* with the CRISPR/Cas9 System" Cell Reports, 2013, 4:220-228.
Bassett, et al., "A Genome-Wide CRISPR Library for High-Throughput Genetic Screening in *Drosophila* Cells," Journal of Genetics and Genomics, vol. 42, pp. 301-309, dated 2015.
Bauer, et al., "An Erythroid Enhancer of BCL11A Subject to Genetic Variation Determines Fetal Hemoglobin Level," Science, vol. 342, pp. 253-257, dated 2013.
Beerli, et al. "Positive and negative regulation of endogenous genes by designed transcription factors:" PNAS, 2000, 97(4):1495-1500.
Beerli, et al. "Toward controlling gene expression at will: Specific regulation of the erbB-2/HER-2 promoter by using polydactyl zinc finger proteins constructed from modular building blocks", Proc. Natl. Acad. Sci., 1998, 95:14628-14633.
Beerli, R., et al., "Engineering polydactyl zinc-finger transcription factors," Nature Biotechnology, vol. 20, pp. 135-141, dated Feb. 2002, 7 pages.
Bennett et al., "Stable transgene expression in rod photoreceptors after recombinant adeno-associated virus-mediated gene transfer to monkey retina", Proc. Natl. Acad. Sci., USA, vol. 96, Aug. 1999, pp. 9920-9925.
Bergemann, et al. Excision of specific DNA-sequences from integrated retroviral vectors via site-specific recombination:, Nucleic Acids Res., 1995, 23(21):4451-4456.
Berns, K., et al. "A Large-Scale RNAi Screen in Human Cells Identifies New Components of the p53 Pathway," Nature 2004, vol. 428, pp. 431-437, dated Mar. 25, 2004, 7 pages.
Bhaya, D., et al., "CRISPR-Cas Systems in Bacteria and Archaea: Versatile Small RNAs for Adaptive Defense and Regulation," Annual Review of Genetics, vol. 45, No. 1, pp. 273-297, dated Dec. 15, 2011, 27 pages.
Bikard, et al. "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.
Bikard, et al. Supplementary Information for: "CRISPR Interference Can Prevent Natural Transformation and Virulence Acquisition During In Vivo Bacterial Infection," Cell Host & Microbe, vol. 12, No. 2, pp. 177-186, dated Aug. 16, 2012, 10 pages.
Birch, et al. "Plant Transformation: Problems and Strategies for Practical Application", Annu. Rev. Plant Physiol. Plant Mol. Biol., 1997, 48:297-326.
Bloom et al., "Inactivation of hepatitis B virus replication in cultured cells and in vivo with engineered transcription activator-like effector nucleases", Molecular Therapy, Aug. 20, 2013, vol. 21, No. 10, pp. 1889-1897.
Bobis-Wozowicz, S., et al., "Targeted genome editing in pluripotent stem cells using zinc-finger nucleases," Methods, vol. 53, pp. 339-346, dated 2011, 8 pages.
Boch, et al. "Breaking the Code of DNA Binding Specificity of TAL-Type III Effectors". Science, 2009, 326:1509-1512.
Boch, et al. "Xanthomonas AvrBs3 Family-Type III Effectors: Discovery and Function", Annu. Rev. Phytopathol, 2010, vol. 48:419-436.
Boden, et al. "Efficient Gene Transfer of HIV-1-Specific Short Hairpin RNA into Human Lymphocytic Cells Using Recombinant Adeno-associated Virus Vectors", Molecular Therapy, 2004, 9(3):396-402.
Bogdanove, et al. "TAL Effectors: Customizable Proteins for DNA Targeting", Science, 2011, 333:1843-1846.
Bohm, "The computer program LUDI: A new method for the de novo design of enzyme inhibitors", Journal of Computer-Aided Molecular Design, 1992, vol. 6, pp. 61-78.
Bouard, et al. "Themed Section: Vector Design and Drug Delivery Review, Viral vectors: from virology to transgene expression", British Journal of Pharmacology, 2009, 157:153-165.
Boutros et al.: "Genome-wide RNAi analysis of growth and viability in *Drosophila* cells," Science, American Association for the Advancement of Science, vol. 303, No. 5659, pp. 832-835, dated Feb. 6, 2004, 4 pages.
Branden, C., and Tooze, J., "Prediction, Engineering, and Design of Protein Structures," Introduction to Protein Structure, Chapter 16, p. 247, Garland Publishing, Inc., New York, dated 1991, 3 pages.
Briner, et al. "Guide RNA Functional Modules Direct Cas9 Activity and Orthogonality", Molecular Cell, Oct. 2014, 56:333-339.
Campeau, et al. "A Versatile Viral System for Expression and Depletion of Proteins in Mammalian Cells", PLoS One, 2009, 4(8):e6529.
Canver, et al., "BCL11A enhancer dissection by Cas9-mediated in situ saturating mutagenesis," Nature, vol. 527, pp. 192-197, including Supplementary Material, dated 2015.
Carr, et al., "Genome engineering", Nature Biotechnology, 2009, 27(12):1151-1162.
Carroll, "Genome Engineering With Zing-Finger Nucleases", Genetics, 2011, 188:773.782.
Carroll, "Progress and prospects: Zinc-finger nucleases as gene therapy agents", Gene Therapy, 2008, 15:1463-1468.
Carroll, D., "A CRISPR Approach to Gene Targeting," Molecular Therapy, vol. 20, No. 9, pp. 1658-1660, dated Sep. 1, 2012, 3 pages.

(56) References Cited

OTHER PUBLICATIONS

Cermak, T., et al., "Efficient design and assembly of custom TALEN and other TAL Effector-Based Constructs for DNA Targeting", Nucleic Acids Research, vol. 39, No. 12, art. e82, pp. 1-11, dated Apr. 14, 2011, 11 pages.
Chan, et al. "Characterization of the Kinetochore Binding Domain of CENP-E Reveals Interactions with the Kinetochore Proteins CENP-F and hBuBR1", The Journal of Cell Biology, 1998, 143:49-63.
Chan, Wai-Ting, et al. "Toxin-Antitoxin Genes of the Gram-Positive Pathogen *Streptococcus pneumoniae*: So Few and Yet So Many", Microbiology and Molecular Biology Reviews, 2012, 76(4):773-791.
Chang, N., et al. "Genome editing with RNA-guided Cas9 nuclease in Zebrafish embryos", Cell Research, vol. 23, pp. 465-472, dated Mar. 26, 2013, 8 pages.
Chen, B., et al., "Dynamic Imaging of Genomic Loci in Living Human Cells by an Optimized CRISPR/Cas System," Cell, vol. 155, No. 7, pp. 1479-1491, dated Dec. 1, 2013, 25 pages.
Chen, Fuqiang et al. "High-frequency genome editing using ssDNA oligonucleotides with zinc-finger nucleases". Nature Methods, 2011, 8(9):753-755, including Supplemental Online Methods.
Chen, S., et al., "Genome-wide CRISPR Screen in a Mouse Model of Tumor Growth and Metastasis", Cell, 2015, 160:1-15, http://dx.doi.org/10.1016/j.cell.2015.02.038.
Chinnasamy, D., et al., "Multicistronic lentiviral vectors containing the FMCV 2A Cleavage factor demonstrate robust expression of encoded genes at limiting MOI," Virology Journal, vol. 3, No. 4, dated Mar. 15, 2006, 16 pages.
Chiu et al, "Engineered GFP as a vital reporter in plants", Current Biology, (1996), 6(3):325-330.
Cho, A., et al., "Generation of Transgenic Mice," Current Protocols in Cell Biology, Chapter Unit 19.11, pp. 1-29, dated Mar. 2009, 29 pages.
Chou, JY, and Mansfield, BC, "Recombinant AAV-directed gene therapy for type I glycogen storage diseases," Expert Opinion on Biological Therapy, vol. 11, No. 8, pp. 1011-1024, dated Apr. 20, 2011, 21 pages.
Choulika, et al., "Transfer of Single Gene-Containing Long Terminal Repeats into the Genome of Mammalian Cells by a Retroviral Vector Carrying the cre Gene and the loxP site", Journal of Virology, 1996, 70(3):1792-1798.
Christian, et al. "Supporting Information-Targeting DNA Double-Strand Breaks With TAL Effector Nucleases", Genetics, 2010, DOI:10.1534/110.120717:1SI-8SI.
Christian, et al. "Targeting DNA Double-Strand Breaks With TAL Effector Nucleases", Genetics, Oct. 2010, vol. 186:757-761.
Chylinski, et al. "Classification and evolution of type II CRISPR-Cas systems", Nucleic Acids Research, 2014, 42(10):6091-6105,doi:10.1093Inarlgku241.
Clark, K., et al., "A TALE of Two Nucleases: Gene Targeting for the Masses?" Zebrafish, vol. 8, No. 3, pp. 147-149, dated 2011, 3 pages.
Cockrell, "Berkeley's Wikipedian-in-residence is a first," NewsCenter, Feb. 25, 2014.
Community Corner, "CRISPR technology for gene therapy," Nature Medicine, vol. 20, No. 5, pp. 476-477, dated May 2014, 3 pages.
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, pp. 819-823, dated Feb. 15, 2013, 36 pages.
Cong, L., et al., "Comprehensive interrogation of natural TALE DNA-binding modules and transcriptional repressor domains," Nature Communications, vol. 3, pp. 968-973, dated Jul. 24, 2012, 6 pages.
Cong, L., et al., "In Vivo Genome Engineering With AAV Vector Carrying CRISPR-Cas9 System," Molecular Therapy, vol. 22, Supplement 1, p. S214, dated May 23, 2014, 1 page.
Cong, L., et al., Supplementary Material for: "Multiplex Genome Engineering Using CRISPR-Cas Systems," Science Express, dated Jul. 5, 2012.
Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.
Costantino, et al., "Enhanced levels of alpha Red-mediated recombinants in mismatch repair mutants", PNAS, 100(26):15748-15753.
Cotropia, et al., "Copying in Patent Law," N.C.L. Rev., Stanford Public Law Working Paper No. 1270160 (2009), 87:1421.
Cummings et al., "Fourteen and counting: unraveling trinucleotide repeat diseases", Human Molecular Genetics, 2000, vol. 9, No. 6, pp. 909-916.
Daboussi, F., et al., "Chromosomal context and epigenetic mechanisms control the efficacy of genome editing by rare-cutting designer endonucleases," Nucleic Acids Research, vol. 40, No. 13, pp. 6367-6379, dated Jul. 13, 2012, 13 pages.
Dahlman, J., et al., "In vivo endothelial siRNA delivery using polymeric nanoparticles with low molecular weight," Nature Nanotechnology, vol. 9, No. 8, pp. 648-655, dated May 11, 2014, 17 pages.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., 2002, 277:24390-24398.
Daley, J., and Wilson, T., "Rejoining of DNA Double-Strand Breaks as a Function of Overhang Length," Molecular and Cellular Biology, vol. 25, No. 3, pp. 896-906, dated Feb. 2005, 11 pages.
Damian, M., and Porteus, M., "A Crisper Look at Genome Editing: RNA-guided Genome Modification," Molecular Therapy, vol. 21, No. 4, pp. 720-722, dated Apr. 2013, 3 pages.
Database GenBank, "*Staphylococcus aureus* subsp.aureus ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. Q0P897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.
Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q0P897, http://www.uniprot.org/uniprot/Q0P897.txt?version=28, dated Oct. 3, 2012, 1 page.
Database UniProtKB/TrEMBL, Accession No. Q6NKI3, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; AN 2014-J79552, XP-002737563, 2 pages.
Datensenko, et al. "Molecular memory of prior infections activates the CRISPR/Cas adaptive bacterial immunity system", Nature Communications, Jul. 10, 2012, 3:935, DOI:10.1038/ncomms1937.
Declaration of Feng Zhang for U.S. Appl. No. 14/054,414 dated Jan. 30, 2014, 10 pages.

(56) References Cited

OTHER PUBLICATIONS

Declaration of Paul Simons dated Dec. 22, 2015.
Deltcheva, et al. "Supplementary Information: CRISPR RNA Maturation by Trans-Encoded Small RNA and Host Factor RNase III" www.Nature.com/doi:10.1038/nature09886:1-35.
Dicarlo, et al. "Genome engineering in *Saccharomyces cerevisiae* using CRISPTR-Cas systems", Nucleic Acids Research, 2013, 41(7):4336-4343, doi:10.1093/nar/gkt135.
Dingwall, et al. "Abstract: A Polypeptide Domain That Specifies Migration of Nucleoplasmin into the Nucleus", Cell, 1982, 30(2):449-58.
Dingwall, et al. "The Nucleoplasmin Nuclear Location Sequence is Larger and More Complex than That of SV-40 Large T Antigen", The Journal of Cell Biology, 1988, 107:841-849.
Do, et al. "Identification of multiple nuclear localization signals in murine Elf3, an ETS transcription factor" FEBS Letters, 2006, 580:1865-1871.
Doench, et al., "Rational design of highly active sgRNAs for CRISPR-Cas9-mediated gene inactivation," Nature Biotechnology, vol. 32, No. 12, pp. 1262-1267, including Supplementary Material, dated 2014.
Dominguez, et al., "Beyond editing: repurposing CRISPR-Cas 9 for precision genome regulation and interrogation" Nat Rev Mol Cell Biol., 2016, 17(1):5-15, doi:10.1038/nrm.2015.2.
Dong, et al. "The crystal structure of Cpf1 in complex with CRISPR RNA," Nature, vol. 532, pp. 523-525, including Research Letter, dated 2016.
Drittanti, et al. "High throughput production, screening and anyalysis of adeno-associated viral vectors", Gene Therapy, 2000, 7:924-929.
Dworetzky, S., et al., "The Effects of Variations in the Number and Sequence of Targeting Signals on Nuclear Uptake," The Journal of Cell Biology, vol. 107, pp. 1279-1287, dated Oct. 1988, 9 pages.
Ebina, H., et al., "Harnessing the CRISPR/Cas9 system to disrupt latent HIV-1 provirus," Scientific Reports, vol. 3, art. 2510, dated Aug. 26, 2013, 7 pages.
Ellis, B., et al., "Zinc-finger nuclease-mediated gene correction using single AAV vector transduction and enhanced by Food and Drug Administration-Approved Drugs," Gene Therapy, vol. 20, No. 1, pp. 35-42, dated Jan. 1, 2013, 8 pages.
Ellis, et al. "Macromolecular Crowding: Obvious But Underappreciated", TRENDS in Biochemical Sciences, Oct. 2001, 26(10):597-604.
Ellis, Hilary, et al. "High efficiency mutagenesis, repair, and engineering of chromosomal DNA using single-stranded oligonucleotids" PNAS, 2001, 98(12):6742-6746.
Enyeart, et al., "Biotechnological applications of mobile group II introns and their reverse transcriptases: gene targeting, RNA-seq, and non-coding RNA analysis", Mobile DNA, 2014, 5:2, http://www.mobilednajournal.com/contents5/1/2.
Espinoza, et al., "Characterization of the structure, function, and mechanism of B2 RNA, an ncRNA repressor of RNA polymerase II transcription", RNA, 2007, 13(4):583-596.
Excerpt from Declaration of Feng Zhang, dated Sep. 9, 2015.
Federal Circuit decision in *Dow Chemical Co. v. Nova Chemicals Corp.*, Appeal Nos. 2014-1431, 2014-1462 (Fed. Cir. Aug. 28, 2015) (*Dow* v. *Nova*), 25 pages.
Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.
Fieck, et al. "Modifications of the *E. coli* Lac repressor for expression in eukaryotic cells: effects of nuclear signal sequences on protein activity and nuclear accumulation", Nucleic Acids Research, 1992, 20(7):1785-1791.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, No. 12, pp. 5495-5503, dated 1988, 10 pages.
Fleming, J., et al.: "Adeno-Associated Virus and Lentivirus Vectors Mediate Efficient and Sustained Transduction of Cultured Mouse and Human Dorsal Root Ganglia Sensory Neurons," Human Gene Therapy, vol. 12, pp. 77-86, dated Jan. 1, 2001, 10 pages.
Foecking, et al. "Powerful and versatile entrance-promoter unit for mammalian expression vectors", Gene, 1986, 101-105.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Freitas, et al. "Mechanisms and Signals for the Nuclear Import of Proteins", Current Genomics, 2009, 10:550-557.
Fu et al, "Targeted genome editing in human cells using CRISPR/Cas nucleases and truncated guide RNAsc", Jan. 1, 2014, The Use of CRISPR/Cas9 ZFNs and Talens in Generating Site-Specific Genome Alterations; Methods in Enzymology; ISSN 1557-7988, vol. 546, Elsevier, NL, pp. 21-45.
Fu, et al. "High-frequency off-target mutagenesis induced by CRISPR-Cas nucleases in human cells", Nature Biotechnology, 2013, 31(9):822-826.
Gabriel, R., et al., "An unbiased genome-wide analysis of zinc-finger nuclease specificity," Nature Biotechnology, vol. 29, No. 9, pp. 816-823, dated Aug. 7, 2011, 10 pages.
Gaj, T., et al., "Targeted Gene knockout by direct delivery of zinc-finger nuclease proteins," Nature Methods, vol. 9, No. 8, pp. 805-807, dated Aug. 2012, 5 pages.
Gama Sosa, M., et al., "Animal transgenesis: an overview," Brain Structure and Function, vol. 214, pp. 91-109, dated 2010, 19 pages.
Gao, et al. "Engineered Cpf1 Enzymes with Altered PAM Specificities", BioRxiv Preprint, XP-002769442, 2016, doi:http://dx.doi.org/10.1101/091611, 1-13, including Figure Legends.
Gao, et al. "Engineered Cpf1 variants with altered PAM specificities", Nature Biotechnology, 2017, 1-4, doi:10.1038/nbt.3900, advanced online publication including Supplementary Information.
Garcia-Bustos, et al. "Nuclear protein localization", Biochimica et Biophysica Acta, 1991, 1071:83-101.
Gardlik, R., et al., "Vectors and delivery systems in gene therapy," Medical Science Monitor, vol. 11, No. 4, pp. RA110-RA121, dated Apr. 1, 2005, 12 pages.
Garg, et al. "Engineering synthetic TAL effectors with orthogonal target sites", Nucleic Acids Research, 2012, 40(15):7584-7595, doi:10.1093/nar/gks404.
Garneau, et al. "The CRISPR-Cas bacterial immune systems cleaves bacteriophage and plasmid DNA", Nature, Nov. 2010, 468:67-71.
Garriga-Canut, M., et al., "Synthetic zinc finger repressors reduce mutant huntingtin expression in the brain of R6/2 mice," Proceedings of the National Academy of Sciences, vol. 109, No. 45, pp. E3136-E3145, dated Nov. 6, 2012, 10 pages.
Geibler, et al. "Tranescriptional Activators of Human Genes with Programmable DNA-Specificity", PLone, 2011, 6(5):e19509. Doi:10.1371/hournal.pone.0019509.
Geisinger et al., "In vivo blunt-end cloning through CRISPR/CAS9-facilitated non-homologous end-joining", Nucleic Acid Research Advance Access, Jan. 13, 2016, pp. 1-15.
Goldfarb, et al. "Synthetic peptides as nuclear localization signals", Nature, Aug. 1986, 322(14):641-644.
Gomaa, et al. "Programmable removal of bacterial strains by use of genome-targeting CRISPR-Cas systems", MBio., 2014, 5(1):e00928-13.
Goncalves, M., et al., "Concerted nicking of donor and chromosomal acceptor DNA promotes homology-directed gene targeting in Human Cells," Nucleic Acids Research, vol. 40, No. 8, pp. 3443-3455, dated Dec. 20, 2011, 13 pages.
Gratz, et al. "Genome Engineering of *Drosophila* with the CRISPR RNA-Guided Cas9 Nuclease", Genetics, 2013, 194:1029-1035.
Greenspan, et al. "Two Nuclear Location Signals in the Influenza Virus NS1 Nonstructural Protein", Journal of Virology, 1988, 62(8):3020-3026.
Grens, "Enzyme Improves CRISPR A smaller Cas9 protein enables in vivo genome engineering via viral vectors", The Scientist, Apr. 1, 2015.
Grieger, J., and Samulski, R., "Packaging Capacity of Adeno-Associated Virus Serotypes: Impact of Larger Genomes on Infectivity and Postentry Steps," Journal of Virology, vol. 79, No. 15, pp. 9933-9944, dated Aug. 2005, 12 pages.

(56) References Cited

OTHER PUBLICATIONS

Grissa, I., et al., "CRISPRFinder: a web tool to identify clustered regularly interspaced short palindromic repeats," Nucleic Acids Research, vol. 35, pp. W52-W57, dated 2007, 6 pages.

Guan, et al. "Heritable endogenous gene regulation in plants with designed polydactyl zinc finger transcription factors", PNAS, 2002, 99(20):13296-13301.

Gustafsson, et al. "Codon Bias and heterologous protein expression", TRENDS in Biotechnology, Jul. 2004, 22(7):346-353.

Habib, N., Assignment to Broad Institute, dated Jun. 9, 2014, 4 pages.

Haft, D., et al., "A Guild of 45 CRISPR-Associated (Cas) Protein Families and Multiple CRISPR/Cas Subtypes Exist in Prokaryotic Genomes," PLoS Computational Biology, vol. 1, No. 6, pp. 0474-0483, dated Nov. 2005, 10 pages.

Haft, D.H., "HMM Summary Page: TIGR04330", 2012, XP-002757584, http://jcvi.org/cgi-bin/tigrfams/HmmReportPage.cgi?acc=TIGR04330.

Hale, et al. "Essential Features and Rational Design of CRISPR RNAs that Function With the Cas RAMP Module Complex to Cleave RNAs", Molecular Cell, 2012, 45(3):292-302.

Hale, et al. "Prokaryotic siliencing (psi) RNAs in Pyrococcus furiosus", RNA, 2008, 14:2572-2579.

Hale, et al. "RNA-Guided RNA Cleavage by a CRISPR RNA-Cas Protein Complex", Cell, 2009, 139:945-956.

Hall, B., et al., "Overview: Generation of Gene Knockout Mice," Current Protocols in Cell Biology, unit 19.12, suppl. 44, pp. 1-17, dated 2009, 17 pages.

Handel, E., et al., "Versatile and Efficient Genome Editing in Human Cells by Combining Zinc-Finger Nucleases With Adeno-Associated Viral-Vectors," Human Gene Therapy, vol. 23, No. 3, pp. 321-329, dated Mar. 2012, 9 pages.

Harrison et al., "A CRISPR view of development", Genes & Development, vol. 28, No. 17, Sep. 1, 2014, pp. 1859-1872.

Heintze, et al. "A CRISPR CASe for high-throughput silencing", Frontiers in Genetics, Oct. 2013, 4(193): DOI:10.3389/gfene.2013. 00193.

Hibbitt, O., et al. "RNAi-mediated knockdown of HMG CoA reductase enhances gene expression from physiologically regulated low-density lipoprotein receptor therapeutic vectors in vivo," Gene Therapy, vol. 19, pp. 463-467, dated 2012, 5 pages.

Hicks, et al. "Protein Import Into the Nucleus: An Integrated View", Annu. Rev. Cell Dev. Biol., 1995, 11:155-188.

Ho, et al, "Targeting non-coding RNAs with the CRISPR/Cas9 system in human cell lines," Nucleic Acids Research, vol. 43, No. 3, p. e17, dated 2015.

Hockemeyer, et al. "Highly efficient gene targeting of expressed and silent genes in human ESCs and iPSCs using zinc finger nucleases", Nat Biotechnol., 2009, 27(9):851-857, doi:10.1038/nbt.1562.

Holkers, M., et al., "Adenoviral vector DNA for accurate genome editing with engineered nucleases," Nature Methods, vol. 11, No. 10, pp. 1051-1057, Aug. 24, 2014, 8 pages (Only Abstract Available).

Holmes, "CRISPR Genome Engineering Resources" XP055167586, Oct. 2, 2013, https://groups.google/forum/#!top1c/crispr/5BpJj_Y3yIG [retrieved on Feb. 5, 2015].

Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-1/rziHxKT76pYJ [retrieved on Feb. 6, 2015].

Horvath, P., and Barrangou, R., "RNA-guidded genome editing a la carte," Cell Research, vol. 23, No. 6, pp. 733-734, dated Jun. 2013, 2 pages.

Hou, Z., et al., "Efficient genome engineering in human pluripotent stem cells using Cas9 from Neisseria meningitides," Proceedings of the National Academy of Sciences, vol. 110, No. 39, pp. 15644-15649, dated Aug. 12, 2013, 6 pages.

Houdebine, L., "The methods to generate transgenic animals and to control transgene expression," Journal of Biotechnology, vol. 98, pp. 145-160, dated 2002, 16 pages.

Hsu et al., "DNA targeting specificity of RNA-guided Cas9 nucleases," Nature Biotechnology, 2013, 31(9):827-834.

Hsu et al., "Supplementary Information-DNA targeting specificity of RNA-guided Cas9 nucleases," Nature Biotechnology, 2013, doi:10.1038/nbt.2647.

*Huang v. California Institute of Technology*, 2004 WL 2296330 (C.D. Cal. Feb. 18, 2004).

Hung, S., et al., "AAV-Mediated CRISPR/Cas Gene Editing of Retinal Cells in Vivo," Investigative Ophthalmology & Visual Science, vol. 57, No. 7, pp. 3470-3476, dated Jun. 2016, 7 pages.

Hwang Woong, et al. "Efficient In Vivo Genome Editing Using RNA-Guided Nucleases", Nat. Biotechnol., 2013, 31(3):227.229. doi. 1.1038/mbt.2501.

Imagawa, et al. "Two nuclear localization signals are required for nuclear translocation of nuclear factor 1-A", FEBS Letters, 2000, 484118-124.

Incontro, S., et al., "Efficient, Complete Deletion of Synaptic Proteins using CRISPR," Neuron, vol. 83, No. 5, pp. 1051-1057, dated Sep. 3, 2014, 13 pages.

Iwamoto et al., "A General Chemical Method to Regulate Protein Stability in the Mammalian Central Nervous System", Chemistry and Biology, Current Biology, London, GB, vol. 17, No. 9, Sep. 24, 2010, pp. 981-988.

Jackson, A., et al. "Widespread siRNA "off-target" transcript silencing mediated by seed region sequence complementarity," RNA 2006, vol. 12, No. 7, dated Mar. 16, 2006, 10 pages.

Janssen, et al., "Mouse Models of K-ras-Initiated Carcinogenesis", Biochimicia et Biophysica Acta, 2005, 1756:145-154.

Jao, et al. "Efficient multiplex biallelic zebrafish genome editing using a CRISPR nuclease system", Proceeding of the National Academy of Sciences, 2013, www.pnas.org/cgi/doi/10.1073/pnas. 1308335110.

Jiang, W., et al., "RNA-guided editing of bacterial genomes using CRISPR-Cas systems," Nature Biotechnology, vol. 31, No. 3, pp. 233-239, dated Mar. 2013, 30 pages, including Supplementary Materials.

Jieliang Chen, et al. "An Efficient Antiviral Strategy for Targeting Hepatitis B Virus Genome Using Transcription Activator-Like Effector Nucleases", Molecular Therapy, 2014, 22(2):303-311.

Jinek, M., et al, "A programmable Dual-RNA-Guided DNA Endonuclease in adaptive bacterial immunity," Science, vol. 337, n.6096, pp. 816-821, dated Aug. 17, 2012, 7 pages.

Jinek, M., et al., "RNA-programmed genome editing in human cells", eLIFE, vol. 2, No. e00471, dated Jan. 29, 2013, 9 pages.

Jinek, M., et al., Figures and figure supplements for: "RNA-programmed genome editing in human cells," eLIFE, vol. 2, No. e00471, dated Jan. 29, 2013, 5 pages.

Jinek, M., et al., Supplementary Materials for: "A Programmable Dual-RNA-Guided DNA Endonuclease in Adaptive Bacterial Immunity," Science, vol. 337, No. 6096, pp. 816-821, dated Jun. 28, 2012, 38 pages.

Joseph, T., and Osman, R., "Thermodynamic basis of selectivity in guide-target-mismatched RNA interference," Proteins, vol. 80, No. 5, pp. 1283-1298, dated May 2012, 26 pages.

Joshi, et al., "Evolution of I-SceI homing endonucleases with increased DNA recognition site specificity", Journal of Molecular Biology, 2011, 405(1):185-200; ePub: Oct. 26, 2010.

Joung, et al. "TALENs: a widely applicable technology for targeted genome editing", Nat Ref. Mol. Cell Biol., 2013, 14(1):49-55. doi:10.1038/nrm3586.

Kalderon, et al. "A Short Amino Acid Sequence Able to Specify Nuclear Location", Cell, 1984, 39:499-509.

Kanasty, R., et al., "Delivery materials for siRNA therapeutics," Nature materials, vol. 12, No. 11, pp. 967-977, dated Oct. 23, 2013, 11 pages.

Karvelis, et al. "crRNA and tracrRNA guide Cas9-mediated DNA interference in *Streptococcus thermophiles*" RNA Biology, 2013, 10(5):841-851.

Karvelis, et al. "Supplemental Material to: crRNA and tracrRNA guide Cas9-mediated DNA interference in *Streptococcus thermophiles*", Landes Bioscience, 2013, 10(5), http://dx.doi.org/10.4161/rna. 24203.

(56) References Cited

OTHER PUBLICATIONS

Kiani, et al. "CAS9 gRNA engineering for genome editing, activation and repression", Nature Methods, Advanced Online Publication, 2015, DOI:10.1038/NMETH.3580.
Kim et al., "High Cleavage Efficiency of a 2A Peptide Derived from Porcine Teschovirus-1 in Human Cell Lines, Zebrafish and Mice," PLoS One, 6(4):e1 8556, (2011).
Kim, E., et al., "Precision genome engineering with programmable DNA-nicking enzymes," Genome Research, vol. 22, pp. 1327-1333, dated 2012, 8 pages.
Kim, et al. "Crystal structure of Cas1 from Archaeoglobus fulgidus and characterization of its nucleolytic activity", Biochemical and Biophysical Research Communications, 2013, 441:720-725.
Kim, S., et al., "CRISPER RNAs trigger innate immune responses in human cells," Genome Research, pp. 1-7, dated Feb. 22, 2018, 8 pages.
Kinnevery, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, No. 1, pp. 524-531, dated Jan. 2013, 8 pages.
Kleinstiver et al., "High-fidelity CRISP-Cas9 nucleases with no detectable genome-wide off-target effects", Nature, vol. 529, No. 7587, Jan. 28, 2016, pp. 490-495.
Kleinstiver, et al. "Engineered CRISPR-Cas9 nucleases with altered PAM specificities," Nature, vol. 523, pp. 481-485, including Research Letter, dated 2015.
Kondo, et al. "Highly Improved Gene Targeting by Germline-Specific Cas9 Expression in *Drosphila*", Genetics, 2013, 195:715-721.
Konermann, et al, "Genome-scale transcriptional activation by an engineered CRISPR-Cas9 complex", Nature, 2015, 517:583-588.
Koornneef, A., et al., "Apoliprotein B Knockdown by AAV-Delivered shRNA Lowers Plasma Cholesterol in Mice," Molecular Therapy, vol. 19, No. 4, pp. 731-740, dated Apr. 2011, 10 pages.
Kosugi, et al. "Six Classes of Nuclear Localization Signals Specific to Different Binding Grooves of Importin a . . . " The Journal of Biological Chemistry, 2009, 284(1):478-485.
Kowalski, Thomas J., PowerPoint Presentation, "Interview Sep. 9, 2015."
Krauer, et al. "Identitication of the nuclear localization signals witnin the Epstein-Barr virus EBNA-6 protein", Journal of General Virology, 2004, 85:165-172.
Kuhlman, et al. "A place for everything$201D Chromosomal intergration of large constructs", Bioengineered Bugs, Jul./Aug. 2010, 1(4)296-299.
Kuhlman, et al. "Site-specific chromosomal integration of large synthetic constructs", Nucleic Acids Research, 2010, 38(6):1-10, doi:10.1093/nar/gkp1193.
Kumar, M., et al., "Systematic Determination of the Packaging Limit of Lentiviral Vectors," Human Gene Therapy, vol. 12, pp. 1893-1905, dated Oct. 10, 2001, 21 pages.
Kuwayama, H., "Enhancement of Homologous Recombination Efficiency by Homologous Oligonucleotides," Cell Interaction Sivakumar Gowder, IntechOpen, DOI: 10.5772/47779, dated Oct. 10, 2012, 12 pages.
Lambowitz, et al. "Group II Introns: Mobile Ribozymes that Invade DNA", Cold Spring Harb Perspect Biol., 2011, 3:a003616.
Lanford, et al. "Induction of Nuclear Transport with a Synthetic Peptide Homologous to the SV40 T Antigen Transport Signal", Cell, 1986, 46:575-582.
Lange, et al. "Classical Nuclear Localization Signals: Definition, Function, and Interaction with Importin$2026" J. Biol. Chem., 2007, 282(8):5101-5105.
Larson, et al. "CRISPR interference (CRISPRi) for sequence-specific control of gene expression", Nature Protocols, 2013, 8(11):2180-2196.
Lebherz, C., et al., "Gene therapy with novel adeno-associated virus vectors substantially diminished atherosclerosis in a murine model of familial hypercholesterolemia," The Journal of Gene Medicine, vol. 6, pp. 663-672, dated Mar. 2, 2004, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al. "Identifying and Visualizing Functional PAM Diversity across CRISPR-Cas Systems", Molecular Cell, 2016, 62:137-147.
Lemay, et al. "Folding of the Adenine Riboswitch", Chemistry & Biology, 2006, 13:857-868.
Levitt, J., et al., "Intrinsic fluorescence and redox changes associated with apoptosis of primary human epithelial cells," Journal of Biomedical Optics, vol. 11, No. 6, pp. 064012 1-10, dated Nov./Dec. 2006, 10 pages.
Lewin, et al. "Nuclear localization sequences target proteins to the nucleus" Cells, 2006, 5:224.
Lewis, et al., "The c-myc and PyMT oncogenes induce different tumor types in a somatic mouse model for pancreatic cancer" Genes & Development, 2003, 17:3127-3138.
Li et al., "Coevolution of CRISPR-Cas system with bacteria and phages", Hereditas, vol. 33, No. 3, Mar. 31, 2011, pp. 213-218.
Li, et al. "In vivo genome editing restores nemostasis in a mouse model of hemophilia" Nature, 2011, 475(7355):217-221. doi: 10.1038/nature10177.
Li, et al. "Multiplex and homologous recombination-mediated genome editing in *Arabidopsis* and *Nicotaina benthamiana* using guide RNA and Cas9" Nature Biotechnology, 2013, 31(9):688-691.
Li, P., et al., "Biallelic knockout of alpha-1,3 galactosyltransferase gene in porcine liver-derived cells using zing finger nucleases," Journal of Surgical Research, vol. 181, No. 1, pp. E39-E45, dated Jul. 3, 2012, 7 pages.
Li, Ting, et al. "Modularly assembled designer TAL effector nucleases for targeted gene knockout and gene replacement in eukaryotes" Nucleic Acids Research, 2011, 39(14):6315-6325.
Liu, et al. "Epstein-Barr Virus DNase Contains Two Nuclear Localization Signals Which Are Different in Sensitivity to the Hydrophobic Regions" Virology, 1998, 247:62-73.
Lombardo, A., et al., "Gene editing in human stem cells using zinc finger nucleases and integrase-defective lentiviral vector delivery," Nature Biotechnology, vol. 25, No. 11, pp. 1298-1306, dated Nov. 1, 2007, 9 pages.
Los, et al. "Halotag Technology: Cell Imaging and Protein Analysis" Cell Notes, 2006, 14:10-14.
Luo, B., et al., "Highly parallel identification of essential genes in cancer cells," Proceeding of the National Academy of Sciences, vol. 105, No. 51, pp. 20380-20385, dated Dec. 23, 2008, 6 pages.
Luo, Ming, et al. "Multiple Nuclear Localization Sequences Allow Modulation of 5-Lipoxygenase Nuclear Import" Traffic, 2004, 5:847-854.
Lyssenko, et al. "Cognate putative nuclear localization signal effects strong nuclear localization of a GFP reporter and facilitates gene expression studies in Caenorhabditis elegans" BioTechniques, 2007, 43:596-600.
Ma, M., et al., "A Guide RNA Sequence Design Platform for the CRISPR/Cas9 System for Model Organism Genomes," Hindawi, vol. 2013, art. 270805, BioMed Research International, dated Sep. 13, 2013, 5 pages.
Ma, M., et al., "A Guide RNA Sequence Design Platform for the CRISPR/Cas9 System for Model Organism Genomes," BioMed Research International, vol. 31, No. 3, pp. 822-824, dated Nov. 2013, 4 pages.
Maczuga, P., et al., "Embedding siRNA sequences targeting Apolipoprotein B100 in shRNA and miRNA scaffolds results in differential processing and in vivo efficacy," Molecular Therapy, vol. 21, No. 1, pp. 217-227, dated Jan. 2013, 11 pages.
Madisen et al., "A robust and high-throughput Cre reporting and characterization system for the whole mouse brain," Nat. Neurosci., 13(1):133-140, (2010) (author manuscript; available in PMC Jul. 1, 2010).
Maeder, et al. "CRISPR RNA-guided activation of endogenous human genes" Nature Methods, 2013, 10(10):977-979. doi.10.1038/nmeth.2556.

(56) References Cited

OTHER PUBLICATIONS

Maeder, M., and Gersbach, C., "Genome-editing Technologies for Gene and Cell Therapy," Molecular Therapy, vol. 24, No. 3, pp. 430-446, dated Mar. 2016, 17 pages.
Maeder, M., et al., "Robust, synergistic regulation of human gene expression using TALE activators," Nature Methods, vol. 10, No. 3, pp. 243-245, dated Mar. 2013, 9 pages.
Mahfouz, et al. "Targeted transcriptional repression using a chimeric TALE-SRDX repressor protein" Plant Mol Biol, 2012, 78:311-321.
Mahfouz, M., et al., "De novo-engineered transcription activator-like effector (TALE) hybrid nuclease with novel DNA binding specificity creates double-strand breaks," Proceedings of the National Academy of Science, vol. 108, No. 6, pp. 2623-2628, dated Feb. 8, 2011, 6 pages.
Makarova, et al. "An updated evolutionary classification of CRISPR-Cas systems" Nature Reviews-Microbiology, 2015, 13:722-736.
Makarova, K., et al., "Evolution and classification of the CRISPR-CAS Systems," Nature Reviews Microbiology, vol. 9, No. 6, pp. 467-477, dated Jun. 2011, 23 pages.
Makarova, K., et al., "Unification of Cas protein families and a simple scenario for the origin and evolution of CRISPR-Cas systems," Biology Direct, vol. 6, No. 38, dated 2011, 27 pages.
Mali et al., "CAS9 transcriptional activators for target specificity screening and paired nickases for cooperative genome engineering", Nature Biotechnology, Sep. 2013, vol. 31, No. 9, pp. 833-837.
Mali, et al, Supplementary Information for "Use of adjacent sgRNA: Cas9 complexes for transcriptional activation and genome engineering," Nature Biotechnology, doi:10.1037/nbt.2675.
Mali, et al. "RNA-Guided Human Genome engineering Via Cas9" Science, vol. 339, pp. 823-826, dated Feb. 15, 2013, 41 pages. (Includes Supplemental Information).
Mali, et al.: "Supplementary Materials for-RNA-Guided Human Genome Engineering Via Cas9" Science, vol. 339, art. 6121, pp. 823-826, dated Feb. 15, 2013, 8 pages.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages (Includes Supplemental Information).
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 8 pages.
Mali, P., et al., Supplementary Information for: "RNA-Guided Human Genome Engineering via Cas9," Science, vol. 339, pp. 823-826, dated Feb. 15, 2013, 36 pages.
Malina, A., et al., "Repurposing CRISPR/Cas9 for in situ functional assays," Genes & Development, vol. 27, No. 23, pp. 2602-2614, dated Dec. 1, 2013, 14 pages.
Manjunath, N., et al., "Newer Gene Editing Technologies toward HIV Gene Therapy," VIRUSES, vol. 5, No. 11, pp. 2748-2766, dated Nov. 14, 2013, 19 pages.
*Manning v. Paradis*, 296 F.3d 1098 (Fed. Cir. 2012).
Marraffini, L., "CRISPR-Cas Immunity against Phages: Its Effects on the Evolution and Survival of Bacterial Pathogens," PLOS, Pathogens, dated Dec. 12, 2013, 6 pages.
Marraffini, L., Assignment to Rockefeller University, dated Dec. 12, 2013, 3 pages.
Marraffini, L., et al., "Self vs. non-self discrimination during CRISPR RNA-directed immunity," Nature, vol. 463, No. 7280, pp. 568-571, dated Jan. 28, 2010, 13 pages.
Mastroianni, et al. "Group II Intron-Based Gene Targeting Reactions in Eukaryotes" Plos One, 2008, 3(9):e3121. Doi:10.1371/journal.pone.0003121.
*Maxwell v. The Stanley Works*, 2006 WL 1967012, *5 (M.D. Tenn. Jul. 11, 2006).
Meshorer, et al. "Chromatin in pluripotent embryonic stem cells and differentiation" Nature Reviews Molecular Cell Biology, 2006, 7:540-546.

Mewburn Ellis, "Publicising Inventions" available at: http://mewburn.com/resource/publicising-inventions.
Miller, et al. "A TALE nuclease architecture for efficient genome editing" Nature Biotechnology, 2011, 29(2):143-150.
Mincer, J., and Simon, S., "Simulations of nuclear pore transport yield mechanistic insights and quantitative predictions," Proceedings of the National Academy of Science, vol. 108, No. 31, pp. E351-E358, dated Aug. 2, 2011, 8 pages.
Minton, "How can biochemical reactions within cells differ from those in test tubes?" Journal of Cell Science, 2006, 119:2863-2869.
Mojica, F. J., et al., "Short motif sequences determine the targets of the prokaryotic CRISPR defence system," Microbiology, vol. 155, No. 3, pp. 733-740, dated Mar. 1, 2009, 8 pages.
Mojica, F. J., et al., Supplementary Material for: "Short motif sequences determine the targets of the prokaryotic CRISPR defence system," Microbiology, vol. 155, No. 3, pp. 733-740, dated Mar. 1, 2009, 8 pages.
Morbitzer, et al. "Assembly of custom TALE-type DNA binding domains by modular cloning" 2011, 39(13):5790-5799.
Morbitzer, et al. "Regulation of selected genome loci using de novo-engineered transcription activator-like effector (TALE)-type transcription factors" PNAS, 2010, 108(50):21617-21622.
Morgan, et al. "Inducible Expression and Cytogenetic Effects of the EcoRI Restriction Endonuclease in Chinese Hamster Ovary Cells" Molecular and Cellular Biology, 1988, 8(10):4204-4211.
Morin, et al. "Nuclear Localization of the Adenovirus DNA-Binding Protein: Requirement for Two Signals and Complementation during Viral Infection" Molecular and Cellular Biology, 1989, 9(10):4372-4380.
Morris et al., "Distributed automated docking of flexible ligands to proteins: Parallel applications of AutoDock 2.4*", Journal of Computer-Aided Molecular Design, 1996, vol. 10, pp. 293-304.
Moscou, et al. "A Simple Cipher Governs DNA Regognition by TAL Effectors" Science, 2009, 326:1501.
Mukhopadyay, R., "On the Same Wavelength," ASBMB Today, http://www.asbmb.org/asbmbtoday/201408/Features/Doudna/, dated Aug. 2014, 6 pages.
Mussolino, et al. "TALE nucleases: tailored genome engineering made easy" Current Opinion in Biotechnology, 2012, 23(5):644-650.
Musunuru, "Abstract 18593: Use of a CRISPR/Cas System for Cardiovascular Disease Modeling and Therapeutic Applications", Circulation, vol. 128, No. 22, Suppl. 1, Nov. 26, 2013, 4 pages (Meeting info: American Heart Association, 2013 Scientific Sessions and Resuscitation Science Symposium, Dallas, TX, US, Nov. 16-20, 2013).
Muther, N., et al.: "Viral Hybrid Vectors for Somatic Integration—Are They the Better Solution?" Viruses, vol. 1, pp. 1295-1324, dated Dec. 15, 2009, 30 pages.
Nagarajan, et al. "A Hierarchy of Nuclear Localization Signals Governs the Import of the Regulatory Factor X Complex Subunits and MHC Class II Expression" The Journal of Immunology, 2004, 173:410.419.
Nakai, et al. "PSORT: a program for detecting sorting signals in proteins and predicting their subcellular localization" Trends in Biochem Sciences, 1999 24:34-35.
Nakamura, et al. "Codon usage tabulated from international DNA sequence databases: status for the year 2000" Nucleic Acids Research, 2000, 28(1): 292.
Nishimasu, et al. Crystal Structure of Cas9 in Complex with Guide RNA and Target DNA, Cell, 2014, 156:935-949.
Nishimasu, H., et al., "Crystal Structure of *Staphylococcus aureus* Cas9," Cell, vol. 162, pp. 1113-1126, dated Aug. 27, 2015, 15 pages.
Noguchi, et al. "PDX-1 Protein Containing Its Own Antennapedia-Like Protein Transduction Domain Can Transduce Pancreatic Duct and Islet Cells" Diabetes, 2003, 52:1732-1737.
Nomura, S., et al., "Low-density lipoprotein receptor gene therapy using helper-dependent adenovirus produces long-term protection against atherosclerosis in a mouse model of familial hypercholesterolemia," Gene Therapy, vol. 11, No. 20, pp. 1540-1548, dated Oct. 22, 2004, 10 pages.
Notice of Opposition filed Aug. 11, 2017 by Schlich against EP Patent No. 2840140.

(56) References Cited

OTHER PUBLICATIONS

Notice of Opposition filed Aug. 14, 2017 by Grund against EP Patent No. 2840140.
Notice of Opposition filed Aug. 16, 2017 by Mathys & Squire LLP against EP Patent No. 2840140.
Notice of Opposition filed by Aug. 16, 2017 by Vossius against EP Patent No. 2840140.
O'Hare, et al. "Transformation of mouse fibroblasts to methotrexate resistance by a recombinant plasmid expressing a prokaryotic dihydrofolate reductase" Proc. Natl. Acad. Sci., 1981, 78(3):1527-1531.
Oost, "New Tool for Genome Surgery" Science, Feb. 15, 2013, 399:768-770.
Opposition Against Appl. Ser. No. EP13818570.7 submitted by Schich dated Oct. 26, 2015, 8 pages.
Opposition Against EP Appl. Ser. No. 2771468-B1 dated Oct. 26, 2015.
Ozawa, K., "Gene therapy using AAV," Uirusu, vol. 57, No. 1, pp. 47-55, dated Nov. 27, 2007, 13 pages (with English Abstract; No English Translation).
Pandika, et al., www.ozy.com/rising-stars-and-provocateurs/jennifer-doudna-crispr-code-killer/4690; 2014 (Jul. 1, 2014).
Panyam, J., and Labhasetwar, V., "Biodegradable nanoparticles for drug and gene delivery to cells and tissue," Advanced Drug Delivery Reviews, vol. 55, No. 3, pp. 329-347, dated Feb. 24, 2003, 19 pages.
Park, et al. "Regulation of Ribosomal S6 Kinase 2 by Mammalian Target of Rapamycin", The Journal of Biological Chemistry, 2002, 277(35):31423-31429.
Pattanayak, et al., "High-throughput profiling of off-target DNA cleavage reveals RNA-programmed Cas9 nuclease specificity," Nature Biotechnology, vol. 31, No. 9, pp. 839-843, dated 2013, including Supplementary Materials.
Patterson, et al. "Codon optimization of bacterial luciferase (lux) for expression in mammalian cells" J. Ind. Microbio. Biotechnology, 2005, 32:115-123.
Perez-Pinera, et al. "Advances in Targeted Genome Editiong" Curr Opin Chem Biol., 2012, 16(3-4):268.277, doi:10.1016/j.cbpa.2012.06.007.
Perez-Pinera, et al. "RNA-guided gene activation by CRISPR-Cas9-based transcription factors" Nature Methods, 2013, 10(10):973-976 (12 pages).
Phillips, A., "The challenge of gene therapy and DNA delivery," The Journal of Pharmacy and Pharmacology, vol. 53, pp. 1169-1174, dated 2001, 6 pages.
Planey, et al. "Mechanisms of Signal Transduction: Inhibition of Glucocorticoid-induced Apoptosis in 697 Pre-B Lymphocytes by the Mineralocorticoid Receptor N-terminal Domain", J. Biol. Chem., 2002, 277:42188-42196.
Platt, R., et al., "CRISPR-Cas9 Knockin Mice for Genome Editing and Cancer Modeling," Cell, vol. 159, No. 2, pp. 440-455, dated Oct. 9, 2014, 16 pages.
Porteus, et al. "Gene targeting using zinc finger nucleases" Nature Biotechnology, 2005, 23(8):967-973.
Porteus, M., and Balitmore, D., "Chimeric Nucleases Stimulate Gene Targeting in Human Cells," Science, vol. 300, p. 763, dated May 2, 2003, 2 pages.
Posfai, et al. "Markerless gene replacement in *Escherichia coli* stimulated by a double-strand break in the chromosome" Nucleic Acids Resarch, 1999, 27(22):4409-4415.
Pougach, et al. "Transcription, Processing and Function of CRISPR Cassettes in *Escherichia coli*" Mol. Microbiol, 2010, 77(6):1367-1379.
Pougach, K.S., et al.: "CRISPR Adaptive Immunity systems of Prokaryotes," Molecular Biology, vol. 46, No. 2, Apr. 2012, pp. 195-203, 1 page (English Abstract).
PowerPoint slide entitled "Development and Applications of CRISPR-Cas9 for Genome Editing" dated Sep. 9, 2015.
Pride, D., et al., "Analysis of Streptococcal CRISPRs from Human Saliva Reveals Substantial Sequence Diversity Within and Between Subjects Over Time," Genome Research, vol. 21, No. 1, pp. 126-136, dated Jan. 2011, 11 pages.
Primo, et al. "Lentiviral vectors for cutaneous RNA managing" Experimental Dermatology, 2012, 21:162-170.
Qi, et al. "Repurposing CRISPR as an RNA-Guided Platform for Sequence-Specific Control of Gene Expression" Cell, 2013, 152(5):1173-1183.
Qi, J., et al., "microRNAs regulate human embryonic stem cell division," Cell Cycle, vol. 8, No. 22, pp. 3729-3741, dated Nov. 15, 2009, 13 pages.
Radecke, S., et al., "Zinc-finger Nuclease-induced Gene Repair With Oligodeoxynucleotides: Wanted and Unwanted Target Locus Modifications," Molecular Therapy, vol. 18, No. 4, pp. 743-753, dated Apr. 2010, 11 pages.
Radulovich, et al. "Modified gateway system for double shRNA expression and Cre/lox based gene expression" BMC Biotechnology, 2011, 11(24):1-9.
Ran, et al., "Double Nicking by RNA-Guided CRISPR Cas9 for Enhanced Genome Editing Specificity," Cell 154, 1-10, Sep. 12, 2013.
Ran, F., et al, "In vivo genome editing using *Staphylococcus aureus* Cas9," Nature, vol. 520, pp. 186-191, dated Apr. 2015, 18 pages.
Ran, F., et al., "Genome engineering using the CRISPR-Cas9 system," Nature Protocols, vol. 8, No. 11, pp. 2281-2308, dated 2013, 28 pages.
Rand, et al. "Argonaute2 Cleaves the Anti-Guide Strand of siRNA during RISC Activation" Cell, 2005, 123:621-629.
Raymond, et al. "High-Efficiency FLP and φC31 Site-Specific Recombination in Mammalian Cells" PLoS ONE, 2007, 2(1):e162. Doi. 10.1371/journal.pone.0000162.
Rebar, et al. "Induction of angiogenesis in a mouse model using engineered transcription factors" Nature Medicine, Dec. 2002, 8(12):1427-1432.
Redeclaration—37 C.F.R. 41.203(c); filed Mar. 17, 2016.
Reiss, et al. "RecA protein stimulates homologous recombination in plants" Proc. Natl. Acad. Sci. USA, 1996, 93:3094-3098.
Request for Ex Parte Reexamination of U.S. Pat. No. 8,771,945 filed Feb. 16, 2016.
Response to Third Party Observations in EP No. 13624232.6 filed Oct. 2, 2014, with Redlined and Clean Amended Claims.
Rho, M., et al., "Diverse CRISPRs Evolving in Human Microbiomes," PLOS Genetics, vol. 8, No. 6, pp. e1002441, dated Jun. 2012, 12 pages.
Rhun, A., and Charpentier, E., "Small RNAs in streptococci," RNA Biology, vol. 9, No. 4, pp. 414-426, dated Apr. 2012, 13 pages.
Roberts, et al. "Nuclear location signal-mediated protein transport" Biochimica et Biophysica Acta, 1989, 1008:263-280.
Roberts, et al. "The Effect of Protein Content on Nuclear Location Signal Function" Cell, 1987, 50:465-475.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodrigues, et al. "Red Fluorescent Protein (DsRed) as a Reporter in *Saccharomyces cerevisiae*" Journal of Bacteriology, 2001, 183(12):3791-3794.
Rodriguez et al., "AAV-CRISPR: A New Therapeutic Approach to Nucleotide Repeat Diseases", Molecular Therapy, vol. 22, Supplement 1, Abstract 247, May 2014, p. S94.
Rolling, "Recombinant AAV-mediated gene transfer to the retina: gene therapy perspectives", Gene Therapy, Vo. 11, 2004, pp. S26-S32.
*Rubin v. The General Hospital Corp.*, 2011-1439 (Fed. Cir. Mar. 28, 2013).
Sadowski, M., and Jones, D., "The sequence-structure relationship and protein function prediction," Current Opinion in Structural Biology, vol. 19, pp. 357-362, dated May 4, 2009, 6 pages.
Sambrook, et al., Molecular Cloning, A Laboratory Manual on the Web, 2001, Chapter 16.
Sander, et al., "CRISPR-Cas systems for editing, regulating and targeting genomes," Nature Biotechnology, vol. 32, pp. 347-355, dated 2014.

(56) References Cited

OTHER PUBLICATIONS

Sanders, et al. "Use of a macromolecular crowding agent to dissect interactions and define functions in transcriptional activation by a DNA-tracking protein: Bacteriophage T4 gene 45 protein and late transcription" PNAS, 1994, 9:7703-7707.
Sanders, UC Berkeley Jan. 7, 2013 Press Release, available at http://newscenter.berkeley.edu/2013/01/07/cheap-and-easy-technique-to-snip-dna-could-revolutionize-gene-therapy/.
Sanjana, et al., "Improved vectors and genome-wide libraries for CRISPR screening," HHS Public Access Author Manuscript, 2014, 11(8):2145-2148.
Sanjana, N., et al., "A Transcription Activator-Like Effector (TALE) Toolbox for Genome Engineering," Nature Protocols, vol. 7, No. 1, pp. 171-192, dated Jan. 1, 2012, 39 pages.
Sapranauskas, R., et al., "The *Streptococcus thermophilus* CRISPR-Cas system provides immunity in *Escherichia coli*," Nucleic Acids Research, vol. 3, No. 21, pp. 9275-9282, dated Aug. 3, 2011, 8 pages.
Sato, et al. "Generation of Adeno-Associated Virus Vector Enabling Functional Expressionof Oxytocin Receptor and Fluorescence Marker Genes Using the Human eIF4G Internal Ribosome Entry Site Elemet" Biosci. Biotechno. Biochem, 2009, 73(9):2145-2148.
Sauer, "Functional Expression of the cre-lox Site-Specific Recombination System in the Yeast *Saccharomyces cerevisiae*" Mol. Cell. Biol., 1987, 7(6):2087-2096.
Sauer, et al. "Site-specific DNA recombination in mammalian cells by the Cre recombinase of bacteriophage P1" Proc. Natl. Acad. Sci. U.S.A., 1988, 85:5166-5170.
Schiffer, et al. "Predictors of Hepatitis B Cure Using Gene Therapy to Deliver DNA Cleavage Enzymes: A Mathematical Modeling Approach" PLOS Computational Biology, 2013, 9(7):e1003131. www.ploscompbiol.org.
Scholze, et al. "TAL effector-DNA specificity" Virulence, 2010, 1(5):428-432, DOI:10.4161/viru.1.5.12863.
Schramm et al. "Recruitment of RNA polymerase III to its target promoters" Genes & Development, 2002, 16:2593-2620.
Schunder, et al. "First indication for a functional CRISPR/Cas system in Francisella tularensis" International Journal of Medical Microbiology, 2013, 303:1438-4221.
Sebastiani, et al., "BCL11A enhancer haplotypes and fetal hemoglobin in sickle cell anemia," Blood Cells, vol. 54, No. 3, pp. 1079-9796, dated 2015.
Sebo, et al. "A simplified and efficient germline-specific CRISPR/Cas9 system for *Drosophila* genomic engineering" Fly, 2014, 8(1):52-57.
Seffernick, J., et al., "Melamine Deaminase and Atrazine Chlorohydrolase: 98 Percent Identical but Functionally Different," Journal of Bacteriology, vol. 183, No. 8, pp. 2405-2410, dated Apr. 2001, 6 pages.
Senis, E., et al., "CRISPR/Cas9-mediated genome engineering: An adeno-associated viral (AAV) vector toolbox," Biotechnology Journal, vol. 9, No. 11, Sp. Iss. SI, pp. 1402-1412, dated Sep. 4, 2014, 12 pages.
Senturk et al., "A rapid and tunable method to temporally control cas9 expression enables the identification of essential genes and the interrogation of functional gene interactions in vitro and in vivo", Jul. 28, 2015, pp. 1-27, XP002756303, doi:10.1101/023366, Retrieved from the Internet: URL:http://biorxiv.org/content/early/2015/07/28/023366 [retrieved on Apr. 11, 2016).
Seung Woo Cho, et al. "Analysis off-target effects of CRISPR/Cas-derived RNA-guided endonucleases and nickases" Genome Research, Nov. 2014, 24:132-141.
Shalem, et al., "High-throughput functional genomics using CRISP-Cas9," Nature Reviews Genetics, vol. 16, No. 5, pp. 1471-0056, dated 2015.
Shalem, O., et al., "Genome-Scale CRISPR-Cas9 Knockout Screening in Human Cells," Science, vol. 343, pp. 84-87, dated Jan. 3, 2014, 5 pages.

Sharan, et al. "Recombineering: A Homologous Recombination-Based Method of Genetic Engineering" Nat. Protoc., 2009, 4(2):206-223, doi:10.1038/nprot.2008.227.
Shen, B., et al. "Generation of gene-modified mice via Cas9/RNA-mediated gene targeting," Cell Research, vol. 23, No. 5, pp. 720-723, dated May 2013, 4 pages.
Shen, et al. "Efficient genome modification by CRISPR-Cas9 mickase with minimal off-target effects" 2014, Nature Methods, 11(4):399-404.
Shengdar Tsai et al., "Dimeric CRISPR RNS-guided FokI nucleases for highly specific genome editing", Nature Biotechnology, vol. 32, No. 6, Apr. 25, 2014, pp. 569-576.
Shieh, et al. "Nuclear Targeting of the Maize R. Protein Requires Two Nuclear Localization Sequences" Plant Physiol, 1993, 101:353-361.
Siegl, et al. "I-Scel endonuclease: a new tool for DNA repair studies and genetic manipulations in streptomycetes" Appl Microbiol Bitotechnol, 2010, 87:1525-1532.
Sims, D., et al., "High-throughput RNA interference screening using pooled shRNA libraries and next generation sequencing," Genome Biology, vol. 12, No. 10, p. R104, dated Oct. 21, 2011, 13 pages.
Singer, et al. "Applications of Lentiviral Vectors for shRNA Delivery and Transgenesis" Curr Gene Ther., 2008, 8(6):483-488.
Slaymaker et al., Rationally engineered Cas9 nucleases with improved specificity, Science, American Association for the Advancement of Science, US, vol. 351, No. 6268, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, htt://groups.molbiosci.northwestern.edu/sontheimer/Sontheimer_cv.php) Molecular Biosciences.
Stolfi, et al, "Tissue-specific genome editing in Ciona embryos by CRISPR/Cas9," Development, 2014, 141:4115-4120 doi:10.1242/dev.114488.
Stoller, J. and Aboussouan, L., "Alpha1-antitrypsin deficiency," The Lancet, Seminar, vol. 365, No. 9478, pp. 2225-2236, dated Jun. 25, 2005, 12 pages.
Stratikopoulos, E., et al., "The hormonal action of IGF1 in postnatal mouse growth," Proceedings of the National Academy of Sciences, vol. 105, No. 49, pp. 19378-19383, dated Dec. 9, 2008, 6 pages.
Straub, C., et al., "CRISPR/Cas9-Mediated Gene Knock-Down in Post-Mitotic Neurons," PLOS One, vol. 9, No. 8, art. E105584, pp. 1-5, dated Aug. 2014, 6 pages.
Suepo Northwestern Working Papers: A Quality Strategy for the EPO, Mark Lemley, Rational Ignorance at the Patent Office, Northwestern University Law Review (2001), vol. 95, No. 4, p. 1495 ff, note 3.
Sung, et al. "An rpsL Cassette, Janus, for Gene Replacement through Negative Selectionin *Streptococcus pneumoniae*" Applied and Environmental Microbiology, 2001, 67(11):5190-5196.
Sung, M., et al., "The importance of valency in enhancing me import and cell routing potential of protein transduction domain-containing molecules," Biochimica et Biophysica Aeta, vol. 1758, pp. 355-363, dated 2006, 9 pages.
Sung, Young Hoon, et al. "Mouse genetics: Catalogue and scissors" BMB Reports, 2012, 45(12):686-692.
Suzuki, K., et al., "In vivo genome editing via CRISPR/Cas9 mediated homology-independent targeted integration," Nature, vol. 540, art. 7631, pp. 144-149, dated Dec. 1, 2016, 44 pages.
Swarthout, J., et al., "Zinc Finger Nucleases: A new era for transgenic animals," Annals of Neurosciences, vol. 18, No. 1, pp. 25-28, dated Jan. 2011, 4 pages.
Swiech et al., "CRISPR-Mediated Genome Editing in the Mammalian Brain", Molecular Therapy, vol. 22, 749, May 2012, p. S289.
Swiech, L., et al., "In vivo interrogation of gene function in the mammalian brain using CRISPR-Cas9," Nature Biotechnology, vol. 33, pp. 102-106, dated Oct. 19, 2014, 9 pages.
Takara Bio USA, Inc., "Lenti-X™ Tet-On © 3G CRISPR/CAS9 System User Manual" 2009, pp. 1-35.
Tang, T., et al., "A mouse knockout library for secreted and transmembrane proteins," Nature Biotechnology, vol. 28, No. 7, pp. 749-755, dated Jul. 2010, 9 pages.

(56) References Cited

OTHER PUBLICATIONS

*The Broad Inst. v. The Regents of University of UCA*—Decision on Motions for Patent Interference No. 106,048 filed Feb. 15, 2017.
Third Party Observation for Application No. EP20130824232 filed Sep. 22, 2014.
Third Party Observation in Application No. PCT/US2013/074819 dated Apr. 10, 2015.
Third Party Observation Under Article 115 EPC in Application No. 13818570.7 dated Oct. 1, 2014.
Third Party Observations Concerning App. No. GB1420270.9 dated Jun. 30, 2015.
Third Party Observations Concerning Appl. No. EP2800811, dated Jul. 24, 2015.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, Feb. 16, 2015.
Third-Party Observation for Application No. EP20130824232 Aug. 9, 2014.
Tinland, et al. "The T-DNA-linked VirD2 protein contains two distinct functional nuclear localization signals" Proc. Natl. Acad. Sci, 1992, 89:7442-7446.
Tiscornia, et al. "Development of Lentiviral Vectors Expressing siRNA" Gene Transfer-Delivery and Expression of DNA and RNA-A Laboratory Manual, 2007, Chapter 3:23-34.
Tolia, et al. "Slicer and the Argonautes" Nature Chemical Biology, 2007, 3(1):36-43.
Trafton, A., "CRISPR-carrying nanoparticles edit the genome," MIT News, dated Nov. 13, 2017, 3 pages.
Trevino, et al. "Genome Editing Using Cas9 Nickases" Methods in Enxymology, 2014, 546:161-174.
Tulpan, D., et al., "Free energy estimation of short DNA duplex hybridizations," BMC Bioinformatics, vol. 11, pp. 105-127, dated 2012, 22 pages.
Type V CRISPR-associated protein Cpf1 [*Acidaminococcus* sp. Bv3L6], 2017, NCBI Reference Sequence: WP_02173622.1, Non-redundant Protein Sequence.
*Ultra-Precision Mfg. Ltd. v. Ford Motor Co.*, 2004 WL 3507671, *7, *11-12 (E.D. Mich. Mar. 30, 2004).
Urnov, et al. "Highly efficient endogenous human gene correction using designed zinc-finger nucleases" Nature, 2005, 435:646-651.
Urnov, F., et al., "Genome editing with engineered zinc finger nucleases," Nature Reviews, Genetics, vol. 11, pp. 637-646, dated Sep. 2010, 11 pages.
Urrutia, et al. "KRAB-containing zing finger repressor proteins" Genome Biology, 2003, 4(10):231-231.8.
Van Den Ackerveken, et al. "Recognition of the Bacterial Avirulence Protein AvrBs3 Occurs inside the Host Plant Cell" Cell, 1996, 87:1307-1316.
Van Der Oost, "New tool for genome surgery", Science, Feb. 2013, vol. 339, pp. 768-770.
Van Nierop, G., et al., "Stimulation of homology-directed gene targeting at an endogenous human locus by a nicking endonuclease," Nucleic Acids Research, vol. 37, No. 17, pp. 5725-5736, dated Aug. 3, 2009, 12 pages.

Vestergaard et al., "CRISPR adaptive immune systems of Archaea", RNA Biology, 2014, vol. 11, No. 2, pp. 156-167.
Villion, et al. "The double-edged sword of CRISPR-Cas systems" Cell Research, 2013, 23:15-17.
Wang, et al. "Genetic Screens in Human Cells Using the CRISPR-Cas9 System", Science, 2014, 343:80-84.
Weber et al., "TALENs Targeting HBV: Designer Endonuclease Therapies for Viral Infections", Molecular Therapy, vol. 21, No. 10, Oct. 2013, pp. 1819-1821.
Welch, et al. "Designing Genes for Successful Protein Expression" Methods in Enzymology, 2011, 498:43-66, DOI: 10.1016/6978-0-12-385120-8.00003-6.
Wienert, B., et al., "In vitro transcribed guide RNAs trigger an innate immune response via the RIG-I pathway," BioRxiv Preprint, dated Mar. 3, 2018, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, pp. 11643-11650, dated Aug. 18, 1999, 8 pages.
Wittmann et al., "Engineered riboswitches: Expanding researchers' toolbox with synthetic RNA regulators", FEBS Letters, vol. 586, No. 15, Feb. 28, 2012, pp. 2076-2083.
Wolff, et al. "Nuclear security breached" Nature Biotechnology, 2001, 19:1118-1120.
Woo Cho, S., et al., "Targeted genome engineering in human cells with the Cas9 RNA-guided endonuclease," Nature Biotechnology, vol. 31, No. 3, pp. 230-232, dated Jan. 29, 2013, including Supplementary Information, 14 pages.
Wu, X., et al., "Genome-wide binding of the CRISPR endonuclease Cas9 in mammalian cells," Nature Biotechnology, Advance Online Publication, dated Apr. 20, 2014, 9 pages.
Wu, Y., et al., "Correction of a Genetic Disease in Mouse via Use of CRISPR-Cas9," Cell Stem Cell, vol. 13, No. 6, pp. 659-662, dated Dec. 5, 2013, 4 pages.
Wu, Z., et al., "Effect of Genome Size on AAV Vector Packaging," The American Society of Gene & Cell Therapy, vol. 18, No. 1, pp. 80-86, dated Jan. 2010, 7 pages.
Xiao, et al. "Chromosomal deletions and inversions mediated by TALENs and CRIPPR/Cas in zebrafish" Nucleic Acids Research, 2013, 41(14):E141. doi:10.1093/nar/gkt464.
Xiao, et al. "Production of High-Titer Recombinant Adeno-Associated Virus Vectors in the Absence of Helper Adenovirus" Journal of Virology, 1998, 72(3):2224-2232.
Xie, et al. "RNA-Guided Genome Editing in Plants Using a CRISPR-Cas System" Molecular Plant, 2013, 6(6):1975-1983.
Yaghmai, et al. "Optimized Regulation of Gene Expression Using Artificial Transcription Factors", Molecular Therapy, 2002, 5(6):685-694.
Yamano, et al. "Crystal Structure of Cpf1 in Complex with Guide RNA and Target DNA" Cell, 2016, 165:949-962.
Yanfang Fu et al., "Improving CRISPR-Cas nuclease specificity using truncated guide RNAs" (with Supplement Table), Nature Biotechnology, vol. 32, No. 3, Jan. 26, 2014, pp. 279-284.
Yang et al., "HIV-1 TAT-mediated protein transduction and subcellular localization using novel expression vectors," FEBS Letters 532:36-44, (2002).
Yang, H., et al., "One-Step Generation of Mice Carrying Reporter and Conditional Alleles by CRISPR/Cas-Mediated Genome Engineering," Cell, vol. 154, No. 6, pp. 1370-1379, dated Sep. 12, 2013, 14 pages.
Yi, et al. "Current Advances in Retroviral Gene Therapy" Current Gene Therapy, 2011, 11:218:228.
Yin, H., et al., "Structure-guided chemical modification of guide RNA enables potent non-viral in vivo genome editing," Nature Biotechnology, vol. 35, pp. 1179-1187, dated Nov. 13, 2017, 22 pages.
Yu, et al. "An efficient recombination system for chromosome engineering in *Escherichia coli*" PNAS, 2000, 97(11):5978-5983.
Yu, W., et al., "Nrl knockdown by AAV-delivered CRISPR/Cas9 prevents retinal degeneration in mice," Nature Communications, vol. 8, art. 14716, dated Mar. 14, 2017, 15 pages.

(56) References Cited

OTHER PUBLICATIONS

Yu, Zhongshen, et al. "Highly Efficient Genome Modifications Mediated by CRISPR/Cas9 in Drosophila" Genetics, 2013, 195:289-291.
Yusuke Miyazaki et al., Destabilizing Domains Derived from the Human Estrogen Receptor:, Journal of the American Chemical Society, vol. 134, No. 9, Mar. 7, 2012, pp. 3942-3945.
Zetsche et al. "A split-Cas9 architecture for inducible genome editing and transcription modulation" Nature biotechnology, 2015, 33(2): 139-142.
Zetsche et al., "Cpf1 is a single RNA-guided endonuclease of a class 2 CRISPR-Cas system", Cell, Oct. 2015, vol. 163, No. 3, pp. 759-771.
Zhang, "Processing-Independent CRISPR RNAs Limit Natural Transformation in Neisseria meningitidis", Molecular Cell, vol. 50, May 23, 2013. pp. 488-503.
Zhang, et al. "Optogenetic interrogation of neural circuits: technology for probing mammalian brain structures" Nat Protoc., 2010, 5(3):439-456, doi:10.1038/nprot.2009.226.
Zhang, et al. "Efficient construction of sequence-specific TAL effectors for modulating mammalian transcription" nature biotechnology, 2011, 29(2):149-154.
Zhang, et al., "Optimized CRISPR Design", MIT, XP055167487, Oct. 23, 2013, URL:http//crispr.mit.edu/about[retrieved on Feb. 5, 2015].
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, pp. 10158-10163, dated Aug. 1998, 6 pages.
Zhang, X. D., et al., "cSSMD: assessing collective activity for addressing off-target effects in genome-scale RNA interference screens," BIOINFORMATICS, vol. 27, No. 20, pp. 2775-2781, dated Oct. 2011, 7 pages.
Zhou, et al., "High-throughput screening of a CRISPR/Cas9 library for functional genomics in human cells," Nature, vol. 509, pp. 487-491, dated 2014.
Zhu, et al. "Crystal structure of Cmr2 suggests a nucleotide cyclase-related enzyme in type III CRISPR-Cas sytems" FEBS Letters, 2012, 939-945. Doi:10.1016/j.febslet2012.02.036.
Zolkiewska, et al. "ADAM Proteases:Ligand Processing and Modulation of the Notch Pathway" Cell Mol Life Sci, 2008, 65(13):2056-2068.
Zuris, et al., "Cationic lipid-mediated delivery of proteins enables efficient protein-based genome editing in vitro and in vivo" Nature Biotechnology, 2014, Advanced Online publication, doi:10.1038/nbt.3081.
Zuris, et al., Supplementary Information—"Cationic lipid-mediated delivery proteins enables efficient protein-based genome editing in vitro and in vivo" Nature Biotechnology, 2014, Advanced Online publication, doi:10.1038/nbt.3081.
U.S. Appl. No. 14/104,900, filed Dec. 12, 2013.
U.S. Appl. No. 14/104,977, filed Dec. 12, 2013.
U.S. Appl. No. 14/104,990, filed Dec. 12, 2013.
U.S. Appl. No. 14/105,017, filed Dec. 12, 2013.
U.S. Appl. No. 14/222,930, filed Mar. 24, 2014.
U.S. Appl. No. 14/226,274, filed Mar. 26, 2014.
U.S. Appl. No. 14/293,498, filed Jun. 2, 2014.
U.S. Appl. No. 14/293,674, filed Jun. 2, 2014.
U.S. Appl. No. 14/463,253, filed Aug. 19, 2014.
U.S. Appl. No. 14/705,719, filed May 6, 2015.
U.S. Appl. No. 14/738,398, filed Jun. 12, 2015.
U.S. Appl. No. 14/738,483, filed Jun. 12, 2015.
U.S. Appl. No. 14/972,927, filed Dec. 17, 2015.
U.S. Appl. No. 15/171,141, filed Jun. 2, 2016.
U.S. Appl. No. 15/172,636, filed Jun. 3, 2016.
U.S. Appl. No. 15/179,711, filed Jun. 10, 2016.
U.S. Appl. No. 15/179,799, filed Jun. 10, 2016.
U.S. Appl. No. 15/179,912, filed Jun. 10, 2016.
U.S. Appl. No. 15/179,938, filed Jun. 10, 2016.
U.S. Appl. No. 15/179,941, filed Jun. 10, 2016.
U.S. Appl. No. 15/330,876, filed Nov. 7, 2016.
U.S. Appl. No. 15/436,396, filed Feb. 17, 2017.
U.S. Appl. No. 15/620,098, filed Jun. 12, 2017.
U.S. Appl. No. 15/620,391, filed Jun. 12, 2017.
U.S. Appl. No. 15/633,126, filed Jun. 26, 2017.
U.S. Appl. No. 15/834,736, filed Dec. 7, 2017.
U.S. Appl. No. 15/838,720, filed Dec. 12, 2017.
U.S. Appl. No. 15/844,528, filed Dec. 16, 2017.
U.S. Appl. No. 16/012,692, filed Jun. 19, 2018.
U.S. Appl. No. 16/158,295, filed Oct. 11, 2018.
U.S. Appl. No. 16/262,905, filed Jan. 30, 2019.
A. Amsterdam et al., "Identification of 315 genes essential for early zebrafish development," proc Natl Acad Sci., vol. 101, Aug. 31, 2004, pp. 12792-12797, 6 pages.
A. Fire et al., "Potent and specific genetic interference by double-stranded RNA in Caenorhabditis elegans," Nature, vol. 391, Feb. 19, 1998, pp. 806-811, 6 pages.
A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.
A.C. Spradling et al., "The Berkeley *Drosophila* Genome Project Gene Disruption Project: Single P-Element Insertions Mutating 25% of Vital *Drosophila* Genes," Genetics, vol. 153, Sep. 1999, pp. 135-177, 43 pages.
A.H. Tong et al., "Global mapping of the yeast genetic interaction network," Science, vol. 303, Feb. 6, 2004, pp. 808-813, 6 pages.
A.L. Lin and D.H Gutmann, "Advances in the treatment of neurofibromatosis-associated tumours," Nature, vol. 10, Nov. 2013, pp. 616-624, 9 pages.
A.P. Blanchard and L. Hood, "Sequence to array: probing the genome's secrets," Nat Biotechnol, vol. 14, Dec. 14, 1996, p. 1649.
Allen, et al., "Liposomal drug delivery systems: From concept to clinical applications" Advanced Drug Delivery Reviews, vol. 65, 2013, pp. 36-48, 13 pages.
B. Langmead et al., "Ultrafast and memory-efficient alignment of short DNA sequences to the human genome," Genome biology, vol. 10, Mar. 4, 2009, 10 pages.
B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counter-selection," Plasmid, vol. 55, 2006, pp. 58-63, 6 pages.
Botta, S. et al, "Transcriptional Repression with Zinc-Finger and Tale Protein Scaffold", Molecular Therapy, 2013, Supplement 1, p. S208, Abstract No. 539.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.

(56) References Cited

OTHER PUBLICATIONS

C.M. Johnston et al., "Large-scale population study of human cell lines indicate that dosage compensation is virtually complete," PLoS Genet., vol. 4, Jan. 2008, p. 88-98, 11 pages.
Carte, J., et al., "Cas6 is an endoribonuclease that generates guide RNAs for invader defense in prokaryotes," Genes Dev., vol. 22, 2008, pp. 3489-3496.
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chevalier et al., "Homing endonuclease: structural and functional insight into the catalysts of intron/intein mobility," Oxford University Press., vol. 29, 2001, pp. 3757-3774.
Cho, Minseon, et al., "Quantitative selection and parallel characterization of aptamers," PNAS, vol. 110, Nov. 12, 2013, pp. 18460-18465.
D.J. Burgess et al., "Topoisomerase levels determine chemotherapy response in vitro and in vivo," Proceedings of the National Academy of Sciences, vol. 105, Jul. 1, 2008, pp. 9053-9058.
Dean., "Recent Advances in Drug Design Methods: Where Will They Lead?", BioEssays, vol. 16, Sep. 1994, pp. 683-687.
Deveau, H. et al., "Phage response to CRISPR-encoded resistance in Streptococcus thermophilus," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
E.S. Lander, "Initial impact of the sequencing of the human genome," Nature, vol. 470, Feb. 10, 2011, p. 187-197.
Edgar, R. and Qimron, U., "The *Escherichia coli* CRISPR system protects from λ lysogenization, lysogens, and prophage induction," Journal of Bacteriology, vol. 192, Dec. 2010, pp. 6291-6294.
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Flannery, J. G., "Ribozyme-Mediated Gene Therapy for Autosomal Dominant Retinal Degeneration", Retinal Degenerative Diseases and Experimental Therapy, 1999, pp. 277-291.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.
Gao, et al., "A Sustained, Cytoplasmic Transgene Expression System delivered by Cationic Liposomes", Biochemical and Biophysical Research Communications, vol. 200, May 16, 1994, pp. 1201-1206.
Gibson, D.G. et al., "Enzymatic assembly of DNA molecules up to several hundred kilobases," Nat methods, vol. 6, 2009, pp. 343-345.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
H. Davies et al., "Mutations of the BRAF gene in human cancer," Nature, vol. 417, Jun. 27, 2002, p. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.

Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.
Hemann et al., "An epi-allelic series of p53 hypomorphs created by stable RNAi produces distinct tumor phenotypes in vivo," Nat Genetics, vol. 33, Mar. 2003, pp. 396-400.
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Husmann, L.K.,et al., "Expression of the Arp protein, a member of the M protein family, is not sufficient to inhibit phagocytosis of *Streptococcus pyogenes*," Infection and immunity, vol. 63, Jan. 1995, pp. 345-348.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist lncRNA exploits three-dimensional genome architecture to spread across the X chromosome," Science, vol. 341, Aug. 16, 2013, pp. 1-8, 8 pages.
Jansen R. et al., "Identification of genes that are associated with DNA repeats in prokaryotes," Molecular Microbiology, vol. 43, 2002, pp. 1565-1575, 11 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Koo et al., "Measuring and Reducing Off-Target Activities of Programmable Nucleases Including CRISPR-Cas9", Molecules and Cells, vol. 38, 2015, pp. 475-481, 7 pages.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.

(56) References Cited

OTHER PUBLICATIONS

M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Moffat J et al., "A lentiviral RNAi library for human and mouse genes applied to an arrayed viral high-content screen," Cell, vol. 124, Mar. 24, 2006, pp. 1283-1298, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Motamedi, M.R., et al., "Double-strand-break repair recombination in *Escherichia coli*: physical evidence for a DNA replication mechanism in vivo," Genes Dev., vol. 13, 1999, pp. 2889-2903.
Paddison et al., "A resource for large-scale RNA-interference-based screens in mammals," Nature, vol. 428, Mar. 25, 2004, pp. 427-31, 5 pages.
Podbielski, A., et al., "R. Novel series of plasmid vectors for gene inactivation and expression analysis in group A streptococci (GAS)," Gene, vol. 177, 1996, pp. 137-147, 11 pages.
R. Rad et al., "PiggyBac transposon mutagenesis: a tool for cancer gene discovery in mice," Science, vol. 330, Nov. 19, 2010, p. 1104-1107, 4 pages.
R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1α localization in erythroblasts," Blood, vol. 117, Jun. 2011, pp. 6928-6938, 11 pages.
S. Huang et al., "MED12 Controls the Response to Multiple Cancer Drugs through Regulation of TGF-ß; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, c1orf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Stewart SA et al., "Lentivirus-delivered stable gene silencing by RNAi in primary cells," RNA, vol. 9, 2003, pp. 493-501, 9 pages.
Symington et al., "Double-Strand Break End Resection and Repair Pathway Choice", Annual Review of Genetics, vol. 45, 2011, pp. 247-271, 25 pages.

T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774-19781, 9 pages.
T.J. Cradick et al., "CRISPR/Cas9 systems targeting ß-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genotoxicity by introducing single-strand breaks to signal a G2-M arrest in MMR-proficient RKO cells," Clinical Cancer Research, vol. 9, Jun. 2003, p. 2327-2334, 9 pages.
V.N. Ngo et al., "A loss-of-function RNA interference screen for molecular targets in cancer," Nature, vol. 441, May 4, 2006, pp. 106-110, 5 pages.
Van Der Oost, J., et al., "CRISPR-based adaptive and heritable immunity in prokaryotes," Trends. Biochem. Sci., vol. 34, 2009, pp. 401-407, 7 pages.
Venken et al., "P[acman]: A BAC Transgenic Platform for Targeted Insertion of Large DNA Fragments in D. melanogaster", Science, vol. 314, Dec. 15, 2006, pp. 1747-1751, 5 pages.
W.G. Kaelin., "Use and Abuse of RNAi to Study Mammalian Gene Function," Science, vol. 337, Jul. 27, 2012, p. 421-422, 2 pages.
Wang, H.H. et al., "Genome-scale promoter engineering by coselection MAGE," Nat methods, vol. 9, Jun. 2012, pp. 591-593, 3 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.
Xu, Zhi-Li et al., "Regulated gene expression from adenovirus vectors: a systematic comparison of various inducible systems," Gene, vol. 309, 2003, pp. 145-151, 7 pages.
Zahner, D. and Hakenbeck, R. "The *Streptococcus pneumoniae* beta-galactosidase is a surface protein," J. Bacteriology, vol. 182, Oct. 2000, pp. 5919-5921, 3 pages.
Zeng Y et al., "Both natural and designed micro RNAs can inhibit the expression of cognate mRNAs when expressed in human cells," Mol Cell., vol. 9, Jun. 2002, pp. 1327-1333, 7 pages.
Hwang, W.Y., et al., "Efficient Genome Editing in Zebrafish Using a CRISPR-Cas System", Nature Biotechnology, vol. 31, No. 3, Jan. 29, 2013, pp. 227-229.
Zuris, et al., "Efficient Delivery of Genome-Editing Proteins In Vitro and In Vivo" Nature Biotechnology, vol. 33, No. 1, Jan. 2015, pp. 1-26.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
GenBank: "CRISPR-associated protein Cas9/Csn1 [*Staphylococcus aureus* subsp. aureus]", GenBank: CCK74173.1, Year: 2012, http://www.ncbi.nlm.nih.gov/protein/403411236?sat=16&satkey=13804560, dated Dec. 14, 2016, 2 pages.
Grosse, et al. "Meganuclease-medicated Inhibition of HSV1 Infection in Cultured Cells", Molecular Therapy, vol. 19, No. 4, Apr. 1, 2011, pp. 694-702.
Schiffer, et al. "Targeted DNA Mutagenesis for the Cure of Chronic Viral Infections" Journal of Virology, vol. 86, No. 17, Jun. 20, 2012, pp. 8920-8936.
Spencer, J.M., et al., "Development of a Nuclease Screen to Improve Cas9 Targeting Specificity", Molecular Therapy, May 2015, vol. 23, Suppl. 1, S136(340).
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
Xiao, W., et al, "Gene Therapy Vectors Based on Adeno-Associated Virus Type 1", Journal of Virology, May 1999, vol. 73, No. 5, p. 3994-4003.

(56) References Cited

OTHER PUBLICATIONS

Decision on Motions—PTAB, *The Regents of the University of California* v. *The Broad Institute, Inc.*, filed Sep. 10, 2020, in Patent Interference No. 106,115 (DK), 113 pages.
Hirano et al., "Structure and Engineering of Francisella novicida Cas9," Cell, vol. 164, Feb. 25, 2016, pp. 950-961.
Ran, F.A., "CRISPR-Cas: Development and Applications for Mammalian Genome Editing", Ph.D. Dissertation, Harvard University, Apr. 2014.
Redeclaration—PTAB, *The Regents of the University of California* v. *The Broad Institute, Inc.*, filed Aug. 26, 2019, in Patent Interference No. 106,115 (DK), 20 pages.
Redeclaration—PTAB, *The Regents of the University of California* v. *The Broad Institute, Inc.*, filed Sep. 10, 2020, in Patent Interference No. 106,115 (DK), 3 pages.
Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.
U.S. Appl. No. 14/054,414, filed Oct. 15, 2013.
U.S. Appl. No. 14/104,837, filed Dec. 12, 2013.
U.S. Appl. No. 14/105,031, filed Dec. 12, 2013.
U.S. Appl. No. 14/105,035, filed Dec. 12, 2013.
U.S. Appl. No. 14/183,429, filed Feb. 18, 2014.
U.S. Appl. No. 14/183,471, filed Feb. 18, 2014.
U.S. Appl. No. 14/183,486, filed Feb. 18, 2014.
U.S. Appl. No. 14/183,512, filed Feb. 18, 2014.
U.S. Appl. No. 14/256,912, filed Apr. 18, 2014.
U.S. Appl. No. 14/258,458, filed Apr. 22, 2014.
U.S. Appl. No. 14/259,420, filed Apr. 23, 2014.
U.S. Appl. No. 14/290,575, filed May 29, 2014.
U.S. Appl. No. 14/324,960, filed Jul. 7, 2014.
U.S. Appl. No. 14/481,339, filed Sep. 9, 2014.
U.S. Appl. No. 14/497,627, filed Sep. 26, 2014.
U.S. Appl. No. 14/523,799, filed Oct. 24, 2014.
U.S. Appl. No. 14/681,382, filed Apr. 8, 2015.
U.S. Appl. No. 14/703,511, filed May 4, 2015.
U.S. Appl. No. 14/704,551, filed May 5, 2015.
U.S. Appl. No. 14/970,967, filed Dec. 16, 2015.
U.S. Appl. No. 14/971,169, filed Dec. 16, 2015.
U.S. Appl. No. 14/971,356, filed Dec. 16, 2015.
U.S. Appl. No. 14/972,523, filed Dec. 17, 2015.
U.S. Appl. No. 14/973,062, filed Dec. 17, 2015.
U.S. Appl. No. 14/990,444, filed Jan. 7, 2016.
U.S. Appl. No. 14/991,083, filed Jan. 8, 2016.
U.S. Appl. No. 15/160,710, filed May 20, 2016.
U.S. Appl. No. 15/217,489, filed Jul. 22, 2016.
U.S. Appl. No. 15/229,702, filed Aug. 5, 2016.
U.S. Appl. No. 15/230,025, filed Aug. 5, 2016.
U.S. Appl. No. 15/230,161, filed Aug. 5, 2016.
U.S. Appl. No. 15/349,603, filed Nov. 11, 2016.
U.S. Appl. No. 15/430,260, filed Feb. 10, 2017.
U.S. Appl. No. 15/838,064, filed Dec. 11, 2017.
U.S. Appl. No. 15/887,377, filed Feb. 2, 2018.
U.S. Appl. No. 15/967,464, filed Apr. 30, 2018.
U.S. Appl. No. 15/967,495, filed Apr. 30, 2018.
U.S. Appl. No. 15/967,510, filed Apr. 30, 2018.
U.S. Appl. No. 16/177,403, filed Oct. 31, 2018.
U.S. Appl. No. 16/178,551, filed Nov. 1, 2018.
U.S. Appl. No. 16/445,150, filed Jun. 18, 2019.
U.S. Appl. No. 16/445,156, filed Jun. 18, 2019.
U.S. Appl. No. 16/532,442, dated Aug. 5, 2019.
U.S. Appl. No. 16/535,043, filed Aug. 7, 2019.
U.S. Appl. No. 16/800,988, filed Feb. 25, 2020.
U.S. Appl. No. 16/844,548, filed Apr. 9, 2020.
U.S. Appl. No. 16/906,580, filed Jun. 19, 2020.
U.S. Appl. No. 16/938,110, filed Jul. 24, 2020.
U.S. Appl. No. 17/027,151, filed Sep. 21, 2020.
Declaration of Interference—PTAB, The Broad Institute, Inc., *Massachusetts Institute of Technology, and President and Fellows of Harvard College* v. *Toolgen, Inc.*, filed Dec. 14, 2020, in Patent Interference No. 106,126 (DK), 19 pages.

\* cited by examiner

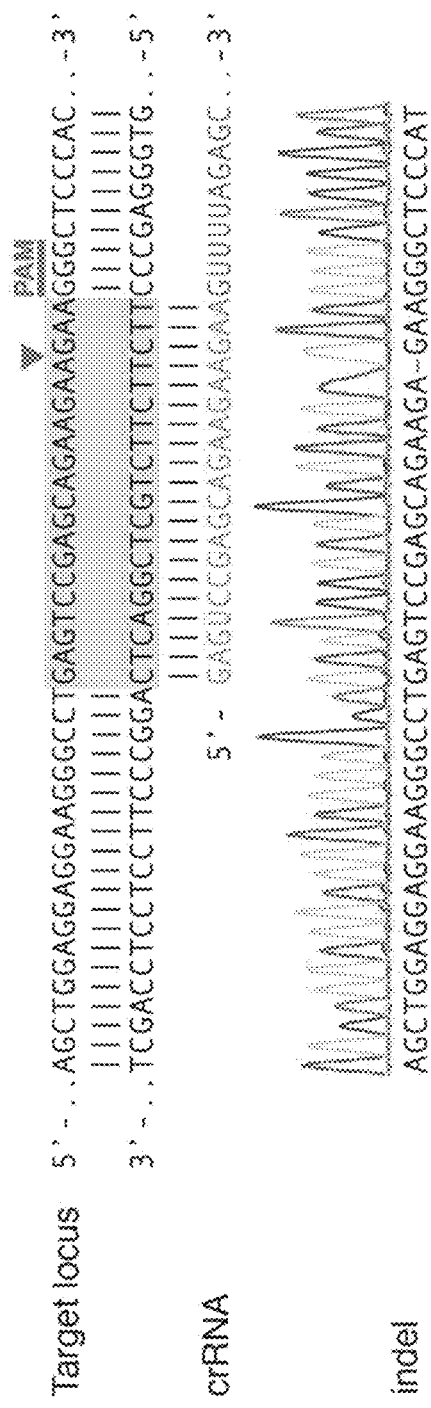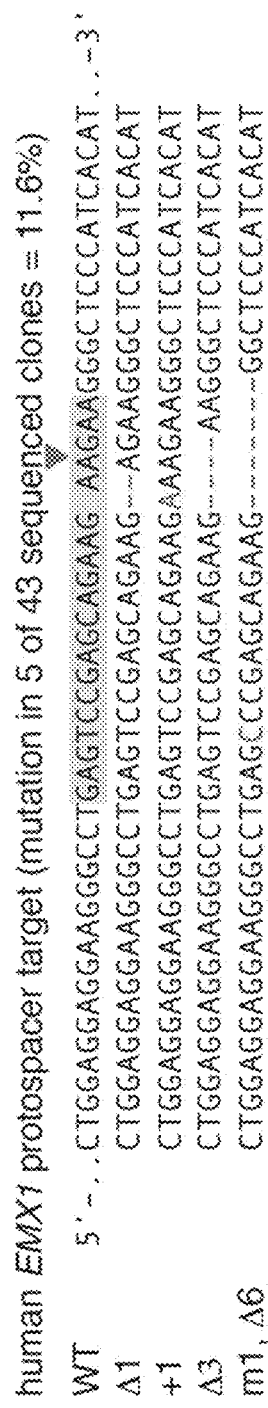
FIG. 2E
FIG. 2F

SpCas9 mutation positions hSpCas9

```
5' ATGGACAAGAAGTACAGCATCGGCCTGGACATCGGCACCAACTCTGTGGGCTGGGCCGTG
                                                                      60
         hSpCas9
              D10
               RuvCI
    M  D  K  Y  S  I  G  L  D  I  G  T  N  S  V  G  W  A  V
    1  2  3  4  5  6  7  8  9  10 11 12 13 14 15 16 17 18 19 20

5' ATCACCGACGAGTACAAGGTGCCCAGCAAGAAATTCAAGGTGCTGGGCAACACCGACCGG
                                                                      120
                              hSpCas9
    R
    I  T  D  E  Y  K  V  P  S  K  K  F  K  V  L  G  N  T  D  R
    21 22 23 24 25 26 27 28 29 30 31 32 33 34 35 36 37 38 39 40

5' CACAGCATCAAGAAGAACCTGATCGGAGCCCTGCTGTTCGACAGCGGCGAAACAGCCGAG
                                                                      180
                              hSpCas9
    H  S  I  K  K  N  L  I  G  A  L  L  F  D  S  G  E  T  A  E
    41 42 43 44 45 46 47 48 49 50 51 52 53 54 55 56 57 58 59 60

5' GCCACCCGGCTGAAGAGAACCGCCAGAAGAAGATACACCAGACGGAAGAACCGGATCTGC
                                                                      240
                              hSpCas9
    A  T  R  L  K  R  T  A  R  R  R  Y  T  R  R  K  N  R  I  C
    61 62 63 64 65 66 67 68 69 70 71 72 73 74 75 76 77 78 79 80

5' TATCTGCAAGAGATCTTCAGCAACGAGATGGCCAAGGTGGACGACAGCTTCTTCCACAGA
                                                                      300
                              hSpCas9
    Y  L  Q  E  I  F  S  N  E  M  A  K  V  D  D  S  F  F  H  R
    81 82 83 84 85 86 87 88 89 90 91 92 93 94 95 96 97 98 99 100
```

FIG. 6A hSpCas9

```
5' CTGGAAGAGTCCTTCCTGGTGGAAGAGGATAAGAAGCACGAGCGGCACCCCATCTTCGGC
                                                                              360
        L   E   E   S   F   L   V   E   E   D   K   K   H   E   R   H   P   I   F   G
       101 102 103 104 105 106 107 108 109 110 111 112 113 114 115 116 117 118 119 120

5' AACATCGTGGACGAGGTGGCCTACCACGAGAAGTACCCCACCATCTACCACCTGAGAAAG
                                                                              420
        N   I   V   D   E   V   A   Y   H   E   K   Y   P   T   I   Y   H   L   R   K
       121 122 123 124 125 126 127 128 129 130 131 132 133 134 135 136 137 138 139 140

5' AAACTGGTGGACAGCACCGACAAGGCCGACCTGCGGCTGATCTATCTGGCCCTGGCCCAC
                                                                              480
        K   L   V   D   S   T   D   K   A   D   L   R   L   I   Y   L   A   L   A   H
       141 142 143 144 145 146 147 148 149 150 151 152 153 154 155 156 157 158 159 160

5' ATGATCAAGTTCCGGGGCCACTTCCTGATCGAGGGCGACCTGAACCCCGACAACAGCGAC
                                                                              540
        M   I   K   F   R   G   H   F   L   I   E   G   D   L   N   P   D   N   S   D
       161 162 163 164 165 166 167 168 169 170 171 172 173 174 175 176 177 178 179 180

5' GTGGACAAGCTGTTCATCCAGCTGGTGCAGACCTACAACCAGCTGTTCGAGGAAAACCCC
                                                                              600
        V   D   K   L   F   I   Q   L   V   Q   T   Y   N   Q   L   F   E   E   N   P
       181 182 183 184 185 186 187 188 189 190 191 192 193 194 195 196 197 198 199 200

5' ATCAACGCCAGCGGCGTGGACGCCAAGGCCATCCTGTCTGCCAGACTGAGCAAGAGCAGA
                                                                              660
        I   N   A   S   G   V   D   A   K   A   I   L   S   A   R   L   S   K   S   R
       201 202 203 204 205 206 207 208 209 210 211 212 213 214 215 216 217 218 219 220
```

FIG. 6B

```
hSpCas9
5' CGGCTGGAAAATCTGATCGCCCAGCTGCCCGGCGAGAAGAAGAATGGCCTGTTCGGCAAC         720
    R  L  E  N  L  I  A  Q  L  P  G  E  K  K  N  G  L  F  G  N
   221 222 223 224 225 226 227 228 229 230 231 232 233 234 235 236 237 238 239 240

5' CTGATTGCCCTGAGCCTGGGCCTGACCCCCAACTTCAAGAGCAACTTCGACCTGGCCGAG        780
    L  I  A  L  S  L  G  L  T  P  N  F  K  S  N  F  D  L  A  E
   241 242 243 244 245 246 247 248 249 250 251 252 253 254 255 256 257 258 259 260

5' GATGCCAAACTGCAGCTGAGCAAGGACACCTACGACGACGACCTGGACAACCTGCTGGCC        840
    D  A  K  L  Q  L  S  K  D  T  Y  D  D  D  L  D  N  L  L  A
   261 262 263 264 265 266 267 268 269 270 271 272 273 274 275 276 277 278 279 280

5' CAGATCGGCGACCAGTACGCCGACCTGTTTCTGGCCGCCAAGAACCTGTCCGACGCCATC        900
    Q  I  G  D  Q  Y  A  D  L  F  L  A  A  K  N  L  S  D  A  I
   281 282 283 284 285 286 287 288 289 290 291 292 293 294 295 296 297 298 299 300

5' CTGCTGAGCGACATCCTGAGAGTGAACACCGAGATCACCAAGGCCCCCCTGAGCGCCTCT        960
    L  L  S  D  I  L  R  V  N  T  E  I  T  K  A  P  L  S  A  S
   301 302 303 304 305 306 307 308 309 310 311 312 313 314 315 316 317 318 319 320

5' ATGATCAAGAGATACGACGAGCACCACCAGGACCTGACCCTGCTGAAAGCTCTCGTGCGG       1020
    M  I  K  R  Y  D  E  H  H  Q  D  L  T  L  L  K  A  L  V  R
   321 322 323 324 325 326 327 328 329 330 331 332 333 334 335 336 337 338 339 340
```

FIG. 6C hSpCas9

```
5' CAGCAGCTGCCTGAGAAGTACAAAGAGATTTTCTTCGACCAGAGCAAGAACGGCTACGCC
                                                                        1080
    Q   Q   L   P   E   K   Y   K   E   I   F   F   D   Q   S   K   N   G   Y   A
   341 342 343 344 345 346 347 348 349 350 351 352 353 354 355 356 357 358 359 360

5' GGCTACATTGACGGCGGAGCCAGCCAGGAAGAGTTCTACAAGTTCATCAAGCCCATCCTG
                                                                        1140
    G   Y   I   D   G   G   A   S   Q   E   E   F   Y   K   F   I   K   P   I   L
   361 362 363 364 365 366 367 368 369 370 371 372 373 374 375 376 377 378 379 380

5' GAAAAGATGGACGGCACCGAGGAACTGCTCGTGAAGCTGAACAGAGAGGACCTGCTGCGG
                                                                        1200
    E   K   M   D   G   T   E   E   L   L   V   K   L   N   R   E   D   L   L   R
   381 382 383 384 385 386 387 388 389 390 391 392 393 394 395 396 397 398 399 400

5' AAGCAGCGGACCTTCGACAACGGCAGCATCCCCCACCAGATCCACCTGGGAGAGCTGCAC
                                                                        1260
    K   Q   R   T   F   D   N   G   S   I   P   H   Q   I   H   L   G   E   L   H
   401 402 403 404 405 406 407 408 409 410 411 412 413 414 415 416 417 418 419 420

5' GCCATTCTGCGGCGGCAGGAAGATTTTTACCCATTCCTGAAGGACAACCGGGAAAAGATC
                                                                        1320
    A   I   L   R   R   Q   E   D   F   Y   P   F   L   K   D   N   R   E   K   I
   421 422 423 424 425 426 427 428 429 430 431 432 433 434 435 436 437 438 439 440

5' GAGAAGATCCTGACCTTCCGCATCCCCTACTACGTGGGCCCTCTGGCCAGGGGAAACAGC
                                                                        1380
    E   K   I   L   T   F   R   I   P   Y   Y   V   G   P   L   A   R   G   N   S
   441 442 443 444 445 446 447 448 449 450 451 452 453 454 455 456 457 458 459 460
```

FIG. 6D hSpCas9

```
5' AGATTCGCCTGGATGACCAGAAAGAGCGAGGAAACCATCACCCCCTGGAACTTCGAGGAA
                                                                          1440
        hSpCas9
        R  F  A  W  M  T  R  K  S  E  E  T  I  T  P  W  N  F  E  E
       461 462 463 464 465 466 467 468 469 470 471 472 473 474 475 476 477 478 479 480

5' GTGGTGGACAAGGGCGCTTCCGCCCAGAGCTTCATCGAGCGGATGACCAACTTCGATAAG
                                                                          1500
        hSpCas9
        V  V  D  K  G  A  S  A  Q  S  F  I  E  R  M  T  N  F  D  K
       481 482 483 484 485 486 487 488 489 490 491 492 493 494 495 496 497 498 499 500

5' AACCTGCCCAACGAGAAGGTGCTGCCCAAGCACAGCCTGCTGTACGAGTACTTCACCGTG
                                                                          1560
        hSpCas9
        N  L  P  N  E  K  V  L  P  K  H  S  L  L  Y  E  Y  F  T  V
       501 502 503 504 505 506 507 508 509 510 511 512 513 514 515 516 517 518 519 520

5' TATAACGAGCTGACCAAAGTGAAATACGTGACCGAGGGAATGAGAAAGCCCGCCTTCCTG
                                                                          1620
        hSpCas9
        Y  N  E  L  T  K  V  K  Y  V  T  E  G  M  R  K  P  A  F  L
       521 522 523 524 525 526 527 528 529 530 531 532 533 534 535 536 537 538 539 540

5' AGCGGCGAGCAGAAAAAGGCCATCGTGGACCTGCTGTTCAAGACCAACCGGAAAGTGACC
                                                                          1680
        hSpCas9
        S  G  E  Q  K  K  A  I  V  D  L  L  F  K  T  N  R  K  V  T
       541 542 543 544 545 546 547 548 549 550 551 552 553 554 555 556 557 558 559 560

5' GTGAAGCAGCTGAAAGAGGACTACTTCAAGAAAATCGAGTGCTTCGACTCCGTGGAAATC
                                                                          1740
        hSpCas9
        V  K  Q  L  K  E  D  Y  F  K  K  I  E  C  F  D  S  V  E  I
       561 562 563 564 565 566 567 568 569 570 571 572 573 574 575 576 577 578 579 580
```

FIG. 6E

```
hSpCas9
5' TCCGGCGTGGAAGATCGGTTCAACGCCTCCCTGGGCACATACCACGATCTGCTGAAAATT
                                                                    1800
                              hSpCas9
    S  G  V  E  D  R  F  N  A  S  L  G  T  Y  H  D  L  L  K  I
   581 582 583 584 585 586 587 588 589 590 591 592 593 594 595 596 597 598 599 600

5' ATCAAGGACAAGGACTTCCTGGACAATGAGGAAAACGAGGACATTCTGGAAGATATCGTG
                                                                    1860
                              hSpCas9
    I  K  D  K  D  F  L  D  N  E  E  N  E  D  I  L  E  D  I  V
   601 602 603 604 605 606 607 608 609 610 611 612 613 614 615 616 617 618 619 620

5' CTGACCCTGACACTGTTTGAGGACAGAGAGATGATCGAGGAACGGCTGAAAACCTATGCC
                                                                    1920
                              hSpCas9
    L  T  L  T  L  F  E  D  R  E  M  I  E  E  R  L  K  T  Y  A
   621 622 623 624 625 626 627 628 629 630 631 632 633 634 635 636 637 638 639 640

5' CACCTGTTCGACGACAAAGTGATGAAGCAGCTGAAGCGGCGGAGATACACCGGCTGGGGC
                                                                    1980
                              hSpCas9
    H  L  F  D  D  K  V  M  K  Q  L  K  R  R  R  Y  T  G  W  G
   641 642 643 644 645 646 647 648 649 650 651 652 653 654 655 656 657 658 659 660

5' AGGCTGAGCCGGAAGCTGATCAACGGCATCCGGGACAAGCAGTCCGGCAAGACAATCCTG
                                                                    2040
                              hSpCas9
    R  L  S  R  K  L  I  N  G  I  R  D  K  Q  S  G  K  T  I  L
   661 662 663 664 665 666 667 668 669 670 671 672 673 674 675 676 677 678 679 680

5' GATTTCCTGAAGTCCGACGGCTTCGCCAACAGAAACTTCATGCAGCTGATCCACGACGAC
                                                                    2100
                              hSpCas9
    D  F  L  K  S  D  G  F  A  N  R  N  F  M  Q  L  I  H  D  D
   681 682 683 684 685 686 687 688 689 690 691 692 693 694 695 696 697 698 699 700
```

```
hSpCas9
5' GTGGAAAACACCCAGCTGCAGAACGAGAAGCTGTACCTGTACTACCTGCAGAATGGGCGG  2460
     V  E  N  T  Q  L  Q  N  E  K  L  Y  L  Y  Y  L  Q  N  G  R
    801 802 803 804 805 806 807 808 809 810 811 812 813 814 815 816 817 818 819 820

5' GATATGTACGTGGACCAGGAACTGGACATCAACCGGCTGTCCGACTACGATGTGGACGCC  2520
     D  M  Y  V  D  Q  E  L  D  I  N  R  L  S  D  Y  D  V  D  A
    821 822 823 824 825 826 827 828 829 830 831 832 833 834 835 836 837 838 839 840

5' ATCGTGCCTCAGAGCTTTCTGAAGGACGACTCCATCGACGCCAAGGTGCTGACCAGAAGC  2580
     I  V  P  Q  S  F  L  K  D  D  S  I  D  A  K  V  L  T  R  S
    841 842 843 844 845 846 847 848 849 850 851 852 853 854 855 856 857 858 859 860

5' GACAAGGCCCGGGGCAAGAGCGACAACGTGCCCTCCGAAGAGGTCGTGAAGAAGATGAAG  2640
     D  K  A  R  G  K  S  D  N  V  P  S  E  E  V  V  K  K  M  K
    861 862 863 864 865 866 867 868 869 870 871 872 873 874 875 876 877 878 879 880

5' AACTACTGGCGGCAGCTGCTGAACGCCAAGCTGATTACCCAGAGAAAGTTCGACAATCTG  2700
     N  Y  W  R  Q  L  L  N  A  K  L  I  T  Q  R  K  F  D  N  L
    881 882 883 884 885 886 887 888 889 890 891 892 893 894 895 896 897 898 899 900
```

FIG. 6H

FIG. 6I hSpCas9

```
5'  TACCCTAAGCTGGAAAGCGAGTTCGTGTACGGCGACTACAAGGTGTACGACGTGCGGAAG
    ++++++++++|++++++++++|++++++++++|++++++++++|++++++++++|++++++++++|  3060
                          hSpCas9
     Y   P   K   L   E   S   E   F   V   Y   G   D   Y   K   V   Y   D   V   R   K
    1001 1002 1003 1004 1005 1006 1007 1008 1009 1010 1011 1012 1013 1014 1015 1016 1017 1018 1019 1020

5'  ATGATCGCCAAGAGCGAGCAGGAAATCGGCAAGGCTACCGCCAAGTACTTCTTCTACAGC
    ++++++++++|++++++++++|++++++++++|++++++++++|++++++++++|++++++++++|  3120
                          hSpCas9
     M   I   A   K   S   E   Q   E   I   G   K   A   T   A   K   Y   F   F   Y   S
    1021 1022 1023 1024 1025 1026 1027 1028 1029 1030 1031 1032 1033 1034 1035 1036 1037 1038 1039 1040

5'  AACATCATGAACTTTTTCAAGACCGAGATTACCCTGGCCAACGGCGAGATCCGGAAGCGG
    ++++++++++|++++++++++|++++++++++|++++++++++|++++++++++|++++++++++|  3180
                          hSpCas9
     N   I   M   N   F   F   K   T   E   I   T   L   A   N   G   E   I   R   K   R
    1041 1042 1043 1044 1045 1046 1047 1048 1049 1050 1051 1052 1053 1054 1055 1056 1057 1058 1059 1060

5'  CCTCTGATCGAGACAAACGGCGAAACCGGGGAGATCGTGTGGGATAAGGGCCGGGATTTT
    ++++++++++|++++++++++|++++++++++|++++++++++|++++++++++|++++++++++|  3240
                          hSpCas9
     P   L   I   E   T   N   G   E   T   G   E   I   V   W   D   K   G   R   D   F
    1061 1062 1063 1064 1065 1066 1067 1068 1069 1070 1071 1072 1073 1074 1075 1076 1077 1078 1079 1080

5'  GCCACCGTGCGGAAAGTGCTGAGCATGCCCCAAGTGAATATCGTGAAAAAGACCGAGGTG
    ++++++++++|++++++++++|++++++++++|++++++++++|++++++++++|++++++++++|  3300
                          hSpCas9
     A   T   V   R   K   V   L   S   M   P   Q   V   N   I   V   K   K   T   E   V
    1081 1082 1083 1084 1085 1086 1087 1088 1089 1090 1091 1092 1093 1094 1095 1096 1097 1098 1099 1100

5'  CAGACAGGCGGCTTCAGCAAAGAGTCTATCCTGCCCAAGAGGAACAGCGATAAGCTGATC
    ++++++++++|++++++++++|++++++++++|++++++++++|++++++++++|++++++++++|  3360
                          hSpCas9
     Q   T   G   G   F   S   K   E   S   I   L   P   K   R   N   S   D   K   L   I
    1101 1102 1103 1104 1105 1106 1107 1108 1109 1110 1111 1112 1113 1114 1115 1116 1117 1118 1119 1120
```

FIG. 6J hSpCas9

```
5'  GCCAGAAAGAAGGACTGGGACCCTAAGAAGTACGGCGGCTTCGACAGCCCCACCGTGGCC
                                                                        3420
         A  R  K  K  D  W  D  P  K  K  Y  G  G  F  D  S  P  T  V  A
       1121 1122 1123 1124 1125 1126 1127 1128 1129 1130 1131 1132 1133 1134 1135 1136 1137 1138 1139 1140

5'  TATTCTGTGCTGGTGGTGGCCAAAGTGGAAAAGGGCAAGTCCAAGAAACTGAAGAGTGTG
                                                                        3480
         Y  S  V  L  V  V  A  K  V  E  K  G  K  S  K  K  L  K  S  V
       1141 1142 1143 1144 1145 1146 1147 1148 1149 1150 1151 1152 1153 1154 1155 1156 1157 1158 1159 1160

5'  AAAGAGCTGCTGGGGATCACCATCATGGAAAGAAGCAGCTTCGAGAAGAATCCCATCGAC
                                                                        3540
         K  E  L  L  G  I  T  I  M  E  R  S  S  F  E  K  N  P  I  D
       1161 1162 1163 1164 1165 1166 1167 1168 1169 1170 1171 1172 1173 1174 1175 1176 1177 1178 1179 1180

5'  TTTCTGGAAGCCAAGGGCTACAAAGAAGTGAAAAAGGACCTGATCATCAAGCTGCCTAAG
                                                                        3600
         F  L  E  A  K  G  Y  K  E  V  K  K  D  L  I  I  K  L  P  K
       1181 1182 1183 1184 1185 1186 1187 1188 1189 1190 1191 1192 1193 1194 1195 1196 1197 1198 1199 1200

5'  TACTCCCTGTTCGAGCTGGAAAACGGCCGGAAGAGAATGCTGGCCTCTGCCGGCGAACTG
                                                                        3660
         Y  S  L  F  E  L  E  N  G  R  K  R  M  L  A  S  A  G  E  L
       1201 1202 1203 1204 1205 1206 1207 1208 1209 1210 1211 1212 1213 1214 1215 1216 1217 1218 1219 1220

5'  CAGAAGGGAAACGAACTGGCCCTGCCCTCCAAATATGTGAACTTCCTGTACCTGGCCAGC
                                                                        3720
         Q  K  G  N  E  L  A  L  P  S  K  Y  V  N  F  L  Y  L  A  S
       1221 1222 1223 1224 1225 1226 1227 1228 1229 1230 1231 1232 1233 1234 1235 1236 1237 1238 1239 1240
```

FIG. 6K hSpCas9

```
5' CACTATGAGAAGCTGAAGGGCTCCCCCGAGGATAATGAGCAGAAACAGCTGTTTGTGGAA 3780
        H  Y  E  K  L  K  G  S  P  E  D  N  E  Q  K  Q  L  F  V  E
       1241 1242 1243 1244 1245 1246 1247 1248 1249 1250 1251 1252 1253 1254 1255 1256 1257 1258 1259 1260

5' CAGCACAAGCACTACCTGGACGAGATCATCGAGCAGATCAGCGAGTTCTCCAAGAGAGTG 3840
        Q  H  K  H  Y  L  D  E  I  I  E  Q  I  S  E  F  S  K  R  V
       1261 1262 1263 1264 1265 1266 1267 1268 1269 1270 1271 1272 1273 1274 1275 1276 1277 1278 1279 1280

5' ATCCTGGCCGACGCTAATCTGGACAAAGTGCTGTCCGCCTACAACAAGCACCGGGATAAG 3900
        I  L  A  D  A  N  L  D  K  V  L  S  A  Y  N  K  H  R  D  K
       1281 1282 1283 1284 1285 1286 1287 1288 1289 1290 1291 1292 1293 1294 1295 1296 1297 1298 1299 1300

5' CCCATCAGAGAGCAGGCCGAGAATATCATCCACCTGTTTACCCTGACCAATCTGGGAGCC 3960
        P  I  R  E  Q  A  E  N  I  I  H  L  F  T  L  T  N  L  G  A
       1301 1302 1303 1304 1305 1306 1307 1308 1309 1310 1311 1312 1313 1314 1315 1316 1317 1318 1319 1320

5' CCTGCCGCCTTCAAGTACTTTGACACCACCATCGACCGGAAGAGGTACACCAGCACCAAA 4020
        P  A  A  F  K  Y  F  D  T  T  I  D  R  K  R  Y  T  S  T  K
       1321 1322 1323 1324 1325 1326 1327 1328 1329 1330 1331 1332 1333 1334 1335 1336 1337 1338 1339 1340

5' GAGGTGCTGGACGCCACCCTGATCCACCAGAGCATCACCGGCCTGTACGAGACACGGATC 4080
        E  V  L  D  A  T  L  I  H  Q  S  I  T  G  L  Y  E  T  R  I
       1341 1342 1343 1344 1345 1346 1347 1348 1349 1350 1351 1352 1353 1354 1355 1356 1357 1358 1359 1360
```

FIG. 6L

```
hSpCas9
5'   GACCTGTCTCAGCTGGGAGGCGAC
     ++++|++++|++++|++++|++++                    4104
     ▓▓▓▓▓▓▓▓hSpCas9▓▓▓▓▓▓▓▓
      D   L   S   Q   L   G   G   D
     1361 1362 1363 1364 1365 1366 1367 1368
```

FIG. 6M

Cas9 Expression in Mouse Hippocampus (AAV)
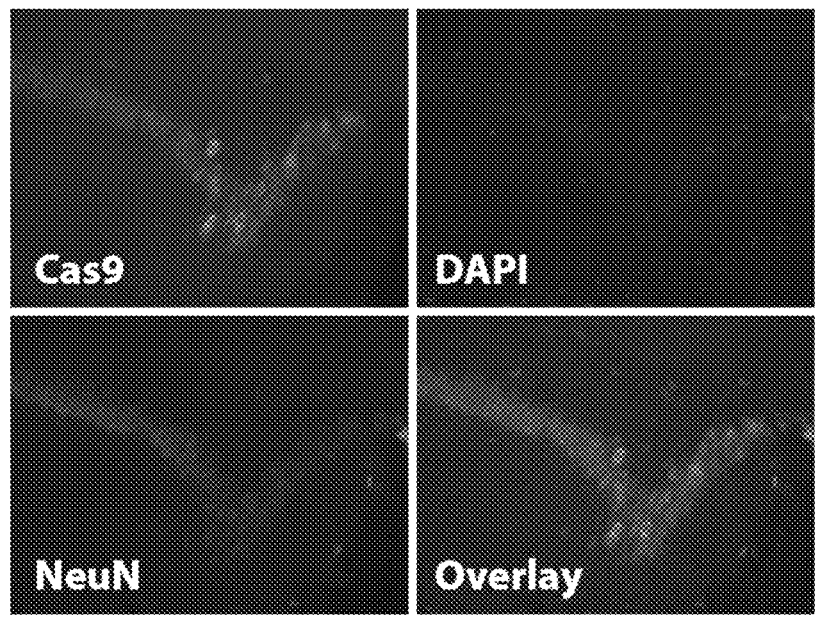
Cas9 Expression in Mouse Cortex (AAV)
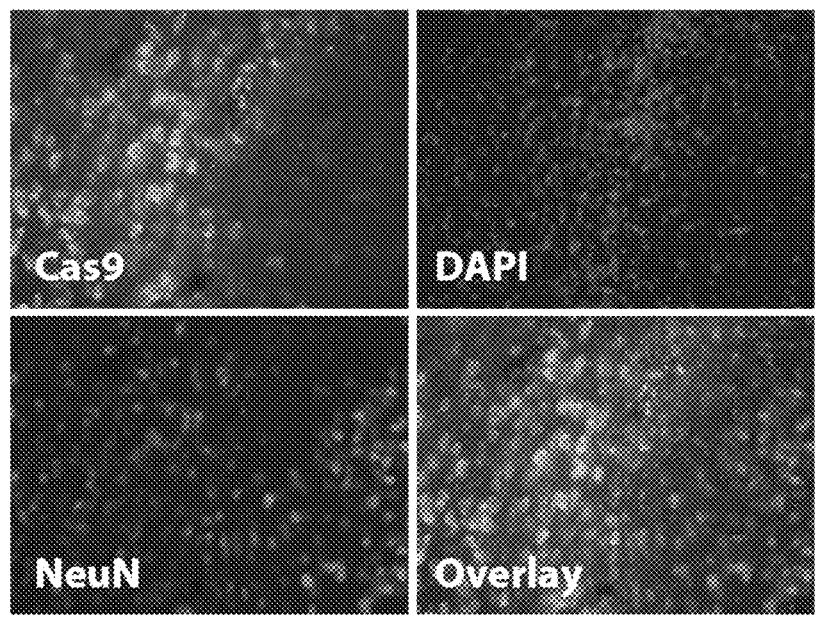
FIG. 9

Repair Strategy for Cystic Fibrosis deltaF508 Mutation

FIG. 13A

```
------------------------------- CFTR gene -------------------------------
 G   T   I   K   E   N   I   I   G   V   S   Y   D   E   Y   R   Y   R   S
500 501 502 503 504 505 506 507 508 509 510 511 512 513 514 515 516 517 518 519
```

1. human CFTR genomic locus

```
GGCACCATTAAAGAAAATATCATTGGTGTTTCCTATGATGAATATAGATACAGAAGC
++++++++++++++++++++++++++++++++++++++++++++++++++++++++
CCGTGGTAATTTCTTTTATAGTAACCACAAAGGATACTACTTATATCTATGTCTTCG
            Cas9 Target Site    *
```

FIG. 13B 2. human CFTRdelta508- targeting chimeric guide RNA

```
5'- NNNNNNNNNNNNNNNNNNNNNNGUUUUAGAGCUAG A
                         *|||||* ||||  A
  GUUCAACUAUUGCCUGAUCGGAAUAAAAUU CGAUA A
 A ||||                         GAA
 A AAAGUGGCACCGA
     *|||||||G
 3'- UUUCGUGGCU
```

FIG. 13C 3. repair template for deltaF508 mutation

```
                            F508
...ATTAAAGAAAATATCATTGGCTTTGTTTCCTATGATGAATATAGATAC...
+++++++++++++++++++++++++++++++++++++++++++++++++++
...TAATTTCTTTTATAGTAACCGAAACAAAGGATACTACTTATATCTATG...
------------------------------- repair template -------------------------------

I   K   E   N   I   I   G   F   V   S   Y   D   E   Y   R   Y
  502 503 504 505 506 507 508 509 510 511 512 513 514 515 516 517
```

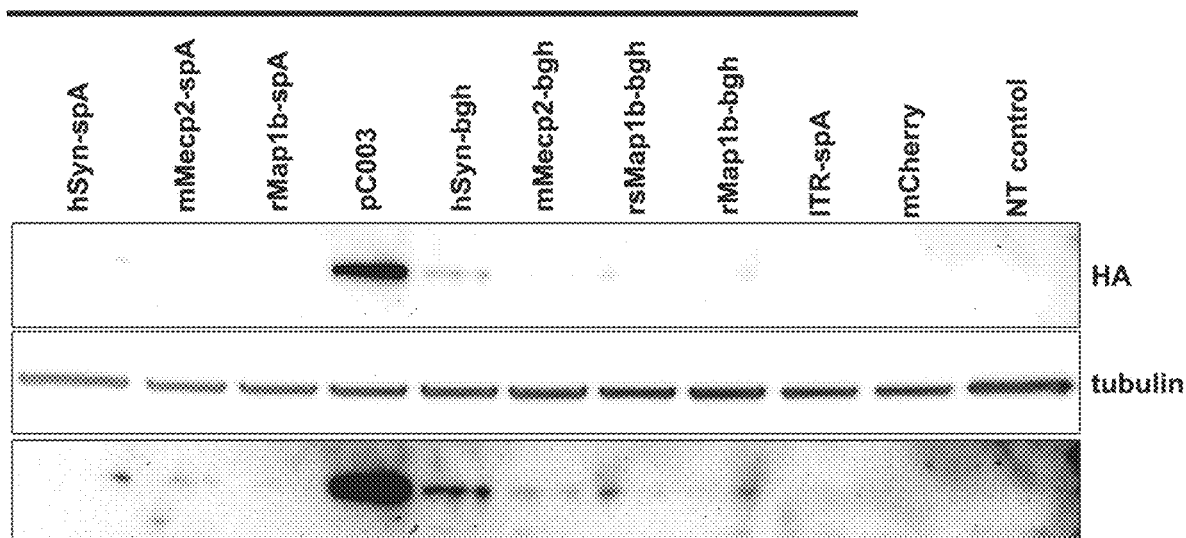
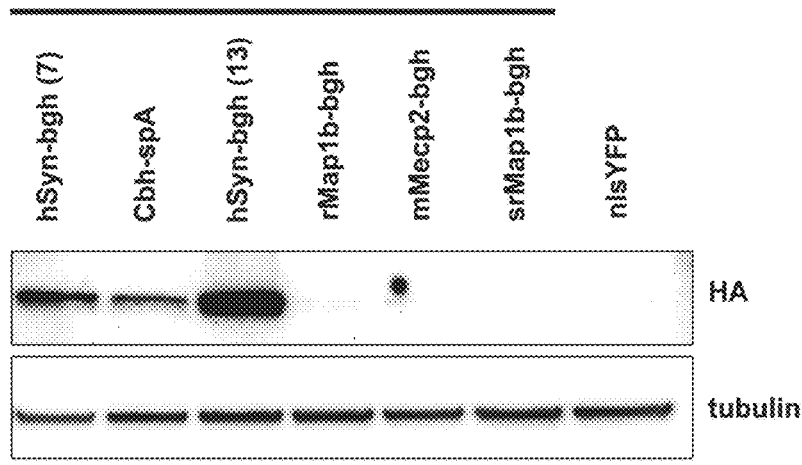
FIG. 24

| | pattern | overhang |
|---|---|---|
| 1 | CCnNNNNNNNNNNNNNNNnnnnnnnnnnnNNNNNNNNNNNNNNNNnGG | 28 |
| 2 | CCnNNNNNNNNNNNNNNNnnnnnnnNNNNNNNNNNNNNNNNnGG | 34 |
| 3 | CCnNNNNNNNNNNNNNNNnnnnnNNNNNNNNNNNNNNNNnGG | 30 |
| 4 | CCnNNNNNNNNNNNNNNNNNNNNNNNNNNNNNNnGG | 28 |
| 5 | CCnNNNNNNNNNNNNNNNNNNNNNNNNNNNnGG | 22 |
| 6 | CCnNNNNNNNNNNNNNNNNNNNNNNNnGG | 18 |
| 7 | CCnNNNNNNNNNNNNNNNNNNNNnGG | 14 |
| 8 | CCnNNNNNNNNNNNNNNNNNnGG | 10 |
| 9 | CCnNNNNNNNNNNNNNnGG | 6 |
| 10 | CCnNNNNNNNNNNNnGG | 4 |
| 11 | CCnNNNNNNNNNNnGG | 3 |
| 12 | CCnNNNNNNNNNnGG | 2 |
| 13 | CCnNNNNNNNNnGG | 1 |
| 14 | CCnNNNNNNNnGG | 0 |
| 15 | CCnNNNNNnGG | 1 |
| 16 | CCnNNNNnGG | 2 |
| 17 | CCnNNNnGG | 3 |
| 18 | CCnnGG | 4 |
| 19 | CCGG | 8 |
| 20 | GGCC | 10 |
| 21 | GGNNCC | 12 |
| 22 | GGNNNCC | 14 |
| 23 | GGNNNNCC | 16 |
| 24 | GGNNNNNNNNNCC | 20 |

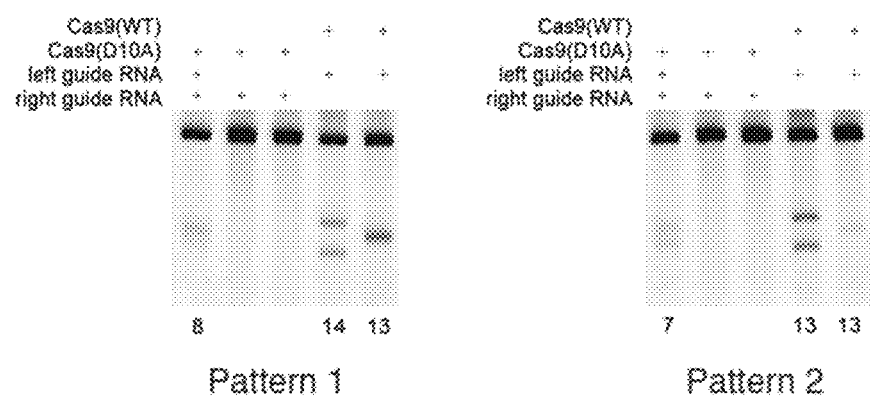

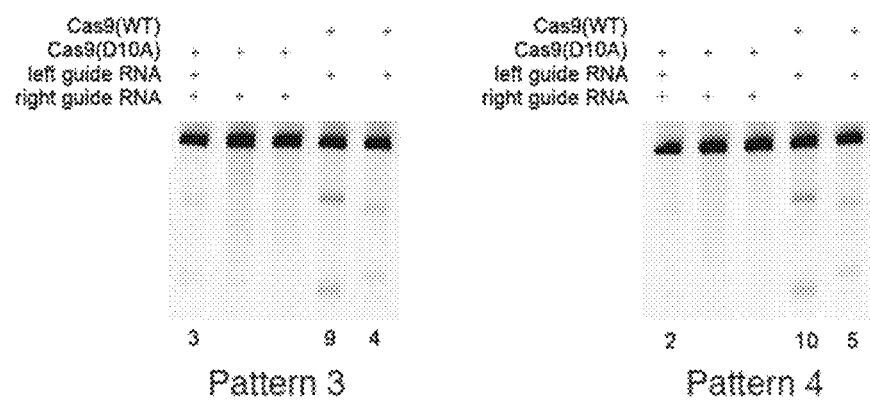

| lane # | Cas9 to use | Left gRNA | Right gRNA | Overhang (D10A) number of bases protruding from 5' |
|---|---|---|---|---|
| 1 | D10A | left 23 | left 12 | -36 |
| 2 | D10A | right 4 | left 9 | -25 |
| 3 | D10A | left 23 | right 23 | -16 |
| 4 | D10A | right 7 | left 10 | -15 |
| 5 | D10A | right 16 | left 3 | -8 |
| 6 | D10A | right 22 | right 6 | 26 |
| 7 | D10A | left 12 | right 16 | 31 |
| 8 | D10A | left 12 | right 13 | 34 |
| 9 | D10A | left 10 | right 1 | 38 |
| 10 | D10A | right 23 | right 16 | 51 |
| 11 | D10A | right 23 | right 13 | 54 |
| 12 | D10A | left 3 | right 7 | 57 |
| 13 | D10A | left 12 | right 4 | 65 |
| 14 | D10A | left 3 | right 3 | 69 |
| 15 | D10A | right 23 | right 10 | 76 |
| 16 | D10A | left 12 | right 4 | 85 |
| 17 | D10A | left 12 | right 9 | 95 |
| 18 | D10A | right 23 | right 10 | 115 |
| 19 | D10A | left 12 | right 10 | 135 |
| 20 | D10A | left 12 | right 2 | 145 |
| 21 | D10A | left 12 | left 22 | 181 |
| 22 | D10A | right 23 | left 22 | 201 |
| 23 | D10A | left 12 | right 6 | 222 |
| 24 | D10A | right 23 | right 6 | 242 |

FIG. 36

Stabilization of distal hairpins in existing chimeric RNA architecture

Tandem single guide RNAs (tsgRNA) driven by a single U6 promoter

FIG. 38D
Tandem Double Nicking Activity with D10A Cas9

FIG. 38C
Tandem sgRNA mediated microdeletion

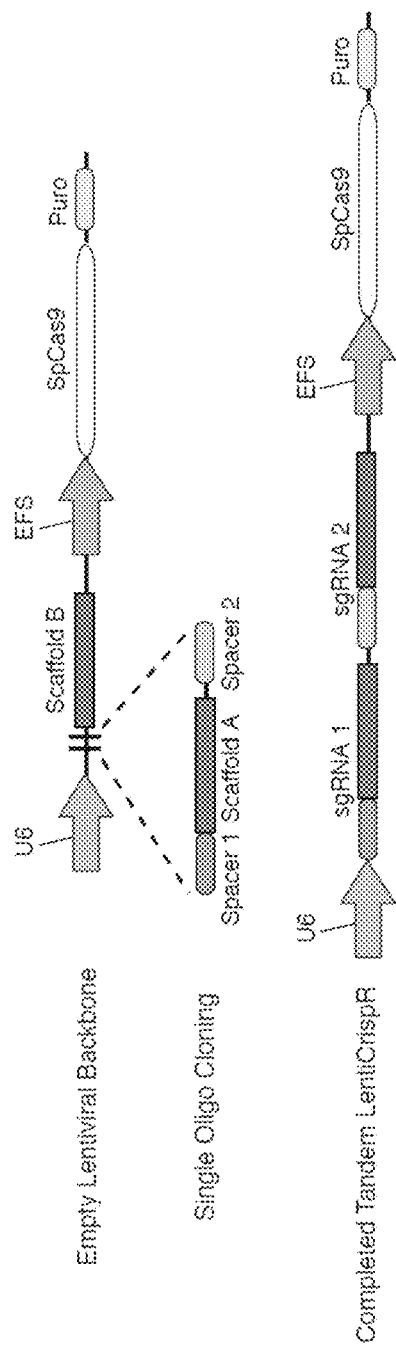
FIG. 39A Tandem LentiCrispR Vector Design
FIG. 39B Scaffold Sequences for LentiCrispr FIG. 44A
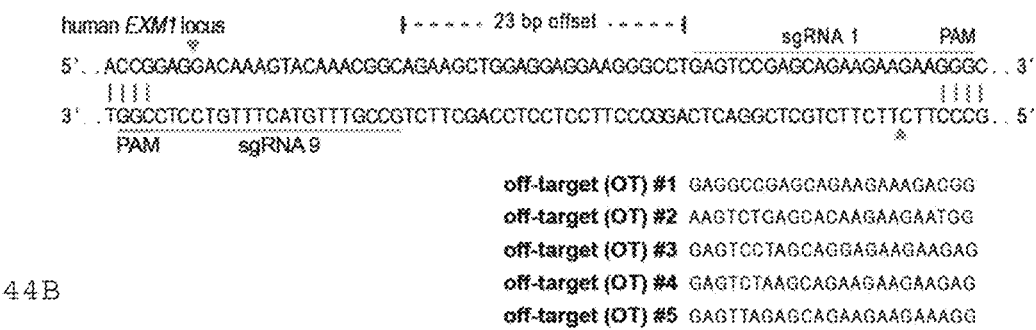
FIG. 44B
FIG. 44C
FIG. 44D
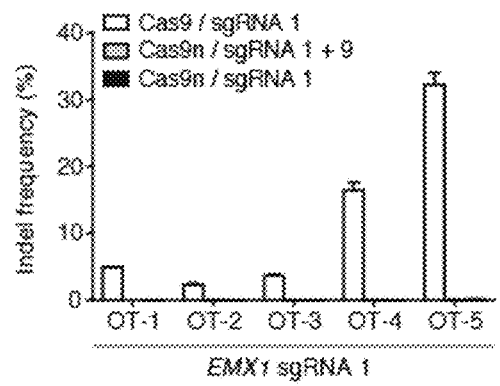
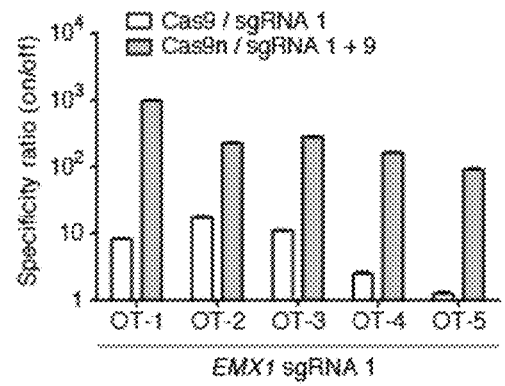

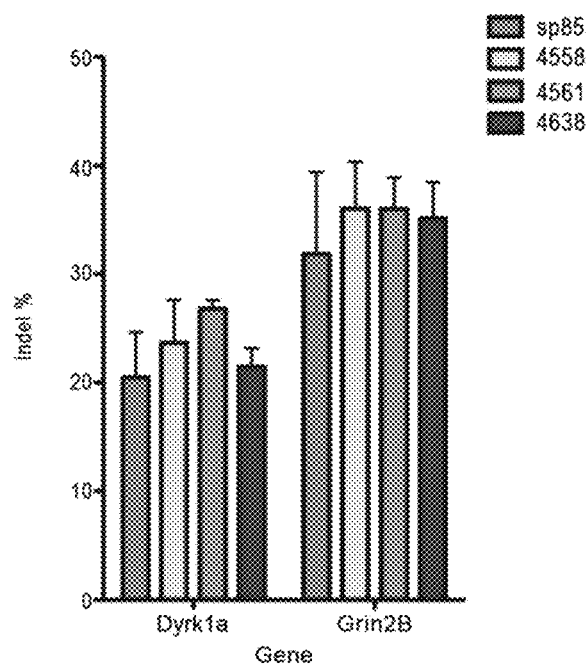
FIG. 46

| Tandem Linker | Length | Sequence |
| --- | --- | --- |
| 0 | 0 | |
| 4 | 4 | ATTA |
| 8 | 8 | AATTATTA |
| 12 | 12 | AATTATTAATTA |
| 16 | 16 | AATTATTAATTATAAT |
| Direct Repeat A | 16 | GTTTTAGAGCTATGCT |
| Direct Repeat B | 20 | GTTTTGAATGGTCCCAAAAC |
| Full Direct Repeat | 36 | GTTTTAGAGCTATGCTGTTTTGAATGGTCCCAAAAC |

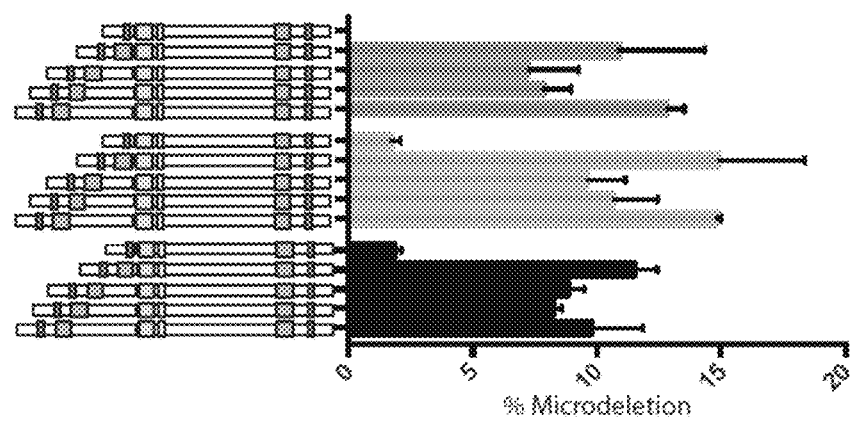
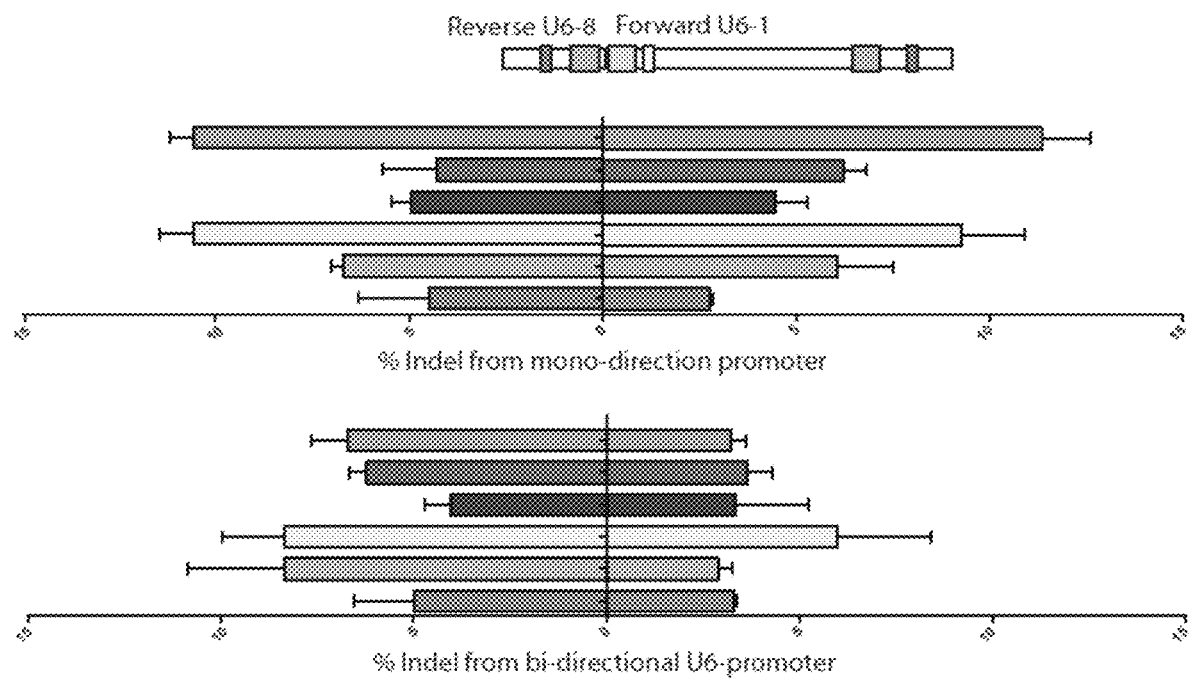
FIG. 52

8-6U U6-1 Smallest

5' tgagaagaagtcacccacaggccttataaggcacgggagtctttcacctattctacttac 60
   Bi-directional U6-8/1 Promoter
   PSE U6-8
   TAT_8
   TGAGAAGAAGTCACCCACAGGCCT 5' ggtgaccgaaccggagggcctatttccatgattccttcatatttgcatgaattaatttg 120
   Bi-directional U6-8/1 Promoter
   OCT
   SPH U6-1
   GAGGGCCTATTTCCCATGATTCCT
   PSE_6-8
   TAAAGGTACTAAGGAAGTATAAGTA 5' actgtaaacacaaagatattagtacaaaatacgtgacgtagaaagtaataatttctggg 180
   Bi-directional U6-8/1 Promoter 5' tagtttgcagttttaaaattatgttttaaaatggactatcatatgcttaccgtaacttga 240
   Bi-directional U6-8/1 Promoter
   PSE 5' aagtatttcgatttcttggctttatatatcttGTGGAAAGGACGAAACACC 291
   Bi-directional U6-8/1 Promoter
   TATA Box
   PSE
   U6-1 Priming Site
   GGACACCTTTCCTGCTTTGTGG

FIG. 53

SEQUENCE LISTING

<160> NUMBER OF SEQ ID NOS: 484

<210> SEQ ID NO 1

```
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120

<210> SEQ ID NO 2
<211> LENGTH: 20
<212> TYPE: DNA
<213> ORGANISM: Homo sapiens

<400> SEQUENCE: 2
gagtccgagc agaagaagaa                                                  20

<210> SEQ ID NO 3
<211> LENGTH: 20
<212> TYPE: DNA
<213> ORGANISM: Homo sapiens

<400> SEQUENCE: 3
gagtcctagc aggagaagaa                                                  20

<210> SEQ ID NO 4
<211> LENGTH: 20
<212> TYPE: DNA
<213> ORGANISM: Homo sapiens

<400> SEQUENCE: 4
gagtctaagc agaagaagaa                                                  20

<210> SEQ ID NO 5
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(44)
<223> OTHER INFORMATION: a, c, u, g, unknown or other
<220> FEATURE:
<221> NAME/KEY: modified_base
<222> LOCATION: (47)..(60)
<223> OTHER INFORMATION: a, c, u, g, unknown or other

<400> SEQUENCE: 5
nnnnnnnnnn nnnnnnnnnn ccnnnnnnnn nnnnnnnnnn nnnggnnnnn nnnnnnnnnn      60

<210> SEQ ID NO 6
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: modified_base
<222> LOCATION: (1)..(14)
<223> OTHER INFORMATION: a, c, u, g, unknown or other
<220> FEATURE:
<221> NAME/KEY: modified_base
<222> LOCATION: (17)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 6
nnnnnnnnnn nnnnccnnnn nnnnnnnnnn nnnnnnnngg nnnnnnnnnn nnnnnnnnnn      60

<210> SEQ ID NO 7
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(43)
<223> OTHER INFORMATION: a, c, u, g, unknown or other
<220> FEATURE:
<221> NAME/KEY: modified_base
<222> LOCATION: (46)..(60)
<223> OTHER INFORMATION: a, c, u, g, unknown or other

<400> SEQUENCE: 7
nnnnnnnnnn nnnnnnnnnn ccnnnnnnnn nnnnnnnnnn nnnggnnnnn nnnnnnnnnn      60

<210> SEQ ID NO 8
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 8
nnnnnnnnnn nnnnnccnnn nnnnnnnnnn nnnnnnnngg nnnnnnnnnn nnnnnnnnnn      60

<210> SEQ ID NO 9
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(42)
<223> OTHER INFORMATION: a, c, u, g, unknown or other
<220> FEATURE:
<221> NAME/KEY: modified_base
<222> LOCATION: (45)..(60)
<223> OTHER INFORMATION: a, c, u, g, unknown or other

<400> SEQUENCE: 9
nnnnnnnnnn nnnnnnnnnn ccnnnnnnnn nnnnnnnnnn nnggnnnnnn nnnnnnnnnn      60

<210> SEQ ID NO 10
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(15)
<223> OTHER INFORMATION: a, c, u, g, unknown or other
<220> FEATURE:
<221> NAME/KEY: modified_base
<222> LOCATION: (18)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 10
nnnnnnnnnn nnnnccnnn nnnnnnnnnn nnnnnnnngg nnnnnnnnnn nnnnnnnnnn      60

<210> SEQ ID NO 11
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(41)
<223> OTHER INFORMATION: a, c, u, g, unknown or other
<220> FEATURE:
<221> NAME/KEY: modified_base
<222> LOCATION: (44)..(60)
<223> OTHER INFORMATION: a, c, u, g, unknown or other

<400> SEQUENCE: 11
nnnnnnnnnn nnnnnnnnnn ccnnnnnnnn nnnnnnnnnn nggnnnnnnn nnnnnnnnnn      60

<210> SEQ ID NO 12
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (1)..(17)
<223> OTHER INFORMATION: a, c, u, g, unknown or other
<220> FEATURE:
<221> NAME/KEY: modified_base
<222> LOCATION: (20)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 12
nnnnnnnnnn nnnnnnnccn nnnnnnnnnn nnnnnnnngg nnnnnnnnnn nnnnnnnnnn      60

<210> SEQ ID NO 13
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(40)
<223> OTHER INFORMATION: a, c, u, g, unknown or other
<220> FEATURE:
<221> NAME/KEY: modified_base
<222> LOCATION: (43)..(60)
<223> OTHER INFORMATION: a, c, u, g, unknown or other

<400> SEQUENCE: 13
nnnnnnnnnn nnnnnnnnnn ccnnnnnnnn nnnnnnnnnn ggnnnnnnnn nnnnnnnnnn      60

<210> SEQ ID NO 14
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(18)
<223> OTHER INFORMATION: a, c, u, g, unknown or other
<220> FEATURE:
<221> NAME/KEY: modified_base
<222> LOCATION: (21)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 14
nnnnnnnnnn nnnnnnnncc nnnnnnnnnn nnnnnnnngg nnnnnnnnnn nnnnnnnnnn      60

<210> SEQ ID NO 15
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
```

<223> OTHER INFORMATION: a, c, u, g, unknown or other
<220> FEATURE:
<221> NAME/KEY: modified_base
<222> LOCATION: (23)..(39)
<223> OTHER INFORMATION: a, c, u, g, unknown or other
<220> FEATURE:
<221> NAME/KEY: modified_base
<222> LOCATION: (42)..(60)
<223> OTHER INFORMATION: a, c, u, g, unknown or other

<400> SEQUENCE: 15
nnnnnnnnnn nnnnnnnnn ccnnnnnnnn nnnnnnnng gnnnnnnnnn nnnnnnnnnn    60

<210> SEQ ID NO 16
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (22)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 16
nnnnnnnnnn nnnnnnnnnc cnnnnnnnnn nnnnnnnngg nnnnnnnnnn nnnnnnnnnn    60

<210> SEQ ID NO 17
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 17
nnnnnnnnnn nnnnnnnnnn ccnnnnnnnn nnnnnnnngg nnnnnnnnnn nnnnnnnnnn    60

<210> SEQ ID NO 18
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

```
<220> FEATURE:
<221> NAME/KEY: modified_base
<222> LOCATION: (23)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 18
nnnnnnnnnn nnnnnnnnnn ccnnnnnnnn nnnnnnnngg nnnnnnnnnn nnnnnnnnnn        60

<210> SEQ ID NO 19
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(37)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 19
nnnnnnnnnn nnnnnnnnnn ccnnnnnnnn nnnnnnnggn nnnnnnnnnn nnnnnnnnnn        60

<210> SEQ ID NO 20
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (24)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 20
nnnnnnnnnn nnnnnnnnnn nccnnnnnnn nnnnnnnngg nnnnnnnnnn nnnnnnnnnn        60

<210> SEQ ID NO 21
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
```

```
<221> NAME/KEY: modified_base
<222> LOCATION: (23)..(36)
<223> OTHER INFORMATION: a, c, u, g, unknown or other
<220> FEATURE:
<221> NAME/KEY: modified_base
<222> LOCATION: (39)..(60)
<223> OTHER INFORMATION: a, c, u, g, unknown or other

<400> SEQUENCE: 21
nnnnnnnnnn nnnnnnnnnn ccnnnnnnnn nnnnnnggnn nnnnnnnnnn nnnnnnnnnn    60

<210> SEQ ID NO 22
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (25)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 22
nnnnnnnnnn nnnnnnnnnn nnccnnnnnn nnnnnnnngg nnnnnnnnnn nnnnnnnnnn    60

<210> SEQ ID NO 23
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 23
nnnnnnnnnn nnnnnnnnnn ccnnnnnnnn nnnnggnnnn nnnnnnnnnn nnnnnnnnnn    60

<210> SEQ ID NO 24
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
```

```
<222> LOCATION: (26)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 24
nnnnnnnnnn nnnnnnnnnn nnnccnnnnn nnnnnnnngg nnnnnnnnnn nnnnnnnnnn      60

<210> SEQ ID NO 25
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(34)
<223> OTHER INFORMATION: a, c, u, g, unknown or other
<220> FEATURE:
<221> NAME/KEY: modified_base
<222> LOCATION: (37)..(60)
<223> OTHER INFORMATION: a, c, u, g, unknown or other

<400> SEQUENCE: 25
nnnnnnnnnn nnnnnnnnnn ccnnnnnnnn nnnggnnnn nnnnnnnnnn nnnnnnnnnn       60

<210> SEQ ID NO 26
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(24)
<223> OTHER INFORMATION: a, c, u, g, unknown or other
<220> FEATURE:
<221> NAME/KEY: modified_base
<222> LOCATION: (27)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 26
nnnnnnnnnn nnnnnnnnnn nnnccnnnn nnnnnnnngg nnnnnnnnnn nnnnnnnnnn       60

<210> SEQ ID NO 27
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(33)
```

```
<223> OTHER INFORMATION: a, c, u, g, unknown or other
<220> FEATURE:
<221> NAME/KEY: modified_base
<222> LOCATION: (36)..(60)
<223> OTHER INFORMATION: a, c, u, g, unknown or other

<400> SEQUENCE: 27
nnnnnnnnnn nnnnnnnnnn ccnnnnnnnn nnnggnnnnn nnnnnnnnnn nnnnnnnnnn      60

<210> SEQ ID NO 28
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(25)
<223> OTHER INFORMATION: a, c, u, g, unknown or other
<220> FEATURE:
<221> NAME/KEY: modified_base
<222> LOCATION: (28)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 28
nnnnnnnnnn nnnnnnnnnn nnnnnccnnn nnnnnnnngg nnnnnnnnnn nnnnnnnnnn      60

<210> SEQ ID NO 29
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(32)
<223> OTHER INFORMATION: a, c, u, g, unknown or other
<220> FEATURE:
<221> NAME/KEY: modified_base
<222> LOCATION: (35)..(60)
<223> OTHER INFORMATION: a, c, u, g, unknown or other

<400> SEQUENCE: 29
nnnnnnnnnn nnnnnnnnnn ccnnnnnnnn nnggnnnnnn nnnnnnnnnn nnnnnnnnnn      60

<210> SEQ ID NO 30
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(26)
<223> OTHER INFORMATION: a, c, u, g, unknown or other
<220> FEATURE:
<221> NAME/KEY: modified_base
<222> LOCATION: (29)..(38)
<223> OTHER INFORMATION: a, c, u, g, unknown or other
```

```
<220> FEATURE:
<221> NAME/KEY: modified_base
<222> LOCATION: (41)..(60)
<223> OTHER INFORMATION: a, c, u, g, unknown or other

<400> SEQUENCE: 30
nnnnnnnnnn nnnnnnnnnn nnnnnnccnn nnnnnnnngg nnnnnnnnnn nnnnnnnnnn      60

<210> SEQ ID NO 31
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(31)
<223> OTHER INFORMATION: a, c, u, g, unknown or other
<220> FEATURE:
<221> NAME/KEY: modified_base
<222> LOCATION: (34)..(60)
<223> OTHER INFORMATION: a, c, u, g, unknown or other

<400> SEQUENCE: 31
nnnnnnnnnn nnnnnnnnnn ccnnnnnnnn nggnnnnnnn nnnnnnnnnn nnnnnnnnnn      60

<210> SEQ ID NO 32
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(27)
<223> OTHER INFORMATION: a, c, u, g, unknown or other
<220> FEATURE:
<221> NAME/KEY: modified_base
<222> LOCATION: (30)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 32
nnnnnnnnnn nnnnnnnnnn nnnnnnnccn nnnnnnnngg nnnnnnnnnn nnnnnnnnnn      60

<210> SEQ ID NO 33
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(30)
<223> OTHER INFORMATION: a, c, u, g, unknown or other
<220> FEATURE:
```

```
<221> NAME/KEY: modified_base
<222> LOCATION: (33)..(60)
<223> OTHER INFORMATION: a, c, u, g, unknown or other

<400> SEQUENCE: 33
nnnnnnnnnn nnnnnnnnnn ccnnnnnnnn ggnnnnnnnn nnnnnnnnnn nnnnnnnnnn      60

<210> SEQ ID NO 34
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 34
nnnnnnnnnn nnnnnnnnnn nnnnnnnncc nnnnnnnngg nnnnnnnnnn nnnnnnnnnn      60

<210> SEQ ID NO 35
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(29)
<223> OTHER INFORMATION: a, c, u, g, unknown or other
<220> FEATURE:
<221> NAME/KEY: modified_base
<222> LOCATION: (32)..(60)
<223> OTHER INFORMATION: a, c, u, g, unknown or other

<400> SEQUENCE: 35
nnnnnnnnnn nnnnnnnnnn ccnnnnnnng gnnnnnnnnn nnnnnnnnnn nnnnnnnnnn      60

<210> SEQ ID NO 36
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(38)
<223> OTHER INFORMATION: a, c, u, g, unknown or other
<220> FEATURE:
<221> NAME/KEY: modified_base
```

```
<222> LOCATION: (41)..(60)
<223> OTHER INFORMATION: a, c, u, g, unknown or other

<400> SEQUENCE: 36
nnnnnnnnnn nnnnnnnnnn nnnnnnnnnc cnnnnnnngg nnnnnnnnnn nnnnnnnnnn      60

<210> SEQ ID NO 37
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(28)
<223> OTHER INFORMATION: a, c, u, g, unknown or other
<220> FEATURE:
<221> NAME/KEY: modified_base
<222> LOCATION: (31)..(60)
<223> OTHER INFORMATION: a, c, u, g, unknown or other

<400> SEQUENCE: 37
nnnnnnnnnn nnnnnnnnnn ccnnnnnngg nnnnnnnnnn nnnnnnnnnn nnnnnnnnnn      60

<210> SEQ ID NO 38
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 38
nnnnnnnnnn nnnnnnnnnn nnnnnnnnnn ccnnnnnngg nnnnnnnnnn nnnnnnnnnn      60

<210> SEQ ID NO 39
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(27)
<223> OTHER INFORMATION: a, c, u, g, unknown or other
<220> FEATURE:
<221> NAME/KEY: modified_base
<222> LOCATION: (30)..(60)
```

<223> OTHER INFORMATION: a, c, u, g, unknown or other

<400> SEQUENCE: 39
nnnnnnnnnn nnnnnnnnnn ccnnnnggn nnnnnnnnnn nnnnnnnnnn nnnnnnnnnn    60

<210> SEQ ID NO 40
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 40
nnnnnnnnnn nnnnnnnnnn nnnnnnnnnn nccnnnnngg nnnnnnnnnn nnnnnnnnnn    60

<210> SEQ ID NO 41
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(26)
<223> OTHER INFORMATION: a, c, u, g, unknown or other
<220> FEATURE:
<221> NAME/KEY: modified_base
<222> LOCATION: (29)..(60)
<223> OTHER INFORMATION: a, c, u, g, unknown or other

<400> SEQUENCE: 41
nnnnnnnnnn nnnnnnnnnn ccnnnnggnn nnnnnnnnnn nnnnnnnnnn nnnnnnnnnn    60

<210> SEQ ID NO 42
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 42
nnnnnnnnnn nnnnnnnnnn nnnnnnnnnn nnccnnnngg nnnnnnnnnn nnnnnnnnnn    60

<210> SEQ ID NO 43
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(25)
<223> OTHER INFORMATION: a, c, u, g, unknown or other
<220> FEATURE:
<221> NAME/KEY: modified_base
<222> LOCATION: (28)..(60)
<223> OTHER INFORMATION: a, c, u, g, unknown or other

<400> SEQUENCE: 43
nnnnnnnnnn nnnnnnnnnn ccnnnggnnn nnnnnnnnnn nnnnnnnnnn nnnnnnnnnn    60

<210> SEQ ID NO 44
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (36)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 44
nnnnnnnnnn nnnnnnnnnn nnnnnnnnnn nnnccnnngg nnnnnnnnnn nnnnnnnnnn    60

<210> SEQ ID NO 45
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(24)
<223> OTHER INFORMATION: a, c, u, g, unknown or other
<220> FEATURE:
<221> NAME/KEY: modified_base
<222> LOCATION: (27)..(60)
<223> OTHER INFORMATION: a, c, u, g, unknown or other

```
<400> SEQUENCE: 45
nnnnnnnnnn nnnnnnnnnn ccnnggnnnn nnnnnnnnnn nnnnnnnnnn nnnnnnnnnn      60

<210> SEQ ID NO 46
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(34)
<223> OTHER INFORMATION: a, c, u, g, unknown or other
<220> FEATURE:
<221> NAME/KEY: modified_base
<222> LOCATION: (37)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 46
nnnnnnnnnn nnnnnnnnnn nnnnnnnnnn nnnnccnngg nnnnnnnnnn nnnnnnnnnn      60

<210> SEQ ID NO 47
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (23)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 47
nnnnnnnnnn nnnnnnnnnn ccnggnnnnn nnnnnnnnnn nnnnnnnnnn nnnnnnnnnn      60

<210> SEQ ID NO 48
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (38)..(38)
<223> OTHER INFORMATION: a, c, u, g, unknown or other
<220> FEATURE:
<221> NAME/KEY: modified_base
<222> LOCATION: (41)..(60)
<223> OTHER INFORMATION: a, c, u, g, unknown or other

<400> SEQUENCE: 48
```
nnnnnnnnnn nnnnnnnnnn nnnnnnnnnn nnnnccngg nnnnnnnnnn nnnnnnnnnn    60

<210> SEQ ID NO 49
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(21)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 49
nnnnnnnnnn nnnnnnnnnn nccggnnnnn nnnnnnnnnn nnnnnnnnnn nnnnnnnnnn    60

<210> SEQ ID NO 50
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(35)
<223> OTHER INFORMATION: a, c, u, g, unknown or other
<220> FEATURE:
<221> NAME/KEY: modified_base
<222> LOCATION: (40)..(60)
<223> OTHER INFORMATION: a, c, u, g, unknown or other

<400> SEQUENCE: 50
nnnnnnnnnn nnnnnnnnnn nnnnnnnnnn nnnnccggn nnnnnnnnnn nnnnnnnnnn    60

<210> SEQ ID NO 51
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(23)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 51
nnnnnnnnnn nnnnnnnnnn nnnggnnnnn nnnnnnnnnn nnnnnnnnnn nnnnnnnnnn    60

<210> SEQ ID NO 52
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:

```
<221> NAME/KEY: modified_base
<222> LOCATION: (1)..(33)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 52
nnnnnnnnnn nnnnnnnnnn nnnnnnnnnn nnnggccnnn nnnnnnnnnn nnnnnnnnnn      60

<210> SEQ ID NO 53
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, u, g, unknown or other
<220> FEATURE:
<221> NAME/KEY: modified_base
<222> LOCATION: (26)..(60)
<223> OTHER INFORMATION: a, c, u, g, unknown or other

<400> SEQUENCE: 53
nnnnnnnnnn nnnnnnnnnn nncggnnnnn nnnnnnnnnn nnnnnnnnnn nnnnnnnnnn      60

<210> SEQ ID NO 54
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(32)
<223> OTHER INFORMATION: a, c, u, g, unknown or other
<220> FEATURE:
<221> NAME/KEY: modified_base
<222> LOCATION: (35)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 54
nnnnnnnnnn nnnnnnnnnn nnnnnnnnnn nnggnccnnn nnnnnnnnnn nnnnnnnnnn      60

<210> SEQ ID NO 55
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
tgagaagaag tcacccacag gcct                                             24

<210> SEQ ID NO 56
<211> LENGTH: 60
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(31)
<223> OTHER INFORMATION: a, c, u, g, unknown or other
<220> FEATURE:
<221> NAME/KEY: modified_base
<222> LOCATION: (34)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 56
nnnnnnnnnn nnnnnnnnnn nnnnnnnnnn nggnnccnnn nnnnnnnnnn nnnnnnnnnn      60

<210> SEQ ID NO 57
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
gagggcctat ttcccatgat tcct                                              24

<210> SEQ ID NO 58
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(30)
<223> OTHER INFORMATION: a, c, u, g, unknown or other
<220> FEATURE:
<221> NAME/KEY: modified_base
<222> LOCATION: (33)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 58
nnnnnnnnnn nnnnnnnnnn nnnnnnnnnn ggnnccnnn nnnnnnnnnn nnnnnnnnnn       60

<210> SEQ ID NO 59
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
taaagggtac taaggaagta taaacgta                                          28

<210> SEQ ID NO 60
<211> LENGTH: 60
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(29)
<223> OTHER INFORMATION: a, c, u, g, unknown or other
<220> FEATURE:
<221> NAME/KEY: modified_base
<222> LOCATION: (32)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 60
nnnnnnnnnn nnnnnnnnnn nnnnnnnnng gnnnccnnn nnnnnnnnnn nnnnnnnnnn      60

<210> SEQ ID NO 61
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
gaacaccttt cctgctttgt gg                                              22

<210> SEQ ID NO 62
<211> LENGTH: 60
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(28)
<223> OTHER INFORMATION: a, c, u, g, unknown or other
<220> FEATURE:
<221> NAME/KEY: modified_base
<222> LOCATION: (31)..(35)
<223> OTHER INFORMATION: a, c, u, g, unknown or other
<220> FEATURE:
<221> NAME/KEY: modified_base
<222> LOCATION: (38)..(60)
<223> OTHER INFORMATION: a, c, u, g, unknown or other

<400> SEQUENCE: 62
nnnnnnnnnn nnnnnnnnnn nnnnnnnngg nnnnccnnn nnnnnnnnnn nnnnnnnnnn      60

<210> SEQ ID NO 63
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
guuuuagagc ua                                                         12

<210> SEQ ID NO 64
<211> LENGTH: 7
```

```
<212> TYPE: PRT
<213> ORGANISM: Simian virus 40

<400> SEQUENCE: 64

Pro Lys Lys Lys Arg Lys Val
1               5

<210> SEQ ID NO 65
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 65

Lys Arg Pro Ala Ala Thr Lys Lys Ala Gly Gln Ala Lys Lys Lys Lys
1               5                   10                  15

<210> SEQ ID NO 66
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 66

Pro Ala Ala Lys Arg Val Lys Leu Asp
1               5

<210> SEQ ID NO 67
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 67

Arg Gln Arg Arg Asn Glu Leu Lys Arg Ser Pro
1               5                   10

<210> SEQ ID NO 68
<211> LENGTH: 38
<212> TYPE: PRT
<213> ORGANISM: Homo sapiens

<400> SEQUENCE: 68

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 69
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"
```

<400> SEQUENCE: 69

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 70
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 70

Val Ser Arg Lys Arg Pro Arg Pro
1               5

<210> SEQ ID NO 71
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 71

Pro Pro Lys Lys Ala Arg Glu Asp
1               5

<210> SEQ ID NO 72
<211> LENGTH: 8
<212> TYPE: PRT
<213> ORGANISM: Homo sapiens

<400> SEQUENCE: 72

Pro Gln Pro Lys Lys Lys Pro Leu
1               5

<210> SEQ ID NO 73
<211> LENGTH: 12
<212> TYPE: PRT
<213> ORGANISM: Mus musculus

<400> SEQUENCE: 73

Ser Ala Leu Ile Lys Lys Lys Lys Lys Met Ala Pro
1               5                   10

<210> SEQ ID NO 74
<211> LENGTH: 5
<212> TYPE: PRT
<213> ORGANISM: Influenza virus

<400> SEQUENCE: 74

Asp Arg Leu Arg Arg
1               5

<210> SEQ ID NO 75
<211> LENGTH: 7
<212> TYPE: PRT

<213> ORGANISM: Influenza virus

<400> SEQUENCE: 75

Pro Lys Gln Lys Lys Arg Lys
1               5

<210> SEQ ID NO 76
<211> LENGTH: 10
<212> TYPE: PRT
<213> ORGANISM: Hepatitis delta virus

<400> SEQUENCE: 76

Arg Lys Leu Lys Lys Lys Ile Lys Lys Leu
1               5                   10

<210> SEQ ID NO 77
<211> LENGTH: 10
<212> TYPE: PRT
<213> ORGANISM: Mus musculus

<400> SEQUENCE: 77

Arg Glu Lys Lys Lys Phe Leu Lys Arg Arg
1               5                   10

<210> SEQ ID NO 78
<211> LENGTH: 20
<212> TYPE: PRT
<213> ORGANISM: Homo sapiens

<400> SEQUENCE: 78

Lys Arg Lys Gly Asp Glu Val Asp Gly Val Asp Glu Val Ala Lys Lys
1               5                   10                  15

Lys Ser Lys Lys
            20

<210> SEQ ID NO 79
<211> LENGTH: 17
<212> TYPE: PRT
<213> ORGANISM: Homo sapiens

<400> SEQUENCE: 79

Arg Lys Cys Leu Gln Ala Gly Met Asn Leu Glu Ala Arg Lys Thr Lys
1               5                   10                  15

Lys

<210> SEQ ID NO 80
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 80
nnnnnnnnnn nnnnnnnnnn nnagaaw                                    27

```
<210> SEQ ID NO 81
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 81
nnnnnnnnnn nnnnagaaw                                                     19

<210> SEQ ID NO 82
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 82
nnnnnnnnnn nnnnnnnnnn nnagaaw                                            27

<210> SEQ ID NO 83
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 83
nnnnnnnnnn nnnagaaw                                                      18

<210> SEQ ID NO 84
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other
```

<400> SEQUENCE: 84
nnnnnnnnnn nnnnnnnnnn gtttttgtac tctcaagatt tagaaataaa tcttgcagaa    60
gctacaaaga taaggcttca tgccgaaatc aacaccctgt catttatgg cagggtgttt    120 tcgttattta atttttt                                                  137

<210> SEQ ID NO 85
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 85
nnnnnnnnnn nnnnnnnnnn gtttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 86
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 86
nnnnnnnnnn nnnnnnnnnn gtttttgtac tctcagaaat gcagaagcta caaagataag    60
gcttcatgcc gaaatcaaca ccctgtcatt ttatggcagg gtgtttttt               110

<210> SEQ ID NO 87
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 87
nnnnnnnnnn nnnnnnnnnn gttttagagc tagaaatagc aagttaaaat aaggctagtc    60
cgttatcaac ttgaaaaagt ggcaccgagt cggtgctttt tt                      102

<210> SEQ ID NO 88
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<220> FEATURE:
<221> NAME/KEY: modified_base
<222> LOCATION: (1)..(20)
<223> OTHER INFORMATION: a, c, t, g, unknown or other

<400> SEQUENCE: 88
nnnnnnnnnn nnnnnnnnnn gttttagagc tagaaatagc aagttaaaat aaggctagtc    60
cgttatcaac ttgaaaaagt gttttttt                                       88

<210> SEQ ID NO 89
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 89
nnnnnnnnnn nnnnnnnnnn gttttagagc tagaaatagc aagttaaaat aaggctagtc    60
cgttatcatt tttttt                                                    76

<210> SEQ ID NO 90
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
aaactctaga gagggcctat ttcccatgat tc                                  32

<210> SEQ ID NO 91
<211> LENGTH: 153
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
acctctagaa aaaaagcacc gactcggtgc cacttttca agttgataac ggactagcct    60
tattttaact tgctatgctg ttttgtttcc aaaacagcat agctctaaaa ccctagtca   120 ttggaggtga cggtgtttcg tcctttccac aag                               153

<210> SEQ ID NO 92
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
taatacgact cactatagga agtgcgccac catggcccca agaagaagc gg            52

<210> SEQ ID NO 93

```
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93 ggttttttt tttttttttt tttttttttt ttttcttact ttttcttttt tgcctggccg    60

<210> SEQ ID NO 94
<211> LENGTH: 984
<212> TYPE: PRT
<213> ORGANISM: Campylobacter jejuni

<400> SEQUENCE: 94
```

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
            20                  25                  30

Thr Lys Val Glu Asn Pro Lys Thr Gly Glu Ser Leu Ala Leu Pro Arg
        35                  40                  45

Arg Leu Ala Arg Ser Ala Arg Lys Arg Leu Ala Arg Arg Lys Ala Arg
    50                  55                  60

Leu Asn His Leu Lys His Leu Ile Ala Asn Glu Phe Lys Leu Asn Tyr
65                  70                  75                  80

Glu Asp Tyr Gln Ser Phe Asp Glu Ser Leu Ala Lys Ala Tyr Lys Gly
                85                  90                  95

Ser Leu Ile Ser Pro Tyr Glu Leu Arg Phe Arg Ala Leu Asn Glu Leu
            100                 105                 110

Leu Ser Lys Gln Asp Phe Ala Arg Val Ile Leu His Ile Ala Lys Arg
        115                 120                 125

Arg Gly Tyr Asp Asp Ile Lys Asn Ser Asp Asp Lys Glu Lys Gly Ala
    130                 135                 140

Ile Leu Lys Ala Ile Lys Gln Asn Glu Glu Lys Leu Ala Asn Tyr Gln
145                 150                 155                 160

Ser Val Gly Glu Tyr Leu Tyr Lys Glu Tyr Phe Gln Lys Phe Lys Glu
                165                 170                 175

Asn Ser Lys Glu Phe Thr Asn Val Arg Asn Lys Lys Glu Ser Tyr Glu
            180                 185                 190

Arg Cys Ile Ala Gln Ser Phe Leu Lys Asp Glu Leu Lys Leu Ile Phe
        195                 200                 205

Lys Lys Gln Arg Glu Phe Gly Phe Ser Phe Ser Lys Lys Phe Glu Glu
    210                 215                 220

Glu Val Leu Ser Val Ala Phe Tyr Lys Arg Ala Leu Lys Asp Phe Ser
225                 230                 235                 240

His Leu Val Gly Asn Cys Ser Phe Phe Thr Asp Glu Lys Arg Ala Pro
                245                 250                 255

Lys Asn Ser Pro Leu Ala Phe Met Phe Val Ala Leu Thr Arg Ile Ile
            260                 265                 270

Asn Leu Leu Asn Asn Leu Lys Asn Thr Glu Gly Ile Leu Tyr Thr Lys
        275                 280                 285

Asp Asp Leu Asn Ala Leu Leu Asn Glu Val Leu Lys Asn Gly Thr Leu
    290                 295                 300

Thr Tyr Lys Gln Thr Lys Lys Leu Leu Gly Leu Ser Asp Asp Tyr Glu
305                 310                 315                 320

```
Phe Lys Gly Glu Lys Gly Thr Tyr Phe Ile Glu Phe Lys Lys Tyr Lys
                325                 330                 335

Glu Phe Ile Lys Ala Leu Gly Glu His Asn Leu Ser Gln Asp Asp Leu
            340                 345                 350

Asn Glu Ile Ala Lys Asp Ile Thr Leu Ile Lys Asp Glu Ile Lys Leu
                355                 360                 365

Lys Lys Ala Leu Ala Lys Tyr Asp Leu Asn Gln Asn Gln Ile Asp Ser
370                 375                 380

Leu Ser Lys Leu Glu Phe Lys Asp His Leu Asn Ile Ser Phe Lys Ala
385                 390                 395                 400

Leu Lys Leu Val Thr Pro Leu Met Leu Glu Gly Lys Lys Tyr Asp Glu
                405                 410                 415

Ala Cys Asn Glu Leu Asn Leu Lys Val Ala Ile Asn Glu Asp Lys Lys
            420                 425                 430

Asp Phe Leu Pro Ala Phe Asn Glu Thr Tyr Tyr Lys Asp Glu Val Thr
        435                 440                 445

Asn Pro Val Val Leu Arg Ala Ile Lys Glu Tyr Arg Lys Val Leu Asn
    450                 455                 460

Ala Leu Leu Lys Lys Tyr Gly Lys Val His Lys Ile Asn Ile Glu Leu
465                 470                 475                 480

Ala Arg Glu Val Gly Lys Asn His Ser Gln Arg Ala Lys Ile Glu Lys
                485                 490                 495

Glu Gln Asn Glu Asn Tyr Lys Ala Lys Lys Asp Ala Glu Leu Glu Cys
            500                 505                 510

Glu Lys Leu Gly Leu Lys Ile Asn Ser Lys Asn Ile Leu Lys Leu Arg
        515                 520                 525

Leu Phe Lys Glu Gln Lys Glu Phe Cys Ala Tyr Ser Gly Glu Lys Ile
    530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
    610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
    690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735
```

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
    770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
    850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910

Thr Ser Ser Thr Val Ser Leu Ile Val Ser Lys His Asp Asn Lys Phe
        915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 95
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
tataatctca taagaaattt aaaaagggac taaaataaag agtttgcggg actctgcggg    60
gttacaatcc cctaaaaccg cttttaaaat t                                   91

<210> SEQ ID NO 96
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
attttaccat aaagaaattt aaaaagggac taaaac                              36

```
<210> SEQ ID NO 97
<211> LENGTH: 95
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 97
nnnnnnnnnn nnnnnnnnnn guuuuagucc cgaaagggac uaaaauaaag aguuugcggg    60
acucugcggg guuacaaucc ccuaaaaccg cuuuu                                95

<210> SEQ ID NO 98
<211> LENGTH: 1115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98
```

| | | | | | | | | | | | | | | |
|---|---|---|---|---|---|---|---|---|---|---|---|---|---|---|
| Met | Ser | Asp | Leu | Val | Leu | Gly | Leu | Asp | Ile | Gly | Ile | Gly | Ser | Val |
| 1 | | | | 5 | | | | | 10 | | | | | 15 |
| Gly | | | | | | | | | | | | | | |
| Val | Gly | Ile | Leu | Asn | Lys | Val | Thr | Gly | Glu | Ile | Ile | His | Lys | Asn |
| | | 20 | | | | | 25 | | | | | 30 | | |
| Ser | | | | | | | | | | | | | | |
| Arg | Ile | Phe | Pro | Ala | Ala | Gln | Ala | Glu | Asn | Asn | Leu | Val | Arg | Arg |
| | | 35 | | | | | 40 | | | | | 45 | | |
| Thr | | | | | | | | | | | | | | |
| Asn | Arg | Gln | Gly | Arg | Arg | Leu | Ala | Arg | Arg | Lys | Lys | His | Arg | Arg |
| | 50 | | | | | 55 | | | | | 60 | | | |
| Val | | | | | | | | | | | | | | |
| Arg | Leu | Asn | Arg | Leu | Phe | Glu | Glu | Ser | Gly | Leu | Ile | Thr | Asp | Phe |
| 65 | | | | | 70 | | | | | 75 | | | | 80 |
| Thr | | | | | | | | | | | | | | |
| Lys | Ile | Ser | Ile | Asn | Leu | Asn | Pro | Tyr | Gln | Leu | Arg | Val | Lys | Gly |
| | | | | 85 | | | | | 90 | | | | | 95 |
| Leu | | | | | | | | | | | | | | |
| Thr | Asp | Glu | Leu | Ser | Asn | Glu | Glu | Leu | Phe | Ile | Ala | Leu | Lys | Asn |
| | | | | 100 | | | | | 105 | | | | | 110 |
| Met | | | | | | | | | | | | | | |
| Val | Lys | His | Arg | Gly | Ile | Ser | Tyr | Leu | Asp | Asp | Ala | Ser | Asp | Asp |
| | | | 115 | | | | | 120 | | | | | 125 | |
| Gly | | | | | | | | | | | | | | |
| Asn | Ser | Ser | Val | Gly | Asp | Tyr | Ala | Gln | Ile | Val | Lys | Glu | Asn | Ser |
| | 130 | | | | | 135 | | | | | 140 | | | |
| Lys | | | | | | | | | | | | | | |
| Gln | Leu | Glu | Thr | Lys | Thr | Pro | Gly | Gln | Ile | Gln | Leu | Glu | Arg | Tyr |
| 145 | | | | | 150 | | | | | 155 | | | | 160 |
| Gln | | | | | | | | | | | | | | |
| Thr | Tyr | Gly | Gln | Leu | Arg | Gly | Asp | Phe | Thr | Val | Glu | Lys | Asp | Gly |
| | | | | 165 | | | | | 170 | | | | | 175 |
| Lys | | | | | | | | | | | | | | |
| Lys | His | Arg | Leu | Ile | Asn | Val | Phe | Pro | Thr | Ser | Ala | Tyr | Arg | Ser |
| | | | | 180 | | | | | 185 | | | | | 190 |
| Glu | | | | | | | | | | | | | | |
| Ala | Leu | Arg | Ile | Leu | Gln | Thr | Gln | Gln | Glu | Phe | Asn | Pro | Gln | Ile |
| | | | 195 | | | | | 200 | | | | | 205 | |
| Thr | | | | | | | | | | | | | | |
| Asp | Glu | Phe | Ile | Asn | Arg | Tyr | Leu | Glu | Ile | Leu | Thr | Gly | Lys | Arg |
| | | | 210 | | | | | 215 | | | | | 220 | |
| Lys | | | | | | | | | | | | | | |
| Tyr | Tyr | His | Gly | Pro | Gly | Asn | Glu | Lys | Ser | Arg | Thr | Asp | Tyr | Gly |
| 225 | | | | | 230 | | | | | 235 | | | | 240 |
| Arg | | | | | | | | | | | | | | |
| Tyr | Arg | Thr | Ser | Gly | Glu | Thr | Leu | Asp | Asn | Ile | Phe | Gly | Ile | Leu |
| | | | | 245 | | | | | 250 | | | | | 255 |
| Ile | | | | | | | | | | | | | | |

-continued

Gly Lys Cys Thr Phe Tyr Pro Asp Glu Phe Arg Ala Ala Lys Ala Ser
          260                 265                 270

Tyr Thr Ala Gln Glu Phe Asn Leu Leu Asn Asp Leu Asn Asn Leu Thr
      275                 280                 285

Val Pro Thr Glu Thr Lys Lys Leu Ser Lys Glu Gln Lys Asn Gln Ile
  290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
              325                 330                 335

Tyr Arg Ile Asp Lys Ser Gly Lys Ala Glu Ile His Thr Phe Glu Ala
          340                 345                 350

Tyr Arg Lys Met Lys Thr Leu Glu Thr Leu Asp Ile Glu Gln Met Asp
      355                 360                 365

Arg Glu Thr Leu Asp Lys Leu Ala Tyr Val Leu Thr Leu Asn Thr Glu
  370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
              405                 410                 415

Ser Ser Ile Phe Gly Lys Gly Trp His Asn Phe Ser Val Lys Leu Met
          420                 425                 430

Met Glu Leu Ile Pro Glu Leu Tyr Glu Thr Ser Glu Glu Gln Met Thr
      435                 440                 445

Ile Leu Thr Arg Leu Gly Lys Gln Lys Thr Thr Ser Ser Ser Asn Lys
  450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
              485                 490                 495

Ile Lys Glu Tyr Gly Asp Phe Asp Asn Ile Val Ile Glu Met Ala Arg
          500                 505                 510

Glu Asn Gln Thr Thr Gln Lys Gly Gln Lys Asn Ser Arg Glu Arg Met
      515                 520                 525

Lys Arg Ile Glu Glu Gly Ile Lys Glu Leu Gly Ser Gln Ile Leu Lys
  530                 535                 540

Glu His Pro Val Glu Asn Thr Gln Leu Gln Asn Glu Lys Leu Tyr Leu
545                 550                 555                 560

Tyr Tyr Leu Gln Asn Gly Arg Asp Met Tyr Val Asp Gln Glu Leu Asp
              565                 570                 575

Ile Asn Arg Leu Ser Asp Tyr Asp Val Asp His Ile Val Pro Gln Ser
          580                 585                 590

Phe Leu Lys Asp Asp Ser Ile Asp Asn Lys Val Leu Thr Arg Ser Asp
      595                 600                 605

Lys Asn Arg Gly Lys Ser Asp Asn Val Pro Ser Glu Glu Val Val Lys
  610                 615                 620

Lys Met Lys Asn Tyr Trp Arg Gln Leu Leu Asn Ala Lys Leu Ile Thr
625                 630                 635                 640

Gln Arg Lys Phe Asp Asn Leu Thr Lys Ala Glu Arg Gly Gly Leu Ser
              645                 650                 655

Glu Leu Asp Lys Ala Gly Phe Ile Lys Arg Gln Leu Val Glu Thr Arg
          660                 665                 670

Gln Ile Thr Lys His Val Ala Gln Ile Leu Asp Ser Arg Met Asn Thr

-continued

```
            675                 680                 685
Lys Tyr Asp Glu Asn Asp Lys Leu Ile Arg Glu Val Lys Val Ile Thr
            690                 695                 700

Leu Lys Ser Lys Leu Val Ser Asp Phe Arg Lys Asp Phe Gln Phe Tyr
705                 710                 715                 720

Lys Val Arg Glu Ile Asn Asn Tyr His His Ala His Asp Ala Tyr Leu
            725                 730                 735

Asn Ala Val Val Gly Thr Ala Leu Ile Lys Lys Tyr Pro Lys Leu Glu
            740                 745                 750

Ser Glu Phe Val Tyr Gly Asp Tyr Lys Val Tyr Asp Val Arg Lys Met
            755                 760                 765

Ile Ala Lys Ser Glu Gln Glu Ile Gly Lys Ala Thr Ala Lys Tyr Phe
            770                 775                 780

Phe Tyr Ser Asn Ile Met Asn Phe Phe Lys Thr Glu Ile Thr Leu Ala
785                 790                 795                 800

Asn Gly Glu Ile Arg Lys Arg Pro Leu Ile Glu Thr Asn Gly Glu Thr
                    805                 810                 815

Gly Glu Ile Val Trp Asp Lys Gly Arg Asp Phe Ala Thr Val Arg Lys
            820                 825                 830

Val Leu Ser Met Pro Gln Val Asn Ile Val Lys Lys Thr Glu Val Gln
            835                 840                 845

Thr Gly Gly Phe Ser Lys Glu Ser Ile Leu Pro Lys Arg Asn Ser Asp
            850                 855                 860

Lys Leu Ile Ala Arg Lys Lys Asp Trp Asp Pro Lys Lys Tyr Gly Gly
865                 870                 875                 880

Phe Asp Ser Pro Thr Val Ala Tyr Ser Val Leu Val Val Ala Lys Val
                    885                 890                 895

Glu Lys Gly Lys Ser Lys Lys Leu Lys Ser Val Lys Glu Leu Leu Gly
            900                 905                 910

Ile Thr Ile Met Glu Arg Ser Ser Phe Glu Lys Asn Pro Ile Asp Phe
            915                 920                 925

Leu Glu Ala Lys Gly Tyr Lys Glu Val Lys Lys Asp Leu Ile Ile Lys
            930                 935                 940

Leu Pro Lys Tyr Ser Leu Phe Glu Leu Glu Asn Gly Arg Lys Arg Met
945                 950                 955                 960

Leu Ala Ser Ala Gly Glu Leu Gln Lys Gly Asn Glu Leu Ala Leu Pro
                    965                 970                 975

Ser Lys Tyr Val Asn Phe Leu Tyr Leu Ala Ser His Tyr Glu Lys Leu
            980                 985                 990

Lys Gly Ser Pro Glu Asp Asn Glu Gln Lys Gln Leu Phe Val Glu Gln
            995                 1000                1005

His Lys His Tyr Leu Asp Glu Ile Ile Glu Gln Ile Ser Glu Phe
            1010                1015                1020

Ser Lys Arg Val Ile Leu Ala Asp Ala Asn Leu Asp Lys Val Leu
            1025                1030                1035

Ser Ala Tyr Asn Lys His Arg Asp Lys Pro Ile Arg Glu Gln Ala
            1040                1045                1050

Glu Asn Ile Ile His Leu Phe Thr Leu Thr Asn Leu Gly Ala Pro
            1055                1060                1065

Ala Ala Phe Lys Tyr Phe Asp Thr Thr Ile Asp Arg Lys Arg Tyr
            1070                1075                1080

Thr Ser Thr Lys Glu Val Leu Asp Ala Thr Leu Ile His Gln Ser
            1085                1090                1095
```

Ile Thr Gly Leu Tyr Glu Thr Arg Ile Asp Leu Ser Gln Leu Gly
            1100                1105                1110

Gly Asp
    1115

<210> SEQ ID NO 99
<211> LENGTH: 1374
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly

-continued

```
                740                 745                 750
Arg His Lys Pro Glu Asn Ile Val Ile Glu Met Ala Arg Glu Thr Asn
                755                 760                 765
Glu Asp Asp Glu Lys Lys Ala Ile Gln Lys Ile Gln Lys Ala Asn Lys
                770                 775                 780
Asp Glu Lys Asp Ala Ala Met Leu Lys Ala Ala Asn Gln Tyr Asn Gly
785                 790                 795                 800
Lys Ala Glu Leu Pro His Ser Val Phe His Gly His Lys Gln Leu Ala
                805                 810                 815
Thr Lys Ile Arg Leu Trp His Gln Gln Gly Glu Arg Cys Leu Tyr Thr
                820                 825                 830
Gly Lys Thr Ile Ser Ile His Asp Leu Ile Asn Asn Ser Asn Gln Phe
                835                 840                 845
Glu Val Asp His Ile Leu Pro Leu Ser Ile Thr Phe Asp Asp Ser Leu
                850                 855                 860
Ala Asn Lys Val Leu Val Tyr Ala Thr Ala Asn Gln Glu Lys Gly Gln
865                 870                 875                 880
Arg Thr Pro Tyr Gln Ala Leu Asp Ser Met Asp Asp Ala Trp Ser Phe
                885                 890                 895
Arg Glu Leu Lys Ala Phe Val Arg Glu Ser Lys Thr Leu Ser Asn Lys
                900                 905                 910
Lys Lys Glu Tyr Leu Leu Thr Glu Glu Asp Ile Ser Lys Phe Asp Val
                915                 920                 925
Arg Lys Lys Phe Ile Glu Arg Asn Leu Val Asp Thr Arg Tyr Ala Ser
                930                 935                 940
Arg Val Val Leu Asn Ala Leu Gln Glu His Phe Arg Ala His Lys Ile
945                 950                 955                 960
Asp Thr Lys Val Ser Val Val Arg Gly Gln Phe Thr Ser Gln Leu Arg
                965                 970                 975
Arg His Trp Gly Ile Glu Lys Thr Arg Asp Thr Tyr His His His Ala
                980                 985                 990
Val Asp Ala Leu Ile Ile Ala Ala Ser Ser Gln Leu Asn Leu Trp Lys
                995                 1000                1005
Lys Gln Lys Asn Thr Leu Val Ser Tyr Ser Glu Asp Gln Leu Leu
                1010                1015                1020
Asp Ile Glu Thr Gly Glu Leu Ile Ser Asp Asp Glu Tyr Lys Glu
                1025                1030                1035
Ser Val Phe Lys Ala Pro Tyr Gln His Phe Val Asp Thr Leu Lys
                1040                1045                1050
Ser Lys Glu Phe Glu Asp Ser Ile Leu Phe Ser Tyr Gln Val Asp
                1055                1060                1065
Ser Lys Phe Asn Arg Lys Ile Ser Asp Ala Thr Ile Tyr Ala Thr
                1070                1075                1080
Arg Gln Ala Lys Val Gly Lys Asp Lys Ala Asp Glu Thr Tyr Val
                1085                1090                1095
Leu Gly Lys Ile Lys Asp Ile Tyr Thr Gln Asp Gly Tyr Asp Ala
                1100                1105                1110
Phe Met Lys Ile Tyr Lys Lys Asp Lys Ser Lys Phe Leu Met Tyr
                1115                1120                1125
Arg His Asp Pro Gln Thr Phe Glu Lys Val Ile Glu Pro Ile Leu
                1130                1135                1140
Glu Asn Tyr Pro Asn Lys Gln Ile Asn Glu Lys Gly Lys Glu Val
                1145                1150                1155
```

```
Pro Cys Asn Pro Phe Leu Lys Tyr Lys Glu Glu His Gly Tyr Ile
        1160                1165                1170

Arg Lys Tyr Ser Lys Lys Gly Asn Gly Pro Glu Ile Lys Ser Leu
    1175                1180                1185

Lys Tyr Tyr Asp Ser Lys Leu Gly Asn His Ile Asp Ile Thr Pro
    1190                1195                1200

Lys Asp Ser Asn Asn Lys Val Val Leu Gln Ser Val Ser Pro Trp
    1205                1210                1215

Arg Ala Asp Val Tyr Phe Asn Lys Thr Thr Gly Lys Tyr Glu Ile
    1220                1225                1230

Leu Gly Leu Lys Tyr Ala Asp Leu Gln Phe Glu Lys Gly Thr Gly
    1235                1240                1245

Thr Tyr Lys Ile Ser Gln Glu Lys Tyr Asn Asp Ile Lys Lys Lys
    1250                1255                1260

Glu Gly Val Asp Ser Asp Ser Glu Phe Lys Phe Thr Leu Tyr Lys
    1265                1270                1275

Asn Asp Leu Leu Leu Val Lys Asp Thr Glu Thr Lys Glu Gln Gln
    1280                1285                1290

Leu Phe Arg Phe Leu Ser Arg Thr Met Pro Lys Gln Lys His Tyr
    1295                1300                1305

Val Glu Leu Lys Pro Tyr Asp Lys Gln Lys Phe Glu Gly Gly Glu
    1310                1315                1320

Ala Leu Ile Lys Val Leu Gly Asn Val Ala Asn Ser Gly Gln Cys
    1325                1330                1335

Lys Lys Gly Leu Gly Lys Ser Asn Ile Ser Ile Tyr Lys Val Arg
    1340                1345                1350

Thr Asp Val Leu Gly Asn Gln His Ile Ile Lys Asn Glu Gly Asp
    1355                1360                1365

Lys Pro Lys Leu Asp Phe
    1370

<210> SEQ ID NO 100
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 100

His His His His His His
1               5

<210> SEQ ID NO 101
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gly Gly Gly Gly Ser Gly Gly Gly Gly Ser Gly Gly Gly Gly Ser
1               5                   10                  15

<210> SEQ ID NO 102
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Glu Ala Ala Ala Lys Glu Ala Ala Ala Lys Glu Ala Ala Ala Lys
1               5                  10                  15

<210> SEQ ID NO 103
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gly Gly Gly Gly Gly Ser Gly Gly Gly Gly Ser Gly Gly Gly Gly
1               5                  10                  15

Gly Ser

<210> SEQ ID NO 104
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
gccaaattgg acgaccctcg cgg                                             23

<210> SEQ ID NO 105
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
cgaggagacc cccgtttcgg tgg                                             23

<210> SEQ ID NO 106
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
cccgccgccg ccgtggctcg agg                                             23

<210> SEQ ID NO 107
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 107
tgagctctac gagatccaca agg          23

<210> SEQ ID NO 108
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
ctcaaaattc ataccggttg tgg          23

<210> SEQ ID NO 109
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
cgttaaacaa caccggact tgg          23

<210> SEQ ID NO 110
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
ttcaccccgc ggcgctgaat ggg          23

<210> SEQ ID NO 111
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
accactacca gtccgtccac agg          23

<210> SEQ ID NO 112
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
agcctttctg aacacatgca cgg          23

<210> SEQ ID NO 113
<211> LENGTH: 39

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
cctgccatca atgtggccat gcatgtgttc agaaaggct                              39

<210> SEQ ID NO 114
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
cctgccatca atgtggccgt gcatgtgttc agaaaggct                              39

<210> SEQ ID NO 115
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
cactgcttaa gcctcgctcg agg                                               23

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
tcaccagcaa tattcgctcg agg                                               23

<210> SEQ ID NO 117
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
caccagcaat attccgctcg agg                                               23

<210> SEQ ID NO 118
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
```
tagcaacaga catacgctcg agg                                         23

<210> SEQ ID NO 119
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
gggcagtagt aatacgctcg agg                                         23

<210> SEQ ID NO 120
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
ccaattccca tacattattg tac                                         23

<210> SEQ ID NO 121
<211> LENGTH: 4677
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 121
tctttcttgc gctatgacac ttccagcaaa aggtagggcg ggctgcgaga cggcttcccg      60
gcgctgcatg caacaccgat gatgcttcga ccccccgaag ctccttcggg gctgcatggg     120
cgctccgatg ccgctccagg gcgagcgctg tttaaatagc caggccccg attgcaaaga     180 cattatagcg agctaccaaa gccatattca aacacctaga tcactaccac ttctacacag     240
gccactcgag cttgtgatcg cactccgcta aggggggcgcc tcttcctctt cgtttcagtc     300
acaacccgca aacatgtacc catacgatgt tccagattac gcttcgccga agaaaaagcg     360
caaggtcgaa gcgtccgaca agaagtacag catcggcctg gacatcggca ccaactctgt     420
gggctgggcc gtgatcaccg acgagtacaa ggtgcccagc aagaaattca aggtgctggg     480
caacaccgac cggcacagca tcaagaagaa cctgatcgga gccctgctgt tcgacagcgg     540
cgaaacagcc gaggccaccc ggctgaagag aaccgccaga agaagataca ccagacggaa     600
gaaccggatc tgctatctgc aagagatctt cagcaacgag atggccaagg tggacgacag     660
cttcttccac agactggaag agtccttcct ggtggaagag gataagaagc acgagcggca     720
ccccatcttc ggcaacatcg tggacgaggt ggcctaccac gagaagtacc ccaccatcta     780
ccacctgaga aagaaactgg tggacagcac cgacaaggcc gacctgcggc tgatctatct     840
ggccctggcc cacatgatca gttccgggg ccacttcctg atcgagggcg acctgaaccc     900
cgacaacagc gacgtggaca gctgttcat ccagctggtg cagacctaca accagctgtt     960
cgaggaaaac cccatcaacg ccagcggcgt ggacgccaag gccatcctgt ctgccagact    1020
gagcaagagc agacgactgg aaaatctgat cgcccagctg cccggcgaga agaagaatggg   1080 cctgttcggc aacctgattg ccctgagcct gggcctgacc cccaacttca gagcaacttt    1140

```
cgacctggcc gaggatgcca aactgcagct gagcaaggac acctacgacg acgacctgga   1200
caacctgctg gcccagatcg gcgaccagta cgccgacctg tttctggccg ccaagaacct   1260
gtccgacgcc atcctgctga gcgacatcct gagagtgaac accgagatca ccaaggcccc   1320
cctgagcgcc tctatgatca agagatacga cgagcaccac caggacctga ccctgctgaa   1380
agctctcgtg cggcagcagc tgcctgagaa gtacaaagag attttcttcg accagagcaa   1440
gaacggctac gccggctaca ttgacggcgg agccagccag gaagagttct acaagttcat   1500
caagcccatc ctggaaaaga tggacggcac cgaggaactg ctcgtgaagc tgaacagaga   1560
ggacctgctg cggaagcagc ggaccttcga caacggcagc atcccccacc agatccacct   1620
gggagagctg cacgccattc tgcggcggca ggaagatttt tacccattcc tgaaggacaa   1680
ccgggaaaag atcgagaaga tcctgacctt ccgcatcccc tactacgtgg ccctctggc    1740
caggggaaac agcagattcg cctggatgac cagaaagagc gaggaaacca tcacccctg    1800
gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg aatgagaaa    1980
gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca taccacga    2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca gcagtccgg    2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga aaccagacc acccagaagg acagaagaa    2700
cagccgcgag agaatgaagc ggatcgaaga gggcatcaaa gagctgggca gccagatcct   2760
gaaagaacac cccgtggaaa cacccagct gcagaacgag aagctgtacc tgtactacct   2820
gcagaatggg cgggatatgt acgtggacca ggaactggac atcaaccggc tgtccgacta   2880
cgatgtggac catatcgtgc ctcagagctt tctgaaggac gactccatcg acaacaaggt   2940
gctgaccaga agcgacaaga accggggcaa gagcgacaac gtgccctccg aagaggtcgt   3000
gaagaagatg aagaactact ggcggcagct gctgaacgcc aagctgatta cccagagaaa   3060
gttcgacaat ctgaccaagg ccgagagagg cggcctgagc gaactggata aggccggctt   3120
catcaagaga cagctggtgg aaacccggca gatcacaaag cacgtggcac agatcctgga   3180
ctcccgatg aacactaagt acgacgaaa tgacaagctg atccgggaag tgaaagtgat   3240
caccctgaag tccaagctgg tgtccgattt ccggaaggat ttccagtttt acaaagtgcg   3300
cgagatcaac aactaccacc acgcccacga cgcctacctg aacgccgtcg tgggaaccgc   3360
cctgatcaaa aagtacccta agctggaaag cgagttcgtg tacggcgact acaaggtgta   3420
cgacgtgcgg aagatgatcg ccaagagcga gcaggaaatc ggcaaggcta ccgccaagta   3480
```

| | |
|---|---|
| cttcttctac agcaacatca tgaactttt caagaccgag attaccctgg ccaacggcga | 3540 |
| gatccggaag cggcctctga tcgagacaaa cggcgaaacc ggggagatcg tgtgggataa | 3600 |
| gggccgggat tttgccaccg tgcggaaagt gctgagcatg ccccaagtga atatcgtgaa | 3660 |
| aaagaccgag gtgcagacag gcggcttcag caaagagtct atcctgccca agaggaacag | 3720 |
| cgataagctg atcgccagaa agaaggactg ggaccctaag aagtacggcg gcttcgacag | 3780 |
| ccccaccgtg gcctattctg tgctggtggt ggccaaagtg aaaagggca agtccaagaa | 3840 |
| actgaagagt gtgaaagagc tgctggggat caccatcatg gaaagaagca gcttcgagaa | 3900 |
| gaatcccatc gactttctgg aagccaaggg ctacaaagaa gtgaaaaagg acctgatcat | 3960 |
| caagctgcct aagtactccc tgttcgagct ggaaaacggc cggaagagaa tgctggcctc | 4020 |
| tgccggcgaa ctgcagaagg gaaacgaact ggccctgccc tccaaatatg tgaacttcct | 4080 |
| gtacctggcc agccactatg agaagctgaa gggctccccc gaggataatg agcagaaaca | 4140 |
| gctgtttgtg gaacagcaca gcactacct ggacgagatc atcgagcaga tcagcgagtt | 4200 |
| ctccaagaga gtgatcctgg ccgacgctaa tctggacaaa gtgctgtccg cctacaacaa | 4260 |
| gcaccgggat aagcccatca gagagcaggc cgagaatatc atccacctgt ttacctgac | 4320 |
| caatctggga gccctgccg ccttcaagta ctttgacacc accatcgacc ggaagaggta | 4380 |
| caccagcacc aaagaggtgc tggacgccac cctgatccac cagagcatca ccggcctgta | 4440 |
| cgagacacga atcgacctgt ctcagctggg aggcgacagc cccaagaaga gagaaaggt | 4500 |
| ggaggccagc taaggatccg gcaagactgg ccccgcttgg caacgcaaca gtgagcccct | 4560 |
| ccctagtgtg tttggggatg tgactatgta ttcgtgtgtt ggccaacggg tcaacccgaa | 4620 |
| cagattgata cccgccttgg catttcctgt cagaatgtaa cgtcagttga tggtact | 4677 |

<210> SEQ ID NO 122
<211> LENGTH: 3150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122

| | |
|---|---|
| tctttcttgc gctatgacac ttccagcaaa aggtagggcg gctgcgaga cggcttcccg | 60 |
| gcgctgcatg caacaccgat gatgcttcga ccccccgaag ctccttcggg gctgcatggg | 120 |
| cgctccgatg ccgctccagg gcgagcgctg tttaaatagc caggccccg attgcaaaga | 180 |
| cattatagcg agctaccaaa gccatattca aacacctaga tcactaccac ttctacacag | 240 |
| gccactcgag cttgtgatcg cactccgcta aggggcgcc tcttcctctt cgtttcagtc | 300 |
| acaacccgca acatgccta agaagaagag gaaggttaac acgattaaca tcgctaagaa | 360 |
| cgacttctct gacatcgaac tggctgctat cccgttcaac actctggctg accattacgg | 420 |
| tgagcgttta gctcgcgaac agttggccct tgagcatgag tcttacgaga tgggtgaagc | 480 |
| acgcttccgc aagatgtttg agcgtcaact aaagctggt gaggttgcgg ataacgctgc | 540 |
| cgccaagcct ctcatcacta ccctactccc taagatgatt gcacgcatca acgactggtt | 600 |
| tgaggaagtg aaagctaagc gcggcaagcg cccgacagcc ttccagttcc tgcaagaaat | 660 |
| caagccggaa gccgtagcgt acatcaccat taagccact ctggcttgcc taaccagtgc | 720 |
| tgacaataca accgttcagg ctgtagcaag cgcaatcggt cgggccattg aggacgaggc | 780 |
| tcgcttcggt cgtatccgtg accttgaagc taagcacttc aagaaaaacg ttgaggaaca | 840 |

-continued

```
actcaacaag cgcgtagggc acgtctacaa gaaagcattt atgcaagttg tcgaggctga      900
catgctctct aagggtctac tcggtggcga ggcgtggtct tcgtggcata aggaagactc      960
tattcatgta ggagtacgct gcatcgagat gctcattgag tcaaccggaa tggttagctt     1020
acaccgccaa aatgctggcg tagtaggtca agactctgag actatcgaac tcgcacctga     1080
atacgctgag gctatcgcaa cccgtgcagg tgcgctggct ggcatctctc cgatgttcca     1140
accttgcgta gttcctccta agccgtggac tggcattact ggtggtggct attgggctaa     1200
cggtcgtcgt cctctggcgc tggtgcgtac tcacagtaag aaagcactga tgcgctacga     1260
agacgtttac atgcctgagg tgtacaaagc gattaacatt gcgcaaaaca ccgcatggaa     1320
aatcaacaag aaagtcctag cggtcgccaa cgtaatcacc aagtggaagc attgtccggt     1380
cgaggacatc cctgcgattg agcgtgaaga actcccgatg aaaccggaag acatcgacat     1440
gaatcctgag gctctcaccg cgtggaaacg tgctgccgct gctgtgtacc gcaaggacaa     1500
ggctcgcaag tctcgccgta tcagccttga gttcatgctt gagcaagcca ataagtttgc     1560
taaccataag gccatctggt tcccttacaa catggactgg cgcggtcgtg tttacgctgt     1620
gtcaatgttc aacccgcaag gtaacgatat gaccaaagga ctgcttacgc tggcgaaagg     1680
taaaccaatc ggtaaggaag gttactactg gctgaaaatc cacggtgcaa actgtgcggg     1740
tgtcgacaag gttccgttcc ctgagcgcat caagttcatt gaggaaaacc acgagaacat     1800
catggcttgc gctaagtctc cactggagaa cacttggtgg gctgagcaag attctccgtt     1860
ctgcttcctt gcgttctgct ttgagtacgc tggggtacag caccacgcc tgagctataa      1920 ctgctccctt ccgctggcgt ttgacgggtc ttgctctggc atccagcact tctccgcgat     1980
gctccgagat gaggtaggtg gtcgcgcggt taacttgctt cctagtgaaa ccgttcagga     2040
catctacggg attgttgcta agaaagtcaa cgagattcta caagcagacg caatcaatgg     2100
gaccgataac gaagtagtta ccgtgaccga tgagaacact ggtgaaatct ctgaaaagt     2160 caagctgggc actaaggcac tggctggtca atggctggct tacggtgtta ctcgcagtgt     2220
gactaagcgt tcagtcatga cgctggctta cgggtccaaa gagttcggct tccgtcaaca     2280
agtgctggaa gataccattc agccagctat tgattccggc aagggtctga tgttcactca     2340
gccgaatcag gctgctggat acatggctaa gctgatttgg gaatctgtga gcgtgacggt     2400
ggtagctgcg gttgaagcaa tgaactggct taagtctgct gctaagctgc tggctgctga     2460
ggtcaaagat aagaagactg gagagattct tcgcaagcgt tgcgctgtgc attgggtaac     2520
tcctgatggt ttccctgtgt ggcaggaata caagaagcct attcagacgc gcttgaacct     2580
gatgttcctc ggtcagttcc gcttacagcc taccattaac accaacaaag atagcgagat     2640
tgatgcacac aaacaggagt ctggtatcgc tcctaacttt gtacacagcc aagacggtag     2700
ccaccttcgt aagactgtag tgtgggcaca cgagaagtac ggaatcgaat cttttgcact     2760
gattcacgac tccttcggta cgattccggc tgacgctgcg aacctgttca agcagtgcg      2820 cgaaactatg gttgacacat atgagtcttg tgatgtactg gctgatttct acgaccagtt     2880
cgctgaccag ttgcacgagt ctcaattgga caaaatgcca gcacttccgg ctaaaggtaa     2940
cttgaacctc cgtgacatct tagagtcgga cttcgcgttc gcgtaaggat ccggcaagac     3000
tggccccgct tggcaacgca acagtgagcc cctccctagt gtgtttgggg atgtgactat     3060
gtattcgtgt gttggccaac gggtcaaccc gaacagattg atacccgcct tggcatttcc     3120
tgtcagaatg taacgtcagt tgatggtact                                      3150
```

<210> SEQ ID NO 123
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (23)..(42)
<223> OTHER INFORMATION: a, c, t, g, unknown or other

<400> SEQUENCE: 123
gaaattaata cgactcacta tannnnnnnn nnnnnnnnnn nngttttaga gctagaaata     60
gcaagttaaa ataaggctag tccgttatca acttgaaaaa gtggcaccga gtcggtgctt    120
ttttt                                                                125

<210> SEQ ID NO 124
<211> LENGTH: 8452
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
tgcggtattt cacaccgcat caggtggcac ttttcgggga atgtgcgcg gaaccctat      60 ttgtttattt ttctaaatac attcaaatat gtatccgctc atgagattat caaaaaggat   120
cttcacctag atccttttaa attaaaaatg aagttttaaa tcaatctaaa gtatatatga   180
gtaaacttgg tctgacagtt accaatgctt aatcagtgag gcacctatct cagcgatctg   240
tctatttcgt tcatccatag ttgcctgact ccccgtcgtg tagataacta cgatacggga   300
gggcttacca tctggcccca gtgctgcaat gataccgcga gacccacgct caccggctcc   360
agatttatca gcaataaacc agccagccgg aagggccgag cgcagaagtg gtcctgcaac   420
tttatccgcc tccatccagt ctattaattg ttgccgggaa gctagagtaa gtagttcgcc   480
agttaatagt ttgcgcaacg ttgttgccat tgctacaggc atcgtggtgt cacgctcgtc   540
gtttggtatg gcttcattca gctccggttc ccaacgatca aggcgagtta catgatcccc   600
catgttgtgc aaaaaagcgg ttagctcctt cggtcctccg atcgttgtca gaagtaagtt   660
ggccgcagtg ttatcactca tggttatggc agcactgcat aattctctta ctgtcatgcc   720
atccgtaaga tgcttttctg tgactggtga gtactcaacc aagtcattct gagaatagtg   780
tatgcggcga ccgagttgct cttgcccggc gtcaatacgg gataataccg cgccacatag   840
cagaacttta aaagtgctca tcattggaaa acgttcttcg gggcgaaaac tctcaaggat   900
cttaccgctg ttgagatcca gttcgatgta acccactcgt gcacccaact gatcttcagc   960
atcttttact ttcaccagcg tttctgggtg agcaaaaaca ggaaggcaaa atgccgcaaa  1020
aaagggaata agggcgacac ggaaatgttg aatactcata ctcttccttt tcaatatta   1080 ttgaagcatt tatcagggtt attgtctcat gaccaaaatc ccttaacgtg agttttcgtt  1140
ccactgagcg tcagaccccg tagaaaagat caaaggatct tcttgagatc cttttttct   1200 gcgcgtaatc tgctgcttgc aaacaaaaaa accaccgcta ccagcggtgg tttgtttgcc  1260
ggatcaagag ctaccaactc tttttccgaa ggtaactggc ttcagcagag cgcagatacc  1320
aaatactgtt cttctagtgt agccgtagtt aggccaccac ttcaagaact ctgtagcacc  1380

```
gcctacatac ctcgctctgc taatcctgtt accagtggct gttgccagtg gcgataagtc    1440
gtgtcttacc gggttggact caagacgata gttaccggat aaggcgcagc ggtcgggctg    1500 aacgggggt  tcgtgcacac agcccagctt ggagcgaacg acctacaccg aactgagata    1560
cctacagcgt gagctatgag aaagcgccac gcttcccgaa gggagaaagg cggacaggta    1620
tccggtaagc ggcagggtcg aacaggaga  gcgcacgagg gagcttccag ggggaaacgc    1680
ctggtatctt tatagtcctg tcgggtttcg ccacctctga cttgagcgtc gattttgtg    1740 atgctcgtca gggggggcgga gcctatggaa aaacgccagc aacgcggcct ttttacggtt    1800
cctggccttt tgctggcctt tgctcacat  gttctttcct gcgttatccc ctgattctgt    1860
ggataaccgt attaccgcct ttgagtgagc tgataccgct cgccgcagcc gaacgaccga    1920
gcgcagcgag tcagtgagcg aggaagcggt cgctgaggct tgacatgatt ggtgcgtatg    1980
tttgtatgaa gctacaggac tgatttggcg ggctatgagg gcggggaag  ctctggaagg    2040 gccgcgatgg ggcgcgcggc gtccagaagg cgccatacgg cccgctggcg cacccatcc    2100 ggtataaaag cccgcgaccc cgaacggtga cctccacttt cagcgacaaa cgagcactta    2160
tacatacgcg actattctgc cgctatacat aaccactcag ctagcttaag atcccatcaa    2220
gcttgcatgc cgggcgcgcc agaaggagcg cagccaaacc aggatgatgt ttgatggggt    2280
atttgagcac ttgcaaccct tatccggaag cccctggcc  cacaaaggct aggcgccaat    2340
gcaagcagtt cgcatgcagc ccctggagcg gtgccctcct gataaaccgg ccaggggcc    2400 tatgttcttt actttttac  aagagaagtc actcaacatc ttaaaatggc caggtgagtc    2460
gacgagcaag cccggcggat caggcagcgt gcttgcagat ttgacttgca acgcccgcat    2520
tgtgtcgacg aaggcttttg gctcctctgt cgctgtctca agcagcatct aaccctgcgt    2580
cgccgtttcc atttgcagga gattcgaggt accatgtacc catacgatgt tccagattac    2640
gcttcgccga gaaaaagcg  caaggtcgaa gcgtccgaca agaagtacag catcggcctg    2700
gacatcggca ccaactctgt gggctgggcc gtgatcaccg acgagtacaa ggtgcccagc    2760
aagaaattca aggtgctggg caacaccgac cggcacagca tcaagaagaa cctgatcgga    2820
gccctgctgt tcgacagcgg cgaaacagcc gaggccaccc ggctgaagag aaccgccaga    2880
agaagataca ccagacggaa gaaccggatc tgctatctgc aagagatctt cagcaacgag    2940
atggccaagg tggacgacag cttcttccac agactgaag  agtccttcct ggtggaagag    3000
gataagaagc acgagcggca ccccatcttc ggcaacatcg tggacgaggt ggcctaccac    3060
gagaagtacc ccaccatcta ccacctgaga aagaaactgg tggacagcac cgacaaggcc    3120
gacctgcggc tgatctatct ggccctggcc cacatgatca gttccgggg  ccacttcctg    3180 atcgagggcg acctgaaccc cgacaacagc gacgtggaca gctgttcat  ccagctggtg    3240 cagacctaca accagctgtt cgaggaaaac cccatcaacg ccagcggcgt ggacgccaag    3300
gccatcctgt ctgccagact gagcaagagc agacggctgg aaaatctgat cgcccagctg    3360
cccggcgaga agaagaatgg cctgttcggc aacctgattg ccctgagcct gggcctgacc    3420
cccaacttca gagcaacttc cgacctggcc gaggatgcca aactgcagct gagcaaggac    3480
acctacgacg acgacctgga caacctgctg gcccagatcg cgaccagta  cgccgacctg    3540 tttctggccg ccaagaacct gtccgacgcc atcctgctga gcgacatcct gagagtgaac    3600
accgagatca ccaaggcccc cctgagcgcc tctatgatca agagatacga cgagcaccac    3660
caggacctga cctgctgaa  agctctcgtg cggcagcagc tgcctgagaa gtacaaagag    3720
```

```
atttcttcg accagagcaa gaacggctac gccggctaca ttgacggcgg agccagccag      3780
gaagagttct acaagttcat caagcccatc ctggaaaaga tggacggcac cgaggaactg      3840
ctcgtgaagc tgaacagaga ggacctgctg cggaagcagc ggaccttcga caacggcagc      3900
atccccacc agatccacct gggagagctg cacgccattc tgcggcggca ggaagatttt      3960
tacccattcc tgaaggacaa ccgggaaaag atcgagaaga tcctgacctt ccgcatcccc      4020
tactacgtgg cccctctggc caggggaaac agcagattcg cctggatgac cagaaagagc      4080
gaggaaacca tcacccctg gaacttcgag gaagtggtgg acaagggcgc ttccgcccag      4140
agcttcatcg agcggatgac caacttcgat aagaacctgc ccaacgagaa ggtgctgccc      4200
aagcacagcc tgctgtacga gtacttcacc gtgtataacg agctgaccaa agtgaaatac      4260
gtgaccgagg gaatgagaaa gcccgccttc ctgagcggcg agcagaaaaa ggccatcgtg      4320
gacctgctgt tcaagaccaa ccggaaagtg accgtgaagc agctgaaaga ggactacttc      4380
aagaaaatcg agtgcttcga ctccgtggaa atctccggcg tggaagatcg gttcaacgcc      4440
tccctgggca cataccacga tctgctgaaa attatcaagg acaaggactt cctggacaat      4500
gaggaaaacg aggacattct ggaagatatc gtgctgaccc tgacactgtt tgaggacaga      4560
gagatgatcg aggaacggct gaaaacctat gcccacctgt tcgacgacaa agtgatgaag      4620
cagctgaagc ggcggagata caccggctgg ggcaggctga gccggaagct gatcaacggc      4680
atccgggaca gcagtccgg caagacaatc ctggatttcc tgaagtccga cggcttcgcc      4740
aacagaaact tcatgcagct gatccacgac gacagcctga cctttaaaga ggacatccag      4800
aaagcccagg tgtccggcca gggcgatagc ctgcacgagc acattgccaa tctggccggc      4860
agccccgcca ttaagaaggg catcctgcag acagtgaagg tggtggacga gctcgtgaaa      4920
gtgatgggcc ggcacaagcc cgagaacatc gtgatcgaaa tggccagaga gaaccagacc      4980
acccagaagg gacagaagaa cagccgcgag agaatgaagc ggatcgaaga gggcatcaaa      5040
gagctgggca gccagatcct gaaagaacac cccgtggaaa acacccagct gcagaacgag      5100
aagctgtacc tgtactacct gcagaatggg cgggatatgt acgtggacca ggaactggac      5160
atcaaccggt gtccgacta cgatgtggac catatcgtgc ctcagagctt tctgaaggac      5220
gactccatcg acaacaaggt gctgaccaga agcgacaaga accggggcaa gagcgacaac      5280
gtgccctccg aagaggtcgt gaagaagatg aagaactact ggcggcagct gctgaacgcc      5340
aagctgatta cccagagaaa gttcgacaat ctgaccaagg ccgagagagg cggcctgagc      5400
gaactggata aggccggctt catcaagaga cagctggtgg aaacccggca gatcacaaag      5460
cacgtggcac agatcctgga ctcccggatg aacactaagt acgacgagaa tgacaagctg      5520
atccgggaag tgaaagtgat cacccctgaag tccaagctgg tgtccgattt ccggaaggat      5580
ttccagtttt acaaagtgcg cgagatcaac aactaccacc acgcccacga cgcctacctg      5640
aacgccgtcg tgggaaccgc cctgatcaaa aagtacccta gctgaaaag cgagttcgtg      5700
tacggcgact acaaggtgta cgacgtgcgg aagatgatcg ccaagagcga gcaggaaatc      5760
ggcaaggcta ccgccaagta cttcttctac agcaacatca tgaacttttt caagaccgag      5820
attaccctgg ccaacggcga gatccggaag cggcctctga tcgagacaaa cggcgaaacc      5880
ggggagatcg tgtgggataa gggccgggat tttgccaccg tgcggaaagt gctgagcatg      5940
ccccaagtga atatcgtgaa aaagaccgag gtgcagacag cggcttcag caaagagtct      6000
atcctgcccc agaggaacag cgataagctg atcgccagaa agaaggactg ggaccctaag      6060
aagtacggcg gcttcgacag ccccaccgtg gcctattctg tgctggtggt ggccaaagtg      6120
```

```
gaaaagggca agtccaagaa actgaagagt gtgaaagagc tgctggggat caccatcatg    6180
gaaagaagca gcttcgagaa gaatcccatc gactttctgg aagccaaggg ctacaaagaa    6240
gtgaaaaagg acctgatcat caagctgcct aagtactccc tgttcgagct ggaaaacggc    6300
cggaagagaa tgctggcctc tgccggcgaa ctgcagaagg gaaacgaact ggccctgccc    6360
tccaaatatg tgaacttcct gtacctggcc agccactatg agaagctgaa gggctccccc    6420
gaggataatg agcagaaaca gctgtttgtg gaacagcaca gcactacct ggacgagatc     6480 atcgagcaga tcagcgagtt ctccaagaga gtgatcctgg ccgacgctaa tctggacaaa    6540
gtgctgtccg cctacaacaa gcaccggat aagcccatca gagagcaggc cgagaatatc     6600
atccacctgt ttaccctgac caatctggga gcccctgccg ccttcaagta ctttgacacc    6660
accatcgacc ggaagaggta caccagcacc aaagaggtgc tggacgccac cctgatccac    6720
cagagcatca ccggcctgta cgagacacgg atcgacctgt ctcagctggg aggcgacagc    6780
cccaagaaga agagaaaggt ggaggccagc taacatatga ttcgaatgtc tttcttgcgc    6840
tatgacactt ccagcaaaag gtagggcggg ctgcgagacg gcttcccggc gctgcatgca    6900
acaccgatga tgcttcgacc ccccgaagct ccttcggggc tgcatgggcg ctccgatgcc    6960
gctccagggc gagcgctgtt taaatagcca ggccccgat tgcaaagaca ttatagcgag      7020
ctaccaaagc catattcaaa cacctagatc actaccactt ctacacaggc cactcgagct    7080
tgtgatcgca ctccgctaag ggggcgcctc ttcctcttcg tttcagtcac aacccgcaaa    7140
catgacacaa gaatccctgt tacttctcga ccgtattgat tcggatgatt cctacgcgag    7200
cctgcggaac gaccaggaat tctgggaggt gagtcgacga gcaagcccgg cggatcaggc    7260
agcgtgcttg cagatttgac ttgcaacgcc cgcattgtgt cgacgaaggc ttttggctcc    7320
tctgtcgctg tctcaagcag catctaaccc tgcgtcgccg tttccatttg cagccgctgg    7380
cccgccgagc cctggaggag ctcgggctgc cggtgccgcc ggtgctgcgg gtgcccggcg    7440
agagcaccaa ccccgtactg gtcggcgagc ccggcccggt gatcaagctg ttcggcgagc    7500
actggtgcgg tccggagagc ctcgcgtcgg agtcggaggc gtacgcgtc ctggcggacg      7560 ccccggtgcc ggtgccccgc ctcctcggcc gcggcgagct gcggcccggc accggagcct    7620
ggccgtggcc ctacctggtg atgagccgga tgaccggcac cacctggcgg tccgcgatgg    7680
acggcacgac cgaccggaac gcgctgctcg ccctggcccg cgaactcggc cgggtgctcg    7740
gccggctgca cagggtgccg ctgaccggga acaccgtgct cacccccat tccgaggtct     7800 tccccggaact gctgcgggaa cgccgcgcgg cgaccgtcga ggaccaccgc gggtggggct    7860
acctctcgcc ccggctgctg gaccgcctgg aggactggct gccggacgtg gacacgctgc    7920
tggccggccg cgaaccccgg ttcgtccacg gcgacctgca cggaccaac atcttcgtgg      7980 acctggccgc gaccgaggtc accgggatcg tcgacttcac cgacgtctat gcgggagact    8040
cccgctacag cctggtgcaa ctgcatctca acgccttccg gggcgaccgc gagatcctgg    8100
ccgcgctgct cgacggggcg cagtggaagc ggaccgagga cttcgcccgc gaactgctcg    8160
ccttcacctt cctgcacgac ttcgaggtgt cgaggagac cccgctggat ctctccggct      8220
tcaccgatcc ggaggaactg gcgcagttcc tctggggcc gccggacacc gccccggcg      8280 cctgataagg atccggcaag actggccccg cttggcaacg caacagtgag cccctcccta    8340
gtgtgtttgg ggatgtgact atgtattcgt gtgttggcca acgggtcaac ccgaacagat    8400
tgatacccgc cttggcattt cctgtcagaa tgtaacgtca gttgatggta ct            8452
```

```
<210> SEQ ID NO 125
<211> LENGTH: 27
<212> TYPE: DNA
<213> ORGANISM: Homo sapiens

<400> SEQUENCE: 125
ccgtgccggg cggggagacc gccatgg                                       27

<210> SEQ ID NO 126
<211> LENGTH: 22
<212> TYPE: DNA
<213> ORGANISM: Homo sapiens

<400> SEQUENCE: 126
ggcccggctg tggctgagga gc                                            22

<210> SEQ ID NO 127
<211> LENGTH: 20
<212> TYPE: DNA
<213> ORGANISM: Homo sapiens

<400> SEQUENCE: 127
cggtctcccg cccggcacgg                                               20

<210> SEQ ID NO 128
<211> LENGTH: 26
<212> TYPE: DNA
<213> ORGANISM: Homo sapiens

<400> SEQUENCE: 128
gctcctcagc cacagccggg ccgggt                                        26

<210> SEQ ID NO 129
<211> LENGTH: 12
<212> TYPE: DNA
<213> ORGANISM: Homo sapiens

<400> SEQUENCE: 129
cgaccctgga aa                                                       12

<210> SEQ ID NO 130
<211> LENGTH: 14
<212> TYPE: DNA
<213> ORGANISM: Homo sapiens

<400> SEQUENCE: 130
ccccgccgcc accc                                                     14

<210> SEQ ID NO 131
<211> LENGTH: 18
<212> TYPE: DNA
<213> ORGANISM: Homo sapiens

<400> SEQUENCE: 131
tttccagggt cgccatgg                                                 18

<210> SEQ ID NO 132
<211> LENGTH: 10
<212> TYPE: DNA
<213> ORGANISM: Homo sapiens

<400> SEQUENCE: 132
ggcggcgggg                                                          10
```

<210> SEQ ID NO 133
<211> LENGTH: 20
<212> TYPE: DNA
<213> ORGANISM: Homo sapiens

<400> SEQUENCE: 133
acccttgtta gccacctccc                                                   20

<210> SEQ ID NO 134
<211> LENGTH: 20
<212> TYPE: DNA
<213> ORGANISM: Homo sapiens

<400> SEQUENCE: 134
gaacgcagtg ctcttcgaag                                                   20

<210> SEQ ID NO 135
<211> LENGTH: 20
<212> TYPE: DNA
<213> ORGANISM: Homo sapiens

<400> SEQUENCE: 135
ctcacgccct gctccgtgta                                                   20

<210> SEQ ID NO 136
<211> LENGTH: 20
<212> TYPE: DNA
<213> ORGANISM: Homo sapiens

<400> SEQUENCE: 136
ggcgacaact acttcctggt                                                   20

<210> SEQ ID NO 137
<211> LENGTH: 20
<212> TYPE: DNA
<213> ORGANISM: Homo sapiens

<400> SEQUENCE: 137
ctcacgccct gctccgtgta                                                   20

<210> SEQ ID NO 138
<211> LENGTH: 20
<212> TYPE: DNA
<213> ORGANISM: Homo sapiens

<400> SEQUENCE: 138
gggcgacaac tacttcctgg                                                   20

<210> SEQ ID NO 139
<211> LENGTH: 20
<212> TYPE: DNA
<213> ORGANISM: Homo sapiens

<400> SEQUENCE: 139
cctcttcagg gccggggtgg                                                   20

<210> SEQ ID NO 140
<211> LENGTH: 20
<212> TYPE: DNA
<213> ORGANISM: Homo sapiens

<400> SEQUENCE: 140
gaggacccag gtggaactgc                                                  20

<210> SEQ ID NO 141
<211> LENGTH: 20
<212> TYPE: DNA
<213> ORGANISM: Homo sapiens

<400> SEQUENCE: 141
tcagctccag gcggtcctgg                                                  20

<210> SEQ ID NO 142
<211> LENGTH: 20
<212> TYPE: DNA
<213> ORGANISM: Homo sapiens

<400> SEQUENCE: 142
agcagcagca gcagtggcag                                                  20

<210> SEQ ID NO 143
<211> LENGTH: 20
<212> TYPE: DNA
<213> ORGANISM: Homo sapiens

<400> SEQUENCE: 143
tgggcaccgt cagctccagg                                                  20

<210> SEQ ID NO 144
<211> LENGTH: 20
<212> TYPE: DNA
<213> ORGANISM: Homo sapiens

<400> SEQUENCE: 144
cagcagtggc agcggccacc                                                  20

<210> SEQ ID NO 145
<211> LENGTH: 20
<212> TYPE: DNA
<213> ORGANISM: Homo sapiens

<400> SEQUENCE: 145
acctctcccc tggccctcat                                                  20

<210> SEQ ID NO 146
<211> LENGTH: 20
<212> TYPE: DNA
<213> ORGANISM: Homo sapiens

<400> SEQUENCE: 146
ccaggaccgc ctggagctga                                                  20

<210> SEQ ID NO 147
<211> LENGTH: 20
<212> TYPE: DNA
<213> ORGANISM: Homo sapiens

<400> SEQUENCE: 147
ccgtcagctc caggcggtcc                                                  20

<210> SEQ ID NO 148
<211> LENGTH: 20
<212> TYPE: DNA
<213> ORGANISM: Homo sapiens

<400> SEQUENCE: 148

```
agcagcagca gcagtggcag                                                   20

<210> SEQ ID NO 149
<211> LENGTH: 20
<212> TYPE: DNA
<213> ORGANISM: Homo sapiens

<400> SEQUENCE: 149
atgtgccaag caaagcctca                                                   20

<210> SEQ ID NO 150
<211> LENGTH: 20
<212> TYPE: DNA
<213> ORGANISM: Homo sapiens

<400> SEQUENCE: 150
ttcggtcatg cccgtggatg                                                   20

<210> SEQ ID NO 151
<211> LENGTH: 20
<212> TYPE: DNA
<213> ORGANISM: Homo sapiens

<400> SEQUENCE: 151
gtcgttgaaa ttcatcgtac                                                   20

<210> SEQ ID NO 152
<211> LENGTH: 20
<212> TYPE: DNA
<213> ORGANISM: Homo sapiens

<400> SEQUENCE: 152
accacctgtg aagagtttcc                                                   20

<210> SEQ ID NO 153
<211> LENGTH: 20
<212> TYPE: DNA
<213> ORGANISM: Homo sapiens

<400> SEQUENCE: 153
cgtcgttgaa attcatcgta                                                   20

<210> SEQ ID NO 154
<211> LENGTH: 20
<212> TYPE: DNA
<213> ORGANISM: Homo sapiens

<400> SEQUENCE: 154
accacctgtg aagagtttcc                                                   20

<210> SEQ ID NO 155
<211> LENGTH: 20
<212> TYPE: DNA
<213> ORGANISM: Mus musculus

<400> SEQUENCE: 155
gaacgcagtg cttttcgagg                                                   20

<210> SEQ ID NO 156
<211> LENGTH: 20
<212> TYPE: DNA
<213> ORGANISM: Mus musculus
```

```
<400> SEQUENCE: 156 accccttgttg gccacctccc                                              20

<210> SEQ ID NO 157
<211> LENGTH: 20
<212> TYPE: DNA
<213> ORGANISM: Mus musculus

<400> SEQUENCE: 157
ggtgacaact actatctggt                                               20

<210> SEQ ID NO 158
<211> LENGTH: 20
<212> TYPE: DNA
<213> ORGANISM: Mus musculus

<400> SEQUENCE: 158
ctcacaccct gctccgtgta                                               20

<210> SEQ ID NO 159
<211> LENGTH: 20
<212> TYPE: DNA
<213> ORGANISM: Mus musculus

<400> SEQUENCE: 159
gggtgacaac tactatctgg                                               20

<210> SEQ ID NO 160
<211> LENGTH: 20
<212> TYPE: DNA
<213> ORGANISM: Mus musculus

<400> SEQUENCE: 160
ctcacaccct gctccgtgta                                               20

<210> SEQ ID NO 161
<211> LENGTH: 20
<212> TYPE: DNA
<213> ORGANISM: Mus musculus

<400> SEQUENCE: 161
cgagaacgca gtgcttttcg                                               20

<210> SEQ ID NO 162
<211> LENGTH: 20
<212> TYPE: DNA
<213> ORGANISM: Mus musculus

<400> SEQUENCE: 162 accccttgttg gccacctccc                                              20

<210> SEQ ID NO 163
<211> LENGTH: 20
<212> TYPE: DNA
<213> ORGANISM: Mus musculus

<400> SEQUENCE: 163
atgagccaag caaatcctca                                               20

<210> SEQ ID NO 164
<211> LENGTH: 20
<212> TYPE: DNA
<213> ORGANISM: Mus musculus
```

-continued

<400> SEQUENCE: 164
ttccgtcatg cccgtggaca								20

<210> SEQ ID NO 165
<211> LENGTH: 20
<212> TYPE: DNA
<213> ORGANISM: Mus musculus

<400> SEQUENCE: 165
cttcgttgaa aaccattgta								20

<210> SEQ ID NO 166
<211> LENGTH: 20
<212> TYPE: DNA
<213> ORGANISM: Mus musculus

<400> SEQUENCE: 166
ccacctctga agagtttcct								20

<210> SEQ ID NO 167
<211> LENGTH: 20
<212> TYPE: DNA
<213> ORGANISM: Mus musculus

<400> SEQUENCE: 167
cttcgttgaa aaccattgta								20

<210> SEQ ID NO 168
<211> LENGTH: 20
<212> TYPE: DNA
<213> ORGANISM: Mus musculus

<400> SEQUENCE: 168
accacctctg aagagtttcc								20

<210> SEQ ID NO 169
<211> LENGTH: 20
<212> TYPE: DNA
<213> ORGANISM: Mus musculus

<400> SEQUENCE: 169
cttccactca ctctgcgatt								20

<210> SEQ ID NO 170
<211> LENGTH: 20
<212> TYPE: DNA
<213> ORGANISM: Mus musculus

<400> SEQUENCE: 170
accatgtctc agtgtcaagc								20

<210> SEQ ID NO 171
<211> LENGTH: 20
<212> TYPE: DNA
<213> ORGANISM: Mus musculus

<400> SEQUENCE: 171
ggcggcaaca gcggcaacag								20

<210> SEQ ID NO 172
<211> LENGTH: 20
<212> TYPE: DNA

-continued

```
<213> ORGANISM: Mus musculus

<400> SEQUENCE: 172
actgctctgc gtggctgcgg                                              20

<210> SEQ ID NO 173
<211> LENGTH: 20
<212> TYPE: DNA
<213> ORGANISM: Mus musculus

<400> SEQUENCE: 173
ccgcagccac gcagagcagt                                              20

<210> SEQ ID NO 174
<211> LENGTH: 20
<212> TYPE: DNA
<213> ORGANISM: Mus musculus

<400> SEQUENCE: 174
gcacctctcc tcgcccgat                                               20

<210> SEQ ID NO 175
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
gagggcctat ttcccatgat tcc                                          23

<210> SEQ ID NO 176
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (84)..(102)
<223> OTHER INFORMATION: a, c, t, g, unknown or other

<400> SEQUENCE: 176
aaaaaaagca ccgactcggt gccactttt caagttgata acggactagc cttatttaa    60 cttgctattt ctagctctaa aacnnnnnnn nnnnnnnnnn nnccggtgtt tcgtcctttc  120
cacaag                                                            126

<210> SEQ ID NO 177
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (6)..(24)
<223> OTHER INFORMATION: a, c, t, g, unknown or other

<400> SEQUENCE: 177
caccgnnnnn nnnnnnnnnn nnnn                                         24
```

```
<210> SEQ ID NO 178
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (5)..(23)
<223> OTHER INFORMATION: a, c, t, g, unknown or other

<400> SEQUENCE: 178
aaacnnnnnn nnnnnnnnnn nnnc                                        24

<210> SEQ ID NO 179
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
aaaaaaagca ccgactcggt gccactttt caagttgata acggactagc cttattttaa    60
cttgctattt ctagctctaa aaccctagt cattggaggt gaccggtgtt tcgtcctttc   120
cacaag                                                             126

<210> SEQ ID NO 180
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180
caccgtcacc tccaatgact aggg                                         24

<210> SEQ ID NO 181
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181
aaacccctag tcattggagg tgac                                         24

<210> SEQ ID NO 182
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
cagaagaaga agggctccca tcacatcaac cggtggcgca ttgccacgaa gcaggccaat    60
```

```
ggggaggaca tcgatgtcac ctccaatgac aagcttgcta gcggtgggca accacaaacc      120
cacgagggca gagtgctgct tgctgctggc caggccctg cgtgggccca agctggactc       180
tggccactcc ct                                                           192
```

<210> SEQ ID NO 183
<211> LENGTH: 192
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183

```
agggagtggc cagagtccag cttgggccca cgcaggggcc tggccagcag caagcagcac       60
tctgccctcg tgggtttgtg gttgcccacc gctagcaagc ttgtcattgg aggtgacatc      120
gatgtcctcc ccattggcct gcttcgtggc aatgcgccac cggttgatgt gatgggagcc      180
cttcttcttc tg                                                           192
```

<210> SEQ ID NO 184
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184

```
ccatcccctt ctgtgaatgt                                                   20
```

<210> SEQ ID NO 185
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185

```
ggagattgga gacacggaga                                                   20
```

<210> SEQ ID NO 186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186

```
ggctccctgg gttcaaagta                                                   20
```

<210> SEQ ID NO 187
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187 agagggggtct ggatgtcgta a                                              21

<210> SEQ ID NO 188
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 188
cgccagggtt ttcccagtca cgac                                            24

<210> SEQ ID NO 189
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
gagggtctcg tccttgcggc cgcgctagcg agggcctatt tcccatgatt c               51

<210> SEQ ID NO 190
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (95)..(114)
<223> OTHER INFORMATION: a, c, t, g, unknown or other

<400> SEQUENCE: 190
ctcggtctcg gtaaaaaagc accgactcgg tgccactttt tcaagttgat aacggactag      60
ccttatttta acttgctatt tctagctcta aaacnnnnnn nnnnnnnnnn nnnnggtgtt    120
tcgtcctttc cac                                                       133

<210> SEQ ID NO 191
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 191
gagggtctct ttaccggtga gggcctattt cccatgattc                            41

<210> SEQ ID NO 192
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (95)..(114)

<223> OTHER INFORMATION: a, c, t, g, unknown or other

<400> SEQUENCE: 192
ctcggtctcc tcaaaaaagc accgactcgg tgccactttt tcaagttgat aacggactag    60
ccttatttta acttgctatt tctagctcta aaacnnnnnn nnnnnnnnnn nnnnggtgtt   120
tcgtcctttc cac    133

<210> SEQ ID NO 193
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 193
gagggtctct ttgagctcga gggcctattt cccatgattc    40

<210> SEQ ID NO 194
<211> LENGTH: 133
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (96)..(115)
<223> OTHER INFORMATION: a, c, t, g, unknown or other

<400> SEQUENCE: 194
ctcggtctcg cgtaaaaaag caccgactcg gtgccacttt ttcaagttga taacggacta    60
gccttatttt aacttgctat ttctagctct aaaacnnnnn nnnnnnnnnn nnnnnggtgt   120
ttcgtccttt cca    133

<210> SEQ ID NO 195
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 195
gagggtctct tacgcgtgtg tctagac    27

<210> SEQ ID NO 196
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 196
ctcggtctca aggacaggga agggagcagt ggttcacgcc tgtaatccca gcaatttggg    60
aggccaaggt gggtagatca cctgagatta ggagttgc    98

<210> SEQ ID NO 197
<211> LENGTH: 30

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 197
cctgtccttg cggccgcgct agcgagggcc                                              30

<210> SEQ ID NO 198
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198
cacgcggccg caaggacagg gaagggagca g                                            31

<210> SEQ ID NO 199
<211> LENGTH: 327
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 199
```

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

| | | | | | | | | | | | | | | |
|---|---|---|---|---|---|---|---|---|---|---|---|---|---|---|
|Val|Thr|Ala|Ala|Gly|Ile|Thr|Leu|Gly|Met|Asp|Glu|Leu|Tyr|Lys|Ser|
|225| | | | |230| | | | |235| | | | |240|

Gly Leu Arg Ser Arg Glu Glu Glu Glu Thr Asp Ser Arg Met Pro
             245                 250                 255

His Leu Asp Ser Pro Gly Ser Ser Gln Pro Arg Arg Ser Phe Leu Ser
             260                 265                 270

Arg Val Ile Arg Ala Ala Leu Pro Leu Gln Leu Leu Leu Leu Leu
             275                 280                 285

Leu Leu Leu Ala Cys Leu Leu Pro Ala Ser Glu Asp Asp Tyr Ser Cys
             290                 295                 300

Thr Gln Ala Asn Asn Phe Ala Arg Ser Phe Tyr Pro Met Leu Arg Tyr
305                 310                 315                 320

Thr Asn Gly Pro Pro Pro Thr
             325

<210> SEQ ID NO 200
<211> LENGTH: 3243
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200

```
accggtgcca ccatgtaccc atacgatgtt ccagattacg cttcgccgaa gaaaaagcgc    60
aaggtcgaag cgtccatgaa aaggaactac attctggggc tggacatcgg gattacaagc   120
gtggggtatg ggattattga ctatgaaaca agggacgtga tcgacgcagg cgtcagactg   180
ttcaaggagg ccaacgtgga aaacaatgag ggacggagaa gcaagagggg agccaggcgc   240
ctgaaacgac ggagaaggca cagaatccag agggtgaaga aactgctgtt cgattacaac   300
ctgctgaccg accattctga gctgagtgga attaatcctt atgaagccag ggtgaaaggc   360
ctgagtcaga agctgtcaga ggaagagttt tccgcagctc tgctgcacct ggctaagcgc   420
cgaggagtgc ataacgtcaa tgaggtggaa gaggacaccg caacgagct gtctacaaag   480 gaacagatct cacgcaatag caaagctctg gaagagaagt atgtcgcaga gctgcagctg   540
gaacggctga gaaagatgg cgaggtgaga gggtcaatta ataggttcaa gacaagcgac   600
tacgtcaaag aagccaagca gctgctgaaa gtgcagaagg cttaccacca gctggatcag   660
agcttcatcg atacttatat cgacctgctg gagactcgga gaacctacta tgagggacca   720
ggagaaggga gcccccttcg gatggaaaga tcaaggaat ggtacgagat gctgatggga   780
cattgcacct attttccaga gagctgaga agcgtcaagt acgcttataa cgcagatctg   840
tacaacgccc tgaatgacct gaacaacctg gtcatcacca gggatgaaaa cgagaaactg   900
gaatactatg agaagttcca gatcatcgaa aacgtgttta gcagaagaa aaagcctaca   960 ctgaaacaga ttgctaagga tcctggtc aacgaagagg acatcaaggg ctaccgggtg  1020
acaagcactg gaaaaccaga gttcaccaat ctgaaagtgt atcacgatat taggacatc  1080 acagcacgga agaaatcat tgagaacgcc gaactgctgg atcagattgc taagatcctg  1140
actatctacc agagctccga ggacatccag gaagagctga ctaacctgaa cagcgagctg  1200
acccaggaag agatcgaaca gattagtaat ctgaagggt acaccggaac acacaacctg  1260
tccctgaaag ctatcaatct gattctggat gagctgtggc atacaaacga caatcagatt  1320
gcaatcttta ccggctgaa gctggtccca aaaaaggtgg acctgagtca gcagaaagag  1380
```

```
atcccaacca cactggtgga cgatttcatt ctgtcacccg tggtcaagcg gagcttcatc    1440
cagagcatca aagtgatcaa cgccatcatc aagaagtacg gcctgcccaa tgatatcatt    1500
atcgagctgg ctagggagaa gaacagcaag gacgcacaga agatgatcaa tgagatgcag    1560
aaacgaaacc ggcagaccaa tgaacgcatt gaagagatta tccgaactac cgggaaagag    1620
aacgcaaagt acctgattga aaaaatcaag ctgcacgata tgcaggaggg aaagtgtctg    1680
tattctctgg aggccatccc cctggaggac ctgctgaaca atccattcaa ctacgaggtc    1740
gatcatatta tccccagaag cgtgtccttc gacaattcct ttaacaacaa ggtgctggtc    1800
aagcaggaag agaactctaa aaagggcaat aggactcctt tccagtacct gtctagttca    1860
gattccaaga tctcttacga aacctttaaa aagcacattc tgaatctggc caaggaaag    1920
ggccgcatca gcaagaccaa aaaggagtac ctgctggaag agcgggacat caacagattc    1980
tccgtccaga aggattttat taaccggaat ctggtggaca caagatacgc tactcgcggc    2040
ctgatgaatc tgctgcgatc ctatttccgg gtgaacaatc tggatgtgaa agtcaagtcc    2100
atcaacggcg ggttcacatc tttctgagg cgcaaatgga agtttaaaaa ggagcgcaac    2160
aaagggtaca agcaccatgc cgaagatgct ctgattatcg caaatgccga cttcatcttt    2220
aaggagtgga aaaagctgga caaagccaag aaagtgatgg agaaccagat gttcgaagag    2280
aagcaggccg aatctatgcc cgaaatcgag acagaacagg agtacaagga gattttcatc    2340
actcctcacc agatcaagca tatcaaggat ttcaaggact acaagtactc tcaccgggtg    2400
gataaaaagc ccaacagaga gctgatcaat gacacccctgt atagtacaag aaaagacgat    2460
aaggggaata ccctgattgt gaacaatctg aacggactgt acgacaaaga taatgacaag    2520
ctgaaaaagc tgatcaacaa aagtcccgag aagctgctga tgtaccacca tgatcctcag    2580
acatatcaga aactgaagct gattatggag cagtacggcg acgagaagaa cccactgtat    2640
aagtactatg aagagactgg gaactacctg accaagtata gcaaaaagga taatggcccc    2700
gtgatcaaga gatcaagta ctatgggaac aagctgaatg cccatctgga catcacagac    2760
gattacccta cagtcgcaa caaggtggtc aagctgtcac tgaagccata cagattcgat    2820
gtctatctgg acaacggcgt gtataaattt gtgactgtca agaatctgga tgtcatcaaa    2880
aaggagaact actatgaagt gaatagcaag tgctacgaag aggctaaaaa gctgaaaaag    2940
attagcaacc aggcagagtt catcgcctcc ttttacaaca acgacctgat taagatcaat    3000
ggcgaactgt atagggtcat cggggtgaac aatgatctgc tgaaccgcat tgaagtgaat    3060
atgattgaca tcacttaccg agagtatctg gaaaacatga atgataagcg ccccccctcga    3120
attatcaaaa caattgcctc taagactcag agtatcaaaa agtactcaac cgacattctg    3180
ggaaacctgt atgaggtgaa gagcaaaaag caccctcaga ttatcaaaaa gggctaagaa    3240
ttc                                                                 3243
```

<210> SEQ ID NO 201
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 201

```
ccaggcttgg                                                            10
```

```
<210> SEQ ID NO 202
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
tgcgccaccg gttgatgtga tgg                                               23

<210> SEQ ID NO 203
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
actctgccct cgtgggtttg tgg                                               23

<210> SEQ ID NO 204
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
caaacggcag aagctggagg agg                                               23

<210> SEQ ID NO 205
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
aggccccagt ggctgctctg ggg                                               23

<210> SEQ ID NO 206
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
tgaaggtgtg gttccagaac cgg                                               23

<210> SEQ ID NO 207
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 207
gccgtttgta ctttgtcctc cgg                                           23

<210> SEQ ID NO 208
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
tcacctgggc cagggaggga ggg                                           23

<210> SEQ ID NO 209
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ggggcacaga tgagaaactc agg                                           23

<210> SEQ ID NO 210
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
tcacctgggc cagggaggga ggg                                           23

<210> SEQ ID NO 211
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
ggggcacaca tgagaaactc agg                                           23

<210> SEQ ID NO 212
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
atctggtcag aatatgataa agg                                           23

<210> SEQ ID NO 213
<211> LENGTH: 23
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 213
gtcactgtac tgatgtgaat tgg                                             23

<210> SEQ ID NO 214
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
catctgaagg ccagcagcat tgg                                             23

<210> SEQ ID NO 215
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
tgataaggca gaaacctgtt tgg                                             23

<210> SEQ ID NO 216
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
gaagataagt gaggtttaaa agg                                             23

<210> SEQ ID NO 217
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
gtatcatttg acatatctaa tgg                                             23

<210> SEQ ID NO 218
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
cagcatggaa tgaaaatgac cgg                                             23
```

```
<210> SEQ ID NO 219
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gcagcatgga atgaaaatga cgg                                            23

<210> SEQ ID NO 220
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
gtgcaagccg aacagatgaa agg                                            23

<210> SEQ ID NO 221
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ggagtatcag aaatgactat tgg                                            23

<210> SEQ ID NO 222
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
ggtcactgta ctgatgtgaa tgg                                            23

<210> SEQ ID NO 223
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
tcactgtact gatgtgaatg ggg                                            23

<210> SEQ ID NO 224
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 224
gttccttaaa taagaactttt agg                                          23

<210> SEQ ID NO 225
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
tcctacaaga agataagtga agg                                           23

<210> SEQ ID NO 226
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
tatcatttga catatctaat tgg                                           23

<210> SEQ ID NO 227
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
aactttctca actacaaaca agg                                           23

<210> SEQ ID NO 228
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
ccaacaccaa ccagaacttg ggg                                           23

<210> SEQ ID NO 229
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
acagcaatgc caatgctggg ggg                                           23

<210> SEQ ID NO 230
<211> LENGTH: 23
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
gtggaaatca tctttctcgt tgg                                              23

<210> SEQ ID NO 231
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
tctgctgcct gacacggcca agg                                              23

<210> SEQ ID NO 232
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
cgagctctgc tgcctgacac cgg                                              23

<210> SEQ ID NO 233
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
tccttgatgg ccacctcgtc cgg                                              23

<210> SEQ ID NO 234
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
atgacagcaa tgccaatgct tgg                                              23

<210> SEQ ID NO 235
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
agcaatgcca atgctggggg ggg                                              23
```

<210> SEQ ID NO 236
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 236
gccaacacca accagaactt tgg                                          23

<210> SEQ ID NO 237
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 237
ggagaacagc actccgctct tgg                                          23

<210> SEQ ID NO 238
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 238
tgacagcaat gccaatgctg ggg                                          23

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
ccggccaaga ccttgaagcc agg                                          23

<210> SEQ ID NO 240
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
tattacagaa tgagagactg tgg                                          23

<210> SEQ ID NO 241
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 241
aaaagaccta aacaaaagaa tgg          23

<210> SEQ ID NO 242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
tcagagcttc ctgacaccca tgg          23

<210> SEQ ID NO 243
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
gagaacagca ctccgctctg ggg          23

<210> SEQ ID NO 244
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
ctgcctgaca cggccaggac cgg          23

<210> SEQ ID NO 245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gagtccgagc agaagaagaa ggg          23

<210> SEQ ID NO 246
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
cacgaagcag gccaatgggg agg          23

<210> SEQ ID NO 247
<211> LENGTH: 23

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
ggagcccttc ttcttctgct cgg                                          23

<210> SEQ ID NO 248
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ggcagagtgc tgcttgctgc tgg                                          23

<210> SEQ ID NO 249
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
ttgccacgaa gcaggccaat ggg                                          23

<210> SEQ ID NO 250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
aggtgtggtt ccagaaccgg agg                                          23

<210> SEQ ID NO 251
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
cggcagaagc tggaggagga agg                                          23

<210> SEQ ID NO 252
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
```
agggctccca tcacatcaac cgg                                            23

<210> SEQ ID NO 253
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
tgagtccgag cagaagaaga agg                                            23

<210> SEQ ID NO 254
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
tcacctccaa tgactagggt ggg                                            23

<210> SEQ ID NO 255
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
aacctcactt atcttcttgt agg                                            23

<210> SEQ ID NO 256
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
ctcacttatc ttcttgtagg agg                                            23

<210> SEQ ID NO 257
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
ccatgctgct ggccttcaga tgg                                            23

<210> SEQ ID NO 258
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 258
gccaaacata agtgaccaac agg                                               23

<210> SEQ ID NO 259
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
tgtcaaatga tacaaacatt agg                                               23

<210> SEQ ID NO 260
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
gctgctggcc ttcagatggc tgg                                               23

<210> SEQ ID NO 261
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
tcagcaacct ctaactaacc agg                                               23

<210> SEQ ID NO 262
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
tcattttcat tccatgctgc tgg                                               23

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
catgcaaacc ttcatctgtt cgg                                               23

<210> SEQ ID NO 264
```

```
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
ctggtagatg gagttgggtt tgg                                          23

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
agtgctgttc tcccaagttc tgg                                          23

<210> SEQ ID NO 266
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
ggcattgctg tcatcctcgt ggg                                          23

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
tcccaagttc tggttggtgt tgg                                          23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
ttggccgtcc tggccgtgtc agg                                          23

<210> SEQ ID NO 269
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
```
ttccgacgag gtggccatca agg    23

<210> SEQ ID NO 270
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
tggcattgct gtcatcctcg tgg    23

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
cctcgtgggc acttccgacg agg    23

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
ctggttgtag gatttgagtt agg    23

<210> SEQ ID NO 273
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
ttatttctga agaatattaa agg    23

<210> SEQ ID NO 274
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
tgtgtgagga taaaagagtt ggg    23

<210> SEQ ID NO 275
<211> LENGTH: 23
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 275
aatacctagt tacaggcatt tgg                                              23

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
cagaagagcc cccccagcat tgg                                              23

<210> SEQ ID NO 277
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
cgtgggcact tccgacgagg tgg                                              23

<210> SEQ ID NO 278
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
tgatttccac catctctccg tgg                                              23

<210> SEQ ID NO 279
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
tgaccggaag atccaggggg tgg                                              23

<210> SEQ ID NO 280
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
ggaagggcct gagtccgagc agaagaagag gg                                    32
```

```
<210> SEQ ID NO 281
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
ggcctccaag gagtccgagc agaagaagaa ggg                                   33

<210> SEQ ID NO 282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
gacatcgatg tcctccccat tgg                                              23

<210> SEQ ID NO 283
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
gtcacctcca atgactaggg tgg                                              23

<210> SEQ ID NO 284
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
gggcaaccac aaacccacga ggg                                              23

<210> SEQ ID NO 285
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
caagcagcac tctgccctcg tgg                                              23

<210> SEQ ID NO 286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 286
ttcttcttct gctcggactc agg                                              23

<210> SEQ ID NO 287
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
ctccccattg gcctgcttcg agg                                              23

<210> SEQ ID NO 288
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
gaacttacct ggttagttag agg                                              23

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
ggtgatgatg ctctttgggt cgg                                              23

<210> SEQ ID NO 290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
tctgtgatct catgtctgac cgg                                              23

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
cagcaatgcc aatgctgggg ggg                                              23

<210> SEQ ID NO 292
<211> LENGTH: 23
<212> TYPE: DNA
<213> ORGANISM: Artificial Sequence
```

<220> FEATURE:
<221> NAME/KEY: source
<223> OTHER INFORMATION: /note="Description of Artificial Sequence:
      Synthetic oligonucleotide"

<400> SEQUENCE: 292
tttctcgtgg gcatccttga tgg                                              23

<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
ggagaacagc actccgctct ggg                                              23

<210> SEQ ID NO 294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
ctggttggtg ttggccgtcc tgg                                              23

<210> SEQ ID NO 295
<211> LENGTH: 81
<212> TYPE: DNA
<213> ORGANISM: Homo sapiens

<400> SEQUENCE: 295
gttttagagc tagaaatagc aagttaaaat aaggctagtc cgttatcaac ttgaaaaagt      60
ggcaccgagt cggtgctttt t                                                81

<210> SEQ ID NO 296
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
gttttagcgc tagaaatagc gttaaaataa ggctagtccg ttatcaactt gaaaaagtgg      60
caccgagtcg gtgcttttt                                                   79

<210> SEQ ID NO 297
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
gccggcgcgc tagaaatagc gtgccggtaa ggctagtccg ttatcaactt gaaaaagtgg      60

```
caccgagtcg gtgctttt                                                    79
```

<210> SEQ ID NO 298
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298

```
gccggcgcga aagtgccggt aaggctagtc cgttatcaac ttgaaaaagt ggcaccgagt    60
cggtgctttt t                                                          71
```

<210> SEQ ID NO 299
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299

```
gccggcgagc tagaaatagc aagtgccggt aaggctagtc cgttatcaac ttgaaaaagt    60
ggcaccgagt cggtgctttt t                                               81
```

<210> SEQ ID NO 300
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300

```
gccccagagc tagaaatagc aagttggggt aaggctagtc cgttatcaac ttgaaaaagt    60
ggcaccgagt cggtgctttt                                                 80
```

<210> SEQ ID NO 301
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (21)..(24)
<223> OTHER INFORMATION: a, c, t, g, unknown or other

<400> SEQUENCE: 301

```
gttttagagc tagaaatagc nnnntaaaat aaggctagtc cgttatcaac ttgaaaaagt    60
ggcaccgagt cggtgctttt t                                               81
```

<210> SEQ ID NO 302
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
gttttagagc tagaaatagc aagttaaaat aaggctagta cttgaaaaag tggcaccgag    60
tcggtgcttt tt    72

<210> SEQ ID NO 303
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
gttttagagc tagaaatagc aagttaaaat acttgaaaaa gtggcaccga gtcggtgctt    60
ttt    63

<210> SEQ ID NO 304
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
gttttagagc tagaaatagc aagttaaaat agatcgtata catcattaac ttgaaaaagt    60
ggcaccgagt cggtgctttt t    81

<210> SEQ ID NO 305
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (31)..(48)
<223> OTHER INFORMATION: a, c, t, g, unknown or other

<400> SEQUENCE: 305
gttttagagc tagaaatagc aagttaaaat nnnnnnnnnn nnnnnnnnac ttgaaaaagt    60
ggcaccgagt cggtgctttt t    81

<210> SEQ ID NO 306
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
gttttagagc tagaaatagc aagttaaaat aaggctagtc cgttatcacg ccgaaaggcg    60
ggcaccgagt cggtgctttt t    81

<210> SEQ ID NO 307
<211> LENGTH: 85
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
gttttagagc tagaaatagc aagttaaaat aaggctagtc cgttatcaac ttgagaaatc    60
aagtggcacc gagtcggtgc ttttt                                          85

<210> SEQ ID NO 308
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
gttttagagc tagaaatagc aagttaaaat aaggctagtc cgttatcaac ttgaaaaagt    60
ggccccgcgg cggggctttt                                                80

<210> SEQ ID NO 309
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
gttttagagc tagaaatagc aagttaaaat aaggctagtc cgttatcaac ttgaaaaagt    60
ggcaccgaaa gtttcggtgc tttt                                           84

<210> SEQ ID NO 310
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
gttttagagc tagaaatagc aagttaaaat aaggctagtc cgttatcacg ccgaaaggcg    60
ggcaccgagt cggtgccttt tt                                             82

<210> SEQ ID NO 311
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
gttttagagc tagaaatagc aagttaaaat aaggctagtc cgttatcacc ttgggccgaa    60
aggcccaagg ggcgccgagt cggcgccttt tt                                  92

<210> SEQ ID NO 312
<211> LENGTH: 82

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
gttttagagc cggaaacggc aagttaaaat aaggctagtc cgttatcacg ccgaaaggcg      60
ggcaccgagt cggtgccttt tt                                               82

<210> SEQ ID NO 313
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
gccccagcgc tagaaatagc aagttggggt aaggctagtc cgttatcacg ccgaaaggcg      60
ggcaccgagt cggtgctttt t                                                81

<210> SEQ ID NO 314
<211> LENGTH: 81
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
gcttcagcgc tagaaatagc aagttgaagt aaggctagtc cgttatcacg ccgaaaggcg      60
ggcaccgagt cggtgctttt t                                                81

<210> SEQ ID NO 315
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
gttttagatg caattatgca aagttaaaat aaggctagtc cgttatcaac ttataccaat      60
aagtcatcgt cgagaagctc gacgatgttt tt                                    92

<210> SEQ ID NO 316
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
gttttagaac tcattagagt aagttaaaat aaggctagtc cgttatcaac atgcaccagc      60
atgttcagga ttcaaagtga atcctgattt tt                                    92

<210> SEQ ID NO 317
```

```
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
gccccagatg caattatgca aagttggggt aaggcaagtc cgttatcaac cgaccacggt     60
cacgtcgaag cgacgtgttt tt                                              82

<210> SEQ ID NO 318
<211> LENGTH: 82
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
gcttcagatg caattatgca aagttgaagt aaggcaagtc cgttatcacc tgaccacagg     60
gtgtcgtaag acgacacttt tt                                              82

<210> SEQ ID NO 319
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
gccccagacc attggaagtt ggggtaaggc aagtccgtta tcaaccgacc acggtcacgt     60
cgaagcgacg tgttttt                                                    77

<210> SEQ ID NO 320
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
gcttcagagg attccaagtt gaagtaaggc aagtccgtta tcacctgacc acagggtgtc     60
gtaagacgac acttttt                                                    77

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 321
ccatcccctt ctgtgaatgt                                                 20

<210> SEQ ID NO 322
<211> LENGTH: 20
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 322
ggagattgga gacacggaga                                            20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 323
ggagctggtc tgttggagaa                                            20

<210> SEQ ID NO 324
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 324
tcccaatcca taatcccacg tt                                         22

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 325
caggagggcc aggagatttg                                            20

<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 326
tgaaatcgag gatctgggcg                                            20

<210> SEQ ID NO 327
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 327
```

```
ggaggacaaa gtacaaacgg c                                              21

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 328
atcgatgtcc tccccattgg                                                20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 329
ccatcccctt ctgtgaatgt                                                20

<210> SEQ ID NO 330
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 330
ggagattgga gacacggaga                                                20

<210> SEQ ID NO 331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 331
tgggagagag accccttctt                                                20

<210> SEQ ID NO 332
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 332
tcctgctctc acttagactt tctc                                           24

<210> SEQ ID NO 333
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 333
gacattcctc ctgagggaaa a                                              21

<210> SEQ ID NO 334
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 334
gataaaatgt attccttctc accattc                                        27

<210> SEQ ID NO 335
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 335
ccagactcag taaagcctgg a                                              21

<210> SEQ ID NO 336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 336
tggccccagt ctctcttcta                                                20

<210> SEQ ID NO 337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 337
cacggccttt gcaaatagag                                                20

<210> SEQ ID NO 338
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 338
catgacttgg cctttgtagg a                                              21

<210> SEQ ID NO 339
```

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 339
tggggttaca gaaagaatag gg                                              22

<210> SEQ ID NO 340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 340
ttctgagggc tgctacctgt                                                 20

<210> SEQ ID NO 341
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 341
gttttagagc tatgctgttt tgaatggtcc caaaacggaa gggcctgagt ccgagcagaa     60
gaagaagttt tagagctatg ctgttttgaa tggtcccaaa ac                       102

<210> SEQ ID NO 342
<211> LENGTH: 100
<212> TYPE: DNA
<213> ORGANISM: Homo sapiens

<400> SEQUENCE: 342
cggaggacaa agtacaaacg gcagaagctg gaggaggaag ggcctgagtc cgagcagaag     60
aagaagggct cccatcacat caaccggtgg cgcattgcca                          100

<210> SEQ ID NO 343
<211> LENGTH: 50
<212> TYPE: DNA
<213> ORGANISM: Homo sapiens

<400> SEQUENCE: 343
agctggagga ggaagggcct gagtccgagc agaagaagaa gggctcccac                50

<210> SEQ ID NO 344
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
gaguccgagc agaagaagaa guuuuagagc                                      30

-continued

```
<210> SEQ ID NO 345
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
agctggagga ggaagggcct gagtccgagc agaagagaag ggctcccat          49

<210> SEQ ID NO 346
<211> LENGTH: 53
<212> TYPE: DNA
<213> ORGANISM: Homo sapiens

<400> SEQUENCE: 346
ctggaggagg aagggcctga gtccgagcag aagaagaagg ctcccatca cat      53

<210> SEQ ID NO 347
<211> LENGTH: 52
<212> TYPE: DNA
<213> ORGANISM: Homo sapiens

<400> SEQUENCE: 347
ctggaggagg aagggcctga gtccgagcag aagagaaggg ctcccatcac at       52

<210> SEQ ID NO 348
<211> LENGTH: 54
<212> TYPE: DNA
<213> ORGANISM: Homo sapiens

<400> SEQUENCE: 348
ctggaggagg aagggcctga gtccgagcag aagaaagaag gctcccatc acat      54

<210> SEQ ID NO 349
<211> LENGTH: 50
<212> TYPE: DNA
<213> ORGANISM: Homo sapiens

<400> SEQUENCE: 349
ctggaggagg aagggcctga gtccgagcag aagaagggct cccatcacat          50

<210> SEQ ID NO 350
<211> LENGTH: 47
<212> TYPE: DNA
<213> ORGANISM: Homo sapiens

<400> SEQUENCE: 350
ctggaggagg aagggcctga gcccgagcag aagggctccc atcacat             47

<210> SEQ ID NO 351
<211> LENGTH: 4104
<212> TYPE: DNA
<213> ORGANISM: Homo sapiens
<220> FEATURE:
<221> NAME/KEY: CDS
<222> LOCATION: (1)..(4104)

<400> SEQUENCE: 351 atg gac aag aag tac agc atc ggc ctg gac atc ggc acc aac tct gtg     48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc     96
```

```
                Gly Trp Ala Val Ile Thr Asp Glu Tyr Lys Val Pro Ser Lys Lys Phe
                             20                  25                  30 aag gtg ctg ggc aac acc gac cgg cac agc atc aag aag aac ctg atc              144
Lys Val Leu Gly Asn Thr Asp Arg His Ser Ile Lys Lys Asn Leu Ile
             35                  40                  45 gga gcc ctg ctg ttc gac agc ggc gaa aca gcc gag gcc acc cgg ctg              192
Gly Ala Leu Leu Phe Asp Ser Gly Glu Thr Ala Glu Ala Thr Arg Leu
 50                  55                  60 aag aga acc gcc aga aga aga tac acc aga cgg aag aac cgg atc tgc              240
Lys Arg Thr Ala Arg Arg Arg Tyr Thr Arg Arg Lys Asn Arg Ile Cys
 65                  70                  75                  80 tat ctg caa gag atc ttc agc aac gag atg gcc aag gtg gac gac agc              288
Tyr Leu Gln Glu Ile Phe Ser Asn Glu Met Ala Lys Val Asp Asp Ser
                 85                  90                  95 ttc ttc cac aga ctg gaa gag tcc ttc ctg gtg gaa gag gat aag aag              336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac              384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac              432
His Glu Lys Tyr Pro Thr Ile Tyr His Leu Arg Lys Lys Leu Val Asp
130                 135                 140 agc acc gac aag gcc gac ctg cgg ctg atc tat ctg gcc ctg gcc cac              480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc              528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac              576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc              624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat              672
Lys Ala Ile Leu Ser Ala Arg Leu Ser Lys Ser Arg Arg Leu Glu Asn
210                 215                 220 ctg atc gcc cag ctg ccc ggc gag aag aag aat ggc ctg ttc ggc aac              720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc              768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac              816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac              864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac              912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct              960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa             1008
Met Ile Lys Arg Tyr Asp Glu His His Gln Asp Leu Thr Leu Leu Lys
                325                 330                 335
```

```
gct ctc gtg cgg cag cag ctg cct gag aag tac aaa gag att ttc ttc    1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc    1104
Asp Gln Ser Lys Asn Gly Tyr Ala Gly Tyr Ile Asp Gly Gly Ala Ser
                355                 360                 365 cag gaa gag ttc tac aag ttc atc aag ccc atc ctg gaa aag atg gac    1152
Gln Glu Glu Phe Tyr Lys Phe Ile Lys Pro Ile Leu Glu Lys Met Asp
370                 375                 380 ggc acc gag gaa ctg ctc gtg aag ctg aac aga gag gac ctg ctg cgg    1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg    1248
Lys Gln Arg Thr Phe Asp Asn Gly Ser Ile Pro His Gln Ile His Leu
            405                 410                 415 gga gag ctg cac gcc att ctg cgg cgg cag gaa gat ttt tac cca ttc    1296
Gly Glu Leu His Ala Ile Leu Arg Arg Gln Glu Asp Phe Tyr Pro Phe
                420                 425                 430 ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
435                 440                 445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
450                 455                 460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
            485                 490                 495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
                500                 505                 510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
515                 520                 525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
            565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
            645                 650                 655
```

```
acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
        675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc    2256
Ile Leu Gln Thr Val Lys Val Val Asp Glu Leu Val Lys Val Met Gly
            740                 745                 750 cgg cac aag ccc gag aac atc gtg atc gcc atg gcc aga gag aac cag    2304
Arg His Lys Pro Glu Asn Ile Val Ile Ala Met Ala Arg Glu Asn Gln
        755                 760                 765 acc acc cag aag gga cag aag aac agc cgc gag aga atg aag cgg atc    2352
Thr Thr Gln Lys Gly Gln Lys Asn Ser Arg Glu Arg Met Lys Arg Ile
770                 775                 780 gaa gag ggc atc aaa gag ctg ggc agc cag atc ctg aaa gaa cac ccc    2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg    2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg    2496
Gln Asn Gly Arg Asp Met Tyr Val Asp Gln Glu Leu Asp Ile Asn Arg
            820                 825                 830 ctg tcc gac tac gat gtg gac gcc atc gtg cct cag agc ttt ctg aag    2544
Leu Ser Asp Tyr Asp Val Asp Ala Ile Val Pro Gln Ser Phe Leu Lys
        835                 840                 845 gac gac tcc atc gac gcc aag gtg ctg acc aga agc gac aag gcc cgg    2592
Asp Asp Ser Ile Asp Ala Lys Val Leu Thr Arg Ser Asp Lys Ala Arg
850                 855                 860 ggc aag agc gac aac gtg ccc tcc gaa gag gtc gtg aag aag atg aag    2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag    2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat    2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca    2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac    2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc    2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc    2928
Lys Leu Val Ser Asp Phe Arg Lys Asp Phe Gln Phe Tyr Lys Val Arg
```

-continued

|  |  |  | 965 |  |  |  | 970 |  |  |  | 975 |  |  |  |
|---|---|---|---|---|---|---|---|---|---|---|---|---|---|---|
| gag | atc | aac | aac | tac | cac | cac | gcc | cac | gcc | gcc | tac | ctg | aac | gcc gtc | 2976
| Glu | Ile | Asn | Asn | Tyr | His | His | Ala | His | Ala | Ala | Tyr | Leu | Asn | Ala Val |
|     |     |     | 980 |     |     |     | 985 |     |     |     | 990 |     |     |         |

```
gag atc aac aac tac cac cac gcc cac gcc gcc tac ctg aac gcc gtc      2976
Glu Ile Asn Asn Tyr His His Ala His Ala Ala Tyr Leu Asn Ala Val
            980                 985                 990 gtg gga acc gcc ctg atc aaa aag tac cct aag ctg gaa agc gag ttc      3024
Val Gly Thr Ala Leu Ile Lys Lys Tyr Pro Lys Leu Glu Ser Glu Phe
            995                 1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
        1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
        1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
        1040                1045                1050 aac ggc gag atc cgg aag cgg cct ctg atc gag aca aac ggc gaa          3204
Asn Gly Glu Ile Arg Lys Arg Pro Leu Ile Glu Thr Asn Gly Glu
        1055                1060                1065 acc ggg gag atc gtg tgg gat aag ggc cgg gat ttt gcc acc gtg          3249
Thr Gly Glu Ile Val Trp Asp Lys Gly Arg Asp Phe Ala Thr Val
        1070                1075                1080 cgg aaa gtg ctg agc atg ccc caa gtg aat atc gtg aaa aag acc          3294
Arg Lys Val Leu Ser Met Pro Gln Val Asn Ile Val Lys Lys Thr
        1085                1090                1095 gag gtg cag aca ggc ggc ttc agc aaa gag tct atc ctg ccc aag          3339
Glu Val Gln Thr Gly Gly Phe Ser Lys Glu Ser Ile Leu Pro Lys
        1100                1105                1110 agg aac agc gat aag ctg atc gcc aga aag aag gac tgg gac cct          3384
Arg Asn Ser Asp Lys Leu Ile Ala Arg Lys Lys Asp Trp Asp Pro
        1115                1120                1125 aag aag tac ggc ggc ttc gac agc ccc acc gtg gcc tat tct gtg          3429
Lys Lys Tyr Gly Gly Phe Asp Ser Pro Thr Val Ala Tyr Ser Val
        1130                1135                1140 ctg gtg gtg gcc aaa gtg gaa aag ggc aag tcc aag aaa ctg aag          3474
Leu Val Val Ala Lys Val Glu Lys Gly Lys Ser Lys Lys Leu Lys
        1145                1150                1155 agt gtg aaa gag ctg ctg ggg atc acc atc atg gaa aga agc agc          3519
Ser Val Lys Glu Leu Leu Gly Ile Thr Ile Met Glu Arg Ser Ser
        1160                1165                1170 ttc gag aag aat ccc atc gac ttt ctg gaa gcc aag ggc tac aaa          3564
Phe Glu Lys Asn Pro Ile Asp Phe Leu Glu Ala Lys Gly Tyr Lys
        1175                1180                1185 gaa gtg aaa aag gac ctg atc atc aag ctg cct aag tac tcc ctg          3609
Glu Val Lys Lys Asp Leu Ile Ile Lys Leu Pro Lys Tyr Ser Leu
        1190                1195                1200 ttc gag ctg gaa aac ggc cgg aag aga atg ctg gcc tct gcc ggc          3654
Phe Glu Leu Glu Asn Gly Arg Lys Arg Met Leu Ala Ser Ala Gly
        1205                1210                1215 gaa ctg cag aag gga aac gaa ctg gcc ctg ccc tcc aaa tat gtg          3699
Glu Leu Gln Lys Gly Asn Glu Leu Ala Leu Pro Ser Lys Tyr Val
        1220                1225                1230 aac ttc ctg tac ctg gcc agc cac tat gag aag ctg aag ggc tcc          3744
Asn Phe Leu Tyr Leu Ala Ser His Tyr Glu Lys Leu Lys Gly Ser
        1235                1240                1245 ccc gag gat aat gag cag aaa cag ctg ttt gtg gaa cag cac aag          3789
Pro Glu Asp Asn Glu Gln Lys Gln Leu Phe Val Glu Gln His Lys
        1250                1255                1260 cac tac ctg gac gag atc atc gag cag atc agc gag ttc tcc aag          3834
```

| | | | | | | | | | | | | |
|---|---|---|---|---|---|---|---|---|---|---|---|---|
| His | Tyr | Leu | Asp | Glu | Ile | Ile | Glu | Gln | Ile | Ser | Glu | Phe | Ser | Lys |
| | 1265 | | | | 1270 | | | | 1275 | | | |

| aga | gtg | atc | ctg | gcc | gac | gct | aat | ctg | gac | aaa | gtg | ctg | tcc | gcc | 3879 |
|---|---|---|---|---|---|---|---|---|---|---|---|---|---|---|---|
| Arg | Val | Ile | Leu | Ala | Asp | Ala | Asn | Leu | Asp | Lys | Val | Leu | Ser | Ala | |
| | 1280 | | | | 1285 | | | | 1290 | | | | | |

| tac | aac | aag | cac | cgg | gat | aag | ccc | atc | aga | gag | cag | gcc | gag | aat | 3924 |
|---|---|---|---|---|---|---|---|---|---|---|---|---|---|---|---|
| Tyr | Asn | Lys | His | Arg | Asp | Lys | Pro | Ile | Arg | Glu | Gln | Ala | Glu | Asn | |
| | 1295 | | | | 1300 | | | | 1305 | | | | | |

| atc | atc | cac | ctg | ttt | acc | ctg | acc | aat | ctg | gga | gcc | cct | gcc | gcc | 3969 |
|---|---|---|---|---|---|---|---|---|---|---|---|---|---|---|---|
| Ile | Ile | His | Leu | Phe | Thr | Leu | Thr | Asn | Leu | Gly | Ala | Pro | Ala | Ala | |
| 1310 | | | | | 1315 | | | | 1320 | | | | | |

| ttc | aag | tac | ttt | gac | acc | acc | atc | gac | cgg | aag | agg | tac | acc | agc | 4014 |
|---|---|---|---|---|---|---|---|---|---|---|---|---|---|---|---|
| Phe | Lys | Tyr | Phe | Asp | Thr | Thr | Ile | Asp | Arg | Lys | Arg | Tyr | Thr | Ser | |
| 1325 | | | | | 1330 | | | | 1335 | | | | | |

| acc | aaa | gag | gtg | ctg | gac | gcc | acc | ctg | atc | cac | cag | agc | atc | acc | 4059 |
|---|---|---|---|---|---|---|---|---|---|---|---|---|---|---|---|
| Thr | Lys | Glu | Val | Leu | Asp | Ala | Thr | Leu | Ile | His | Gln | Ser | Ile | Thr | |
| 1340 | | | | | 1345 | | | | 1350 | | | | | |

| ggc | ctg | tac | gag | aca | cgg | atc | gac | ctg | tct | cag | ctg | gga | ggc | gac | 4104 |
|---|---|---|---|---|---|---|---|---|---|---|---|---|---|---|---|
| Gly | Leu | Tyr | Glu | Thr | Arg | Ile | Asp | Leu | Ser | Gln | Leu | Gly | Gly | Asp | |
| 1355 | | | | | 1360 | | | | 1365 | | | | | |

<210> SEQ ID NO 352
<211> LENGTH: 1368
<212> TYPE: PRT
<213> ORGANISM: Homo sapiens

<400> SEQUENCE: 352

| Met | Asp | Lys | Lys | Tyr | Ser | Ile | Gly | Leu | Asp | Ile | Gly | Thr | Asn | Ser | Val |
|---|---|---|---|---|---|---|---|---|---|---|---|---|---|---|---|
| 1 | | | | 5 | | | | | 10 | | | | | 15 | |

| Gly | Trp | Ala | Val | Ile | Thr | Asp | Glu | Tyr | Lys | Val | Pro | Ser | Lys | Lys | Phe |
|---|---|---|---|---|---|---|---|---|---|---|---|---|---|---|---|
| | | | 20 | | | | | 25 | | | | | 30 | | |

| Lys | Val | Leu | Gly | Asn | Thr | Asp | Arg | His | Ser | Ile | Lys | Lys | Asn | Leu | Ile |
|---|---|---|---|---|---|---|---|---|---|---|---|---|---|---|---|
| | | 35 | | | | | 40 | | | | | 45 | | | |

| Gly | Ala | Leu | Leu | Phe | Asp | Ser | Gly | Glu | Thr | Ala | Glu | Ala | Thr | Arg | Leu |
|---|---|---|---|---|---|---|---|---|---|---|---|---|---|---|---|
| | 50 | | | | | 55 | | | | | 60 | | | | |

| Lys | Arg | Thr | Ala | Arg | Arg | Arg | Tyr | Thr | Arg | Arg | Lys | Asn | Arg | Ile | Cys |
|---|---|---|---|---|---|---|---|---|---|---|---|---|---|---|---|
| 65 | | | | | 70 | | | | | 75 | | | | | 80 |

| Tyr | Leu | Gln | Glu | Ile | Phe | Ser | Asn | Glu | Met | Ala | Lys | Val | Asp | Asp | Ser |
|---|---|---|---|---|---|---|---|---|---|---|---|---|---|---|---|
| | | | | 85 | | | | | 90 | | | | | 95 | |

| Phe | Phe | His | Arg | Leu | Glu | Glu | Ser | Phe | Leu | Val | Glu | Glu | Asp | Lys | Lys |
|---|---|---|---|---|---|---|---|---|---|---|---|---|---|---|---|
| | | | | 100 | | | | | 105 | | | | | 110 | |

| His | Glu | Arg | His | Pro | Ile | Phe | Gly | Asn | Ile | Val | Asp | Glu | Val | Ala | Tyr |
|---|---|---|---|---|---|---|---|---|---|---|---|---|---|---|---|
| | | | 115 | | | | | 120 | | | | | 125 | | |

| His | Glu | Lys | Tyr | Pro | Thr | Ile | Tyr | His | Leu | Arg | Lys | Lys | Leu | Val | Asp |
|---|---|---|---|---|---|---|---|---|---|---|---|---|---|---|---|
| | 130 | | | | | 135 | | | | | 140 | | | | |

| Ser | Thr | Asp | Lys | Ala | Asp | Leu | Arg | Leu | Ile | Tyr | Leu | Ala | Leu | Ala | His |
|---|---|---|---|---|---|---|---|---|---|---|---|---|---|---|---|
| 145 | | | | | 150 | | | | | 155 | | | | | 160 |

| Met | Ile | Lys | Phe | Arg | Gly | His | Phe | Leu | Ile | Glu | Gly | Asp | Leu | Asn | Pro |
|---|---|---|---|---|---|---|---|---|---|---|---|---|---|---|---|
| | | | | 165 | | | | | 170 | | | | | 175 | |

| Asp | Asn | Ser | Asp | Val | Asp | Lys | Leu | Phe | Ile | Gln | Leu | Val | Gln | Thr | Tyr |
|---|---|---|---|---|---|---|---|---|---|---|---|---|---|---|---|
| | | | 180 | | | | | 185 | | | | | 190 | | |

| Asn | Gln | Leu | Phe | Glu | Glu | Asn | Pro | Ile | Asn | Ala | Ser | Gly | Val | Asp | Ala |
|---|---|---|---|---|---|---|---|---|---|---|---|---|---|---|---|
| | | 195 | | | | | 200 | | | | | 205 | | | |

| Lys | Ala | Ile | Leu | Ser | Ala | Arg | Leu | Ser | Lys | Ser | Arg | Arg | Leu | Glu | Asn |
|---|---|---|---|---|---|---|---|---|---|---|---|---|---|---|---|
| | 210 | | | | | 215 | | | | | 220 | | | | |

| Leu | Ile | Ala | Gln | Leu | Pro | Gly | Glu | Lys | Lys | Asn | Gly | Leu | Phe | Gly | Asn |
|---|---|---|---|---|---|---|---|---|---|---|---|---|---|---|---|
| 225 | | | | | 230 | | | | | 235 | | | | | 240 |

```
Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655
```

-continued

```
Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Ala Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Ala Lys Val Leu Thr Arg Ser Asp Lys Ala Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Ala Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
```

```
                1070                1075                1080
Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 353
<211> LENGTH: 15
<212> TYPE: DNA
<213> ORGANISM: Homo sapiens

<400> SEQUENCE: 353
cagaagaaga agggc                                               15

<210> SEQ ID NO 354
<211> LENGTH: 51
<212> TYPE: DNA
<213> ORGANISM: Homo sapiens

<400> SEQUENCE: 354
ccaatgggga ggacatcgat gtcacctcca atgactaggg tggtgggcaa c       51
```

```
<210> SEQ ID NO 355
<211> LENGTH: 15
<212> TYPE: DNA
<213> ORGANISM: Homo sapiens

<400> SEQUENCE: 355
ctctggccac tccct                                                  15

<210> SEQ ID NO 356
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
acatcgatgt cacctccaat gacaagcttg ctagcggtgg gcaaccacaa ac         52

<210> SEQ ID NO 357
<211> LENGTH: 57
<212> TYPE: DNA
<213> ORGANISM: Homo sapiens
<220> FEATURE:
<221> NAME/KEY: CDS
<222> LOCATION: (1)..(57)

<400> SEQUENCE: 357 ggc acc att aaa gaa aat atc att ggt gtt tcc tat gat gaa tat aga   48
Gly Thr Ile Lys Glu Asn Ile Ile Gly Val Ser Tyr Asp Glu Tyr Arg
1               5                   10                  15 tac aga agc                                                       57
Tyr Arg Ser <210> SEQ ID NO 358
<211> LENGTH: 19
<212> TYPE: PRT
<213> ORGANISM: Homo sapiens

<400> SEQUENCE: 358

Gly Thr Ile Lys Glu Asn Ile Ile Gly Val Ser Tyr Asp Glu Tyr Arg
1               5                   10                  15

Tyr Arg Ser

<210> SEQ ID NO 359
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: CDS
<222> LOCATION: (1)..(48)

<400> SEQUENCE: 359 att aaa gaa aat atc att ggc ttt gtt tcc tat gat gaa tat aga tac   48
Ile Lys Glu Asn Ile Ile Gly Phe Val Ser Tyr Asp Glu Tyr Arg Tyr
1               5                   10                  15

<210> SEQ ID NO 360
<211> LENGTH: 16
<212> TYPE: PRT
<213> ORGANISM: Artificial Sequence
<220> FEATURE:
```

<221> NAME/KEY: source
<223> OTHER INFORMATION: /note="Description of Artificial Sequence:
      Synthetic peptide"

<400> SEQUENCE: 360

Ile Lys Glu Asn Ile Ile Gly Phe Val Ser Tyr Asp Glu Tyr Arg Tyr
1               5                   10                  15

<210> SEQ ID NO 361
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(48)
<223> OTHER INFORMATION: a, c, t, g, unknown or other

<400> SEQUENCE: 361
ccnnnnnnnn nnnnnnnnnn nnnnnnnnnn nnnnnnnnnn nnnnnnnngg                50

<210> SEQ ID NO 362
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(44)
<223> OTHER INFORMATION: a, c, t, g, unknown or other

<400> SEQUENCE: 362
ccnnnnnnnn nnnnnnnnnn nnnnnnnnnn nnnnnnnnnn nnnngg                    46

<210> SEQ ID NO 363
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(40)
<223> OTHER INFORMATION: a, c, t, g, unknown or other

<400> SEQUENCE: 363
ccnnnnnnnn nnnnnnnnnn nnnnnnnnnn nnnnnnnnnn gg                        42

<210> SEQ ID NO 364
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(36)
<223> OTHER INFORMATION: a, c, t, g, unknown or other

<400> SEQUENCE: 364
ccnnnnnnnn nnnnnnnnnn nnnnnnnnnn nnnnnngg                            38

<210> SEQ ID NO 365
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(32)
<223> OTHER INFORMATION: a, c, t, g, unknown or other

<400> SEQUENCE: 365
ccnnnnnnnn nnnnnnnnnn nnnnnnnnnn nngg                                34

<210> SEQ ID NO 366
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(28)
<223> OTHER INFORMATION: a, c, t, g, unknown or other

<400> SEQUENCE: 366
ccnnnnnnnn nnnnnnnnnn nnnnnnnngg                                     30

<210> SEQ ID NO 367
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(24)
<223> OTHER INFORMATION: a, c, t, g, unknown or other

<400> SEQUENCE: 367
ccnnnnnnnn nnnnnnnnnn nnnngg                                         26

<210> SEQ ID NO 368
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(20)
<223> OTHER INFORMATION: a, c, t, g, unknown or other

<400> SEQUENCE: 368
ccnnnnnnnn nnnnnnnnnn gg                                             22

<210> SEQ ID NO 369
<211> LENGTH: 18
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(16)
<223> OTHER INFORMATION: a, c, t, g, unknown or other

<400> SEQUENCE: 369
ccnnnnnnnn nnnnnngg                                                  18

<210> SEQ ID NO 370
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(14)
<223> OTHER INFORMATION: a, c, t, g, unknown or other

<400> SEQUENCE: 370
ccnnnnnnnn nnnngg                                                    16

<210> SEQ ID NO 371
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(13)
<223> OTHER INFORMATION: a, c, t, g, unknown or other

<400> SEQUENCE: 371
ccnnnnnnnn nnngg                                                     15

<210> SEQ ID NO 372
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(12)
<223> OTHER INFORMATION: a, c, t, g, unknown or other

<400> SEQUENCE: 372
ccnnnnnnnn nngg                                                      14

<210> SEQ ID NO 373
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(11)
```

```
<223> OTHER INFORMATION: a, c, t, g, unknown or other

<400> SEQUENCE: 373
ccnnnnnnnn ngg                                                    13

<210> SEQ ID NO 374
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 374
ccnnnnnnnn gg                                                     12

<210> SEQ ID NO 375
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(9)
<223> OTHER INFORMATION: a, c, t, g, unknown or other

<400> SEQUENCE: 375
ccnnnnnnng g                                                      11

<210> SEQ ID NO 376
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(8)
<223> OTHER INFORMATION: a, c, t, g, unknown or other

<400> SEQUENCE: 376 ccnnnnnngg                                                        10

<210> SEQ ID NO 377
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (3)..(10)
<223> OTHER INFORMATION: a, c, t, g, unknown or other

<400> SEQUENCE: 377
ggnnnnnnnn cc                                                     12
```

<210> SEQ ID NO 378
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 378
gcactgaggg cctatttccc atgattc                                27

<210> SEQ ID NO 379
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 379
aaaaaaagca ccgactcggt gccactttt caagttgata acggactagc cttattttaa     60
cttgctattt ctagctctaa aactcacatc aaccggtggc gcaggtgttt cgtccttcc    120 acaag                                                               125

<210> SEQ ID NO 380
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 380
aaaaaaagca ccgactcggt gccactttt caagttgata acggactagc cttattttaa     60
cttgctattt ctagctctaa aactcacatc aaccggtggc gcaggtgttt cgtccttcc    120 acaag                                                               125

<210> SEQ ID NO 381
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 381
aaaaaaagca ccgactcggt gccactttt caagttgata acggactagc cttattttaa     60
cttgctattt ctagctctaa aacgaggaca aagtacaaac ggcggtgttt cgtccttcc    120 acaag                                                               125

<210> SEQ ID NO 382
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 382
aaaaaaagca ccgactcggt gccactttt caagttgata acggactagc cttattttaa      60
cttgctattt ctagctctaa aacgaggaca aagtacaaac ggcggtgttt cgtcctttcc     120
acaag                                                                 125

<210> SEQ ID NO 383
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 383
aaaaaaagca ccgactcggt gccactttt caagttgata acggactagc cttattttaa      60
cttgctattt ctagctctaa aacgtggcgc attgccacga agcggtgttt cgtcctttcc    120
acaag                                                                 125

<210> SEQ ID NO 384
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 384
aaaaaaagca ccgactcggt gccactttt caagttgata acggactagc cttattttaa      60
cttgctattt ctagctctaa aaccgagggc agagtgctgc ttgggtgttt cgtcctttcc    120
acaag                                                                 125

<210> SEQ ID NO 385
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 385
aaaaaaagca ccgactcggt gccactttt caagttgata acggactagc cttattttaa      60
cttgctattt ctagctctaa aacgagtccg agcagaagaa gaaggtgttt cgtcctttcc    120
acaag                                                                 125

<210> SEQ ID NO 386
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 386
aaaaaaagca ccgactcggt gccactttt caagttgata acggactagc cttattttaa      60
cttgctattt ctagctctaa aacgaggaca aagtacaaac ggcggtgttt cgtcctttcc    120
acaag                                                                 125

<210> SEQ ID NO 387
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 387
aaaaaaagca ccgactcggt gccactttt caagttgata acggactagc cttatttaa      60 cttgctattt ctagctctaa aacagcagaa gaagaagggc tccggtgttt cgtccttcc    120 acaag                                                                125

<210> SEQ ID NO 388
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 388
aaaaaaagca ccgactcggt gccactttt caagttgata acggactagc cttatttaa      60 cttgctattt ctagctctaa aactcacatc aaccggtggc gcaggtgttt cgtccttcc    120 acaag                                                                125

<210> SEQ ID NO 389
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 389
aaaaaaagca ccgactcggt gccactttt caagttgata acggactagc cttatttaa      60 cttgctattt ctagctctaa aaccccctggc ccaggtgaag gtgggtgttt cgtcctttcc    120
acaag                                                                125

<210> SEQ ID NO 390
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 390
aaaaaaagca ccgactcggt gccactttt caagttgata acggactagc cttatttaa      60 cttgctattt ctagctctaa aactccctcc ctggcccagg tgaggtgttt cgtcctttcc    120
acaag                                                                125

<210> SEQ ID NO 391
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 391
aaaaaaagca ccgactcggt gccactttt caagttgata acggactagc cttatttaa    60 cttgctattt ctagctctaa aacgaaccgg aggacaaagt acaggtgttt cgtccttcc   120 acaag                                                              125

<210> SEQ ID NO 392
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 392
aaaaaaagca ccgactcggt gccactttt caagttgata acggactagc cttatttaa    60 cttgctattt ctagctctaa aacaggtgaa ggtgtggttc cagggtgttt cgtcctttcc  120
acaag                                                              125

<210> SEQ ID NO 393
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 393
aaaaaaagca ccgactcggt gccactttt caagttgata acggactagc cttatttaa    60 cttgctattt ctagctctaa aacggtgaag gtgtggttcc agaggtgttt cgtcctttcc  120
acaag                                                              125

<210> SEQ ID NO 394
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 394
aaaaaaagca ccgactcggt gccactttt caagttgata acggactagc cttatttaa    60 cttgctattt ctagctctaa aacgaaccgg aggacaaagt acaggtgttt cgtcctttcc  120
acaag                                                              125

<210> SEQ ID NO 395
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 395
aaaaaaagca ccgactcggt gccactttt caagttgata acggactagc cttatttaa    60 cttgctattt ctagctctaa aaccccctggc ccaggtgaag gtgggtgttt cgtcctttcc 120

```
acaag                                                              125

<210> SEQ ID NO 396
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 396
aaaaaaagca ccgactcggt gccactttt caagttgata acggactagc cttatttaa        60 cttgctattt ctagctctaa aacaggtgaa ggtgtggttc cagggtgttt cgtccttcc      120 acaag                                                              125

<210> SEQ ID NO 397
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 397
aaaaaaagca ccgactcggt gccactttt caagttgata acggactagc cttatttaa        60 cttgctattt ctagctctaa aacgaggaca aagtacaaac ggcggtgttt cgtccttcc      120 acaag                                                              125

<210> SEQ ID NO 398
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 398
aaaaaaagca ccgactcggt gccactttt caagttgata acggactagc cttatttaa        60 cttgctattt ctagctctaa aacgggaggg aggggcacag atgggtgttt cgtccttcc      120 acaag                                                              125

<210> SEQ ID NO 399
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 399
aaaaaaagca ccgactcggt gccactttt caagttgata acggactagc cttatttaa        60 cttgctattt ctagctctaa aaccaccttc acctgggcca ggggtgttt cgtccttcc      120 acaag                                                              125

<210> SEQ ID NO 400
<211> LENGTH: 125
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 400
aaaaaaagca ccgactcggt gccactttt caagttgata acggactagc cttattttaa      60
cttgctattt ctagctctaa aacaccctag tcattggagg tgaggtgttt cgtcctttcc    120
acaag                                                                125

<210> SEQ ID NO 401
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 401
aaaaaaagca ccgactcggt gccactttt caagttgata acggactagc cttattttaa      60
cttgctattt ctagctctaa aaccagagca gccactgggg cctggtgttt cgtcctttcc    120
acaag                                                                125

<210> SEQ ID NO 402
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 402
aaaaaaagca ccgactcggt gccactttt caagttgata acggactagc cttattttaa      60
cttgctattt ctagctctaa aaccaccttc acctgggcca ggggtgttt cgtcctttcc     120 acaag                                                                125

<210> SEQ ID NO 403
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 403
aaaaaaagca ccgactcggt gccactttt caagttgata acggactagc cttattttaa      60
cttgctattt ctagctctaa aaccccccatt ggcctgcttc gtgggtgttt cgtcctttcc   120
acaag                                                                125

<210> SEQ ID NO 404
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 404
```

```
aaaaaaagca ccgactcggt gccactttt caagttgata acggactagc cttattttaa    60
cttgctattt ctagctctaa aacattggcc tgcttcgtgg caaggtgttt cgtccttttcc   120 acaag                                                               125
```

<210> SEQ ID NO 405
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 405

```
aaaaaaagca ccgactcggt gccactttt caagttgata acggactagc cttattttaa    60
cttgctattt ctagctctaa aactcctcct ccagcttctg ccgggtgttt cgtccttttcc  120 acaag                                                               125
```

<210> SEQ ID NO 406
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 406

```
aaaaaaagca ccgactcggt gccactttt caagttgata acggactagc cttattttaa    60
cttgctattt ctagctctaa aaccctccag cttctgccgt ttgggtgttt cgtccttttcc  120 acaag                                                               125
```

<210> SEQ ID NO 407
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 407

```
aaaaaaagca ccgactcggt gccactttt caagttgata acggactagc cttattttaa    60
cttgctattt ctagctctaa aacattggcc tgcttcgtgg caaggtgttt cgtccttttcc  120 acaag                                                               125
```

<210> SEQ ID NO 408
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 408

```
aaaaaaagca ccgactcggt gccactttt caagttgata acggactagc cttattttaa    60
cttgctattt ctagctctaa aacgcagcaa gcagcactct gccggtgttt cgtccttttcc  120 acaag                                                               125
```

```
<210> SEQ ID NO 409
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 409
aaaaaaagca ccgactcggt gccactttt caagttgata acggactagc cttattttaa    60
cttgctattt ctagctctaa aacttcttct tctgctcgga ctcggtgttt cgtccttcc   120 acaag                                                              125

<210> SEQ ID NO 410
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 410
aaaaaaagca ccgactcggt gccactttt caagttgata acggactagc cttattttaa    60
cttgctattt ctagctctaa aacaccggag gacaaagtac aaaggtgttt cgtccttcc   120 acaag                                                              125

<210> SEQ ID NO 411
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 411
aaaaaaagca ccgactcggt gccactttt caagttgata acggactagc cttattttaa    60
cttgctattt ctagctctaa aactcttctt ctgctcggac tcaggtgttt cgtccttcc   120 acaag                                                              125

<210> SEQ ID NO 412
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 412
aaaaaaagca ccgactcggt gccactttt caagttgata acggactagc cttattttaa    60
cttgctattt ctagctctaa aacgttgatg tgatgggagc cctggtgttt cgtccttcc   120 acaag                                                              125

<210> SEQ ID NO 413
<211> LENGTH: 125
<212> TYPE: DNA
<213> ORGANISM: Artificial Sequence
<220> FEATURE:
<221> NAME/KEY: source
```

<223> OTHER INFORMATION: /note="Description of Artificial Sequence:
     Synthetic primer"

<400> SEQUENCE: 413
aaaaaaagca ccgactcggt gccactttt caagttgata acggactagc cttattttaa    60
cttgctattt ctagctctaa aacgggccag ggagggaggg gcaggtgttt cgtccttcc   120 acaag                                                             125

<210> SEQ ID NO 414
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 414
aaaaaaagca ccgactcggt gccactttt caagttgata acggactagc cttattttaa    60
cttgctattt ctagctctaa aacgggaggg aggggcacag atgggtgttt cgtccttcc   120 acaag                                                             125

<210> SEQ ID NO 415
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 415
aaaaaaagca ccgactcggt gccactttt caagttgata acggactagc cttattttaa    60
cttgctattt ctagctctaa aacccggttc tggaaccaca cctggtgttt cgtccttcc   120 acaag                                                             125

<210> SEQ ID NO 416
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 416
aaaaaaagca ccgactcggt gccactttt caagttgata acggactagc cttattttaa    60
cttgctattt ctagctctaa aactcacctg ggccagggag ggaggtgttt cgtccttcc   120 acaag                                                             125

<210> SEQ ID NO 417
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic primer"

<400> SEQUENCE: 417
aaaaaaagca ccgactcggt gccactttt caagttgata acggactagc cttattttaa    60
cttgctattt ctagctctaa aactcacctg ggccagggag ggaggtgttt cgtccttttcc    120 acaag                                                                125

<210> SEQ ID NO 418
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 418
aaaaaaagca ccgactcggt gccacttttt caagttgata acggactagc cttattttaa    60
cttgctattt ctagctctaa aacgttctgg aaccacacct tcaggtgttt cgtccttttcc   120 acaag                                                                125

<210> SEQ ID NO 419
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 419
aaaaaaagca ccgactcggt gccacttttt caagttgata acggactagc cttattttaa    60
cttgctattt ctagctctaa aacgggaggg aggggcacag atgggtgttt cgtccttttcc   120 acaag                                                                125

<210> SEQ ID NO 420
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 420
aaaaaaagca ccgactcggt gccacttttt caagttgata acggactagc cttattttaa    60
cttgctattt ctagctctaa aacgggccag ggagggaggg gcaggtgttt cgtccttttcc   120 acaag                                                                125

<210> SEQ ID NO 421
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 421
aaaaaaagca ccgactcggt gccacttttt caagttgata acggactagc cttattttaa    60
cttgctattt ctagctctaa aacgttctgg aaccacacct tcaggtgttt cgtccttttcc   120 acaag                                                                125

<210> SEQ ID NO 422
<211> LENGTH: 125

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 422
aaaaaaagca ccgactcggt gccactttt caagttgata acggactagc cttatttaa      60 cttgctattt ctagctctaa aacaggtgaa ggtgtggttc cagggtgttt cgtccttcc    120 acaag                                                                125

<210> SEQ ID NO 423
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 423
aaaaaaagca ccgactcggt gccactttt caagttgata acggactagc cttatttaa      60 cttgctattt ctagctctaa aacgaaccgg aggacaaagt acaggtgttt cgtcctttcc    120
acaag                                                                125

<210> SEQ ID NO 424
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 424
aaaaaaagca ccgactcggt gccactttt caagttgata acggactagc cttatttaa      60 cttgctattt ctagctctaa aaccaaaccc acgagggcag agtggtgttt cgtcctttcc    120
acaag                                                                125

<210> SEQ ID NO 425
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 425
aaaaaaagca ccgactcggt gccactttt caagttgata acggactagc cttatttaa      60 cttgctattt ctagctctaa aacgagtttc tcatctgtgc ccggtgttt cgtcctttcc    120 acaag                                                                125

<210> SEQ ID NO 426
<211> LENGTH: 684
<212> TYPE: DNA
<213> ORGANISM: Homo sapiens
<220> FEATURE:
<221> NAME/KEY: CDS
<222> LOCATION: (1)..(123)
<220> FEATURE:
<221> NAME/KEY: CDS

```
<222> LOCATION: (127)..(159)
<220> FEATURE:
<221> NAME/KEY: CDS
<222> LOCATION: (163)..(399)
<220> FEATURE:
<221> NAME/KEY: CDS
<222> LOCATION: (403)..(684)

<400> SEQUENCE: 426 aaa acc acc ctt ctc tct ggc cca ctg tgt cct ctt cct gcc ctg cca        48
Lys Thr Thr Leu Leu Ser Gly Pro Leu Cys Pro Leu Pro Ala Leu Pro
1               5                   10                  15 tcc cct tct gtg aat gtt aga ccc atg gga gca gct ggt cag agg gga        96
Ser Pro Ser Val Asn Val Arg Pro Met Gly Ala Ala Gly Gln Arg Gly
            20                  25                  30 ccc cgg cct ggg gcc cct aac cct atg tag cct cag tct tcc cat cag       144
Pro Arg Pro Gly Ala Pro Asn Pro Met     Pro Gln Ser Ser His Gln
        35                  40                  45 gct ctc agc tca gcc tga gtg ttg agg ccc cag tgg ctg ctc tgg ggg       192
Ala Leu Ser Ser Ala     Val Leu Arg Pro Gln Trp Leu Leu Trp Gly
    50                      55                  60 cct cct gag ttt ctc atc tgt gcc cct ccc tcc ctg gcc cag gtg aag       240
Pro Pro Glu Phe Leu Ile Cys Ala Pro Pro Ser Leu Ala Gln Val Lys
65                  70                  75 gtg tgg ttc cag aac cgg agg aca aag tac aaa cgg cag aag ctg gag       288
Val Trp Phe Gln Asn Arg Arg Thr Lys Tyr Lys Arg Gln Lys Leu Glu
        80                  85                  90 gag gaa ggg cct gag tcc gag cag aag aag aag ggc tcc cat cac atc       336
Glu Glu Gly Pro Glu Ser Glu Gln Lys Lys Lys Gly Ser His His Ile
95                  100                 105                 110 aac cgg tgg cgc att gcc acg aag cag gcc aat ggg gag gac atc gat       384
Asn Arg Trp Arg Ile Ala Thr Lys Gln Ala Asn Gly Glu Asp Ile Asp
                115                 120                 125 gtc acc tcc aat gac tag ggt ggg caa cca caa acc cac gag ggc aga       432
Val Thr Ser Asn Asp     Gly Gly Gln Pro Gln Thr His Glu Gly Arg
            130                 135                 140 gtg ctg ctt gct gct ggc cag gcc cct gcg tgg gcc caa gct gga ctc       480
Val Leu Leu Ala Ala Gly Gln Ala Pro Ala Trp Ala Gln Ala Gly Leu
        145                 150                 155 tgg cca ctc cct ggc cag gct ttg ggg agg cct gga gtc atg gcc cca       528
Trp Pro Leu Pro Gly Gln Ala Leu Gly Arg Pro Gly Val Met Ala Pro
    160                 165                 170 cag ggc ttg aag ccc ggg gcc gcc att gac aga ggg aca agc aat ggg       576
Gln Gly Leu Lys Pro Gly Ala Ala Ile Asp Arg Gly Thr Ser Asn Gly
175                 180                 185 ctg gct gag gcc tgg gac cac ttg gcc ttc tcc tcg gag agc ctg cct       624
Leu Ala Glu Ala Trp Asp His Leu Ala Phe Ser Ser Glu Ser Leu Pro
            190                 195                 200                 205 gcc tgg gcg ggc ccg ccc gcc acc gca gcc tcc cag ctg ctc tcc gtg       672
Ala Trp Ala Gly Pro Pro Ala Thr Ala Ala Ser Gln Leu Leu Ser Val
        210                 215                 220 tct cca atc tcc                                                       684
Ser Pro Ile Ser
            225

<210> SEQ ID NO 427
<211> LENGTH: 41
<212> TYPE: PRT
<213> ORGANISM: Homo sapiens

<400> SEQUENCE: 427

Lys Thr Thr Leu Leu Ser Gly Pro Leu Cys Pro Leu Pro Ala Leu Pro
```

```
                1               5                   10                  15
Ser Pro Ser Val Asn Val Arg Pro Met Gly Ala Ala Gly Gln Arg Gly
                    20                  25                  30

Pro Arg Pro Gly Ala Pro Asn Pro Met
        35                  40

<210> SEQ ID NO 428
<211> LENGTH: 11
<212> TYPE: PRT
<213> ORGANISM: Homo sapiens

<400> SEQUENCE: 428

Pro Gln Ser Ser His Gln Ala Leu Ser Ser Ala
1               5                   10

<210> SEQ ID NO 429
<211> LENGTH: 79
<212> TYPE: PRT
<213> ORGANISM: Homo sapiens

<400> SEQUENCE: 429

Val Leu Arg Pro Gln Trp Leu Leu Trp Gly Pro Pro Glu Phe Leu Ile
1               5                   10                  15

Cys Ala Pro Pro Ser Leu Ala Gln Val Lys Val Trp Phe Gln Asn Arg
                20                  25                  30

Arg Thr Lys Tyr Lys Arg Gln Lys Leu Glu Glu Glu Gly Pro Glu Ser
            35                  40                  45

Glu Gln Lys Lys Lys Gly Ser His His Ile Asn Arg Trp Arg Ile Ala
        50                  55                  60

Thr Lys Gln Ala Asn Gly Glu Asp Ile Asp Val Thr Ser Asn Asp
65                  70                  75

<210> SEQ ID NO 430
<211> LENGTH: 94
<212> TYPE: PRT
<213> ORGANISM: Homo sapiens

<400> SEQUENCE: 430

Gly Gly Gln Pro Gln Thr His Glu Gly Arg Val Leu Leu Ala Ala Gly
1               5                   10                  15

Gln Ala Pro Ala Trp Ala Gln Ala Gly Leu Trp Pro Leu Pro Gly Gln
                20                  25                  30

Ala Leu Gly Arg Pro Gly Val Met Ala Pro Gln Gly Leu Lys Pro Gly
            35                  40                  45

Ala Ala Ile Asp Arg Gly Thr Ser Asn Gly Leu Ala Glu Ala Trp Asp
        50                  55                  60

His Leu Ala Phe Ser Ser Glu Ser Leu Pro Ala Trp Ala Gly Pro Pro
65                  70                  75                  80

Ala Thr Ala Ala Ser Gln Leu Leu Ser Val Ser Pro Ile Ser
                85                  90

<210> SEQ ID NO 431
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
```

```
<222> LOCATION: (1)..(20)
<223> OTHER INFORMATION: a, c, u, g, unknown or other

<400> SEQUENCE: 431
nnnnnnnnnn nnnnnnnnnn guuuuagagc uagaaauagc aaguuaaaau aaggcuaguc      60
cguuaucacg ccgaaaggcg ggcgccgagu cggcgcuuu                             99

<210> SEQ ID NO 432
<211> LENGTH: 109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (1)..(20)
<223> OTHER INFORMATION: a, c, t, g, u, unknown or other

<400> SEQUENCE: 432
nnnnnnnnnn nnnnnnnnnn guuuuagagc uagaaauagc aaguuaaaau aaggcuaguc      60
cguuaucacc ttgggccgaa aggcccaagg ggcgccgagu cggcgcuuu                  109

<210> SEQ ID NO 433
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
gtagcctcag tcttcccatc aggctctc                                         28

<210> SEQ ID NO 434
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
agggtgggca accacaaacc cacgaggggg gcagagt                               37

<210> SEQ ID NO 435
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
tggggcccct aaccctatgt agcctcagtc ttccccgagg gcagagtgct gcttgctgct      60
ggccagg                                                                67

<210> SEQ ID NO 436
```

<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 436
gttttagagc tagaaacggc aagttaaaat aaggctagtc cgttatcacg ccgaaaggcg    60
ggcgccgagt cggcgcc                                                  77

<210> SEQ ID NO 437
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 437
gttttagagc tagaaatagc aagttaaaat aaggctagtc cgttatcacc ttgggccgaa    60
aggcccaagg ggcgccgagt cggcgcc                                       87

<210> SEQ ID NO 438
<211> LENGTH: 77
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 438
gttttagagc cggaaacggc aagttaaaat aaggctagtc cgttatcacg ccgaaaggcg    60
ggcgccgagt cggcgcc                                                  77

<210> SEQ ID NO 439
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 439
gttttagatg caattatgca aagttaaaat aaggctagtc cgttatcaac ttataccaat    60
aagtcatcgt cgagaagctc gacgatg                                       87

<210> SEQ ID NO 440
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 440
gttttagaac tcattagagt aagttaaaat aaggctagtc cgttatcaac atgcaccagc    60
atgttcagga ttcaaagtga atcctga                                       87

| | |
|---|---|
| <210> SEQ ID NO 441 | |
| <211> LENGTH: 20 | |
| <212> TYPE: RNA | |
| <213> ORGANISM: Artificial Sequence | |
| <220> FEATURE: | |
| <221> NAME/KEY: source | |
| <223> OTHER INFORMATION: /note="Description of Artificial Sequence: Synthetic oligonucleotide" | |
| | |
| <400> SEQUENCE: 441 | |
| | |
| ugcgccaccg guugauguga | 20 |
| | |
| <210> SEQ ID NO 442 | |
| <211> LENGTH: 83 | |
| <212> TYPE: DNA | |
| <213> ORGANISM: Homo sapiens | |
| | |
| <400> SEQUENCE: 442 | |
| | |
| tccgagcaga agaagaaggg ctcccatcac atcaaccggt ggcgcattgc cacgaagcag | 60 |
| | |
| gccaatgggg aggacatcga tgt | 83 |
| | |
| <210> SEQ ID NO 443 | |
| <211> LENGTH: 20 | |
| <212> TYPE: RNA | |
| <213> ORGANISM: Artificial Sequence | |
| <220> FEATURE: | |
| <221> NAME/KEY: source | |
| <223> OTHER INFORMATION: /note="Description of Artificial Sequence: Synthetic oligonucleotide" | |
| | |
| <400> SEQUENCE: 443 | |
| | |
| cacgaagcag gccaaugggg | 20 |
| | |
| <210> SEQ ID NO 444 | |
| <211> LENGTH: 77 | |
| <212> TYPE: DNA | |
| <213> ORGANISM: Homo sapiens | |
| | |
| <400> SEQUENCE: 444 | |
| | |
| agaagaaggg ctcccatcac atcaaccggt ggcgcattgc cacgaagcag gccaatgggg | 60 |
| | |
| aggacatcga tgtcacc | 77 |
| | |
| <210> SEQ ID NO 445 | |
| <211> LENGTH: 99 | |
| <212> TYPE: RNA | |
| <213> ORGANISM: Artificial Sequence | |
| <220> FEATURE: | |
| <221> NAME/KEY: source | |
| <223> OTHER INFORMATION: /note="Description of Artificial Sequence: Synthetic oligonucleotide" | |
| <220> FEATURE: | |
| <221> NAME/KEY: modified_base | |
| <222> LOCATION: (1)..(20) | |
| <223> OTHER INFORMATION: a, c, u, g, unknown or other | |
| | |
| <400> SEQUENCE: 445 | |
| | |
| nnnnnnnnnn nnnnnnnnnn guuuuagagc uagaaauagc aaguuaaaau aaggcuaguc | 60 |
| | |
| cguuaucaac uugaaaaagu ggcaccgagu cggugcuuu | 99 |
| | |
| <210> SEQ ID NO 446 | |
| <211> LENGTH: 30 | |
| <212> TYPE: DNA | |
| <213> ORGANISM: Homo sapiens | |
| | |
| <400> SEQUENCE: 446 | | agaagaaggg ctcccatcat cgatgtcacc                                    30

<210> SEQ ID NO 447
<211> LENGTH: 41
<212> TYPE: DNA
<213> ORGANISM: Homo sapiens

<400> SEQUENCE: 447
agaagaaggg ctcccatcac agggaggaca tcgatgtcac c                        41

<210> SEQ ID NO 448
<211> LENGTH: 41
<212> TYPE: DNA
<213> ORGANISM: Homo sapiens

<400> SEQUENCE: 448
agaagaaggg ctcccatcac atcaaccggt gggatgtcac c                        41

<210> SEQ ID NO 449
<211> LENGTH: 69
<212> TYPE: DNA
<213> ORGANISM: Homo sapiens

<400> SEQUENCE: 449
agaagaaggg ctcccatcac atcaaccggt ggcgcattgc cacgaagcag gccaatgatc    60
gatgtcacc                                                            69

<210> SEQ ID NO 450
<211> LENGTH: 72
<212> TYPE: DNA
<213> ORGANISM: Homo sapiens

<400> SEQUENCE: 450
agaagaaggg ctcccatcac atcaaccggt ggcgccacga agcaggccaa tggggaggac    60
atcgatgtca cc                                                        72

<210> SEQ ID NO 451
<211> LENGTH: 74
<212> TYPE: DNA
<213> ORGANISM: Homo sapiens

<400> SEQUENCE: 451
agaagaaggg ctcccatctc aaccggtggc gcattgccac gaagcaggcc aatggggagg    60
acatcgatgt cacc                                                      74

<210> SEQ ID NO 452
<211> LENGTH: 74
<212> TYPE: DNA
<213> ORGANISM: Homo sapiens

<400> SEQUENCE: 452
agaagaaggg ctcccatcac atcaaccggt ggcgcattgc cacgaagcag gccggggagg    60
acatcgatgt cacc                                                      74

<210> SEQ ID NO 453
<211> LENGTH: 64
<212> TYPE: DNA
<213> ORGANISM: Homo sapiens

<400> SEQUENCE: 453
ccaatgggga ggacatcgat gtcacctcca atgactaggg tgggcaacca caaacccacg    60

-continued aggg 64

<210> SEQ ID NO 454
<211> LENGTH: 64
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 454
ggtttgtggt tgcccaccgc tagcaagctt gtcattggag gtgacatcga tgtcctcccc    60
attg    64

<210> SEQ ID NO 455
<211> LENGTH: 71
<212> TYPE: DNA
<213> ORGANISM: Homo sapiens

<400> SEQUENCE: 455
accggaggac aaagtacaaa cggcagaagc tggaggagga agggcctgag tccgagcaga    60
agaagaaggg c    71

<210> SEQ ID NO 456
<211> LENGTH: 23
<212> TYPE: DNA
<213> ORGANISM: Homo sapiens

<400> SEQUENCE: 456
gaggccgagc agaagaaaga cgg    23

<210> SEQ ID NO 457
<211> LENGTH: 23
<212> TYPE: DNA
<213> ORGANISM: Homo sapiens

<400> SEQUENCE: 457
aagtctgagc acaagaagaa tgg    23

<210> SEQ ID NO 458
<211> LENGTH: 23
<212> TYPE: DNA
<213> ORGANISM: Homo sapiens

<400> SEQUENCE: 458
gagtcctagc aggagaagaa gag    23

<210> SEQ ID NO 459
<211> LENGTH: 23
<212> TYPE: DNA
<213> ORGANISM: Homo sapiens

<400> SEQUENCE: 459
gagtctaagc agaagaagaa gag    23

<210> SEQ ID NO 460
<211> LENGTH: 23
<212> TYPE: DNA
<213> ORGANISM: Homo sapiens

<400> SEQUENCE: 460

```
gagttagagc agaagaagaa agg                                            23
```

<210> SEQ ID NO 461
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 461

```
nnnnnnnnnn nnnnnnnnnn guuuuagagc cggaaacggc aaguuaaaau aaggcuaguc    60
cguuaucacg ccgaaaggcg ggcgccgagu cggcgcuuu                           99
```

<210> SEQ ID NO 462
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462

```
aattattaat ta                                                        12
```

<210> SEQ ID NO 463
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463

```
aattattaat tataat                                                    16
```

<210> SEQ ID NO 464
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464

```
gttttagagc tatgct                                                    16
```

<210> SEQ ID NO 465
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465

```
gttttgaatg gtcccaaaac                                                20
```

<210> SEQ ID NO 466
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
gttttagagc tatgctgttt tgaatggtcc caaaac                              36

<210> SEQ ID NO 467
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 467
gyuuyagagc uagaaaurgc aaguuraaru aaggcuaguc cguuaucacc gccgaaaggc    60
gggcgccgag ucgrcgccga                                                80

<210> SEQ ID NO 468
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
guuuuagagc uagaaauagc aaguuaaaau aaggcuaguc cguuaucaac uugaaaagu     60 ggcaccgagu cggugc                                                    76

<210> SEQ ID NO 469
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
guuuuagagc uagaaauagc aaguuaaaau aaggcuaguc cguuaucacc uugggccgaa    60
aggcccaagg ggcgccgagu cggcgcc                                        87

<210> SEQ ID NO 470
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
guuuuagagc cggaaacggc aaguuaaaau aaggcuaguc cguuaucacg ccgaaaggcg    60

```
ggcgccgagu cggcgcc                                              77

<210> SEQ ID NO 471
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
guuuuagagc uagaaacggc aaguuaaaau aaggcuaguc cguuaucacg ccgaaaggcg   60
ggcgccgagu cggcgcc                                              77

<210> SEQ ID NO 472
<211> LENGTH: 76
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
gcuucagcgc uagaaauagc aaguugaagu aaggcuaguc cguuaucacg ccgaaaggcg   60
ggcaccgagu cggugc                                               76

<210> SEQ ID NO 473
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 473
gccccagcgc tagaaatagc aagttggggt aaggctagtc cgttatcacg ccgaaaggcg   60
ggcaccgagt cggtgc                                               76

<210> SEQ ID NO 474
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
guuuuagaac ucauuagagu aaguuaaaau aaggcuaguc cguuaucaac augcaccagc   60
auguucagga uucaaaguga auccuga                                   87

<210> SEQ ID NO 475
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
guuuuagaug caauuaugca aaguuaaaau aaggcuaguc cguuaucaac uuauaccaau   60
```
aagucaucgu cgagaagcuc gacgaug            87

<210> SEQ ID NO 476
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
gccccagaug caauuaugca aaguuggggu aaggcaaguc cguuaucaac cgaccacggu    60
cacgucgaag cgacgug                                                  77

<210> SEQ ID NO 477
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
gccccagacc attggaagtt ggggtaaggc aagtccgtta tcaaccgacc acggtcacgt    60
cgaagcgacg tg                                                       72

<210> SEQ ID NO 478
<211> LENGTH: 77
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
gcuucagaug caauuaugca aaguugaagu aaggcaaguc cguuaucacc ugaccacagg    60
gugucguaag acgacac                                                  77

<210> SEQ ID NO 479
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
gcttcagagg attccaagtt gaagtaaggc aagtccgtta tcacctgacc acagggtgtc    60
gtaagacgac ac                                                       72

<210> SEQ ID NO 480
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 480

```
tgagaagaag tcacccacag gccttataag gcacgggagt ctttcaccta ttctacttac        60
ggtgaccgaa ccggagggcc tatttcccat gattccttca tatttgcatg aattaatttg       120
actgtaaaca caaagatatt agtacaaaat acgtgacgta gaaagtaata atttcttggg       180
tagtttgcag ttttaaaatt atgttttaaa atggactatc atatgcttac cgtaacttga       240
aagtatttcg atttcttggc tttatatatc ttgtggaaag gacgaaacac c                291

<210> SEQ ID NO 481
<211> LENGTH: 15
<212> TYPE: DNA
<213> ORGANISM: Homo sapiens

<400> SEQUENCE: 481
agggagtggc cagag                                                         15

<210> SEQ ID NO 482
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
gtttgtggtt gcccaccgct agcaagcttg tcattggagg tgacatcgat gt                52

<210> SEQ ID NO 483
<211> LENGTH: 15
<212> TYPE: DNA
<213> ORGANISM: Homo sapiens

<400> SEQUENCE: 483
gcccttcttc ttctg                                                         15

<210> SEQ ID NO 484
<211> LENGTH: 48
<212> TYPE: DNA
<213> ORGANISM: Homo sapiens

<400> SEQUENCE: 484
gtatctatat tcatcatagg aaacaaagcc aatgatattt tctttaat                     48
```

DELIVERY, ENGINEERING AND OPTIMIZATION OF TANDEM GUIDE SYSTEMS, METHODS AND COMPOSITIONS FOR SEQUENCE MANIPULATION

RELATED APPLICATIONS AND INCORPORATION BY REFERENCE

This application is a Continuation-In-Part of International Application Number PCT/US2014/041800 filed on Jun. 10, 2014 which published as PCT Number WO2014/204724 on Dec. 24, 2014. Priority is claimed from U.S. Provisional applications 61/836,123, filed Jun. 17, 2013; 61/847,537, filed Jul. 17, 2013; 61/862,355, filed Aug. 5, 2013; 61/862,468, filed Aug. 5, 2013; 61/871,301, filed Aug. 28, 2013; 61/915,407, filed Dec. 12, 2013; and 61/979,942, filed Apr. 15, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant no. MH100706 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 29, 2018, is named 44790032034_SL.txt and is 241,049 bytes in size.

FIELD OF THE INVENTION

The present invention generally relates to the delivery, engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

The CRISPR-Cas system does not require the generation of customized proteins to target specific sequences but rather a single Cas enzyme can be programmed by a short RNA molecule to recognize a specific DNA target. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

There exists a pressing need for alternative and robust systems and techniques for sequence targeting with a wide array of applications. Aspects of this invention address this need and provides related advantages. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one aspect, the invention provides methods for using one or more elements of a CRISPR system. The CRISPR complex of the invention provides an effective means for modifying a target polynucleotide. The CRISPR complex of the invention has a wide variety of utilities including modifying (e.g., deleting, inserting, translocating, inactivating, activating) a target polynucleotide in a multiplicity of cell types. As such the CRISPR complex of the invention has a broad spectrum of applications in, e.g., gene or genome editing, gene therapy, drug discovery, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

Aspects of the invention relate to Cas9 enzymes having improved target specificity in a CRISPR-Cas9 system having guide RNAs having optimal activity, smaller in length than wild-type Cas9 enzymes and nucleic acid molecules coding therefor, and chimeric Cas9 enzymes, as well as methods of improving the target specificity of a Cas9 enzyme or of designing a CRISPR-Cas9 system comprising designing or preparing guide RNAs having optimal activity and/or selecting or preparing a Cas9 enzyme having a smaller size or length than wild-type Cas9 whereby packaging a nucleic acid coding therefor into a delivery vector is advanced as there is less coding therefor in the delivery vector than for wild-type Cas9, and/or generating chimeric Cas9 enzymes.

Also provided are uses of the present sequences, vectors, enzymes or systems, in medicine. Also provided are uses of the same in gene or genome editing.

In an additional aspect of the invention, a Cas9 enzyme may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (D10 and H840). Further mutations have been characterized. In one aspect of the invention, the transcriptional activation domain may be VP64. Other aspects of the invention relate to the mutated Cas 9 enzyme being fused to domains which include but are not limited to a transcriptional repressor, a recombinase, a transposase, a histone remodeler, a DNA methyltransferase, a cryptochrome, a light inducible/controllable domain or a chemically inducible/controllable domain.

In a further embodiment, the invention provides for methods to generate mutant tracrRNA and direct repeat sequences or mutant chimeric guide sequences that allow for enhancing performance of these RNAs in cells. Aspects of the invention also provide for selection of said sequences.

Aspects of the invention also provide for methods of simplifying the cloning and delivery of components of the CRISPR complex. In the preferred embodiment of the invention, a suitable promoter, such as the U6 promoter, is amplified with a DNA oligo and added onto the guide RNA. The resulting PCR product can then be transfected into cells to drive expression of the guide RNA. Aspects of the invention also relate to the guide RNA being transcribed in vitro or ordered from a synthesis company and directly transfected.

In one aspect, the invention provides for methods to improve activity by using a more active polymerase. In a preferred embodiment, the expression of guide RNAs under the control of the T7 promoter is driven by the expression of the T7 polymerase in the cell. In an advantageous embodiment, the cell is a eukaryotic cell. In a preferred embodiment the eukaryotic cell is a human cell. In a more preferred embodiment the human cell is a patient specific cell.

In one aspect, the invention provides for methods of reducing the toxicity of Cas enzymes. In certain aspects, the Cas enzyme is any Cas9 as described herein, for instance any naturally-occurring bacterial Cas9 as well as any chimaeras, mutants, homologs or orthologs. In a preferred embodiment, the Cas9 is delivered into the cell in the form of mRNA. This allows for the transient expression of the enzyme thereby reducing toxicity. In another preferred embodiment, the invention also provides for methods of expressing Cas9 under the control of an inducible promoter the constructs used therein.

In another aspect, the invention provides for methods of improving the in vivo applications of the CRISPR-Cas system. In the preferred embodiment, the Cas enzyme is wildtype Cas9 or any of the modified versions described herein, including any naturally-occurring bacterial Cas9 as well as any chimaeras, mutants, homologs or orthologs. An advantageous aspect of the invention provides for the selection of Cas9 homologs that are easily packaged into viral vectors for delivery. Cas9 orthologs typically share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

In some embodiments, the CRISPR enzyme is a type I or III CRISPR enzyme, preferably a type II CRISPR enzyme. This type II CRISPR enzyme may be any Cas enzyme. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCas9, St1Cas9 and so forth. Further examples are provided herein.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

In further embodiments, the invention provides for methods of enhancing the function of Cas9 by generating chimeric Cas9 proteins. These methods may comprise fusing N-terminal fragments of one Cas9 homolog with C-terminal fragments of another Cas9 homolog. These methods also allow for the selection of new properties displayed by the chimeric proteins.

It will be appreciated that in the present methods, where the organism is an animal or a plant, the modification may occur ex vivo or in vitro, for instance in a cell culture and in some instances not in vivo. In other embodiments, it may occur in vivo.

In one aspect the invention provides for a method of modifying an organism or a non-human organism by manipulation of a first and a second target sequence on opposite strands of a DNA duplex in a genomic locus of interest in a cell comprising delivering a non-naturally occurring or engineered composition comprising: I. a CRISPR-Cas system chimeric RNA (chiRNA) polynucleotide sequence, wherein the polynucleotide sequence may comprise: (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and II. a polynucleotide sequence encoding a CRISPR enzyme comprising at least one or more nuclear localization sequences, wherein (a), (b), (c), (d), (e) and (f) may be arranged in a 5' to 3' orientation, wherein the polynucleotide sequence may comprise a linker sequence between the first tracr sequence and the second guide sequence, whereby the first guide sequence and the second guide sequence are in tandem, wherein when transcribed, the first and the second tracr mate sequence may hybridize to the first and second tracr sequence respectively and the first and the second guide sequence directs sequence-specific binding of a first and a second CRISPR complex to the first and second target sequences respectively, wherein the first CRISPR complex may comprise the CRISPR enzyme complexed with (1) the first guide sequence that is hybridized to the first target sequence, and (2) the first tracr mate sequence that is hybridized to the first tracr sequence, wherein the second CRISPR complex may comprise the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism.

The invention also comprehends a method of modifying an organism or a non-human organism by manipulation of a first and a second target sequence on opposite strands of a DNA duplex in a genomic locus of interest in a cell comprising delivering a non-naturally occurring or engineered composition comprising a vector system comprising one or more vectors comprising I. a first regulatory element operably linked to (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and wherein a linker sequence is present between the first tracr sequence and the second guide sequence, whereby the first guide sequence and the second guide sequence are in tandem, and II. a second regulatory element operably linked to an enzyme-coding sequence encoding a CRISPR enzyme, and wherein components I and II are located on the same or different vectors of the system, when transcribed, a first tracr mate sequence hybridizes to a first tracr sequence and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism with a reduction in likelihood of off-target modifications. In some instances, the second tracr may hybridize with the first tracr-mate.

The invention also comprehends a non-naturally occurring or engineered composition for modifying an organism or a non-human organism by manipulation of a first and a second target sequence on opposite strands of a DNA duplex in a genomic locus of interest in a cell comprising: 1. a CRISPR-Cas system chimeric RNA (chiRNA) polynucleotide sequence, wherein the polynucleotide sequence comprises: (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and II. a polynucleotide sequence encoding a CRISPR enzyme comprising at least one or more nuclear localization sequences, wherein (a), (b), (c), (d), (e) and (f) may be arranged in a 5' to 3' orientation, wherein the polynucleotide sequence comprises a linker sequence between the first tracr sequence and the second guide sequence, whereby the first guide sequence and the second guide sequence are in tandem, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break to modify the organism or the non-human organism with a reduction in likelihood of off-target modifications.

In embodiments of the methods and compositions of the invention, the modifying of the organism or the non-human organism with a reduction in likelihood of off-target modifications may comprise inducing a microdeletion, wherein the microdeletion may comprise deletion of a sequence between the first and second target sequences. In embodiments of the invention, the linker sequence may comprise at least 5 nucleotides, or at least 10 nucleotides or at least 20 nucleotides. In an advantageous embodiment, the linker sequence has 8 or 12 nucleotides. In other embodiments, the first or second guide sequence, the first or second tracr sequence and/or the first or second tracr mate sequences are modified, wherein the modification comprises optimized first or second tracr sequence and/or optimized first or second guide sequence and/or, co-fold structure of first or second tracr sequence and/or first or second tracr mate sequence(s) respectively and/or stabilizing secondary structures (hair pins) of first or second tracr sequence and/or first or second tracr sequence with a reduced region of base-pairing and/or first or second tracr sequence fused RNA elements.

In a further embodiments of the methods and compositions of the invention, any or all of the polynucleotide sequence encoding the CRISPR enzyme, the first and the second guide sequence, the first and the second tracr mate sequence or the first and the second tracr sequence, is/are RNA. The invention also comprehends the polynucleotides encoding the sequence encoding the CRISPR enzyme, the first and the second guide sequence, the first and the second tracr mate sequence or the first and the second tracr sequence, is/are RNA and are delivered via nanoparticles, exosomes, microvesicles, or a gene-gun. In a further embodiment, the first and second tracr mate sequence share 100% identity and/or the first and second tracr sequence share 100% identity. In a preferred embodiment, the CRISPR enzyme is a Cas9 enzyme, e.g. SpCas9. It is not necessarily the case for 100% identity between the first tracr and second tracr sequence: Many of the altered scaffolds have changes to the DR/TracR sequences as well as the distal hairpins. It is also possible to have tandems involving alternate scaffolds that have distinct DR/TRACR sequences.

In another aspect, the invention comprehends a method of modifying an organism or a non-human organism by manipulation of a first and a second target sequence on opposite strands of a DNA duplex in a genomic locus of interest in a cell comprising delivering a non-naturally occurring or engineered composition comprising: I. a CRISPR-Cas system chimeric RNA (chiRNA) polynucleotide sequence, wherein the polynucleotide sequence comprises: (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and II. a polynucleotide sequence encoding a CRISPR enzyme comprising at least one or more nuclear localization sequences and comprising one or more mutations, wherein (a), (b), (c), (d), (e) and (f) are may be in a 5' to 3' orientation, wherein the polynucleotide sequence comprises a linker sequence between the first tracr sequence and the second guide sequence, whereby the first guide sequence and the second guide sequence are in tandem, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism.

The invention comprehends a method of modifying an organism or a non-human organism by manipulation of a first and a second target sequence on opposite strands of a DNA duplex in a genomic locus of interest in a cell comprising delivering a non-naturally occurring or engineered composition comprising a vector system comprising one or more vectors comprising I. a first regulatory element operably linked to (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and wherein a linker sequence is present between the first tracr sequence and the second guide sequence, whereby the first guide sequence and the second guide sequence are in tandem, and II. a second regulatory element operably linked to an enzyme-coding sequence encoding a CRISPR enzyme, and wherein components I and II are located on the same or different vectors of the system, when transcribed, a first tracr mate sequence hybridizes to a first tracr sequence and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism. In an embodiment of the invention, the one or more of the viral vectors are delivered via nanoparticles, exosomes, microvesicles, or a gene-gun. In some instances, the second tracr may hybridize with the first tracr-mate.

The invention also comprehends a non-naturally occurring or engineered composition modifying an organism or a non-human organism by manipulation of a first and a second target sequence on opposite strands of a DNA duplex in a genomic locus of interest in a cell comprising: I. a CRISPR-Cas system chimeric RNA (chiRNA) polynucleotide sequence, wherein the polynucleotide sequence comprises: (a) a first guide sequence capable of hybridizing to the first target sequence, (b) a first tracr mate sequence, (c) a first tracr sequence, (d) a second guide sequence capable of hybridizing to the second target sequence, (e) a second tracr mate sequence, and (f) a second tracr sequence, and II. a polynucleotide sequence encoding a CRISPR enzyme comprising at least one or more nuclear localization sequences and comprising one or more mutations, wherein (a), (b), (c), (d), (e) and (f) may be arranged in a 5' to 3' orientation, wherein the polynucleotide sequence comprises a linker sequence between the first tracr sequence and the second guide sequence, whereby the first guide sequence and the second guide sequence are in tandem, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break to modify the organism or the non-human organism.

In embodiments of the methods and compositions of the invention, the first guide sequence directing cleavage of one strand of the DNA duplex near the first target sequence and the second guide sequence directing cleavage of other strand near the second target sequence results in a 5' overhang. In some embodiments, the 5' overhang is at most 200 base pairs, or at most 100 base pairs, or at most 50 base pairs or at least 26 base pairs or at least 30 base pairs. In a preferred embodiment, the 5' overhang is 34-50 base pairs. The invention comprehends any or all of the polynucleotide sequence encoding the CRISPR enzyme, the first and the second guide sequence, the first and the second tracr mate sequence or the first and the second tracr sequence, is/are RNA. In embodiments of the invention, the first and second tracr mate sequence share 100% identity and/or the first and second tracr sequence share 100% identity. It is not necessarily the case for 100% identity between the first tracr and second tracr sequence: Many of the altered scaffolds have changes to the DR/TracR sequences as well as the distal hairpins. It is also possible to have tandems involving alternate scaffolds that have distinct DR/TRACR sequences. In a preferred embodiment, the CRISPR enzyme is a Cas9 enzyme, e.g. SpCas9. In a further embodiment, the CRISPR enzyme comprises one or more mutations in a catalytic domain, wherein the one or more mutations selected from the group consisting of D10A, E762A, H840A, N854A, N863A and D986A. In a preferred embodiment, the CRISPR enzyme has the D10A mutation. In yet another embodiment, the modification comprises optimized first or second tracr sequence and/or optimized first or second guide sequence and/or, co-fold structure of first or second tracr sequence and/or first or second tracr mate sequence(s) respectively and/or stabilizing secondary structures (hair pins) of first or second tracr sequence and/or first or second tracr sequence with a reduced region of base-pairing and/or first or second tracr sequence fused RNA elements. In embodiments of the invention, the linker sequence may comprise at least 5 nucleotides, or at least 10 nucleotides or at least 20 nucleotides. In an advantageous embodiment, the linker sequence has 8 or 12 nucleotides.

In other aspects of the methods and compositions of the invention, more than two guide sequences may be in tandem. The term "tandem single guide RNA" or "tsgRNA" is used to refer to one or more single guide RNAs (sgRNAs) connected by one or more linker sequences. In a preferred embodiment, two guide sequences are in tandem in the polynucleotide sequence. A key aspect of the invention is the utilization of a single promoter or operable element to drive the expression of more than one guide RNA.

In one aspect, the invention provides a method of modifying an organism or a non-human organism by manipulation of a target sequence in a genomic locus of interest comprising:

delivering a non-naturally occurring or engineered composition comprising:

A)-I. a CRISPR-Cas system chimeric RNA (chiRNA) polynucleotide sequence, wherein the polynucleotide sequence comprises:

(a) a guide sequence capable of hybridizing to a target sequence in a eukaryotic cell, (b) a tracr mate sequence, and (c) a tracr sequence, and II. a polynucleotide sequence encoding a CRISPR enzyme comprising at least one or more nuclear localization sequences, wherein (a), (b) and (c) are arranged in a 5' to 3' orientation, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence and the polynucleotide sequence encoding a CRISPR enzyme is DNA or RNA, or (B) I. polynucleotides comprising:

(a) a guide sequence capable of hybridizing to a target sequence in a prokaryotic cell, and (b) at least one or more tracr mate sequences, II. a polynucleotide sequence encoding a CRISPR enzyme, and III. a polynucleotide sequence comprising a tracr sequence, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, and the polynucleotide sequence encoding a CRISPR enzyme is DNA or RNA.

Any or all of the polynucleotide sequence encoding a CRISPR enzyme, guide sequence, tracr mate sequence or tracr sequence, may be RNA. The polynucleotides encoding the sequence encoding a CRISPR enzyme, the guide sequence, tracr mate sequence or tracr sequence may be RNA and are delivered via nanoparticles, exosomes, microvesicles, or a gene-gun.

It will be appreciated that where reference is made to a polynucleotide, which is RNA and is said to 'comprise' a feature such a tracr mate sequence, the RNA sequence includes the feature. Where the polynucleotide is DNA and is said to comprise a feature such a tracr mate sequence, the DNA sequence is or can be transcribed into the RNA the feature at issue. Where the feature is a protein, such as the CRISPR enzyme, the DNA or RNA sequence referred to is, or can be, translated (and in the case of DNA transcribed first).

Accordingly, in certain embodiments the invention provides method of modifying an organism, e.g., mammal including human or a non-human mammal or organism by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS), wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence.

Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via nanoparticles, exosomes, microvesicles, or a gene-gun.

By manipulation of a target sequence, Applicants also mean the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting or reducing 3D folding.

It will be appreciated that where reference is made to a method of modifying an organism or mammal including human or a non-human mammal or organism by manipulation of a target sequence in a genomic locus of interest, this may apply to the organism (or mammal) as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject (e.g., mammal or human) or a non-human subject (e.g., mammal) in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV vector system comprising one or more AAV vectors comprising operably encoding a composition for expression thereof, wherein the target sequence is manipulated by the composition when expressed, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence.

Some methods of the invention can include inducing expression. In some methods of the invention the organism or subject is a eukaryote (including mammal including human) or a non-human eukaryote or a non-human animal or a non-human mammal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the CRISPR enzyme is a Cas9. In some methods of the invention the expression of the guide sequence is under the control of the T7 promoter is driven by the expression of T7 polymerase.

By manipulation of a target sequence, Applicants also mean the epigenetic manipulation of a target sequence. This may be of the chromatin state of a target sequence, such as by modification of the methylation state of the target sequence (i.e. addition or removal of methylation or methylation patterns or CpG islands), histone modification, increasing or reducing accessibility to the target sequence, or by promoting or reducing 3D folding.

It will be appreciated that where reference is made to a method of modifying an organism or a non-human organism by manipulation of a target sequence in a genomic locus of interest, this may apply to the organism as a whole or just a single cell or population of cells from that organism (if the organism is multicellular). In the case of humans, for instance, Applicants envisage, inter alia, a single cell or a population of cells and these may preferably be modified ex vivo and then re-introduced. In this case, a biopsy or other tissue or biological fluid sample may be necessary. Stem cells are also particularly preferred in this regard. But, of course, in vivo embodiments are also envisaged.

In certain embodiments the invention provides a method of treating or inhibiting a condition caused by a defect in a target sequence in a genomic locus of interest in a subject or a non-human subject in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV vector system comprising one or more AAV vectors comprising operably encoding a composition for expression thereof, wherein the target sequence is manipulated by the composition when expressed, wherein the composition comprises: (A) a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to a target sequence in a eukaryotic cell, (b) a tracr mate sequence, and (c) a tracr sequence, and II. a second regulatory element operably linked to an enzyme-coding sequence encoding a CRISPR enzyme comprising at least one or more nuclear localization sequences (or optionally at least one or more nuclear localization sequences as some embodiments can involve no NLS) wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence, or (B) a non-naturally occurring or engineered composition comprising a vector system comprising one or more vectors comprising I. a first regulatory element operably linked to (a) a guide sequence capable of hybridizing to a target sequence in a prokaryotic cell, and (b) at least one or more tracr mate sequences, II. a second regulatory element operably linked to an enzyme-coding sequence encoding a CRISPR enzyme, and III. a third regulatory element operably linked to a tracr sequence, wherein components I, II and III are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence.

Some methods of the invention can include inducing expression. In some methods of the invention the organism or subject is a eukaryote or a non-human eukaryote or a non-human animal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the CRISPR enzyme is a Cas9. In some methods of the invention the expression of the guide sequence is under the control of the T7 promoter is driven by the expression of T7 polymerase.

The invention in some embodiments comprehends a method of delivering a CRISPR enzyme comprising delivering to a cell mRNA encoding the CRISPR enzyme. In some of these methods the CRISPR enzyme is a Cas9.

The invention in some embodiments comprehends a method of preparing the AAV of the invention comprising transfecting plasmid(s) containing or consisting essentially of nucleic acid molecule(s) coding for the AAV into AAV-infected cells, and supplying AAV rep and/or cap obligatory for replication and packaging of the AAV. In some embodiments the AAV rep and/or cap obligatory for replication and packaging of the AAV are supplied by transfecting the cells with helper plasmid(s) or helper virus(es). In some embodiments the helper virus is a poxvirus, adenovirus, herpesvirus or baculovirus. In some embodiments the poxvirus is a vaccinia virus. In some embodiments the cells are mammalian cells. And in some embodiments the cells are insect cells and the helper virus is baculovirus.

In plants, pathogens are often host-specific. For example, *Fusarium oxysporum* f. sp. *lycopersici* causes tomato wilt but attacks only tomato, and *F. oxysporum* f. *dianthii* *Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

The invention further comprehends a composition of the invention or a CRISPR enzyme thereof (including or alternatively mRNA encoding the CRISPR enzyme) for use in medicine. In some embodiments the invention comprehends a composition according to the invention or a CRISPR enzyme thereof (including or alternatively mRNA encoding the CRISPR enzyme) for use in a method according to the invention. In some embodiments the invention provides for the use of a composition of the invention or a CRISPR enzyme thereof (including or alternatively mRNA encoding the CRISPR enzyme) in ex vivo gene or genome editing. In certain embodiments the invention comprehends use of a composition of the invention or a CRISPR enzyme thereof (including or alternatively mRNA encoding the CRISPR enzyme) in the manufacture of a medicament for ex vivo gene or genome editing or for use in a method according of the invention. The invention comprehends in some embodiments a composition of the invention or a CRISPR enzyme thereof (including or alternatively mRNA encoding the CRISPR enzyme), wherein the target sequence is flanked at its 3' end by 5'-motif (where N is any Nucleotide), especially where the Cas9 is (or is derived from) S. pyogenes or S. aureus Cas9. For example, a suitable PAM is 5'-NRG or 5'-NNGRR for SpCas9 or SaCas9 enzymes (or derived enzymes), respectively, as mentioned below.

It will be appreciated that SpCas9 or SaCas9 are those from or derived from S. pyogenes or S. aureus Cas9.

Aspects of the invention comprehend improving the specificity of a CRISPR enzyme, e.g. Cas9, mediated gene targeting and reducing the likelihood of off-target modification by the CRISPR enzyme, e.g. Cas9. The invention in some embodiments comprehends a method of modifying an organism or a non-human organism with a reduction in likelihood of off-target modifications by manipulation of a first and a second target sequence on opposite strands of a DNA duplex in a genomic locus of interest in a cell comprising delivering a non-naturally occurring or engineered composition comprising:

I. a first CRISPR-Cas system chimeric RNA (chiRNA) polynucleotide sequence, wherein the first polynucleotide sequence comprises:
(a) a first guide sequence capable of hybridizing to the first target sequence,
(b) a first tracr mate sequence, and
(c) a first tracr sequence,
II. a second CRISPR-Cas system chiRNA polynucleotide sequence, wherein the second polynucleotide sequence comprises:
(a) a second guide sequence capable of hybridizing to the second target sequence,
(b) a second tracr mate sequence, and
(c) a second tracr sequence, and
III. a polynucleotide sequence encoding a CRISPR enzyme comprising at least one or more nuclear localization sequences and comprising one or more mutations, wherein (a), (b) and (c) are arranged in a 5' to 3' orientation, wherein when transcribed, the first and the second tracr mate sequence hybridize to the first and second tracr sequence respectively and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the first tracr mate sequence that is hybridized to the first tracr sequence, wherein the second CRISPR complex comprises the CRISPR enzyme complexed with (1) the second guide sequence that is hybridized to the second target sequence, and (2) the second tracr mate sequence that is hybridized to the second tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism with a reduction in likelihood of off-target modifications.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the polynucleotides encoding the sequence encoding the CRISPR enzyme, the first and the second guide sequence, the first and the second tracr mate sequence or the first and the second tracr sequence, is/are RNA and are delivered via nanoparticles, exosomes, microvesicles, or a gene-gun. In certain embodiments of the invention, the first and second tracr mate sequence share 100% identity and/or the first and second tracr sequence share 100% identity. It is not necessarily the case for 100% identity between the first tracr and second tracr sequence: Many of the altered scaffolds have changes to the DR/TracR sequences as well as the distal hairpins. It is also possible to have tandems involving alternate scaffolds that have distinct DR/TRACR sequences. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation.

In preferred methods of the invention the first guide sequence directing cleavage of one strand of the DNA duplex near the first target sequence and the second guide sequence directing cleavage of other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

The invention in some embodiments comprehends a method of modifying an organism or a non-human organism with a reduction in likelihood of off-target modifications by manipulation of a first and a second target sequence on opposite strands of a DNA duplex in a genomic locus of interest in a cell comprising delivering a non-naturally occurring or engineered composition comprising a vector system comprising one or more vectors comprising
I. a first regulatory element operably linked to
(a) a first guide sequence capable of hybridizing to the first target sequence, and
(b) at least one or more tracr mate sequences,
II. a second regulatory element operably linked to
(a) a second guide sequence capable of hybridizing to the second target sequence, and
(b) at least one or more tracr mate sequences,
III. a third regulatory element operably linked to an enzyme-coding sequence encoding a CRISPR enzyme, and
IV. a fourth regulatory element operably linked to a tracr sequence,
wherein components I, II, III and IV are located on the same or different vectors of the system, when transcribed, the tracr mate sequence hybridizes to the tracr sequence and the first and the second guide sequence directs sequence-specific binding of a first and a second CRISPR complex to the first and second target sequences respectively, wherein the first CRISPR complex comprises the CRISPR enzyme complexed with (1) the first guide sequence that is hybridized to the first target sequence, and (2) the tracr mate sequence that is hybridized to the tracr sequence, wherein the second CRISPR complex comprises the CRISPR enzyme complexed with (1) the second guide sequence that is hybridized to the second target sequence, and (2) the tracr mate sequence that is hybridized to the tracr sequence, wherein the polynucleotide sequence encoding a CRISPR enzyme is DNA or RNA, and wherein the first guide sequence directs cleavage of one strand of the DNA duplex near the first target sequence and the second guide sequence directs cleavage of other strand near the second target sequence inducing a double strand break, thereby modifying the organism or the non-human organism with a reduction in likelihood of off-target modifications.

In some methods of the invention any or all of the polynucleotide sequence encoding the CRISPR enzyme, the first and the second guide sequence, the first and the second tracr mate sequence or the first and the second tracr sequence, is/are RNA. In further embodiments of the invention the first and second tracr mate sequence share 100% identity and/or the first and second tracr sequence share 100% identity. It is not necessarily the case for 100% identity between the first tracr and second tracr sequence: Many of the altered scaffolds have changes to the DR/TracR sequences as well as the distal hairpins. It is also possible to have tandems involving alternate scaffolds that have distinct DR/TRACR sequences. In preferred embodiments of the invention the CRISPR enzyme is a Cas9 enzyme, e.g. SpCas9. In an aspect of the invention the CRISPR enzyme comprises one or more mutations in a catalytic domain, wherein the one or more mutations are selected from the group consisting of D10A, E762A, H840A, N854A, N863A and D986A. In a highly preferred embodiment the CRISPR enzyme has the D10A mutation. In a further embodiment of the invention, one or more of the viral vectors are delivered via nanoparticles, exosomes, microvesicles, or a gene-gun.

In preferred methods of the invention the first guide sequence directing cleavage of one strand of the DNA duplex near the first target sequence and the second guide sequence directing cleavage of other strand near the second target sequence results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

The invention in some embodiments comprises a method of modifying a genomic locus of interest with a reduction in likelihood of off-target modifications by introducing into a cell containing and expressing a double stranded DNA molecule encoding the gene product an engineered, non-naturally occurring CRISPR-Cas system comprising a Cas protein having one or more mutations and two guide RNAs that target a first strand and a second strand of the DNA molecule respectively, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In preferred methods of the invention the Cas protein nicking each of the first strand and the second strand of the DNA molecule encoding the gene product results in a 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs.

Embodiments of the invention also comprehend the guide RNAs comprising a guide sequence fused to a tracr mate sequence and a tracr sequence. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring CRISPR-Cas system comprising a Cas protein having one or more mutations and two guide RNAs that target a first strand and a second strand respectively of a double stranded DNA molecule encoding a gene product in a cell, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

The invention also comprehends an engineered, non-naturally occurring vector system comprising one or more vectors comprising:

a) a first regulatory element operably linked to each of two CRISPR-Cas system guide RNAs that target a first strand and a second strand respectively of a double stranded DNA molecule encoding a gene product, b) a second regulatory element operably linked to a Cas protein, wherein components (a) and (b) are located on same or different vectors of the system, whereby the guide RNAs target the DNA molecule encoding the gene product and the Cas protein nicks each of the first strand and the second strand of the DNA molecule encoding the gene product, whereby expression of the gene product is altered; and, wherein the Cas protein and the two guide RNAs do not naturally occur together.

In aspects of the invention the guide RNAs may comprise a guide sequence fused to a tracr mate sequence and a tracr sequence. In an embodiment of the invention the Cas protein is a type II CRISPR-Cas protein. In an aspect of the invention the Cas protein is codon optimized for expression in a eukaryotic cell, wherein it may be a mammalian cell or a human cell. In further embodiments of the invention the Cas protein is a type II CRISPR-Cas protein, e.g. a Cas 9 protein. In a highly preferred embodiment the Cas protein is a Cas9 protein, e.g. SpCas9. In aspects of the invention the Cas protein has one or more mutations selected from the group consisting of D10A, E762A, H840A, N854A, N863A and D986A. In a highly preferred embodiment the Cas protein has the D10A mutation.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. In preferred embodiments of the invention the vectors of the system are viral vectors. In a further embodiment, the vectors of the system are delivered via nanoparticles, exosomes, microvesicles, or a gene-gun.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more prokaryotic cell(s) by introducing one or more mutations in a gene in the one or more prokaryotic cell (s), the method comprising: introducing one or more vectors into the prokaryotic cell (s), wherein the one or more vectors drive expression of one or more of: a CRISPR enzyme, a guide sequence linked to a tracr mate sequence, a tracr sequence, and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, wherein binding of the CRISPR complex to the target polynucleotide induces cell death, thereby allowing one or more prokaryotic cell(s) in which one or more mutations have been introduced to be selected. In a preferred embodiment, the CRISPR enzyme is Cas9. In another aspect of the invention the cell to be selected may be a eukaryotic cell. Aspects of the invention allow for selection of specific cells without requiring a selection marker or a two-step process that may include a counter-selection system.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In other embodiments, this invention provides a method of modifying expression of a polynucleotide in a eukaryotic cell. The method comprises increasing or decreasing expression of a target polynucleotide by using a CRISPR complex that binds to the polynucleotide.

Where desired, to effect the modification of the expression in a cell, one or more vectors comprising a tracr sequence, a guide sequence linked to the tracr mate sequence, a sequence encoding a CRISPR enzyme is delivered to a cell. In some methods, the one or more vectors comprises a regulatory element operably linked to an enzyme-coding sequence encoding said CRISPR enzyme comprising a nuclear localization sequence; and a regulatory element operably linked to a tracr mate sequence and one or more insertion sites for inserting a guide sequence upstream of the tracr mate sequence. When expressed, the guide sequence directs sequence-specific binding of a CRISPR complex to a target sequence in a cell. Typically, the CRISPR complex comprises a CRISPR enzyme complexed with (1) the guide sequence that is hybridized to the target sequence, and (2) the tracr mate sequence that is hybridized to the tracr sequence.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations D10A, E762A, H840A, N854A, N863A or D986A and/or the one or more mutations is in a RuvC1 or HNH domain of the CRISPR enzyme or is a mutation as otherwise as discussed herein. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain. In some embodiments, a transcriptional activation domain is VP64. In some embodiments, a transcription repression domains is KRAB. In some embodiments, a transcription repression domain is SID, or concatemers of SID (i.e. SID4X). In some embodiments, an epigenetic modifying enzyme is provided. In some embodiments, an activation domain is provided, which may be the P65 activation domain.

In some embodiments, the CRISPR enzyme is a type I or III CRISPR enzyme, preferably a type II CRISPR enzyme. This type II CRISPR enzyme may be any Cas enzyme. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in Streptococcus pyogenes. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

Preferably, delivery is in the form of a vector which may be a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. A vector may mean not only a viral or yeast system (for instance, where the nucleic acids of interest may be operably linked to and under the control (in terms of expression, such as to ultimately provide a processed RNA) a promoter), but also direct delivery of nucleic acids into a host cell. While in herein methods the vector may be a viral vector and this is advantageously an AAV, other viral vectors as herein discussed can be employed. For example, baculoviruses may be used for expression in insect cells. These insect cells may, in turn be useful for producing large quantities of further vectors, such as AAV vectors adapted for delivery of the present invention. Also envisaged is a method of delivering the present CRISPR enzyme comprising delivering to a cell mRNA encoding the CRISPR enzyme. It will be appreciated that the CRISPR enzyme is truncated, comprised of less than one thousand amino acids or less than four thousand amino acids, is a nuclease or nickase, is codon-optimized comprises one or more mutations, and/or comprises a chimeric CRISPR enzyme, or the other options as herein discussed. AAV viral vectors are preferred.

In certain embodiments, the target sequence is flanked or followed, at its 3' end, by a PAM suitable for the CRISPR enzyme, typically a Cas and in particular a Cas9.

For example, a suitable PAM is 5'-NRG or 5'-NNGRR for SpCas9 or SaCas9 enzymes (or derived enzymes), respectively.

It will be appreciated that SpCas9 or SaCas9 are those from or derived from S. pyogenes or S. aureus Cas9.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-F shows a schematic representation assay carried out to evaluate the cleavage specificity of Cas9 form *Streptococcus pyogenes*. Single base pair mismatches between the guide RNA sequence and the target DNA are mapped against cleavage efficiency in %.

FIG. 2C discloses a pre-crRNA array consisting of a single spacer flanked by two direct repeats (DRs) SEQ ID NO: 341 and the 33-base-pair (bp) target site (30-bp protospacer plus a 3-bp CRISPR motif (PAM) sequence in the human EMX1 genomic locus (SEQ ID NO: 342). FIG. 2E discloses SEQ ID NOS 343-345, respectively, in order of appearance. FIG. 2F discloses SEQ ID NOS 346-350, respectively, in order of appearance.

Figure 4A:
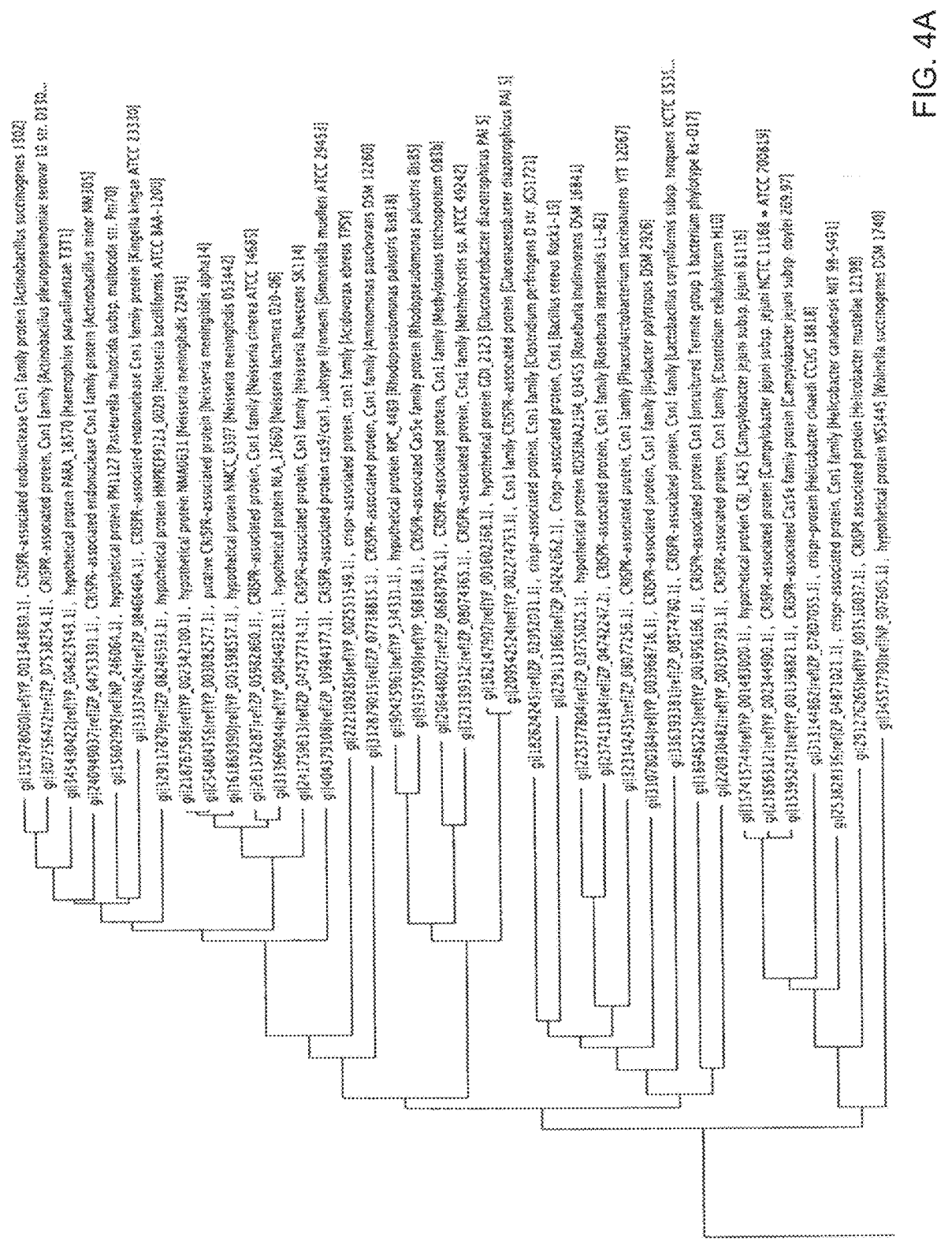
Figure 4C:
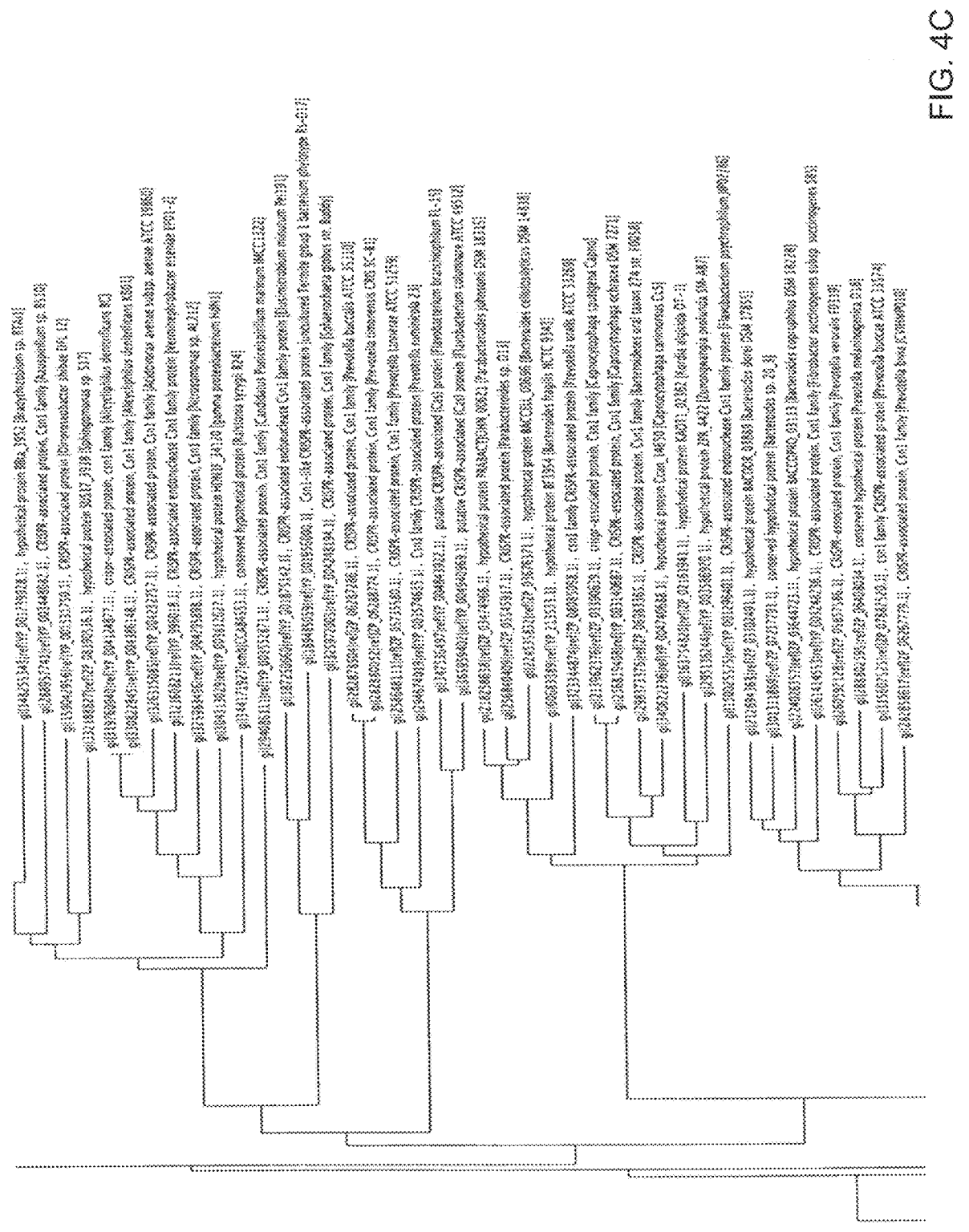
Figure 4E:
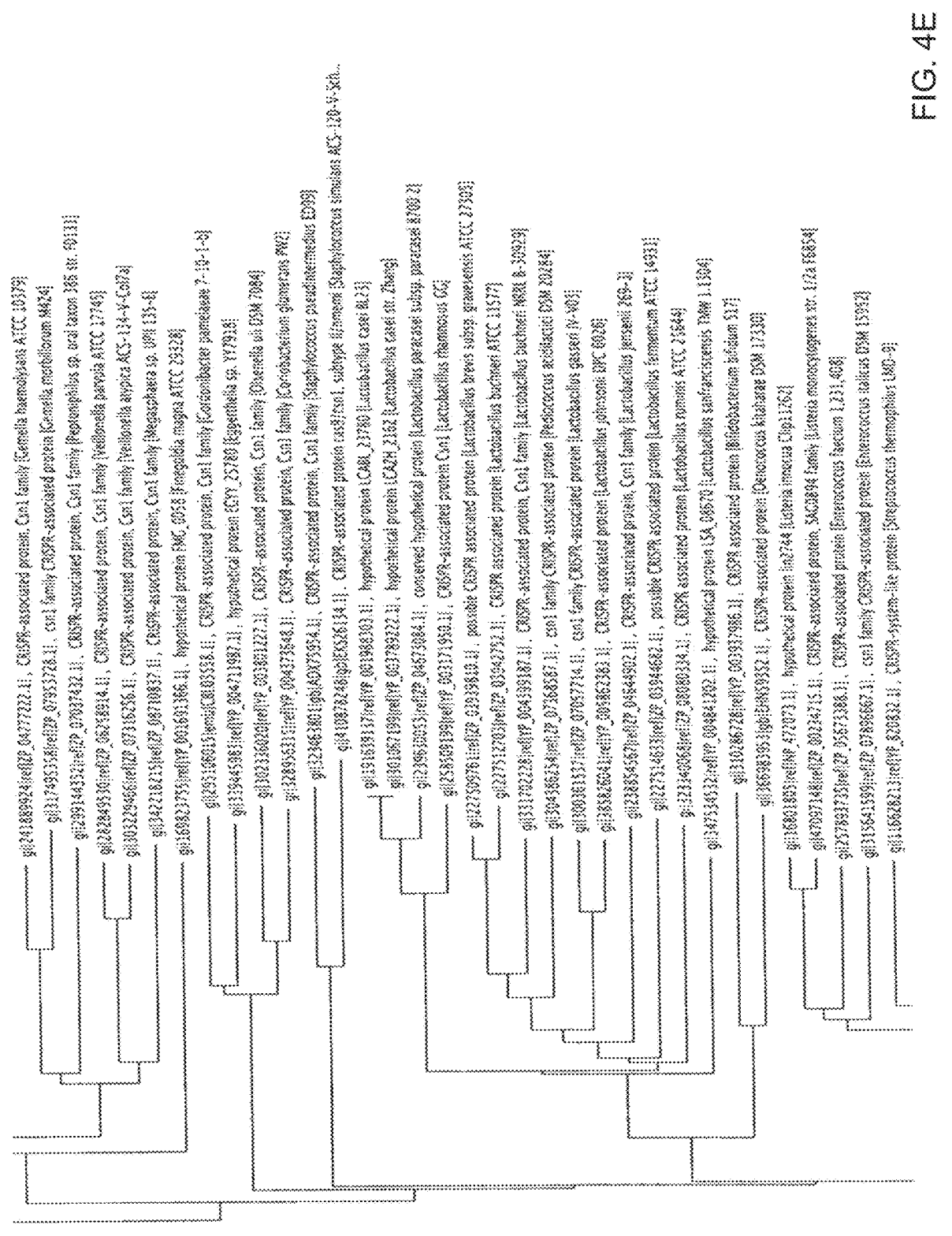
Figure 4F:
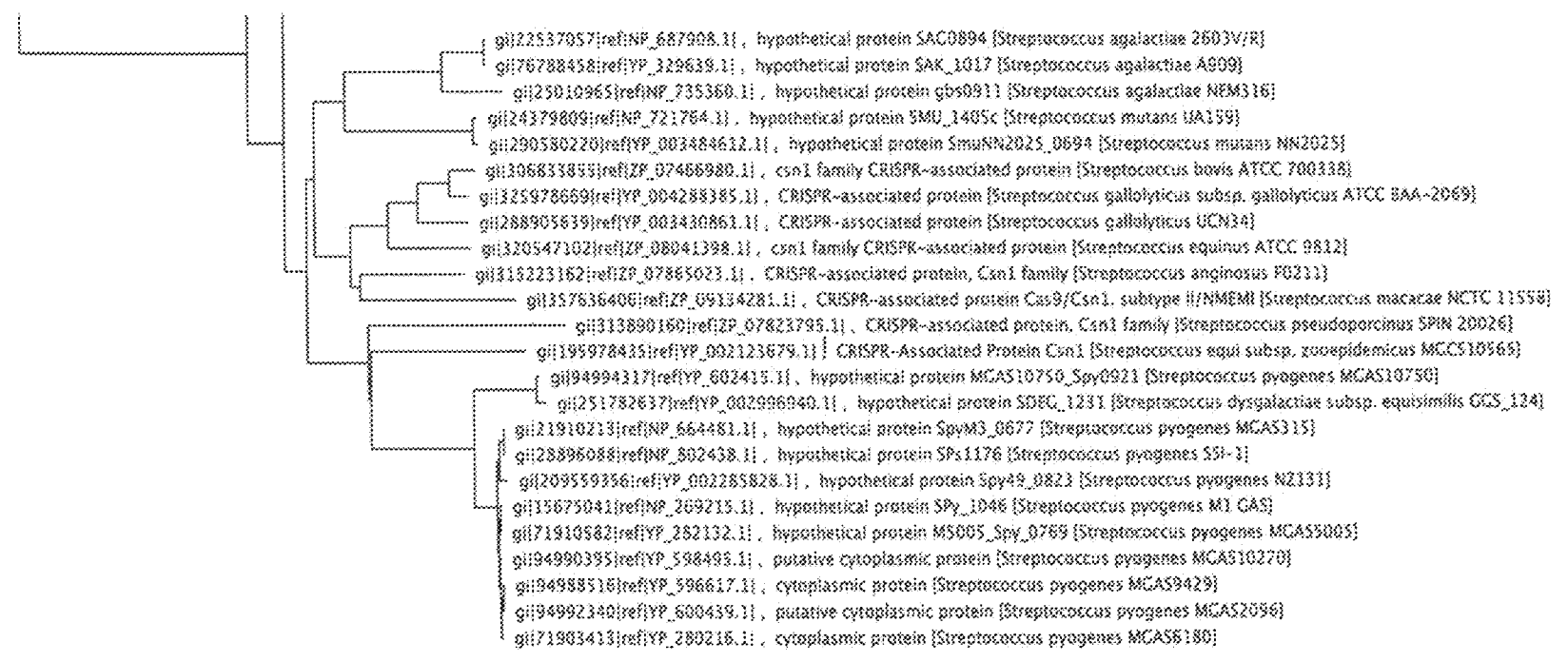

FIG. 4A-F shows the linear phylogenetic analysis revealing five families of Cas9s, including three groups of large Cas9s (~1400 amino acids) and two of small Cas9s (~1100 amino acids).

Figure 6G:
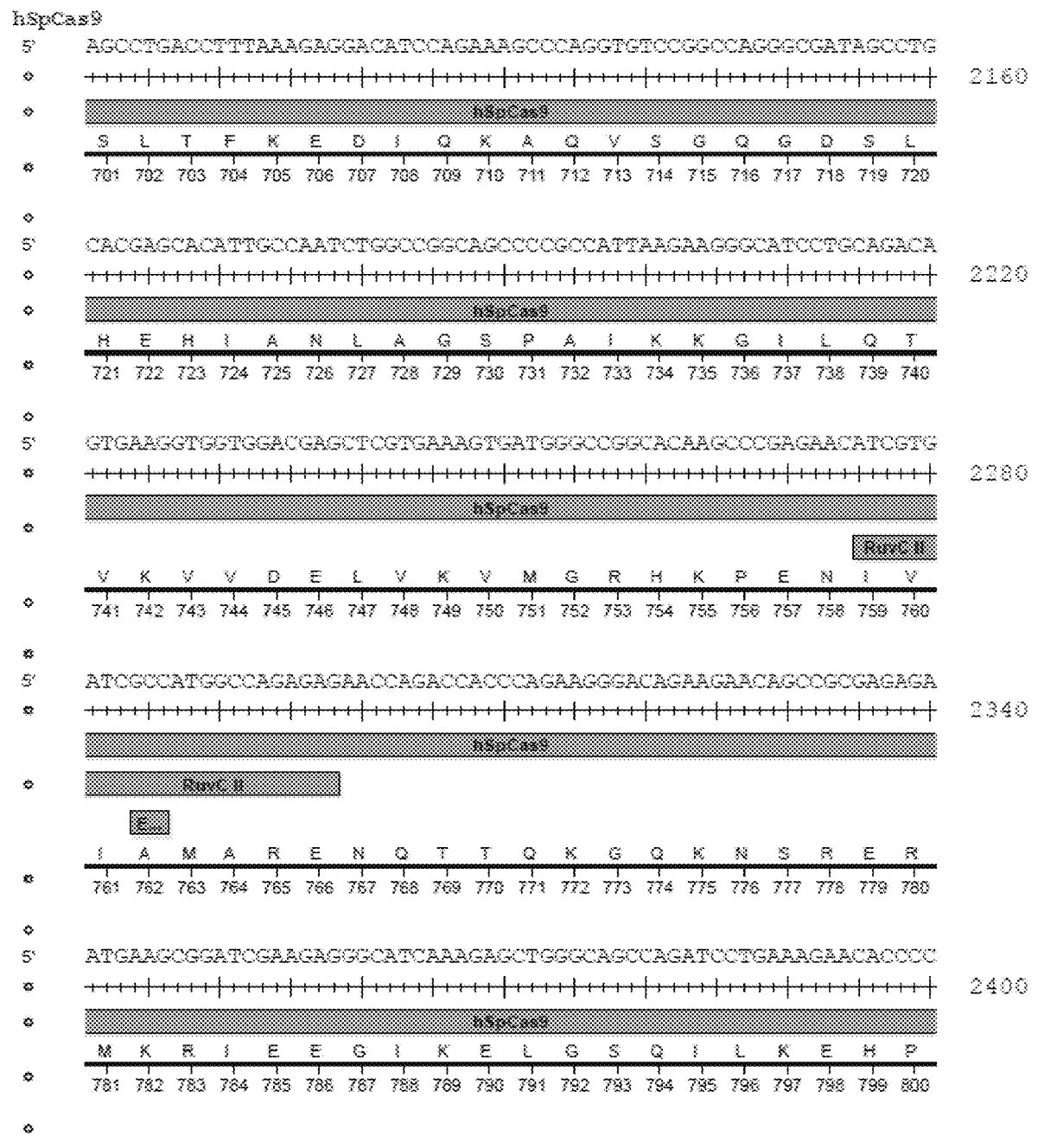
Figure 6I:
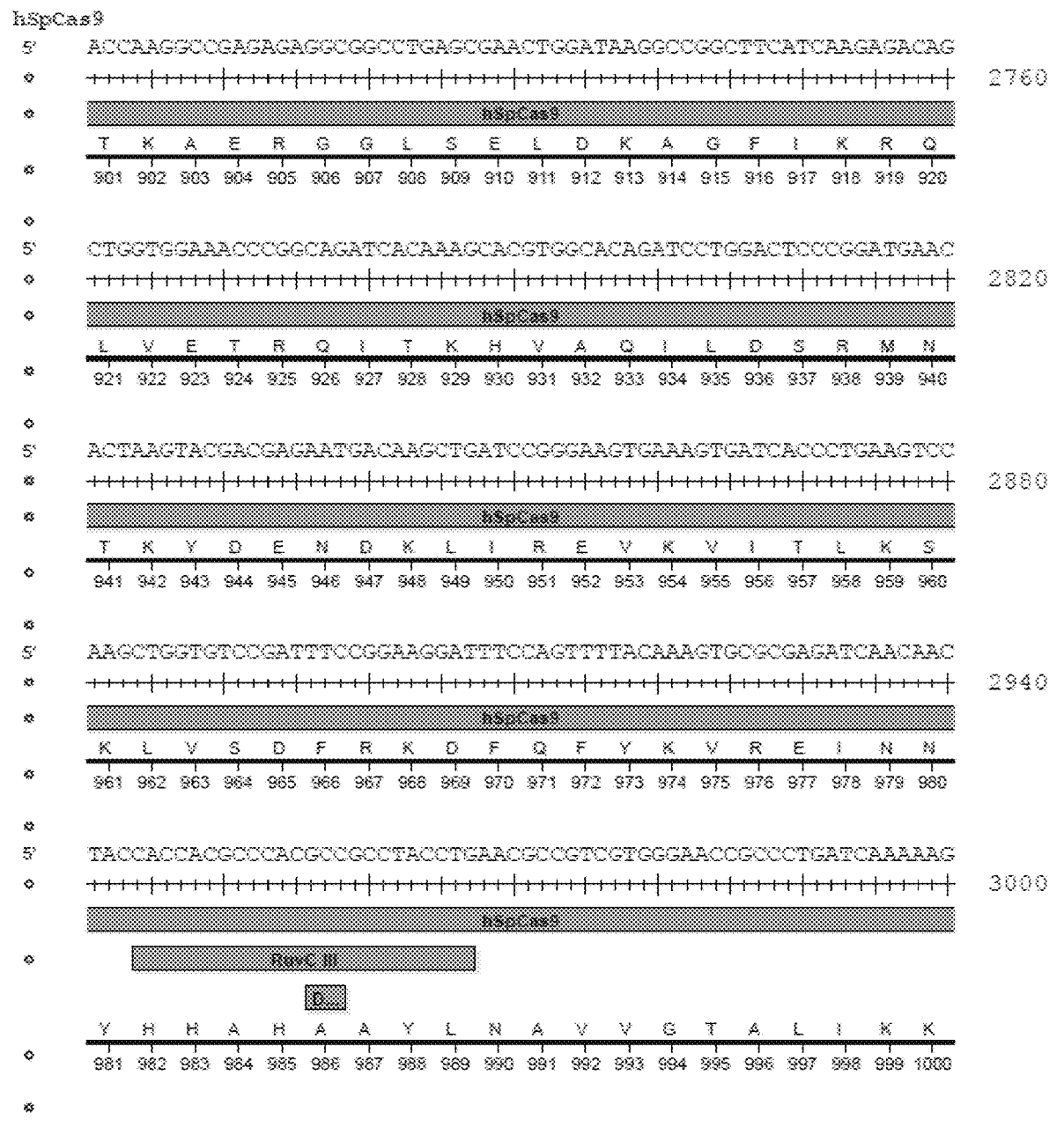

FIG. 6A-M shows sequences where the mutation points are located within the SpCas9 gene. FIG. 6A-M discloses the nucleotide sequence as SEQ ID NO: 351 and the amino acid sequence as SEQ ID NO: 352.

FIG. 9 shows delivery and in vivo mouse brain Cas9 expression data.

FIG. 12B discloses from top to bottom, a genomic locus comprising, in order, SEQ ID NOS: 353, 354, and 355, a repair template oriented in the sense direction comprising, in order, SEQ ID NOS: 353, 356 and 355, and a repair template oriented in the antisense direction comprising SEQ ID NOS: 481, 482, and 483.

FIG. 13A-C shows the repair strategy for Cystic Fibrosis delta F508 mutation. FIG. 13A discloses the nucleotide sequence of a segment of the human CFTR genomic locus (SEQ ID NO: 357) and the encoded amino acid sequence SEQ ID NO:358). FIG. 13B discloses SEQ ID NO: 445. FIG. 13C discloses repair templates for the deltaF508 mutation (SEQ ID NOS: 359 and 484 and the encoded amino acid sequence (SEQ ID NO: 360).

FIG. 24 shows expression of SpCas9 and SaCas9 in cortical primary neurons in culture 7 days after transduction. Representative Western blot of HA-tagged SpCas9 and SaCas9 versions under the control of different promoters and with bgh or short polyA (spA) sequences. Tubulin is loading control.

FIG. 33 shows (top) a list of spacing (as indicated by the pattern of arrangement for two PAM sequences) between pairs of guide RNAs (SEQ ID NOS 361-377, respectively, in order of appearance). Only guide RNA pairs satisfying patterns 1, 2, 3, 4 exhibited indels when used with SpCas9 (D10A) nickase. (bottom) Gel images showing that combination of SpCas9(D10A) with pairs of guide RNA satisfying patterns 1, 2, 3, 4 led to the formation of indels in the target site.

FIG. 34 shows a list of U6 reverse primer sequences (SEQ ID NOS 379-425 and 381, respectively, in order of appearance) used to generate U6-guide RNA expression cassettes. Each primer needs to be paired with the U6 forward primer "gcactgagggcctatttcccatgattc" (SEQ ID NO: 378) to generate amplicons containing U6 and the desired guide RNA.

FIG. 35 shows a Genomic sequence map from the human Emx1 locus showing the locations of the 24 patterns listed in FIG. 33. FIG. 35 discloses the hEMX1 target locus (SEQ ID NO: 426) and the four amino acid sequences encoded in Frame 1 (SEQ ID NOS 427-430, respectively, in order of appearance).

FIG. 36 shows on (right) a gel image indicating the formation of indels at the target site when variable 5' overhangs are present after cleavage by the Cas9 nickase targeted by different pairs of guide RNAs. on (left) a table indicating the lane numbers of the gel on the right and various parameters including identifying the guide RNA pairs used and the length of the 5' overhang present following cleavage by the Cas9 nickase.

FIG. 37 discloses the hEMX1 target locus (SEQ ID NO: 426) and the four amino acid sequences encoded in Frame 1 (SEQ ID NOS 427-430, respectively, in order of appearance).

FIG. 38A-D shows (A) Optimization of sgRNA scaffold for additional stability; Architectures A (SEQ ID NO: 431) and B (SEQ ID NO: 432) are indicated. (B) a schematic illustrating a tandem sgRNA (2 sgRNAs connected by a linker) driven by a single U6 promoter (C) a gel figure indicating tsgRNAs are designed to target a region of EMX1 so that, when co-transfected into HEK cells with wt Cas9, mediates a genomic microdeletion. Here, the targets flank the last exon of EMX1. tsgRNAs are synthesized with either custom scaffold A or B that differ from the wt sgRNA scaffold (as indicated above). A single tsgRNA encoding 2 spacers, with either architecture A or B, when co-delivered with wt Cas9, mediates a similar level of genomic microdeletion as two wt sgRNAs co-delivered with wt Cas9. FIG. 38C discloses a tsgRNA encoding two spacers comprising SEQ ID NOS 433 and 434, and genomic microdeletion (SEQ ID NO:435). (D) a gel figure where, alternatively, tsgRNAs are designed to target a region of EMX1 so that, when co-transfected into HEK cells with D10A Cas9, mediates an indel as previously described in double nickase experiments. Spacers are chosen so that the left and right targets are offset with at least 0, or 4-bp of non-overlap in between the 20-bp targets, and resulting cuts from D10A would generate 5'-overhangs. The gel image shows SURVEYOR assay measuring indels from either D10A Cas9 co-transfected with either a single tsgRNA encoding 2 spacers or two separate sgRNA, where the former can mediate a similar level of indels as the latter.

FIG. 39A-C shows (A) tandem lentiviral vector design. (B) the scaffold sequences for LentiCRISPR (SEQ ID NOS 436-440, respectively, in order of appearance). (C) a schematic and gel image indicating that the tandem guide RNAs constructed of modified scaffolds are more efficiently processed to individual units.

FIG. 40A discloses SEQ ID NOS 441-443, respectively, in order of appearance. (B) Representative gel image showing Cas9n mediated indel in the EMX1 locus of the human genome, as detected using the SURVEYOR nuclease assay with 650 bp band representing the unmodified genomic target and bands around 300 bp indicating the presence of indels.

FIG. 42A discloses sequence of the human EMX1 genomic locus (SEQ ID NOS 453) showing location of nicks from targeting with depicted sgRNAs and ssODN template (SEQ ID NO:454). (B) Restriction digest assay gel showing successful insertion of HindIII cleavage sites by double nicking-facilitated HDR in HEK 293FT cells. Upper bands are unmodified template; lower bands are HindIII cleavage product. (C) Double nicking enhances HDR in HUES62 cells. HDR frequencies determined using deep sequencing. (n=3; error bars show mean±s.e.)

FIG. 44A-D shows double-nicking reduces non-specific activity at known off-target sites. (A) Schematic showing the target human EMX1 genomic locus (SEQ ID NO: 455) and target and nicking sites of two different sgRNAs with a 23 bp offset that target opposite strands of the duplex. Genomic off-target sites for the right sgRNA (sgRNA1) are listed below (SEQ ID NOS 456-460, respectively, in order of appearance). Off-target sites were identified previously as described in Hsu et al 48. (B) SURVEYOR gels showing modification at the on-target site by Cas9n with two sgRNAs as well as by wild-type Cas9 with individual sgRNA. Indels at off-target 5 were only observed for wild-type Cas9 with sgRNA 1. (C) The levels of off-target modification are quantified using deep sequencing at all five off-target loci. (D) Specificity comparison of Cas9n and wild-type Cas9. The specificity ratio is calculated by taking the ratio of on-target and off-target modification rates. (n=3; error bars show mean±s.e.)

FIG. 46 shows distal hairpin and DDR stabilization retains comparable indel activity (SEQ ID NOS 431-432 and 461, respectively, in order of appearance). Schematic showing sequence of three alternative scaffold architectures aimed at stabilization of the hairpins with changes base-pairs denoted in black. Indel-inducing activity of corresponding scaffolds compared to the wild-type sp85 architecture is shown at right.

FIG. 47C discloses a tsgRNA encoding two spacers comprising SEQ ID NOS 433 and 434, and genomic microdeletion (SEQ ID NO:435).

FIG. 52 shows different truncations of the Bi-directional U6 promoter and associated microdeletion activity and quantification of indel-inducing activity coming off of either side of the bi-directional promoter.

FIG. 53 shows a sequence of the smallest U6-8/U6-1 bi-directional reporter (SEQ ID NO:480) and four primers for assembly (SEQ ID NOS: 55, 57, 59 and 61, respectively, in order of appearance).

DETAILED DESCRIPTION OF THE INVENTION

Figure 1:
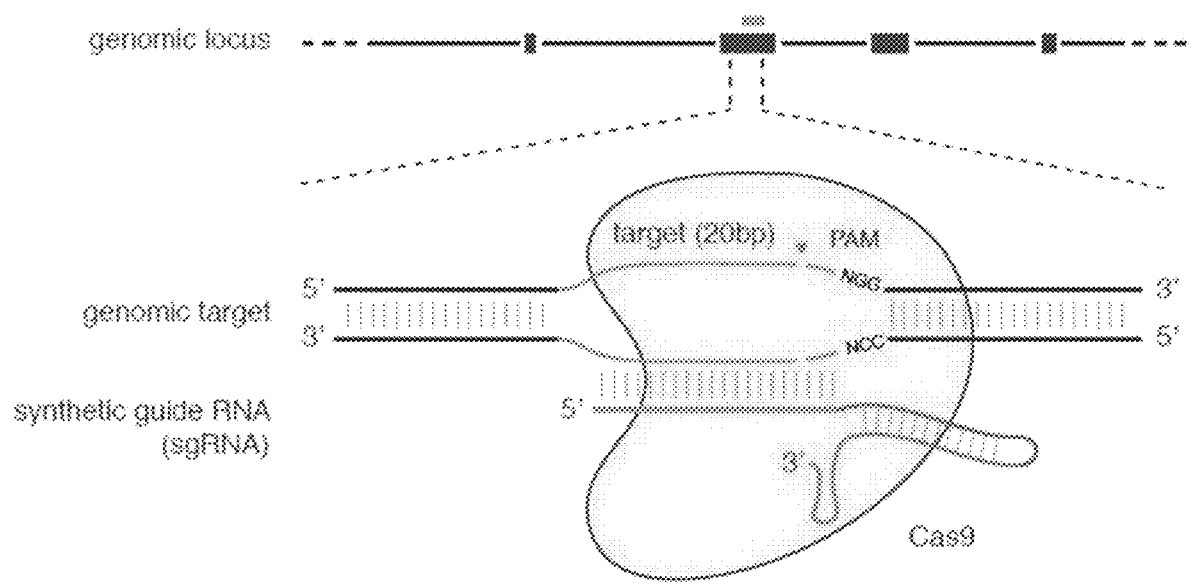
FIG. 1 shows a schematic model of the CRISPR system. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

Reference is made to U.S. provisional patent application 61/862,468, filed on Aug. 8, 2013. Reference is made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent applications 61/836,123 and 61/847,537, filed on Jun. 17, 2013 and Jul. 17, 2013 respectively. Reference is also made to U.S. provisional patent applications 61/736,527 and 61/748,427, filed on Dec. 12, 2012 and Jan. 2, 2013, respectively. Reference is also made to U.S. provisional patent application 61/791,409, filed on Mar. 15, 2013. Reference is also made to U.S. provisional patent application 61/799,800, filed Mar. 15, 2013. Reference is also made to U.S. provisional patent applications 61/835,936, 61/836,127, 61/836, 101, 61/836,123, 61/836,080 and 61/835,973, each filed Jun. 17, 2013. Reference is also made to U.S. provisional patent application 61/842,322 and U.S. patent application Ser. No. 14/054,414, filed on Jul. 2, 2013 and Oct. 15, 2013 respectively. Reference is also made to U.S. provisional patent application 61/915,407, filed Dec. 12, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems.* Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121):819-23 (2013);

*RNA-guided editing of bacterial genomes using CRISPR-Cas systems.* Jiang W., Bikard D., Cox D., Zhang F, Marraffini L A. *Nat Biotechnol* March; 31(3):233-9 (2013);

*One-Step Generation of Mice Carrying Mutations in Multiple Genes by CRISPR/Cas-Mediated Genome Engineering.* Wang H., Yang H., Shivalila C S., Dawlaty M M., Cheng A W., Zhang F., Jaenisch R. *Cell* May 9; 153(4): 910-8 (2013);

*Optical control of mammalian endogenous transcription and epigenetic states.* Konermann S, Brigham M D, Trevino A E, Hsu P D, Heidenreich M, Cong L, Platt R J, Scott D A, Church G M, Zhang F. *Nature.* 2013 Aug. 22; 500(7463):472-6. doi: 10.1038/Nature12466. Epub 2013 Aug. 23;

*Double Nicking by RNA-Guided CRISPR Cas9 for Enhanced Genome Editing Specificity.* Ran, F A., Hsu, P D., Lin, C Y., Gootenberg, J S., Konermann, S., Trevino, A E., Scott, D A., Inoue, A., Matoba, S., Zhang, Y., & Zhang, F. *Cell* August 28. pii: S0092-8674(13)01015-5. (2013);

*DNA targeting specificity of RNA-guided Cas9 nucleases.* Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system.* Ran, F A., Hsu, P D., Wright, J., Agarwala, V., Scott, D A., Zhang, F. *Nature Protocols* November; 8(11):2281-308. (2013);

*Genome-Scale CRISPR-Cas9 Knockout Screening in Human Cells.* Shalem, O., Sanjana, N E., Hartenian, E., Shi, X., Scott, D A., Mikkelson, T., Heckl, D., Ebert, B L., Root, D E., Doench, J G., Zhang, F. *Science* December 12. (2013). [Epub ahead of print];

*Crystal structure of cas9 in complex with guide RNA and target DNA.* Nishimasu, H., Ran, F A., Hsu, P D., Konermann, S., Shehata, S I., Dohmae, N., Ishitani, R., Zhang, F., Nureki, O. *Cell* February 27. (2014). 156(5):935-49;

*Genome-wide binding of the CRISPR endonuclease Cas9 in mammalian cells.* Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol.* (2014) April 20. doi: 10.1038/nbt.2889, and

*Development and Applications of CRISPR-Cas9 for Genome Engineering,* Hsu et al, Cell 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9.

An advantage of the present methods is that the CRISPR system avoids off-target binding and its resulting side effects. This is achieved using systems arranged to have a high degree of sequence specificity for the target DNA.

Cas9 optimization may be used to enhance function or to develop new functions, one can generate chimeric Cas9 proteins. Examples that the Applicants have generated are provided in Example 6. Chimeric Cas9 proteins can be made by combining fragments from different Cas9 homologs. For example, two example chimeric Cas9 proteins from the Cas9s described herein. For example, Applicants fused the N-term of St1Cas9 (fragment from this protein is in bold) with C-term of SpCas9. The benefit of making chimeric Cas9s include any or all of:
  reduced toxicity;
  improved expression in eukaryotic cells;
  enhanced specificity;
  reduced molecular weight of protein, make protein smaller by combining the smallest domains from different Cas9 homologs; and/or
  altering the PAM sequence requirement.

The Cas9 may be used as a generic DNA binding protein. For example, and as shown in Example 7, Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9. Other transcriptional activation domains are known. As shown in Example 11, transcriptional activation is possible. As also shown in Example 11, gene repression (in this case of the beta-catenin gene) is possible using a Cas9 repressor (DNA-binding domain) that binds to the target gene sequence, thus repressing its activity.

Figure 7A:
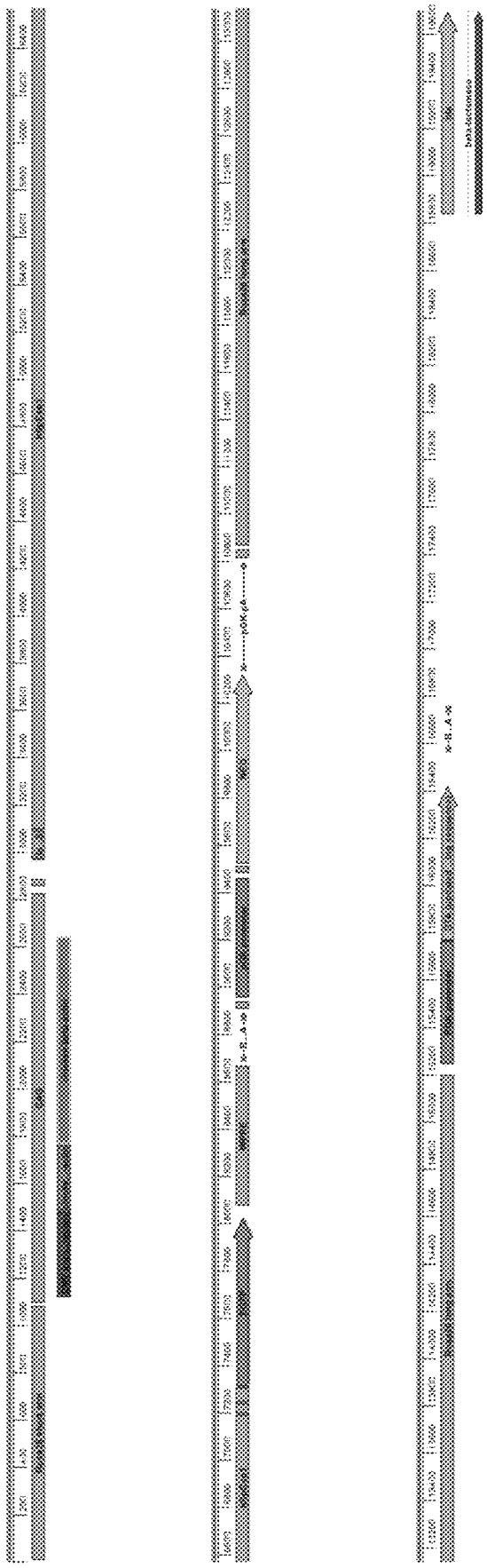
FIG. 7A shows the Conditional Cas9, Rosa26 targeting vector map.
Figure 7B:
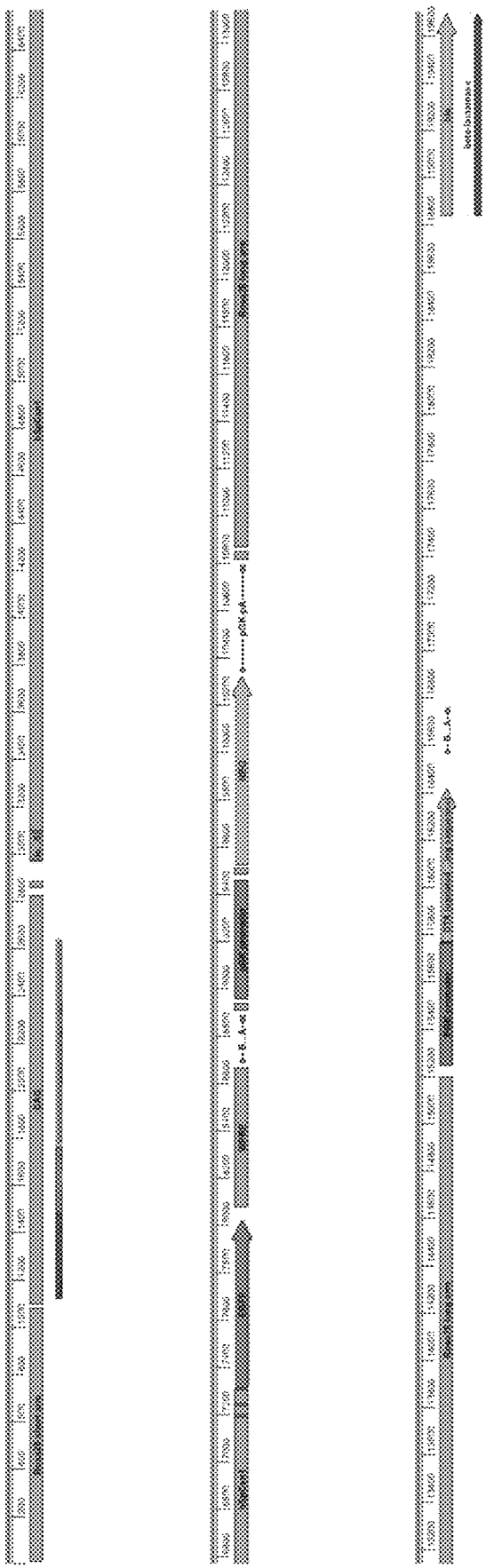
FIG. 7B shows the Constitutive Cas9, Rosa26 targeting vector map.
Figure 8:
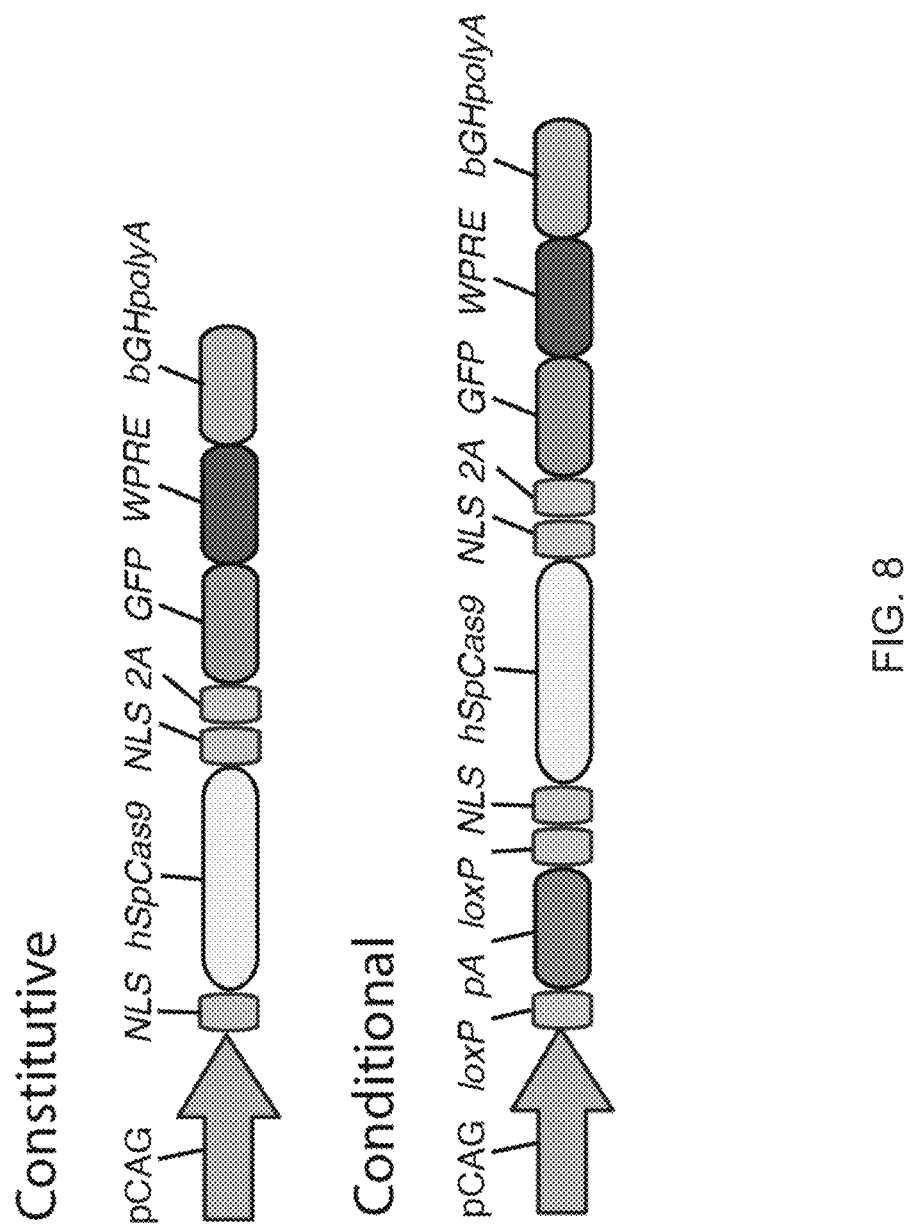
FIG. 8 shows a schematic of the important elements in the Constitutive and Conditional Cas9 constructs.

Transgenic animals are also provided. Preferred examples include animals comprising Cas9, in terms of polynucleotides encoding Cas9 or the protein itself. Mice, rats and rabbits are preferred. To generate transgenic mice with the constructs, as exemplified herein one may inject pure, linear DNA into the pronucleus of a zygote from a pseudo pregnant female, e.g. a CB56 female. Founders may then be identified are identified, genotyped, and backcrossed to CB57 mice. The constructs may then be cloned and optionally verified, for instance by Sanger sequencing. Knock outs are envisaged where for instance one or more genes are knocked out in a model. However, are knockins are also envisaged (alone or in combination). An example Knock in Cas9 mouse was generated and this is exemplified, but Cas9 knockins are preferred. To generate a Cas9 knock in mice one may target the same constitutive and conditional constructs to the Rosa26 locus, as described herein (FIGS. 7A-B and 8).

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. Applicants have shown Cas9 activation in mESCs. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

As mentioned above, transgenic animals are also provided, as are transgenic plants, especially crops and algae. The transgenic may be useful in applications outside of providing a disease model. These may include food of feed production through expression of, for instance, higher protein, carbohydrate, nutrient or vitamins levels than would normally be seen in the wildtype. In this regard, transgenic plants, especially pulses and tubers, and animals, especially mammals such as livestock (cows, sheep, goats and pigs), but also poultry and edible insects, are preferred.

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

In terms of in vivo delivery, AAV is advantageous over other viral vectors for a couple of reasons:
  Low toxicity (this may be due to the purification method not requiring ultra centrifugation of cell particles that can activate the immune response)
  Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species. Applicants have shown delivery and in vivo mouse brain Cas9 expression data.

Two ways to package Cas9 coding nucleic acid molecules, e.g., DNA, into viral vectors to mediate genome modification in vivo are preferred:

To achieve NHEJ-mediated gene knockout:
Single virus vector:
Vector containing two or more expression cassettes:
Promoter-Cas9 coding nucleic acid molecule-terminator
Promoter-gRNA1-terminator
Promoter-gRNA2-terminator
Promoter-gRNA(N)-terminator (up to size limit of vector)
Double virus vector:
Vector 1 containing one expression cassette for driving the expression of Cas9
Promoter-Cas9 coding nucleic acid molecule-terminator
Vector 2 containing one or more expression cassettes for driving the expression of one or more guideRNAs
Promoter-gRNA1-terminator
Promoter-gRNA(N)-terminator (up to size limit of vector)
To mediate homology-directed repair. In addition to the single and double virus vector approaches described above, an additional vector is used to deliver a homology-direct repair template.

Promoter used to drive Cas9 coding nucleic acid molecule expression can include:
AAV ITR can serve as a promoter: this is advantageous for eliminating the need for an additional promoter element (which can take up space in the vector). The additional space freed up can be used to drive the expression of additional elements (gRNA, etc). Also, ITR activity is relatively weaker, so can be used to reduce toxicity due to over expression of Cas9.

For ubiquitous expression, can use promoters: CMV, CAG, CBh, PGK, SV40, Ferritin heavy or light chains, etc.
For brain expression, can use promoters: SynapsinI for all neurons, CaMKIIalpha for excitatory neurons, GAD67 or GAD65 or VGAT for GABAergic neurons, etc.
For liver expression, can use Albumin promoter
For lung expression, can use SP-B
For endothelial cells, can use ICAM
For hematopoietic cells can use IFNbeta or CD45
For Osteoblasts can use OG-2
Promoter used to drive guide RNA can include:
Pol III promoters such as U6 or H1
Use of Pol II promoter and intronic cassettes to express gRNA As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

RNA delivery is also a useful method of in vivo delivery. FIG. 9 shows delivery and in vivo mouse brain Cas9 expression data. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as Invivofectamine from Life Technologies and other reagents on the market can effectively deliver RNA molecules into the liver.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Various means of delivery are described herein, and further discussed in this section.

Viral delivery: The CRISPR enzyme, for instance a Cas9, and/or any of the present RNAs, for instance a guide RNA, can be delivered using adeno associated virus (AAV), lentivirus, adenovirus or other viral vector types, or combinations thereof. Cas9 and one or more guide RNAs can be packaged into one or more viral vectors. In some embodiments, the viral vector is delivered to the tissue of interest by, for example, an intramuscular injection, while other times the viral delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector chose, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. Such a dosage formulation is readily ascertainable by one skilled in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg.

The doses herein are based on an average 70 kg individual. The frequency of administration is within the ambit of the medical or veterinary practitioner (e.g., physician, veterinarian), or scientist skilled in the art. A mouse used in experiments is typically considered 20 g, and one skilled in the art can extrapolate dosages from a 20 g mouse to a 70 kg individual.

Cas9 and one or more guide RNA can be delivered using adeno associated virus (AAV), lentivirus, adenovirus or other plasmid or viral vector types, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual, and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed.

The viral vectors can be injected into the tissue of interest. For cell-type specific genome modification, the expression of Cas9 can be driven by a cell-type specific promoter. For example, liver-specific expression might use the Albumin promoter and neuron-specific expression might use the Synapsin I promoter.

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines (SEQ ID NO: 1)). The cassette can be used for transcription by T7 polymerase. Guide RNAs can also be transcribed using in vitro transcription from a cassette containing T7_promoter-GG-guide RNA sequence.

To enhance expression and reduce toxicity, the CRISPR enzyme and/or guide RNA can be modified using pseudo-U or 5-Methyl-C.

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(DJ-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Furthermore, Michael S D Kormann et al. ("Expression of therapeutic proteins after delivery of chemically modified mRNA in mice: Nature Biotechnology, Volume: 29, Pages: 154-157 (2011) Published online 9 Jan. 2011) describes the use of lipid envelopes to deliver RNA. Use of lipid envelopes is also preferred in the present invention.

mRNA delivery methods are especially promising for liver delivery currently.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

Additional administrations of CRISPR enzyme mRNA and/or guide RNA might be useful to achieve the most efficient levels of genome modification.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 2) in the EMX1 gene of the human genome, deep sequencing can be used to assess the level of modification at the following two off-target loci, 1: 5'-GAGTCCTAGCAGGAGAAGAA-3' (SEQ ID NO: 3) and 2: 5'-GAGTCTAAGCAGAAGAAGAA-3' (SEQ ID NO: 4). The concentration that gives the highest level of on-target modification while minimizing or with a reduction in likelihood of the level of off-target modification should be chosen for in vivo delivery.

Alternatively, to minimize the level of toxicity and off-target effect, CRISPR enzyme nickase mRNA (for example S. pyogenes Cas9 with the D10A mutation) can be delivered with a pair of guide RNAs targeting a site of interest. The two guide RNAs need to be spaced as follows. Guide sequences in red (single underline) and blue (double underline) respectively these examples are based on the PAM requirement for Streptococcus pyogenes Cas9.

| Overhang length (bp) | Guide RNA design (guide sequence and PAM color coded) | SEQ ID NO: |
|---|---|---|
| 14 | 5'-NNNNNNNNNNNNNNNNNNNNCCNNNNNNNNNNNNNNNNNNNNGGNNNNNNNNNNNNNNNN-3' | 5 |
|    | 3'-NNNNNNNNNNNNNNNNNNNNNNGGNNNNNNNNNNNNNNNNNNNNCCNNNNNNNNNNNNNN-5' | 6 |
| 13 | 5'-NNNNNNNNNNNNNNNNNNNNCCNNNNNNNNNNNNNNNNNNNNNGGNNNNNNNNNNNNNNN-3' | 7 |
|    | 3'-NNNNNNNNNNNNNNNNNNNNNGGNNNNNNNNNNNNNNNNNNNNNCCNNNNNNNNNNNNNN-5' | 8 |
| 12 | 5'-NNNNNNNNNNNNNNNNNNNNCCNNNNNNNNNNNNNNNNNNNNNNGGNNNNNNNNNNNNNN-3' | 9 |
|    | 3'-NNNNNNNNNNNNNNNNNNNNGGNNNNNNNNNNNNNNNNNNNNNNCCNNNNNNNNNNNNNN-5' | 10 |
| 11 | 5'-NNNNNNNNNNNNNNNNNNNCCNNNNNNNNNNNNNNNNNNNNNNNGGNNNNNNNNNNNNNN-3' | 11 |
|    | 5'-NNNNNNNNNNNNNNNNNNNGGNNNNNNNNNNNNNNNNNNNNNNNCCNNNNNNNNNNNNNN-3' | 12 |
| 10 | 5'-NNNNNNNNNNNNNNNNNNNCCNNNNNNNNNNNNNNNNNNNNNNGGNNNNNNNNNNNNNNN-3' | 13 |
|    | 3'-NNNNNNNNNNNNNNNNNNNNGGNNNNNNNNNNNNNNNNNNNNNCCNNNNNNNNNNNNNNN-5' | 14 |
| 9  | 5'-NNNNNNNNNNNNNNNNNNNNCCNNNNNNNNNNNNNNNNNNNNNGGNNNNNNNNNNNNNNN-3' | 15 |
|    | 3'-NNNNNNNNNNNNNNNNNNNNGGNNNNNNNNNNNNNNNNNNNNCCNNNNNNNNNNNNNNNN-5' | 16 |
| 8  | 5'-NNNNNNNNNNNNNNNNNNNNNCCNNNNNNNNNNNNNNNNNNNGGNNNNNNNNNNNNNNNN-3' | 17 |
|    | 3'-NNNNNNNNNNNNNNNNNNNNGGNNNNNNNNNNNNNNNNNNNCCNNNNNNNNNNNNNNNNN-5' | 18 |
| 7  | 5'-NNNNNNNNNNNNNNNNNNNNNCCNNNNNNNNNNNNNNNNNNGGNNNNNNNNNNNNNNNNN-3' | 19 |
|    | 3'-NNNNNNNNNNNNNNNNNNNNGGNNNNNNNNNNNNNNNNNNCCNNNNNNNNNNNNNNNNNN-5' | 20 |
| 6  | 5'-NNNNNNNNNNNNNNNNNNNNNCCNNNNNNNNNNNNNNNNNGGNNNNNNNNNNNNNNNNNN-3' | 21 |
|    | 3'-NNNNNNNNNNNNNNNNNNNNGGNNNNNNNNNNNNNNNNNCCNNNNNNNNNNNNNNNNNNN-5' | 22 |
| 5  | 5'-NNNNNNNNNNNNNNNNNNNNNCCNNNNNNNNNNNNNNNNGGNNNNNNNNNNNNNNNNNNN-3' | 23 |
|    | 3'-NNNNNNNNNNNNNNNNNNNNGGNNNNNNNNNNNNNNNNCCNNNNNNNNNNNNNNNNNNNN-5' | 24 |
| 4  | 5'-NNNNNNNNNNNNNNNNNNNNNCCNNNNNNNNNNNNNNNGGNNNNNNNNNNNNNNNNNNNN-3' | 25 |
|    | 3'-NNNNNNNNNNNNNNNNNNNNGGNNNNNNNNNNNNNNNCCNNNNNNNNNNNNNNNNNNNNN-5' | 26 |
| 3  | 5'-NNNNNNNNNNNNNNNNNNNNNCCNNNNNNNNNNNNNNGGNNNNNNNNNNNNNNNNNNNNN-3' | 27 |
|    | 3'-NNNNNNNNNNNNNNNNNNNNGGNNNNNNNNNNNNNNCCNNNNNNNNNNNNNNNNNNNNNN-5' | 28 |
| 2  | 5'-NNNNNNNNNNNNNNNNNNNNNCCNNNNNNNNNNNNNGGNNNNNNNNNNNNNNNNNNNNNN-3' | 29 |
|    | 3'-NNNNNNNNNNNNNNNNNNNNGGNNNNNNNNNNNNNCCNNNNNNNNNNNNNNNNNNNNNNN-5' | 30 |
| 1  | 5'-NNNNNNNNNNNNNNNNNNNNNCCNNNNNNNNNNNNGGNNNNNNNNNNNNNNNNNNNNNNN-3' | 31 |
|    | 3'-NNNNNNNNNNNNNNNNNNNNGGNNNNNNNNNNNNCCNNNNNNNNNNNNNNNNNNNNNNNN-5' | 32 |

| Overhang length (bp) | Guide RNA design (guide sequence and PAM color coded) | SEQ ID NO: |
|---|---|---|
| blunt | 5'-NNNNNNNNNNNNNNNNNNNNNCCNNNNNNNNGGNNNNNNNNNNNNNNNNNNNNNNNNNNNN-3'<br>3'-NNNNNNNNNNNNNNNNNNNNNNNNGGNNNNNNNNCCNNNNNNNNNNNNNNNNNNNNNNNNNNNN-5' | 33<br>34 |
| 1 | 5'-NNNNNNNNNNNNNNNNNNNNNNCCNNNNNNNGGNNNNNNNNNNNNNNNNNNNNNNNNNNNN-3'<br>3'-NNNNNNNNNNNNNNNNNNNNNNNNGGNNNNNNNCCNNNNNNNNNNNNNNNNNNNNNNNNNNNN-5' | 35<br>36 |
| 2 | 5'-NNNNNNNNNNNNNNNNNNNNNNCCNNNNNNGGNNNNNNNNNNNNNNNNNNNNNNNNNNNN-3'<br>3'-NNNNNNNNNNNNNNNNNNNNNNNNGGNNNNNNCCNNNNNNNNNNNNNNNNNNNNNNNNNNNN-5' | 37<br>38 |
| 3 | 5'-NNNNNNNNNNNNNNNNNNNNNNCCNNNNNGGNNNNNNNNNNNNNNNNNNNNNNNNNNNN-3'<br>3'-NNNNNNNNNNNNNNNNNNNNNNNNGGNNNNNCCNNNNNNNNNNNNNNNNNNNNNNNNNNNN-5' | 39<br>40 |
| 4 | 5'-NNNNNNNNNNNNNNNNNNNNNNCCNNNNGGNNNNNNNNNNNNNNNNNNNNNNNNNNNN-3'<br>3'-NNNNNNNNNNNNNNNNNNNNNNNNGGNNNNCCNNNNNNNNNNNNNNNNNNNNNNNNNNNN-5' | 41<br>42 |
| 5 | 5'-NNNNNNNNNNNNNNNNNNNNNNCCNNNGGNNNNNNNNNNNNNNNNNNNNNNNNNNNN-3'<br>3'-NNNNNNNNNNNNNNNNNNNNNNNNGGNNNCCNNNNNNNNNNNNNNNNNNNNNNNNNNNN-5' | 43<br>44 |
| 6 | 5'-NNNNNNNNNNNNNNNNNNNNNNCCNNGGNNNNNNNNNNNNNNNNNNNNNNNNNNNN-3'<br>3'-NNNNNNNNNNNNNNNNNNNNNNNNGGNNCCNNNNNNNNNNNNNNNNNNNNNNNNNNNN-5' | 45<br>46 |
| 7 | 5'-NNNNNNNNNNNNNNNNNNNNNNCCNGGNNNNNNNNNNNNNNNNNNNNNNNNNNNN-3'<br>3'-NNNNNNNNNNNNNNNNNNNNNNNNGGNCCNNNNNNNNNNNNNNNNNNNNNNNNNNNN-5' | 47<br>48 |
| 8 | 5'-NNNNNNNNNNNNNNNNNNNNNNCCGGNNNNNNNNNNNNNNNNNNNNNNNNNNNN-3'<br>3'-NNNNNNNNNNNNNNNNNNNNNNNNGGCCNNNNNNNNNNNNNNNNNNNNNNNNNNNN-5' | 49<br>50 |
| 12 | 5'-NNNNNNNNNNNNNNNNNNNNNNGGNNNNNNNNNNNNNNNNNNNNNNNNNNNN-3'<br>3'-NNNNNNNNNNNNNNNNNNNNNNNNCCGGNNNNNNNNNNNNNNNNNNNNNNNNNNNN-5' | 51<br>52 |
| 13 | 5'-NNNNNNNNNNNNNNNNNNNNNNCGGNNNNNNNNNNNNNNNNNNNNNNNNNNNN-3'<br>3'-NNNNNNNNNNNNNNNNNNNNNNNNCCNGGNNNNNNNNNNNNNNNNNNNNNNNNNNNN-5' | 53<br>54 |
| 14 | 5'-NNNNNNNNNNNNNNNNNNNNNNCGGNNNNNNNNNNNNNNNNNNNNNNNNNNNN-3'<br>3'-NNNNNNNNNNNNNNNNNNNNNNNNCCNNGGNNNNNNNNNNNNNNNNNNNNNNNNNNNN-5' | 53<br>56 |
| 15 | 5'-NNNNNNNNNNNNNNNNNNNNNNCGGNNNNNNNNNNNNNNNNNNNNNNNNNNNN-3'<br>3'-NNNNNNNNNNNNNNNNNNNNNNNNCCNNNGGNNNNNNNNNNNNNNNNNNNNNNNNNNNN-5' | 53<br>58 |
| 16 | 5'-NNNNNNNNNNNNNNNNNNNNNNCGGNNNNNNNNNNNNNNNNNNNNNNNNNNNN-3'<br>3'-NNNNNNNNNNNNNNNNNNNNNNNNCCNNNNGGNNNNNNNNNNNNNNNNNNNNNNNNNNNN-5' | 53<br>60 |
| 17 | 5'-NNNNNNNNNNNNNNNNNNNNNNCGGNNNNNNNNNNNNNNNNNNNNNNNNNNNN-3'<br>3'-NNNNNNNNNNNNNNNNNNNNNNNNCCNNNNNGGNNNNNNNNNNNNNNNNNNNNNNNNNNNN-5' | 53<br>62 |

Further interrogation of the system have given Applicants evidence of the 5' overhang (see, e.g., Ran et al., Cell. 2013 Sep. 12; 154(6):1380-9 and U.S. Provisional Patent Application Ser. No. 61/871,301 filed Aug. 28, 2013). Applicants have further identified parameters that relate to efficient cleavage by the Cas9 nickase mutant when combined with two guide RNAs and these parameters include but are not limited to the length of the 5' overhang. In embodiments of the invention the 5' overhang is at most 200 base pairs, preferably at most 100 base pairs, or more preferably at most 50 base pairs. In embodiments of the invention the 5' overhang is at least 26 base pairs, preferably at least 30 base pairs or more preferably 34-50 base pairs or 1-34 base pairs. In other preferred methods of the invention the first guide sequence directing cleavage of one strand of the DNA duplex near the first target sequence and the second guide sequence directing cleavage of other strand near the second target sequence results in a blunt cut or a 3' overhang. In embodiments of the invention the 3' overhang is at most 150, 100 or 25 base pairs or at least 15, 10 or 1 base pairs. In preferred embodiments the 3' overhang is 1-100 base pairs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein.

Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity.

Since Cas9n and Cas9H840A nick opposite strands of DNA, substitution of Cas9n with Cas9H840A with a given sgRNA pair should result in the inversion of the overhang type. For example, a pair of sgRNAs that will generate a 5' overhang with Cas9n should in principle generate the corresponding 3' overhang instead. Therefore, sgRNA pairs that lead to the generation of a 3' overhang with Cas9n might be used with Cas9H840A to generate a 5' overhang. Unexpectedly, Applicants tested Cas9H840A with a set of sgRNA pairs designed to generate both 5' and 3' overhangs (offset range from −278 to +58 bp), but were unable to observe indel formation. Further work may be needed to identify the necessary design rules for sgRNA pairing to allow double nicking by Cas9H840A.

Additional delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang Y, Schlachetzki F, Pardridge W M. ("Global non-viral gene transfer to the primate brain following intravenous administration." Mol Ther. 2003 January; 7(1):11-8.) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjunction with antibodies to target specific tissues or cell surface proteins.

Other means of delivery or RNA are also preferred, such as via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exozomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then siRNA is loaded into the exosomes.

Targeted deletion of genes is preferred. Examples are exemplified in Example 12. Preferred are, therefore, genes involved in cholesterol biosynthesis, fatty acid biosynthesis, and other metabolic disorders, genes encoding mis-folded proteins involved in amyloid and other diseases, oncogenes leading to cellular transformation, latent viral genes, and genes leading to dominant-negative disorders, amongst other disorders. As exemplified here, Applicants prefer gene delivery of a CRISPR-Cas system to the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Therapeutic applications of the CRISPR-Cas system include Glaucoma, Amyloidosis, and Huntington's disease. These are exemplified in Example 14 and the features described therein are preferred alone or in combination.

As an example, chronic infection by HIV-1 may be treated or prevented. In order to accomplish this, one may generate CRISPR-Cas guide RNAs that target the vast majority of the HIV-1 genome while taking into account HIV-1 strain variants for maximal coverage and effectiveness. One may accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host. This is discussed in more detail in the Examples section.

It is also envisaged that the present invention generates a gene knockout cell library. Each cell may have a single gene knocked out. This is exemplified in Example 17.

One may make a library of ES cells where each cell has a single gene knocked out, and the entire library of ES cells will have every single gene knocked out. This library is useful for the screening of gene function in cellular processes as well as diseases. To make this cell library, one may integrate Cas9 driven by an inducible promoter (e.g. doxycycline inducible promoter) into the ES cell. In addition, one may integrate a single guide RNA targeting a specific gene in the ES cell. To make the ES cell library, one may simply mix ES cells with a library of genes encoding guide RNAs targeting each gene in the human genome. One may first introduce a single BxB1 attB site into the AAVS1 locus of the human ES cell. Then one may use the BxB1 integrase to facilitate the integration of individual guide RNA genes into the BxB1 attB site in AAVS1 locus. To facilitate integration, each guide RNA gene may be contained on a plasmid that carries of a single attP site. This way BxB1 will recombine the attB site in the genome with the attP site on the guide RNA containing plasmid. To generate the cell library, one may take the library of cells that have single guide RNAs integrated and induce Cas9 expression. After induction, Cas9 mediates double strand break at sites specified by the guide RNA.

Chronic administration of protein therapeutics may elicit unacceptable immune responses to the specific protein. The immunogenicity of protein drugs can be ascribed to a few immunodominant helper T lymphocyte (HTL) epitopes. Reducing the MHC binding affinity of these HTL epitopes contained within these proteins can generate drugs with lower immunogenicity (Tangri S, et al. ("Rationally engineered therapeutic proteins with reduced immunogenicity" J Immunol. 2005 Mar. 15; 174(6):3187-96.) In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cas9) in the host species (human or other species).

In Example 28, Applicants used 3 guideRNAs of interest and able to visualize efficient DNA cleavage in vivo occurring only in a small subset of cells. Essentially, what Applicants have shown here is targeted in vivo cleavage. In particular, this provides proof of concept that specific targeting in higher organisms such as mammals can also be achieved. It also highlights multiplex aspect in that multiple guide sequences (i.e. separate targets) can be used simultaneously (in the sense of co-delivery). In other words, Applicants used a multiple approach, with several different sequences targeted at the same time, but independently.

A suitable example of a protocol for producing AAV, a preferred vector of the invention is provided in Example 29.

Trinucleotide repeat disorders are preferred conditions to be treated. These are also exemplified herein.

According to another aspect, a method of gene therapy for the treatment of a subject having a mutation in the CFTR gene is provided and comprises administering a therapeutically effective amount of a CRISPR-Cas gene therapy particle, optionally via a biocompatible pharmaceutical carrier, to the cells of a subject. Preferably, the target DNA comprises the mutation deltaF508. In general, it is of preferred that the mutation is repaired to the wildtype. In this case, the mutation is a deletion of the three nucleotides that comprise the codon for phenylalanine (F) at position 508. Accordingly, repair in this instance requires reintroduction of the missing codon into the mutant.

To implement this Gene Repair Strategy, it is preferred that an adenovirus/AAV vector system is introduced into the host cell, cells or patient. Preferably, the system comprises a Cas9 (or Cas9 nickase) and the guide RNA along with a adenovirus/AAV vector system comprising the homology repair template containing the F508 residue. This may be introduced into the subject via one of the methods of delivery discussed earlier. The CRISPR-Cas system may be guided by the CFTRdelta 508 chimeric guide RNA. It targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

For an example of CFTRdelta508 chimeric guide RNA, see Example which demonstrates gene transfer or gene delivery of a CRISPR-Cas system in airways of subject or a patient in need thereof, suffering from cystic fibrosis or from cystic fibrosis (CF) related symptoms, using adeno-associated virus (AAV) particles. In particular, they exemplify a repair strategy for Cystic Fibrosis delta F508 mutation. This type of strategy should apply across all organisms. With particular reference to CF, suitable patients may include: Human, non-primate human, canine, feline, bovine, equine and other domestic animals. In this instance, Applicants utilized a CRISPR-Cas system comprising a Cas9 enzyme to target deltaF508 or other CFTR-inducing mutations.

The treated subjects in this instance receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas9, U6 or H1 promoter for chimeric guide RNA): A preferred arrangement is to use a CFTRdelta508 targeting chimeric guide, a repair template for deltaF508 mutation and a codon optimized Cas9 enzyme (preferred Cas9s are those with nuclease or nickase activity) with optionally one or more nuclear localization signal or sequence(s) (NLS(s)), e.g., two (2) NLSs. Constructs without NLS are also envisaged.

In order to identify the Cas9 target site, Applicants analyzed the human CFTR genomic locus and identified the Cas9 target site. Preferably, in general and in this CF case, the PAM may contain a NGG or a NNAGAAW motif.

Accordingly, in the case of CF, the present method comprises manipulation of a target sequence in a genomic locus of interest comprising delivering a non-naturally occurring or engineered composition comprising a viral vector system comprising one or more viral vectors operably encoding a composition for expression thereof, wherein the composition comprises:

a non-naturally occurring or engineered composition comprising a vector system comprising one or more vectors comprising I. a first regulatory element operably linked to a CRISPR-Cas system chimeric RNA (chiRNA) polynucleotide sequence, wherein the polynucleotide sequence comprises (a) a guide sequence capable of hybridizing to the CF target sequence in a suitable mammalian cell, (b) a tracr mate sequence, and (c) a tracr sequence, and II. a second regulatory element operably linked to an enzyme-coding sequence encoding a CRISPR enzyme comprising at least one or more nuclear localization sequences, wherein (a), (b) and (c) are arranged in a 5' to 3' orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex comprises the CRISPR enzyme complexed with (1) the guide sequence that is hybridized to the target sequence, and (2) the tracr mate sequence that is hybridized to the tracr sequence. In respect of CF, preferred target DNA sequences comprise the CFTRdelta508 mutation. A preferred PAM is described above. A preferred CRISPR enzyme is any Cas (described herein, but particularly that described in Example 16).

Alternatives to CF include any genetic disorder and examples of these are well known. Another preferred method or use of the invention is for correcting defects in the EMP2A and EMP2B genes that have been identified to be associated with Lafora disease.

In some embodiments, a "guide sequence" may be distinct from "guide RNA". A guide sequence may refer to an approx. 20 bp sequence, within the guide RNA, that specifies the target site.

In some embodiments, the Cas9 is (or is derived from) the SpCas9. In such embodiments, preferred mutations are at any or all or positions 10, 762, 840, 854, 863 and/or 986 of SpCas9 or corresponding positions in other Cas9s (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. These are advantageous as they provide nickase activity.

It will be readily apparent that a host of other diseases can be treated in a similar fashion. Some examples of genetic diseases caused by mutations are provided herein, but many more are known. The above strategy can be applied to these diseases.

The invention uses nucleic acids to bind target DNA sequences. This is advantageous as nucleic acids are much easier and cheaper to produce and the specificity can be varied according to the length of the stretch where homology is sought. Complex 3-D positioning of multiple fingers, for example is not required.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., WO 97/03211; WO 96/39154. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

As used herein, the term "domain" or "protein domain" refers to a part of a protein sequence that may exist and function independently of the rest of the protein chain.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity.

However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see *FEMS Microbiol Lett.* 1999 174 (2): 247-50; *FEMS Microbiol Lett.* 1999 177(1): 187-8 and the website of the National Center for Biotechnology information at the website of the National Institutes for Health).

Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244). Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| SET | | SUB-SET | |
|---|---|---|---|
| Hydrophobic | F W Y H K M I L V<br>A G C | Aromatic<br>Aliphatic | F W Y H<br>I L V |
| Polar | W Y H K R E D C S<br>T N Q | Charged<br>Positively charged<br>Negatively charged | H K R E D<br>H K R<br>E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

In one aspect, the invention provides for vectors that are used in the engineering and optimization of CRISPR-Cas systems.

A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUA-GAGCUA (SEQ ID NO: 63). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

In one embodiment, the U6 promoter may be a bi-directional promoter. FIG. 52 depicts panels of data: the first showing different truncations of the Bi-directional U6 promoter and associated microdeletion activity and the second quantifying the indel-inducing activity coming off of either side of the bi-directional promoter. FIG. 52 represents yet another means by which it is possible to deliver two independent sgRNAs off of a single U6 promoter that is independent of and complementary to the tandem sgRNA approach. The increase in size of the U6 promoter is minimal, which makes this amenable and attractive to in vivo/AAV delivery applications where vector size represents a significant constraint. The sequence of the smallest U6-8/U6-1 bi-directional reporter that retains good function in both directions which consists of joining end to end of the U6-1 promoter in the forward direction and a truncated version of the U6-8 promoter in the reverse direction (see FIG. 53). Additionally, this may address the issue that the first spacer tends to work significantly better than the second in the current iteration of the tandem sgRNA architecture as processing of independent sgRNAS does not have to occur with the BiU6 approach. See, e.g., WO2005035718 for additional disclosure on bi-directional promoters.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis*

(See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In embodiments of the invention the terms guide sequence and guide RNA are used interchangeably. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell.

In some embodiments, direct repeats may be identified in silico by searching for repetitive motifs that fulfill any or all of the following criteria:
1. found in a 2 Kb window of genomic sequence flanking the type II CRISPR locus;
2. span from 20 to 50 bp; and
3. interspaced by 20 to 50 bp.

In some embodiments, 2 of these criteria may be used, for instance 1 and 2, 2 and 3, or 1 and 3. In some embodiments, all 3 criteria may be used.

In some embodiments, candidate tracrRNA may be subsequently predicted by sequences that fulfill any or all of the following criteria:
1. sequence homology to direct repeats (motif search in Geneious with up to 18-bp mismatches);
2. presence of a predicted Rho-independent transcriptional terminator in direction of transcription; and
3. stable hairpin secondary structure between tracrRNA and direct repeat.

In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

In preferred embodiments of the invention, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defense in bacteria and archaea, Mole Cell 2010 Jan. 15; 37(1): 7.

Figure 2A:
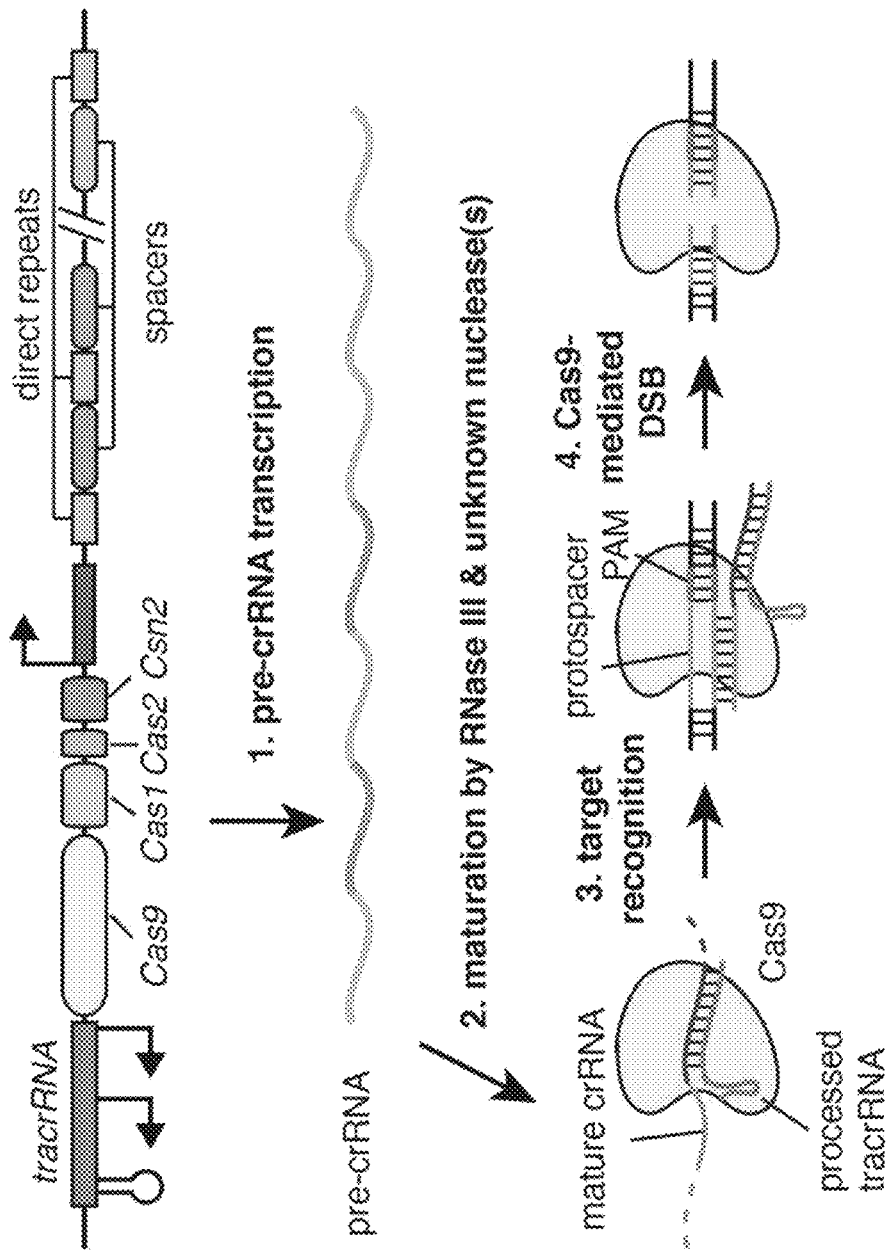
Figure 2B:
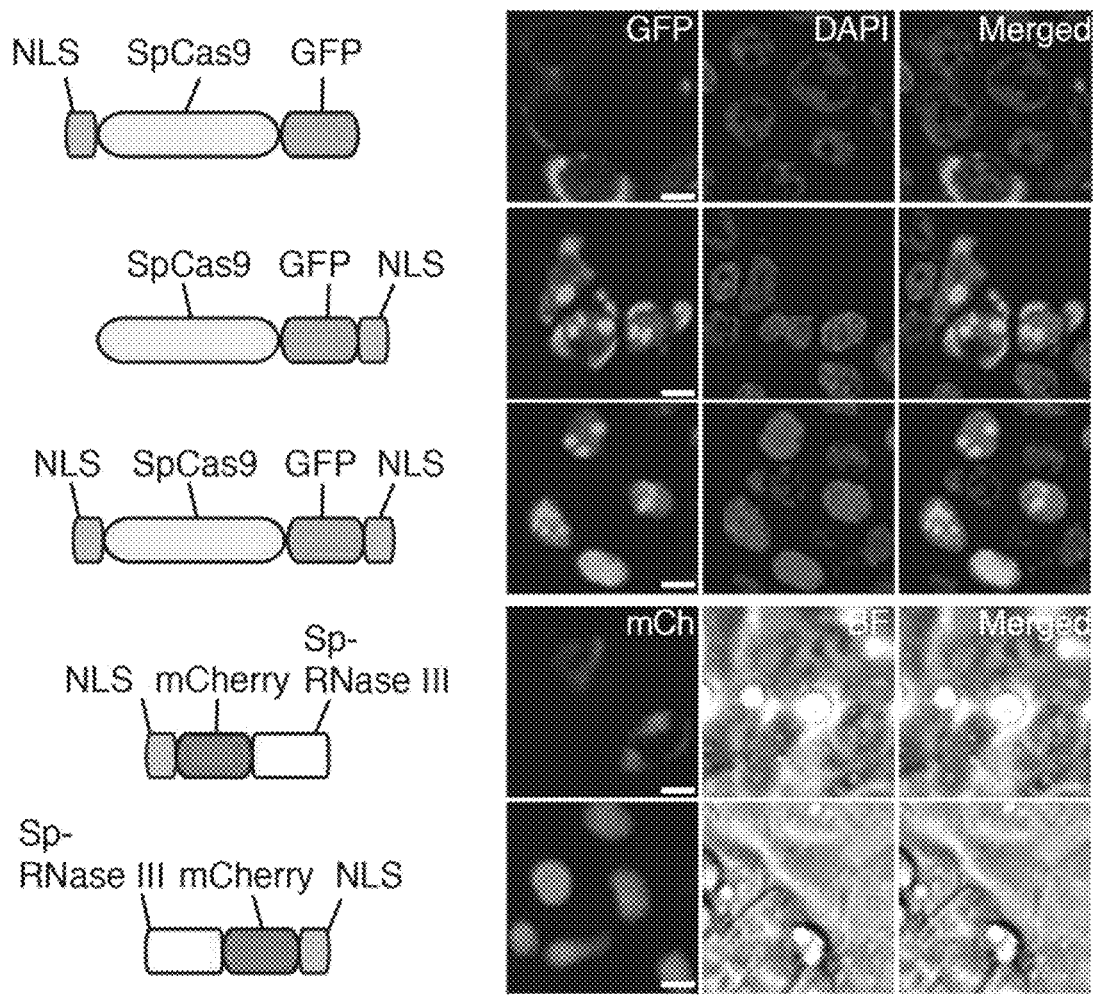
Figure 2C:
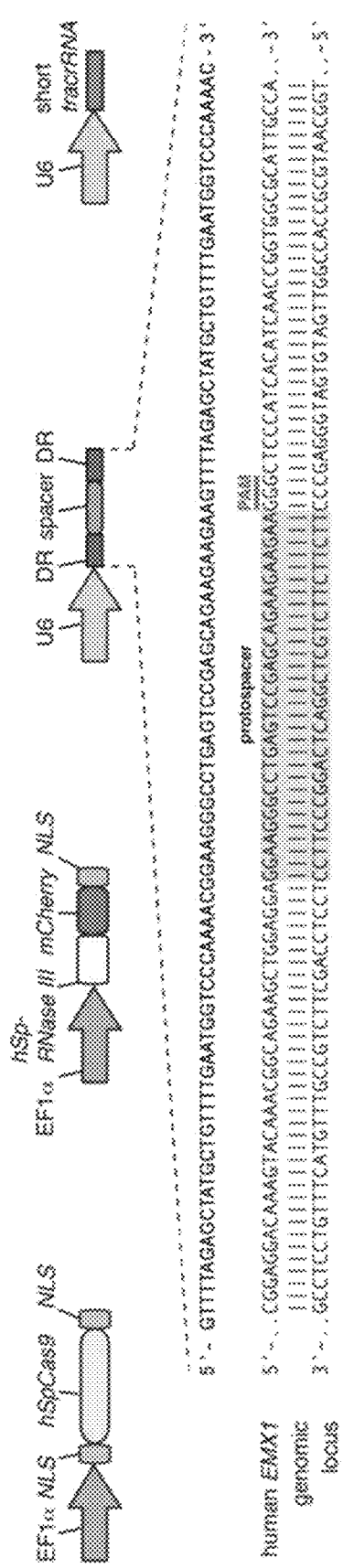
Figure 2D:
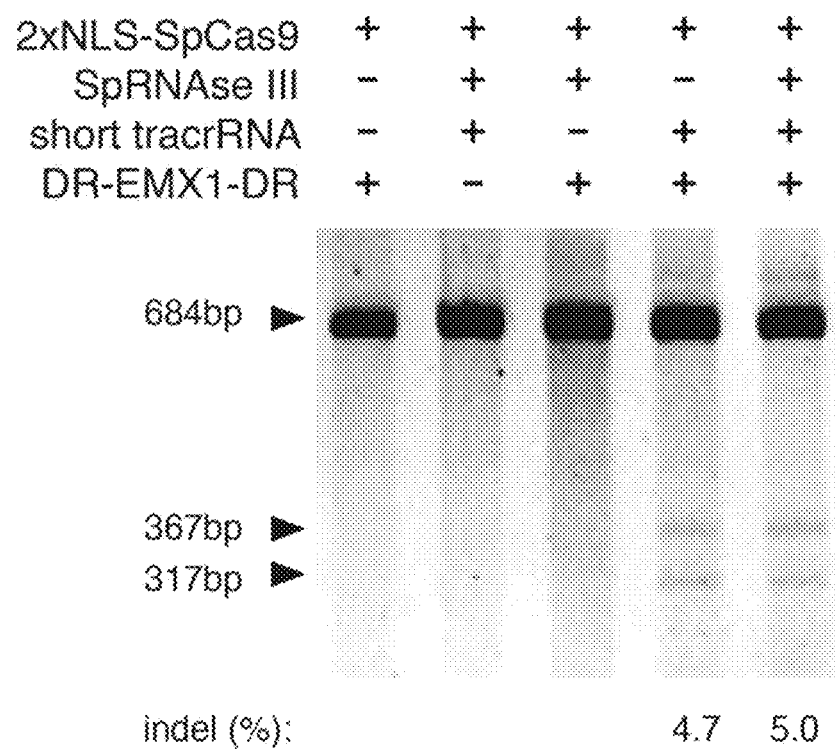
Figure 3A:
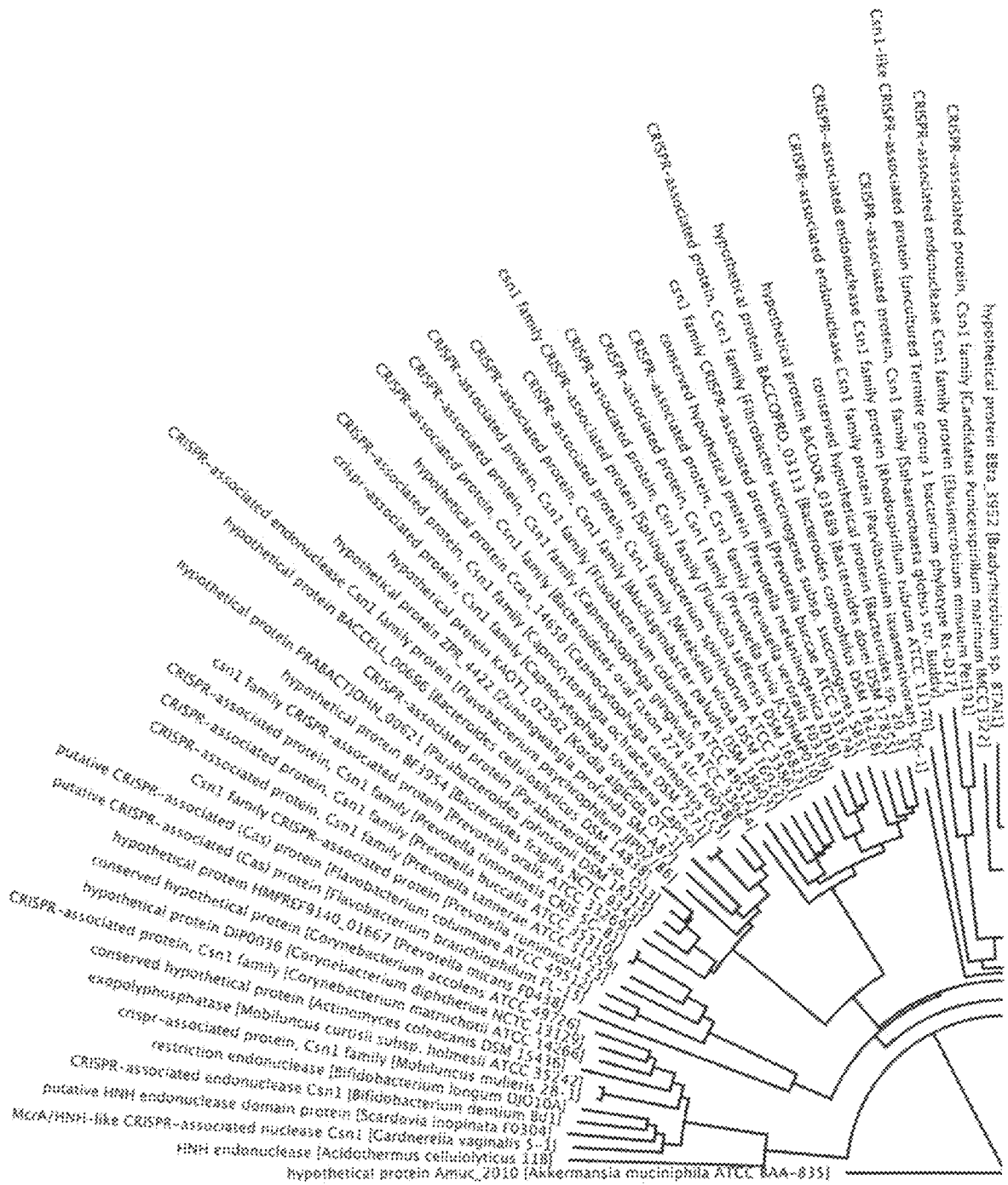
FIG. 3A-D is a circular phylogenetic tree of Cas genes
Figure 3B:
Figure 3C:
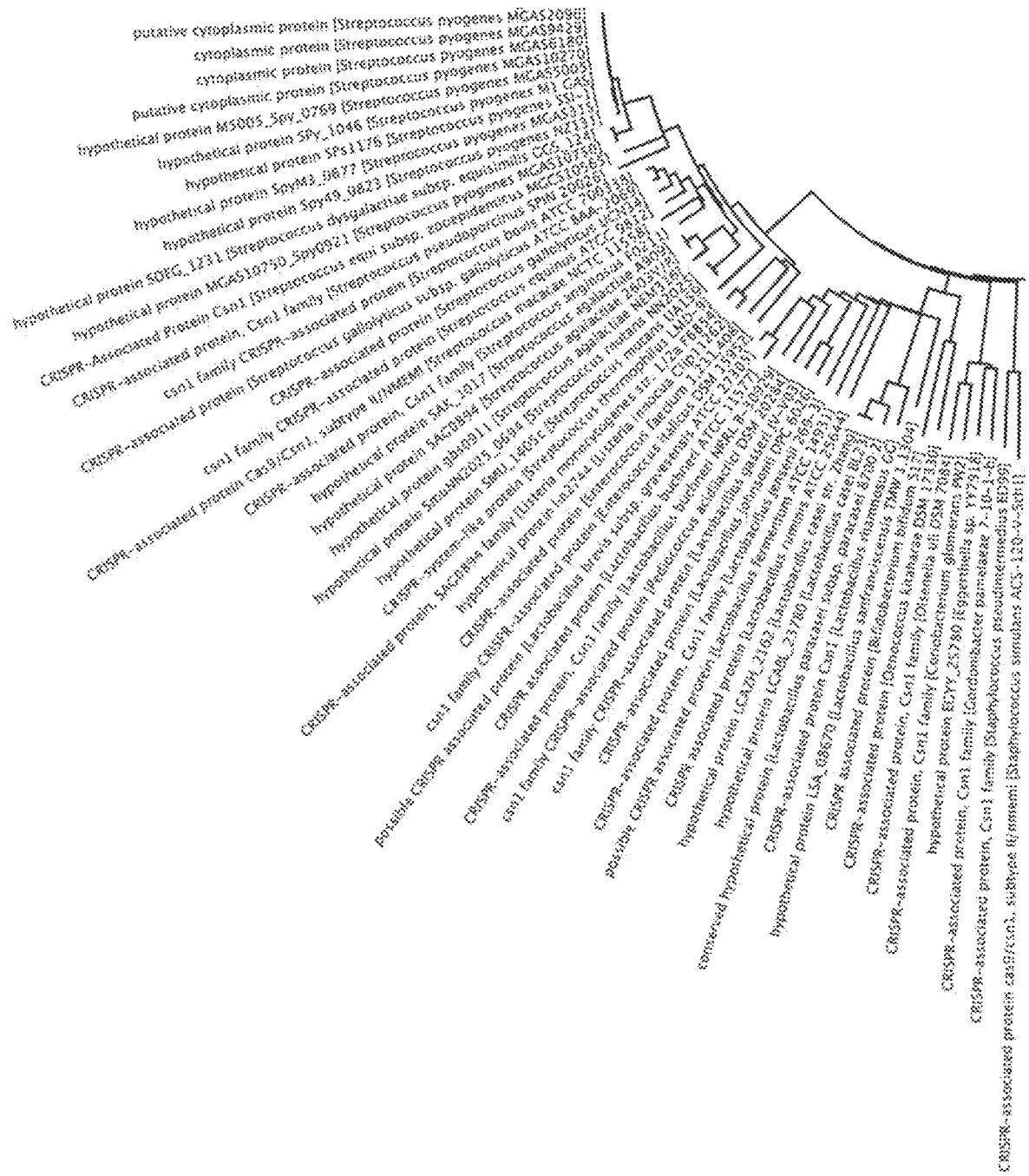
Figure 3D:
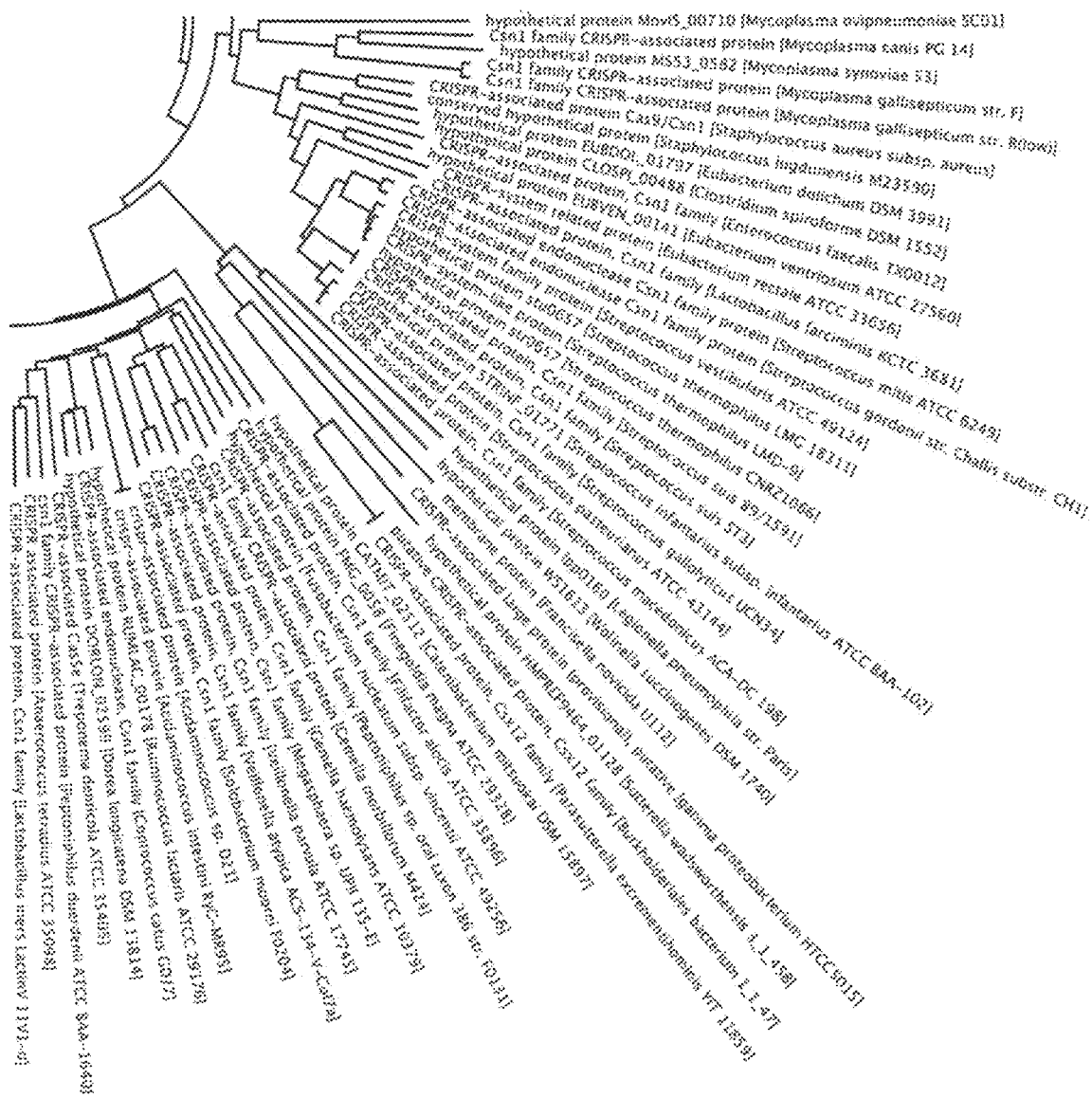
Figure 4B:
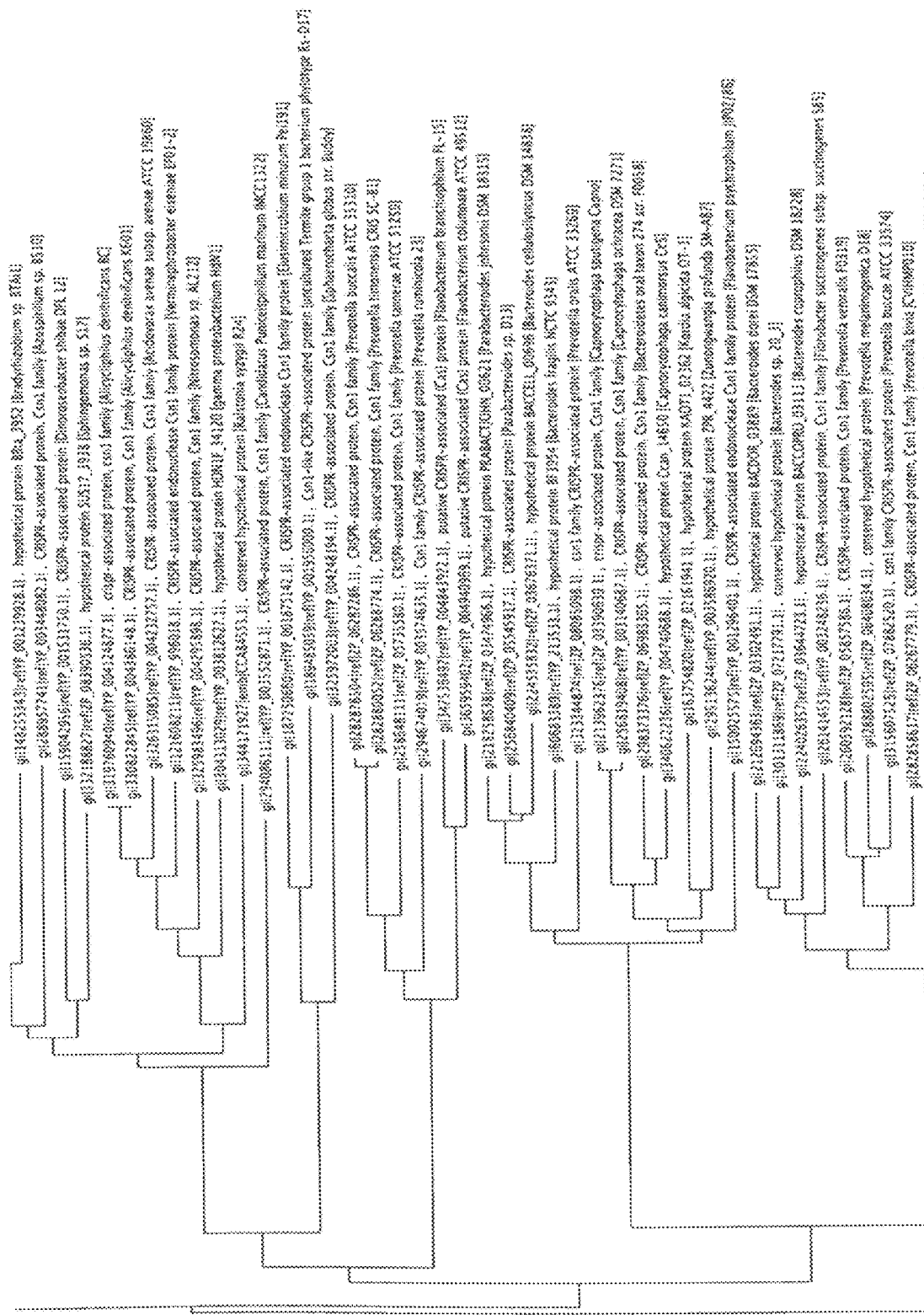
Figure 4D:
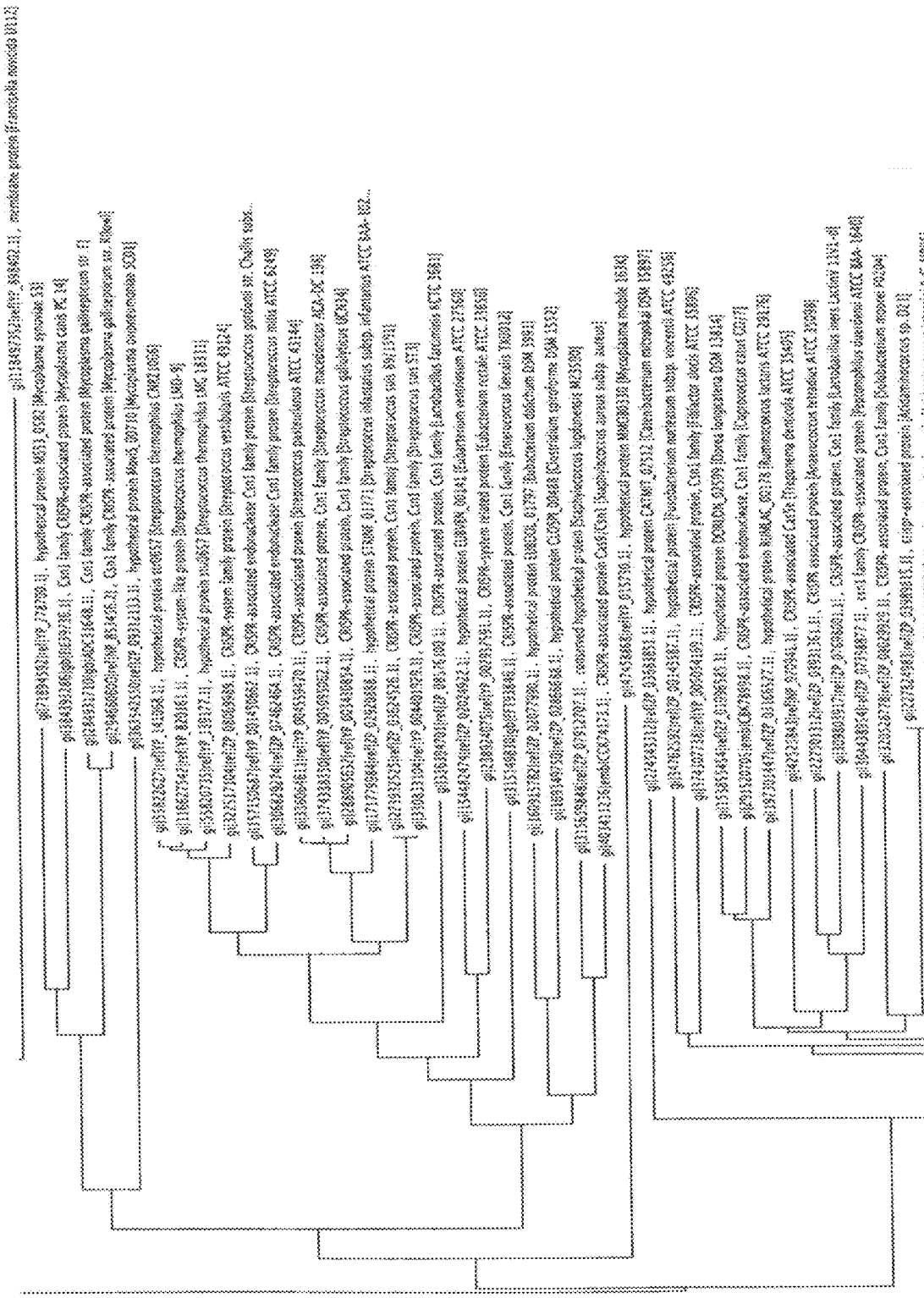

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). FIG. 2B demonstrates the nuclear localization of the codon optimized Cas9. To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form.

An aspartate-to-alanine substitution (D10A) in the RuvC I catalytic domain of SpCas9 was engineered to convert the nuclease into a nickase (SpCas9n) (see e.g. Sapranauskas et al., 2011, Nucleic Acid Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. Co-expression of EMX1-targeting chimeric crRNA (having the tracrRNA component as well) with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer.

Preferred orthologs are described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, Applicants mean that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth.

An example of a codon optimized sequence, in this instance optimized for humans (i.e. being optimized for expression in humans) is provided herein, see the SaCas9 human codon optimized sequence. Whilst this is preferred, it will be appreciated that other examples are possible and codon optimization for a host species is known.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded.

In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ (visited Jul. 9, 2002), and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 64); the NLS from nucleoplasmin (e.g. the nucleoplasmin bipartite NLS with the sequence KRPAATKKAGQAKKKK (SEQ ID NO: 65)); the c-myc NLS having the amino acid sequence PAAKRVKLD (SEQ ID NO: 66) or RQRRNELKRSP (SEQ ID NO: 67); the hRNPA1 M9 NLS having the sequence NQSSNFGPMKGGNFGGRSSGPYGGGGQYFAK-PRNQGGY (SEQ ID NO: 68); the sequence RMRIZFKNKGKDTAELRRRRVEVSVELRKAKKD-EQILKRRNV (SEQ ID NO: 69) of the IBB domain from importin-alpha; the sequences VSRKRPRP (SEQ ID NO: 70) and PPKKARED (SEQ ID NO: 71) of the myoma T protein; the sequence PQPKKKPL (SEQ ID NO: 72) of human p53; the sequence SALIKKKKMAP (SEQ ID NO: 73) of mouse c-abl IV; the sequences DRLRR (SEQ ID NO: 74) and PKQKKRK (SEQ ID NO: 75) of the influenza virus NS1; the sequence RKLKKKIKKL (SEQ ID NO: 76) of the Hepatitis virus delta antigen; the sequence REKKKFLKRR (SEQ ID NO: 77) of the mouse Mx1 protein; the sequence KRKGDEVDGVDEVAKKKSKK (SEQ ID NO: 78) of the human poly(ADP-ribose) polymerase; and the sequence RKCLQAGMNLEARKTKK (SEQ ID NO: 79) of the steroid hormone receptors (human) glucocorticoid.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome. A unique target sequence in a genome may include an S. pyogenes Cas9 target site of the form MMMMMMMMMNNNNNNNNNXGG where NNNNNNNNNXGG (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 80) where NNNNNNNNNNNNXXAGAAW (SEQ ID NO: 81) (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNNXXAGAAW (SEQ ID NO: 82) where NNNNNNNNNNNXXAGAAW (SEQ ID NO: 83) (N is A, G, T, or C; X can be anything; and W is A or T) has a single occurrence in the genome. For the S. pyogenes Cas9, a unique target sequence in a genome may include a Cas9 target site of the form MMMMMMMMMNNNNNNNNNNNNXGGXG where NNNNNNNNNNNNXGGXG (N is A, G, T, or C; and X can be anything) has a single occurrence in the genome. A unique target sequence in a genome may include an S. pyogenes Cas9 target site of the form MMMMMMMMMNNNNNNNNNNNXGGXG where NNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa ggcttcatgccgaaat-caacaccctgtcattttatggcagggtgttttcgttatttaaTTTTTT (SEQ ID NO: 84); (2) NNNNNNNNNNNNNNNNNNNNgttttgtactctca GAAAtgcagaagctacaaagataaggcttcatgccg aaatcaacaccctgt-cattttatggcagggtgttttcgttatttaaTTTTTT (SEQ ID NO: 85); (3) NNNNNNNNNNNNNNNNNNNNgttttgtactctcaGAAA tgcagaagctacaaagataaggcttcatgccg aaatcaacaccctgtcattt-tatggcagggtgtTTTTTT (SEQ ID NO: 86); (4) NNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 87); (5) NNNNNNNNNNNNNNNNNNNNgttt-tagagctaGAAATAGcaagttaaaataaggctagtccgttatcaac ttgaaaaagtgTTTTTTT (SEQ ID NO: 88); and (6) NNNNNNNNNNNNNNNNNNNNgttt-tagagctagAAATAGcaagttaaaataaggctagtccgttatcaTT TTTTTT (SEQ ID NO: 89). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

3) In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cryptochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In some aspects, the invention provides methods comprising delivering one or more polynucleotides, such as or one or more vectors as described herein, one or more transcripts thereof, and/or one or more proteins transcribed therefrom, to a host cell. In some aspects, the invention further provides cells produced by such methods, and animals comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36

(1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system.

Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producer a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

Accordingly, AAV is considered an ideal candidate for use as a transducing vector. Such AAV transducing vectors can comprise sufficient cis-acting functions to replicate in the presence of adenovirus or herpesvirus or poxvirus (e.g., vaccinia virus) helper functions provided in trans. Recombinant AAV (rAAV) can be used to carry exogenous genes into cells of a variety of lineages. In these vectors, the AAV cap and/or rep genes are deleted from the viral genome and replaced with a DNA segment of choice. Current AAV vectors may accommodate up to 4300 bases of inserted DNA.

There are a number of ways to produce rAAV, and the invention provides rAAV and methods for preparing rAAV. For example, plasmid(s) containing or consisting essentially of the desired construct are transfected into AAV-infected cells. In addition, a second or additional helper plasmid is cotransfected into these cells to provide the AAV rep and/or cap genes which are obligatory for replication and packaging of the recombinant viral construct. Under these conditions, the rep and/or cap proteins of AAV act in trans to stimulate replication and packaging of the rAAV construct. Two to Three days after transfection, rAAV is harvested. Traditionally rAAV is harvested from the cells along with adenovirus. The contaminating adenovirus is then inactivated by heat treatment. In the instant invention, rAAV is advantageously harvested not from the cells themselves, but from cell supernatant. Accordingly, in an initial aspect the invention provides for preparing rAAV, and in addition to the foregoing, rAAV can be prepared by a method that comprises or consists essentially of: infecting susceptible cells with a rAAV containing exogenous DNA including DNA for expression, and helper virus (e.g., adenovirus, herpesvirus, poxvirus such as vaccinia virus) wherein the rAAV lacks functioning cap and/or rep (and the helper virus (e.g., adenovirus, herpesvirus, poxvirus such as vaccinia virus) provides the cap and/or rev function that the rAAV lacks); or infecting susceptible cells with a rAAV containing exogenous DNA including DNA for expression, wherein the recombinant lacks functioning cap and/or rep, and transfecting said cells with a plasmid supplying cap and/or rep function that the rAAV lacks; or infecting susceptible cells with a rAAV containing exogenous DNA including DNA for expression, wherein the recombinant lacks functioning cap and/or rep, wherein said cells supply cap and/or rep function that the recombinant lacks; or transfecting the susceptible cells with an AAV lacking functioning cap and/or rep and plasmids for inserting exogenous DNA into the recombinant so that the exogenous DNA is expressed by the recombinant and for supplying rep and/or cap functions whereby transfection results in an rAAV containing the exogenous DNA including DNA for expression that lacks functioning cap and/or rep.

The rAAV can be from an AAV as herein described, and advantageously can be an rAAV1, rAAV2, AAV5 or rAAV having hybrid capsid which may comprise AAV1, AAV2, AAV5 or any combination thereof. One can select the AAV of the rAAV with regard to the cells to be targeted by the rAAV; e.g., one can select AAV serotypes 1, 2, 5 or a hybrid capsid AAV1, AAV2, AAV5 or any combination thereof for targeting brain or neuronal cells; and one can select AAV4 for targeting cardiac tissue.

In addition to 293 cells, other cells that can be used in the practice of the invention and the relative infectivity of certain AAV serotypes in vitro as to these cells (see Grimm, D. et al, J. Virol. 82: 5887-5911 (2008)) are as follows:

nucleic acid molecule encoding guide RNA (gRNA) and a terminator (e.g., each cassette schematically represented as Promoter-gRNA1-terminator, Promoter-gRNA2-terminator . . . Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator. Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn).

Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, CR, Rat6, CV1, RPTE, A10, T24, J82, A375, ARH-77, Calu1, SW480, SW620, SKOV3, SK-UT, CaCo2,

| Cell Line | AAV-1 | AAV-2 | AAV-3 | AAV-4 | AAV-5 | AAV-6 | AAV-8 | AAV-9 |
| --- | --- | --- | --- | --- | --- | --- | --- | --- |
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The invention provides rAAV that contains or consists essentially of an exogenous nucleic acid molecule encoding a CRISPR (Clustered Regularly Interspaced Short Palindromic Repeats) system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/

CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. Methods for producing transgenic plants and animals are known in the art, and generally begin with a method of cell transfection, such as described herein.

With recent advances in crop genomics, the ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications" Nat Rev Genet. 2011 Dec. 29; 13(2):85-96 are also herein incorporated by reference in their entirety. In an advantageous embodiment of the invention, the CRISPR/Cas9 system is used to engineer microalgae. That the CRISPR-Cas system is able to be employed in plant systems is also provided in the manuscript "Efficient Genome Editing in Plants using a CRISPR/Cas System", by Feng et al. submitted for publication to Nature Biotechnology in July 2013, incorporated by reference in its entirety, wherein it is demonstrated that engineered CRISPR/Cas complexes may be used to create double strand breaks at specific sites of the plant genome to achieve targeted genome modifications in both dicot and monocot plants. Accordingly, reference herein to animal cells may also apply, mutatis mutandis, to plant cells unless otherwise apparent.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae). For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence. Similar considerations and conditions apply as above for methods of modifying a target polynucleotide.

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell.

Figure 11:
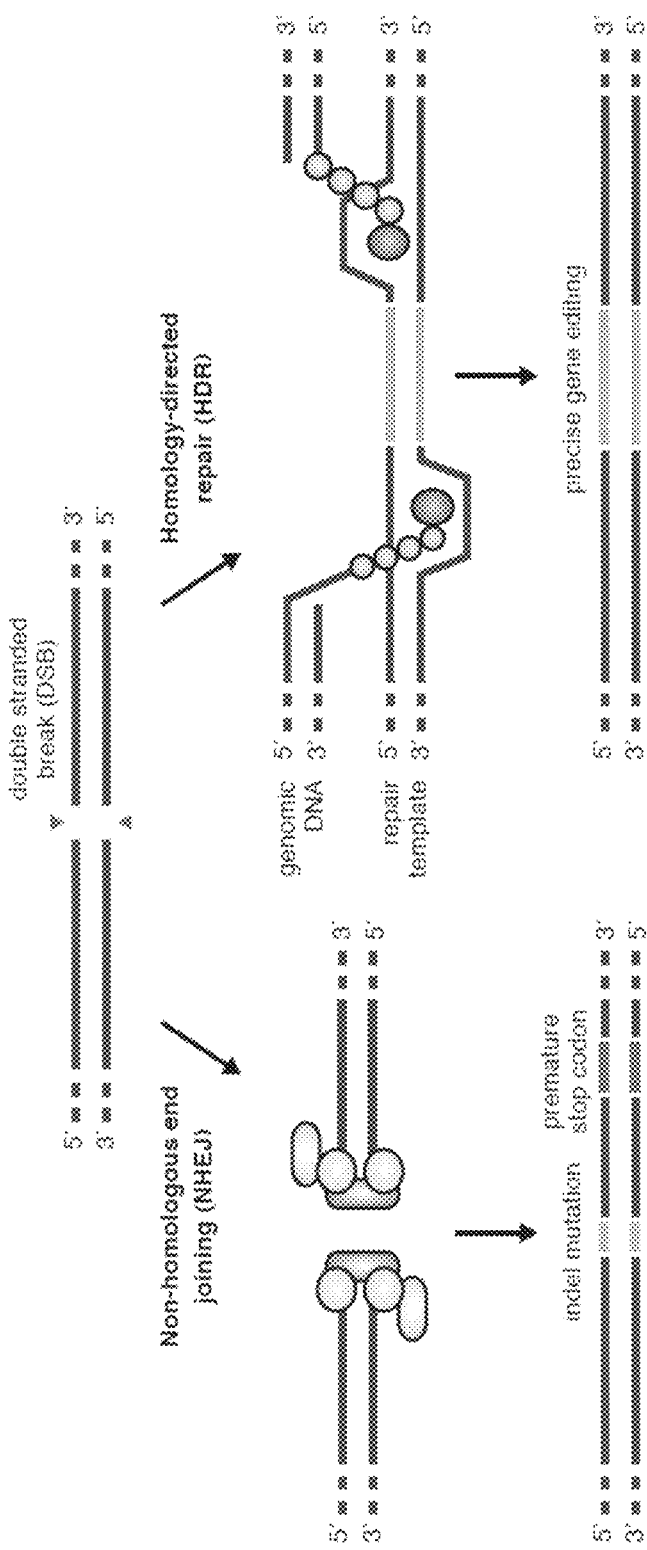
FIG. 11 shows how DNA double-strand break (DSB) repair promotes gene editing. In the error-prone non-homologous end joining (NHEJ) pathway, the ends of a DSB are processed by endogenous DNA repair machineries and rejoined together, which can result in random insertion/deletion (indel) mutations at the site of junction. Indel mutations occurring within the coding region of a gene can result in frame-shift and a premature stop codon, leading to gene knockout. Alternatively, a repair template in the form of a plasmid or single-stranded oligodeoxynucleotides (ssODN) can be supplied to leverage the homology-directed repair (HDR) pathway, which allows high fidelity and precise editing.

The break created by the CRISPR complex can be repaired by a repair processes such as the error prone non-homologous end joining (NHEJ) pathway or the high fidelity homology-directed repair (HDR) (FIG. 11). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome.

Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In an exemplary method for modifying a target polynucleotide by integrating an exogenous polynucleotide template, a double stranded break is introduced into the genome sequence by the CRISPR complex, the break is repaired via homologous recombination by an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences.

The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knock-out" of the target sequence.

A method of the invention may be used to create a plant, an animal or cell that may be used as a disease model. As used herein, "disease" refers to a disease, disorder, or indication in a subject. For example, a method of the invention may be used to create an animal or cell that comprises a modification in one or more nucleic acid sequences associated with a disease, or a plant, animal or cell in which the expression of one or more nucleic acid sequences associated with a disease are altered. Such a nucleic acid sequence may encode a disease associated protein sequence or may be a disease associated control sequence. Accordingly, it is understood that in embodiments of the invention, a plant, subject, patient, organism or cell can be a non-human subject, patient, organism or cell. Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants. In the instance where the cell is in cultured, a cell line may be established if appropriate culturing conditions are met and preferably if the cell is suitably adapted for this purpose (for instance a stem cell). Bacterial cell lines produced by the invention are also envisaged. Hence, cell lines are also envisaged.

In some methods, the disease model can be used to study the effects of mutations on the animal or cell and development and/or progression of the disease using measures commonly used in the study of the disease. Alternatively, such a disease model is useful for studying the effect of a pharmaceutically active compound on the disease.

In some methods, the disease model can be used to assess the efficacy of a potential gene therapy strategy. That is, a disease-associated gene or polynucleotide can be modified such that the disease development and/or progression is inhibited or reduced. In particular, the method comprises modifying a disease-associated gene or polynucleotide such that an altered protein is produced and, as a result, the animal or cell has an altered response. Accordingly, in some methods, a genetically modified animal may be compared with an animal predisposed to development of the disease such that the effect of the gene therapy event may be assessed.

In another embodiment, this invention provides a method of developing a biologically active agent that modulates a cell signaling event associated with a disease gene. The method comprises contacting a test compound with a cell comprising one or more vectors that drive expression of one or more of a CRISPR enzyme, a guide sequence linked to a tracr mate sequence, and a tracr sequence; and detecting a change in a readout that is indicative of a reduction or an augmentation of a cell signaling event associated with, e.g., a mutation in a disease gene contained in the cell.

A cell model or animal model can be constructed in combination with the method of the invention for screening a cellular function change. Such a model may be used to study the effects of a genome sequence modified by the CRISPR complex of the invention on a cellular function of interest. For example, a cellular function model may be used to study the effect of a modified genome sequence on intracellular signaling or extracellular signaling. Alternatively, a cellular function model may be used to study the effects of a modified genome sequence on sensory perception. In some such models, one or more genome sequences associated with a signaling biochemical pathway in the model are modified.

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but serve to show the broad applicability of the invention across genes and corresponding models.

An altered expression of one or more genome sequences associated with a signaling biochemical pathway can be determined by assaying for a difference in the mRNA levels of the corresponding genes between the test model cell and a control cell, when they are contacted with a candidate agent. Alternatively, the differential expression of the sequences associated with a signaling biochemical pathway is determined by detecting a difference in the level of the encoded polypeptide or gene product.

To assay for an agent-induced alteration in the level of mRNA transcripts or corresponding polynucleotides, nucleic acid contained in a sample is first extracted according to standard methods in the art. For instance, mRNA can be isolated using various lytic enzymes or chemical solutions according to the procedures set forth in Sambrook et al. (1989), or extracted by nucleic-acid-binding resins following the accompanying instructions provided by the manufacturers. The mRNA contained in the extracted nucleic acid sample is then detected by amplification procedures or conventional hybridization assays (e.g. Northern blot analysis) according to methods widely known in the art or based on the methods exemplified herein.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

In yet another aspect, conventional hybridization assays using hybridization probes that share sequence homology with sequences associated with a signaling biochemical pathway can be performed. Typically, probes are allowed to form stable complexes with the sequences associated with a signaling biochemical pathway contained within the biological sample derived from the test subject in a hybridization reaction. It will be appreciated by one of skill in the art that where antisense is used as the probe nucleic acid, the target polynucleotides provided in the sample are chosen to be complementary to sequences of the antisense nucleic acids. Conversely, where the nucleotide probe is a sense nucleic acid, the target polynucleotide is selected to be complementary to sequences of the sense nucleic acid.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, B-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

An agent-induced change in expression of sequences associated with a signaling biochemical pathway can also be determined by examining the corresponding gene products. Determining the protein level typically involves a) contacting the protein contained in a biological sample with an agent that specifically bind to a protein associated with a signaling biochemical pathway; and (b) identifying any agent:protein complex so formed. In one aspect of this embodiment, the agent that specifically binds a protein associated with a signaling biochemical pathway is an antibody, preferably a monoclonal antibody.

The reaction is performed by contacting the agent with a sample of the proteins associated with a signaling biochemical pathway derived from the test samples under conditions that will allow a complex to form between the agent and the proteins associated with a signaling biochemical pathway. The formation of the complex can be detected directly or indirectly according to standard procedures in the art. In the direct detection method, the agents are supplied with a detectable label and unreacted agents may be removed from the complex; the amount of remaining label thereby indicating the amount of complex formed. For such method, it is preferable to select labels that remain attached to the agents even during stringent washing conditions. It is preferable that the label does not interfere with the binding reaction. In the alternative, an indirect detection procedure may use an agent that contains a label introduced either chemically or enzymatically. A desirable label generally does not interfere with binding or the stability of the resulting agent:polypeptide complex. However, the label is typically designed to be accessible to an antibody for an effective binding and hence generating a detectable signal.

A wide variety of labels suitable for detecting protein levels are known in the art. Non-limiting examples include radioisotopes, enzymes, colloidal metals, fluorescent compounds, bioluminescent compounds, and chemiluminescent compounds.

The amount of agent:polypeptide complexes formed during the binding reaction can be quantified by standard quantitative assays. As illustrated above, the formation of agent:polypeptide complex can be measured directly by the amount of label remained at the site of binding. In an alternative, the protein associated with a signaling biochemical pathway is tested for its ability to compete with a labeled analog for binding sites on the specific agent. In this competitive assay, the amount of label captured is inversely proportional to the amount of protein sequences associated with a signaling biochemical pathway present in a test sample.

A number of techniques for protein analysis based on the general principles outlined above are available in the art. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunofluorescent assays, and SDS-PAGE.

Antibodies that specifically recognize or bind to proteins associated with a signaling biochemical pathway are preferable for conducting the aforementioned protein analyses. Where desired, antibodies that recognize a specific type of post-translational modifications (e.g., signaling biochemical pathway inducible modifications) can be used. Post-translational modifications include but are not limited to glycosylation, lipidation, acetylation, and phosphorylation. These antibodies may be purchased from commercial vendors. For example, anti-phosphotyrosine antibodies that specifically recognize tyrosine-phosphorylated proteins are available from a number of vendors including Invitrogen and Perkin Elmer. Anti-phosphotyrosine antibodies are particularly useful in detecting proteins that are differentially phosphorylated on their tyrosine residues in response to an ER stress. Such proteins include but are not limited to eukaryotic translation initiation factor 2 alpha (eIF-2α). Alternatively, these antibodies can be generated using conventional polyclonal or monoclonal antibody technologies by immunizing a host animal or an antibody-producing cell with a target protein that exhibits the desired post-translational modification.

In practicing the subject method, it may be desirable to discern the expression pattern of an protein associated with a signaling biochemical pathway in different bodily tissue, in different cell types, and/or in different subcellular structures. These studies can be performed with the use of tissue-specific, cell-specific or subcellular structure specific antibodies capable of binding to protein markers that are preferentially expressed in certain tissues, cell types, or subcellular structures.

An altered expression of a gene associated with a signaling biochemical pathway can also be determined by examining a change in activity of the gene product relative to a control cell. The assay for an agent-induced change in the activity of a protein associated with a signaling biochemical pathway will dependent on the biological activity and/or the signal transduction pathway that is under investigation. For example, where the protein is a kinase, a change in its ability to phosphorylate the downstream substrate(s) can be determined by a variety of assays known in the art. Representative assays include but are not limited to immunoblotting and immunoprecipitation with antibodies such as anti-phosphotyrosine antibodies that recognize phosphorylated proteins. In addition, kinase activity can be detected by high throughput chemiluminescent assays such as AlphaScreen™ (available from Perkin Elmer) and eTag™ assay (Chan-Hui, et al. (2003) Clinical Immunology 111: 162-174).

Where the protein associated with a signaling biochemical pathway is part of a signaling cascade leading to a fluctuation of intracellular pH condition, pH sensitive molecules such as fluorescent pH dyes can be used as the reporter molecules. In another example where the protein associated with a signaling biochemical pathway is an ion channel, fluctuations in membrane potential and/or intracellular ion concentration can be monitored. A number of commercial kits and high-throughput devices are particularly suited for a rapid and robust screening for modulators of ion channels. Representative instruments include FLIPR™ (Molecular Devices, Inc.) and VIPR (Aurora Biosciences). These instruments are capable of detecting reactions in over 1000 sample wells of a microplate simultaneously, and providing real-time measurement and functional data within a second or even a minisecond.

In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR and BI-2011/008/WSGR respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 and 61/748,427. Such genes, proteins and pathways may be the target polynucleotide of a CRISPR complex.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1 ; BRCA2; AR (Androgen Receptor); TSG101; IGF; IGF Receptor; Igf 1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia Disorders | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b<br>5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-B)-global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD; FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1,, P2RX7, P2X7, BCR, CML, PHL, ALL, GRAF, NF1, VRNF, WSS, NFNS, PTPN11, PTP2C, SHP2, |

TABLE B-continued

| | |
|---|---|
| Inflammation and immune related diseases and disorders | NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), Il-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PC, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2), Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260; AUTSX2); Fragile X Syndrome (FMR2, EMU, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1); Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxics), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT71); |

TABLE B-continued

Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3, PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNKTA1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A: EIF4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; AREGEF7; GRK6; ROCK2; MAPK1; RAC2; PLK1; AKT2; PIK3CA; CDK8; PTK2; CFL 1; P1K3CB; MYH9; DIAPH1; PIK3C3; MAPK8; |

TABLE C-continued

| CELLULAR FUNCTION | GENES |
|---|---|
| | F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2, IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NTKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKO; PTK2; PIK3CB; CXCL12; PIK3C3; MAPK8; PRKCI; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2: CTNND1; PIK3R1; CTNNB1; CLDN1; CDC42; F11R; ITK; CRKL; VAV3; CTTN; PRKCA; MMP1; MMP9 |
| Integtin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TFRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1: EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; |

TABLE C-continued

| CELLULAR FUNCTION | GENES |
|---|---|
| | CDKN1A; NCOA2; APAF1; NFKB1; CCND1; ATM; ESR1; CDKN2A; MYC; JUN; ESR2; BAX; IL6; CYPB1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1: CREBBP; MAP2K2; PIK3R1; PPP2RSC; MAP2K1; NIFKB1; KEAP1; PRKCA.; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1: GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; TRAF6; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK: NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; |

TABLE C-continued

| CELLULAR FUNCTION | GENES |
|---|---|
| | NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNT; INSR; RAF1; IKBKG; RELB; MAP3K7; CREBBP; MAP2K2; CHUK; PDGFRA; MAP2K1; NTKB1; JUN; IL1R1; HSP90AA1 |
| Fc-Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NTKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1 ; NFKB1; BRAT; ATF4; AKT3 PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NGKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; |

TABLE C-continued

| CELLULAR FUNCTION | GENES |
|---|---|
| | PTPN6; PIK3C2A; RAF1: CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CLF1; GNAQ; CAMK2A; CXCL12; MAPK8; MAPK3; KRAS; MAPK13; RHOA; CCR3; SRC; PPP1CC; MAPK14; NOM; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB, FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF |
| FXR/RXR Activation | INS; PPARA; FASN; RXRA; AKT2; SDC1; MAPK8; APOB; MAPK10; PPARG; MTTP; MAPK9; .PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA: FOS; PIK3CB; PIK3C3, MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |

TABLE C-continued

| CELLULAR FUNCTION | GENES |
|---|---|
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1.; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQOI; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNIVIT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |

TABLE C-continued

| CELLULAR FUNCTION | GENES |
| --- | --- |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dabl; unc-86 (Pou4f1 or Brn3a); Numb; Rein |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN and so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion—related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK, Parkin, UCHL1, Synphilin-1, and NURR1.

Examples of addiction-related proteins may include ABAT for example.

Examples of inflammation-related proteins may include the monocyte chemoattractant protein-1 (MCP1) encoded by the Ccr2 gene, the C—C chemokine receptor type 5 (CCR5) encoded by the Ccr5 gene, the IgG receptor IIB (FCGR2b, also termed CD32) encoded by the Fcgr2b gene, or the Fc epsilon R1 g (FCER1 g) protein encoded by the Fcer1 g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C—C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (C. elegans)), CTSB (cathepsin B), PSEN1 (presenilin 1), APP (amyloid beta (A4) precursor protein), APH1B (anterior pharynx defective 1 homolog B (C. elegans)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutières Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia *Punctata* Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

For example, "wild type StCas9" refers to wild type Cas9 from *S. thermophilus*, the protein sequence of which is given in the SwissProt database under accession number G3ECR1. Similarly, *S. pyogenes* Cas9 is included in SwissProt under accession number Q99ZW2.

The ability to use CRISPR-Cas systems to perform efficient and cost effective gene editing and manipulation will allow the rapid selection and comparison of single and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Methodological Improvement to Simplify Cloning and Delivery

Rather than encoding the U6-promoter and guide RNA on a plasmid, Applicants amplified the U6 promoter with a DNA oligo to add on the guide RNA. The resulting PCR product may be transfected into cells to drive expression of the guide RNA.

Example primer pair that allows the generation a PCR product consisting of U6-promoter::guideRNA targeting human Emx1 locus:

```
Forward Primer:
                                      (SEQ ID NO: 90)
AAACTCTAGAgagggcctatttcccatgattc Reverse Primer
(carrying the guide RNA, which is underlined):
                                      (SEQ ID NO: 91)
acctctagAAAAAAAGCACCGACTCGGTGCCACTTTTTCAAGTTGATAA

CGGACTAGCCTTATTTTAACTTGCTATGCTGTTTTGTTTCCAAAACAG

CATAGCTCTAAAACCCCTAGTCATTGGAGGTGACGGTGTTTCGTCCT

TTCCACaag
```

Example 2: Methodological Improvement to Improve Activity

Rather than use pol3 promoters, in particular RNA polymerase III (e.g. U6 or H1 promoters), to express guide RNAs in eukaryotic cells, Applicants express the T7 polymerase in eukaryotic cells to drive expression of guide RNAs using the T7 promoter.

One example of this system may involve introduction of three pieces of DNA:
1. expression vector for Cas9
2. expression vector for T7 polymerase
3. expression vector containing guideRNA fused to the T7 promoter Example 3: Methodological Improvement to Reduce Toxicity of Cas9: Delivery of Cas9 in the Form of mRNA Delivery of Cas9 in the form of mRNA enables transient expression of Cas9 in cells, to reduce toxicity. For example, humanized SpCas9 may be amplified using the following primer pair:

```
Forward Primer (to add on T7 promoter
for in vitro transcription):
                                      (SEQ ID NO: 92)
TAATACGACTCACTATAGGAAGTGCGCCACCATGGCCCCAAAGAAGAAGC

GG

Reverse Primer (to add on polyA tail):
                                      (SEQ ID NO: 93)
GGTTTTTTTTTTTTTTTTTTTTTTTTTTTTTttcttaCTTTTTCTTTT

TTGCCTGGCCG
```

Applicants transfect the Cas9 mRNA into cells with either guide RNA in the form of RNA or DNA cassettes to drive guide RNA expression in eukaryotic cells.

Example 4: Methodological Improvement to Reduce Toxicity of Cas9: Use of an Inducible Promoter Applicants transiently turn on Cas9 expression only when it is needed for carrying out genome modification. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome).

Example 5: Improvement of the Cas9 System for In Vivo Application

Figure 5:
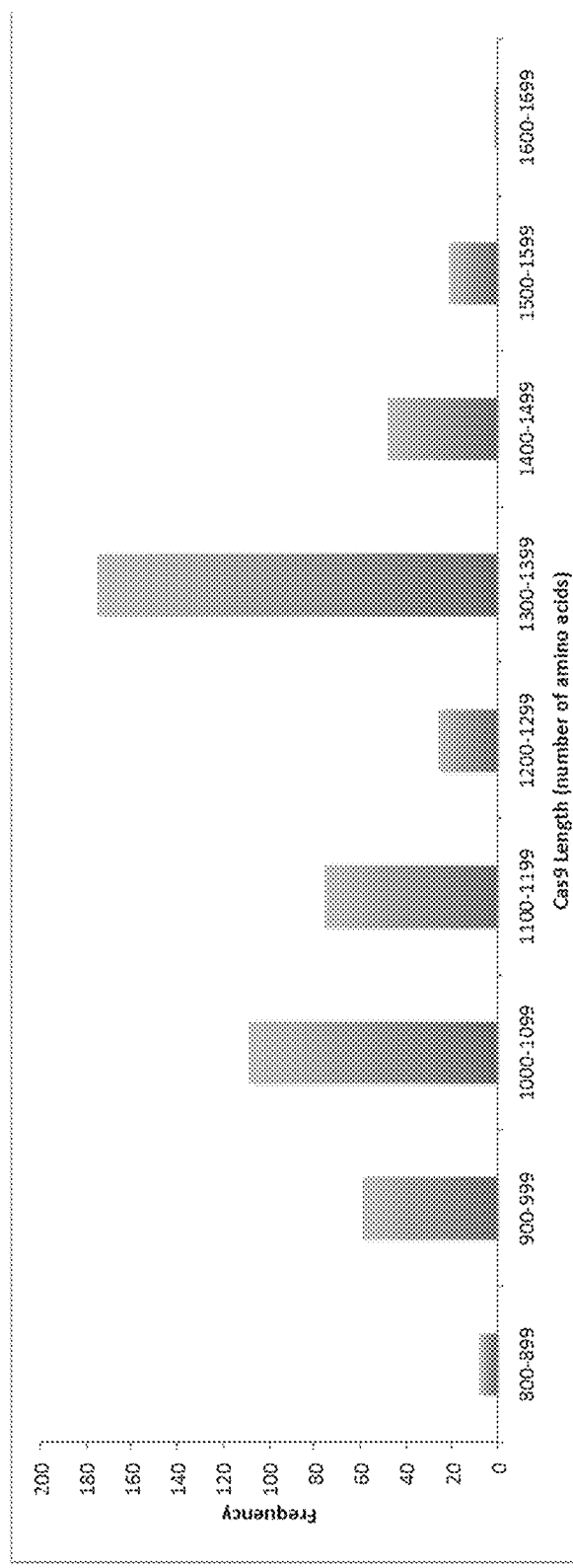
FIG. 5 shows a graph representing the length distribution of Cas9 orthologs.

Applicants conducted a Metagenomic search for a Cas9 with small molecular weight. Most Cas9 homologs are fairly large. For example the SpCas9 is around 1368aa long, which is too large to be easily packaged into viral vectors for delivery. A graph representing the length distribution of Cas9 homologs is generated from sequences deposited in GenBank (FIG. 5). Some of the sequences may have been mis-annotated and therefore the exact frequency for each length may not necessarily be accurate. Nevertheless it provides a glimpse at distribution of Cas9 proteins and suggest that there are shorter Cas9 homologs.

Through computational analysis, Applicants found that in the bacterial strain *Campylobacter*, there are two Cas9 proteins with less than 1000 amino acids. The sequence for one Cas9 from *Campylobacter jejuni* is presented below. At this length, CjCas9 can be easily packaged into AAV, lentiviruses, Adenoviruses, and other viral vectors for robust delivery into primary cells and in vivo in animal models. In a preferred embodiment of the invention, the Cas9 protein from *S. aureus* is used.

>Campylobacter jejuni Cas9 (CjCas9)
(SEQ ID NO: 94)
MARILAFDIGISSIGWAFSENDELKDCGVRIFTKVENPKTGESLALPRRL

ARSARKRLARRKARLNHLKHLIANEFKLNYEDYQSFDESLAKAYKGSLIS

PYELRFRALNELLSKQDFARVILHIAKRRGYDDIKNSDDKEKGAILKAIK

QNEEKLANYQSVGEYLYKEYFQKFKENSKEFTNVRNKKESYERCIAQSFL

KDELKLIFKKQREFGFSFSKKFEEEVLSVAFYKRALKDFSHLVGNCSFFT

DEKRAPKNSPLAFMFVALTRIINLLNNLKNTEGILYTKDDLNALLNEVLK

NGTLTYKQTKKLLGLSDDYEFKGEKGTYFIEFKKYKEFIKALGEHNLSQD

DLNEIAKDITLIKDEIKLKKALAKYDLNQNQIDSLSKLEFKDHLNISFKA

LKLVTPLMLEGKKYDEACNELNLKVAINEDKKDFLPAFNETYYKDEVTNP

VVLRAIKEYRKVLNALLKKYGKVHKINIELAREVGKNHSQRAKIEKEQNE

NYKAKKDAELECEKLGLKINSKNILKLRLFKEQKEFCAYSGEKIKISDLQ

DEKMLEIDHIYPYSRSFDDSYMNKVLVFTKQNQEKLNQTPFEAFGNDSAK

WQKIEVLAKNLPTKKQKRILDKNYKDKEQKNFKDRNLNDTRYIARLVLNY

TKDYLDFLPLSDDENTKLNDTQKGSKVHVEAKSGMLTSALRHTWGFSAKD

RNNHLHHAIDAVIIAYANNSIVKAFSDFKKEQESNSAELYAKKISELDYK

NKRKFFEPFSGFRQKVLDKIDEIFVSKPERKKPSGALHEETFRKEEEFYQ

SYGGKEGVLKALELGKIRKVNGKIVKNGDMFRVDIFKHKKTNKFYAVPIY

TMDFALKVLPNKAVARSKKGEIKDWILMDENYEFCFSLYKDSLILIQTKD

MQEPEFVYYNAFTSSTVSLIVSKHDNKFETLSKNQKILFKNANEKEVIAK

SIGIQNLKVFEKYIVSALGEVTKAEFRQREDFKK.

The putative tracrRNA element for this CjCas9 is:

(SEQ ID NO: 95)
TATAATCTCATAAGAAATTTAAAAAGGGACTAAAATAAAGAGTTTGCG

GGACTCTGCGGGGTTACAATCCCCTAAAACCGCTTTTAAAATT

The Direct Repeat sequence is:
ATTTTACCATAAAGAAATT-
TAAAAAGGGACTAAAAC (SEQ ID NO: 96)

An example of a chimeric guideRNA for CjCas9 is:

(SEQ ID NO: 97)
NNNNNNNNNNNNNNNNNNNNNNGUUUUAGUCCCGAAAGGGACUAAAAU

AAAGAGUUUGCGGGACUCUGCGGGGUUACAAUCCCCUAAAACCGCUUUU

Example 6: Cas9 Optimization

For enhanced function or to develop new functions, Applicants generate chimeric Cas9 proteins by combining fragments from different Cas9 homologs. For example, two example chimeric Cas9 proteins:

For example, Applicants fused the N-term of St1Cas9 (fragment from this protein is in bold) with C-term of SpCas9 (fragment from this protein is underlined).

>St1(N)Sp(C)Cas9
(SEQ ID NO: 98)
MSDLVLGLDIGIGSVGVGILNKVTGEIIHKNSRIFPAAQAENNLVRRTN

RQGRRLARRKKHRRVRLNRLFEESGLITDFTKISINLNPYQLRVKGLTDE

LSNEELFIALKNMVKHRGISYLDDASDDGNSSVGDYAQIVKENSKQLETK

TPGQIQLERYQTYGQLRGDFTVEKDGKKHRLINVFPTSAYRSEALRILQT

QQEFNPQITDEFINRYLEILTGKRKYYHGPGNEKSRTDYGRYRTSGETLD

NIFGILIGKCTFYPDEFRAAKASYTAQEFNLLNDLNNLTVPTETKKLSKE

QKNQIINYVKNEKAMGPAKLFKYIAKLLSCDVADIKGYRIDKSGKAEIHT

FEAYRKMKTLETLDIEQMDRETLDKLAYVLTLNTEREGIQEALEHEFADG

SFSQKQVDELVQFRKANSSIFGKGWHNFSVKLMMELIPELYETSEEQMTI

LTRLGKQKTTSSSNKTKYIDEKLLTEEIYNPVVAKSVRQAIKIVNAAIKE

YGDFDNIVIEMARENQTTQKGQKNSRERMKRIEEGIKELGSQILKEHPVE

NTQLQNEKLYLYYLQNGRDMYVDQELDINRLSDYDVDHIVPQSFLKDDSI

DNKVLTRSDKNRGKSDNVPSEEVVKKMKNYWRQLLNAKLITQRKFDNLTK

AERGGLSELDKAGFIKRQLVETRQITKHVAQILDSRMNTKYDENDKLIRE

VKVITLKSKLVSDFRKDFQFYKVREINNYHHAHDAYLNAVVGTALIKKYP

KLESEFVYGDYKVYDVRKMIAKSEQEIGKATAKYFFYSNIMNFFKTEITL

ANGEIRKRPLIETNGETGEIVWDKGRDFATVRKVLSMPQVNIVKKTEVQT

GGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYS

-continued

LFELENGRKRMLASAGELQKGNELALPSKYVNFLYLASHYEKLKGSPEDN

EQKQLFVEQHKHYLDEIIEQISEFSKRVILADANLDKVLSAYNKHRDKPI

REQAENIIHLFTLTNLGAPAAFKYFDTTIDRKRYTSTKEVLDATLIHQSI

TGLYETRIDLSQLGGD

\>Sp(N)St1(C)Cas9

(SEQ ID NO: 99)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARETNEDDEKKAIQKIQKANKDEKDAAMLKAANQYNG

KAELPHSVFHGHKQLATKIRLWHQQGERCLYTGKTISIHDLINNSNQFEV

DHILPLSITFDDSLANKVLVYATANQEKGQRTPYQALDSMDDAWSFRELK

AFVRESKTLSNKKKEYLLTEEDISKFDVRKKFIERNLVDTRYASRVVLNA

LQEHFRAHKIDTKVSVVRGQFTSQLRRHWGIEKTRDTYHHHAVDALIIAA

SSQLNLWKKQKNTLVSYSEDQLLDIETGELISDDEYKESVFKAPYQHFVD

TLKSKEFEDSILFSYQVDSKFNRKISDATIYATRQAKVGKDKADETYVLG

KIKDIYTQDGYDAFMKIYKKDKSKFLMYRHDPQTFEKVIEPILENYPNKQ

INEKGKEVPCNPFLKYKEEHGYIRKYSKKGNGPEIKSLKYYDSKLGNHID

ITPKDSNNKVVLQSVSPWRADVYFNKTTGKYEILGLKYADLQFEKGTGTY

KISQEKYNDIKKKEGVDSDSEFKFTLYKNDLLLVKDTETKEQQLFRFLSR

TMPKQKHYVELKPYDKQKFEGGEALIKVLGNVANSGQCKKGLGKSNISIY

KVRTDVLGNQHIIKNEGDKPKLDF

The benefit of making chimeric Cas9 include:

reduce toxicity improve expression in eukaryotic cells enhance specificity reduce molecular weight of protein, make protein smaller by combining the smallest domains from different Cas9 homologs.

Altering the PAM sequence requirement

Example 7: Utilization of Cas9 as a Generic DNA Binding Protein

Applicants used Cas9 as a generic DNA binding protein by mutating the two catalytic domains (D10 and H840) responsible for cleaving both strands of the DNA target. In order to upregulate gene transcription at a target locus Applicants fused the transcriptional activation domain (VP64) to Cas9. Applicants hypothesized that it would be important to see strong nuclear localization of the Cas9-VP64 fusion protein because transcription factor activation strength is a function of time spent at the target. Therefore, Applicants cloned a set of Cas9-VP64-GFP constructs, transfected them into 293 cells and assessed their localization under a fluorescent microscope 12 hours post-transfection.

The same constructs were cloned as a 2A-GFP rather than a direct fusion in order to functionally test the constructs without a bulky GFP present to interfere. Applicants elected to target the Sox2 locus with the Cas9 transactivator because it could be useful for cellular reprogram and the locus has already been validated as a target for TALE-TF mediated transcriptional activation. For the Sox2 locus Applicants chose eight targets near the transcriptional start site (TSS). Each target was 20 bp long with a neighboring NGG protospacer adjacent motif (PAM). Each Cas9-VP64 construct was co-transfected with each PCR generated chimeric crispr RNA (chiRNA) in 293 cells. 72 hours post transfection the transcriptional activation was assessed using RT-qPCR.

To further optimize the transcriptional activator, Applicants titrated the ratio of chiRNA (Sox2.1 and Sox2.5) to Cas9 (NLS-VP64-NLS-hSpCas9-NLS-VP64-NLS), transfected into 293 cells, and quantified using RT-qPCR. These results indicate that Cas9 can be used as a generic DNA binding domain to upregulate gene transcription at a target locus.

Applicants designed a second generation of constructs. (Table below).

--- pLenti-EF1a-GFP-2A-6xHis-NLS-VP64-NLS-hSpCsn1(D10A, H840A)-NLS ("6xHis" disclosed as SEQ ID NO: 100)
pLenti-EF1a-GFP-2A-6xHis-NLS-VP64-NLS-hSpCsn1(D10A, H840A) ("6xHis" disclosed as SEQ ID NO: 100)
pLenti-EF1a-GFP-2A-6xHis-NLS-VP64-NLS-NLS-hSpCsn1 (D10A, H840A) "6xHis" disclosed as SEQ ID NO: 100)
pLenti-EF1a-GFP-2A-6xHis-NLS-hSpCsn1(D10A, H840A)-NLS ("6xHis" disclosed as SEQ ID NO: 100)
pLenti-EF1a-GFP-2A-6xHis-NLS-hSpCsn1(D10A, H840A) ("6xHis" disclosed as SEQ ID NO: 100)
pLenti-EF1a-GFP-2A-6xHis-NLS-NLS-hSpCsn1(D10A, H840A) ("6xHis" disclosed as SEQ ID NO: 100)

---

Applicants use these constructs to assess transcriptional activation (VP64 fused constructs) and repression (Cas9 only) by RT-qPCR. Applicants assess the cellular localization of each construct using anti-His antibody, nuclease activity using a Surveyor nuclease assay, and DNA binding affinity using a gel shift assay. In a preferred embodiment of the invention, the gel shift assay is an EMSA gel shift assay.

Example 8: Cas9 Transgenic and Knock in Mice

To generate a mouse that expresses the Cas9 nuclease Applicants submit two general strategies, transgenic and knock in. These strategies may be applied to generate any other model organism of interest, for e.g. Rat. For each of the general strategies Applicants made a constitutively active Cas9 and a Cas9 that is conditionally expressed (Cre recombinase dependent). The constitutively active Cas9 nuclease is expressed in the following context: pCAG-NLS-Cas9-NLS-P2A-EGFP-WPRE-bGHpolyA. pCAG is the promoter, NLS is a nuclear localization signal, P2A is the peptide cleavage sequence, EGFP is enhanced green fluorescent protein, WPRE is the woodchuck hepatitis virus posttranscriptional regulatory element, and bGHpolyA is the bovine growth hormone poly-A signal sequence (FIGS. 7A-B). The conditional version has one additional stop cassette element, loxP-SV40 polyA x3-loxP, after the promoter and before NLS-Cas9-NLS (i.e. pCAG-oxP-SV40polyAx3-loxP-NLS-Cas9-NLS-P2A-EGFP-WPRE-bGHpolyA). The important expression elements can be visualized as in FIG. 8. The constitutive construct should be expressed in all cell types throughout development, whereas, the conditional construct will only allow Cas9 expression when the same cell is expressing the Cre recombinase. This latter version will allow for tissue specific expression of Cas9 when Cre is under the expression of a tissue specific promoter. Moreover, Cas9 expression could be induced in adult mice by putting Cre under the expression of an inducible promoter such as the TET on or off system.

Validation of Cas9 constructs: Each plasmid was functionally validated in three ways: 1) transient transfection in 293 cells followed by confirmation of GFP expression; 2) transient transfection in 293 cells followed by immunofluorescence using an antibody recognizing the P2A sequence; and 3) transient transfection followed by Surveyor nuclease assay. The 293 cells may be 293FT or 293 T cells depending on the cells that are of interest. In a preferred embodiment the cells are 293FT cells. The results of the Surveyor were run out on the top and bottom row of the gel for the conditional and constitutive constructs, respectively. Each was tested in the presence and absence of chimeric RNA targeted to the hEMX1 locus (chimeric RNA hEMX1.1). The results indicate that the construct can successfully target the hEMX1 locus only in the presence of chimeric RNA (and Cre in the conditional case). The gel was quantified and the results are presented as average cutting efficiency and standard deviation for three samples.

Transgenic Cas9 mouse: To generate transgenic mice with constructs, Applicants inject pure, linear DNA into the pronucleus of a zygote from a pseudo pregnant CB56 female. Founders are identified, genotyped, and backcrossed to CB57 mice. The constructs were successfully cloned and verified by Sanger sequencing.

Knock in Cas9 mouse: To generate Cas9 knock in mice Applicants target the same constitutive and conditional constructs to the Rosa26 locus. Applicants did this by cloning each into a Rosa26 targeting vector with the following elements: Rosa26 short homology arm—constitutive/conditional Cas9 expression cassette—pPGK-Neo-Rosa26 long homology arm—pPGK-DTA. pPGK is the promoter for the positive selection marker Neo, which confers resistance to neomycin, a 1 kb short arm, a 4.3 kb long arm, and a negative selection diphtheria toxin (DTA) driven by PGK.

The two constructs were electroporated into R1 mESCs and allowed to grow for 2 days before neomycin selection was applied. Individual colonies that had survived by days 5-7 were picked and grown in individual wells. 5-7 days later the colonies were harvested, half were frozen and the other half were used for genotyping. Genotyping was done by genomic PCR, where one primer annealed within the donor plasmid (AttpF) and the other outside of the short homology arm (Rosa26-R) Of the 22 colonies harvested for the conditional case, 7 were positive (Left). Of the 27 colonies harvested for the constitutive case, zero were positive (Right). It is likely that Cas9 causes some level of toxicity in the mESC and for this reason there were no positive clones. To test this Applicants introduced a Cre expression plasmid into correctly targeted conditional Cas9 cells and found very low toxicity after many days in culture. The reduced copy number of Cas9 in correctly targeted conditional Cas9 cells (1-2 copies per cell) is enough to allow stable expression and relatively no cytotoxicity. Moreover, this data indicates that the Cas9 copy number determines toxicity. After electroporation each cell should get several copies of Cas9 and this is likely why no positive colonies were found in the case of the constitutive Cas9 construct. This provides strong evidence that utilizing a conditional, Cre-dependent strategy should show reduced toxicity. Applicants inject correctly targeted cells into a blastocyst and implant into a female mouse. Chimerics are identified and backcrossed. Founders are identified and genotyped.

Utility of the conditional Cas9 mouse: Applicants have shown in 293 cells that the Cas9 conditional expression construct can be activated by co-expression with Cre. Applicants also show that the correctly targeted R1 mESCs can have active Cas9 when Cre is expressed. Because Cas9 is followed by the P2A peptide cleavage sequence and then EGFP Applicants identify successful expression by observing EGFP. This same concept is what makes the conditional Cas9 mouse so useful. Applicants may cross their conditional Cas9 mouse with a mouse that ubiquitously expresses Cre (ACTB-Cre line) and may arrive at a mouse that expresses Cas9 in every cell. It should only take the delivery of chimeric RNA to induce genome editing in embryonic or adult mice. Interestingly, if the conditional Cas9 mouse is crossed with a mouse expressing Cre under a tissue specific promoter, there should only be Cas9 in the tissues that also express Cre. This approach may be used to edit the genome in only precise tissues by delivering chimeric RNA to the same tissue.

Example 9: Cas9 Diversity and Chimeric RNAs

The CRISPR-Cas system is an adaptive immune mechanism against invading exogenous DNA employed by diverse species across bacteria and archaea. The type II CRISPR-Cas system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracrRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~100 amino acids) (FIGS. 3 and 4A-F).

Applicants have also optimized Cas9 guide RNA using in vitro methods.

Example 10: Cas9 Mutations

In this example, Applicants show that the following mutations can convert SpCas9 into a nicking enzyme: D10A, E762A, H840A, N854A, N863A, D986A.

Applicants provide sequences showing where the mutation points are located within the SpCas9 gene (FIG. 6A-M). Applicants also show that the nickases are still able to mediate homologous recombination. Furthermore, Applicants show that SpCas9 with these mutations (individually) do not induce double strand break.

Cas9 orthologs all share the general organization of 3-4 RuvC domains and a HNH domain. The 5' most RuvC domain cleaves the non-complementary strand, and the HNH domain cleaves the complementary strand. All notations are in reference to the guide sequence.

The catalytic residue in the 5' RuvC domain is identified through homology comparison of the Cas9 of interest with other Cas9 orthologs (from *S. pyogenes* type II CRISPR locus, *S. thermophilus* CRISPR locus 1, *S. thermophilus* CRISPR locus 3, and *Franciscilla novicida* type II CRISPR locus), and the conserved Asp residue is mutated to alanine to convert Cas9 into a complementary-strand nicking enzyme. Similarly, the conserved His and Asn residues in the HNH domains are mutated to Alanine to convert Cas9 into a non-complementary-strand nicking enzyme.

Example 11: Cas9 Transcriptional Activation and Cas9 Repressor

Cas9 Transcriptional Activation

A second generation of constructs have been designed and are in the pipeline to be tested (Table 1). These constructs will be used to assess transcriptional activation (VP64 fused constructs) and repression (Cas9 only) by RT-qPCR. Applicants will also assess the cellular localization of each construct using anti-His antibody, nuclease activity using a Surveyor nuclease assay, and DNA binding affinity using a gel shift assay.

Cas Repressor

It has been shown previously that dCas9 can be used as a generic DNA binding domain to repress gene expression. Applicants report an improved dCas9 design as well as dCas9 fusions to the repressor domains KRAB and SID4x. From the plasmid library created for modulating transcription using Cas9 in Table 1, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Each dCas9 repressor plasmid was co-transfected with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP## control". The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4x (pXRP48 and pXRP49).

Further work investigates: repeating the above experiment, targeting different genes, utilizing other gRNAs to determine the optimal targeting position, and multiplexed repression.

TABLE 1

(Table 1 discloses "GGGGS$_3$" as SEQ ID NO: 101, "EAAAK$_3$" as SEQ ID NO: 102 and "GGGGGS$_3$" as SEQ ID NO: 103)

pXRP024-pLenti2-EF1a-VP64-NLS-FLAG-Linker-dCas9-NLS-gLuc-2A-GFP-WPRE pXRP025-pLenti2-EF1a-VP64-NLS-GGGGS$_3$Linker-dCas9-NLS-gLuc-2A-GFP-WPRE pXRP026-pLenti2-EF1a-VP64-NLS-EAAAK$_3$Linker-dCas9-NLS-gLuc-2A-GFP-WPRE pXRP027-pLenti2-EF1a-NLS-FLAG-Linker-dCas9-NLS-gLuc-2A-GFP-WPRE pXRP028-pLenti2-EF1a-NLS-GGGGS$_3$Linker-dCas9-NLS-gLuc-2A-GFP-WPRE pXRP029-pLenti2-EF1a-NLS-EAAAK$_3$Linker-dCas9-NLS-gLuc-2A-GFP-WPRE pXRP030-pLenti2-pSV40-VP64-NLS-FLAG-Linker-dCas9-NLS-gLuc-2A-GFP-WPRE pXRP031-pLenti2-pPGK-VP64-NLS-FLAG-Linker-dCas9-NLS-gLuc-2A-GFP-WPRE pXRP032-pLenti2-LTR-VP64-NLS-FLAG-Linker-dCas9-NLS-gLuc-2A-GFP-WPRE pXRP033-pLenti2-pSV40-VP64-NLS-GGGGS$_3$Linker-dCas9-NLS-gLuc-2A-GFP-WPRE pXRP034-pLenti2-pPGK-VP64-NLS-GGGGS$_3$Linker-dCas9-NLS-gLuc-2A-GFP-WPRE pXRP035-pLenti2-LTR-VP64-NLS-GGGGS$_3$Linker-dCas9-NLS-gLuc-2A-GFP-WPRE pXRP036-pLenti2-pSV40-VP64-NLS-EAAAK$_3$Linker-dCas9-NLS-gLuc-2A-GFP-WPRE pXRP037-pLenti2-pPGK-VP64-NLS-EAAAK$_3$Linker-dCas9-NLS-gLuc-2A-GFP-WPRE TABLE 1-continued (Table 1 discloses "GGGGS₃" as SEQ ID NO: 101, "EAAAK₃" as SEQ ID NO: 102 and "GGGGGS₃" as SEQ ID NO: 103)

pXRP038-pLenti2-LTR-VP64-NLS-EAAAK₃Linker-dCas9-NLS-gLuc-2A-GFP-WPRE pXRP048-pLenti2-EF1a-SID4x-NLS-FLAG-Linker-dCas9-NLS-gLuc-2A-GFP-WPRE pXRP049-pLenti2-EF1a-SID4X-NLS-GGGGS₃Linker-dCas9-NLS-gLuc-2A-GFP-WPRE pXRP050-pLenti2-EF1a-SID4X-NLS-EAAAK₃Linker-dCas9-NLS-gLuc-2A-GFP-WPRE pXRP051-pLenti2-EF1a-KRAB-NLS-FLAG-Linker-dCas9-NLS-gLuc-2A-GFP-WPRE pXRP052-pLenti2-EF1a-KRAB-NLS-GGGGS₃Linker-dCas9-NLS-gLuc-2A-GFP-WPRE pXRP053-pLenti2-EF1a-KRAB-NLS-EAAAK₃Linker-dCas9-NLS-gLuc-2A-GFP-WPRE pXRP054-pLenti2-EF1a-dCas9-Linker-FLAG-NLS-VP64-gLuc-2A-GFP-WPRE pXRP055-pLenti2-EF1a-dCas9-Linker-FLAG-NLS-SID4X-gLuc-2A-GFP-WPRE pXRP056-pLenti2-EF1a-dCas9-Linker-FLAG-NLS-KRAB-gLuc-2A-GFP-WPRE pXRP057-pLenti2-EF1a-dCas9-GGGGGS₃-NLS-VP64-gLuc-2A-GFP-WPRE pXRP058-pLenti2-EF1a-dCas9-GGGGGS₃-NLS-SID4X-gLuc-2A-GFP-WPRE pXRP059-pLenti2-EF1a-dCas9-GGGGGS₃-NLS-KRAB-gLuc-2A-GFP-WPRE pXRP060-pLenti2-EF1a-dCas9-EAAAK₃-NLS-VP64-gLuc-2A-GFP-WPRE pXRP061-pLenti2-EF1a-dCas9-EAAAK₃-NLS-SID4X-gLuc-2A-GFP-WPRE pXRP062-pLenti2-EF1a-dCas9-EAAAK₃-NLS-KRAB-gLuc-2A-GFP-WPRE pXRP024-pLenti2-EF1a-VP64-NLS-FLAG-Linker-Cas9-NLS-gLuc-2A-GFP-WPRE pXRP025-pLenti2-EF1a-VP64-NLS-GGGGS₃Linker-Cas9-NLS-gLuc-2A-GFP-WPRE pXRP026-pLenti2-EF1a-VP64-NLS-EAAAK₃Linker-Cas9-NLS-gLuc-2A-GFP-WPRE pXRP027-pLenti2-EF1a-NLS-FLAG-Linker-Cas9-NLS-gLuc-2A-GFP-WPRE pXRP028-pLenti2-EF1a-NLS-GGGGS₃Linker-Cas9-NLS-gLuc-2A-GFP-WPRE pXRP029-pLenti2-EF1a-NLS-EAAAK₃Linker-Cas9-NLS-gLuc-2A-GFP-WPRE pXRP030-pLenti2-pSV40-VP64-NLS-FLAG-Linker-Cas9-NLS-gLuc-2A-GFP-WPRE pXRP031-pLenti2-pPGK-VP64-NLS-FLAG-Linker-Cas9-NLS-gLuc-2A-GFP-WPRE pXRP032-pLenti2-LTR-VP64-NLS-FLAG-Linker-Cas9-NLS-gLuc-2A-GFP-WPRE pXRP033-pLenti2-pSV40-VP64-NLS-GGGGS₃Linker-Cas9-NLS-gLuc-2A-GFP-WPRE pXRP034-pLenti2-pPGK-VP64-NLS-GGGGS₃Linker-Cas9-NLS-gLuc-2A-GFP-WPRE pXRP035-pLenti2-LTR-VP64-NLS-GGGGS₃Linker-Cas9-NLS-gLuc-2A-GFP-WPRE pXRP036-pLenti2-pSV40-VP64-NLS-EAAAK₃Linker-Cas9-NLS-gLuc-2A-GFP-WPRE pXRP037-pLenti2-pPGK-VP64-NLS-EAAAK₃Linker-Cas9-NLS-gLuc-2A-GFP-WPRE pXRP038-pLenti2-LTR-VP64-NLS-EAAAK₃Linker-Cas9-NLS-gLuc-2A-GFP-WPRE pXRP048-pLenti2-EF1a-SID4x-NLS-FLAG-Linker-Cas9-NLS-gLuc-2A-GFP-WPRE pXRP049-pLenti2-EF1a-SID4X-NLS-GGGGS₃Linker-Cas9-NLS-gLuc-2A-GFP-WPRE pXRP050-pLenti2-EF1a-SID4X-NLS-EAAAK₃Linker-Cas9-NLS-gLuc-2A-GFP-WPRE pXRP051-pLenti2-EF1a-KRAB-NLS-FLAG-Linker-Cas9-NLS-gLuc-2A-GFP-WPRE pXRP052-pLenti2-EF1a-KRAB-NLS-GGGGS₃Linker-Cas9-NLS-gLuc-2A-GFP-WPRE pXRP053-pLenti2-EF1a-KRAB-NLS-EAAAK₃Linker-Cas9-NLS-gLuc-2A-GFP-WPRE pXRP054-pLenti2-EF1a-Cas9-Linker-FLAG-NLS-VP64-gLuc-2A-GFP-WPRE pXRP055-pLenti2-EF1a-Cas9-Linker-FLAG-NLS-SID4X-gLuc-2A-GFP-WPRE

TABLE 1-continued (Table 1 discloses "GGGGS$_3$" as SEQ ID NO: 101, "EAAAK$_3$" as SEQ ID NO: 102 and "GGGGGS$_3$" as SEQ ID NO: 103)

pXRP056-pLenti2-EF1a-Cas9-Linker-FLAG-NLS-KRAB-gLuc-2A-GFP-WPRE pXRP057-pLenti2-EF1a-Cas9-GGGGGS$_3$-NLS-VP64-gLuc-2A-GFP-WPRE pXRP058-pLenti2-EF1a-Cas9-GGGGGS$_3$-NLS-SID4X-gLuc-2A-GFP-WPRE pXRP059-pLenti2-EF1a-Cas9-GGGGGS$_3$-NLS-KRAB-gLuc-2A-GFP-WPRE pXRP060-pLenti2-EF1a-Cas9-EAAAK$_3$-NLS-VP64-gLuc-2A-GFP-WPRE pXRP061-pLenti2-EF1a-Cas9-EAAAK$_3$-NLS-SID4X-gLuc-2A-GFP-WPRE pXRP062-pLenti2-EF1a-Cas9-EAAAK$_3$-NLS-KRAB-gLuc-2A-GFP-WPRE Example 12: Targeted Deletion of Genes Involved in Cholesterol Biosynthesis, Fatty Acid Biosynthesis, and Other Metabolic Disorders, Genes Encoding Mis-Folded Proteins Involved in Amyloid and Other Diseases, Oncogenes Leading to Cellular Transformation, Latent Viral Genes, and Genes Leading to Dominant-Negative Disorders, Amongst Other Disorders Applicants demonstrate gene delivery of a CRISPR-Cas system in the liver, brain, ocular, epithelial, hematopoetic, or another tissue of a subject or a patient in need thereof, suffering from metabolic disorders, amyloidosis and protein-aggregation related diseases, cellular transformation arising from genetic mutations and translocations, dominant negative effects of gene mutations, latent viral infections, and other related symptoms, using either viral or nanoparticle delivery system.

Study Design: Subjects or patients in need thereof suffering from metabolic disorders, amyloidosis and protein aggregation related disease which include but are not limited to human, non-primate human, canine, feline, bovine, equine, other domestic animals and related mammals. The CRISPR-Cas system is guided by a chimeric guide RNA and targets a specific site of the human genomic loci to be cleaved. After cleavage and non-homologous end-joining mediated repair, frame-shift mutation results in knock out of genes.

Applicants select guide-RNAs targeting genes involved in above-mentioned disorders to be specific to endogenous loci with minimal off-target activity. Two or more guide RNAs may be encoded into a single CRISPR array to induce simultaneous double-stranded breaks in DNA leading to micro-deletions of affected genes or chromosomal regions.

Identification and Design of Gene Targets

For each candidate disease gene, Applicants select DNA sequences of interest include protein-coding exons, sequences including and flanking known dominant negative mutation sites, sequences including and flanking pathological repetitive sequences. For gene-knockout approaches, early coding exons closest to the start codon offer best options for achieving complete knockout and minimize possibility of truncated protein products retaining partial function.

Applicants analyze sequences of interest for all possible targetable 20-bp sequences immediately 5' to a NGG motif (for SpCas9 system) or a NNAGAAW (for St1Cas9 system). Applicants choose sequences for unique, single RNA-guided Cas9 recognition in the genome to minimize off-target effects based on computational algorithm to determine specificity.

Cloning of Guide Sequences into a Delivery System

Guide sequences are synthesized as double-stranded 20-24 bp oligonucleotides. After 5'-phosphorylation treatment of oligos and annealing to form duplexes, oligos are ligated into suitable vector depending on the delivery method:

Virus-Based Delivery Methods

AAV-based vectors (PX260, 330, 334, 335) have been described elsewhere

Lentiviral-based vectors use a similar cloning strategy of directly ligating guide sequences into a single vector carrying a U6 promoter-driven chimeric RNA scaffold and a EF1a promoter-driven Cas9 or Cas9 nickase.

Virus production is described elsewhere.

Nanoparticle-based RNA delivery methods

1. Guide sequences are synthesized as an oligonucleotide duplex encoding T7 promoter—guide sequence—chimeric RNA. A T7 promoter is added 5' of Cas9 by PCR method.

2. T7-driven Cas9 and guide-chimeric RNAs are transcribed in vitro, and Cas9 mRNA is further capped and A-tailed using commercial kits. RNA products are purified per kit instructions.

Hydrodynamic Tail Vein Delivery Methods (for Mouse)

Guide sequences are cloned into AAV plasmids as described above and elsewhere in this application.

In Vitro Validation on Cell Lines

Transfection

1. DNA Plasmid Transfection

Plasmids carrying guide sequences are transfected into human embryonic kidney (HEK293T) or human embryonic stem (hES) cells, other relevant cell types using lipid-, chemical-, or electroporation-based methods. For a 24-well transfection of HEK293T cells (~260,000 cells), 500 ng of total DNA is transfected into each single well using Lipofectamine 2000. For a 12-well transfection of hES cells, 1 ug of total DNA is transfected into a single well using Fugene HD.

2. RNA Transfection

Figure 10:
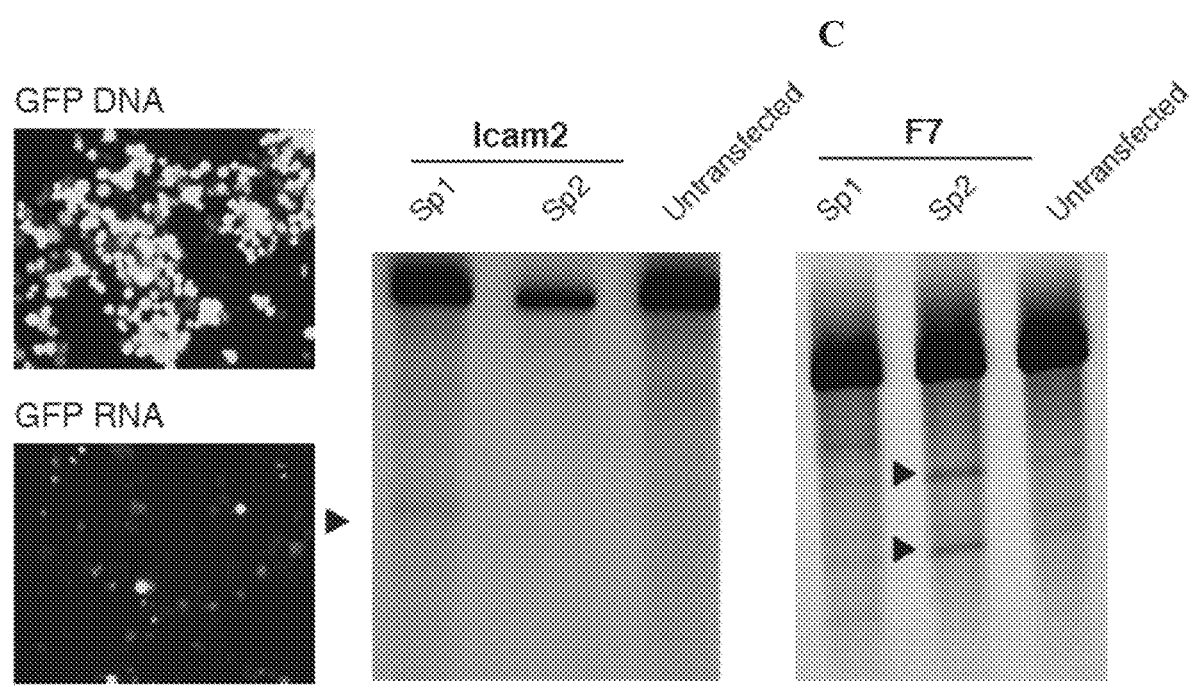
FIG. 10 shows RNA delivery of Cas9 and chimeric RNA into cells (A) Delivery of a GFP reporter as either DNA or mRNA into Neuro-2A cells. (B) Delivery of Cas9 and chimeric RNA against the Icam2 gene as RNA results in cutting for one of two spacers tested. (C) Delivery of Cas9 and chimeric RNA against the F7 gene as RNA results in cutting for one of two spacers tested.

Purified RNA described above is used for transfection into HEK293T cells. 1-2 ug of RNA may be transfected into ~260,000 using Lipofectamine 2000 per manufacturer's instruction. RNA delivery of Cas9 and chimeric RNA is shown in FIG. 10.

Assay of Indel Formation In Vitro

Cells are harvested 72-hours post-transfection and assayed for indel formation as an indication of double-stranded breaks.

Briefly, genomic region around target sequence is PCR amplified (~400-600 bp amplicon size) using high-fidelity polymerase. Products are purified, normalized to equal concentration, and slowly annealed from 95° C. to 4° C. to allow formation of DNA heteroduplexes. Post annealing, the Cel-I enzyme is used to cleave heteroduplexes, and resulting products are separated on a polyacrylamide gel and indel efficiency calculated.

In Vivo Proof of Principle in Animal

Delivery Mechanisms

AAV or Lentivirus production is described elsewhere.

Nanoparticle formulation: RNA mixed into nanoparticle formulation

Hydrodynamic tail vein injections with DNA plasmids in mice are conducted using a commercial kit Cas9 and guide sequences are delivered as virus, nanoparticle-coated RNA mixture, or DNA plasmids, and injected into subject animals. A parallel set of control animals is injected with sterile saline, Cas9 and GFP, or guide sequence and GFP alone.

Three weeks after injection, animals are tested for amelioration of symptoms and sacrificed. Relevant organ systems analyzed for indel formation. Phenotypic assays include blood levels of HDL, LDL, lipids, Assay for Indel Formation DNA is extracted from tissue using commercial kits; indel assay will be performed as described for in vitro demonstration.

Therapeutic applications of the CRISPR-Cas system are amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Examples of a Single Guide-RNA to Introduce Targeted Indels at a Gene Locus

| Disease | GENE | SPACER | PAM | SEQ ID NO: | Mechanism | References |
| --- | --- | --- | --- | --- | --- | --- |
| Hypercholesterolemia | HMG-CR | GCCAAATTGGACGACCCTCG | CGG | 104 | Knockout | Fluvastatin: a review of its pharmacology and use in the management of hypercholesterolaemia. (Plosker GL et al. Drugs 1996, 51(3): 433-459) |
| Hypercholesterolemia | SQLE | CGAGGAGACCCCCGTTTCGG | TGG | 105 | Knockout | Potential role of nonstatin cholesterol lowering agents (Trapani et al. IUBMB Life, Volume 63, Issue 11, pages 964-971, November 2011) |
| Hyperlipidemia | DGAT1 | CCCGCCGCCGCCGTGGCTCG | AGG | 106 | Knockout | DGAT1 inhibitors as anti-obesity and anti-diabetic agents. (Birch AM et al. Current Opinion in Drug Discovery & Development [2010, 13(4): 489-496) |
| Leukemia | BCR-ABL | TGAGCTCTACGAGATCCACA | AGG | 107 | Knockout | Killing of leukemic cells with a BCR/ABL fusion gene by RNA interference (RNAi). (Fuchs et al. Oncogene 2002, 21(37): 5716-5724) |

Examples of a Pair of Guide-RNA to Introduce Chromosomal Microdeletion at a Gene Locus

| Disease | GENE | SPACER | PAM | SEQ ID NO: | Mechanism | References |
|---|---|---|---|---|---|---|
| Hyperlipidemia | PLIN2 guide1 | CTCAAAATT CATACCGGT TG | TGG | 108 | Microdeletion | Perilipin-2 Null Mice are Protected Against Diet-Induced Obesity, Adipose Inflammation and Fatty Liver Disease (McManaman JL et al. The Journal of Lipid Research, jlr.M035063. First Published on Feb. 12, 2013) |
| Hyperlipidemia | PLIN2 guide2 | CGTTAAACA ACAACCGGA CT | TGG | 109 | Microdeletion | |
| Hyperlipidemia | SREBP guide1 | TTCACCCCG CGGCGCTGA AT | ggg | 110 | Microdeletion | Inhibition of SREBP by a Small Molecule, Betulin, Improves Hyperlipidemia and Insulin Resistance and Reduces Atherosclerotic Plaques (Tang J et al. Cell Metabolism, Volume 13, Issue 1, 44-56, 5 Jan. 2011) |
| Hyperlipidemia | SREBP guide2 | ACCACTACC AGTCCGTCC AC | agg | 111 | Microdeletion | |

Resistance and Reduces Atherosclerotic Plaques (Tang J et al. 1, 44-56, 5 Jan. 2011)

Example 13: Targeted Integration of Repair for Genes Carrying Disease-Causing Mutations; Reconstitution of Enzyme Deficiencies and Other Related Diseases Study Design I. Identification and design of gene targets Described in Example 16

II. Cloning of guide sequences and repair templates into a delivery system

Described above in Example 16

Applicants clone DNA repair templates to include homology arms with diseased allele as well a wild-type repair template III. In vitro validation on cell lines a. Transfection is described above in Example 16; Cas9, guide RNAs, and repair template are co-transfected into relevant cell types.

b. Assay for repair in vitro i. Applicants harvest cells 72-hours post-transfection and assay for repair ii. Briefly, Applicants amplify genomic region around repair template PCR using high-fidelity polymerase. Applicants sequence products for decreased incidence of mutant allele.

IV. In vivo proof of principle in animal a. Delivery mechanisms are described above Examples 16 and 29.

b. Assay for repair in vivo i. Applicants perform the repair assay as described in the in vitro demonstration.

V. Therapeutic applications

The CRISPR-Cas system is amenable for achieving tissue-specific and temporally controlled targeted deletion of candidate disease genes. Examples include genes involved in cholesterol and fatty acid metabolism, amyloid diseases, dominant negative diseases, latent viral infections, among other disorders.

Example of one single missense mutation with repair template (sequence disclosed as SEQ ID NO: 112):

| Disease | GENE | SPACER | PAM |
|---|---|---|---|
| Familial amyloid polyneuropathy | TTR | AGCCTTTCTGAACACATGCA | CGG |

| Mechanism | References |
|---|---|
| V30M repair | Transthyretin mutations in health and disease (Joao et al. Human Mutation, Volume 5, Issue 3, pages 191-196, 1995) |

```
V30M    CCTGCCATCAATGTGGCCATGCATGTGTTCAGAAAGGCT
allele  (SEQ ID NO: 113)

WT      CCTGCCATCAATGTGGCCGTGCATGTGTTCAGAAAGGCT
allele  (SEQ ID NO: 114)
```

Example 14: Therapeutic Application of the CRISPR-Cas System in Glaucoma, Amyloidosis, and Huntington's Disease Glaucoma: Applicants design guide RNAs to target the first exon of the mycilin (MYOC) gene. Applicants use adenovirus vectors (Ad5) to package both Cas9 as well as a guide RNA targeting the MYOC gene. Applicants inject adenoviral vectors into the trabecular meshwork where cells have been implicated in the pathophysiology of glaucoma. Applicants initially test this out in mouse models carrying the mutated MYOC gene to see whether they improve visual acuity and decrease pressure in the eyes. Therapeutic application in humans employ a similar strategy.

Amyloidosis: Applicants design guide RNAs to target the first exon of the transthyretin (TTR) gene in the liver. Applicants use AAV8 to package Cas9 as well as guide RNA targeting the first exon of the TTR gene. AAV8 has been shown to have efficient targeting of the liver and will be administered intravenously. Cas9 can be driven either using liver specific promoters such as the albumin promoter, or using a constitutive promoter. A pol3 promoter drives the guide RNA.

Alternatively, Applicants utilize hydrodynamic delivery of plasmid DNA to knockout the TTR gene. Applicants deliver a plasmid encoding Cas9 and the guideRNA targeting Exon1 of TTR.

As a further alternative approach, Applicants administer a combination of RNA (mRNA for Cas9, and guide RNA). RNA can be packaged using liposomes such as Invivofectamine from Life Technologies and delivered intravenously. To reduce RNA-induced immunogenicity, increase the level of Cas9 expression and guide RNA stability, Applicants modify the Cas9 mRNA using 5′ capping. Applicants also incorporate modified RNA nucleotides into Cas9 mRNA and guide RNA to increase their stability and reduce immunogenicity (e.g. activation of TLR). To increase efficiency, Applicants administer multiple doses of the virus, DNA, or RNA.

Huntington's Disease: Applicants design guide RNA based on allele specific mutations in the HTT gene of patients. For example, in a patient who is heterozygous for HTT with expanded CAG repeat, Applicants identify nucleotide sequences unique to the mutant HTT allele and use it to design guideRNA. Applicants ensure that the mutant base is located within the last 9 bp of the guide RNA (which Applicants have ascertained has the ability to discriminate between single DNA base mismatches between the target size and the guide RNA).

Applicants package the mutant HTT allele specific guide RNA and Cas9 into AAV9 and deliver into the striatum of Huntington's patients. Virus is injected into the striatum stereotactically via a craniotomy. AAV9 is known to transduce neurons efficiently. Applicants drive Cas9 using a neuron specific promoter such as human Synapsin I.

Example 15: Therapeutic Application of the CRISPR-Cas System in HIV

Chronic viral infection is a source of significant morbidity and mortality. While there exists for many of these viruses conventional antiviral therapies that effectively target various aspects of viral replication, current therapeutic modalities are usually non-curative in nature due to "viral latency." By its nature, viral latency is characterized by a dormant phase in the viral life cycle without active viral production. During this period, the virus is largely able to evade both immune surveillance and conventional therapeutics allowing for it to establish long-standing viral reservoirs within the host from which subsequent re-activation can permit continued propagation and transmission of virus. Key to viral latency is the ability to stably maintain the viral genome, accomplished either through episomal or proviral latency, which stores the viral genome in the cytoplasm or integrates it into the host genome, respectively. In the absence of effective vaccinations which would prevent primary infection, chronic viral infections characterized by latent reservoirs and episodes of lytic activity can have significant consequences: human papilloma virus (HPV) can result in cervical cancer, hepatitis C virus (HCV) predisposes to hepatocellular carcinoma, and human immunodeficiency virus eventually destroys the host immune system resulting in susceptibility to opportunistic infections. As such, these infections require life-long use of currently available antiviral therapeutics. Further complicating matters is the high mutability of many of these viral genomes which lead to the evolution of resistant strains for which there exists no effective therapy.

The CRISPR-Cas system is a bacterial adaptive immune system able to induce double-stranded DNA breaks (DSB) in a multiplex-able, sequence-specific manner and has been recently re-constituted within mammalian cell systems. It has been shown that targeting DNA with one or numerous guide-RNAs can result in both indels and deletions of the intervening sequences, respectively. As such, this new technology represents a means by which targeted and multiplexed DNA mutagenesis can be accomplished within a single cell with high efficiency and specificity. Consequently, delivery of the CRISPR-Cas system directed against viral DNA sequences could allow for targeted disruption and deletion of latent viral genomes even in the absence of ongoing viral production.

As an example, chronic infection by HIV-1 represents a global health issue with 33 million individuals infected and an annual incidence of 2.6 million infections. The use of the multimodal highly active antiretroviral therapy (HAART), which simultaneously targets multiple aspects of viral replication, has allowed HIV infection to be largely managed as a chronic, not terminal, illness. Without treatment, progression of HIV to AIDS occurs usually within 9-10 years resulting in depletion of the host immune system and occurrence of opportunistic infections usually leading to death soon thereafter. Secondary to viral latency, discontinuation of HAART invariably leads to viral rebound. Moreover, even temporary disruptions in therapy can select for resistant strains of HIV uncontrollable by available means. Additionally, the costs of HAART therapy are significant: within the US $10,000-15,0000 per person per year. As such, treatment approaches directly targeting the HIV genome rather than the process of viral replication represents a means by which eradication of latent reservoirs could allow for a curative therapeutic option.

Development and delivery of an HIV-1 targeted CRISPR-Cas system represents a unique approach differentiable from existing means of targeted DNA mutagenesis, i.e. ZFN and TALENs, with numerous therapeutic implications. Targeted disruption and deletion of the HIV-1 genome by CRISPR-mediated DSB and indels in conjunction with HAART could allow for simultaneous prevention of active viral production as well as depletion of latent viral reservoirs within the host.

Once integrated within the host immune system, the CRISPR-Cas system allows for generation of a HIV-1 resistant sub-population that, even in the absence of complete viral eradication, could allow for maintenance and re-constitution of host immune activity. This could potentially prevent primary infection by disruption of the viral genome preventing viral production and integration, representing a means to "vaccination". Multiplexed nature of the CRISPR-Cas system allows targeting of multiple aspects of the genome simultaneously within individual cells.

As in HAART, viral escape by mutagenesis is minimized by requiring acquisition of multiple adaptive mutations concurrently. Multiple strains of HIV-1 can be targeted simultaneously which minimizes the chance of super-infection and prevents subsequent creation of new recombinants strains. Nucleotide, rather than protein, mediated sequence-specificity of the CRISPR-Cas system allows for rapid generation of therapeutics without need for significantly altering delivery mechanism.

In order to accomplish this, Applicants generate CRISPR-Cas guide RNAs that target the vast majority of the HIV-1 genome while taking into account HIV-1 strain variants for maximal coverage and effectiveness. Sequence analyses of genomic conservation between HIV-1 subtypes and variants should allow for targeting of flanking conserved regions of the genome with the aims of deleting intervening viral sequences or induction of frame-shift mutations which would disrupt viral gene functions.

Applicants accomplish delivery of the CRISPR-Cas system by conventional adenoviral or lentiviral-mediated infection of the host immune system. Depending on approach, host immune cells could be a) isolated, transduced with CRISPR-Cas, selected, and re-introduced in to the host or b) transduced in vivo by systemic delivery of the CRISPR-Cas system. The first approach allows for generation of a resistant immune population whereas the second is more likely to target latent viral reservoirs within the host.

| Examples of potential HIV-1 targeted spacers adapted from Mcintyre et al, which generated shRNAs against HIV-1 optimized for maximal coverage of HIV-1 variants | |
|---|---|
| CACTGCTTAAGCCTCGCTCGAGG | (SEQ ID NO: 115) |
| TCACCAGCAATATTCGCTCGAGG | (SEQ ID NO: 116) |
| CACCAGCAATATTCCGCTCGAGG | (SEQ ID NO: 117) |
| TAGCAACAGACATACGCTCGAGG | (SEQ ID NO: 118) |
| GGGCAGTAGTAATACGCTCGAGG | (SEQ ID NO: 119) |
| CCAATTCCCATACATTATTGTAC | (SEQ ID NO: 120) |

Example 16: Targeted Correction of deltaF508 or Other Mutations in Cystic Fibrosis An aspect of the invention provides for a pharmaceutical composition that may comprise an CRISPR-Cas gene therapy particle and a biocompatible pharmaceutical carrier. According to another aspect, a method of gene therapy for the treatment of a subject having a mutation in the CFTR gene comprises administering a therapeutically effective amount of a CRISPR-Cas gene therapy particle to the cells of a subject.

This Example demonstrates gene transfer or gene delivery of a CRISPR-Cas system in airways of subject or a patient in need thereof, suffering from cystic fibrosis or from cystic fibrosis related symptoms, using adeno-associated virus (AAV) particles.

Study Design: Subjects or patients in need there of: Human, non-primate human, canine, feline, bovine, equine and other domestic animals, related. This study tests efficacy of gene transfer of a CRISPR-Cas system by a AAV vector. Applicants determine transgene levels sufficient for gene expression and utilize a CRISPR-Cas system comprising a Cas9 enzyme to target deltaF508 or other CFTR-inducing mutations.

The treated subjects receive pharmaceutically effective amount of aerosolized AAV vector system per lung endobronchially delivered while spontaneously breathing. The control subjects receive equivalent amount of a pseudotyped AAV vector system with an internal control gene. The vector system may be delivered along with a pharmaceutically acceptable or biocompatible pharmaceutical carrier. Three weeks or an appropriate time interval following vector administration, treated subjects are tested for amelioration of cystic fibrosis related symptoms.

Applicants use an adenovirus or an AAV particle.

Applicants clone the following gene constructs, each operably linked to one or more regulatory sequences (Cbh or EF1a promoter for Cas9, U6 or H1 promoter for chimeric guide RNA), into one or more adenovirus or AAV vectors or any other compatible vector: A CFTRdelta508 targeting chimeric guide RNA (FIG. 13B), a repair template for deltaF508 mutation (FIG. 13C) and a codon optimized Cas9 enzyme with optionally one or more nuclear localization signal or sequence(s) (NLS(s)), e.g., two (2) NLSs.

Identification of Cas9 Target Site

Applicants analyzed the human CFTR genomic locus and identified the Cas9 target site (FIG. 13A). (PAM may contain a NGG or a NNAGAAW motif).

Gene Repair Strategy

Applicants introduce an adenovirus/AAV vector system comprising a Cas9 (or Cas9 nickase) and the guide RNA along with a adenovirus/AAV vector system comprising the homology repair template containing the F508 residue into the subject via one of the methods of delivery discussed earlier. The CRISPR-Cas system is guided by the CFTRdelta 508 chimeric guide RNA and targets a specific site of the CFTR genomic locus to be nicked or cleaved. After cleavage, the repair template is inserted into the cleavage site via homologous recombination correcting the deletion that results in cystic fibrosis or causes cystic fibrosis related symptoms. This strategy to direct delivery and provide systemic introduction of CRISPR systems with appropriate guide RNAs can be employed to target genetic mutations to edit or otherwise manipulate genes that cause metabolic, liver, kidney and protein diseases and disorders such as those in Table B.

Example 17: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 18: Engineering of Microalgae Using Cas9

Methods of Delivering Cas9

Method 1: Applicants deliver Cas9 and guide RNA using a vector that expresses Cas9 under the control of a constitutive promoter such as Hsp70A-Rbc S2 or Beta2-tubulin.

Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.

Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

(SEQ ID NO: 121)
TCTTTCTTGCGCTATGACACTTCCAGCAAAAGGTAGGGCGGGCTGCGA

GACGGCTTCCCGGCGCTGCATGCAACACCGATGATGCTTCGACCCCCCGA

AGCTCCTTCGGGGCTGCATGGGCGCTCCGATGCCGCTCCAGGGCGAGCGC

TGTTTAAATAGCCAGGCCCCCGATTGCAAAGACATTATAGCGAGCTACCA

AAGCCATATTCAAACACCTAGATCACTACCACTTCTACACAGGCCACTCG

AGCTTGTGATCGCACTCCGCTAAGGGGGCGCCTCTTCCTCTTCGTTTCAG

TCACAACCCGCAAACATGTACCCATACGATGTTCCAGATTACGCTTCGCC

GAAGAAAAAGCGCAAGGTCGAAGCGTCCGACAAGAAGTACAGCATCGGCC

TGGACATCGGCACCAACTCTGTGGGCTGGGCCGTGATCACCGACGAGTAC

AAGGTGCCCAGCAAGAAATTCAAGGTGCTGGGCAACACCGACCGGCACAG

CATCAAGAAGAACCTGATCGGAGCCCTGCTGTTCGACAGCGGCGAAACAG

CCGAGGCCACCCGGCTGAAGAGAACCGCCAGAAGAAGATACACCAGACGG

AAGAACCGGATCTGCTATCTGCAAGAGATCTTCAGCAACGAGATGGCCAA

GGTGGACGACAGCTTCTTCCACAGACTGGAAGAGTCCTTCCTGGTGGAAG

AGGATAAGAAGCACGAGCGGCACCCCATCTTCGGCAACATCGTGGACGAG

GTGGCCTACCACGAGAAGTACCCCACCATCTACCACCTGAGAAAGAAACT

GGTGGACAGCACCGACAAGGCCGACCTGCGGCTGATCTATCTGGCCCTGG

CCCACATGATCAAGTTCCGGGGCCACTTCCTGATCGAGGGCGACCTGAAC

CCCGACAACAGCGACGTGGACAAGCTGTTCATCCAGCTGGTGCAGACCTA

CAACCAGCTGTTCGAGGAAAACCCCATCAACGCCAGCGGCGTGGACGCCA

AGGCCATCCTGTCTGCCAGACTGAGCAAGAGCAGACGGCTGGAAAATCTG

ATCGCCCAGCTGCCCGGCGAGAAGAAGAATGGCCTGTTCGGCAACCTGAT

TGCCCTGAGCCTGGGCCTGACCCCCAACTTCAAGAGCAACTTCGACCTGG

CCGAGGATGCCAAACTGCAGCTGAGCAAGGACACCTACGACGACGACCTG

GACAACCTGCTGGCCCAGATCGGCGACCAGTACGCCGACCTGTTTCTGGC

CGCCAAGAACCTGTCCGACGCCATCCTGCTGAGCGACATCCTGAGAGTGA

ACACCGAGATCACCAAGGCCCCCCTGAGCGCCTCTATGATCAAGAGATAC

GACGAGCACCACCAGGACCTGACCCTGCTGAAAGCTCTCGTGCGGCAGCA

GCTGCCTGAGAAGTACAAAGAGATTTTCTTCGACCAGAGCAAGAACGGCT

ACGCCGGCTACATTGACGGCGGAGCCAGCCAGGAAGAGTTCTACAAGTTC

ATCAAGCCCATCCTGGAAAAGATGGACGGCACCGAGGAACTGCTCGTGAA

GCTGAACAGAGAGGACCTGCTGCGGAAGCAGCGGACCTTCGACAACGGCA

```
GCATCCCCCACCAGATCCACCTGGGAGAGCTGCACGCCATTCTGCGGCGG
CAGGAAGATTTTTACCCATTCCTGAAGGACAACCGGGAAAAGATCGAGAA
GATCCTGACCTTCCGCATCCCCTACTACGTGGGCCCTCTGGCCAGGGGAA
ACAGCAGATTCGCCTGGATGACCAGAAAGAGCGAGGAAACCATCACCCCC
TGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGC
CCAAGCACAGCCTGCTGTACGAGTACTTCACCGTGTATAACGAGCTGACC
AAAGTGAAATACGTGACCGAGGGAATGAGAAAGCCCGCCTTCCTGAGCGG
CGAGCAGAAAAAGGCCATCGTGGACCTGCTGTTCAAGACCAACCGGAAAG
TGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGG
CACATACCACGATCTGCTGAAAATTATCAAGGACAAGGACTTCCTGGACA
ATGAGGAAAACGAGGACATTCTGGAAGATATCGTGCTGACCCTGACACTG
TTTGAGGACAGAGAGATGATCGAGGAACGGCTGAAAACCTATGCCCACCT
GTTCGACGACAAAGTGATGAAGCAGCTGAAGCGGCGGAGATACACCGGCT
GGGGCAGGCTGAGCCGGAAGCTGATCAACGGCATCCGGGACAAGCAGTCC
GGCAAGACAATCCTGGATTTCCTGAAGTCCGACGGCTTCGCCAACAGAAA
CTTCATGCAGCTGATCCACGACGACAGCCTGACCTTTAAAGAGGACATCC
AGAAAGCCCAGGTGTCCGGCCAGGGCGATAGCCTGCACGAGCACATTGCC
AATCTGGCCGGCAGCCCCGCCATTAAGAAGGGCATCCTGCAGACAGTGAA
GGTGGTGGACGAGCTCGTGAAAGTGATGGGCCGGCACAAGCCCGAGAACA
TCGTGATCGAAATGGCCAGAGAGAACCAGACCACCCAGAAGGGACAGAAG
AACAGCCGCGAGAGAATGAAGCGGATCGAAGAGGGCATCAAAGAGCTGGG
CAGCCAGATCCTGAAAGAACACCCCGTGGAAAACACCCAGCTGCAGAACG
AGAAGCTGTACCTGTACTACCTGCAGAATGGGCGGGATATGTACGTGGAC
CAGGAACTGGACATCAACCGGCTGTCCGACTACGATGTGGACCATATCGT
GCCTCAGAGCTTTCTGAAGGACGACTCCATCGACAACAAGGTGCTGACCA
GAAGCGACAAGAACCGGGGCAAGAGCGACAACGTGCCCTCCGAAGAGGTC
GTGAAGAAGATGAAGAACTACTGGCGGCAGCTGCTGAACGCCAAGCTGAT
TACCCAGAGAAAGTTCGACAATCTGACCAAGGCCGAGAGAGGCGGCCTGA
GCGAACTGGATAAGGCCGGCTTCATCAAGAGACAGCTGGTGGAAACCCGG
CAGATCACAAAGCACGTGGCACAGATCCTGGACTCCCGGATGAACACTAA
GTACGACGAGAATGACAAGCTGATCCGGGAAGTGAAAGTGATCACCCTGA
AGTCCAAGCTGGTGTCCGATTTCCGGAAGGATTTCCAGTTTTACAAAGTG
CGCGAGATCAACAACTACCACCACGCCCACGACGCCTACCTGAACGCCGT
CGTGGGAACCGCCCTGATCAAAAAGTACCCTAAGCTGGAAAGCGAGTTCG
TGTACGGCGACTACAAGGTGTACGACGTGCGGAAGATGATCGCCAAGAGC
GAGCAGGAAATCGGCAAGGCTACCGCCAAGTACTTCTTCTACAGCAACAT
CATGAACTTTTTCAAGACCGAGATTACCCTGGCCAACGGCGAGATCCGGA
AGCGGCCTCTGATCGAGACAAACGGCGAAACCGGGGAGATCGTGTGGGAT
AAGGGCCGGGATTTTGCCACCGTGCGGAAAGTGCTGAGCATGCCCCAAGT
GAATATCGTGAAAAAGACCGAGGTGCAGACAGGCGGCTTCAGCAAAGAGT
CTATCCTGCCCAAGAGGAACAGCGATAAGCTGATCGCCAGAAAGAAGGAC
TGGGACCCTAAGAAGTACGGCGGCTTCGACAGCCCCACCGTGGCCTATTC
TGTGCTGGTGGTGGCCAAAGTGGAAAAGGGCAAGTCCAAGAAACTGAAGA
GTGTGAAAGAGCTGCTGGGGATCACCATCATGGAAAGAAGCAGCTTCGAG
AAGAATCCCATCGACTTTCTGGAAGCCAAGGGCTACAAAGAAGTGAAAAA
GGACCTGATCATCAAGCTGCCTAAGTACTCCCTGTTCGAGCTGGAAAACG
GCCGGAAGAGAATGCTGGCCTCTGCCGGCGAACTGCAGAAGGGAAACGAA
CTGGCCCTGCCCTCCAAATATGTGAACTTCCTGTACCTGGCCAGCCACTA
TGAGAAGCTGAAGGGCTCCCCCGAGGATAATGAGCAGAAACAGCTGTTTG
TGGAACAGCACAAGCACTACCTGGACGAGATCATCGAGCAGATCAGCGAG
TTCTCCAAGAGAGTGATCCTGGCCGACGCTAATCTGGACAAAGTGCTGTC
CGCCTACAACAAGCACCGGGATAAGCCCATCAGAGAGCAGGCCGAGAATA
TCATCCACCTGTTTACCCTGACCAATCTGGGAGCCCCTGCCGCCTTCAAG
TACTTTGACACCACCATCGACCGGAAGAGGTACACCAGCACCAAAGAGGT
GCTGGACGCCACCCTGATCCACCAGAGCATCACCGGCCTGTACGAGACAC
GGATCGACCTGTCTCAGCTGGGAGGCGACAGCCCCAAGAAGAAGAGAAAG
GTGGAGGCCAGCTAAGGATCCGGCAAGACTGGCCCCGCTTGGCAACGCAA
CAGTGAGCCCCTCCCTAGTGTGTTTGGGGATGTGACTATGTATTCGTGTG
TTGGCCAACGGGTCAACCCGAACAGATTGATACCCGCCTTGGCATTTCCT
GTCAGAATGTAACGTCAGTTGATGGTACT
```

Sequence for a cassette driving the expression of T7 polymerase under the control of beta-2 tubulin promoter, followed by the 3' UTR of Cop:

```
                                              (SEQ ID NO: 122)
TCTTTCTTGCGCTATGACACTTCCAGCAAAAGGTAGGGCGGGCTGCGA
GACGGCTTCCCGGCGCTGCATGCAACACCGATGATGCTTCGACCCCCCGA
AGCTCCTTCGGGGCTGCATGGGCGCTCCGATGCCGCTCCAGGGCGAGCGC
TGTTTAAATAGCCAGGCCCCCGATTGCAAAGACATTATAGCGAGCTACCA
AAGCCATATTCAAACACCTAGATCACTACCACTTCTACACAGGCCACTCG
AGCTTGTGATCGCACTCCGCTAAGGGGGCGCCTCTTCCTCTTCGTTTCAG
TCACAACCCGCAAAatgcctaagaagaagaggaaggttaacacgattaa
catcgctaagaacgacttctctgacatcgaactggctgctatcccgttca
acactctggctgaccattacggtgagcgtttagctcgcgaacagttggcc
cttgagcatgagtcttacgagatgggtgaagcacgcttccgcaagatgtt
tgagcgtcaacttaaagctggtgaggttgcggataacgctgccgccaagc
ctctcatcactaccctactccctaagatgattgcacgcatcaacgactgg
tttgaggaagtgaaagctaagcgcggcaagcgcccgacagccttccagtt
cctgcaagaaatcaagccggaagccgtagcgtacatcaccattaagacca
ctctggcttgcctaaccagtgctgacaatacaaccgttcaggctgtagca
agcgcaatcggtcgggccattgaggacgaggctcgcttcggtcgtatccg
```

-continued

```
tgaccttgaagctaagcacttcaagaaaaacgttgaggaacaactcaaca
agcgcgtagggcacgtctacaagaaagcatttatgcaagttgtcgaggct
gacatgctctctaagggtctactcggtggcgaggcgtggtcttcgtggca
taaggaagactctattcatgtaggagtacgctgcatcgagatgctcattg
agtcaaccggaatggttagcttacaccgccaaaatgctggcgtagtaggt
caagactctgagactatcgaactcgcacctgaatacgctgaggctatcgc
aacccgtgcaggtgcgctggctggcatctctccgatgttccaaccttgcg
tagttcctcctaagccgtggactggcattactggtggtggctattgggct
aacggtcgtcgtcctctggcgctggtgcgtactcacagtaagaaagcact
gatgcgctacgaagacgtttacatgcctgaggtgtacaaagcgattaaca
ttgcgcaaaacaccgcatggaaaatcaacaagaaagtcctagcggtcgcc
aacgtaatcaccaagtggaagcattgtccggtcgaggacatccctgcgat
tgagcgtgaagaactcccgatgaaaccggaagacatcgacatgaatcctg
aggctctcaccgcgtggaaacgtgctgccgctgctgtgtaccgcaaggac
aaggctcgcaagtctcgccgtatcagccttgagttcatgcttgagcaagc
caataagtttgctaaccataaggccatctggttcccttacaacatggact
ggcgcggtcgtgtttacgctgtgtcaatgttcaaccgcaaggtaacgat
atgaccaaaggactgcttacgctggcgaaaggtaaaccaatcggtaagga
aggttactactggctgaaaatccacggtgcaaactgtgcgggtgtcgaca
aggttccgttccctgagcgcatcaagttcattgaggaaaaccacgagaac
atcatggcttgcgctaagtctccactggagaacacttggtgggctgagca
agattctccgttctgcttccttgcgttctgctttgagtacgctggggtac
agcaccacggcctgagctataactgctcccttccgctggcgtttgacggg
tcttgctctggcatccagcacttctccgcgatgctccgagatgaggtagg
tggtcgcgcggttaacttgcttcctagtgaaaccgttcaggacatctacg
ggattgttgctaagaaagtcaacgagattctacaagcagacgcaatcaat
gggaccgataacgaagtagttaccgtgaccgatgagaacactggtgaaat
ctctgagaaagtcaagctgggcactaaggcactggctggtcaatggctgg
cttacggtgttactcgcagtgtgactaagcgttcagtcatgacgctggct
tacgggtccaaagagttcggcttccgtcaacaagtgctggaagataccat
tcagccagctattgattccggcaagggtctgatgttcactcagccgaatc
aggctgctggatacatggctaagctgatttgggaatctgtgagcgtgacg
gtggtagctgcggttgaagcaatgaactggcttaagtctgctgctaagct
gctggctgctgaggtcaaagataagaagactggagagattcttcgcaagc
gttgcgctgtgcattgggtaactcctgatggtttccctgtgtggcaggaa
tacaagaagcctattcagacgcgcttgaacctgatgttcctcggtcagtt
ccgcttacagcctaccattaacaccaacaaagatagcgagattgatgcac
acaaacaggagtctggtatcgctcctaactttgtacacagccaagacggt
agccaccttcgtaagactgtagtgtgggcacacgagaagtacggaatcga
atcttttgcactgattcacgactccttcggtacgattccggctgacgctg
```

-continued

```
cgaacctgttcaaagcagtgcgcgaaactatggttgacacatatgagtct
tgtgatgtactggctgatttctacgaccagttcgctgaccagttgcacga
gtctcaattggacaaaatgccagcacttccggctaaaggtaacttgaacc
tccgtgacatcttagagtcggacttcgcgttcgcgtaaGGATCCGGCAAG
ACTGGCCCCGCTTGGCAACGCAACAGTGAGCCCCTCCCTAGTGTGTTTGG
GGATGTGACTATGTATTCGTGTGTTGGCCAACGGGTCAACCCGAACAGAT
TGATACCCGCCTTGGCATTTCCTGTCAGAATGTAACGTCAGTTGATGGTA
CT
```

Sequence of guide RNA driven by the T7 promoter (T7 promoter, Ns represent targeting sequence):

(SEQ ID NO: 123)
```
gaaatTAATACGACTCACTATANNNNNNNNNNNNNNNNNNNNgttttaga
gctaGAAAtagcaagttaaaataaggctagtccgttatcaacttgaaaaa
gtggcaccgagtcggtgcttttttt
```

Gene Delivery:

*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit.

Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 124)
```
TGCGGTATTTCACACCGCATCAGGTGGCACTTTTCGGGGAAATGTGC
GCGGAACCCCTATTTGTTTATTTTTCTAAATACATTCAAATATGTATCCG
CTCATGAGATTATCAAAAAGGATCTTCACCTAGATCCTTTTAAATTAAAA
ATGAAGTTTTAAATCAATCTAAAGTATATATGAGTAAACTTGGTCTGACA
GTTACCAATGCTTAATCAGTGAGGCACCTATCTCAGCGATCTGTCTATTT
CGTTCATCCATAGTTGCCTGACTCCCCGTCGTGTAGATAACTACGATACG
GGAGGGCTTACCATCTGGCCCCAGTGCTGCAATGATACCGCGAGACCCAC
GCTCACCGGCTCCAGATTTATCAGCAATAAACCAGCCAGCCGGAAGGGCC
GAGCGCAGAAGTGGTCCTGCAACTTTATCCGCCTCCATCCAGTCTATTAA
TTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGT
ATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTG
TCAGAAGTAAGTTGGCCGCAGTGTTATCACTCATGGTTATGGCAGCACTG
CATAATTCTCTTACTGTCATGCCATCCGTAAGATGCTTTTCTGTGACTGG
TGAGTACTCAACCAAGTCATTCTGAGAATAGTGTATGCGGCGACCGAGTT
```

GCTCTTGCCCGGCGTCAATACGGGATAATACCGCGCCACATAGCAGAACT

TTAAAAGTGCTCATCATTGGAAAACGTTCTTCGGGGCGAAAACTCTCAAG

GATCTTACCGCTGTTGAGATCCAGTTCGATGTAACCCACTCGTGCACCCA

ACTGATCTTCAGCATCTTTTACTTTCACCAGCGTTTCTGGGTGAGCAAAA

ACAGGAAGGCAAAATGCCGCAAAAAAGGGAATAAGGGCGACACGGAAATG

TTGAATACTCATACTCTTCCTTTTTCAATATTATTGAAGCATTTATCAGG

GTTATTGTCTCATGACCAAAATCCCTTAACGTGAGTTTTCGTTCCACTGA

GCGTCAGACCCCGTAGAAAAGATCAAAGGATCTTCTTGAGATCCTTTTTT

TCTGCGCGTAATCTGCTGCTTGCAAACAAAAAAACCACCGCTACCAGCGG

TGGTTTGTTTGCCGGATCAAGAGCTACCAACTCTTTTTCCGAAGGTAACT

GGCTTCAGCAGAGCGCAGATACCAAATACTGTTCTTCTAGTGTAGCCGTA

GTTAGGCCACCACTTCAAGAACTCTGTAGCACCGCCTACATACCTCGCTC

TGCTAATCCTGTTACCAGTGGCTGTTGCCAGTGGCGATAAGTCGTGTCTT

ACCGGGTTGGACTCAAGACGATAGTTACCGGATAAGGCGCAGCGGTCGGG

CTGAACGGGGGGTTCGTGCACACAGCCCAGCTTGGAGCGAACGACCTACA

CCGAACTGAGATACCTACAGCGTGAGCTATGAGAAAGCGCCACGCTTCCC

GAAGGGAGAAAGGCGGACAGGTATCCGGTAAGCGGCAGGGTCGGAACAGG

AGAGCGCACGAGGGAGCTTCCAGGGGGAAACGCCTGGTATCTTTATAGTC

CTGTCGGGTTTCGCCACCTCTGACTTGAGCGTCGATTTTTGTGATGCTCG

TCAGGGGGGCGGAGCCTATGGAAAAACGCCAGCAACGCGGCCTTTTTACG

GTTCCTGGCCTTTTGCTGGCCTTTTGCTCACATGTTCTTTCCTGCGTTAT

CCCCTGATTCTGTGGATAACCGTATTACCGCCTTTGAGTGAGCTGATACC

GCTCGCCGCAGCCGAACGACCGAGCGCAGCGAGTCAGTGAGCGAGGAAGC

GGTCGCTGAGGCTTGACATGATTGGTGCGTATGTTTGTATGAAGCTACAG

GACTGATTTGGCGGGCTATGAGGGCGGGGGAAGCTCTGGAAGGGCCGCGA

TGGGGCGCGCGGCGTCCAGAAGGCGCCATACGGCCCGCTGGCGGCACCCA

TCCGGTATAAAAGCCCGCGACCCCGAACGGTGACCTCCACTTTCAGCGAC

AAACGAGCACTTATACATACGCGACTATTCTGCCGCTATACATAACCACT

CAGCTAGCTTAAGATCCCATCAAGCTTGCATGCCGGGCGCGCCAGAAGGA

GCGCAGCCAAACCAGGATGATGTTTGATGGGGTATTTGAGCACTTGCAAC

CCTTATCCGGAAGCCCCCTGGCCCACAAAGGCTAGGCGCCAATGCAAGCA

GTTCGCATGCAGCCCCTGGAGCGGTGCCCTCCTGATAAACCGGCCAGGGG

GCCTATGTTCTTTACTTTTTTACAAGAGAAGTCACTCAACATCTTAAAAT

GGCCAGGTGAGTCGACGAGCAAGCCCGGCGGATCAGGCAGCGTGCTTGCA

GATTTGACTTGCAACGCCCGCATTGTGTCGACGAAGGCTTTTGGCTCCTC

TGTCGCTGTCTCAAGCAGCATCTAACCCTGCGTCGCCGTTTCCATTTGCA

GGAGATTCGAGGTACCATGTACCCATACGATGTTCCAGATTACGCTTCGC

CGAAGAAAAAGCGCAAGGTCGAAGCGTCCGACAAGAAGTACAGCATCGGC

CTGGACATCGGCACCAACTCTGTGGGCTGGGCCGTGATCACCGACGAGTA

CAAGGTGCCCAGCAAGAAATTCAAGGTGCTGGGCAACACCGACCGGCACA

GCATCAAGAAGAACCTGATCGGAGCCCTGCTGTTCGACAGCGGCGAAACA

GCCGAGGCCACCCGGCTGAAGAGAACCGCCAGAAGAAGATACACCAGACG

GAAGAACCGGATCTGCTATCTGCAAGAGATCTTCAGCAACGAGATGGCCA

AGGTGGACGACAGCTTCTTCCACAGACTGGAAGAGTCCTTCCTGGTGGAA

GAGGATAAGAAGCACGAGCGGCACCCCATCTTCGGCAACATCGTGGACGA

GGTGGCCTACCACGAGAAGTACCCCACCATCTACCACCTGAGAAAGAAAC

TGGTGGACAGCACCGACAAGGCCGACCTGCGGCTGATCTATCTGGCCCTG

GCCCACATGATCAAGTTCCGGGGCCACTTCCTGATCGAGGGCGACCTGAA

CCCCGACAACAGCGACGTGGACAAGCTGTTCATCCAGCTGGTGCAGACCT

ACAACCAGCTGTTCGAGGAAAACCCCATCAACGCCAGCGGCGTGGACGCC

AAGGCCATCCTGTCTGCCAGACTGAGCAAGAGCAGACGGCTGGAAAATCT

GATCGCCCAGCTGCCCGGCGAGAAGAAGAATGGCCTGTTCGGCAACCTGA

TTGCCCTGAGCCTGGGCCTGACCCCCAACTTCAAGAGCAACTTCGACCTG

GCCGAGGATGCCAAACTGCAGCTGAGCAAGGACACCTACGACGACGACCT

GGACAACCTGCTGGCCCAGATCGGCGACCAGTACGCCGACCTGTTTCTGG

CCGCCAAGAACCTGTCCGACGCCATCCTGCTGAGCGACATCCTGAGAGTG

AACACCGAGATCACCAAGGCCCCCCTGAGCGCCTCTATGATCAAGAGATA

CGACGAGCACCACCAGGACCTGACCCTGCTGAAAGCTCTCGTGCGGCAGC

AGCTGCCTGAGAAGTACAAAGAGATTTTCTTCGACCAGAGCAAGAACGGC

TACGCCGGCTACATTGACGGCGGAGCCAGCCAGGAAGAGTTCTACAAGTT

CATCAAGCCCATCCTGGAAAAGATGGACGGCACCGAGGAACTGCTCGTGA

AGCTGAACAGAGAGGACCTGCTGCGGAAGCAGCGGACCTTCGACAACGGC

AGCATCCCCCACCAGATCCACCTGGGAGAGCTGCACGCCATTCTGCGGCG

GCAGGAAGATTTTTACCCATTCCTGAAGGACAACCGGGAAAAGATCGAGA

AGATCCTGACCTTCCGCATCCCCTACTACGTGGGCCCTCTGGCCAGGGGA

AACAGCAGATTCGCCTGGATGACCAGAAAGAGCGAGGAAACCATCACCCC

CTGGAACTTCGAGGAAGTGGTGGACAAGGGCGCTTCCGCCCAGAGCTTCA

TCGAGCGGATGACCAACTTCGATAAGAACCTGCCCAACGAGAAGGTGCTG

CCCAAGCACAGCCTGCTGTACGAGTACTTCACCGTGTATAACGAGCTGAC

CAAAGTGAAATACGTGACCGAGGGAATGAGAAAGCCCGCCTTCCTGAGCG

GCGAGCAGAAAAAGGCCATCGTGGACCTGCTGTTCAAGACCAACCGGAAA

GTGACCGTGAAGCAGCTGAAAGAGGACTACTTCAAGAAAATCGAGTGCTT

CGACTCCGTGGAAATCTCCGGCGTGGAAGATCGGTTCAACGCCTCCCTGG

GCACATACCACGATCTGCTGAAAATTATCAAGGACAAGGACTTCCTGGAC

AATGAGGAAAACGAGGACATTCTGGAAGATATCGTGCTGACCCTGACACT

GTTTGAGGACAGAGAGATGATCGAGGAACGGCTGAAAACCTATGCCCACC

TGTTCGACGACAAAGTGATGAAGCAGCTGAAGCGGCGGAGATACACCGGC

TGGGGCAGGCTGAGCCGGAAGCTGATCAACGGCATCCGGGACAAGCAGTC

CGGCAAGACAATCCTGGATTTCCTGAAGTCCGACGGCTTCGCCAACAGAA

ACTTCATGCAGCTGATCCACGACGACAGCCTGACCTTTAAAGAGGACATC

CAGAAAGCCCAGGTGTCCGGCCAGGGCGATAGCCTGCACGAGCACATTGC

```
CAATCTGGCCGGCAGCCCCGCCATTAAGAAGGGCATCCTGCAGACAGTGA
AGGTGGTGGACGAGCTCGTGAAAGTGATGGGCCGGCACAAGCCCGAGAAC
ATCGTGATCGAAATGGCCAGAGAGAACCAGACCACCCAGAAGGGACAGAA
GAACAGCCGCGAGAGAATGAAGCGGATCGAAGAGGGCATCAAAGAGCTGG
GCAGCCAGATCCTGAAAGAACACCCCGTGGAAAACACCCAGCTGCAGAAC
GAGAAGCTGTACCTGTACTACCTGCAGAATGGGCGGGATATGTACGTGGA
CCAGGAACTGGACATCAACCGGCTGTCCGACTACGATGTGGACCATATCG
TGCCTCAGAGCTTTCTGAAGGACGACTCCATCGACAACAAGGTGCTGACC
AGAAGCGACAAGAACCGGGGCAAGAGCGACAACGTGCCCTCCGAAGAGGT
CGTGAAGAAGATGAAGAACTACTGGCGGCAGCTGCTGAACGCCAAGCTGA
TTACCCAGAGAAAGTTCGACAATCTGACCAAGGCCGAGAGAGGCGGCCTG
AGCGAACTGGATAAGGCCGGCTTCATCAAGAGACAGCTGGTGGAAACCCG
GCAGATCACAAAGCACGTGGCACAGATCCTGGACTCCCGGATGAACACTA
AGTACGACGAGAATGACAAGCTGATCCGGGAAGTGAAAGTGATCACCCTG
AAGTCCAAGCTGGTGTCCGATTTCCGGAAGGATTTCCAGTTTTACAAAGT
GCGCGAGATCAACAACTACCACCACGCCCACGACGCCTACCTGAACGCCG
TCGTGGGAACCGCCCTGATCAAAAAGTACCCTAAGCTGGAAAGCGAGTTC
GTGTACGGCGACTACAAGGTGTACGACGTGCGGAAGATGATCGCCAAGAG
CGAGCAGGAAATCGGCAAGGCTACCGCCAAGTACTTCTTCTACAGCAACA
TCATGAACTTTTTCAAGACCGAGATTACCCTGGCCAACGGCGAGATCCGG
AAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAG
TGAATATCGTGAAAAAGACCGAGGTGCAGACAGGCGGCTTCAGCAAAGAG
TCTATCCTGCCCAAGAGGAACAGCGATAAGCTGATCGCCAGAAAGAAGGA
CTGGGACCCTAAGAAGTACGGCGGCTTCGACAGCCCCACCGTGGCCTATT
CTGTGCTGGTGGTGGCCAAAGTGGAAAAGGGCAAGTCCAAGAAACTGAAG
AGTGTGAAAGAGCTGCTGGGGATCACCATCATGGAAAGAAGCAGCTTCGA
GAAGAATCCCATCGACTTTCTGGAAGCCAAGGGCTACAAAGAAGTGAAAA
AGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACT
ATGAGAAGCTGAAGGGCTCCCCCGAGGATAATGAGCAGAAACAGCTGTTT
GTGGAACAGCACAAGCACTACCTGGACGAGATCATCGAGCAGATCAGCGA
GTTCTCCAAGAGAGTGATCCTGGCCGACGCTAATCTGGACAAAGTGCTGT
CCGCCTACAACAAGCACCGGGATAAGCCCATCAGAGAGCAGGCCGAGAAT
ATCATCCACCTGTTTACCCTGACCAATCTGGGAGCCCCTGCCGCCTTCAA
GTACTTTGACACCACCATCGACCGGAAGAGGTACACCAGCACCAAAGAGG
TGCTGGACGCCACCCTGATCCACCAGAGCATCACCGGCCTGTACGAGACA
CGGATCGACCTGTCTCAGCTGGGAGGCGACAGCCCCAAGAAGAAGAGAAA
GGTGGAGGCCAGCTAACATATGATTCGAATGTCTTTCTTGCGCTATGACA
CTTCCAGCAAAAGGTAGGGCGGGCTGCGAGACGGCTTCCCGGCGCTGCAT
GCAACACCGATGATGCTTCGACCCCCCGAAGCTCCTTCGGGGCTGCATGG
GCGCTCCGATGCCGCTCCAGGGCGAGCGCTGTTTAAATAGCCAGGCCCCC
GATTGCAAAGACATTATAGCGAGCTACCAAAGCCATATTCAAACACCTAG
ATCACTACCACTTCTACACAGGCCACTCGAGCTTGTGATCGCACTCCGCT
AAGGGGGCGCCTCTTCCTCTTCGTTTCAGTCACAACCCGCAAACATGACA
CAAGAATCCCTGTTACTTCTCGACCGTATTGATTCGGATGATTCCTACGC
GAGCCTGCGGAACGACCAGGAATTCTGGGAGGTGAGTCGACGAGCAAGCC
CGGCGGATCAGGCAGCGTGCTTGCAGATTTGACTTGCAACGCCCGCATTG
TGTCGACGAAGGCTTTTGGCTCCTCTGTCGCTGTCTCAAGCAGCATCTAA
CCCTGCGTCGCCGTTTCCATTTGCAGCCGCTGGCCCGCCGAGCCCTGGAG
GAGCTCGGGCTGCCGGTGCCGCCGGTGCTGCGGGTGCCCGGCGAGAGCAC
CAACCCCGTACTGGTCGGCGAGCCCGGCCCGGTGATCAAGCTGTTCGGCG
AGCACTGGTGCGGTCCGGAGAGCCTCGCGTCGGAGTCGGAGGCGTACGCG
GTCCTGGCGGACGCCCCGGTGCCGGTGCCCCGCCTCCTCGGCCGCGGCGA
GCTGCGGCCCGGCACCGGAGCCTGGCCGTGGCCCTACCTGGTGATGAGCC
GGATGACCGGCACCACCTGGCGGTCCGCGATGGACGGCACGACCGACCGG
AACGCGCTGCTCGCCCTGGCCCGCGAACTCGGCCGGGTGCTCGGCCGGCT
GCACAGGGTGCCGCTGACCGGGAACACCGTGCTCACCCCCCATTCCGAGG
TCTTCCCGGAACTGCTGCGGGAACGCCGCGCGGCGACCGTCGAGGACCAC
CGCGGGTGGGGCTACCTCTCGCCCCGGCTGCTGGACCGCCTGGAGGACTG
GCTGCCGGACGTGGACACGCTGCTGGCCGGCCGCGAACCCCGGTTCGTCC
ACGGCGACCTGCACGGGACCAACATCTTCGTGGACCTGGCCGCGACCGAG
GTCACCGGGATCGTCGACTTCACCGACGTCTATGCGGGAGACTCCCGCTA
CAGCCTGGTGCAACTGCATCTCAACGCCTTCCGGGGCGACCGCGAGATCC
TGGCCGCGCTGCTCGACGGGCGCAGTGGAAGCGGACCGAGGACTTCGCC
CGCGAACTGCTCGCCTTCACCTTCCTGCACGACTTCGAGGTGTTCGAGGA
GACCCCGCTGGATCTCTCCGGCTTCACCGATCCGGAGGAACTGGCGCAGT
TCCTCTGGGGGCCGCCGGACACCGCCCCGGCGCCTGATAAGGATCCGGC
AAGACTGGCCCCGCTTGGCAACGCAACAGTGAGCCCCTCCCTAGTGTGTT
TGGGGATGTGACTATGTATTCGTGTGTTGGCCAACGGGTCAACCCGAACA
GATTGATACCCGCCTTGGCATTTCCTGTCAGAATGTAACGTCAGTTGATG
GTACT
```

For all modified *Chlamydomonas reinhardtii* cells, Applicants use PCR, SURVEYOR nuclease assay, and DNA sequencing to verify successful modification.

Example 19: Use of Cas9 to Target a Variety of Disease Types

Diseases that Involve Mutations in Protein Coding Sequence:

Dominant disorders may be targeted by inactivating the dominant negative allele. Applicants use Cas9 to target a unique sequence in the dominant negative allele and introduce a mutation via NHEJ. The NHEJ-induced indel may be able to introduce a frame-shift mutation in the dominant negative allele and eliminate the dominant negative protein. This may work if the gene is haplo-sufficient (e.g. MYOC mutation induced glaucoma and Huntington's disease).

Recessive disorders may be targeted by repairing the disease mutation in both alleles. For dividing cells, Applicants use Cas9 to introduce double strand breaks near the mutation site and increase the rate of homologous recombination using an exogenous recombination template. For dividing cells, this may be achieved using multiplexed nickase activity to catalyze the replacement of the mutant sequence in both alleles via NHEJ-mediated ligation of an exogenous DNA fragment carrying complementary overhangs.

Applicants also use Cas9 to introduce protective mutations (e.g. inactivation of CCR5 to prevent HIV infection, inactivation of PCSK9 for cholesterol reduction, or introduction of the A673T into APP to reduce the likelihood of Alzheimer's disease).

Diseases that Involve Non-Coding Sequences

Applicants use Cas9 to disrupt non-coding sequences in the promoter region, to alter transcription factor binding sites and alter enhancer or repressor elements. For example, Cas9 may be used to excise out the Klf1 enhancer EHS1 in hematopoietic stem cells to reduce BCL11a levels and reactivate fetal globin gene expression in differentiated erythrocytes Applicants also use Cas9 to disrupt functional motifs in the 5' or 3' untranslated regions. For example, for the treatment of myotonic dystrophy, Cas9 may be used to remove CTG repeat expansions in the DMPK gene.

Example 20: Multiplexed Nickase

Aspects of optimization and the teachings of Cas9 detailed in this application may also be used to generate Cas9 nickases. Applicants use Cas9 nickases in combination with pairs of guide RNAs to generate DNA double strand breaks with defined overhangs. When two pairs of guide RNAs are used, it is possible to excise an intervening DNA fragment. If an exogenous piece of DNA is cleaved by the two pairs of guide RNAs to generate compatible overhangs with the genomic DNA, then the exogenous DNA fragment may be ligated into the genomic DNA to replace the excised fragment. For example, this may be used to remove trinucleotide repeat expansion in the huntintin (HTT) gene to treat Huntington's Disease.

If an exogenous DNA that bears fewer number of CAG repeats is provided, then it may be able to generate a fragment of DNA that bears the same overhangs and can be ligated into the HTT genomic locus and replace the excised fragment (fragments below disclosed as SEQ ID NOS 125-132, respectively, in order of appearance).

```
HTT locus with    ...CCGTGCCGGGCGGGAGACCGCCATGG          GGCCCGGCTGTGGCTGAGGAGC...
fragment          ...GGCACGGCCCGCCCTCTGGC                TGGGCCGGGCCGACACCGACTCCTCG...
excised by
Cas9 nickase
and two
pairs of
guide RNAs

+ exogenous DNA     CGACCCTGGAAA.....    reduced number of CAG repeats   .....CCCCGCCGCCACCC
fragment with     GGTACCGCTGGGACCTTT.....                              .....GGGGCGGCGG
fewer number
of CAG repeats
also cleaved
by Cas9
nicakse and
the two pairs
of guide
RNAs
```

The ligation of the exogenous DNA fragment into the genome does not require homologous recombination machineries and therefore this method may be used in post-mitotic cells such as neurons.

Example 21: Delivery of CRISPR System

Cas9 and its chimeric guide RNA, or combination of tracrRNA and crRNA, can be delivered either as DNA or RNA. Delivery of Cas9 and guide RNA both as RNA (normal or containing base or backbone modifications) molecules can be used to reduce the amount of time that Cas9 protein persist in the cell. This may reduce the level of off-target cleavage activity in the target cell. Since delivery of Cas9 as mRNA takes time to be translated into protein, it might be advantageous to deliver the guide RNA several hours following the delivery of Cas9 mRNA, to maximize the level of guide RNA available for interaction with Cas9 protein.

In situations where guide RNA amount is limiting, it may be desirable to introduce Cas9 as mRNA and guide RNA in the form of a DNA expression cassette with a promoter driving the expression of the guide RNA. This way the amount of guide RNA available will be amplified via transcription.

A variety of delivery systems can be introduced to introduce Cas9 (DNA or RNA) and guide RNA (DNA or RNA) into the host cell. These include the use of liposomes, viral vectors, electroporation, nanoparticles, nanowires (Shalek et al., Nano Letters, 2012), exosomes. Molecular trojan horses liposomes (Pardridge et al., Cold Spring Harb Protoc; 2010; doi:10.1101/pdb.prot5407) may be used to deliver Cas9 and guide RNA across the blood brain barrier.

Example 22: Cas9 Orthologs

Applicants analyzed Cas9 orthologs (FIGS. 3 and 4A-F) to identify the relevant PAM sequences and the corresponding chimeric guide RNAs. This expanded set of PAMs may provide broader targeting across the genome and also significantly increases the number of unique target sites and provides potential for identifying novel Cas9s with increased levels of specificity in the genome. Applicants determined the PAM for Staphylococcus aureus sp. Aureus Cas9 to be NNGRR Staphylococcus aureus sp. Aureus Cas9 is also known as SaCas9.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species.

Example 23: Therapeutic Strategies for Trinucleotide Repeat Disorders

As previously mentioned in the application, the target polynucleotide of a CRISPR complex may include a number of disease-associated genes and polynucleotides and some of these disease associated gene may belong to a set of genetic disorders referred to as Trinucleotide repeat disorders (referred to as also trinucleotide repeat expansion disorders, triplet repeat expansion disorders or codon reiteration disorders).

These diseases are caused by mutations in which the trinucleotide repeats of certain genes exceed the normal, stable threshold which may usually differ in a gene. The discovery of more repeat expansion disorders has allowed for the classification of these disorders into a number of categories based on underlying similar characteristics. Huntington's disease (HD) and the spinocerebellar ataxias that are caused by a CAG repeat expansion in protein-coding portions of specific genes are included in Category I. Diseases or disorders with expansions that tend to make them phenotypically diverse and include expansions are usually small in magnitude and also found in exons of genes are included in Category II. Category III includes disorders or diseases which are characterized by much larger repeat expansions than either Category I or II and are generally located outside protein coding regions. Examples of Category III diseases or disorders include but are not limited to Fragile X syndrome, myotonic dystrophy, two of the spinocerebellar ataxias, juvenile myoclonic epilepsy, and Friedreich's ataxia.

Figure 14A:
FIG. 14A-B shows (a) a schematic of the GAA repeat expansion in FXN intron 1 and (b) a schematic of the strategy adopted to excise the GAA expansion region using the CRISPR/Cas system.

Similar therapeutic strategies, like the one mentioned for Friedreich's ataxia below may be adopted to address other trinucleotide repeat or expansion disorders as well. For example, another triple repeat disease that can be treated using almost identical strategy is dystrophia myotonica 1 (DM1), where there is an expanded CTG motif in the 3' UTR. In Friedreich's ataxia, the disease results from expansion of GAA trinucleotides in the first intron of frataxin (FXN). One therapeutic strategy using CRISPR is to excise the GAA repeat from the first intron. The expanded GAA repeat is thought to affect the DNA structure and leads to recruit the formation of heterochromatin which turn off the frataxin gene (FIG. 14A).

Competitive Advantage over other therapeutic strategies are listed below:

siRNA knockdown is not applicable in this case, as disease is due to reduced expression of frataxin. Viral gene therapy is currently being explored. HSV-1 based vectors were used to deliver the frataxin gene in animal models and have shown therapeutic effect. However, long term efficacy of virus-based frataxin delivery suffer from several problems: First, it is difficult to regulate the expression of frataxin to match natural levels in health individuals, and second, long term over expression of frataxin leads to cell death.

Nucleases may be used to excise the GAA repeat to restore healthy genotype, but Zinc Finger Nuclease and TALEN strategies require delivery of two pairs of high efficacy nucleases, which is difficult for both delivery as well as nuclease engineering (efficient excision of genomic DNA by ZFN or TALEN is difficult to achieve).

In contrast to above strategies, the CRISPR-Cas system has clear advantages. The Cas9 enzyme is more efficient and more multiplexible, by which it is meant that one or more targets can be set at the same time. So far, efficient excision of genomic DNA>30% by Cas9 in human cells and may be as high as 30%, and may be improved in the future. Furthermore, with regard to certain trinucleotide repeat disorders like Huntington's disease (HD), trinucleotide repeats in the coding region may be addressed if there are differences between the two alleles. Specifically, if a HD patient is heterozygous for mutant HTT and there are nucleotide differences such as SNPs between the wt and mutant HTT alleles, then Cas9 may be used to specifically target the mutant HTT allele. ZFN or TALENs will not have the ability to distinguish two alleles based on single base differences.

Figure 14B:
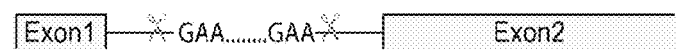

In adopting a strategy using the CRISPR-Cas 9 enzyme to address Friedreich's ataxia, Applicants design a number of guide RNAs targeting sites flanking the GAA expansion and the most efficient and specific ones are chosen (FIG. 14B).

Applicants deliver a combination of guide RNAs targeting the intron 1 of FXN along with Cas9 to mediate excision of the GAA expansion region. AAV9 may be used to mediate efficient delivery of Cas9 and in the spinal cord.

If the Alu element adjacent to the GAA expansion is considered important, there may be constraints to the number of sites that can be targeted but Applicants may adopt strategies to avoid disrupting it.

Alternative Strategies:

Rather than modifying the genome using Cas9, Applicants may also directly activate the FXN gene using Cas9 (nuclease activity deficient)-based DNA binding domain to target a transcription activation domain to the FXN gene.

Example 24: Strategies for Minimizing Off-Target Cleavage Using Cas9 Nickase As previously mentioned in the application, Cas9 may be mutated to mediate single strand cleavage via one or more of the following mutations: D10A, E762A, and H840A.

To mediate gene knockout via NHEJ, Applicants use a nickase version of Cas9 along with two guide RNAs. Off-target nicking by each individual guide RNA may be primarily repaired without mutation, double strand breaks (which can lead to mutations via NHEJ) only occur when the target sites are adjacent to each other. Since double strand breaks introduced by double nicking are not blunt, co-expression of end-processing enzymes such as TREX1 will increase the level of NHEJ activity.

The following list of targets in tabular form are for genes involved in the following diseases:

Lafora's Disease—target GSY1 or PPP1R3C (PTG) to reduce glycogen in neurons.

Hypercholesterolemia—target PCSK9

Target sequences are listed in pairs (L and R) with different number of nucleotides in the spacer (0 to 3 bp). Each spacer may also be used by itself with the wild type Cas9 to introduce double strand break at the target locus.

```
GYS1 (human)
                               (SEQ ID NO: 133)
GGCC-L  ACCCTTGTTAGCCACCTCCC (SEQ ID NO: 134)
GGCC-R  GAACGCAGTGCTCTTCGAAG (SEQ ID NO: 135)
GGNCC-L  CTCACGCCCTGCTCCGTGTA (SEQ ID NO: 136)
GGNCC-R  GGCGACAACTACTTCCTGGT (SEQ ID NO: 137)
GGNNCC-L  CTCACGCCCTGCTCCGTGTA (SEQ ID NO: 138)
GGNNCC-R  GGGCGACAACTACTTCCTGG (SEQ ID NO: 139)
GGNNNCC-L  CCTCTTCAGGGCCGGGGTGG (SEQ ID NO: 140)
GGNNNCC-R  GAGGACCCAGGTGGAACTGC PCSK9 (human)
                               (SEQ ID NO: 141)
GGCC-L  TCAGCTCCAGGCGGTCCTGG (SEQ ID NO: 142)
GGCC-R  AGCAGCAGCAGCAGTGGCAG (SEQ ID NO: 143)
GGNCC-L  TGGGCACCGTCAGCTCCAGG (SEQ ID NO: 144)
GGNCC-R  CAGCAGTGGCAGCGGCCACC (SEQ ID NO: 145)
GGNNCC-L  ACCTCTCCCCTGGCCCTCAT (SEQ ID NO: 146)
GGNNCC-R  CCAGGACCGCCTGGAGCTGA (SEQ ID NO: 147)
GGNNNCC-L  CCGTCAGCTCCAGGCGGTCC (SEQ ID NO: 148)
GGNNNCC-R  AGCAGCAGCAGCAGTGGCAG PPP1R3C (PTG) (human)
                               (SEQ ID NO: 149)
GGCC-L  ATGTGCCAAGCAAAGCCTCA (SEQ ID NO: 150)
GGCC-R  TTCGGTCATGCCCGTGGATG (SEQ ID NO: 151)
GGNCC-L  GTCGTTGAAATTCATCGTAC (SEQ ID NO: 152)
GGNCC-R  ACCACCTGTGAAGAGTTTCC (SEQ ID NO: 153)
GGNNCC-L  CGTCGTTGAAATTCATCGTA (SEQ ID NO: 154)
GGNNCC-R  ACCACCTGTGAAGAGTTTCC Gys1 (mouse)
                               (SEQ ID NO: 155)
GGCC-L  GAACGCAGTGCTTTTCGAGG (SEQ ID NO: 156)
GGCC-R  ACCCTTGTTGGCCACCTCCC (SEQ ID NO: 157)
GGNCC-L  GGTGACAACTACTATCTGGT (SEQ ID NO: 158)
GGNCC-R  CTCACACCCTGCTCCGTGTA (SEQ ID NO: 159)
GGNNCC-L  GGGTGACAACTACTATCTGG (SEQ ID NO: 160)
GGNNCC-R  CTCACACCCTGCTCCGTGTA (SEQ ID NO: 161)
GGNNNCC-L  CGAGAACGCAGTGCTTTTCG (SEQ ID NO: 162)
GGNNNCC-R  ACCCTTGTTGGCCACCTCCC PPP1R3C (PTG) (mouse)
                               (SEQ ID NO: 163)
GGCC-L  ATGAGCCAAGCAAATCCTCA (SEQ ID NO: 164)
GGCC-R  TTCCGTCATGCCCGTGGACA (SEQ ID NO: 165)
GGNCC-L  CTTCGTTGAAAACCATTGTA (SEQ ID NO: 166)
GGNCC-R  CCACCTCTGAAGAGTTTCCT (SEQ ID NO: 167)
GGNNCC-L  CTTCGTTGAAAACCATTGTA (SEQ ID NO: 168)
GGNNCC-R  ACCACCTCTGAAGAGTTTCC (SEQ ID NO: 169)
GGNNNCC-L  CTTCCACTCACTCTGCGATT (SEQ ID NO: 170)
GGNNNCC-R  ACCATGTCTCAGTGTCAAGC PCSK9 (mouse)
                               (SEQ ID NO: 171)
GGCC-L  GGCGGCAACAGCGGCAACAG (SEQ ID NO: 172)
GGCC-R  ACTGCTCTGCGTGGCTGCGG (SEQ ID NO: 173)
GGNNCC-L  CCGCAGCCACGCAGAGCAGT (SEQ ID NO: 174)
GGNNCC-R  GCACCTCTCCTCGCCCCGAT
```

Alternative strategies for improving stability of guide RNA and increasing specificity 1. Nucleotides in the 5' of the guide RNA may be linked via thiolester linkages rather than phosphoester linkage like in natural RNA. Thiolester linkage may prevent the guide RNA from being digested by endogenous RNA degradation machinery.

2. Nucleotides in the guide sequence (5' 20 bp) of the guide RNA can use bridged nucleic acids (BNA) as the bases to improve the binding specificity.

Example 25: CRISPR-Cas for Rapid, Multiplex Genome Editing

Aspects of the invention relate to protocols and methods by which efficiency and specificity of gene modification may be tested within 3-4 days after target design, and modified clonal cell lines may be derived within 2-3 weeks.

Programmable nucleases are powerful technologies for mediating genome alteration with high precision. The RNA-guided Cas9 nuclease from the microbial CRISPR adaptive immune system can be used to facilitate efficient genome editing in eukaryotic cells by simply specifying a 20-nt targeting sequence in its guide RNA. Applicants describe a set of protocols for applying Cas9 to facilitate efficient genome editing in mammalian cells and generate cell lines for downstream functional studies. Beginning with target design, efficient and specific gene modification can be achieved within 3-4 days, and modified clonal cell lines can be derived within 2-3 weeks.

The ability to engineer biological systems and organisms holds enormous potential for applications across basic science, medicine, and biotechnology. Programmable sequence-specific endonucleases that facilitate precise editing of endogenous genomic loci are now enabling systematic interrogation of genetic elements and causal genetic variations in a broad range of species, including those that have not been genetically tractable previously. A number of genome editing technologies have emerged in recent years, including zinc finger nucleases (ZFNs), transcription activator-like effector nucleases (TALENs), and the RNA-guided CRISPR-Cas nuclease system. The first two technologies use a common strategy of tethering endonuclease catalytic domains to modular DNA-binding proteins for inducing targeted DNA double stranded breaks (DSB) at specific genomic loci. By contrast, Cas9 is a nuclease guided by small RNAs through Watson-Crick base-pairing with target DNA, presenting a system that is easy to design, efficient, and well-suited for high-throughput and multiplexed gene editing for a variety of cell types and organisms. Here Applicants describe a set of protocols for applying the recently developed Cas9 nuclease to facilitate efficient genome editing in mammalian cells and generate cell lines for downstream functional studies.

Like ZFNs and TALENs, Cas9 promotes genome editing by stimulating DSB at the target genomic loci. Upon cleavage by Cas9, the target locus undergoes one of two major pathways for DNA damage repair, the error-prone non-homologous end joining (NHEJ) or the high-fidelity homology directed repair (HDR) pathway. Both pathways may be utilized to achieve the desired editing outcome.

NHEJ: In the absence of a repair template, the NHEJ process re-ligates DSBs, which may leave a scar in the form of indel mutations. This process can be harnessed to achieve gene knockouts, as indels occurring within a coding exon may lead to frameshift mutations and a premature stop codon. Multiple DSBs may also be exploited to mediate larger deletions in the genome.

HDR: Homology directed repair is an alternate major DNA repair pathway to NHEJ. Although HDR typically occurs at lower frequencies than NHEJ, it may be harnessed to generate precise, defined modifications at a target locus in the presence of an exogenously introduced repair template. The repair template may be either in the form of double stranded DNA, designed similarly to conventional DNA targeting constructs with homology arms flanking the insertion sequence, or single-stranded DNA oligonucleotides (ssODNs). The latter provides an effective and simple method for making small edits in the genome, such as the introduction of single nucleotide mutations for probing causal genetic variations. Unlike NHEJ, HDR is generally active only in dividing cells and its efficiency varies depending on the cell type and state.

Overview of CRISPR: The CRISPR-Cas system, by contrast, is at minimum a two-component system consisting of the Cas9 nuclease and a short guide RNA. Re-targeting of Cas9 to different loci or simultaneous editing of multiple genes simply requires cloning a different 20-bp oligonucleotide. Although specificity of the Cas9 nuclease has yet to be thoroughly elucidated, the simple Watson-Crick base-pairing of the CRISPR-Cas system is likely more predictable than that of ZFN or TALEN domains.

The type II CRISPR-Cas (clustered regularly interspaced short palindromic repeats) is a bacterial adaptive immune system that uses Cas9, to cleave foreign genetic elements. Cas9 is guided by a pair of non-coding RNAs, a variable crRNA and a required auxiliary tracrRNA. The crRNA contains a 20-nt guide sequence determines specificity by locating the target DNA via Watson-Crick base-pairing. In the native bacterial system, multiple crRNAs are co-transcribed to direct Cas9 against various targets. In the CRISPR-Cas system derived from *Streptococcus pyogenes*, the target DNA must immediately precede a 5'-NGG/NRG protospacer adjacent motif (PAM), which can vary for other CRISPR systems.

CRISPR-Cas is reconstituted in mammalian cells through the heterologous expression of human codon-optimized Cas9 and the requisite RNA components. Furthermore, the crRNA and tracrRNA can be fused to create a chimeric, synthetic guide RNA (sgRNA). Cas9 can thus be re-directed toward any target of interest by altering the 20-nt guide sequence within the sgRNA.

Given its ease of implementation and multiplex capability, Cas9 has been used to generate engineered eukaryotic cells carrying specific mutations via both NHEJ and HDR. In addition, direct injection of sgRNA and mRNA encoding Cas9 into embryos has enabled the rapid generation of transgenic mice with multiple modified alleles; these results hold promise for editing organisms that are otherwise genetically intractable.

A mutant Cas9 carrying a disruption in one of its catalytic domains has been engineered to nick rather than cleave DNA, allowing for single-stranded breaks and preferential repair through HDR, potentially ameliorating unwanted indel mutations from off-target DSBs. Additionally, a Cas9 mutant with both DNA-cleaving catalytic residues mutated has been adapted to enable transcriptional regulation in *E. coli*, demonstrating the potential of functionalizing Cas9 for diverse applications. Certain aspects of the invention relate to the construction and application of Cas9 for multiplexed editing of human cells.

Applicants have provided a human codon-optimized, nuclear localization sequence-flanked Cas9 to facilitate eukaryotic gene editing. Applicants describe considerations for designing the 20-nt guide sequence, protocols for rapid construction and functional validation of sgRNAs, and finally use of the Cas9 nuclease to mediate both NHEJ- and HDR-based genome modifications in human embryonic kidney (HEK-293FT) and human stem cell (HUES9) lines. This protocol can likewise be applied to other cell types and organisms.

Target selection for sgRNA: There are two main considerations in the selection of the 20-nt guide sequence for gene targeting: 1) the target sequence should precede the 5'-NGG PAM for S. pyogenes Cas9, and 2) guide sequences should be chosen to minimize off-target activity. Applicants provided an online Cas9 targeting design tool that takes an input sequence of interest and identifies suitable target sites. To experimentally assess off-target modifications for each sgRNA, Applicants also provide computationally predicted off-target sites for each intended target, ranked according to Applicants' quantitative specificity analysis on the effects of base-pairing mismatch identity, position, and distribution.

The detailed information on computationally predicted off-target sites is as follows:

Considerations for Off-target Cleavage Activities: Similar to other nucleases, Cas9 can cleave off-target DNA targets in the genome at reduced frequencies. The extent to which a given guide sequence exhibit off-target activity depends on a combination of factors including enzyme concentration, thermodynamics of the specific guide sequence employed, and the abundance of similar sequences in the target genome. For routine application of Cas9, it is important to consider ways to minimize the degree of off-target cleavage and also to be able to detect the presence of off-target cleavage.

Minimizing off-target activity: For application in cell lines, Applicants recommend following two steps to reduce the degree of off-target genome modification. First, using our online CRISPR target selection tool, it is possible to computationally assess the likelihood of a given guide sequence to have off-target sites. These analyses are performed through an exhaustive search in the genome for off-target sequences that are similar sequences as the guide sequence. Comprehensive experimental investigation of the effect of mismatching bases between the sgRNA and its target DNA revealed that mismatch tolerance is 1) position dependent—the 8-14 bp on the 3' end of the guide sequence are less tolerant of mismatches than the 5' bases, 2) quantity dependent—in general more than 3 mismatches are not tolerated, 3) guide sequence dependent—some guide sequences are less tolerant of mismatches than others, and 4) concentration dependent—off-target cleavage is highly sensitive to the amount of transfected DNA. The Applicants' target site analysis web tool (available at the website genome-engineering.org/tools) integrates these criteria to provide predictions for likely off-target sites in the target genome. Second, Applicants recommend titrating the amount of Cas9 and sgRNA expression plasmid to minimize off-target activity.

Detection of off-target activities: Using Applicants' CRISPR targeting web tool, it is possible to generate a list of most likely off-target sites as well as primers performing SURVEYOR or sequencing analysis of those sites. For isogenic clones generated using Cas9, Applicants strongly recommend sequencing these candidate off-target sites to check for any undesired mutations. It is worth noting that there may be off target modifications in sites that are not included in the predicted candidate list and full genome sequence should be performed to completely verify the absence of off-target sites. Furthermore, in multiplex assays where several DSBs are induced within the same genome, there may be low rates of translocation events and can be evaluated using a variety of techniques such as deep sequencing.

The online tool provides the sequences for all oligos and primers necessary for 1) preparing the sgRNA constructs, 2) assaying target modification efficiency, and 3) assessing cleavage at potential off-target sites. It is worth noting that because the U6 RNA polymerase III promoter used to express the sgRNA prefers a guanine (G) nucleotide as the first base of its transcript, an extra G is appended at the 5' of the sgRNA where the 20-nt guide sequence does not begin with G.

Approaches for sgRNA construction and delivery: Depending on the desired application, sgRNAs may be delivered as either 1) PCR amplicons containing an expression cassette or 2) sgRNA-expressing plasmids. PCR-based sgRNA delivery appends the custom sgRNA sequence onto the reverse PCR primer used to amplify a U6 promoter template. The resulting amplicon may be co-transfected with a plasmid containing Cas9 (PX165). This method is optimal for rapid screening of multiple candidate sgRNAs, as cell transfections for functional testing can be performed mere hours after obtaining the sgRNA-encoding primers. Because this simple method obviates the need for plasmid-based cloning and sequence verification, it is well suited for testing or co-transfecting a large number of sgRNAs for generating large knockout libraries or other scale-sensitive applications. Note that the sgRNA-encoding primers are over 100-bp, compared to the ~20-bp oligos required for plasmid-based sgRNA delivery.

Construction of an expression plasmid for sgRNA is also simple and rapid, involving a single cloning step with a pair of partially complementary oligonucleotides. After annealing the oligo pairs, the resulting guide sequences may be inserted into a plasmid bearing both Cas9 and an invariant scaffold bearing the remainder of the sgRNA sequence (PX330). The transfection plasmids may also be modified to enable virus production for in vivo delivery.

In addition to PCR and plasmid-based delivery methods, both Cas9 and sgRNA can be introduced into cells as RNA.

Design of repair template: Traditionally, targeted DNA modifications have required use of plasmid-based donor repair templates that contain homology arms flanking the site of alteration. The homology arms on each side can vary in length, but are typically longer than 500 bp. This method can be used to generate large modifications, including insertion of reporter genes such as fluorescent proteins or antibiotic resistance markers. The design and construction of targeting plasmids has been described elsewhere.

More recently, single-stranded DNA oligonucleotides (ssODNs) have been used in place of targeting plasmids for short modifications within a defined locus without cloning. To achieve high HDR efficiencies, ssODNs contain flanking sequences of at least 40 bp on each side that are homologous to the target region, and can be oriented in either the sense or antisense direction relative to the target locus.

Functional Testing

SURVEYOR nuclease assay: Applicants detected indel mutations either by the SURVEYOR nuclease assay (or PCR amplicon sequencing. Applicants online CRISPR target design tool provides recommended primers for both approaches. However, SURVEYOR or sequencing primers may also be designed manually to amplify the region of interest from genomic DNA and to avoid non-specific amplicons using NCBI Primer-BLAST. SURVEYOR primers should be designed to amplify 300-400 bp (for a 600-800 bp total amplicon) on either side of the Cas9 target for allowing clear visualization of cleavage bands by gel electrophoresis. To prevent excessive primer dimer formation, SURVEYOR primers should be designed to be typically under 25-nt long with melting temperatures of ~60° C. Applicants recommend testing each pair of candidate primers for specific PCR amplicons as well as for the absence of non-specific cleavage during the SURVEYOR nuclease digestion process.

Plasmid- or ssODN-mediated HDR: HDR can be detected via PCR-amplification and sequencing of the modified region. PCR primers for this purpose should anneal outside the region spanned by the homology arms to avoid false detection of residual repair template (HDR Fwd and Rev, FIG. 12). For ssODN-mediated HDR, SURVEYOR PCR primers can be used.

Detection of indels or HDR by sequencing: Applicants detected targeted genome modifications by either Sanger or next-generation deep sequencing (NGS). For the former, genomic DNA from modified region can be amplified using either SURVEYOR or HDR primers. Amplicons should be subcloned into a plasmid such as pUC19 for transformation; individual colonies can be sequenced to reveal clonal genotype.

Applicants designed next-generation sequencing (NGS) primers for shorter amplicons, typically in the 100-200 bp size range. For detecting NHEJ mutations, it is important to design primers with at least 10-20 bp between the priming regions and the Cas9 target site to allow detection of longer indels. Applicants provide guidelines for a two-step PCR method to attach barcoded adapters for multiplex deep sequencing. Applicants recommend the Illumina platform, due to its generally low levels of false positive indels. Off-target analysis (described previously) can then be performed through read alignment programs such as ClustalW, Geneious, or simple sequence analysis scripts.

Materials and Reagents
sgRNA Preparation:
UltraPure DNaseRNase-free distilled water (Life Technologies, cat. no. 10977-023)
Herculase II fusion polymerase (Agilent Technologies, cat. no. 600679)
CRITICAL. Standard Taq polymerase, which lacks 3'-5' exonuclease proofreading activity, has lower fidelity and can lead to amplification errors. Herculase II is a high-fidelity polymerase (equivalent fidelity to Pfu) that produces high yields of PCR product with minimal optimization. Other high-fidelity polymerases may be substituted.
Herculase II reaction buffer (5×; Agilent Technologies, included with polymerase)
dNTP solution mix (25 mM each; Enzymatics, cat. no. N205L)
MgCl2 (25 mM; ThermoScientific, cat. no. R0971)
QIAquick gel extraction kit (Qiagen, cat. no. 28704)
QIAprep spin miniprep kit (Qiagen, cat. no. 27106)
UltraPure TBE buffer (10×; Life Technologies, cat. no. 15581-028)
SeaKem LE agarose (Lonza, cat. no. 50004)
SYBR Safe DNA stain (10,000×; Life Technologies, cat. no. S33102)
1-kb Plus DNA ladder (Life Technologies, cat. no. 10787-018)
TrackIt CyanOrange loading buffer (Life Technologies, cat. no. 10482-028)
FastDigest BbsI (BpiI) (Fermentas/ThermoScientific, cat. no. FD1014)
Fermentas Tango Buffer (Fermentas/ThermoScientific, cat. no. BY5)
DL-dithiothreitol (DTT; Fermentas/ThermoScientific, cat. no. R0862)
T7 DNA ligase (Enzymatics, cat. no. L602L)
Critical: Do not substitute the more commonly used T4 ligase. T7 ligase has 1,000-fold higher activity on the sticky ends than on the blunt ends and higher overall activity than commercially available concentrated T4 ligases.
T7 2× Rapid Ligation Buffer (included with T7 DNA ligase, Enzymatics, cat. no. L602L)
T4 Polynucleotide Kinase (New England Biolabs, cat. no M0201S)
T4 DNA Ligase Reaction Buffer (10×; New England Biolabs, cat. no B0202S)
Adenosine 5'-triphosphate (10 mM; New England Biolabs, cat. no. P0756S)
PlasmidSafe ATP-dependent DNase (Epicentre, cat. no. E3101K)
One Shot Stbl3 chemically competent *Escherichia coli* (*E. coli*) (Life Technologies, cat. no. C7373-03)
SOC medium (New England Biolabs, cat. no. B9020S)
LB medium (Sigma, cat. no. L3022)
LB agar medium (Sigma, cat. no. L2897)
Ampicillin, sterile filtered (100 mg ml-1; Sigma, cat. no. A5354)
Mammalian Cell Culture:
HEK293FT cells (Life Technologies, cat. no. R700-07)
Dulbecco's minimum Eagle's medium (DMEM, 1×, high glucose; Life Technologies, cat. no. 10313-039)
Dulbecco's minimum Eagle's medium (DMEM, IX, high glucose, no phenol red; Life Technologies, cat. no. 31053-028)
Dulbecco's phosphate-buffered saline (DPBS, 1×; Life Technologies, cat. no. 14190-250)
Fetal bovine serum, qualified and heat inactivated (Life Technologies, cat. no. 10438-034)
Opti-MEM I reduced-serum medium (FBS; Life Technologies, cat. no. 11058-021)
Penicillin-streptomycin (100×; Life Technologies, cat. no. 15140-163)
TrypLE™ Express (1×, no Phenol Red; Life Technologies, cat. no. 12604-013)
Lipofectamine 2000 transfection reagent (Life Technologies, cat. no. 11668027)
Amaxa SF Cell Line 4D-Nucleofector® X Kit S (32 RCT; Lonza, cat. no V4XC-2032)
HUES 9 cell line (HARVARD STEM CELL SCIENCE)
Geltrex LDEV-Free Reduced Growth Factor Basement Membrane Matrix (Life Technologies, cat. no. A1413201)
mTeSR1 medium (Stemcell Technologies, cat. no. 05850)
Accutase cell detachment solution (Stemcell Technologies, cat. no. 07920)
ROCK Inhibitor (Y-27632; Millipore, cat. no. SCM075)
Amaxa P3 Primary Cell 4D-Nucleofector® X Kit S (32 RCT; Lonza cat. no. V4XP-3032)
Genotyping Analysis:
QuickExtract DNA extraction solution (Epicentre, cat. no. QE09050)
PCR primers for SURVEYOR, RFLP analysis, or sequencing (see Primer table)
Herculase II fusion polymerase (Agilent Technologies, cat. no. 600679)
CRITICAL. As Surveyor assay is sensitive to single-base mismatches, it is particularly important to use a high-fidelity polymerase. Other high-fidelity polymerases may be substituted.
Herculase II reaction buffer (5×; Agilent Technologies, included with polymerase)
dNTP solution mix (25 mM each; Enzymatics, cat. no. N205L)

QIAquick gel extraction kit (Qiagen, cat. no. 28704)

Taq Buffer (Ox; Genscript, cat. no. B0005)

SURVEYOR mutation detection kit for standard gel electrophoresis (Transgenomic, cat. no. 706025)

UltraPure TBE buffer (10×; Life Technologies, cat. no. 15581-028)

SeaKem LE agarose (Lonza, cat. no. 50004)

4-20% TBE Gels 1.0 mm, 15 Well (Life Technologies, cat. no. EC62255BOX)

Novex® Hi-Density TBE Sample Buffer (5×; Life Technologies, cat. no. LC6678)

SYBR Gold Nucleic Acid Gel Stain (10,000×; Life Technologies, cat. no. S-11494)

1-kb Plus DNA ladder (Life Technologies, cat. no. 10787-018)

TrackIt CyanOrange loading buffer (Life Technologies, cat. no. 10482-028) FastDigest HindIII (Fermentas/ThermoScientific, cat. no. FD0504)

Equipment

Filtered sterile pipette tips (Corning)

Standard 1.5 ml microcentrifuge tubes (Eppendorf, cat. no. 0030 125.150)

Axygen 96-well PCR plates (VWR, cat. no. PCR-96M2-HSC) Axygen 8-Strip PCR tubes (Fischer Scientific, cat. no. 14-222-250)

Falcon tubes, polypropylene, 15 ml (BD Falcon, cat. no. 352097)

Falcon tubes, polypropylene, 50 ml (BD Falcon, cat. no. 352070)

Round-bottom Tube with cell strainer cap, 5 ml (BD Falcon, cat. no. 352235)

Petri dishes (60 mm×15 mm; BD Biosciences, cat. no. 351007)

Tissue culture plate (24 well; BD Falcon, cat. no. 353047)

Tissue culture plate (96 well, flat bottom; BD Falcon, cat. no. 353075)

Tissue culture dish (100 mm; BD Falcon, 353003)

96-well thermocycler with programmable temperature stepping functionality (Applied Biosystems Veriti, cat. no. 4375786).

Desktop microcentrifuges 5424, 5804 (Eppendorf)

Gel electrophoresis system (PowerPac basic power supply, Bio-Rad, cat. no. 164-5050, and Sub-Cell GT System gel tray, Bio-Rad, cat. no. 170-4401)

Novex XCell SureLock Mini-Cell (Life Technologies, cat. no. E10001)

Digital gel imaging system (GelDoc EZ, Bio-Rad, cat. no. 170-8270, and blue sample tray, Bio-Rad, cat. no. 170-8273)

Blue light transilluminator and orange filter goggles (SafeImager 2.0; Invitrogen, cat. no. G6600)

Gel quantification software (Bio-Rad, ImageLab, included with GelDoc EZ, or open-source ImageJ from the National Institutes of Health, available at the website rsbweb.nih.gov/ij/) UV spectrophotometer (NanoDrop 2000c, Thermo Scientific)

Reagent Setup

Tris-borate EDTA (TBE) electrophoresis solution Dilute TBE buffer in distilled water to 1× working solution for casting agarose gels and for use as a buffer for gel electrophoresis. Buffer may be stored at room temperature (18-22° C.) for at least 1 year.

ATP, 10 mM Divide 10 mM ATP into 50-µl aliquots and store at −20° C. for up to 1 year; avoid repeated freeze-thaw cycles.

DTT, 10 mM Prepare 10 mM DTT solution in distilled water and store in 20-µl aliquots at −70° C. for up to 2 years; for each reaction, use a new aliquot, as DTT is easily oxidized.

D10 culture medium For culture of HEK293FT cells, prepare D10 culture medium by supplementing DMEM with 1× GlutaMAX and 10% (vol/vol) fetal bovine serum. As indicated in the protocol, this medium can also be supplemented with 1× penicillin-streptomycin. D10 medium can be made in advance and stored at 4° C. for up to I month.

mTeSR1 culture medium For culture of human embryonic stem cells, prepare mTeSR1 medium by supplementing the 5× supplement (included with mTeSR1 basal medium), and 100 ug/ml Normocin.

Procedure

Design of Targeting Components and Use of the Online Tool • Timing 1 d

1| Input target genomic DNA sequence. Applicants provide an online Cas9 targeting design tool that takes an input sequence of interest, identifies and ranks suitable target sites, and computationally predicts off-target sites for each intended target. Alternatively, one can manually select guide sequence by identifying the 20-bp sequence directly upstream of any 5'-NGG.

2| Order necessary oligos and primers as specified by the online tool. If the site is chosen manually, the oligos and primers should be designed.

Preparation of sgRNA Expression Construct

3| To generate the sgRNA expression construct, either the PCR- or plasmid-based protocol can be used.

(A) Via PCR Amplification • Timing 2 h (i) Applicants prepare diluted U6 PCR template. Applicants recommend using PX330 as a PCR template, but any U6-containing plasmid may likewise be used as the PCR template. Applicants diluted template with ddH$_2$O to a concentration of 10 ng/ul. Note that if a plasmid or cassette already containing an U6-driven sgRNA is used as a template, a gel extraction needs to be performed to ensure that the product contains only the intended sgRNA and no trace sgRNA carryover from template.

(ii) Applicants prepared diluted PCR oligos. U6-Fwd and U6-sgRNA-Rev primers are diluted to a final concentration of 10 uM in ddH$_2$O (add 10 ul of 100 uM primer to 90 ul ddH$_2$O).

(iii) U6-sgRNA PCR reaction. Applicants set up the following reaction for each U6-sgRNA-Rev primer and mastermix as needed:

| Component: | Amount (ul) | Final concentration |
| --- | --- | --- |
| Herculase II PCR buffer, 5X | 10 | 1X |
| dNTP, 100 mM (25 mM each) | 0.5 | 1 mM |
| U6 template (PX330) | 1 | 0.2 ng/ul |
| U6-Fwd primer | 1 | 0.2 uM |
| U6-sgRNA-Rev primer (variable) | 1 | 0.2 uM |
| Herculase II Fusion polymerase | 0.5 | |
| Distilled water | 36 | |
| Total | 50 | |

(iv) Applicants performed PCR reaction on the reactions from step (iii) using the following cycling conditions:

| Cycle number | Denature | Anneal | Extend |
|---|---|---|---|
| 1 | 95° C., 2 m | | |
| 2-31 | 95° C., 20 s | 60° C., 20 s | 72° C., 20 s |
| 32 | | | 72° C., 3 m |

(v) After the reaction is completed, Applicants ran the product on a gel to verify successful, single-band amplification. Cast a 2% (wt/vol) agarose gel in 1× TBE buffer with 1× SYBR Safe dye. Run 5 ul of the PCR product in the gel at 15 V cm-1 for 20-30 min. Successful amplicons should yield one single 370-bp product and the template should be invisible. It should not be necessary to gel extract the PCR amplicon.

(vi) Applicants purified the PCR product using the QIAquick PCR purification kit according to the manufacturer's directions. Elute the DNA in 35 ul of Buffer EB or water. Purified PCR products may be stored at 4° C. or −20° C.

(B) Cloning sgRNA into Cas9-Containing Bicistronic Expression Vector • Timing 3d (i) Prepare the sgRNA oligo inserts. Applicants resuspended the top and bottom strands of oligos for each sgRNA design to a final concentration of 100 uM. Phosphorylate and anneal the oligo as follows:

| | |
|---|---|
| Oligo 1 (100 uM) | 1 ul |
| Oligo 2 (100 uM) | 1 ul |
| T4 Ligation Buffer, 10X | 1 ul |
| T4 PNK | 1 ul |
| ddH$_2$O | 6 ul |
| Total | 10 ul |

(ii) Anneal in a thermocycler using the following parameters:
37° C. for 30 m
95° C. for 5 m
Ramp down to 25° C. at 5° C. per m (iii) Applicants diluted phosphorylated and annealed oligos 1:200 by add 1 ul of oligo to 199 ul room temperature ddH$_2$O.

(iv) Clone sgRNA oligo into PX330. Applicants set up Golden Gate reaction for each sgRNA. Applicants recommend also setting up a no-insert, PX330 only negative control.

| | |
|---|---|
| PX330 (100 ng) | x ul |
| Diluted oligo duplex from step (iii) | 2 ul |
| Tango Buffer, 10X | 2 ul |
| DTT, 10 mM | 1 ul |
| ATP, 10 mM | 1 ul |
| FastDigest BbsI | 1 ul |
| T7 Ligase | 0.5 ul |
| ddH$_2$O | x ul |
| Total | 20 ul |

(v) Incubate the Golden Gate reaction for a total of 1 h:

| Cycle number | Condition |
|---|---|
| 1-6 | 37° C. for 5 m, 21° C. for 5 m |

(vi) Applicants treated Golden Gate reaction with PlasmidSafe exonuclease to digest any residual linearized DNA. This step is optional but highly recommended.

| | |
|---|---|
| Golden Gate reaction from step 4 | 11 ul |
| 10X PlasmidSafe Buffer | 1.5 ul |
| ATP, 10 mM | 1.5 ul |
| PlasmidSafe exonuclease | 1 ul |
| Total | 15 ul |

(vii) Applicants incubated the PlasmidSafe reaction at 37° C. for 30 min, followed by inactivation at 70° C. for 30 min. Pause point: after completion, the reaction may be frozen and continued later. The circular DNA should be stable for at least 1 week.

(viii) Transformation. Applicants transformed the PlasmidSafe-treated plasmid into a competent E. coli strain, according to the protocol supplied with the cells. Applicants recommend Stbl3 for quick transformation. Briefly, Applicants added 5 ul of the product from step (vii) into 20 ul of ice-cold chemically competent Stbl3 cells. This is then incubated on ice for 10 m, heat shocked at 42° C. for 30 s, returned immediately to ice for 2 m, 100 ul of SOC medium is added, and this is plated onto an LB plate containing 100 ug/ml ampicillin with incubation overnight at 37° C.

(ix) Day 2: Applicants inspected plates for colony growth. Typically, there are no colonies on the negative control plates (ligation of BbsI-digested PX330 only, no annealed sgRNA oligo), and tens to hundreds of colonies on the PX330-sgRNA cloning plates.

(x) From each plate, Applicants picked 2-3 colonies to check correct insertion of sgRNA. Applicants used a sterile pipette tip to inoculate a single colony into a 3 ml culture of LB medium with 100 ug/ml ampicillin. Incubate and shake at 37° C. overnight.

(xi) Day 3: Applicants isolated plasmid DNA from overnight cultures using a QiAprep Spin miniprep kit according to the manufacturer's instructions.

(xii) Sequence validate CRISPR plasmid. Applicants verified the sequence of each colony by sequencing from the U6 promoter using the U6-Fwd primer. Optional: sequence the Cas9 gene using primers listed in the following Primer table.

| Primer | Sequence (5' to 3') | Purpose |
|---|---|---|
| U6-For | GAGGGCCTATTTCCCATGATTCC (SEQ ID NO: 175) | Amplify U6-sgRNA |
| U6-Rev | AAAAAAAGCACCGACTCGGTGCCACTTTTTCAAGTTGA TAACGGACTAGCCTTATTTTAACTTGCTATTTCTAG CTCTAAAACNNNNNNNNNNNNNNNNNNNNCCGGTGTTTC GTCCTTTCCACAAG (SEQ ID NO: 176) | Amplify U6-sgRNA; N is reverse complement of target |

-continued

| Primer | Sequence (5' to 3') | Purpose |
|---|---|---|
| sgRNA-top | CACCGNNNNNNNNNNNNNNNNNNNN (SEQ ID NO: 177) | Clone sgRNA into PX330 |
| sgRNA-bottom | AAACNNNNNNNNNNNNNNNNNNNNC (SEQ ID NO: 178) | Clone sgRNA into PX330 |
| U6-EMX1-Rev | AAAAAAAGCACCGACTCGGTGCCACTTTTTCAAGTTGATAACGGACTAGCCTTATTTTAACTTGCTATTTCTAGCTCTAAAACCCCTAGTCATTGGAGGTGACCGGTGTTTCGTCCTTTCCACAAG (SEQ ID NO: 179) | Amplify U6-EMX1 sgRNA |
| EMX1-top | CACCGTCACCTCCAATGACTAGGG (SEQ ID NO: 180) | Clone EMX1 sgRNA into PX330 |
| EMX1-bottom | AAACCCCTAGTCATTGGAGGTGAC (SEQ ID NO: 181) | Clone EMX1 sgRNA into PX330 |
| ssODN-sense | CAGAAGAAGAAGGGCTCCCATCACATCAACCGGTGGCGCATTGCCACGAAGCAGGCCAATGGGGAGGACATCGATGTCACCTCCAATGAC<u>AAGCTTGCTAGC</u>GGTGGGCAACCACAAACCCACGAGGGCAGAGTGCTGCTTGCTGCTGGCCAGGCCCCTGCGTGGGCCCAAGCTGGACTCTGGCCACTCCCT (SEQ ID NO: 182) | EMX1 HDR (sense; insertion underlined) |
| ssODN-antisense | AGGGAGTGGCCAGAGTCCAGCTTGGGCCCACGCAGGGGCCTGGCCAGCAGCAAGCAGCACTCTGCCCTCGTGGGTTTGTGGTTGCCCACCG<u>CTAGCAAGCTT</u>GTCATTGGAGGTGACATCGATGTCCTCCCCATTGGCCTGCTTCGTGGCAATGCGCCACCGGTTGATGTGATGGGAGCCCTTCTTCTTCTG (SEQ ID NO: 183) | EMX1 HDR (antisense; insertion underlined) |
| EMX1-SURV-F | CCATCCCCTTCTGTGAATGT (SEQ ID NO: 184) | EMX1 SURVEYOR assay PCR, sequencing |
| EMX1-SURV-R | GGAGATTGGAGACACGGAGA (SEQ ID NO: 185) | EMX1 SURVEYOR assay PCR, sequencing |
| EMX1-HDR-F | GGCTCCCTGGGTTCAAAGTA (SEQ ID NO: 186) | EMX1 RFLP analysis PCR, sequencing |
| EMX1-HDR-R | AGAGGGGTCTGGATGTCGTAA (SEQ ID NO: 187) | EMX1 RFLP analysis PCR, sequencing |
| pUC19-F | CGCCAGGGTTTTCCCAGTCACGAC (SEQ ID NO: 188) | pUC19 multiple cloning site F primer, for Sanger sequencing |

Applicants referenced the sequencing results against the PX330 cloning vector sequence to check that the 20 bp guide sequence was inserted between the U6 promoter and the remainder of the sgRNA scaffold. Details and sequence of the PX330 map in GenBank vector map format (*.gb file) can be found at the website crispr.genome-engineering.org.

(Optional) Design of ssODN Template • Timing 3 d Planning Ahead

3| Design and order ssODN. Either the sense or antisense ssODN can be purchased directly from supplier. Applicants recommend designing homology arms of at least 40 bp on either side and 90 bp for optimal HDR efficiency. In Applicants' experience, antisense oligos have slightly higher modification efficiencies.

4| Applicants resuspended and diluted ssODN ultramers to a final concentration of 10 uM. Do not combine or anneal the sense and antisense ssODNs. Store at −20° C.

5| Note for HDR applications, Applicants recommend cloning sgRNA into the PX330 plasmid.

Functional Validation of sgRNAs: Cell Culture and Transfections • Timing 3-4 d

The CRISPR-Cas system has been used in a number of mammalian cell lines. Conditions may vary for each cell line. The protocols below details transfection conditions for HEK239FT cells. Note for ssODN-mediated HDR transfections, the Amaxa SF Cell Line Nucleofector Kit is used for optimal delivery of ssODNs. This is described in the next section.

7| HEK293FT maintenance. Cells are maintained according to the manufacturer's recommendations. Briefly, Applicants cultured cells in D10 medium (GlutaMax DMEM supplemented with 10% Fetal Bovine Serum), at 37° C. and 5% CO2.

8| To passage, Applicants removed medium and rinsed once by gently adding DPBS to side of vessel, so as not to dislodge cells. Applicants added 2 ml of TrypLE to a T75 flask and incubated for 5 m at 37° C. 10 ml of warm D10 medium is added to inactivate and transferred to a 50 ml Falcon tube. Applicants dissociated cells by triturating gently, and re-seeded new flasks as necessary. Applicants typically passage cells every 2-3 d at a split ratio of 1:4 or 1:8, never allowing cells to reach more than 70% confluency. Cell lines are restarted upon reaching passage number 15.

9| Prepare cells for transfection. Applicants plated well-dissociated cells onto 24-well plates in D10 medium without antibiotics 16-24 h before transfection at a seeding density of $1.3 \times 10^5$ cells per well and a seeding volume of 500 ul. Scale up or down according to the manufacturer's manual as needed. It is suggested to not plate more cells than recommended density as doing so may reduce transfection efficiency.

10| On the day of transfection, cells are optimal at 70-90% confluency. Cells may be transfected with Lipofectamine 2000 or Amaxa SF Cell Line Nucleofector Kit according to the manufacturers' protocols.

(A) For sgRNAs cloned into PX330, Applicants transfected 500 ng of sequence-verified CRISPR plasmid; if transfecting more than one plasmid, mix at equimolar ratio and no more than 500 ng total.

(B) For sgRNA amplified by PCR, Applicants mixed the following:

| PX165 (Cas9 only) | 200 ng |
| sgRNA amplicon (each) | 40 ng |
| pUC19 | fill up total DNA to 500 ng |

Applicants recommend transfecting in technical triplicates for reliable quantification and including transfection controls (e.g. GFP plasmid) to monitor transfection efficiency. In addition, PX330 cloning plasmid and/or sgRNA amplicon may be transfected alone as a negative control for downstream functional assays.

11| Applicants added Lipofectamine complex to cells gently as HEK293FT cells may detach easily from plate easily and result in lower transfection efficiency.

12| Applicants checked cells 24 h after transfection for efficiency by estimating the fraction of fluorescent cells in the control (e.g., GFP) transfection using a fluorescence microscope. Typically cells are more than 70% transfected.

13| Applicants supplemented the culture medium with an additional 500 ul of warm D10 medium. Add D10 very slowly to the side of the well and do not use cold medium, as cells can detach easily.

14| Cells are incubated for a total of 48-72 h post-transfection before harvested for indel analysis. Indel efficiency does not increase noticeably after 48 h.

(Optional) Co-Transfection of CRISPR Plasmids and ssODNs or Targeting Plasmids for HR • Timing 3-4 d 15| Linearize targeting plasmid. Targeting vector is linearized if possible by cutting once at a restriction site in the vector backbone near one of the homology arms or at the distal end of either homology arm.

16| Applicants ran a small amount of the linearized plasmid alongside uncut plasmid on a 0.8-1% agarose gel to check successful linearization. Linearized plasmid should run above the supercoiled plasmid.

17| Applicants purified linearized plasmid with the QIAQuick PCR Purification kit.

18| Prepare cells for transfection. Applicants cultured HEK293FT in T75 or T225 flasks. Sufficient cell count before day of transfection is planned for. For the Amaxa strip-cuvette format, $2 \times 10^6$ cells are used per transfection.

19| Prepare plates for transfection. Applicants added 1 ml of warm D10 medium into each well of a 12 well plate. Plates are placed into the incubator to keep medium warm.

20| Nucleofection. Applicants transfected HEK293FT cells according to the Amaxa SF Cell Line Nucleofector 4D Kit manufacturer's instructions, adapted in the steps below.

a. For ssODN and CRISPR cotransfection, pre-mix the following DNA in PCR tubes:

| pCRISPR plasmid (Cas9 + sgRNA) | 500 ng |
| ssODN template (10 uM) | 1 ul | b. For HDR targeting plasmid and CRISPR cotransfection, pre-mix the following DNA in PCR tubes:

| CRISPR plasmid (Cas9 + sgRNA) | 500 ng |
| Linearized targeting plasmid | 500 ng |

For transfection controls, see previous section. In addition, Applicants recommend transfecting ssODN or targeting plasmid alone as a negative control.

21| Dissociate to single cells. Applicants removed medium and rinsed once gently with DPBS, taking care not to dislodge cells. 2 ml of TrypLE is added to a T75 flask and incubated for 5 m at 37° C. 10 ml of warm D10 medium is added to inactivate and triturated gently in a 50 ml Falcon tube. It is recommended that cells are triturated gently and dissociated to single cells. Large clumps will reduce transfection efficiency. Applicants took a 10 ul aliquot from the suspension and diluted into 90 ul of D10 medium for counting. Applicants counted cells and calculated the number of cells and volume of suspension needed for transfection. Applicants typically transfected $2 \times 10^5$ cells per condition using the Amaxa Nucleocuvette strips, and recommend calculating for 20% more cells than required to adjust for volume loss in subsequent pipetting steps. The volume needed is transferred into a new Falcon tube.

23| Applicants spun down the new tube at 200×g for 5 m.

Applicants prepared the transfection solution by mixing the SF solution and S1 supplement as recommended by Amaxa. For Amaxa strip-cuvettes, a total of 20 ul of supplemented SF solution is needed per transfection. Likewise, Applicants recommend calculating for 20% more volume than required.

25| Applicants removed medium completely from pelleted cells from step 23 and gently resuspended in appropriate volume (20 ul per $2 \times 10^5$ cells) of S-supplemented SF solution. Do not leave cells in SF solution for extended period of time.

26| 20 ul of resuspended cells is pipetted into each DNA pre-mix from step 20. Pipette gently to mix and transfer to Nucleocuvette strip chamber. This is repeated for each transfection condition.

Electroporate cells using the Nucleofector 4D program recommended by Amaxa, CM-130.

28| Applicants gently and slowly pipetted 100 ul of warm D10 medium into each Nucleocuvette strip chamber, and transferred all volume into the pre-warmed plate from step 19. CRITICAL. Cells are very fragile at this stage and harsh pipetting can cause cell death. Incubate for 24 h. At this point, transfection efficiency can be estimated from fraction of fluorescent cells in positive transfection control. Nucleofection typically results in greater than 70-80% transfection efficiency. Applicants slowly added 1 ml warm D10 medium to each well without dislodging the cells. Incubate cells for a total of 72 h.

Human Embryonic Stem Cell (HUES 9) Culture and Transfection • Timing 3-4 d

Maintaining hESC (HUES9) line. Applicants routinely maintain HUES9 cell line in feeder-free conditions with mTesR1 medium. Applicants prepared mTeSR1 medium by adding the 5× supplement included with basal medium and 100 ug/ml Normocin. Applicants prepared a 10 ml aliquot of mTeSR1 medium supplemented further with 10 uM Rock Inhibitor. Coat tissue culture plate. Dilute cold GelTrex 1:100 in cold DMEM and coat the entire surface of a 100 mm tissue culture plate.

Place plate in incubator for at least 30 m at 37° C. Thaw out a vial of cells at 37° C. in a 15 ml Falcon tube, add 5 ml of mTeSR1 medium, and pellet at 200×g for 5 m. Aspirate off GelTrex coating and seed ~1×106 cells with 10 ml mTeSR1 medium containing Rock Inhibitor. Change to normal mTeSR1 medium 24 h after transfection and re-feed daily. Passaging cells. Re-feed cells with fresh mTeSR1 medium daily and passage before reaching 70% confluency. Aspirate off mTeSR1 medium and wash cells once with DPBS. Dissociate cells by adding 2 ml Accutase and incubating at 37° C. for 3-5 m. Add 10 ml mTeSR1 medium to detached cells, transfer to 15 ml Falcon tube and resuspend gently. Re-plate onto GelTrex-coated plates in mTeSR1 medium with 10 uM Rock Inhibitor. Change to normal mTeSR1 medium 24 h after plating.

Transfection. Applicants recommend culturing cells for at least 1 week post-thaw before transfecting using the Amaxa P3 Primary Cell 4-D Nucleofector Kit (Lonza). Re-feed log-phase growing cells with fresh medium 2 h before transfection. Dissociate to single cells or small clusters of no more than 10 cells with accutase and gentle resuspension. Count the number of cells needed for nucleofection and spin down at 200×g for 5 m. Remove medium completely and resuspend in recommended volume of S1-supplemented P3 nucleofection solution. Gently plate electroporated cells into coated plates in presence of 1× Rock Inhibitor.

Check transfection success and re-feed daily with regular mTeSR1 medium beginning 24 h after nucleofection. Typically, Applicants observe greater than 70% transfection efficiency with Amaxa Nucleofection. Harvest DNA. 48-72 h post transfection, dissociate cells using accutase and inactivate by adding 5× volume of mTeSR1. Spin cells down at 200×g for 5 m. Pelleted cells can be directed processed for DNA extraction with QuickExtract solution. It is recommended to not mechanically dissociate cells without accutase. It is recommended to not spin cells down without inactivating accutase or above the recommended speed; doing so may cause cells to lyse.

Isolation of Clonal Cell Lines by FACS. Timing • 2-3 h Hands-on; 2-3 Weeks Expansion Clonal isolation may be performed 24 h post-transfection by FACS or by serial dilution.

54| Prepare FACS buffer. Cells that do not need sorting using colored fluorescence may be sorted in regular D10 medium supplemented with 1× penicillin/streptinomycin. If colored fluorescence sorting is also required, a phenol-free DMEM or DPBS is substituted for normal DMEM. Supplement with 1× penicillin/streptinomycin and filter through a 0.22 um Steriflip filter.

55| Prepare 96 well plates. Applicants added 100 ul of D10 media supplemented with IX penicillin/streptinomycin per well and prepared the number of plates as needed for the desired number of clones.

56| Prepare cells for FACS. Applicants dissociated cells by aspirating the medium completely and adding 100 ul TrypLE per well of a 24-well plate. Incubate for 5 m and add 400 ul warm D10 media.

57| Resuspended cells are transferred into a 15 ml Falcon tube and gently triturated 20 times. Recommended to check under the microscope to ensure dissociation to single cells.

58| Spin down cells at 200×g for 5 minutes.

59| Applicants aspirated the media, and resuspended the cells in 200 ul of FACS media.

60| Cells are filtered through a 35 um mesh filter into labeled FACS tubes. Applicants recommend using the BD Falcon 12×75 mm Tube with Cell Strainer cap. Place cells on ice until sorting.

61| Applicants sorted single cells into 96-well plates prepared from step 55. Applicants recommend that in one single designated well on each plate, sort 100 cells as a positive control.

NOTE. The remainder of the cells may be kept and used for genotyping at the population level to gauge overall modification efficiency.

62| Applicants returned cells into the incubator and allowed them to expand for 2-3 weeks. 100 ul of warm D10 medium is added 5 d post sorting. Change 100 ul of medium every 3-5 d as necessary.

63| Colonies are inspected for "clonal" appearance 1 week post sorting: rounded colonies radiating from a central point. Mark off wells that are empty or may have been seeded with doublets or multiplets.

64| When cells are more than 60% confluent, Applicants prepared a set of replica plates for passaging. 100 ul of D10 medium is added to each well in the replica plates. Applicants dissociated cells directly by pipetting up and down vigorously 20 times. 20% of the resuspended volume was plated into the prepared replica plates to keep the clonal lines. Change the medium every 2-3 d thereafter and passage accordingly.

65| Use the remainder 80% of cells for DNA isolation and genotyping.

Optional: Isolation of Clonal Cell Lines by Dilution. Timing • 2-3 h Hands-on; 2-3 Weeks Expansion 66| Applicants dissociated cells from 24-well plates as described above. Make sure to dissociate to single cells. A cell strainer can be used to prevent clumping of cells.

67| The number of cells are counted in each condition. Serially dilute each condition in D10 medium to a final concentration of 0.5 cells per 100 ul. For each 96 well plate, Applicants recommend diluting to a final count of 60 cells in 12 ml of D10. Accurate count of cell number is recommended for appropriate clonal dilution. Cells may be recounted at an intermediate serial dilution stage to ensure accuracy.

68| Multichannel pipette was used to pipette 100 ul of diluted cells to each well of a 96 well plate.

NOTE. The remainder of the cells may be kept and used for genotyping at the population level to gauge overall modification efficiency.

69| Applicants inspected colonies for "clonal" appearance ~1 week post plating: rounded colonies radiating from a central point. Mark off wells that may have seeded with doublets or multiplets.

70| Applicants returned cells to the incubator and allowed them to expand for 2-3 weeks. Re-feed cells as needed as detailed in previous section.

SURVEYOR Assay for CRISPR Cleavage Efficiency. Timing • 5-6 h

Before assaying cleavage efficiency of transfected cells, Applicants recommend testing each new SURVEYOR primer on negative (untransfected) control samples through the step of SURVEYOR nuclease digestion using the protocol described below. Occasionally, even single-band clean SURVEYOR PCR products can yield non-specific SURVEYOR nuclease cleavage bands and potentially interfere with accurate indel analysis.

71| Harvest cells for DNA. Dissociate cells and spin down at 200×g for 5 m. NOTE. Replica plate at this stage as needed to keep transfected cell lines.

72| Aspirate the supernatant completely.

73| Applicants used QuickExtract DNA extraction solution according to the manufacturer's instructions. Applicants typically used 50 ul of the solution for each well of a 24 well plate and 10 ul for a 96 well plate.

74| Applicants normalized extracted DNA to a final concentration of 100-200 ng/ul with ddH2O. Pause point: Extracted DNA may be stored at −20° C. for several months.

75| Set up the SURVEYOR PCR. Master mix the following using SURVEYOR primers provided by Applicants online/computer algorithm tool:

| Component: | Amount (ul) | Final concentration |
|---|---|---|
| Herculase II PCR buffer, 5X | 10 | 1X |
| dNTP, 100 mM (25 mM each) | 1 | 1 mM |
| SURVEYOR Fwd primer (10 uM) | 1 | 0.2 uM |
| SURVEYOR Rev primer (10 uM) | 1 | 0.2 uM |
| Herculase II Fusion polymerase | 1 | |
| $MgCl_2$ (25 mM) | 2 | 1 mM |
| Distilled water | 33 | |
| Total | 49 (for each reaction) | |

76| Applicants added 100-200 ng of normalized genomic DNA template from step 74 for each reaction.

77| PCR reaction was performed using the following cycling conditions, for no more than 30 amplification cycles:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 min |

78| Applicants ran 2-5 ul of PCR product on a 1% gel to check for single-band product. Although these PCR conditions are designed to work with most pairs of SURVEYOR primers, some primers may need additional optimization by adjusting the template concentration, $MgCl_2$ concentration, and/or the annealing temperature.

79| Applicants purified the PCR reactions using the QIAQuick PCR purification kit and normalized eluant to 20 ng/ul. Pause point: Purified PCR product may be stored at −20° C.

80| DNA heteroduplex formation. The annealing reaction was set up as follows:

| | |
|---|---|
| Taq PCR buffer, 10X | 2 ul |
| Normalized DNA (20 ng/ul) | 18 ul |
| Total volume | 20 ul |

81| Anneal the reaction using the following conditions:

| Cycle number | Condition |
|---|---|
| 1 | 95° C., 10 mn |
| 2 | 95° C.-85° C., −2° C./s |
| 3 | 85° C., 1 min |
| 4 | 85° C.-75° C., −0.3° C./s |
| 5 | 75° C., 1 min |
| 6 | 75° C.-65° C., −0.3° C./s |
| 7 | 65° C., 1 min |
| 8 | 65° C.-55° C., −0.3° C./s |
| 9 | 55° C., 1 min |
| 10 | 55° C.-45° C., −0.3° C./s |
| 11 | 45° C., 1 min |
| 12 | 45° C.-35° C., −0.3° C./s |
| 13 | 35° C., 1 min |
| 14 | 35° C.-25° C., −0.3° C./s |
| 15 | 25° C., 1 min |

82| SURVEYOR nuclease S digestion. Applicants prepared master-mix and added the following components on ice to annealed heteroduplexes from step 81 for a total final volume of 25 ul:

| Component | Amount (ul) | Final Concentration |
|---|---|---|
| $MgCl_2$ solution, 0.15M | 2.5 | 15 mM |
| $ddH_2O$ | 0.5 | |
| SURVEYOR nuclease S | 1 | 1X |
| SURVEYOR enhancer S | 1 | 1X |
| Total | 5 | |

83| Vortex well and spin down. Incubate the reaction at 42° C. for 1 h.

84| Optional: 2 ul of the Stop Solution from the SURVEYOR kit may be added. Pause point. The digested product may be stored at −20° C. for analysis at a later time.

85| Visualize the SURVEYOR reaction. SURVEYOR nuclease digestion products may be visualized on a 2% agarose gel. For better resolution, products may be run on a 4-20% gradient Polyacrylamide TBE gel. Applicants loaded 10 ul of product with the recommended loading buffer and ran the gel according to manufacturer's instructions. Typically, Applicants run until the bromophenol blue dye has migrated to the bottom of the gel. Include DNA ladder and negative controls on the same gel.

86| Applicants stained the gel with 1× SYBR Gold dye diluted in TBE. The gel was gently rocked for 15 m.

87| Applicants imaged the gel using a quantitative imaging system without overexposing the bands. The negative controls should have only one band corresponding to the size of the PCR product, but may have occasionally non-specific cleavage bands of other sizes. These will not interfere with analysis if they are different in size from target cleavage bands. The sum of target cleavage band sizes, provided by Applicants online/computer algorithm tool, should be equal to the size of the PCR product.

88| Estimate the cleavage intensity. Applicants quantified the integrated intensity of each band using ImageJ or other gel quantification software.

89| For each lane, Applicants calculated the fraction of the PCR product cleaved ($f_{cut}$) using the following formula: $f_{cut}=(b+c)/(a+b+c)$, where a is the integrated intensity of the undigested PCR product and b and c are the integrated intensities of each cleavage product. 90| Cleavage efficiency may be estimated using the following formula, based on the binomial probability distribution of duplex formation:

91| indel (%)=100×$(1-\sqrt{(1-f_{cut})})$|IPSpecs_L2|ZZMPTAG|

Sanger Sequencing for Assessing CRISPR Cleavage Efficiency. Timing • 3 d

Initial steps are identical to Steps 71-79 of the SURVEYOR assay. Note: SURVEYOR primers may be used for Sanger sequencing if appropriate restriction sites are appended to the Forward and Reverse primers. For cloning into the recommended pUC19 backbone, EcoRI may be used for the Fwd primer and HindIII for the Rev primer.

92| Amplicon digestion. Set up the digestion reaction as follows:

| Component | Amount (ul) |
| --- | --- |
| Fast Digest buffer, 10X | 3 |
| FastDigest EcoRI | 1 |
| FastDigest HindIII | 1 |
| Normalized DNA (20 ng/ul) | 10 |
| ddH$_2$O | 15 |
| Total volume | 30 |

93| pUC19 backbone digestion. Set up the digestion reaction as follows:

| Component | Amount (ul) |
| --- | --- |
| Fast Digest buffer, 10X | 3 |
| FastDigest EcoRI | 1 |
| FastDigest HindIII | 1 |
| FastAP Alkaline Phosphatase | 1 |
| pUC19 vector (200 ng/ul) | 5 |
| ddH$_2$O | 20 |
| Total volume | 30 |

94| Applicants purified the digestion reactions using the QIAQuick PCR purification kit. Pause point: Purified PCR product may be stored at −20° C.

95| Applicants ligated the digested pUC19 backbone and Sanger amplicons at a 1:3 vector:insert ratio as follows:

| Component | Amount (ul) |
| --- | --- |
| Digested pUC19 | x (50 ng) |
| Digested insert | x (1:3 vector:insert molar ratio) |
| T7 ligase | 1 |
| 2X Rapid Ligation Buffer | 10 |
| ddH$_2$O | x |
| Total volume | 20 |

96| Transformation. Applicants transformed the Plasmid-Safe-treated plasmid into a competent *E. coli* strain, according to the protocol supplied with the cells. Applicants recommend Stbl3 for quick transformation. Briefly, 5 ul of the product from step 95 is added into 20 ul of ice-cold chemically competent Stbl3 cells, incubated on ice for 10 m, heat shocked at 42° C. for 30 s, returned immediately to ice for 2 m, 100 ul of SOC medium is added, and plated onto an LB plate containing 100 ug/ml ampicillin. This is incubated overnight at 37° C.

97| Day 2: Applicants inspected plates for colony growth. Typically, there are no colonies on the negative control plates (ligation of EcoRI-HindIII digested pUC19 only, no Sanger amplicon insert), and tens to hundreds of colonies on the pUC19-Sanger amplicon cloning plates.

98| Day 3: Applicants isolated plasmid DNA from overnight cultures using a QIAprep Spin miniprep kit according to the manufacturer's instructions.

99| Sanger sequencing. Applicants verified the sequence of each colony by sequencing from the pUC19 backbone using the pUC19-For primer. Applicants referenced the sequencing results against the expected genomic DNA sequence to check for the presence of Cas9-induced NHEJ mutations. % editing efficiency=(# modified clones)/(# total clones). It is important to pick a reasonable number of clones (>24) to generate accurate modification efficiencies.

Genotyping for Microdeletion. Timing • 2-3 d Hands on; 2-3 Weeks Expansion

100| Cells were transfected as described above with a pair of sgRNAs targeting the region to be deleted.

101| 24 h post-transfection, clonal lines are isolated by FACS or serial dilution as described above.

102| Cells are expanded for 2-3 weeks.

103| Applicants harvested DNA from clonal lines as described above using 10 ul QuickExtract solution and normalized genomic DNA with ddH$_2$O to a final concentration of 50-100 ng/ul.

104| PCR Amplify the modified region. The PCR reaction is set up as follows:

| Component: | Amount (ul) | Final concentration |
| --- | --- | --- |
| Herculase II PCR buffer, 5X | 10 | 1X |
| dNTP, 100 mM (25 mM each) | 1 | 1 mM |
| Out Fwd primer (10 uM) | 1 | 0.2 uM |
| Out Rev primer (10 uM) | 1 | 0.2 uM |
| Herculase II Fusion polymerase | 1 | |
| MgCl2 (25 mM) | 2 | 1 mM |
| ddH$_2$O | 32 | |
| Total | 48 (for each reaction) | |

Note: if deletion size is more than 1 kb, set up a parallel set of PCR reactions with In-Fwd and In-Rev primers to screen for the presence of the wt allele.

105| To screen for inversions, a PCR reaction is set up as follows:

| Component: | Amount (ul) | Final concentration |
| --- | --- | --- |
| Herculase II PCR buffer, 5X | 10 | 1X |
| dNTP, 100 mM (25 mM each) | 1 | 1 mM |
| Out Fwd or Out-Rev primer (10 uM) | 1 | 0.2 uM |
| In Fwd or In-Rev primer (10 uM) | 1 | 0.2 uM |
| Herculase II Fusion polymerase | 1 | |
| MgCl$_2$ (25 mM) | 2 | 1 mM |
| ddH$_2$O | 32 | |
| Total | 48 (for each reaction) | |

Note: primers are paired either as Out-Fwd+In Fwd, or Out-Rev+In-Rev.

106| Applicants added 100-200 ng of normalized genomic DNA template from step 103 for each reaction.

107| PCR reaction was performed using the following cycling conditions:

| Cycle number | Denature | Anneal | Extend |
|---|---|---|---|
| 1 | 95° C., 2 min | | |
| 2-31 | 95° C., 20 s | 60° C., 20 s | 72° C., 30 s |
| 32 | | | 72° C., 3 m |

108| Applicants run 2-5 ul of PCR product on a 1-2% gel to check for product. Although these PCR conditions are designed to work with most primers, some primers may need additional optimization by adjusting the template concentration, $MgCl_2$ concentration, and/or the annealing temperature.

Genotyping for Targeted Modifications Via HDR. Timing • 2-3 d, 2-3 h Hands on

109| Applicants harvested DNA as described above using QuickExtract solution and normalized genomic DNA with TE to a final concentration of 100-200 ng/ul.

110| PCR Amplify the modified region. The PCR reaction is set up as follows:

| Component: | Amount (ul) | Final concentration |
|---|---|---|
| Herculase II PCR buffer, 5X | 10 | 1X |
| dNTP, 100 mM (25 mM each) | 1 | 1 mM |
| HDR Fwd primer (10 uM) | 1 | 0.2 uM |
| HDR Rev primer (10 uM) | 1 | 0.2 uM |
| Herculase II Fusion polymerase | 1 | |
| $MgCl_2$ (25 mM) | 2 | 1 mM |
| $ddH_2O$ | 33 | |
| Total | 49 | (for each reaction) |

111| Applicants added 100-200 ng of genomic DNA template from step 109 for each reaction and run the following program.

| Cycle number | Denature | Anneal | Extend |
|---|---|---|---|
| 1 | 95° C., 2 min | | |
| 2-31 | 95° C., 20 s | 60° C., 20 s | 72° C., 30-60 s per kb |
| 32 | | | 72° C., 3 min |

112| Applicants ran 5 ul of PCR product on a 0.8-1% gel to check for single-band product. Primers may need additional optimization by adjusting the template concentration, $MgCl_2$ concentration, and/or the annealing temperature.

113| Applicants purified the PCR reactions using the QIAQuick PCR purification kit.

114| In the HDR example, a HindIII restriction site is inserted into the EMX1 gene. These are detected by a restriction digest of the PCR amplicon:

| Component | Amount (ul) |
|---|---|
| Purified PCR amplicon (200-300 ng) | x |
| F.D. buffer, Green | 1 |
| HindIII | 0.5 |
| ddH2O | x |
| Total | 10 | i. The DNA is digested for 10 m at 37° C.:

ii. Applicants ran 10 ul of the digested product with loading dye on a 4-20% gradient polyacrylamide TBE gel until the xylene cyanol band had migrated to the bottom of the gel.

iii. Applicants stained the gel with 1× SYBR Gold dye while rocking for 15 m.

iv. The cleavage products are imaged and quantified as described above in the SURVEYOR assay section. HDR efficiency is estimated by the formula: $(b+c)/(a+b+c)$, where a is the integrated intensity for the undigested HDR PCR product, and b and c are the integrated intensities for the HindIII-cut fragments.

115| Alternatively, purified PCR amplicons from step 113 may be cloned and genotyped using Sanger sequencing or NGS.

Deep Sequencing and Off-Target Analysis • Timing 1-2 d

The online CRISPR target design tool generates candidate genomic off-target sites for each identified target site. Off-target analysis at these sites can be performed by SURVEYOR nuclease assay, Sanger sequencing, or next-generation deep sequencing. Given the likelihood of low or undetectable modification rates at many of these sites, Applicants recommend deep sequencing with the Illumina Miseq platform for high sensitivity and accuracy. Protocols will vary with sequencing platform; here, Applicants briefly describe a fusion PCR method for attaching sequencing adapters.

116| Design deep sequencing primers. Next-generation sequencing (NGS) primers are designed for shorter amplicons, typically in the 100-200 bp size range. Primers may be manually designed using NCBI Primer-Blast or generated with online CRISPR target design tools (website at genome-engineering.org/tools).

117| Harvest genomic DNA from Cas9-targeted cells. Normalize QuickExtract genomic DNA to 100-200 ng/ul with ddH2O.

118| Initial library preparation PCR. Using the NGS primers from step 116, prepare the initial library preparation PCR

| Component: | Amount (ul) | Final concentration |
|---|---|---|
| Herculase II PCR buffer, 5X | 10 | 1X |
| dNTP, 100 mM (25 mM each) | 1 | 1 mM |
| NGS Fwd primer (10 uM) | 1 | 0.2 uM |
| NGS Rev primer (10 uM) | 1 | 0.2 uM |
| Herculase II Fusion polymerase | 1 | |
| MgCl2 (25 mM) | 2 | 1 mM |
| ddH2O | 33 | |
| Total | 49 | (for each reaction) |

119| Add 100-200 ng of normalized genomic DNA template for each reaction.

120| Perform PCR reaction using the following cycling conditions, for no more than 20 amplification cycles:

| Cycle number | Denature | Anneal | Extend |
|---|---|---|---|
| 1 | 95° C., 2 min | | |
| 2-21 | 95° C., 20 s | 60° C., 20 s | 72° C., 15 s |
| 22 | | | 72° C., 3 min |

121| Run 2-5 ul of PCR product on a 1% gel to check for single-band product. As with all genomic DNA PCRs, NGS primers may require additional optimization by adjusting the template concentration, $MgCl_2$ concentration, and/or the annealing temperature.

122| Purify the PCR reactions using the QIAQuick PCR purification kit and normalize eluant to 20 ng/ul. Pause point: Purified PCR product may be stored at −20° C.

123| Nextera XT DNA Sample Preparation Kit. Following the manufacturer's protocol, generate Miseq sequencing-ready libraries with unique barcodes for each sample.

124| Analyze sequencing data. Off-target analysis may be performed through read alignment programs such as ClustalW, Geneious, or simple sequence analysis scripts.

Timing

Steps 1-2 Design and synthesis of sgRNA oligos and ssODNs: 1-5d, variable depending on supplier Steps 3-5 Construction of CRISPR plasmid or PCR expression cassette: 2 h to 3 d Steps 6-53 Transfection into cell lines: 3 (1 h hands-on time)

Steps 54-70 Optional derivation of clonal lines: 1-3 weeks, variable depending on cell type Steps 71-91 Functional validation of NHEJ via SURVEYOR: 5-6 h Steps 92-124 Genotyping via Sanger or next-gen deep sequencing: 2-3 d (3-4 h hands on time)

Figure 12A:
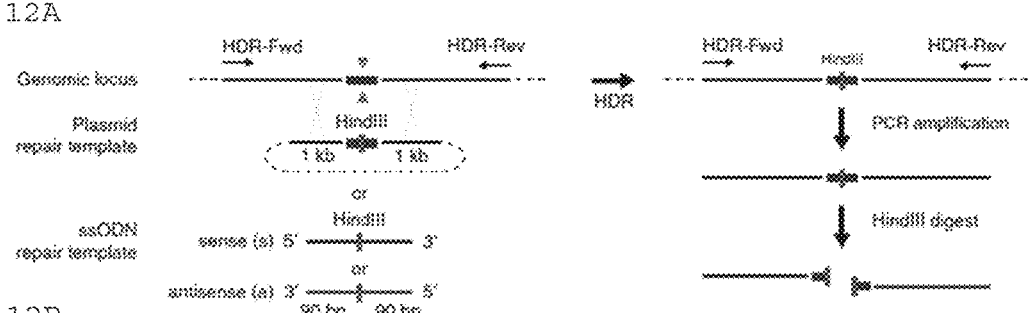
FIG. 12A-C shows anticipated results for HDR in HEK and HUES9 cells. (a) Either a targeting plasmid or an ssODN (sense or antisense) with homology arms can be used to edit the sequence at a target genomic locus cleaved by Cas9 (red triangle). To assay the efficiency of HDR, we introduced a HindIII site (red bar) into the target locus, which was PCR-amplified with primers that anneal outside of the region of homology. Digestion of the PCR product with HindIII reveals the occurrence of HDR events. (b) ssODNs, oriented in either the sense or the antisense (s or a) direction relative to the locus of interest, can be used in combination with Cas9 to achieve efficient HDR-mediated editing at the target locus. A minimal homology region of 40 bp, and preferably 90 bp, is recommended on either side of the modification (red bar). (c) Example of the effect of ssODNs on HDR in the EMX1 locus is shown using both wild-type Cas9 and Cas9 nickase (D10A). Each ssODN contains homology arms of 90 bp flanking a 12-bp insertion of two restriction sites.
Figure 12B:
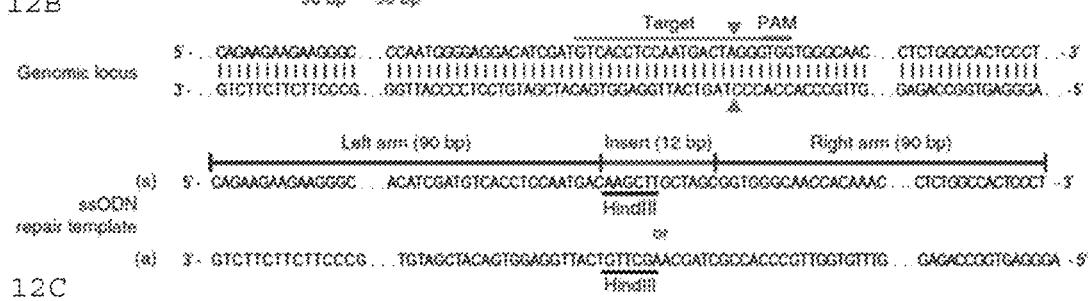
Figure 12C:
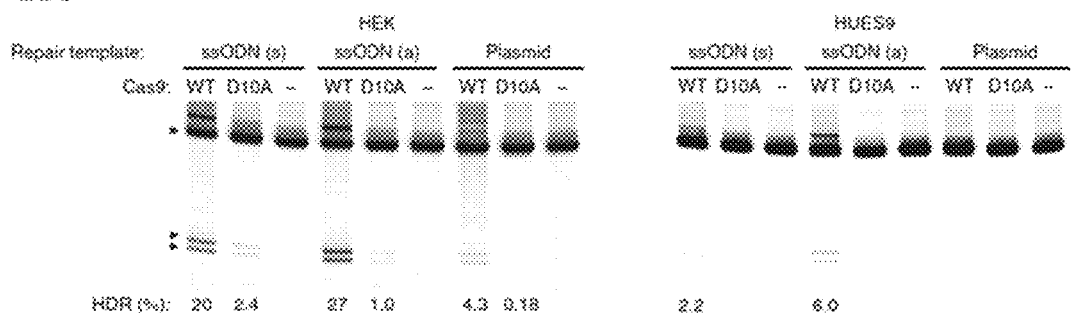

Addressing Situations Concerning Herein Examples chromosomal microdeletions at high efficiencies. Applicants used two sgRNAs to demonstrate simultaneous targeting of the human GRIN2B and DYRK1A loci at efficiencies of up to 68% in HEK293FT cells. Likewise, a pair of sgRNAs may be used to mediate microdeletions, such as excision of an exon, which can be genotyped by PCR on a clonal level. Note that the precise location of exon junctions can vary. Applicants also demonstrated the use of ssODNs and targeting vector to mediate HDR with both wildtype and nickase mutant of Cas9 in HEK 293FT and HUES9 cells (FIG. 12). Note that Applicants have not been able to detect HDR in HUES9 cells using the Cas9 nickase, which may be due to low efficiency or a potential difference in repair activities in HUES9 cells. Although these values are typical, there is some variability in the cleavage efficiency of a given sgRNA, and on rare occasions certain sgRNAs may not work for reasons yet unknown. Applicants recommend designing two sgRNAs for each locus, and testing their efficiencies in the intended cell type.

Example 26: NLSs

Cas9 Transcriptional Modulator: Applicants set out to turn the Cas9/gRNA CRISPR system into a generalized DNA binding system in which functions beyond DNA cleavage can be executed. For instance, by fusing functional domain(s) onto a catalytically inactive Cas9 Applicants have imparted novel functions, such as transcriptional activation/repression, methylation/demethylation, or chromatin modifications. To accomplish this goal Applicants made a catalytically inactive Cas9 mutant by changing two residues essential for nuclease activity, D10 and H840, to alanine. By mutating these two residues the nuclease activity of Cas9 is abolished while maintaining the ability to bind target DNA. The functional domains Applicants decided to focus on to test Applicants' hypothesis are the transcriptional activator VP64 and the transcriptional repressors SID and KRAB.

Cas9 Nuclear localization: Applicants hypothesized that the most effective Cas9 transcriptional modulator would be

| Situation | Solution |
|---|---|
| No amplification of sgRNA | Titrate U6-template concentration |
| SURVEYOR or HDR PCR dirty or no amplification | Titrate MgCl2; normalize and titrate template concentration; annealing temp gradient; redesign primers |
| Unequal amplification of alleles in microdeletion PCRs | Set up separate PCRs to detect wildtype and deletion alleles; Redesign primers with similar sized amplicons |
| Colonies on negative control plate | Increase BbsI; increase Golden Gate reaction cycle number, cut PX330 separately with Antarctic Phosphate treatment |
| No sgRNA sequences or wrong sequences | Screen additional colonies |
| Low lipofectamine transfection efficiency | Check cell health and density; titrate DNA; add GFP transfection control |
| Low nucleofection transfection efficiency | Check cell health and density; titrate DNA; suspend to single cell |
| Clumps or no cells after FACS | Filter cells before FACS; dissociate to single cells; resuspend in appropriate density |
| Clumps or no cells in serial dilution | Recount cells; dissociate to single cells and filter through strainer; check serial dilution |
| High SURVEYOR background on negative sample | Redesign primers to prime from different locations |
| Dirty SURVEYOR result on gel | Purify PCR product; reduce input DNA; reduce 42° C. incubation to 30 m |
| No SURVEYOR cleavage | Purify and normalize PCR product; re-anneal with TaqB buffer; Redesign sgRNAs; sequence verify Cas9 on px330 backbone |
| Samples do not sink in TBE acrylamide gel | Supplement with MgCl2 to a final concentration of 15 mM or add loading buffer containing glycerol |

Discussion

CRISPR-Cas may be easily multiplexed to facilitate simultaneous modification of several genes and mediate strongly localized to the nucleus where it would have its greatest influence on transcription. Moreover, any residual Cas9 in the cytoplasm could have unwanted effects. Applicants determined that wild-type Cas9 does not localize into the nucleus without including multiple nuclear localization signals (NLSs) (although a CRISPR system need not have one or more NLSs but advantageously has at least one or more NLS(s)). Because multiple NLS sequences were required it was reasoned that it is difficult to get Cas9 into the nucleus and any additional domain that is fused to Cas9 could disrupt the nuclear localization. Therefore, Applicants made four Cas9-VP64-GFP fusion constructs with different NLS sequences (pXRP02-pLenti2-EF1a-NLS-hSpCsn1 (10A,840A)-NLS-VP64-EGFP, pXRP04-pLenti2-EF1a-NLS-hSpCsn1(10A,840A)-NLS-VP64-2A-EGFP-NLS, pXRP06-pLenti2-EF1a-NLS-EGFP-VP64-NLS-hSpCsn1 (10A,840A)-NLS, pXRP08-pLenti2-EF1a-NLS-VP64-NLS-hSpCsn1(10A,840A)-NLS-VP64-EGFP-NLS). These constructs were cloned into a lenti backbone under the expression of the human EF1a promoter. The WPRE element was also added for more robust protein expression. Each construct was transfected into HEK 293FT cells using Lipofectame 2000 and imaged 24 hours post-transfection. The best nuclear localization is obtained when the fusion proteins have NLS sequences on both the N- and C-term of the fusion protein. The highest observed nuclear localization occurred in the construct with four NLS elements.

To more robustly understand the influence of NLS elements on Cas9 Applicants made 16 Cas9-GFP fusions by adding the same alpha importin NLS sequence on either the N- or C-term looking at zero to three tandem repeats. Each construct was transfected into HEK 293FT cells using Lipofectame 2000 and imaged 24 hours post-transfection. Notably, the number of NLS elements does not directly correlate with the extent of nuclear localization. Adding an NLS on the C-term has a greater influence on nuclear localization than adding on the N-term.

Cas9 Transcriptional Activator: Applicants functionally tested the Cas9-VP64 protein by targeting the Sox2 locus and quantifying transcriptional activation by RT-qPCR. Eight DNA target sites were chosen to span the promoter of Sox2. Each construct was transfected into HEK 293FT cells using Lipofectame 2000 and 72 hours post-transfection total RNA was extracted from the cells. 1 ug of RNA was reverse transcribed into cDNA (qScript Supermix) in a 40 ul reaction. 2 ul of reaction product was added into a single 20 ul TaqMan assay qPCR reaction. Each experiment was performed in biological and technical triplicates. No RT control and no template control reactions showed no amplification. Constructs that do not show strong nuclear localization, pXRP02 and pXRP04, result in no activation. For the construct that did show strong nuclear localization, pXRP08, moderate activation was observed. Statistically significant activation was observed in the case of guide RNAs Sox2.4 and Sox2.5.

Example 27: In Vivo Mouse Data

Material and Reagents
Herculase II fusion polymerase (Agilent Technologies, cat. no. 600679)
10× NEBuffer 4 (NEB, cat. No. B7004S)
BsaI HF (NEB, cat. No. R3535S)
T7 DNA ligase (Enzymatics, cat. no. L602L)
Fast Digest buffer, 10× (ThermoScientific, cat. No. B64)
FastDigest NotI (ThermoScientific, cat. No. FD0594)
FastAP Alkaline Phosphatase (ThermoScientific, cat. No. EF0651)
Lipofectamine2000 (Life Technologies, cat. No. 11668-019)
Trypsin (Life Technologies, cat. No. 15400054)
Forceps #4 (Sigma, cat. No. Z168777-IEA)
Forceps #5 (Sigma, cat. No. F6521-IEA)
10× Hank's Balanced Salt Solution (Sigma, cat. No. H4641-500ML)
Penicillin/Streptomycin solution (Life Technologies, cat. No. P4333)
Neurobasal (Life Technologies, cat. No. 21103049)
B27 Supplement (Life Technologies, cat. No. 17504044)
L-glutamine (Life Technologies, cat. No. 25030081)
Glutamate (Sigma, cat. No. RES5063G-A7)
β-mercaptoethanol (Sigma, cat. No. M6250-100ML)
HA rabbit antibody (Cell Signaling, cat. No. 3724S)
LIVE/DEAD® Cell Imaging Kit (Life Technologies, cat. No. R37601)
30G World Precision Instrument syringe (World Precision Instruments, cat. No. NANOFIL)
Stereotaxic apparatus (Kopf Instruments)
UltraMicroPump3 (World Precision Instruments, cat. No. UMP3-4)
Sucrose (Sigma, cat. No. S7903)
Calcium chloride (Sigma, cat. No. C1016)
Magnesium acetate (Sigma, cat. No. M0631)
Tris-HCl (Sigma, cat. no T5941)
EDTA (Sigma, cat. No. E6758)
NP-40 (Sigma, cat. No. NP40)
Phenylmethanesulfonyl fluoride (Sigma, cat. No. 78830)
Magnesium chloride (Sigma, cat. No. M8266)
Potassium chloride (Sigma, cat. No. P9333)
β-glycerophosphate (Sigma, cat. No. G9422)
Glycerol (Sigma, cat. No. G9012)
Vybrant® DyeCycle™ Ruby Stain (Life technologies, cat. No. S4942)
FACS Aria Flu-act-cell sorter (Koch Institute of MIT, Cambridge US)
DNAeasy Blood & Tissue Kit (Qiagen, cat. No. 69504)

Procedure

Constructing gRNA Multiplexes for Using In Vivo in the Brain

Figure 15:
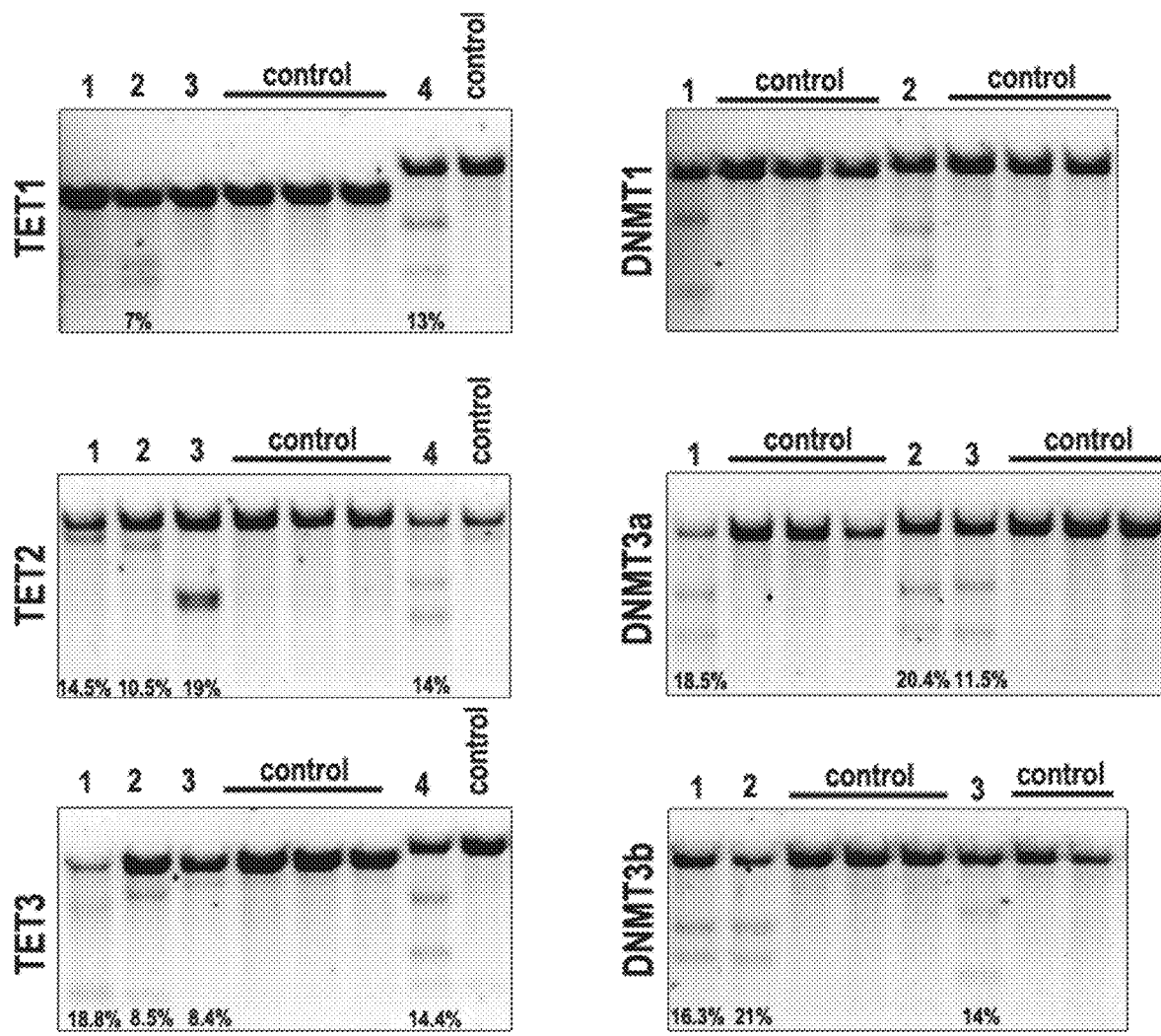
FIG. 15 shows a screen for efficient SpCas9 mediated targeting of Tet1-3 and Dnmt1, 3a and 3b gene loci. Surveyor assay on DNA from transfected N2A cells demonstrates efficient DNA cleavage by using different gRNAs.
Figure 16:
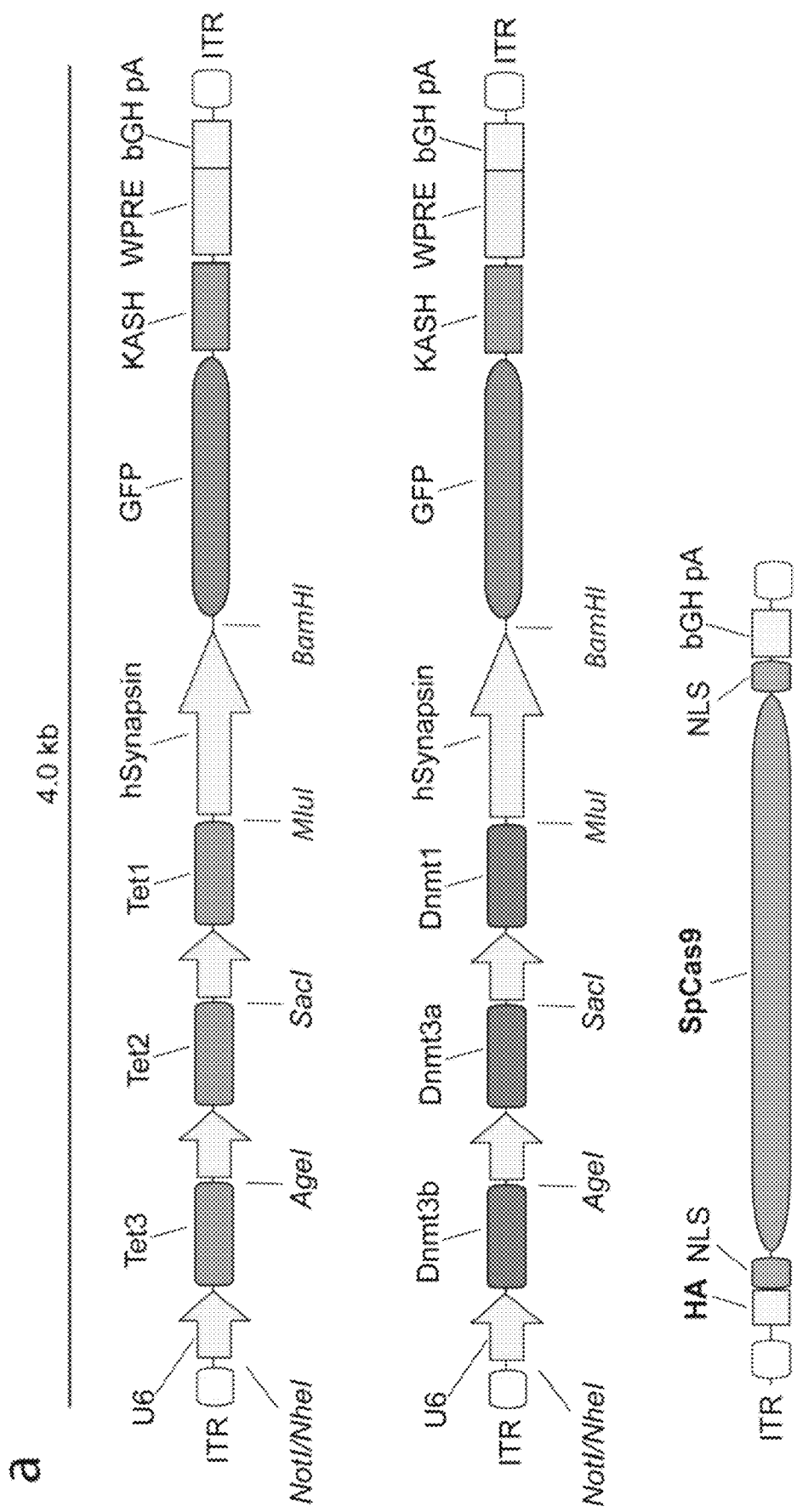
FIG. 16 shows a strategy of multiplex genome targeting using a 2-vector system in an AAV1/2 delivery system. Tet1-3 and Dnmt1, 3a and 3b gRNA under the control of the U6 promoter. GFP-KASH under the control of the human synapsin promoter. Restriction sides shows simple gRNA replacement strategy by subcloning. HA-tagged SpCas9 flanked by two nuclear localization signals (NLS) is shown. Both vectors are delivered into the brain by AAV1/2 virus in a 1:1 ratio.

Applicants designed and PCR amplified single gRNAs targeting mouse TET and DNMT family members (as described herein) Targeting efficiency was assessed in N2a cell line (FIG. 15). To obtain simultaneous modification of several genes in vivo, efficient gRNA was multiplexed in AAV-packaging vector (FIG. 16). To facilitate further analysis of system efficiency applicants added to the system expression cassette consistent of GFP-KASH domain fusion protein under control of human Synapsin I promoter (FIG. 16). This modification allows for further analysis of system efficiency in neuronal population (more detail procedure in section Sorting nuclei and in vivo results).

All 4 parts of the system were PCR amplified using Herculase II Fusion polymerase using following primers:

1st U6 Fw:
(SEQ ID NO: 189)
gagggtctcgtccttgcggccgcgctagcgagggcctatttcccatgat
tc 1st gRNA Rv:
(SEQ ID NO: 190)
ctcggtctcggtAAAAAAgcaccgactcggtgccactttttcaagttgat aacggactagccttattttaacttgctaTTTCtagctctaaaacNNNNN

NNNNNNNNNNNNNNNNGGTGTTTCGTCCTTTCCAC

-continued

2nd U6 Fw:
(SEQ ID NO: 191)
gagggtctcTTTaccggtgagggcctatttcccatgattcc

2nd gRNA Rv:
(SEQ ID NO: 192)
ctcggtctcctcAAAAAgcaccgactcggtgccactttttcaagttgat aacggactagc cttattttaacttgctaTTTCtagctctaaaacNNNN

NNNNNNNNNNNNNNNNNGGTGTTTCGTCCTTTCCAC

3rd U6 Fw:
(SEQ ID NO: 193)
gagggtctcTTTgagctcgagggcctatttcccatgattc

3rd gRNA Rv:
(SEQ ID NO: 194)
ctcggtctcgcgtAAAAAgcaccgactcggtgccactttttcaagttga taacggactag ccttattttaacttgctaTTTCtagctctaaaacNNNN

NNNNNNNNNNNNNNNNNGGTGTTTCGTCCTTTCCA hSyn_GFP-kash Fw:
(SEQ ID NO: 195)
gagggtctcTTacgcgtgtgtctagac hSyn_GFP-kash Rv:
(SEQ ID NO: 196)
ctcggtctcAaggaCAGGGAAGGGAGCAGTGGTTCACGCCTGTAATCCCA

GCAATTTGGGA GGCCAAGGTGGGTAGATCACCTGAGATTAGGAGTTGC (NNNNNNNNNNNNNNNNNNNNNN is a reverse compliment targeted genomic sequence)

Applicants used Golden Gate strategy to assemble all parts (1:1 molecular ratio) of the system in a single step reaction:

| 1st U6_gRNA | 18 ng |
| 2nd U6_gRNA | 18 ng |
| 3rd U6_gRNA | 18 ng |
| Syn_GFP-kash | 100 ng |
| 10X NEBuffer 4 | 1.0 μl |
| 10x BSA | 1.0 μl |
| 10 mM ATP | 1.0 μl |
| BsaI HF | 0.75 μl |
| T7 ligase | 0.25 μl |
| ddH$_2$O | 10 μl |

| Cycle number | Condition |
| --- | --- |
| 1-50 | 37° C. for 5 m, 21° C. for 5 m |

Golden Gate reaction product was PCR amplified using Herculase II fusion polymerase and following primers:

Fw
(SEQ ID NO: 197)
5' cctgtccttgcggccgcgctagcgagggcc

Rv
(SEQ ID NO: 198)
5' cacgcggccgcaaggacagggaagggagcag

PCR product was cloned into AAV backbone, between ITR sequences using NotI restriction sites:

PCR Product Digestion:

| Fast Digest buffer, 10X | 3 μl |
| FastDigest NotI | 1 μl |
| DNA | 1 μg |
| ddH$_2$O | up to 30 μl |

AAV Backbone Digestion:

| Fast Digest buffer, 10X | 3 μl |
| FastDigest NotI | 1 μl |
| FastAP Alkaline Phosphatase | 1 μl |
| AAV backbone | 1 μg |
| ddH$_2$O | up to 30 μl |

After 20 min incubation in 37° C. samples were purified using QIAQuick PCR purification kit. Standardized samples were ligated at a 1:3 vector:insert ratio as follows:

| Digested pUC19 | 50 ng |
| Digested insert | 1:3 vector:insert molar ratio |
| T7 ligase | 1 μl |
| 2X Rapid Ligation Buffer | 5 μl |
| ddH$_2$O | up to 10 μl |

After transformation of bacteria with ligation reaction product, applicants confirmed obtained clones with Sanger sequencing.

Figure 17:
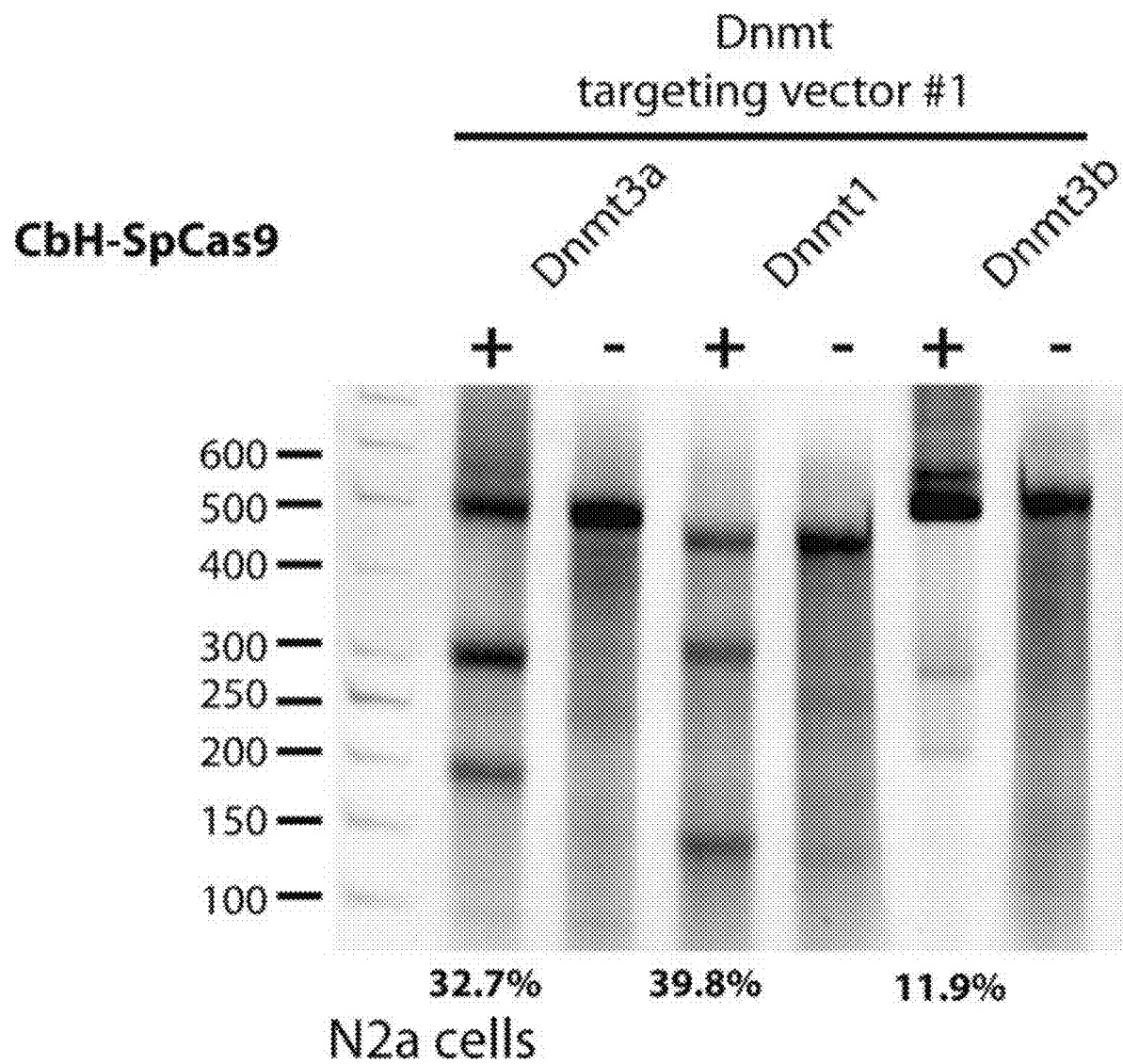
FIG. 17 shows verification of multiplex DNMT targeting vector #1 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.
Figure 18:
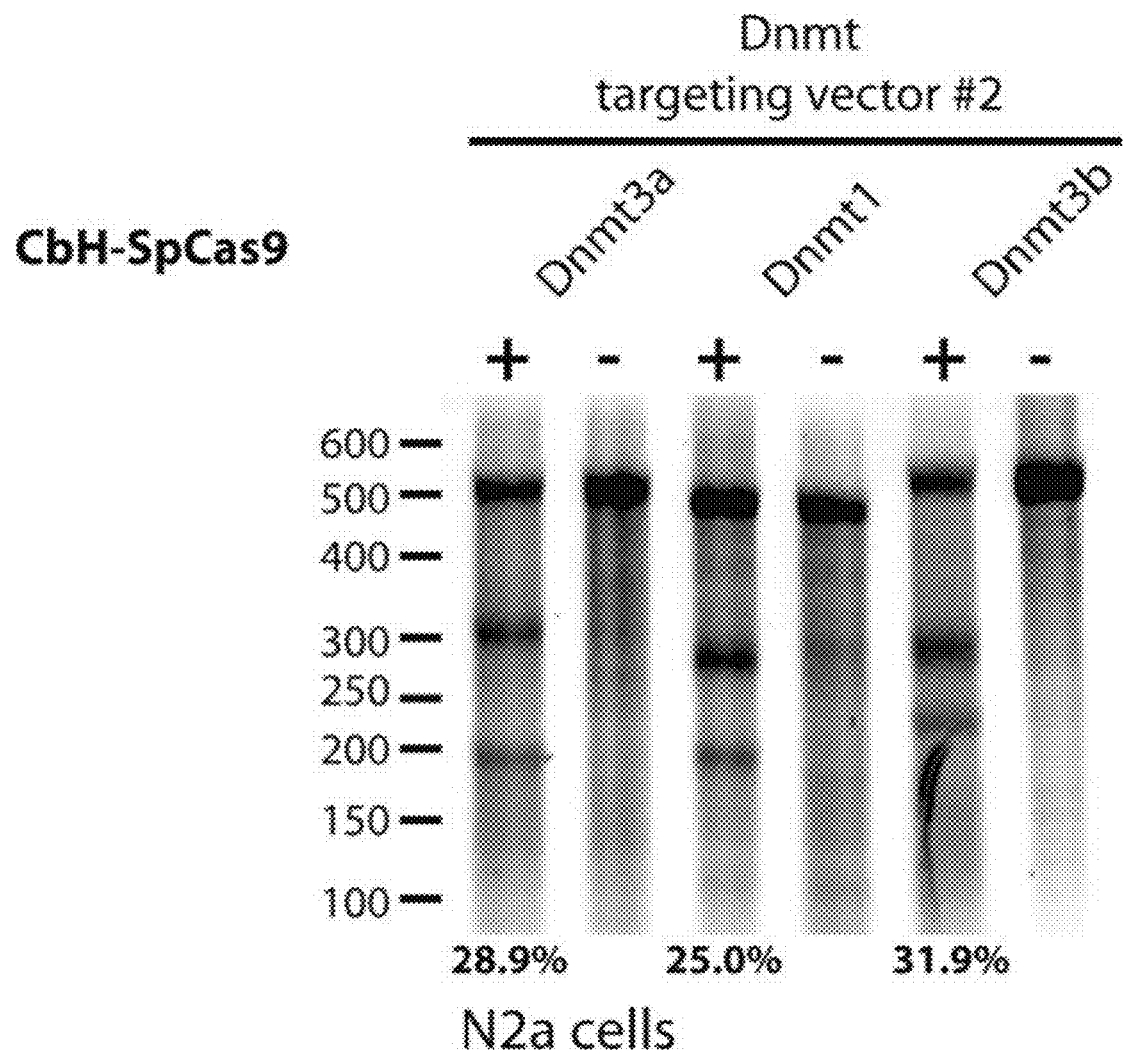
FIG. 18 shows verification of multiplex DNMT targeting vector #2 functionality using Surveyor assay. N2A cells were co-transfected with the DNMT targeting vector #1 (+) and the SpCas9 encoding vector for testing SpCas9 mediated cleavage of DNMTs genes family loci. gRNA only (−) is negative control. Cells were harvested for DNA purification and downstream processing 48 h after transfection.

Positive DNA clones were tested in N2a cells after co-transfection with Cas9 construct (FIGS. 17 and 18).

Design of New Cas9 Constructs for AAV Delivery

Figure 19:
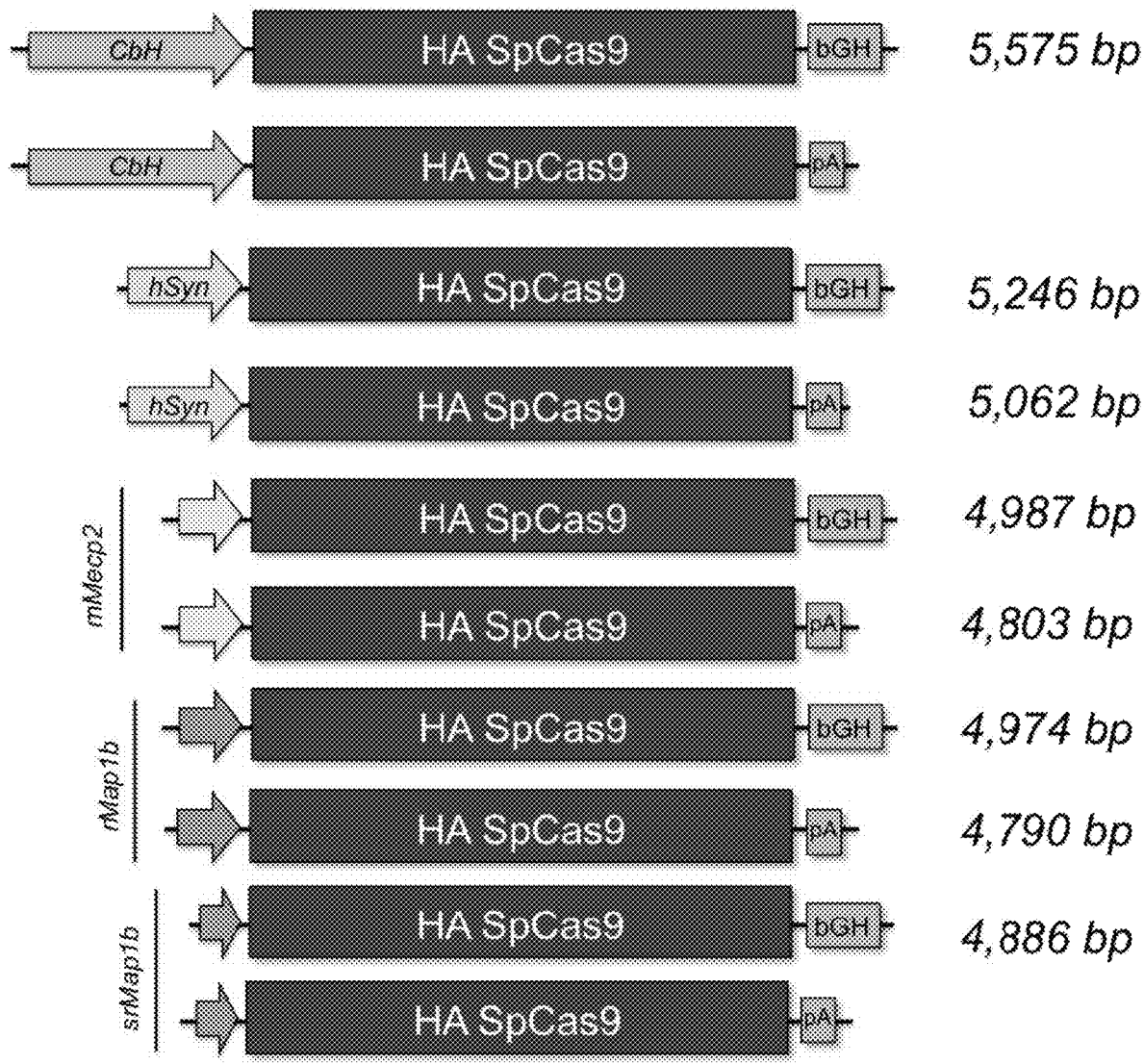
FIG. 19 shows schematic overview of short promoters and short polyA versions used for HA-SpCas9 expression in vivo. Sizes of the encoding region from L-ITR to R-ITR are shown on the right.
Figure 20:
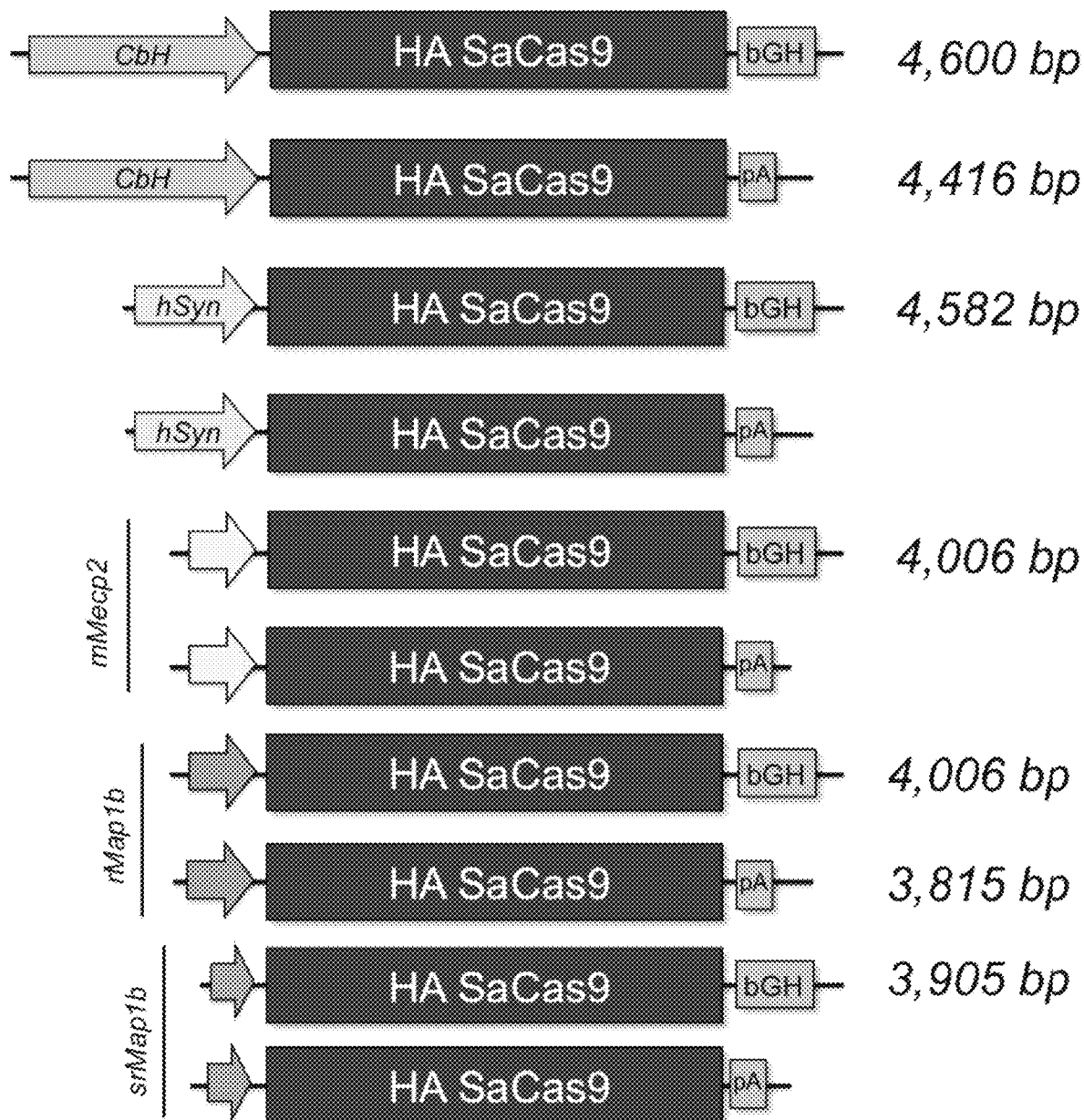
FIG. 20 shows schematic overview of short promoters and short polyA versions used for HA-SaCas9 expression in vivo. Sizes of the encoding region from L-ITR to R-ITR are shown on the right.
Figure 21:
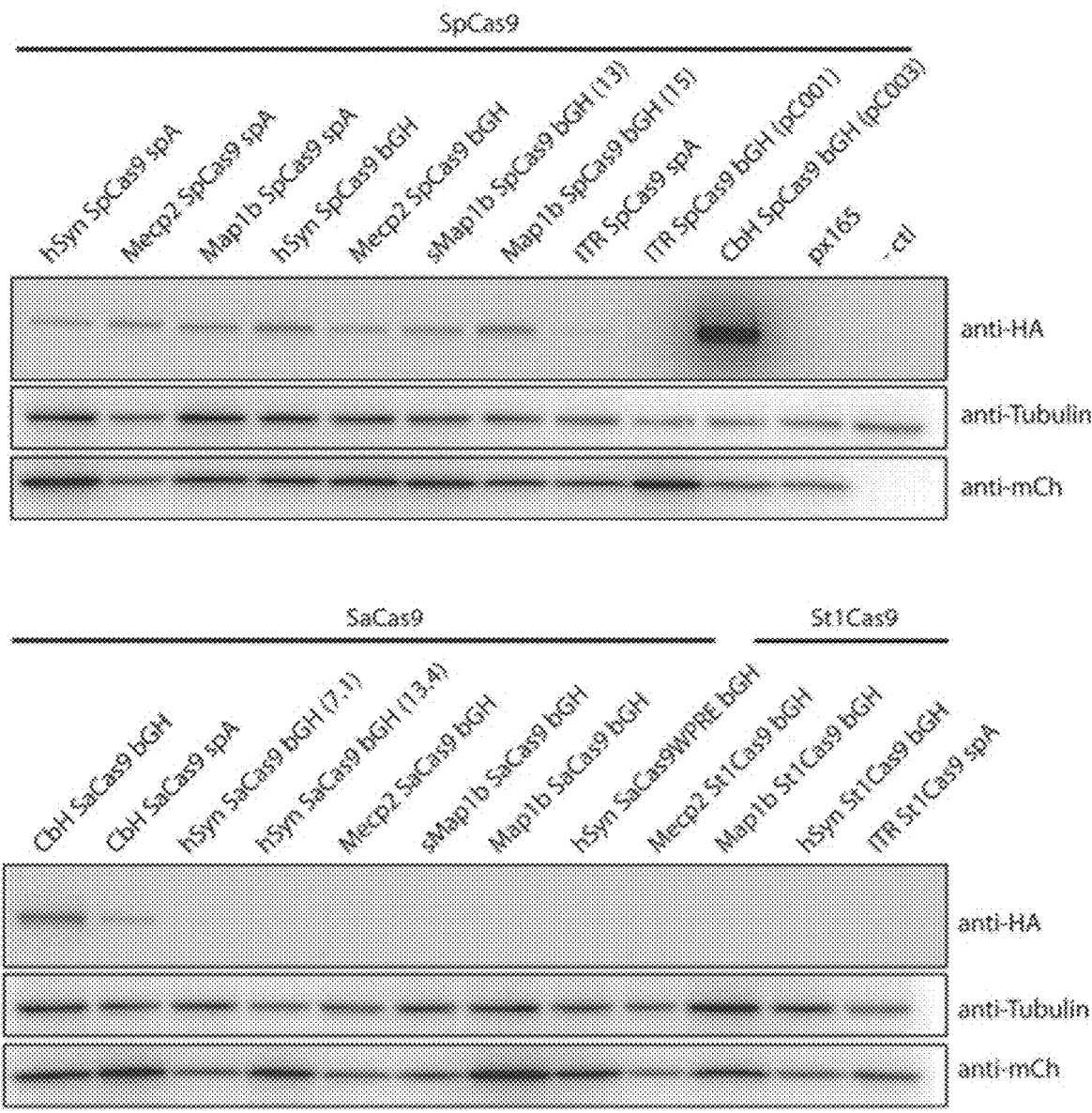
FIG. 21 shows expression of SpCas9 and SaCas9 in N2A cells. Representative Western blot of HA-tagged SpCas9 and SaCas9 versions under the control of different short promoters and with or short polyA (spA) sequences. Tubulin is loading control. mCherry (mCh) is a transfection control. Cells were harvested and further processed for Western blotting 48 h after transfection.
Figure 22:
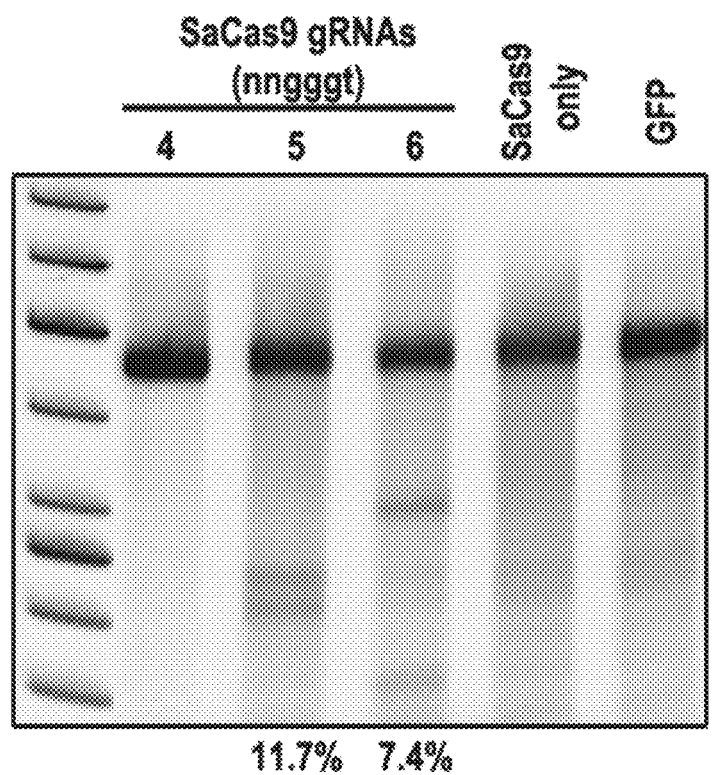
FIG. 22 shows screen for efficient SaCas9 mediated targeting of Tet3 gene locus. Surveyor assay on DNA from transfected N2A cells demonstrates efficient DNA cleavage by using different gRNAs with NNGGGT PUM sequence. GFP transfected cells and cells expressing only SaCas9 are controls.
Figure 23:
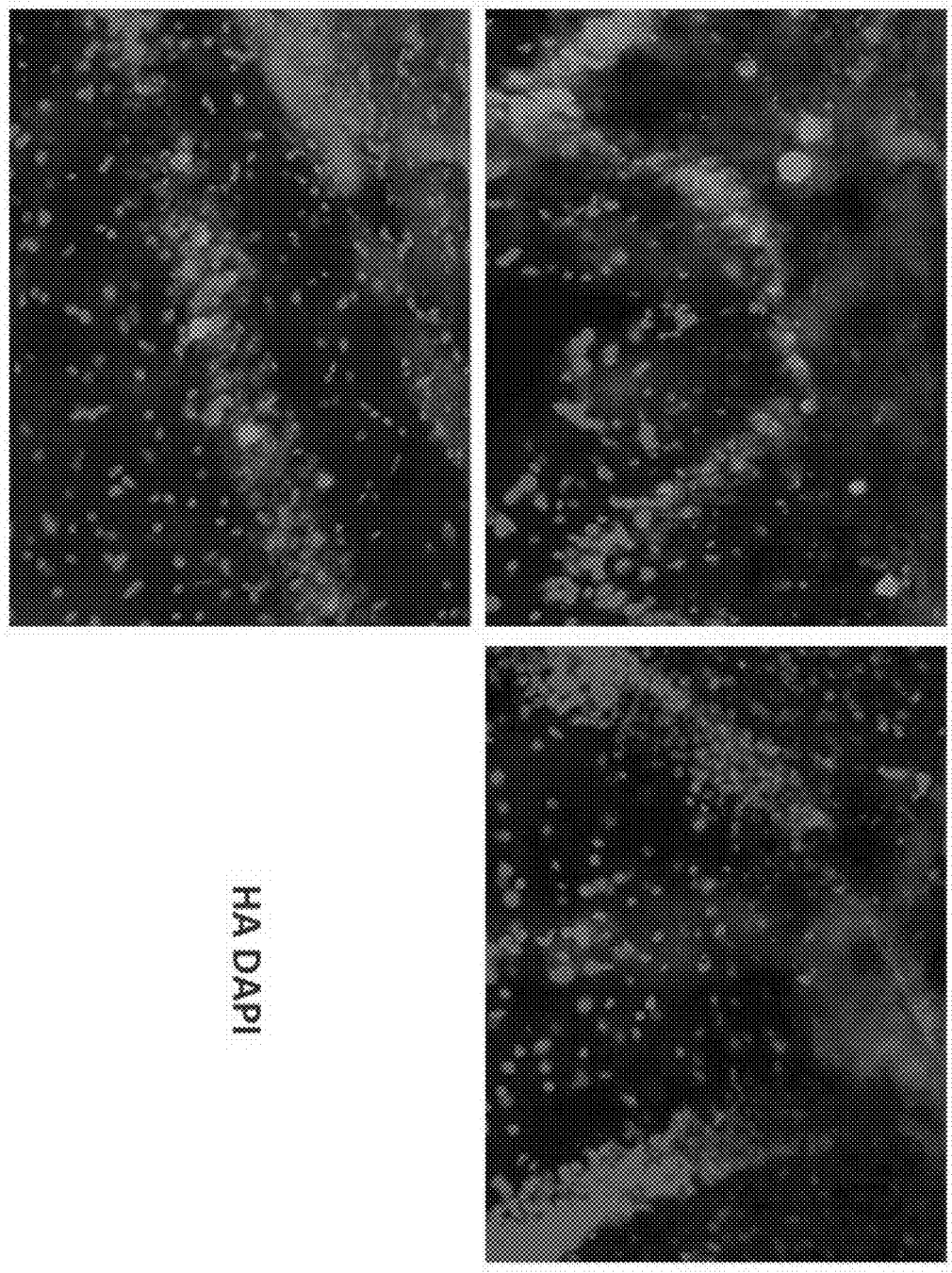
FIG. 23 shows expression of HA-SaCas9 in the mouse brain. Animals were injected into dentate gyri with virus driving expression of HA-SaCas9 under the control of human Synapsin promoter. Animals were sacrificed 2 weeks after surgery. HA tag was detected using rabbit monoclonal antibody C29F4 (Cell Signaling). Cell nuclei stained in blue with DAPI stain.

AAV delivery system despite its unique features has packing limitation—to successfully deliver expressing cassette in vivo it has to be in size <then 4.7 kb. To decrease the size of SpCas9 expressing cassette and facilitate delivery applicants tested several alteration: different promoters, shorter polyA signal and finally a smaller version of Cas9 from *Staphylococcus aureus* (SaCas9) (FIGS. 19 and 20). All tested promoters were previously tested and published to be active in neurons, including mouse Mecp2 (Gray et al., 2011), rat Map1b and truncated rat Map1b (Liu and Fischer, 1996). Alternative synthetic polyA sequence was previously shown to be functional as well (Levitt et al., 1989; Gray et al., 2011). All cloned constructs were expressed in N2a cells after transfection with Lipofectamine 2000, and tested with Western blotting method (FIG. 21).

Testing AAV Multiplex System in Primary Neurons

To confirm functionality of developed system in neurons, Applicants use primary neuronal cultures in vitro. Mouse cortical neurons was prepared according to the protocol published previously by Banker and Goslin (Banker and Goslin, 1988).

Neuronal cells are obtained from embryonic day 16. Embryos are extracted from the euthanized pregnant female and decapitated, and the heads are placed in ice-cold HBSS. The brains are then extracted from the skulls with forceps (#4 and #5) and transferred to another change of ice-cold HBSS. Further steps are performed with the aid of a stereoscopic microscope in a Petri dish filled with ice-cold HBSS and #5 forceps. The hemispheres are separated from each other and the brainstem and cleared of meninges. The hippocampi are then very carefully dissected and placed in a 15 ml conical tube filled with ice-cold HBSS. Cortices that remain after hippocampal dissection can be used for further cell isolation using an analogous protocol after removing the brain steam residuals and olfactory bulbs. Isolated hippocampi are washed three times with 10 ml ice-cold HBSS and dissociated by 15 min incubation with trypsin in HBSS (4 ml HBSS with the addition of 10 µl 2.5% trypsin per hippocampus) at 37° C. After trypsinization, the hippocampi are very carefully washed three times to remove any traces of trypsin with HBSS preheated to 37° C. and dissociated in warm HBSS. Applicants usually dissociate cells obtained from 10-12 embryos in 1 ml HBSS using 1 ml pipette tips and dilute dissociated cells up to 4 ml. Cells are plated at a density of 250 cells/mm2 and cultured at 37° C. and 5% CO2 for up to 3 week HBSS
435 ml H2O
50 ml 10× Hank's Balanced Salt Solution
16.5 ml 0.3M HEPES pH 7.3
5 ml penicillin-streptomycin solution
Filter (0.2 µm) and store 4° C.
Neuron Plating Medium (100 ml)
97 ml Neurobasal
2 ml B27 Supplement
1 ml penicillin-streptomycin solution
250 µl glutamine
125 µl glutamate Neurons are transduced with concentrated AAV1/2 virus or AAV1 virus from filtered medium of HEK293FT cells, between 4-7 days in culture and keep for at least one week in culture after transduction to allow for delivered gene expression.

AAV-Driven Expression of the System

Applicants confirmed expression of SpCas9 and SaCas9 in neuronal cultures after AAV delivery using Western blot method (FIG. 24). One week after transduction neurons were collected in NuPage SDS loading buffer with β-mercaptoethanol to denaturate proteins in 95° C. for 5 min. Samples were separated on SDS PAGE gel and transferred on PVDF membrane for WB protein detection. Cas9 proteins were detected with HA antibody.

Figure 32:
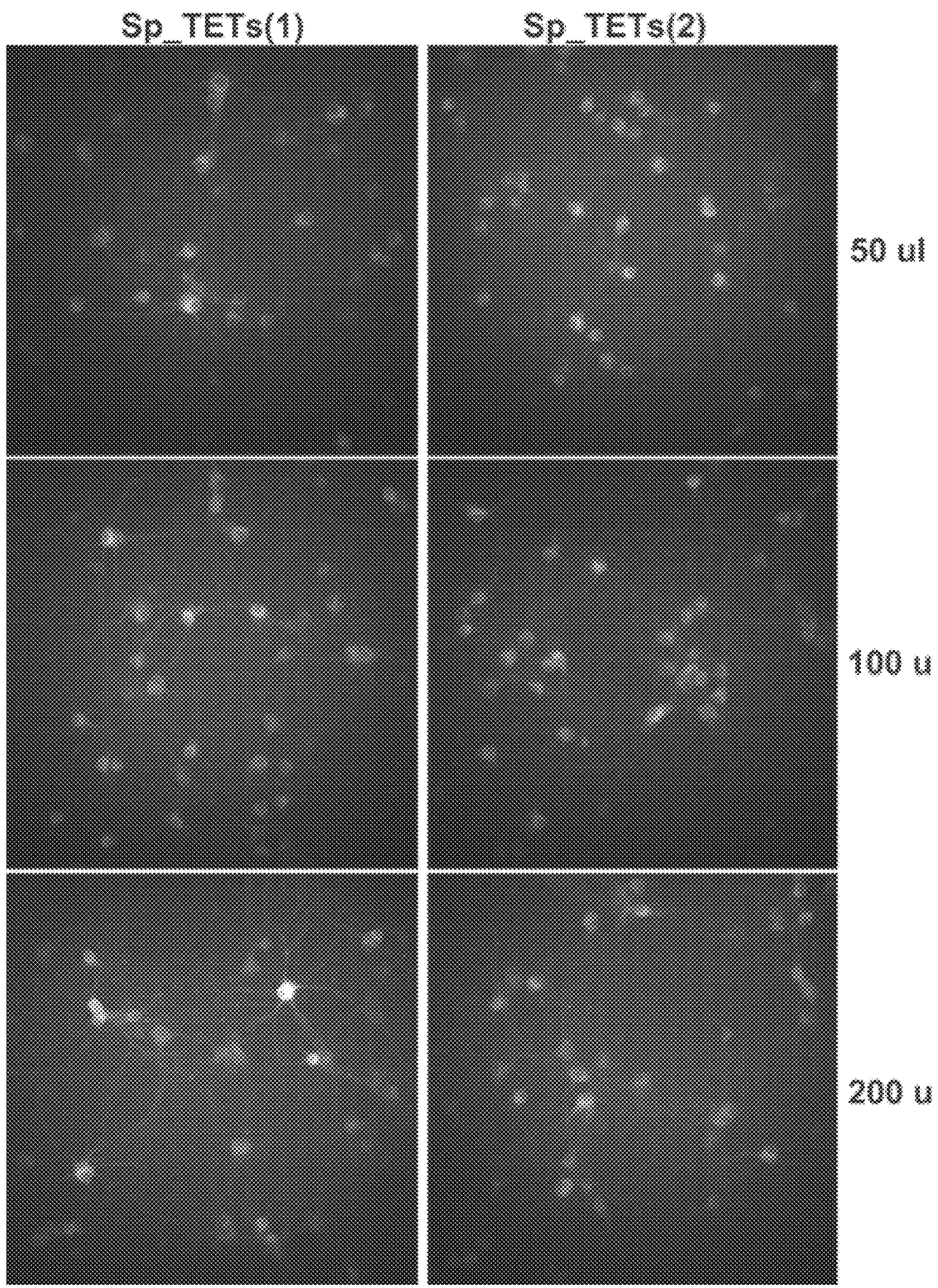
FIG. 32 shows GFP-KASH expression in cortical neurons in culture. Neurons were transduced with AAV1 virus carrying gRNA multiplex constructs targeting TET genes loci. The strongest signal localize around cells nuclei due to KASH domain localization.

Expression of Syn-GFP-kash from gRNA multiplex AAV was confirmed with fluorescent microscopy (FIG. 32).

Toxicity

Figure 25:
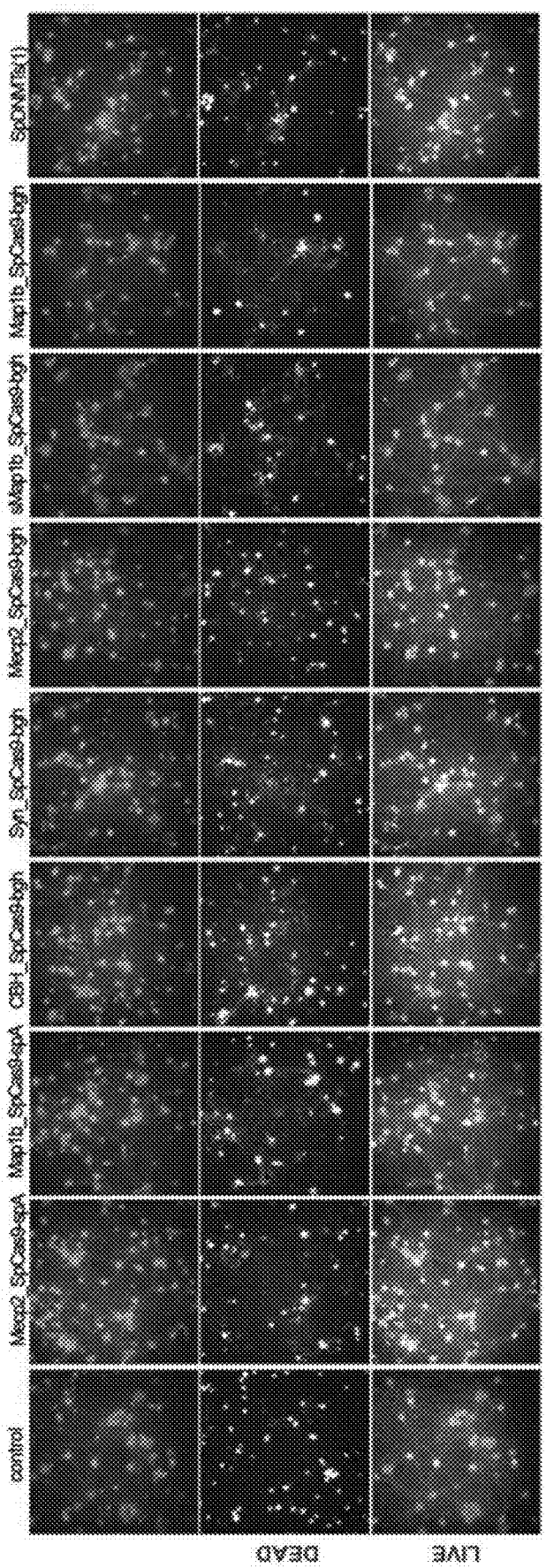
FIG. 25 shows LIVE/DEAD stain of primary cortical neurons 7 days after transduction with AAV1 particles carrying SpCas9 with different promoters and multiplex gRNAs constructs (example shown on the last panel for DNMTs). Neurons after AAV transduction were compared with control untransduced neurons. Red nuclei indicate permeabilized, dead cells (second line of panels). Live cells are marked in green color (third line of panels).
Figure 26:
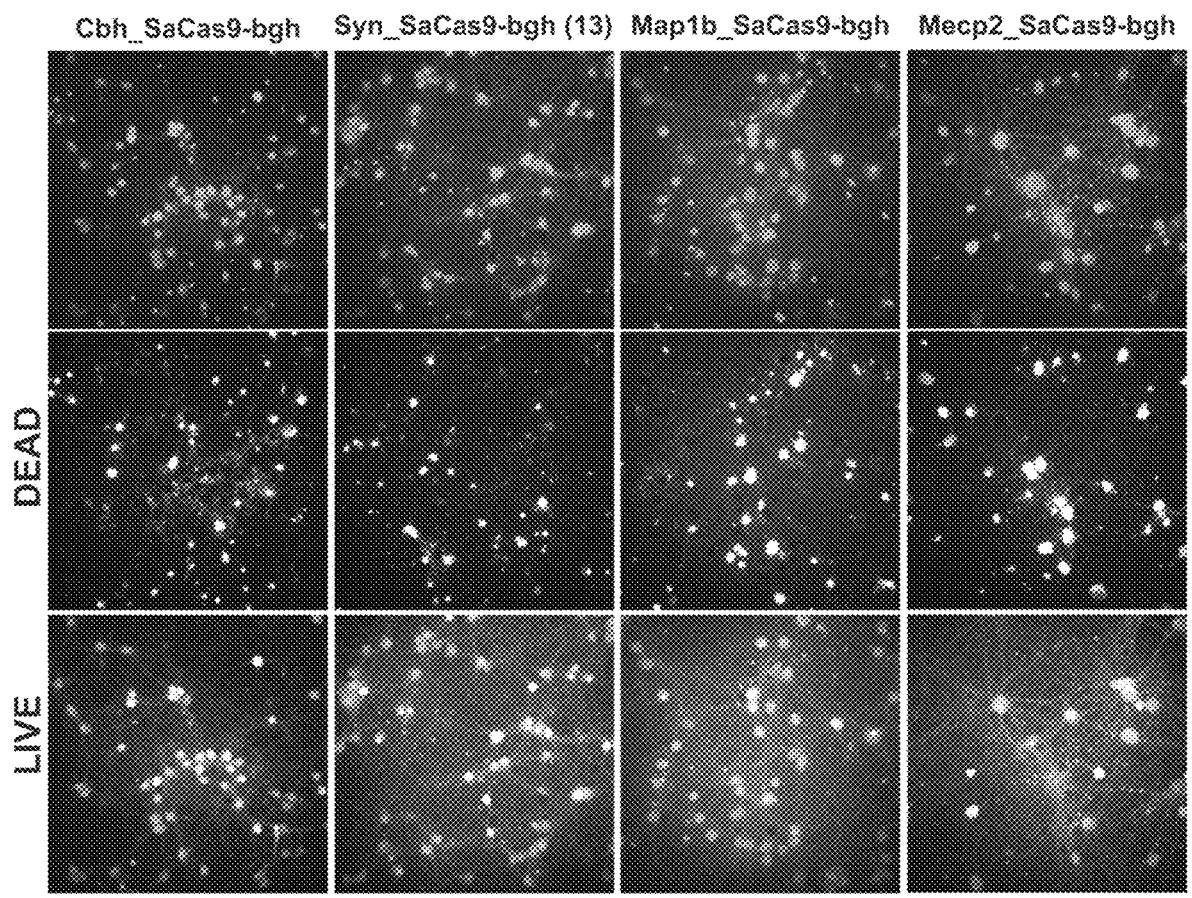
FIG. 26 shows LIVE/DEAD stain of primary cortical neurons 7 days after transduction with AAV1 particles carrying SaCas9 with different promoters. Red nuclei indicate permeabilized, dead cells (second line of panels). Live cells are marked in green color (third line of panels).
Figure 27:
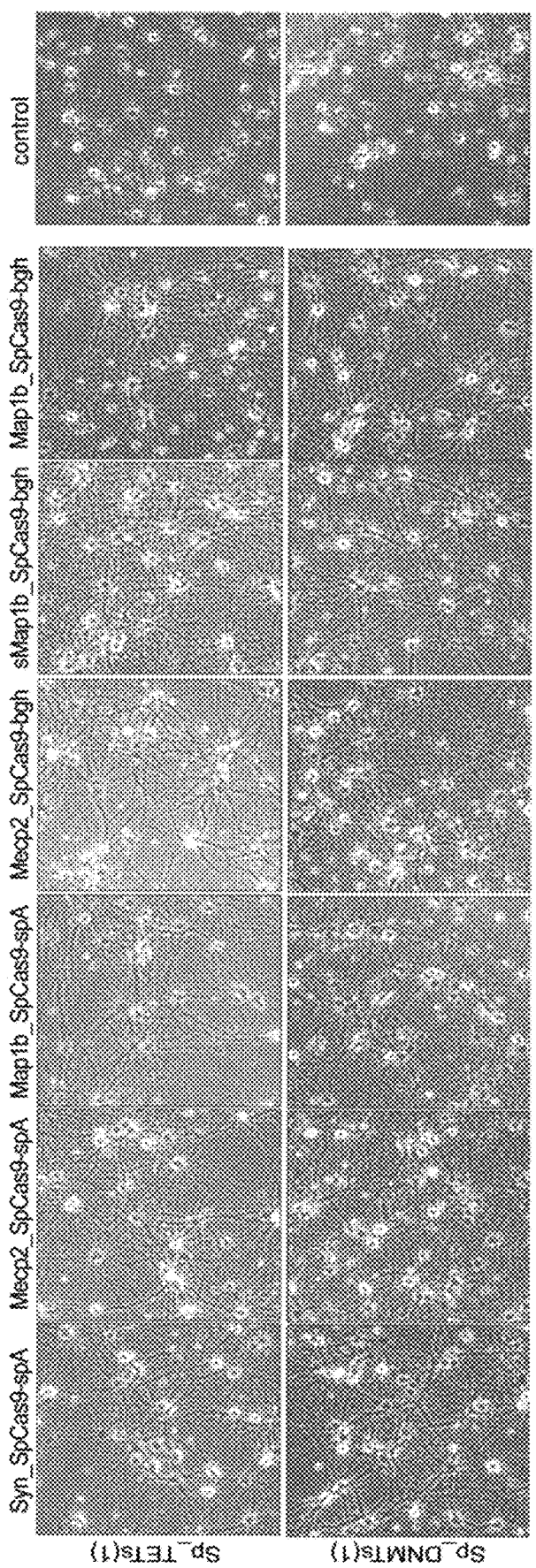
FIG. 27 shows comparison of morphology of neurons after transduction with AAV1 virus carrying SpCas9 and gRNA multiplexes for TETs and DNMTs genes loci. Neurons without transduction are shown as a control.
Figure 28:
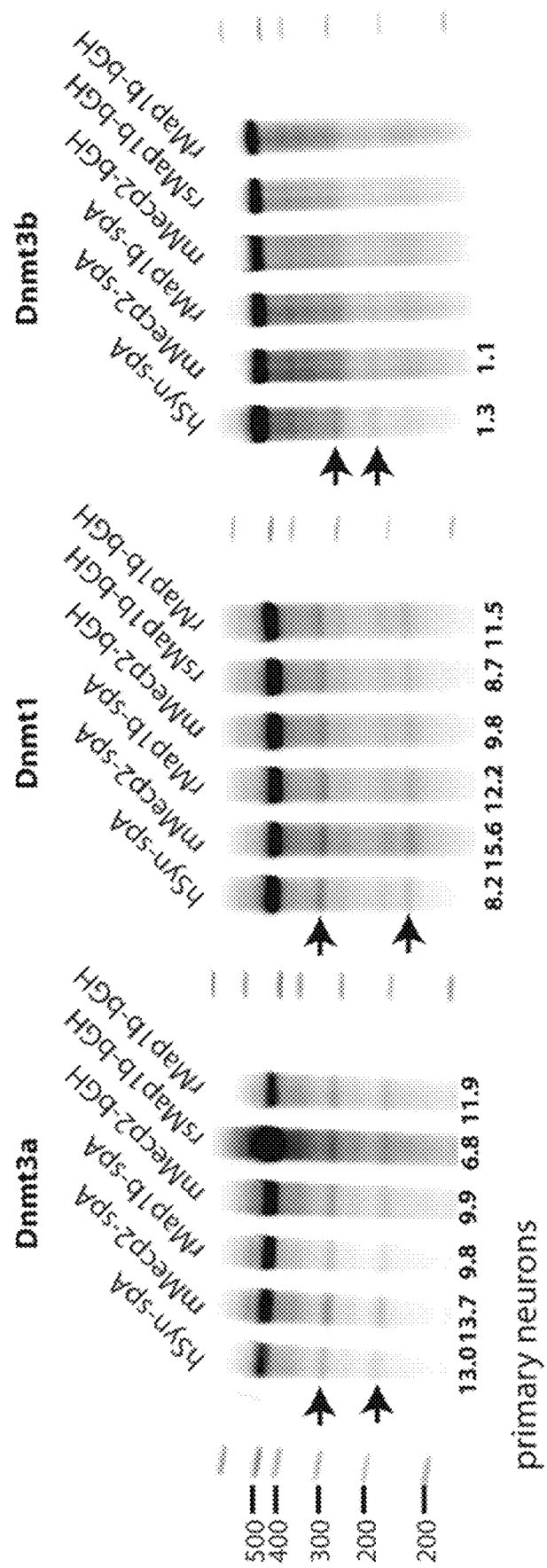
FIG. 28 shows verification of multiplex DNMT targeting vector #1 functionality using Surveyor assay in primary cortical neurons. Cells were co-transduced with the DNMT targeting vector #1 and the SpCas9 viruses with different promoters for testing SpCas9 mediated cleavage of DNMTs genes family loci.
Figure 29:
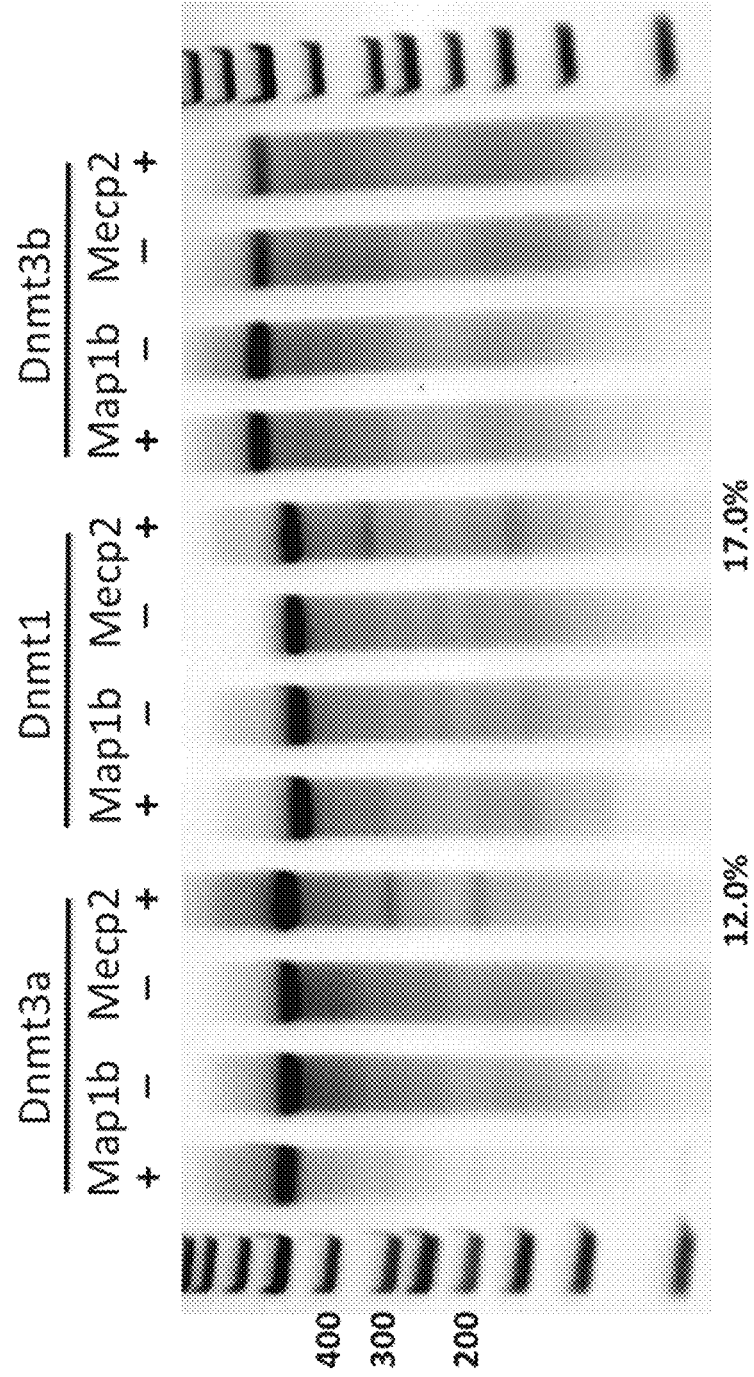
FIG. 29 shows in vivo efficiency of SpCas9 cleavage in the brain. Mice were injected with AAV1/2 virus carrying gRNA multiplex targeting DNMT family genes loci together with SpCas9 viruses under control of 2 different promoters: mouse Mecp2 and rat Map1b. Two weeks after injection brain tissue was extracted and nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.
Figure 30:
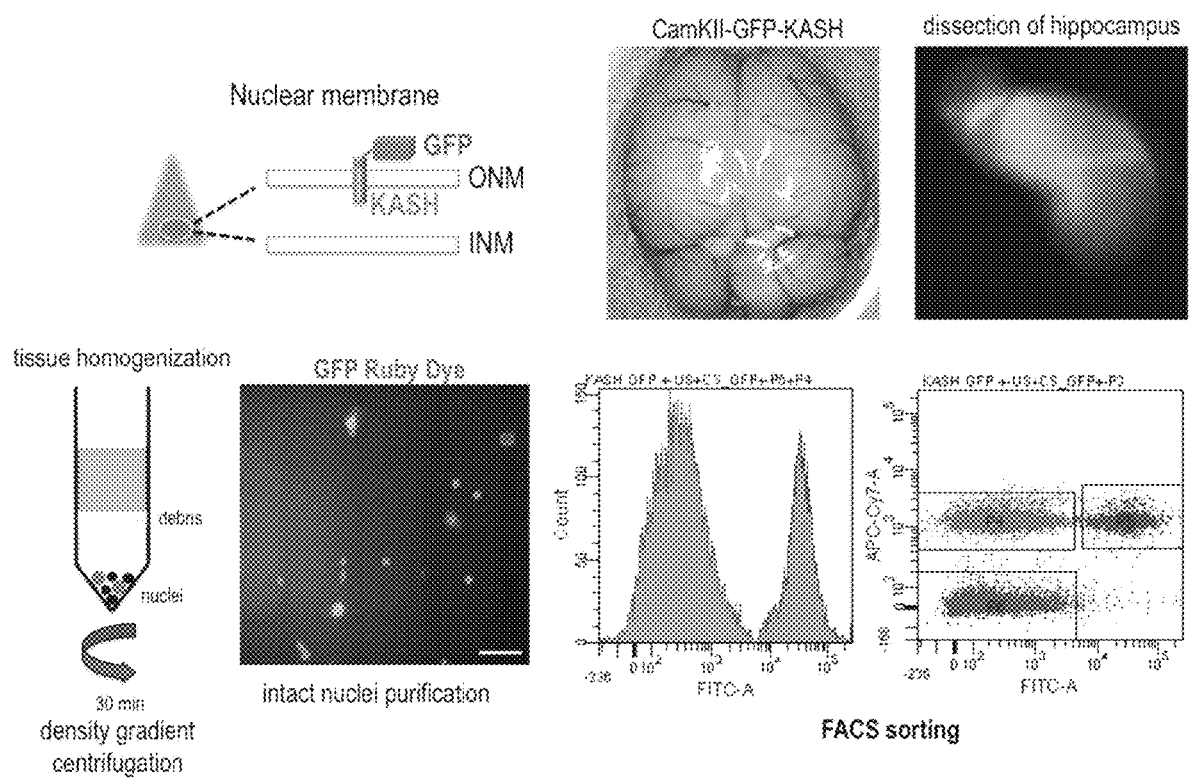
FIG. 30 shows purification of GFP-KASH labeled cell nuclei from hippocampal neurons. The outer nuclear membrane (ONM) of the cell nuclear membrane is tagged with a fusion of GFP and the KASH protein transmembrane domain. Strong GFP expression in the brain after one week of stereotactic surgery and AAV1/2 injection. Density gradient centrifugation step to purify cell nuclei from intact brain. Purified nuclei are shown. Chromatin stain by Vybrant® DyeCycle™ Ruby Stain is shown in red, GFP labeled nuclei are green. Representative FACS profile of GFP+ and GFP− cell nuclei (Magenta: Vybrant® DyeCycle™ Ruby Stain, Green: GFP).
Figure 31:
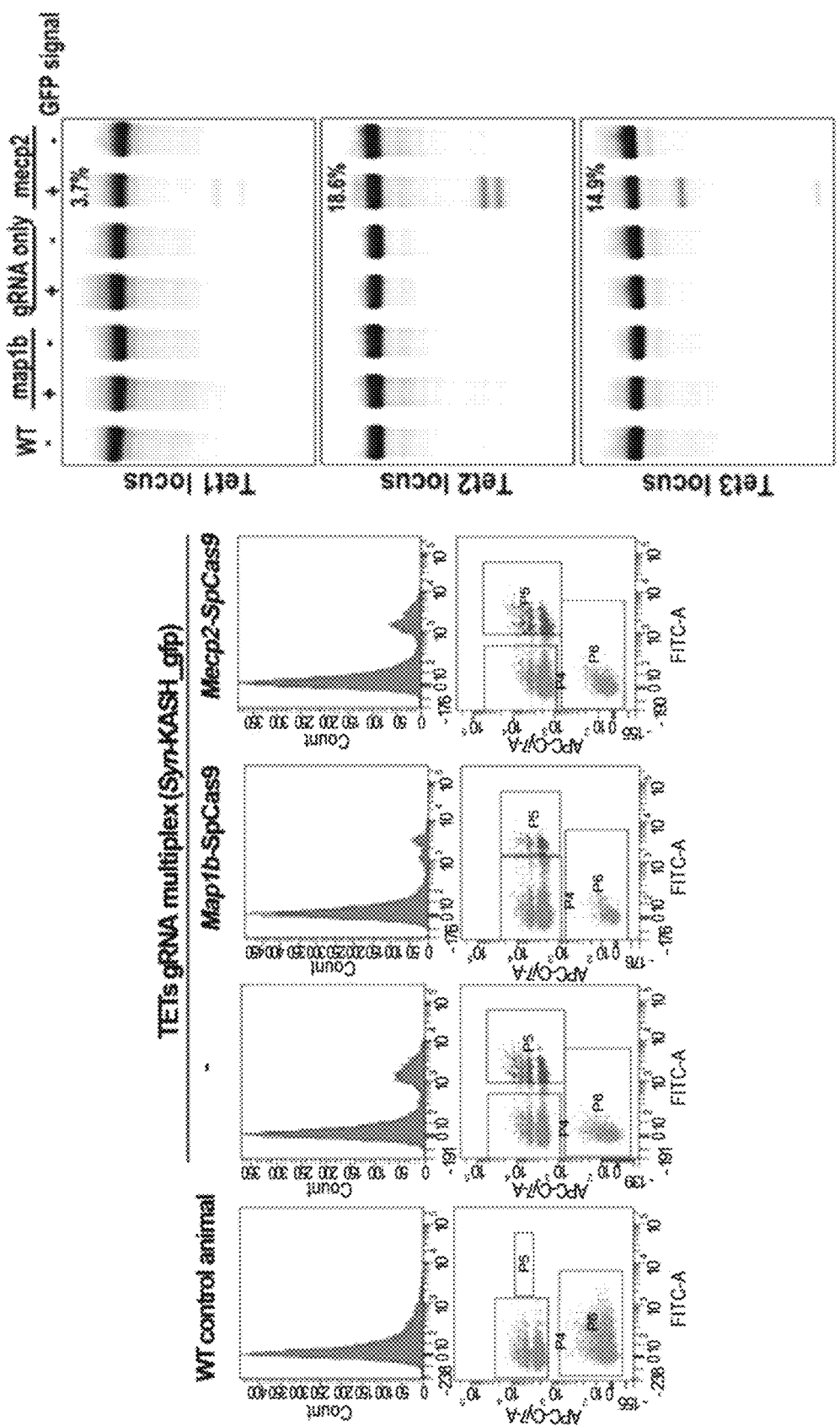
FIG. 31 shows efficiency of SpCas9 cleavage in the mouse brain. Mice were injected with AAV1/2 virus carrying gRNA multiplex targeting TET family genes loci together with SpCas9 viruses under control of 2 different promoters: mouse Mecp2 and rat Map1b. Three weeks after injection brain tissue was extracted, nuclei were prepped and sorted using FACS, based on the GFP expression driven by Synapsin promoter from gRNA multiplex construct. After gDNA extraction Surveyor assay was run. + indicates GFP positive nuclei and − control, GFP-negative nuclei from the same animal. Numbers on the gel indicate assessed SpCas9 efficiency.

To assess the toxicity of AAV with CRISPR system Applicants tested overall morphology of neurons one week after virus transduction (FIG. 27). Additionally, Applicants tested potential toxicity of designed system with the LIVE/DEAD® Cell Imaging Kit, which allows to distinguish live and dead cells in culture. It is based on the presence of intracellular esterase activity (as determined by the enzymatic conversion of the non-fluorescent calcein AM to the intensely green fluorescent calcein). On the other hand, the red, cell-impermeant component of the Kit enters cells with damaged membranes only and bind to DNA generating fluorescence in dead cells. Both flourophores can be easily visualized in living cells with fluorescent microscopy. AAV-driven expression of Cas9 proteins and multiplex gRNA constructs in the primary cortical neurons was well tolerated and not toxic (FIGS. 25 and 26), what indicates that designed AAV system is suitable for in vivo tests.

Virus Production

Concentrated virus was produced according to the methods described in McClure et al., 2011. Supernatant virus production occurred in HEK293FT cells.

Brain Surgeries

For viral vector injections 10-15 week old male C57BL/6N mice were anesthetized with a Ketamine/Xylazine cocktail (Ketamine dose of 100 mg/kg and Xylazine dose of 10 mg/kg) by intraperitoneal injection. Intraperitonial administration of Buprenex was used as a pre-emptive analgesic (1 mg/kg). Animals were immobilized in a Kopf stereotaxic apparatus using intra-aural positioning studs and tooth bar to maintain an immobile skull. Using a hand-held drill, a hole (1-2 mm) at −3.0 mm posterior to Bregma and 3.5 mm lateral for injection in the CA1 region of the hippocampus was made. Using 30G World Precision Instrument syringe at a depth of 2.5 mm, the solution of AAV viral particles in a total volume of 1 ul was injected. The injection was monitored by a 'World Precision Instruments UltraMicroPump3' injection pump at a flow rate of 0.5 ul/min to prevent tissue damage. When the injection was complete, the injection needle was removed slowly, at a rate of 0.5 mm/min. After injection, the skin was sealed with 6-0 Ethilon sutures. Animals were postoperatively hydrated with 1 mL lactated Ringer's (subcutaneous) and housed in a temperature controlled (37° C.) environment until achieving an ambulatory recovery. 3 weeks after surgery animals were euthanized by deep anesthesia followed by tissue removal for nuclei sorting or with 4% paraformaldehyde perfusion for immunochemistry.

Sorting Nuclei and In Vivo Results

Applicants designed a method to specifically genetically tag the gRNA targeted neuronal cell nuclei with GFP for Fluorescent Activated Cell Sorting (FACS) of the labeled cell nuclei and downstream processing of DNA, RNA and nuclear proteins. To that purpose the applicants' multiplex targeting vector was designed to express both a fusion protein between GFP and the mouse nuclear membrane protein domain KASH (Starr D A, 2011, Current biology) and the 3 gRNAs to target specific gene loci of interest (FIG. 16). GFP-KASH was expressed under the control of the human Synapsin promoter to specifically label neurons. The amino acid of the fusion protein GFP-KASH was:

(SEQ ID NO: 199)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYKSGLRSREEEEE

TDSRMPHLDSPGSSQPRRSFLSRVIRAALPLQLLLLLLLLLACLLPASED

DYSCTQANNFARSFYPMLRYTNGPPPT

One week after AAV1/2 mediated delivery into the brain a robust expression of GFP-KASH was observed. For FACS and downstream processing of labeled nuclei, the hippocampi were dissected 3 weeks after surgery and processed for cell nuclei purification using a gradient centrifugation step. For that purpose the tissue was homogenized in 320 mM Sucrose, 5 mM CaCl, 3 mM Mg(Ac)2, 10 mM Tris pH 7.8, 0.1 mM EDTA, 0.1% NP40, 0.1 mM Phenylmethanesulfonyl fluoride (PMSF), 1 mM β-mercaptoethanol using 2 ml Dounce homogenizer (Sigma) The homogenisate was centrifuged on a 25% to 29% Optiprep® gradient according to the manufacture's protocol for 30 min at 3.500 rpm at 4° C. The nuclear pellet was resuspended in 340 mM Sucrose, 2 mM MgCl2, 25 mM KC, 65 mM glycerophosphate, 5% glycerol, 0.1 mM PMSF, 1 mM β-mercaptoethanol and Vybrant® DyeCycle™ Ruby Stain (Life technologies) was added to label cell nuclei (offers near-infrared emission for DNA). The labeled and purified nuclei were sorted by FACS using an Aria Flu-act-cell sorter and BDFACS Diva software. The sorted GFP+ and GFP− nuclei were finally used to purify genomic DNA using DNAeasy Blood & Tissue Kit (Qiagen) for Surveyor assay analysis of the targeted genomic regions. The same approach can be easily used to purify nuclear RNA or protein from targeted cells for downstream processing. Due to the 2-vector system (FIG. 16) the applicants using in this approach efficient Cas9 mediated DNA cleavage was expected to occur only in a small subset of cells in the brain (cells which were co-infected with both the multiplex targeting vector and the Cas9 encoding vector). The method described here enables the applicants to specifically purify DNA, RNA and nuclear proteins from the cell population expressing the 3 gRNAs of interest and therefore are supposed to undergo Cas9 mediated DNA cleavage. By using this method the applicants were able to visualize efficient DNA cleavage in vivo occurring only in a small subset of cells.

Essentially, what Applicants have shown here is targeted in vivo cleavage. Furthermore, Applicants used a multiple approach, with several different sequences targeted at the same time, but independently. Presented system can be applied for studying brain pathologic conditions (gene knock out, e.g. Parkinson disease) and also open a field for further development of genome editing tools in the brain. By replacing nuclease activity with gene transcription regulators or epigenetic regulators it will be possible to answer whole spectrum of scientific question about role of gene regulation and epigenetic changes in the brain in not only in the pathologic conditions but also in physiological process as learning and memory formation. Finally, presented technology can be applied in more complex mammalian system as primates, what allows to overcome current technology limitations.

Example 28: Model Data

Several disease models have been specifically investigated. These include de novo autism risk genes CHD8, KATNAL2, and SCN2A; and the syndromic autism (Angelman Syndrome) gene UBE3A. These genes and resulting autism models are of course preferred, but show that the invention may be applied to any gene and therefore any model is possible.

Applicants have made these cells lines using Cas9 nuclease in human embryonic stem cells (hESCs). The lines were created by transient transfection of hESCs with Cbh-Cas9-2A-EGFP and pU6-sgRNA. Two sgRNAs are designed for each gene targeting most often the same exons in which patient nonsense (knock-out) mutations have been recently described from whole exome sequencing studies of autistic patients. The Cas9-2A-EGFP and pU6 plasmids were created specifically for this project.

Example 29: AAV Production System or Protocol

An AAV production system or protocol that was developed for, and works particularly well with, high through put screening uses is provided herein, but it has broader applicability in the present invention as well. Manipulating endogenous gene expression presents various challenges, as the rate of expression depends on many factors, including regulatory elements, mRNA processing, and transcript stability. To overcome this challenge, Applicants developed an adeno-associated virus (AAV)-based vector for the delivery. AAV has an ssDNA-based genome and is therefore less susceptible to recombination.

AAV1/2 (serotype AAV/2, i.e., hybrid or mosaic AAV1/AAV2 capsid AAV) heparin purified concentrated virus protocol Media: D10+HEPES
500 ml bottle DMEM high glucose+Glutamax (GIBCO)
50 ml Hyclone FBS (heat-inactivated) (Thermo Fischer)
5.5 ml HEPES solution (1M, GIBCO)
Cells: low passage HEK293FT (passage <10 at time of virus production, thaw new cells of passage 2-4 for virus production, grow up for 3-5 passages)
Transfection Reagent: Polyethylenimine (PEI) "Max"
Dissolve 50 mg PEI "Max" in 50 ml sterile Ultrapure H20
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES
Passage everyday between 1:2 and 1:2.5
Advantageously do not allow cells to reach more than 85% confluency
For T75
  Warm 10 ml HBSS (-Mg2+, -Ca2+, GIBCO)+1 ml TrypLE Express (GIBCO) per flask to 37° C. (Waterbath)
Aspirate Media Fully
  Add 10 ml warm HBSS gently (to wash out media completely)
  Add 1 ml TrypLE per Flask
  Place flask in incubator (37° C.) for 1 min
  Rock flask to detach cells
  Add 9 ml D10+HEPES media (37° C.)
  Pipette up and down 5 times to generate single cell suspension
  Split at 1:2-1:2.5 (12 ml media for T75) ratio (if cells are growing more slowly, discard and thaw a new batch, they are not in optimal growth)
  transfer to T225 as soon as enough cells are present (for ease of handling large amounts of cells)
AAV Production (5*15 cm Dish Scale Per Construct):
Plate 10 million cells in 21.5 ml media into a 15 cm dish
Incubate for 18-22 hours at 37° C.
Transfection is ideal at 80% confluence
  Per Plate
Prewarm 22 ml media (D10+HEPES)
  Prepare Tube with DNA Mixture (Use Endofree Maxiprep DNA):
5.2 ug vector of interest plasmid
4.35 ug AAV 1 serotype plasmid
4.35 ug AAV 2 serotype plasmid
10.4 ug pDF6 plasmid (adenovirus helper genes) ☐ Vortex to mix
Add 434 uL DMEM (no serum!)
Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48 h before harvesting (make sure medium isn't turning too acidic)

Virus Harvest:
1. aspirate media carefully from 15 cm dish dishes (advantageously do not dislodge cells)
2. Add 25 ml RT DPBS (Invitrogen) to each plate and gently remove cells with a cell scraper. Collect suspension in 50 ml tubes.
3. Pellet cells at 800×g for 10 minutes.
4. Discard supernatant
Pause Point: Freeze Cell Pellet at −80 C if Desired
5. resuspend pellet in 150 mM NaCl, 20 mM Tris pH 8.0, use 10 ml per tissue culture plate.
6. Prepare a fresh solution of 10% sodium deoxycholate in dH2O. Add 1.25 ml of this per tissue culture plate for a final concentration of 0.5%. Add benzonase nuclease to a final concentration of 50 units per ml. Mix tube thoroughly.
7. Incubate at 37° C. for 1 hour (Waterbath).
8. Remove cellular debris by centrifuging at 3000×g for 15 mins. Transfer to fresh 50 ml tube and ensure all cell debris has been removed to prevent blocking of heparin columns.

Heparin Column Purification of AAV1/2:
1. Set up HiTrap heparin columns using a peristaltic pump so that solutions flow through the column at 1 ml per minute. It is important to ensure no air bubbles are introduced into the heparin column.
2. Equilibrate the column with 10 ml 150 mM NaCl, 20 mM Tris, pH 8.0 using the peristaltic pump.
3. Binding of virus: Apply 50 ml virus solution to column and allow to flow through.
4. Wash step 1: column with 20 ml 100 mM NaCl, 20 mM Tris, pH 8.0. (using the peristaltic pump)
5. Wash step 2: Using a 3 ml or 5 ml syringe continue to wash the column with 1 ml 200 mM NaCl, 20 mM Tris, pH 8.0, followed by 1 ml 300 mM NaCl, 20 mM Tris, pH 8.0. Discard the flow-through.
(prepare the syringes with different buffers during the 50 min flow through of virus solution above)
6. Elution Using 5 ml syringes and gentle pressure (flow rate of <1 ml/min) elute the virus from the column by applying:
1.5 ml 400 mM NaCl, 20 mM Tris, pH 8.0
3.0 ml 450 mM NaCl, 20 mM Tris, pH 8.0
1.5 ml 500 mM NaCl, 20 mM Tris, pH 8.0
Collect these in a 15 ml centrifuge tube.

Concentration of AAV1/2:
1. Concentration step 1: Concentrate the eluted virus using Amicon ultra 15 ml centrifugal filter units with a 100,000 molecular weight cutoff. Load column eluate into the concentrator and centrifuge at 2000×g for 2 minutes (at room temperature. Check concentrated volume—it should be approximately 500 µl. If necessary, centrifuge in 1 min intervals until correct volume is reached.
2. buffer exchange: Add 1 ml sterile DPBS to filter unit, centrifuge in 1 min intervals until correct volume (500 ul) is reached.
3. Concentration step 2: Add 500 ul concentrate to an Amicon Ultra 0.5 ml 100K filter unit. Centrifuge at 6000 g for 2 min. Check concentrated volume—it should be approximately 100 µl. If necessary, centrifuge in 1 min intervals until correct volume is reached.
4. Recovery: Invert filter insert and insert into fresh collection tube. Centrifuge at 1000 g for 2 min.
Aliquot and freeze at −80° C.
1 ul is typically required per injection site, small aliquots (e.g. 5 ul) are therefore recommended (avoid freeze-thaw of virus).
determine DNaseI-resistant GC particle titer using qPCR (see separate protocol)

Materials
Amicon Ultra, 0.5 ml, 100K; MILLIPORE; UFC510024
Amicon Ultra, 15 ml, 100K; MILLIPORE; UFC910024
Benzonase nuclease; Sigma-Aldrich, E1014
HiTrap Heparin cartridge; Sigma-Aldrich; 54836
Sodium deoxycholate; Sigma-Aldrich; D5670

AAV1 Supernatant Production Protocol
Media: D10+HEPES
500 ml bottle DMEM high glucose+Glutamax (Invitrogen)
50 ml Hyclone FBS (heat-inactivated) (Thermo Fischer)
5.5 ml HEPES solution (IM, GIBCO)
Cells: low passage HEK293FT (passage <10 at time of virus production)
Thaw new cells of passage 2-4 for virus production, grow up for 2-5 passages
Transfection reagent: Polyethylenimine (PEI) "Max"
Dissolve 50 mg PEI "Max" in 50 ml sterile Ultrapure H20
Adjust pH to 7.1
Filter with 0.22 um fliptop filter
Seal tube and wrap with parafilm
Freeze aliquots at −20° C. (for storage, can also be used immediately)
Cell Culture
Culture low passage HEK293FT in D10+HEPES Passage everyday between 1:2 and 1:2.5
Advantageously do let cells reach more than 85% confluency
For T75
    Warm 10 ml HBSS (-Mg2+, -Ca2+, GIBCO)+1 ml TrypLE Express (GIBCO) per flask to 37° C. (Waterbath)
    Aspirate media fully
    Add 10 ml warm HBSS gently (to wash out media completely)
    Add 1 ml TrypLE per Flask
    Place flask in incubator (37° C.) for 1 min
    Rock flask to detach cells
    Add 9 ml D10+HEPES media (37° C.)
    Pipette up and down 5 times to generate single cell suspension
    Split at 1:2-1:2.5 (12 ml media for T75) ratio (if cells are growing more slowly, discard and thaw a new batch, they are not in optimal growth)
    transfer to T225 as soon as enough cells are present (for ease of handling large amounts of cells)
AAV production (single 15 cm dish scale)
Plate 10 million cells in 21.5 ml media into a 15 cm dish
Incubate for 18-22 hours at 37° C.
Transfection is ideal at 80% confluence per plate
Prewarm 22 ml media (D10+HEPES)
Prepare tube with DNA mixture (use endofree maxiprep DNA):
5.2 ug vector of interest plasmid
8.7 ug AAV 1 serotype plasmid
10.4 ug DF6 plasmid (adenovirus helper genes)
Vortex to mix
Add 434 uL DMEM (no serum!) Add 130 ul PEI solution
Vortex 5-10 seconds
Add DNA/DMEM/PEI mixture to prewarmed media
Vortex briefly to mix
Replace media in 15 cm dish with DNA/DMEM/PEI mixture
Return to 37° C. incubator
Incubate 48 h before harvesting (advantageously monitor to ensure medium is not turning too acidic)

Virus Harvest:
Remove supernatant from 15 cm dish
Filter with 0.45 um filter (low protein binding) Aliquot and freeze at −80° C.
Transduction (primary neuron cultures in 24-well format, 5 DIV)
Replace complete neurobasal media in each well of neurons to be transduced with fresh neurobasal (usually 400 ul out of 500 ul per well is replaced)
Thaw AAV supernatant in 37° C. waterbath
Let equilibrate in incubator for 30 min
Add 250 ul AAV supernatant to each well
Incubate 24 h at 37° C.
Remove media/supernatant and replace with fresh complete neurobasal
Expression starts to be visible after 48 h, saturates around 6-7 Days Post Infection
Constructs for pAAV plasmid with GOI should not exceed 4.8 kb including both ITRS.

Example of a human codon optimized sequence (i.e. being optimized for expression in humans) sequence: SaCas9 is provided below:

(SEQ ID NO: 200)
ACCGGTGCCACCATGTACCCATACGATGTTCCAGATTACGCTTCGCCGAA

GAAAAAGCGCAAGGTCGAAGCGTCCATGAAAAGGAACTACATTCTGGGGC

TGGACATCGGGATTACAAGCGTGGGGTATGGGATTATTGACTATGAAACA

AGGGACGTGATCGACGCAGGCGTCAGACTGTTCAAGGAGGCCAACGTGGA

AAACAATGAGGGACGGAGAAGCAAGAGGGGAGCCAGGCGCCTGAAACGAC

GGAGAAGGCACAGAATCCAGAGGGTGAAGAAACTGCTGTTCGATTACAAC

CTGCTGACCGACCATTCTGAGCTGAGTGGAATTAATCCTTATGAAGCCAG

GGTGAAAGGCCTGAGTCAGAAGCTGTCAGAGGAAGAGTTTTCCGCAGCTC

TGCTGCACCTGGCTAAGCGCCGAGGAGTGCATAACGTCAATGAGGTGGAA

GAGGACACCGGCAACGAGCTGTCTACAAAGGAACAGATCTCACGCAATAG

CAAAGCTCTGGAAGAGAAGTATGTCGCAGAGCTGCAGCTGGAACGGCTGA

AGAAAGATGGCGAGGTGAGAGGGTCAATTAATAGGTTCAAGACAAGCGAC

TACGTCAAAGAAGCCAAGCAGCTGCTGAAAGTGCAGAAGGCTTACCACCA

GCTGGATCAGAGCTTCATCGATACTTATATCGACCTGCTGGAGACTCGGA

GAACCTACTATGAGGGACCAGGAGAAGGGAGCCCCTTCGGATGGAAAGAC

ATCAAGGAATGGTACGAGATGCTGATGGGACATTGCACCTATTTTCCAGA

AGAGCTGAGAAGCGTCAAGTACGCTTATAACGCAGATCTGTACAACGCCC

TGAATGACCTGAACAACCTGGTCATCACCAGGGATGAAAACGAGAAACTG

GAATACTATGAGAAGTTCCAGATCATCGAAAACGTGTTTAAGCAGAAGAA

AAAGCCTACACTGAAACAGATTGCTAAGGAGATCCTGGTCAACGAAGAGG

ACATCAAGGGCTACCGGGTGACAAGCACTGGAAACCAGAGTTCACCAAT

CTGAAAGTGTATCACGATATTAAGGACATCACAGCACGGAAAGAAATCAT

TGAGAACGCCGAACTGCTGGATCAGATTGCTAAGATCCTGACTATCTACC

AGAGCTCCGAGGACATCCAGGAAGAGCTGACTAACCTGAACAGCGAGCTG

ACCCAGGAAGAGATCGAACAGATTAGTAATCTGAAGGGGTACACCGGAAC

ACACAACCTGTCCCTGAAAGCTATCAATCTGATTCTGGATGAGCTGTGGC

ATACAAACGACAATCAGATTGCAATCTTTAACCGGCTGAAGCTGGTCCCA

AAAAAGGTGGACCTGAGTCAGCAGAAAGAGATCCCAACCACACTGGTGGA

CGATTTCATTCTGTCACCCGTGGTCAAGCGGAGCTTCATCCAGAGCATCA

AAGTGATCAACGCCATCATCAAGAAGTACGGCCTGCCCAATGATATCATT

ATCGAGCTGGCTAGGGAGAAGAACAGCAAGGACGCACAGAAGATGATCAA

TGAGATGCAGAAACGAAACCGGCAGACCAATGAACGCATTGAAGAGATTA

TCCGAACTACCGGGAAAGAGAACGCAAAGTACCTGATTGAAAAAATCAAG

CTGCACGATATGCAGGAGGGAAAGTGTCTGTATTCTCTGGAGGCCATCCC

CCTGGAGGACCTGCTGAACAATCCATTCAACTACGAGGTCGATCATATTA

TCCCCAGAAGCGTGTCCTTCGACAATTCCTTTAACAACAAGGTGCTGGTC

AAGCAGGAAGAGAACTCTAAAAAGGGCAATAGGACTCCTTTCCAGTACCT

GTCTAGTTCAGATTCCAAGATCTCTTACGAAACCTTTAAAAAGCACATTC

TGAATCTGGCCAAAGGAAAGGGCCGCATCAGCAAGACCAAAAAGGAGTAC

CTGCTGGAAGAGCGGGACATCAACAGATTCTCCGTCCAGAAGGATTTTAT

TAACCGGAATCTGGTGGACACAAGATACGCTACTCGCGGCCTGATGAATC

TGCTGCGATCCTATTTCCGGGTGAACAATCTGGATGTGAAAGTCAAGTCC

ATCAACGGCGGGTTCACATCTTTTCTGAGGCGCAAATGGAAGTTTAAAAA

GGAGCGCAACAAAGGGTACAAGCACCATGCCGAAGATGCTCTGATTATCG

CAAATGCCGACTTCATCTTTAAGGAGTGGAAAAAGCTGGACAAAGCCAAG

AAAGTGATGGAAACCAGATGTTCGAAGAGAAGCAGGCCGAATCTATGCC

CGAAATCGAGACAGAACAGGAGTACAAGGAGATTTTCATCACTCCTCACC

AGATCAAGCATATCAAGGATTTCAAGGACTACAAGTACTCTCACCGGGTG

GATAAAAAGCCCAACAGAGAGCTGATCAATGACACCCTGTATAGTACAAG

AAAAGACGATAAGGGGAATACCCTGATTGTGAACAATCTGAACGGACTGT

ACGACAAAGATAATGACAAGCTGAAAAAGCTGATCAACAAAAGTCCCGAG

AAGCTGCTGATGTACCACCATGATCCTCAGACATATCAGAAACTGAAGCT

GATTATGGAGCAGTACGGCGACGAGAAGAACCCACTGTATAAGTACTATG

AAGAGACTGGGAACTACCTGACCAAGTATAGCAAAAAGGATAATGGCCCC

GTGATCAAGAAGATCAAGTACTATGGGAACAAGCTGAATGCCCATCTGGA

CATCACAGACGATTACCCTAACAGTCGCAACAAGGTGGTCAAGCTGTCAC

TGAAGCCATACAGATTCGATGTCTATCTGGACAACGGCGTGTATAAATTT

GTGACTGTCAAGAATCTGGATGTCATCAAAAAGGAGAACTACTATGAAGT

GAATAGCAAGTGCTACGAAGAGGCTAAAAAGCTGAAAAAGATTAGCAACC

AGGCAGAGTTCATCGCCTCCTTTTACAACAACGACCTGATTAAGATCAAT

GGCGAACTGTATAGGGTCATCGGGGTGAACAATGATCTGCTGAACCGCAT

TGAAGTGAATATGATTGACATCACTTACCGAGAGTATCTGGAAAACATGA

ATGATAAGCGCCCCCCTCGAATTATCAAAACAATTGCCTCTAAGACTCAG

AGTATCAAAAAGTACTCAACCGACATTCTGGGAAACCTGTATGAGGTGAA

GAGCAAAAAGCACCCTCAGATTATCAAAAAGGGCTAAGAATTC

Example 30: Minimizing Off-Target Cleavage Using Cas9 Nickase and Two Guide RNAs Cas9 is a RNA-guided DNA nuclease that may be targeted to specific locations in the genome with the help of a 20 bp RNA guide. However the guide sequence may tolerate some mismatches between the guide sequence and the DNA-target sequence. The flexibility is undesirable due to the potential for off-target cleavage, when the guide RNA targets Cas9 to a an off-target sequence that has a few bases different from the guide sequence. For all experimental applications (gene targeting, crop engineering, therapeutic applications, etc) it is important to be able to improve the specificity of Cas9 mediated gene targeting and reduce the likelihood of off-target modification by Cas9.

Applicants developed a method of using a Cas9 nickase mutant in combination with two guide RNAs to facilitate targeted double strand breaks in the genome without off-target modifications. The Cas9 nickase mutant may be generated from a Cas9 nuclease by disabling its cleavage activity so that instead of both strands of the DNA duplex being cleaved only one strand is cleaved. The Cas9 nickase may be generated by inducing mutations in one ore more domains of the Cas9 nuclease, e.g. Ruvc1 or HNH. These mutations may include but are not limited to mutations in a Cas9 catalytic domain, e.g in SpCas9 these mutations may be at positions D10 or H840. These mutations may include but are not limited to D10A, E762A, H840A, N854A, N863A or D986A in SpCas9 but nickases may be generated by inducing mutations at corresponding positions in other CRISPR enzymes or Cas9 orthologs. In a most preferred embodiment of the invention the Cas9 nickase mutant is a SpCas9 nickase with a D10A mutation.

The way this works is that each guide RNA in combination with Cas9 nickase would induce the targeted single strand break of a duplex DNA target. Since each guide RNA nicks one strand, the net result is a double strand break. The reason this method eliminates off-target mutations is because it is very unlikely to have an off-target site that has high degrees of similarity for both guide sequences (20 bp+2 bp(PAM)=22 bp specificity for each guide, and two guides means any off-target site will have to have close to 44 bp of homologous sequence). Although it is still likely that individual guides may have off-targets, but those off-targets will only be nicked, which is unlikely to be repaired by the mutagenic NHEJ process. Therefore the multiplexing of DNA double strand nicking provides a powerful way of introducing targeted DNA double strand breaks without off-target mutagenic effects.

Figure 34:
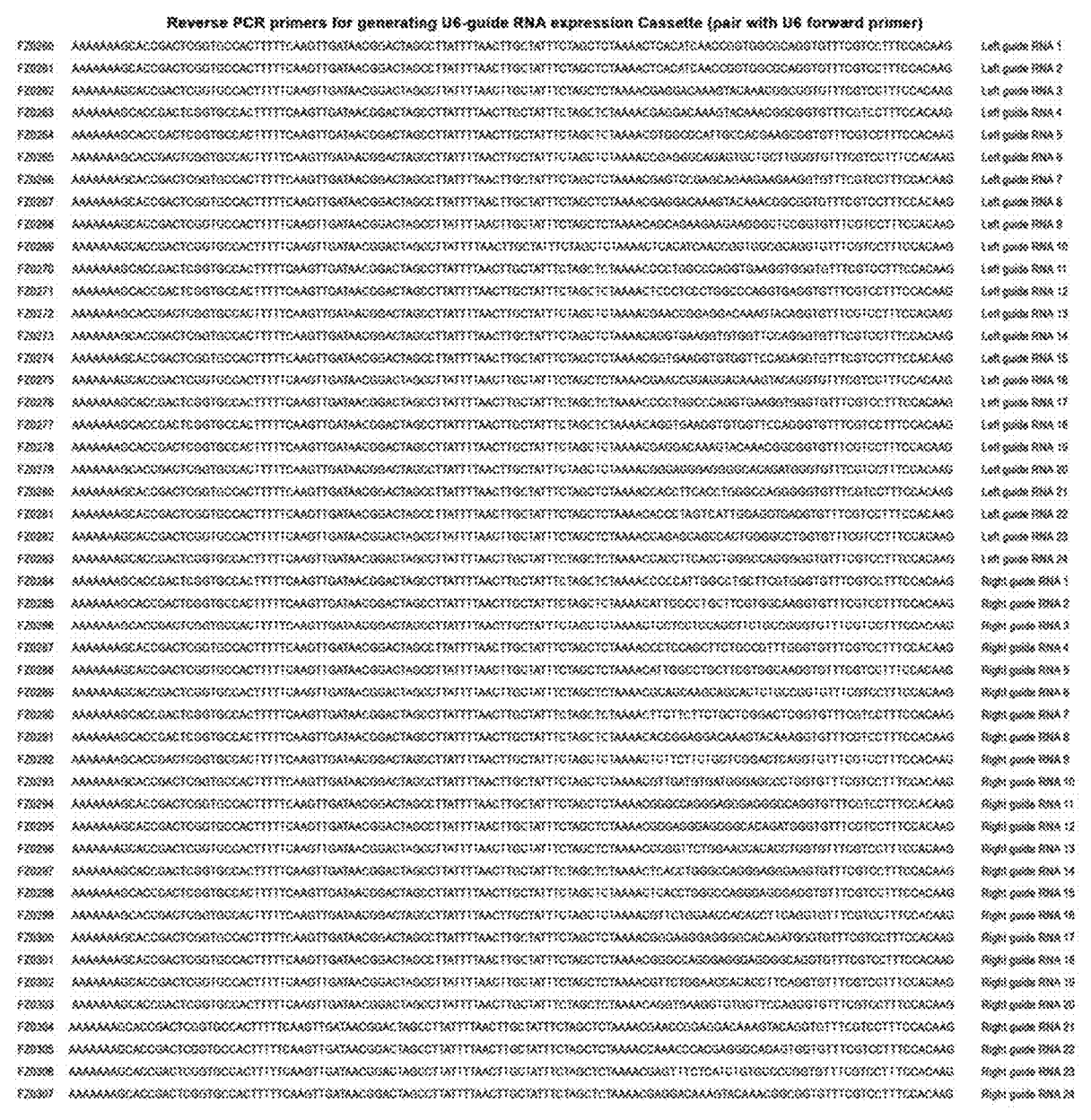
Figure 35:
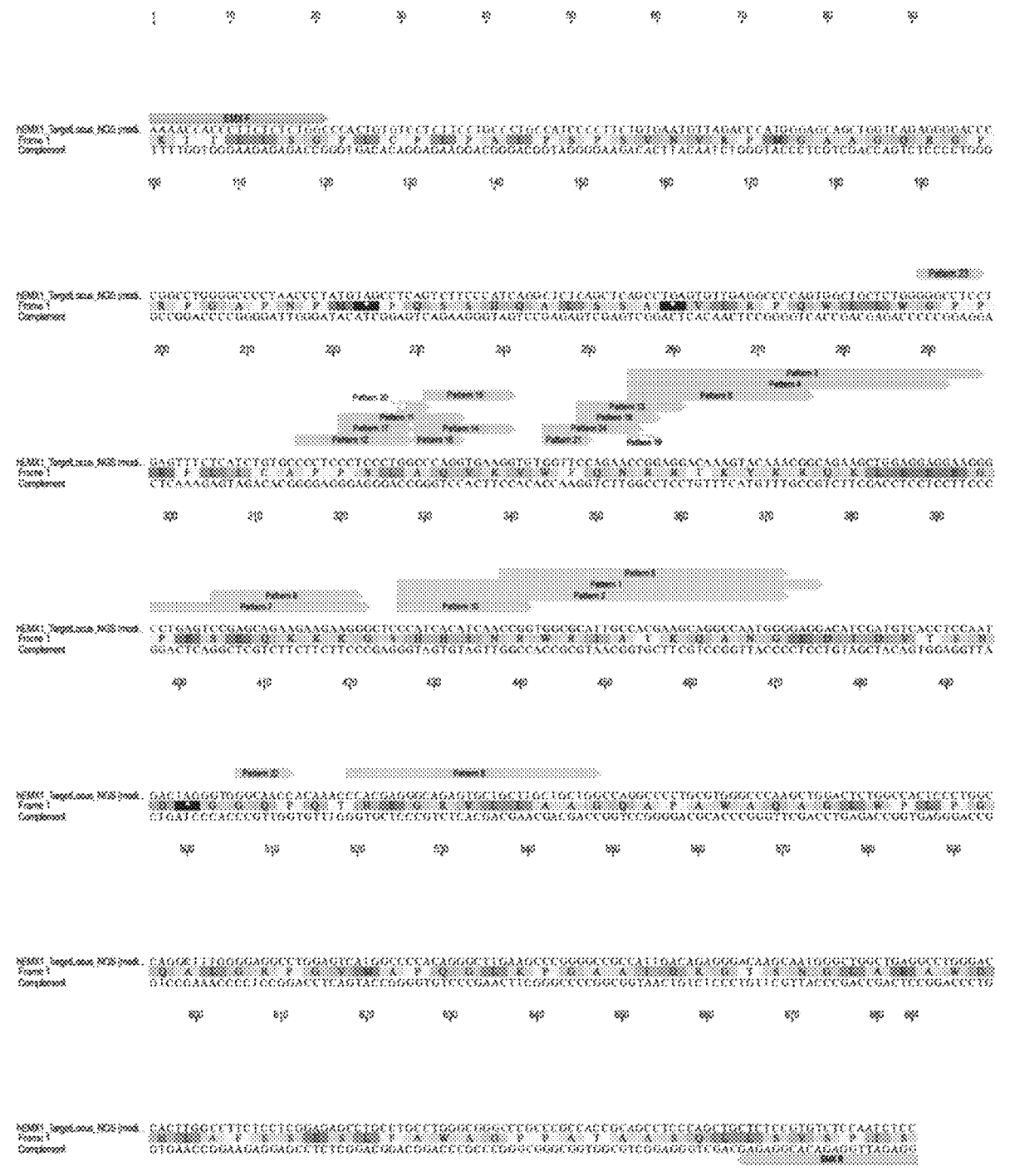

Applicants carried out experiments involving the co-transfection of HEK293FT cells with a plasmid encoding Cas9(D10A) nickase as well as DNA expression cassettes for one or more guides. Applicants transfected cells using Lipofectamine 2000, and transfected cells were harvested 48 or 72 hours after transfections. Double nicking-induced NHEJ were detected using the SURVEYOR nuclease assay as described previously herein (FIGS. 33, 34 and 35).

Figure 37:
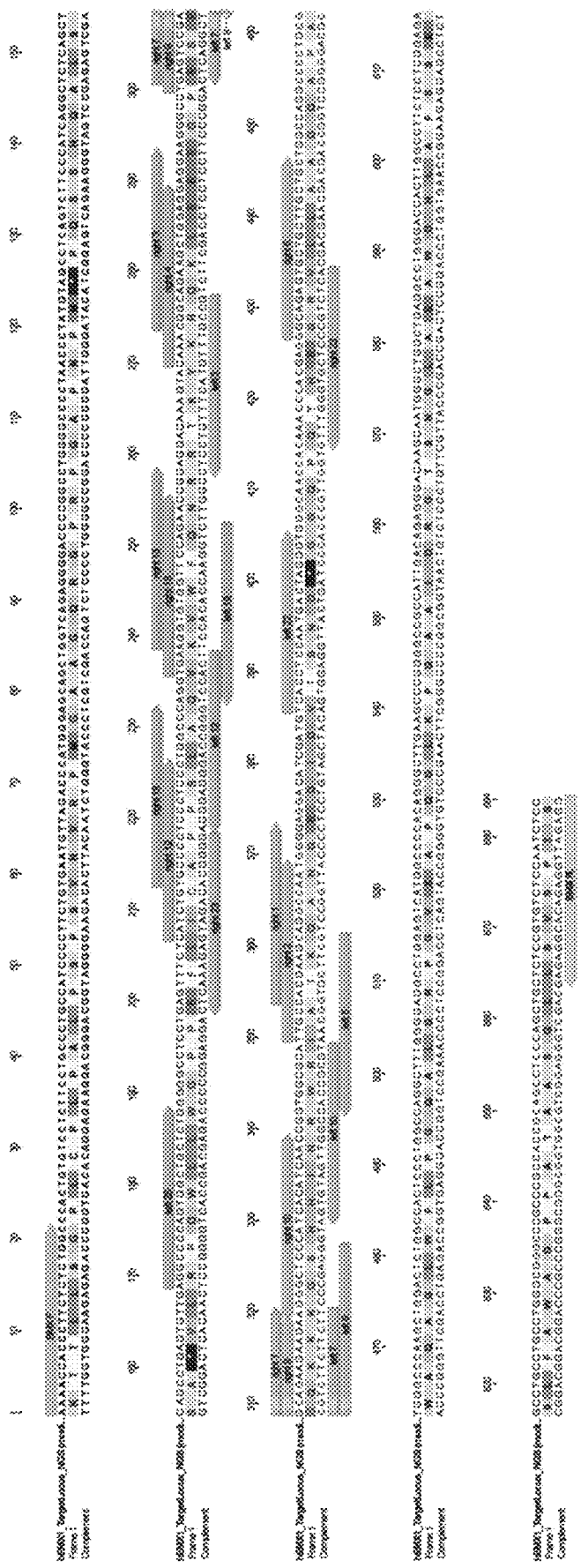
FIG. 37 shows a Genomic sequence map from the human Emx1 locus showing the locations of the different pairs of guide RNAs that result in the gel patterns of FIG. 36 (right) and which are further described in Example 30.

Applicants have further identified parameters that relate to efficient cleavage by the Cas9 nickase mutant when combined with two guide RNAs and these parameters include but are not limited to the length of the 5' overhang. Efficient cleavage is reported for 5' overhang of at least 26 base pairs. In a preferred embodiment of the invention, the 5' overhang is at least 30 base pairs and more preferably at least 34 base pairs. Overhangs of up to 200 base pairs may be acceptable for cleavage, while 5' overhangs less than 100 base pairs are preferred and 5' overhangs less than 50 base pairs are most preferred (FIGS. 36 and 37).

Example 31: Tandem Single Guide RNAs (tsgRNAs)

The bacterial CRISPR-Cas system is an RNA-guided endonuclease that Applicants have shown can induce targeted modification of the eukaryotic genome predictably, precisely, and efficiently. The minimal components required to reconstitute this system in mammalian cells consist of delivery of the Cas9 endonuclease as well as a guide RNA carrying a 20 bp specificity sequence complementary to the target site of interest. Until now, delivery of multiple individual guide RNAs was required to achieve multiplex genome editing. While co-transfection of multiple guides is relative simple in tissue culture, many in vivo and therapeutic applications for the CRISPR-Cas system would benefit from a single-vector system that could still allow multiplex editing.

Figure 38A:
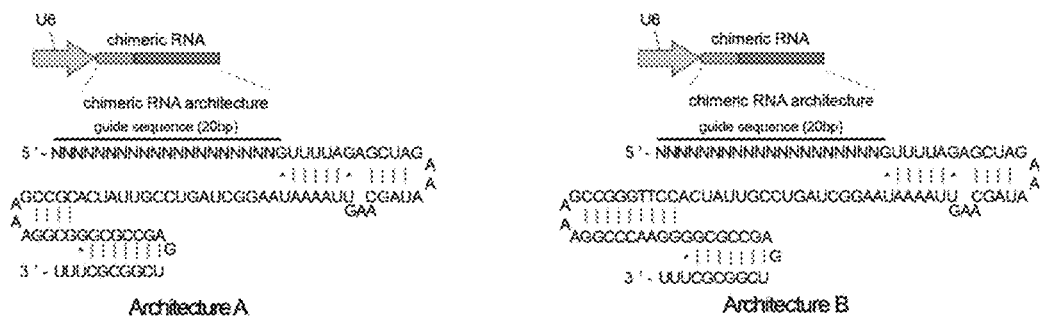

Applicants mutagenized different parts of the original chimeric guide RNA architecture to determine what portions of the chimeric guide RNA would be amenable for alteration or improvement. From these studies, Applicants found that the two distal hairpins appear primarily to function in stabilization of the chimeric RNA. Alteration of the direct-repeat-and-tracrRNA duplex region, as well as the unstructured region between the duplex and the first hairpin of the tracrRNA abolished cleavage activity. However, increased stabilization of the two tracrRNA tail hairpins through introduction of G-C pairs (Architectures A and B in FIG. 38A) did not decrease the ability of Cas9 to induce targeted indels.

Figure 38B:
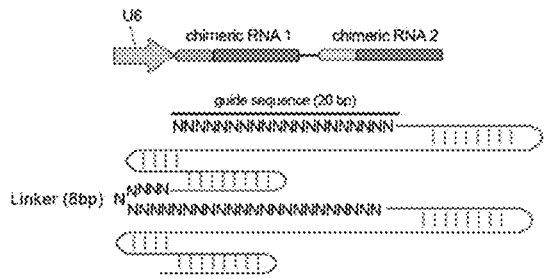

In the native bacterial CRISPR system, Cas9 processes a continuous repetitive transcript of DR-flanked spacers into discrete units upon assembly with tracrRNA. Applicants reasoned that multiple preassembled sgRNA could likewise be processed into discrete functional units. To create tandem sgRNA (tsgRNA), an 8-nt linker was introduced between the tracrRNA end of the first sgRNA and the spacer of the following sgRNA (FIG. 38B). Applicants tested the tsgRNA in two assays: microdeletion induction with wild-type Cas9 (FIG. 38C) and indel formation with nickase Cas9n (FIG. 38D). Applicants found that both tsgRNAs created with either Architecture A or B scaffolds were able to achieve targeted modification at levels comparable to individual delivery of both guide RNAs.

Tandem sgRNA are synthesized in a 2-round PCR as follows:

Round 1: Amplification using U6 promoter as template, U6-Fwd primer (as in previous PCR expression cassette experiments for sgRNA delivery), and a modified Reverse primer that contains from 5' to 3' (in reverse complement direction): spacer-2, sgRNA modified scaffold, spacer-1, U6 priming region.

Round 2: Amplifies using product from round 1 as template, using U6-Fwd primer as previously described, and a reverse primer 5' to 3' (in reverse complement direction): modified scaffold, spacer-2. (FIG. 38).

After 2 rounds of PCR, the full-length tsgRNA product is purified and co-transfected with Cas9 for testing in cells.

Example 32: Tandem Single Guide RNAs (tsgRNAs)

Figure 39C:
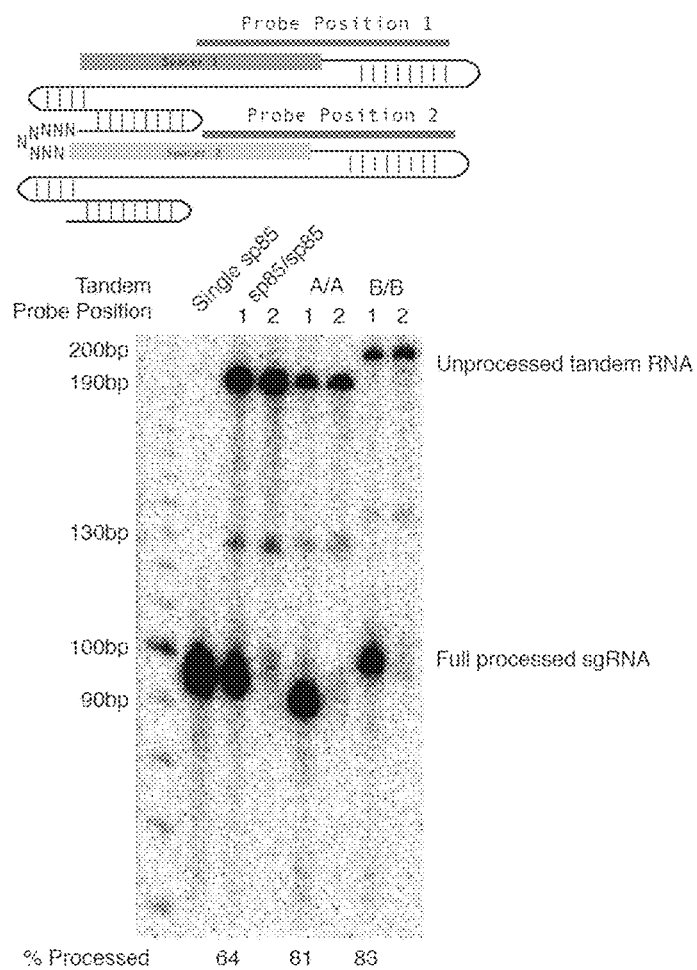

The ability to simultaneously deliver more than a single guide RNA on a single vector is particularly tractable for lentiviral screening methodologies. The propensity of lentivirus to recombine has limited the ability to drive expression of multiple short RNAs from a single vector with the requirement of utilizing multiple unique promoters. A tandem approach may allow a single promoter to drive expression of at least two guide RNAs. In addition to allowing one to target combinations of genomic targets, placing two guide RNAs immediately adjacent to one another facilitates cloning in a single-step high-throughput fashion (FIG. 39A). To further decrease homology between adjacent scaffolds to lessen viral recombination and to increase guide stability within the tandem array, Applicants have created and are validating divergent scaffold sequences that conserve secondary structure (FIG. 39B). Finally, through Northern blot analyses using a probe targeted against a particular spacer-scaffold combination, Applicants have observed that tandem guide RNAs are indeed processed to single sgRNA units and that the efficiency of processing is increased with the modified scaffolds relative to the wild-type+85 scaffold (FIG. 39C). Assembly of tandem guides can be accomplished by annealing of ultramers containing Spacer1-Scaffold-Spacer 2 (FIG. 39A), two-step PCR, or by Golden Gate assembly, which would be most amenable to construction of longer arrays.

Example 33: Characterization and Optimization of the CRISPR/Cas System for Applications in Genome Engineering Recent studies of Cas9 specificity have shown that although each base within the 20-nt guide sequence contributes to overall specificity, multiple mismatches between the guide RNA and its complementary DNA can be tolerated in a quantity-, position-, and base identity-sensitive manner. As a result, Cas9 can cleave genomic loci that share imperfect homology with the target 20-nt guide sequence, leading to off-target DSBs and NHEJ repair. Subsequent indel formation at off-target cleavage sites can lead to significant levels of unwanted mutations, which limit the utility of Cas9 for genome editing applications requiring high levels of precision, including generation of isogenic cell lines for testing causal genetic variations as well as in vivo and ex vivo genome editing-based therapies.

To improve the specificity of Cas9-mediated genome editing, Applicants developed a novel strategy that combines the D10A mutant nickase version of Cas9 (Cas9n) with a pair of offset sgRNAs targeting opposite strands of the target site. Nicking of both DNA strands at the target site by a pair of Cas9 nickases leads to site-specific DSBs, while individual nicks are predominantly repaired by the high-fidelity base excision repair pathway (BER) as opposed to error-prone NHEJ. This strategy would minimize off-target mutagenesis by each Cas9n-sgRNA complex while maximizing on-target NHEJ comparable to wild-type Cas9 and would be analogous to dimeric zinc finger nucleases (ZFNs) and transcription activator-like effector nucleases (TALENs), where DNA cleavage relies upon the synergistic interaction of two independent specificity-encoding modules. ZFNs and TALENs generate DSBs through the proximity-induced dimerization of two FokI monomers, each of which nicks one DNA strand. Similarly, Applicants paired Cas9n with two sgRNAs targeting opposite strands of a desired locus. This 'double nicking' strategy would effectively magnify the targeting specificity of Cas9 by requiring simultaneous targeting by two sgRNAs.

Finally, to facilitate the co-delivery of multiple sgRNA, Applicants have developed a system for expressing pairs of sgRNAs under a single promoter. Applicants first studied the structural components of sgRNA critical for function, and secondly used this knowledge to inform the design of sequence-divergent new sgRNA scaffolds that facilitate tandem sgRNA transcription.

Materials and Methods

PCR amplification of U6-promoter-driven sgRNAs and tandem sgRNAs.

Spacer selection for targeting by Cas9 and subsequent generation of PCR amplicon was performed as described in Ran et al. Briefly, oligo ultramers consisting of U6 priming site, spacer sequence, and guide RNA scaffold were synthesized by IDT for amplification of U6-driven PCR cassettes for cellular transfections. In both cases, either QiaQuick (Qiagen) or EconoSpin (Epoch Life Sciences) spin columns were used to clean up PCR reactions prior to transfections. Tandem sgRNA are synthesized in a 2-round PCR as follows: Round 1: Amplification using U6 promoter as template, U6-Fwd primer (as in previous PCR expression cassette experiments for sgRNA delivery), and a modified Reverse primer that contains from 5' to 3' (in reverse complement direction): spacer-2, sgRNA modified scaffold, spacer-1, U6 priming region. Round 2: Amplifies using product from round 1 as template, using U6-Fwd primer as previously described, and a reverse primer 5' to 3' (in reverse complement direction): modified scaffold, spacer-2. After 2 rounds of PCR, the full-length tsgRNA product is purified and co-transfected with Cas9 for testing in cells. In both cases, either QiaQuick (Qiagen) or EconoSpin (Epoch Life Sciences) spin columns were used to clean up PCR reactions prior to transfections. A list of the sgRNAs used and their genomic targets can be found in Table E.

Cell Culture and Transfection

Human embryonic kidney (HEK) cell line 293FT (Life Technologies) was maintained in Dulbecco's modified Eagle's Medium (DMEM) supplemented with 10% fetal bovine serum (HyClone), 2 mM GlutaMAX (Life Technologies), 100U/mL penicillin, and 100 µg/mL streptomycin at 37° C. with 5% CO2 incubation. Cells are passaged at regular intervals and seeded onto 24-well plates (Corning) at a density of 120,000 cells/well, 24 hours prior to transfection. Cells were transfected using Lipofectamine 2000 (Life Technologies) at 80-90% confluency per manufacturer recommended protocol: A total of 400 ng Cas9 plasmid and 100 ng of U6-sgRNA PCR product was transfected per well of a 24-well plate. For double-nicking experiments or transfections involving more than a single guide, 100 ng of each sgRNA was transfected. In the case of tandem sgRNAs, 200 ng of purified U6-tsgRNA PCR product was transfected per well.

Human embryonic stem cell line HUES62 (Harvard Stem Cell Institute core) was maintained in feeder-free conditions on GelTrex (Life Technologies) in mTesR medium (Stemcell Technologies) supplemented with 100 ug/ml Normocin (InvivoGen). HUES62 cells were transfected with Amaxa P3 Primary Cell 4-D Nucleofector Kit (Lonza) following the manufacturer's protocol.

SURVEYOR Nuclease Assay for Genome Modification

293FT and HUES62 cells were transfected with DNA as described above. Cells were incubated at 37° C. for 72 hours post-transfection prior to genomic DNA extraction. Genomic DNA was extracted using the QuickExtract DNA Extraction Solution (Epicentre) following the manufacturer's protocol. Briefly, pelleted cells were resuspended in QuickExtract solution and incubated at 65° C. for 15 minutes, 68° C. for 15 minutes, and 98° C. for 10 minutes.

The genomic region flanking the CRISPR target site for each gene was PCR amplified (primers listed in Table G), and products were purified using QiaQuick Spin Column (Qiagen) following the manufacturer's protocol. 400 ng total of the purified PCR products were mixed with 2 µl 10× Taq DNA Polymerase PCR buffer (Enzymatics) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with SURVEYOR nuclease and SURVEYOR enhancer S (Transgenomics) following the manufacturer's recommended protocol, and analyzed on 4-20% Novex TBE poly-acrylamide gels (Life Technologies). Gels were stained with SYBR Gold DNA stain (Life Technologies) for 30 minutes and imaged with a Gel Doc gel imaging system (Bio-rad). Quantification was based on relative band intensities. Indel percentage was determined by the formula, $100\times(1-(1-(b+c)/(a+b+c))1/2)$, where a is the integrated intensity of the undigested PCR product, and b and c are the integrated intensities of each cleavage product.

Deep Sequencing to Assess Targeting Specificity

HEK 293FT cells were plated and transfected as described above, 72 hours prior to genomic DNA extraction. The genomic region flanking the CRISPR target site for each gene was amplified (primers listed in Table H) by a fusion PCR method to attach the Illumina P5 adapters as well as unique sample-specific barcodes to the target. PCR products were purified using EconoSpin 96-well Filter Plates (Epoch Life Sciences) following the manufacturer's recommended protocol.

Barcoded and purified DNA samples were quantified by Qubit 2.0 Fluorometer (Life Technologies) and pooled in an equimolar ratio. Sequencing libraries were then sequenced with the Illumina MiSeq Personal Sequencer (Life Technologies).

Sequencing data analysis, indel detection, and homologous recombination detection MiSeq reads were filtered by requiring an average Phred quality (Q score) of at least 30, as well as perfect sequence matches to barcodes and amplicon forward primers. Reads from on- and off-target loci were analyzed by performing Ratcliff-Obershelp string comparison, as implemented in the Python difflib module, against loci sequences that included 30 nucleotides upstream and downstream of the target site (a total of 80 bp). The resulting edit operations were parsed, and reads were counted as indels if insertion or deletion operations were found. Analyzed target regions were discarded if part of their alignment fell outside the MiSeq read itself or if more than 5 bases were uncalled.

Negative controls for each sample provided a gauge for the inclusion or exclusion of indels as putative cutting events. For quantification of homologous recombination, reads were first processed as in the indel detection workflow, and then checked for presence of homologous recombination template CCAGGCTTGG (SEQ ID NO: 201).

Flow Cytometric Analysis for Cas9 Self-Targeting Indel Induction

Cells were transfected as above using the Cas9 plasmid PX475 encoding SpCas9-t2a-GFP in the presence of guide RNAs targeting Cas9 itself. Three days following transfection, cells were washed once with PBS, trypsinized and triturated to single cell suspension, and re-suspended in PBS buffer supplemented with 5% FBS and 2 mM EDTA. Fluorescent intensity was subsequently measured using the Accuri C6 flow cytometer.

Northern blot analysis of sgRNA processing Cells were transfected as described above and incubated for 72 hrs at 37 C. RNA was subsequently extracted from the cells per mirVana miRNA isolation kit protocol (Life Technologies) to enrich for small RNAs. Purified small RNAs were resolved on a denaturing gel, transferred to BrightStar Positively-Charged Nylon Membrane (Ambion), and probed overnight using radioactive or biotinylated oligonucleotides targeted against specific sgRNA spacer sequences. Visualization was performed through the use of a Typhoon imager or Li-Cor CLx machine depending on probe modality.

Results

Cas9 Nickase Generates Efficient NHEJ with Closely Approximated Dual Guide RNAs

Figure 40A:
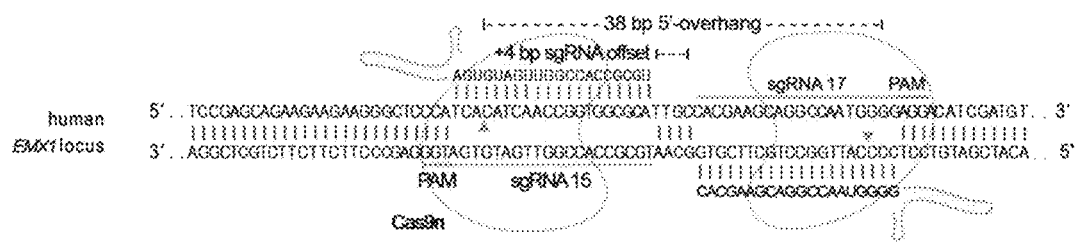
FIG. 40A-B shows paired sgRNAs induce indels via double-nicking with the nickase Cas9n (A) Schematic illustrating DNA double strand break using a pair of Cas9 D10A nickases (Cas9n). Two sgRNA target Cas9n to nick both strands of DNA. The D10A mutation renders Cas9 capable of only cleaving the DNA strand that is complementary to the sgRNA. The offset distance refers to the length of DNA between the closest ends of the paired sgRNAs, in this case 4 bp.
Figure 40B:
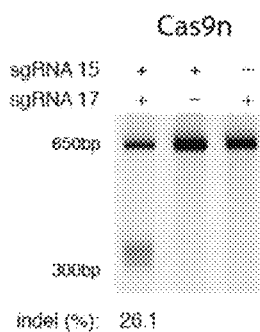

The targeting specificity and activity of the Cas9 nuclease is dependent on base-pairing interaction between the 20 nt guide sequence within the sgRNA and the target DNA. Applicants therefore reasoned that lengthening the guide sequence might increase guide:target basepairing and increase Cas9 targeting specificity. However, this failed to improve Cas9 targeting specificity as a majority of the lengthened guide sequence is processed back to a 20-nt length. Applicants therefore explored an alternate strategy for increasing the overall base-pairing length between guide sequence and DNA target based on simultaneous nicking of both strands of DNA by two separate Cas9-sgRNA complexes. Single-strand nicks by Cas9n are preferentially repaired by the BER pathway, which typically results in extremely low levels of mutagenesis. Applicants reasoned that two nicking enzymes directed by a pair of sgRNAs targeting opposite strands of a target locus, requiring double the number of sgRNA bases paired to target DNA, might still be able to mediate DSBs while loci nicked by a single sgRNA-Cas9 duplex would be perfectly repaired (schematized in FIG. 40A). By co-transfecting sgRNAs and the Cas9 D10A nickase (Cas9n), which nicks the strand of DNA complementary to the sgRNA, into human embryonic kidney (HEK293FT) cells, Applicants observed that whereas Cas9n in combination with guide pairs could efficiently induce indel formation, Cas9n with single guides alone did not result in detectable modification of the target locus by SURVEYOR assay (FIG. 40B).

Figure 41A:
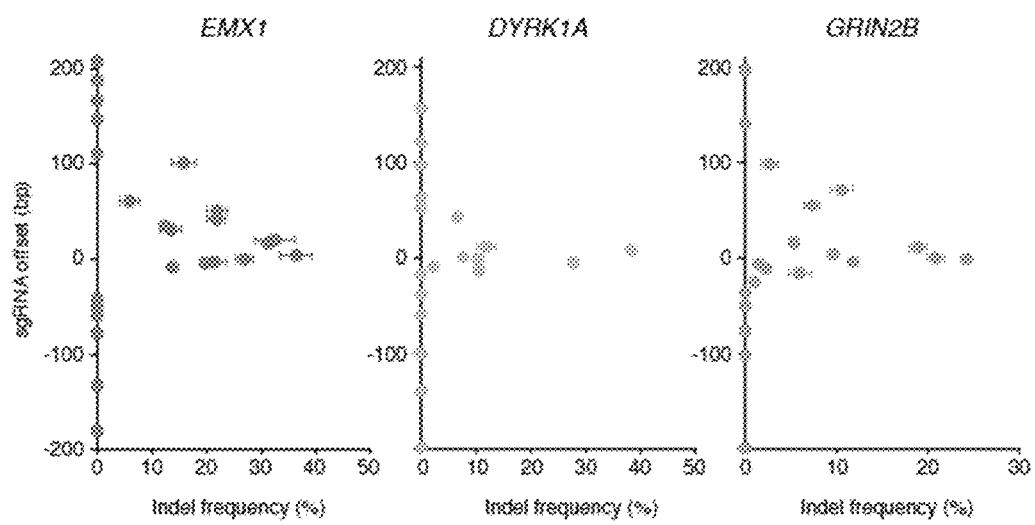
FIG. 41A-B. shows double-nicking is able to induce indels (A) Graphs showing indel frequency corresponding to indicated sgRNA offset distances across three different human genes: EMX1, DYRK1A, GRIN2B. (B) As an example, sequence of the human EMX1 genomic locus (SEQ ID NO: 444) targeted by Cas9n showing location of double nicks and resulting overhang. sgRNA target sites and PAMs are indicated by blue and magenta bars respectively. Below, selected sequences showing representative indels (SEQ ID NOS 446-452, respectively, in order of appearance).
Figure 41B:
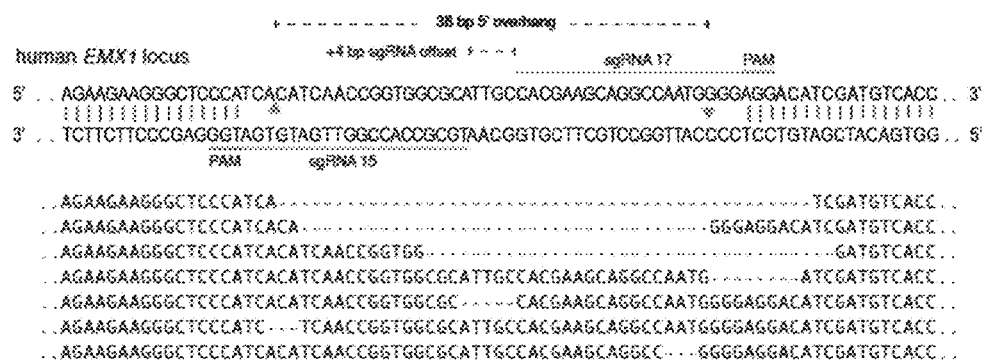

Given that the double-nicking strategy requires two Cas9n-sgRNA complexes to simultaneously target the same locus, steric hindrance is likely to be of concern in determining whether any pair of sgRNAs targeting opposite strands of DNA may be used for generating DSBs. To thoroughly characterize the parameters of paired guide RNAs that would be amenable to indel formation, Applicants systematically designed sgRNA pairings targeting three different human genes separated by a range of offset distances from −200 to 200 bp, creating both 5'- and 3'-overhang products, and tested each for NHEJ (pairs listed in Table D). Significantly, across all three genes, Applicants observed substantial indel frequency (up to 40%) for sgRNA pair offsets from −4 to 20 bp (FIG. 41A). Notably, indels formed by double-nicking with paired guide RNAs can result in larger and more varied types of mutations (representative indels observed by deep sequencing shown in FIG. 41B) than usually observed with single guides, which typically result in small deletions in the target sequence 4-6 bp upstream from the PAM. Occasionally, sgRNAs offset by up to 100 bp were observed to mediate on-target modification, which suggests a wide range of possible spacings for targeting. Importantly, all single sgRNAs transfections with wild-type Cas9, but not Cas9n, mediated efficient indel formation (summarized in Table D), consistent with relative spacing between guide pairs being the primary determinant of double-nickase induced genome modification. Impressively, double nickase indel frequencies were generally comparable to those mediated by wild-type Cas9 nuclease targeting the same locus. Taken together, these results indicate that double nicking can serve as a generalizable and predictable solution for efficiently mediating precisely targeted DSBs.

Double Nicking Allows High-Efficiency Homologous Recombination

While induction of double-stranded DNA breaks can introduce mutagenic indels at targeted genomic loci and mediate gene knockout, it can also be a mechanism by which to facilitate homology directed repair (HDR) to enable highly precise editing or gene replacement of target sites. Given the wealth of SNP data that is being generated and the increasing association with and appreciation of small or single base-pair mutations in disease tissues through genome- or exome-wide sequencing efforts, the ability to reliably and efficiently alter small genomic regions for downstream functional testing or disease modeling would prove enormously useful.

Figure 42A:
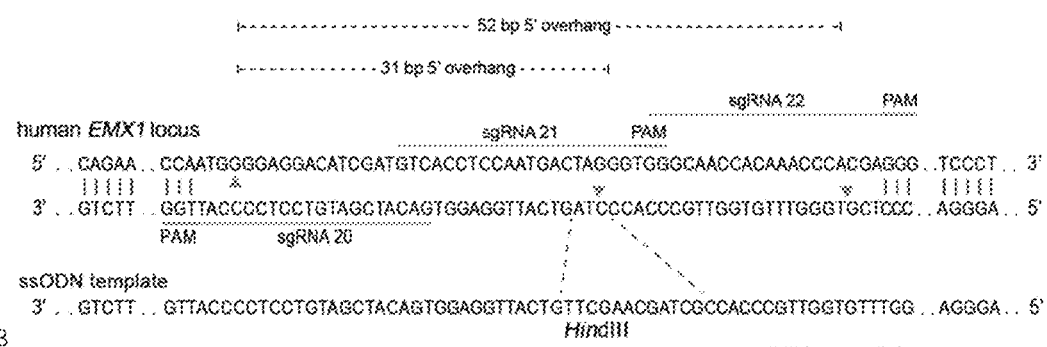
FIG. 42A-C shows double nicking strategy is able to facilitate homologous recombination (A) Schematic illustrating HDR targeted via a single stranded oligodeoxynucleotide (ssODN) template at a DSB created by a pair of Cas9n. Successful recombination at the DSB site introduces a HindIII restriction site.
Figure 42B:
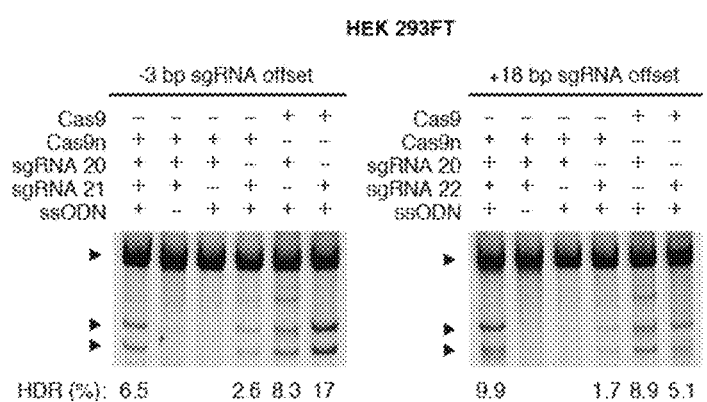

Previously, Applicants have shown that Cas9n, when used with a single sgRNA to nick DNA, can initiate HDR. However, HDR occurs at a much lower frequency when mediated by nicking rather than DSB, which can further vary among cell types. To test the efficiency of HDR with using a double-nicking strategy, Applicants targeted the human EMX1 locus with two pairs of sgRNAs offset by −3 and 17 bp (generating 31- and 52-bp 5' overhangs, respectively) and introduced a single-stranded oligonucleotide (ssODN) bearing a HindIII restriction site as the HDR repair template in order to introduce a restriction fragment length polymorphism (RFLP) into the genomic locus (FIG. 42A). Subsequent RFLP demonstrated that both sgRNA pairs were able to successfully introduce the HR template at frequencies significantly higher than those of single-guide Cas9n transfections and comparable to those of wild-type Cas9 (FIG. 42B).

Figure 42C:
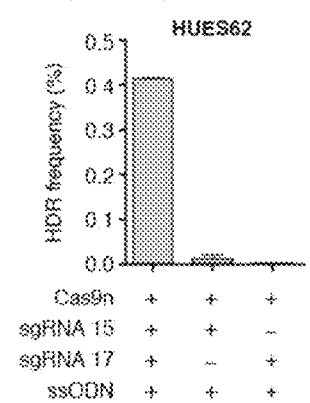

The growing interest and development in stem cells (ESC) or patient derived induced pluripotent stem cells (iPSC) biology represents simultaneously a key opportunity for generating new disease paradigms and developing new therapeutics, as well as an increasing need to develop ever more precise and efficient means of genome modification. While double-stranded breaks have been shown to efficiently facilitate HDR in ESC and iPSCs, there is still much interest in using nicking approaches for HDR in these sensitive applications due to their lower off-target activity. However, single nick approaches to inducing HDR in human embryonic stem cells using the CRISPR-Cas system have met with limited success. To improve HDR efficiency in ES cells, Applicants subsequently attempted double-nicking induced HDR in the HUES62 cell line observed significantly increased rates of incorporation of the HDR template (FIG. 42C).

Figure 43:
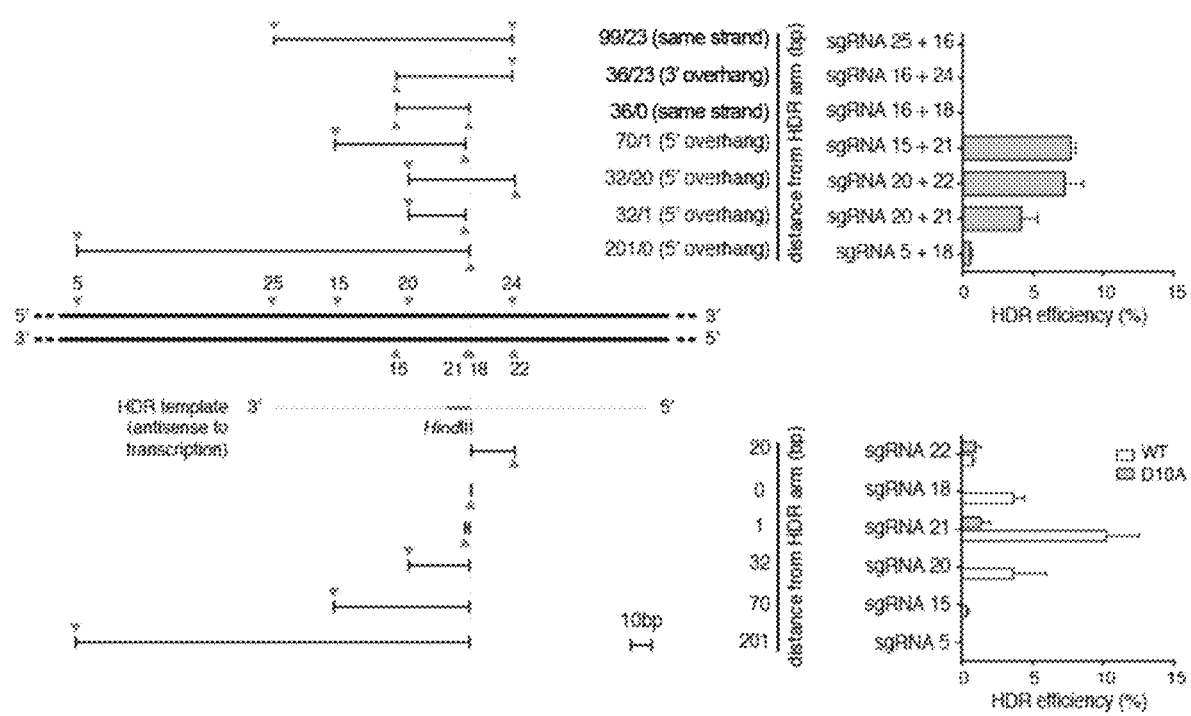
FIG. 43 shows characterization of double nicking spacing for homologous recombination. Schematic illustrating HDR with ssODN template (shown in blue, introduced HindIII site in red). Red arrowheads indicate binding site of respective sgRNA with black bars corresponding putative overhangs resulting from paired nicking activity. Panels at right show efficiency of recombination with the indicated sgRNA pairs, overhang length and type, and offset distances between paired sgRNAs.

Analogous to defining optimal sgRNA spacing for indel generation by double-nicking, Applicants next sought to determine the ideal parameters for potentiating HDR. Applicants posited that to most efficiently facilitate strand invasion and subsequent conversion, at least one of the sgRNA paired RNAs should be targeted close to the site of integration. Applicants tested a variety of sgRNA pairs wherein at least one of the targeted cleavage sites was close to the site of recombination (FIG. 43). Applicants observed that sgRNA pairs predicted to generate a 5' overhang with at least one target within 22 bp of the site of integration were able to incorporate the provided HDR template at frequencies comparable to wild-type Cas9 nuclease mediated HDR. In contrast, sgRNA pairs that targeted the same strand of DNA, spaced by negative offsets, or that had neither sgRNAs close to the site of integration were unable to facilitate HDR at detectable levels.

Double Nicking Mediates Highly Specific Genome Editing

Having shown that double-nicking mediates high efficiency induction of both NHEJ and HDR at levels comparable to those induced by wild-type Cas9, Applicants next sought to determine whether this approach results in improved specificity over Cas9 through quantification of off-target activities. Applicants co-delivered Cas9n with two sgRNAs spaced by a 23-bp offset to target the human EMX1 locus (FIG. 44A). As expected, this configuration of paired sgRNAs resulted in on-target indel levels comparable to those of wild-type Cas9 transfected with either sgRNA singly (FIG. 44B, left panel). Strikingly, Applicants did not detect any modification by SURVEYOR assay at one of the sgRNA 1 off-target sites (OT-4) in the case of double-nicking where the wild-type Cas9 showed 10% modification (FIG. 43, right panel). Applicants subsequently used deep sequencing to assess modification at 5 different sgRNA 1 off-target loci and observed significant mutagenesis at all sites with wild-type Cas9+sgRNA 1 alone (FIG. 43). In contrast, off-target cleavage by Cas9n was barely detectable and difficult to distinguish from sequencing error. Normalized to a specificity ratio (on- to off-target indel percentage ratio), Cas9n with two sgRNAs could achieve over 100-fold greater specificity relative to wild-type Cas9 (FIG. 43).

In summary, the strategy of using the nickase Cas9n with closely approximated pairs of guide RNAs is as efficient at inducing NHEJ and facilitating HDR as the wild-type nuclease, while achieving much higher targeting specificity. Furthermore, the relatively wide range of off-set distances between the double guides that is compatible with robust activity renders double-nicking an attractive and easily implemented method.

Systematic Mutagenesis of sgRNA Architecture Identifies Regions for Further Optimization One of the critical elements of the type II CRISPR-Cas nuclease system is the trans-activating crRNA (tracrRNA), which shares partial sequence homology and base-pairs with the repeat region of the crRNA and is required for the assembly of the final Cas9-crRNA-tracrRNA complex. While elements from tracrRNA and crRNA have been adapted to form a single artificially linked sgRNA (hereafter referred to as the wild-type sp85 scaffold) (Jinek Science, HSU), the effects of sgRNA scaffold modification and tolerance towards mutagenesis has in general not been comprehensively studied.

Figure 45A:
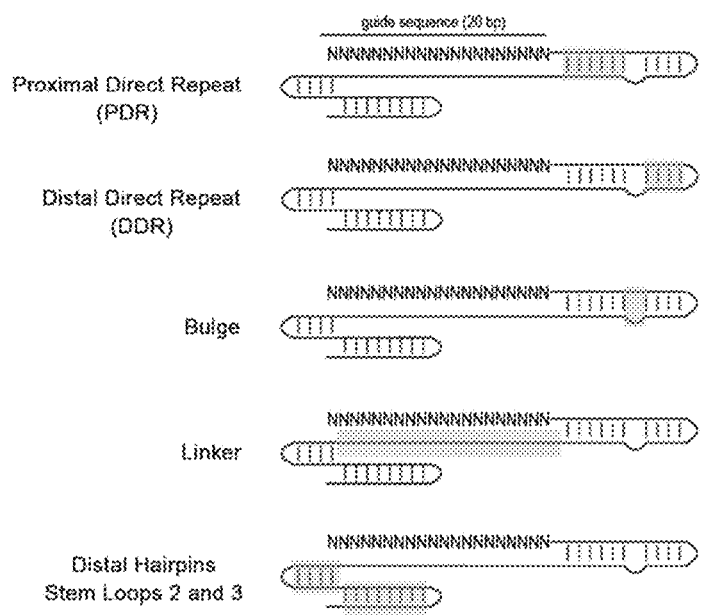
FIG. 45A-B shows rational mutagenesis of sgRNA architecture. (A) Schematic of the chimeric sgRNA architecture with 20-bp guide sequence encoding for the target specificity. The different regions of the sgRNA interrogated by mutagenesis are named and highlighted above. (B) Description of mutations made and corresponding indel activity at human EMX1 locus.

The sgRNA scaffold can be functionally and structurally divided into several components. The crRNA portion includes the guide sequence and the direct repeat regions. The tracrRNA begins with a 14-nt anti-repeat that partially basepairs with the direct repeat to form a stem loop (stem loop 1), and further contains an 18-bp linker to two additional stem loops (stem loop 2 and 3). Importantly, there are several unpaired bases within the direct repeat and tracrRNA anti-repeat stem loop 1, which create a bulge separating the proximal and distal direct repeat regions (FIG. 45A). Applicants hypothesized that optimization of the sgRNA architecture could improve the genome editing activity of Cas9 and subsequently performed a systematic interrogation of the sgRNA scaffold to gain a better functional understanding of each component.

Figure 45B:
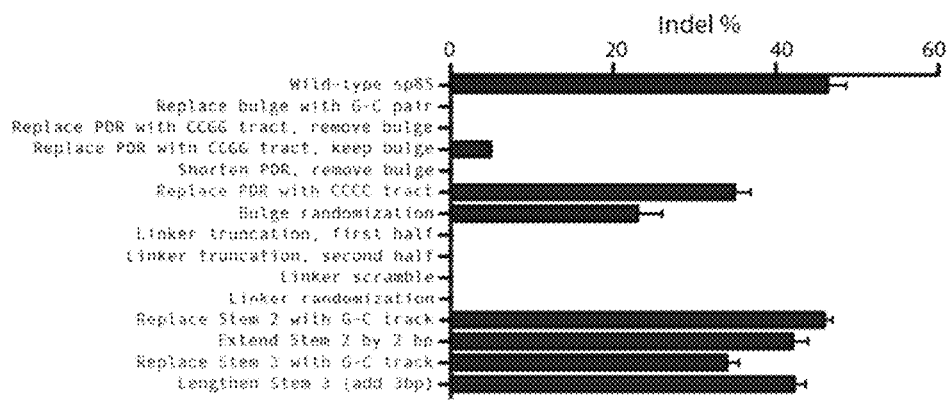

Applicants first identified regions of the sgRNA likely important for binding and recognition by Cas9. Strikingly, replacement of the stem loop 1 bulge with perfectly base-pairing sequences completely abolished Cas9-mediated indel activity, while substituting other non-base pairing nucleotides and thus retaining the bulge structure still allowed maintenance of modest activity. Within stem loop 1, mutations in the proximal direct repeat was not uniformly tolerated: whereas shortening the proximal direct repeat duplex or mutating the poly-T tract to mixed pyrimidines and purines abolished Cas9 activity, mutating the poly-T tract to pyrimidines alone was well-tolerated (FIG. 45B). Finally, truncation, shuffling, or randomization of the 18-bp linker sequence likewise resulted in complete loss of activity. However, it is possible that this longer linker forms additional secondary structures not predicted by RNA-folding, and further finer mapping mutagenesis experiments will be needed to elucidate its structural role.

Consistent with previous studies showing that stem loops 2 and 3 are not critical for Cas9 activity even though they significantly improve cleavage efficiency, alterations of the distal hairpins are largely well tolerated. For instance, both stem loops 2 and 3 could be largely replaced with G-C basepairs or extended in length without adversely affecting activity (FIG. 45B). Together, these findings suggest that while the proximal direct repeat, bulge, and linker may be involved in Cas9 recognition and binding, the two distal hairpins are likely more important for sgRNA folding and stability. Indeed, simultaneous stabilization of both distal hairpins along with mutating the distal direct repeat region was well tolerated, yielding indel activity comparable to the original scaffold (FIG. 46).

U6-Driven Tandem Guide RNAs are Able to Deliver Two Functional sgRNAs

The programmable nature of the CRISPR-Cas system by small RNAs makes it inherently more tractable than purely protein module-based tools such as ZFNs and TALENs for applications requiring multiplex targeting. Indeed, Applicants and others have already shown that this can be readily achieved by co-delivering multiple sgRNAs in a variety of applications. While this approach works well for in vitro studies, in vivo or therapeutic applications would benefit from using a single vector system such as AAV. One of the major limitations of such systems is the amount genetic information that can be delivered (~4.8 kb for AAV), above which the efficiency of AAV particle assembly rapidly declines. Furthermore, the alternative approach of using pooled delivery of independently transcribed sgRNAs is stochastic in nature and less reproducible than a single vector system, especially in applications where target saturation may not be desired or achievable. Many endogenous microbial CRISPR systems naturally occur as a single-promoter driven array of direct repeats interspaced by protospacers, which are transcribed as a single transcript prior to their processing into individual mature crRNAs. However, given that the chimeric sgRNA system works much more efficiently than the native crRNA:tracrRNA duplex, Applicants sought to develop a system by which a single promoter may drive the expression of multiple sgRNAs arranged in tandem, similar to the native microbial CRISPR loci.

Figure 47A:
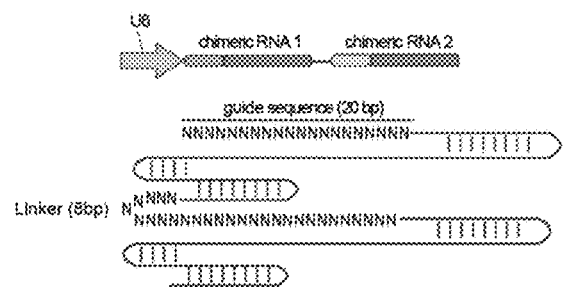
FIG. 47A-C shows U6-driven tandem guide RNAs are able to efficiently target two genomic loci. (A) Schematic illustrating a tandem sgRNA (2 sgRNAs connected by a linker) driven by a single U6 promoter. Images of PAGE gels of SURVEYOR assays demonstrate that tsgRNAs using modified RNA scaffolds delivered with the nickase Cas9n or wild-type Cas9 are able to induce genomic indels or microdeletions, (B and C, respectively) with frequencies comparable to co-delivery of two independent sgRNAs.
Figure 47B:
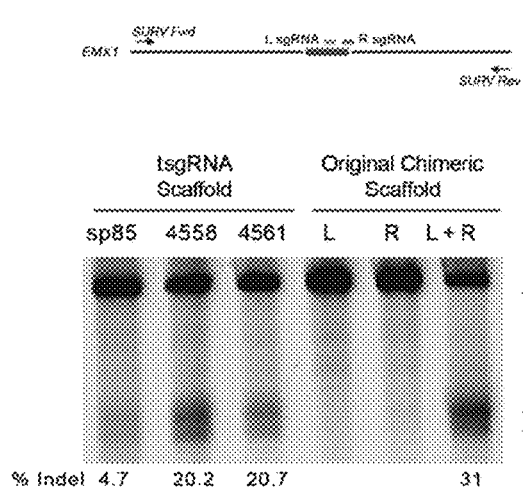
Figure 47C:
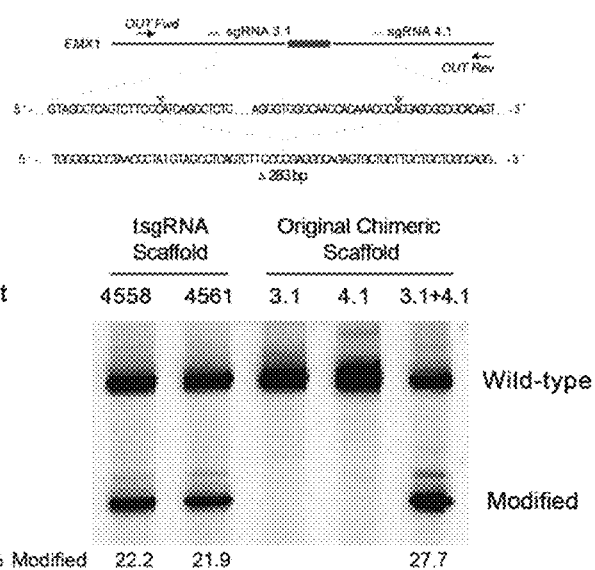

Applicants hypothesized that structurally stable sgRNA scaffolds would be more likely to fold into independent, functionally active units when multiple units are transcribed together in the same transcript. To test this, Applicants began by inserting an 8-nt linker between tandem adjacent sgRNAs (FIG. 47A); for each the invariant sgRNA scaffold (non-guide region), we used either pairs of original sp85 sgRNA or scaffolds with stabilized distal hairpins (4558 and 4561). Strikingly, Applicants observed that when the tsgRNAs targeted closely approximated genomic loci previously shown to induce indels with Cas9 nickase, the stabilized scaffolds 4558 and 4561 were able to induce indels at frequencies similar to those induced by co-transfected individual sgRNAs (FIG. 47B). Moreover, when paired with wild-type Cas9 nuclease, tsgRNAs were similarly able to induce genomic microdeletions in the human EMX1 locus at levels comparable to multiplexed, individual sgRNAs (FIG. 47C).

Optimization of Tandem sgRNA Scaffold Architecture

Figure 48:
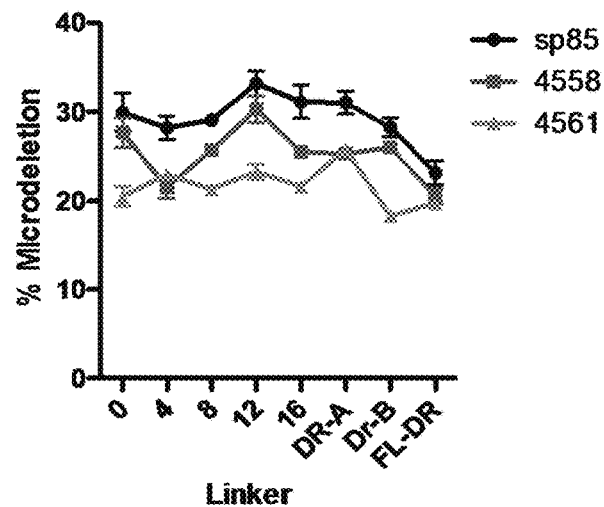
FIG. 48 shows optimization of tandem sgRNA linker length and structure. Gel quantification of band intensities from PCR amplification of the human EMX1 target loci comparing relative abundance of wild-type and modified DNA with varying tandem linkers of 0, 4, 8, 12, 16 base pairs, half direct repeat or full direct repeat (listed in bottom panel) (SEQ ID NOS 462-466, for linkers 8 nt or longer respectively, in order of appearance).

Having shown that sgRNAs transcribed in tandem are able to simultaneously target two genomic loci, Applicants next sought to determine the optimal linker for connecting the adjacent guide-scaffolds. Applicants designed tsgRNAs using linker sequences of varying lengths in a genomic microdeletion assay with two sgRNAs. Given that endogenous individual protospacers are separated by 36-nt long direct repeat sequences, we also tested linkers that encoded for either half of a direct repeat or a full-length direct repeat. Interestingly, Applicants observed there was not a strong correlation between linker sequence length and the efficiency of genome modification, even in cases where there was no linker separating the distal end of the sgRNA from the guide sequence of the second (FIG. 48). However, it appeared that inclusion of direct repeat sequences adversely affected activity while there's a modest preference towards 12-nt linker length for cleavage efficiency, although more studies are needed to confirm these observations.

Figure 49A:
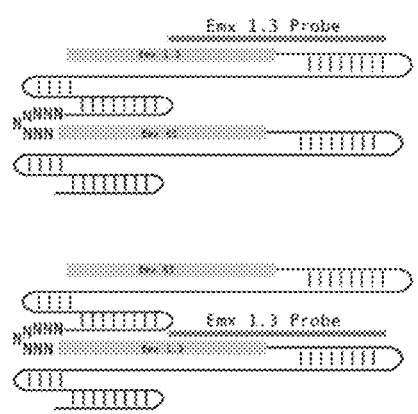
FIG. 49A-C shows tandem guide RNAs are efficiently processed in only the first position. (A) Schematic showing tandem guide RNA scaffolds encoding for either EMX1.3 or EMX63 in the first or second position with position of Emx1.3 Northern probe shown in red. (B) Northern blot analysis examining processing of tandem sgRNA in cells. (C) SURVEYOR assay examining independent sgRNA activity targeting two genomic loci, DYRK1A and GRIN2B. The three left lanes in both panels are tsgRNAs targeting DYRK1A in the first position and GRIN2B in the second position. Conversely, three right lanes target GRIN2B first and then DYRK1A second.
Figure 49B:
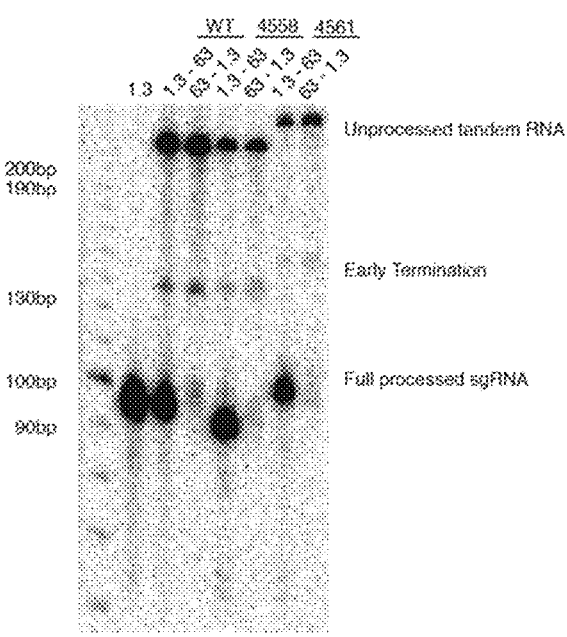

Processing of Tandem sgRNAS into Individual Subunits Occurs, is Position-Dependent An obvious question to transcribing multiple sgRNAs under the same promoter is whether or not the co-transcribed tandem sgRNAs are processed to individual guide-scaffold units. To answer this, Applicants designed tandem sgRNAs that carried the same guide in either the first or second position (FIG. 49A). Subsequent Northern blot analyses of transfected cells showed three distinct RNA species, corresponding to a 200+nt (likely unprocessed tandem RNA transcript), a ~140 nt transcript (consistent with premature transcriptional termination signaled by the poly-U tract in the second scaffold), and a ~100 nt fully processed sgRNA (FIG. 49B).

Figure 49C:
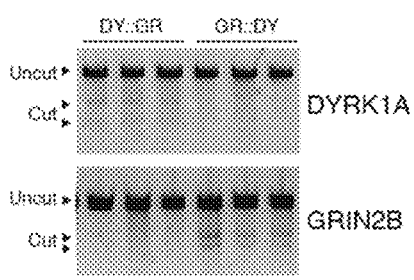

When the target spacer is in the first position in the tsgRNA, Applicants observed abundant fully processed sgRNA of the same size as individually U6-transcribed sgRNAs. However, when placed in the second position, there were only trace amounts of fully processed sgRNA present. Consistent with this, Applicants observed that reversing spacer order in microdeletion assays could significantly alter the efficiency of genomic modification (data not shown). Furthermore, when testing other pairs of sgRNAs targeting different genomic loci, Applicants observed that the same guide sequence typically has better activity when placed in the first rather than the second position (FIG. 49C). These observations suggest that while most spacers are compatible with a single guide transcript, the sequence of the second spacer may be more likely to influence activity of the second sgRNA in the context of a tandem sgRNA.

Figure 50A:
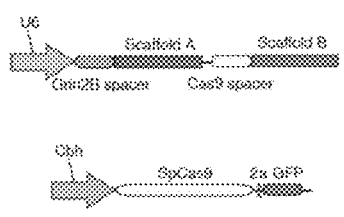
FIG. 50A-C shows optimization of tsgRNA scaffold pairings. (A) Schematic of tandem scaffold design with first spacer targeting Grin2B using Scaffold A and second spacer targeting Cas9 itself using Scaffold B in a Cas9-T2A-GFP expressing plasmid. (B) Single U6-guide controls show both an increase in the percentage of GFP-negative cells as well as a decrease in mean fluorescence intensity of the positive fraction. (C) 12×12 matrix of tandem scaffold pairings and results of subsequent analyses by flow cytometry.
Figure 50B:
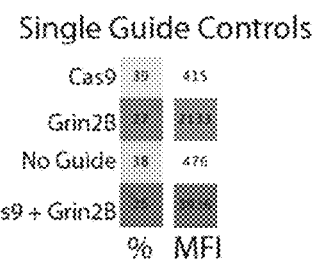

Pairing of Sequence-Divergent Scaffolds Results in Better Second Spacer Activity To optimize the activity of the second spacer, Applicants devised an assay for assessing its activity by fluorescence cytometry. By targeting the second guide against Cas9 itself in a plasmid expressing Cas9-2A-GFP, Applicants can assess indel activity by measuring the fluorescence fraction and intensity of transfected cells (FIG. 50A). Applicants observed that transfecting cells with single sgRNAs targeting Cas9 or co-delivering Cas9-targeting sgRNA with another sgRNA significantly reduced the mean fluorescence intensity (MFI) of the Cas9-2A-GFP-transfected GFP-positive fraction, whereas cells transfected with Cas9-2A-EGFP and a non-Cas9-targeting sgRNA maintained high MFI (FIG. 50B).

Figure 50C:
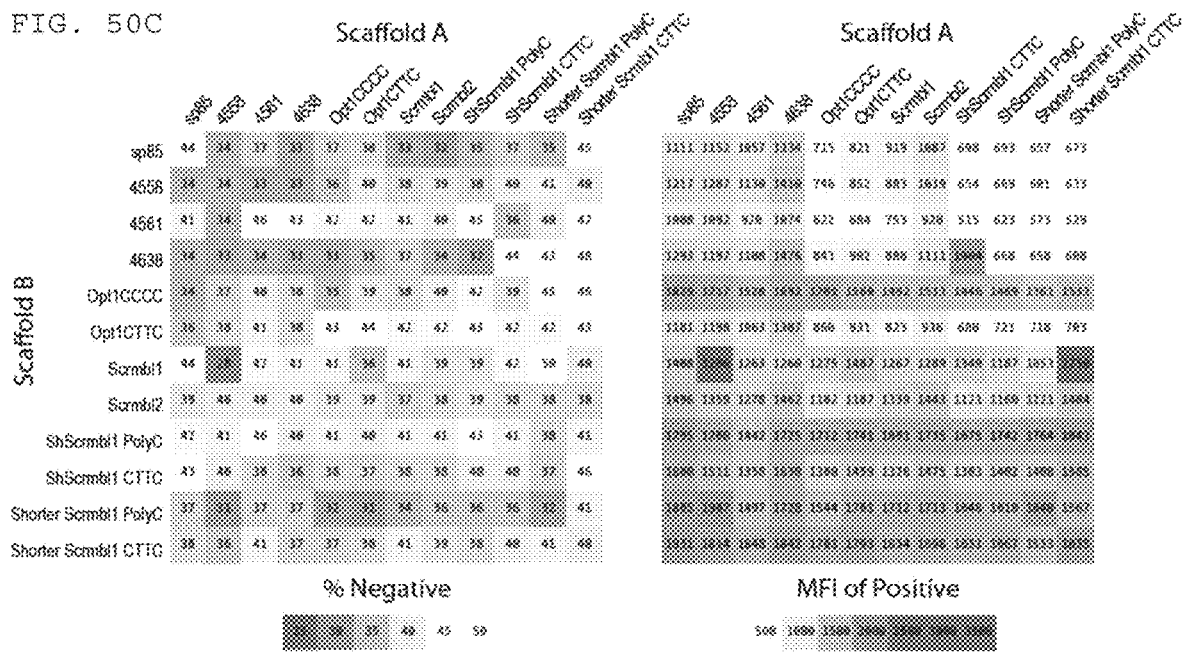
Figure 51:
FIG. 51 shows tandem pairs between divergent scaffolds improve second spacer activity. Sequence alignment of the sgRNA scaffolds used in the previous study to the sp85 scaffold (SEQ ID NOS 467-479, respectively, in order of appearance).

Given that each sgRNA scaffold needs to fold into a stable secondary structure, Applicants hypothesized that a potential reason for the decreased activity of the second spacer may be due to secondary structure interactions not within a single but between the two sgRNA scaffolds. Applicants surmised that the use of divergent, minimally homologous sgRNA scaffolds that are less likely to base-pair with each other could reduce interactions between the pair and aid individual folding. To test this hypothesis, Applicants designed a set of twelve distinct sgRNA scaffolds, each with the first guide targeting GRIN2B and the second targeting Cas9, and performed a pair-wise comparison of all scaffold combinations. Subsequent flow-cytometric analyses identified five potential candidate sgRNA scaffolds that significantly reduced both the MFI of the GFP-positive fraction as well as the overall percentage of GFP-positive cells; the levels of reductions are similar to those obtained by transfecting singly transcribed Cas9-targeting sgRNA (FIG. 50C). Consistent with the notion that inter-scaffold interactions may be disrupting proper sgRNA folding and processing, most of the five scaffolds showed relatively poor activity when transcribed in tandem with highly homologous sgRNAs. Indeed, sequence alignment analysis of the twelve scaffolds showed that the pairs of tandem scaffolds that showed the highest activity had the greatest sequence divergence between the two sgRNAs (FIG. 51). In summary, tandem-arrayed sgRNAs represents a potentially useful approach for co-delivery of two sgRNAs in a single RNA transcript. While some guide sequences appear to function well in the second position, optimization of the sgRNA architecture to maximize inter-scaffold sequence divergence and improve structural stability will likely aid processing and activity of tandem sgRNAs.once with PBS, trypsinized and triturated to single cell suspension, and re-suspended in PBS buffer supplemented with 5% FBS and 2 mM EDTA. Fluorescent intensity was subsequently measured using the Accuri C6 flow cytometer.

Discussion

Double Nicking Approach to Genome Editing with CRISPR

Specificity is of paramount importance when introducing permanent genomic alterations, especially for highly sensitive applications such as gene therapy or studies aimed at linking causal genetic variants with biological processes or disease phenotypes. Designer nucleases such as ZFNs62 and TALENs63 have reported off-target activities over 15%. Given that both approaches are based on complex, evolved protein-DNA interactions, prediction or optimization of specificity through protein engineering can prove quite challenging. Nonetheless, efforts have been made to increase TALEN specificity, such as extending the number of bases recognized by protein monomers.

Strategies for improving the targeting accuracy of the CRISPR-Cas system can optimize either of its two essential components—the Cas9 nuclease or sgRNA. While Applicants' work has shown that extending the guide length does not improve specificity, it has recently been reported that shorter guide lengths could potentially significantly decrease non-specific activity at known off-target sites. However, given that shorter guide sequence also increases the number of possible similar targets across a genome, it remains to be seen whether this strategy will decrease overall genome-wide off-target mutation frequencies. Here, Applicants have demonstrated that combining two sgRNAs with Cas9 nickases is able to effectively generate DSBs while avoiding mutagenic events arising from single-stranded DNA break mutations as they are typically repaired with high fidelity.

In the context of delivering gene repair or replacement templates, Cas9n nicking of DNA with a single sgRNA has been previously shown to facilitate HDR without generating indels. However, it is substantially less efficient at doing so relative to wild-type Cas9, and can be susceptible to differences in HDR efficiency among different cell types 48,52. However, Applicants have demonstrated that using two closely approximated guides to target the Cas9n nickase to the same genomic locus can mediate HDR at high efficiencies while keeping off-target modifications to background levels. Moreover, the characterization of spacing parameters governing successful Cas9 double nickase-mediated gene targeting reveals an effective window of over 100-bp in which sgRNAs targeting opposite strands can be paired for double-nicking applications, allowing for a high degree of flexibility in their design. Applicants have additionally demonstrated that double nicking-mediated indel frequencies are comparable to those of wild-type Cas9 modification at multiple loci in both human and mouse cells, confirming the reproducibility of this strategy for high-precision genome engineering.

Though the ability to potentiate specific, targeted indel mutations greatly enables functional analyses by gene knock-out, the use of double-nicking to precisely target homologous recombination has practical implications in the generation of model systems and organisms. It has been reported that blastocyst injection of Cas9 nuclease with sgRNA and HDR template can generate conditional and reporter mice in a single step. While this finding immensely streamlines an otherwise laborious and prolonged process, the relatively high dose of Cas9 mRNA and guide RNA injected into each blastocyst can become a real concern for off-target modifications. Indeed, concurrent work by collaborators and other members of the lab has already demonstrated that analogous blastocyst delivery of Cas9n with two sgRNAs can induce efficient targeted gene modification at the mouse Mecp2 locus. Further studies investigating the efficiency and specificity of the double-nicking approach in facilitating homologous recombination in the context of mouse model generation will be immensely informative.

While significant off-target mutagenesis has been previously reported for Cas9 nucleases in human cells, the double-nicking approach provides a generalizable solution for rapid and accurate genome editing. Even though double-nicking is conceptually similar to ZFN- and TALEN-based genome editing systems, which utilize hemi-nuclease domains to induce DSBs, the ease, flexibility, and improved predictably of using an RNA-guided DNA targeting system significantly increases its potential downstream applications. Given that it has been observed that cooperative nicking at off-target sites can still occur in the context of ZFNs and TALENs, significant and thorough characterization of the true genome-wide off-target activity of the CRISPR-Cas system is still prerequisite to its further development as means of efficient, ultrahigh-precision genome editing. Even so, Applicants believe that double nicking with Cas9n represents a solid step-forward in establishing CRISPR-Cas system as a versatile tool for genome manipulation in both basic science research and medicine.

sgRNA Optimization and Creation of Tandem Guide RNAs

Following the initial derivation of the chimeric sgRNA41 from elements of tracrRNA and crRNA, the subsequent sp85 sgRNA scaffold40,48 was developed from full-length tracrRNA and has become the most commonly architecture used for genome editing applications. However, aside from relatively few studies aimed at improving sgRNA stability, there has not yet been any reported fine mapping of sgRNA structure-function relationships or optimization of the sgRNA architecture through sequence replacement. The targeted, functional studies Applicants performed have identified a number of regions within the sgRNA that may be amenable to further modification or addition of functional groups that may broaden the range of applications for the CRISPR-Cas9 system. Notably, despite having tested a wide-range of scaffold modifications, Applicants observed few changes that significantly improve the indel activity of Cas9. Further elucidation of the structure-function relationship of the sgRNA interacting with its nuclease will be informative in making more targeted changes to both the sgRNA and Cas9 simultaneously that may allow further gains in on-target efficiency.

The ribonuclease RNAseIII has been shown as necessary for processing and maturation of the crRNA following binding to tracrRNA in the type II CRISPR systems. However, processing at the 5' end remains largely unknown in both microbial and eukaryotic contexts. A recent report investigating processing of *Neisseria* spp. CRISPR RNA processing identified transcriptional promoters located in the direct repeat preceding each spacer sequence that drives transcription of individual crRNA units. Applicants have previously observed that lengthening of the spacer sequence to 30-nt does not result in a longer sgRNA: Northern blot analysis shows still the same length transcript as with sgRNAs with 20-nt guide sequences. Furthermore, Applicants' observation that sgRNA units can be fully processed—albeit at low levels—from the second position of the tsgRNA might point to the existence of potential endonucleases involved with end-maturation of sgRNAs.

RNA-sequencing analyses have shown that spacers located at the promoter-proximal end of the CRISPR arrays tend to be of higher abundance than those located more distally, suggesting that transcriptional processivity may be an important parameter in determining relative efficiency of mature crRNA units. Consistent with Applicants' findings, this study also reports that certain spacer sequences predicted to form secondary interactions with adjacent RNA are often under-represented. Thus, while developing synthetic CRISPR arrays, consideration of spacer sequence is likely to become of increasing importance.

There have been a number of recent studies using CRISPR-Cas9 lentiviral libraries for genome-wide knockout screens that have shown greater reproducibility and sensitivity than analogous RNAi-libraries. The ability to simultaneously deliver more than a single guide RNA on a single vector would be particularly interesting in the context of lentiviral screening methodologies, which would open the door for both high-throughput deletion as well as pairwise screens. In the context of commonly used shRNA libraries, the propensity of lentivirus to recombine has limited our ability to drive expression of multiple short RNAs from a single vector with the requirement of utilizing multiple unique promoters. Although it remains to be seen how many sgRNAs can be efficiently arrayed in tandem, this approach allows for a single promoter to drive expression of at least two sgRNAs. Furthermore, the knowledge that sequence-divergent yet structurally similar sgRNA scaffolds can remain active will be useful in a variety of applications where recombination between structural elements has been a limitation.

TABLE D

List of sgRNA pairs to identify optimal spacing.

| Gene | Overhang Length (bp) | Overhang Type | Offset Length (bp) | Left sgRNA ID | Right sgRNA ID | Cas9n with left and right sgRNA indel (%) | left sgRNA guide sequence (5' to 3') | left sgRNA target site PAM | left sgRNA Cas9 indel with wildtype (%) | right sgRNA guide sequence (5' to 3') | right sgRNA target site PAM | right sgRNA Cas9 indel with wildtype (%) |
|---|---|---|---|---|---|---|---|---|---|---|---|---|
| EMX1 | 148 | 3' | -182 | 15 | 4 | N.D. | TGCGCCACCGGTTGATGTGA | TGG | 13.15 | AGGCCCCAGTGGCTGCTCTG | GGG | 27.29 |
| EMX1 | 101 | 3' | -135 | 23 | 1 | N.D. | ACTCTGCCCTCGTGGGTTTG | TGG | 24.7 | GAGTCCGAGCAGAGAAGAA | GGG | 21.9 |
| EMX1 | 48 | 3' | -82 | 23 | 17 | N.D. | ACTCTGCCCTCGTGGGTTTG | TGG | 24.7 | CACGAAGCAGGCCAATGGGG | AGG | 13.57 |
| EMX1 | 25 | 3' | -59 | 10 | 13 | N.D. | CAAACGGCAGAAGCTGGAGG | AGG | 26.15 | GGAGCCCTTCTTCTTCTGCT | CGG | 33.17 |
| EMX1 | 15 | 3' | -49 | 4 | 5 | N.D. | AGGCCCCAGTGGCTGCTCTG | GGG | 27.29 | GGGGCACAGATGAGAAACTC | AGG | 26.56 |
| EMX1 | 8 | 3' | -42 | 7 | 9 | N.D. | TGAAGGTGTGTTCCAGAAC | CGG | 36.02 | GCCGTTTGTACTTTGTCCTC | CGG | 30.49 |
| EMX1 | 26 | 5' | -8 | 9 | 39 | 13.7 ± 1.27 | GCCGTTTGTACTTTGTCCTC | CGG | 9.82 | GGCAGAGTGCTGCTTGCTGC | TGG | 26.15 |
| EMX1 | 30 | 5' | -4 | 9 | 10 | 19.72 ± 0.32 | GCCGTTTGTACTTTGTCCTC | CGG | 30.49 | CAAACGGCAGAAGCTGGAGG | AGG | 22.06 |
| EMX1 | 31 | 5' | -3 | 6 | 7 | 21.35 ± 2.23 | TCACCTGGGCCAGGGAGGGA | GGG | 10.75 | TGAAGGTGTGTTCCAGAAC | CGG | 36.02 |
| EMX1 | 34 | 5' | 0 | 15 | 16 | 26.89 ± 1.54 | TGCGCCACCGGTTGATGTGA | TGG | 13.15 | TTGCCACGAAGCAGGCCAAT | GGG | 13.77 |
| EMX1 | 38 | 5' | 4 | 15 | 17 | 36.31 ± 2.97 | TGCGCCACCGGTTGATGTGA | TGG | 14.49 | CACGAAGCAGGCCAATGGGG | AGG | 13.57 |
| EMX1 | 51 | 5' | 17 | 5 | 7 | 31.12 ± 0.25 | GGGGCACAGATGAGAAACTC | AGG | 26.56 | TGAAGGTGTGTTCCAGAAC | CGG | 36.02 |
| EMX1 | 54 | 5' | 20 | 5 | 8 | 32.41 ± 3.68 | GGGGCACAGATGAGAAACTC | AGG | 26.56 | AGTGTGTTCCAGAACCGG | AGG | 35.53 |
| EMX1 | 65 | 5' | 31 | 6 | 10 | 13.45 ± 1.99 | TCACCTGGGCCAGGGAGGGA | GGG | 10.75 | CAAACGGCAGAAGCTGGAGG | AGG | 26.15 |
| EMX1 | 69 | 5' | 35 | 6 | 11 | 12.39 ± 1.29 | TCACCTGGGCCAGGGAGGGA | GGG | 10.75 | CGGCAGAAGCTGGAGGAGGA | GGG | 22.06 |
| EMX1 | 76 | 5' | 42 | 9 | 14 | 21.71 ± 1.66 | GCCGTTTGTACTTTGTCCTC | CGG | 30.49 | AGGGCTCCCATCACATCAAC | CGG | 41.27 |
| EMX1 | 85 | 5' | 51 | 5 | 10 | 21.89 ± 1.88 | GGGGCACAGATGAGAAACTC | AGG | 26.56 | CAAACGGCAGAAGCTGGAGG | AGG | 26.15 |
| EMX1 | 95 | 5' | 61 | 6 | 12 | 5.88 ± 1.81 | TCACCTGGGCCAGGGAGGGA | GGG | 10.75 | TGAGTCCGAGCAGAAGAAGA | AGG | 29.06 |
| EMX1 | 135 | 5' | 101 | 9 | 14 | 15.78 ± 2.19 | GCCGTTTGTACTTTGTCCTC | CGG | 30.49 | AGGGCTCCCATCACATCAAC | CGG | 41.27 |
| EMX1 | 145 | 5' | 111 | 6 | 16 | N.D. | TCACCTGGGCCAGGGAGGGA | GGG | 10.75 | TTGCCACGAAGCAGGCCAAT | GGG | 13.77 |
| EMX1 | 181 | 5' | 147 | 6 | 18 | N.D. | TCACCTGGGCCAGGGAGGGA | GGG | 10.75 | TCACCTCCAATGACTAGGGT | GGG | 25.14 |
| EMX1 | 201 | 5' | 167 | 5 | 18 | N.D. | GGGGCACAGATGAGAAACTC | AGG | 26.56 | TCACCTCCAATGACTAGGGT | GGG | 25.14 |

TABLE D-continued

List of sgRNA pairs to identify optimal spacing.

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| EMX1 | 222 | 5' | 188 | 6 | 19 | N.D. | TCACCTGGGCCAGGGAGGGA | GGG | 10.75 | GGCAGAGTGCTGCTTGCTGC | TGG | 10.75 |
| EMX1 | 242 | 5' | 208 | 5 | 19 | N.D. | GGGGCACAGATGAGAAACTC | AGG | 26.56 | GGCAGAGTGCTGCTTGCTGC | TGG | 17.22 |
| DYRK1A | 164 | 3' | -198 | 34 | 47 | N.D. | ATCTGGTCAGAATATGATAA | AGG | 10.65 ± 2.05 | AACCTCACTTATCTTCTTGT | AGG | 19.02 ± 4.32 |
| DYRK1A | 105 | 3' | -139 | 35 | 47 | N.D. | GTCACTGTACTGATGTGAAT | TGG | 16.71 ± 2.47 | AACCTCACTTATCTTCTTGT | AGG | 17.04 ± 1.30 |
| DYRK1A | 66 | 3' | -100 | 36 | 48 | N.D. | CATCTGAAGGCCAGCAGCAT | TGG | 8.82 ± 1.01 | CTCACTTATCTTCTTGTAGG | AGG | 18.79 ± 2.71 |
| DYRK1A | 25 | 3' | -59 | 35 | 49 | N.D. | GTCACTGTACTGATGTGAAT | TGG | 17.83 ± 0.43 | CCATGCTGCTGGCCTTCAGA | TGG | 17.15 ± 3.29 |
| DYRK1A | 4 | 3' | -38 | 37 | 31 | N.D. | TGATAAGGCAGAAACCTGTT | TGG | 4.95 ± 0.66 | GCCAAACATAAGTGACCAAC | AGG | 16.38 ± 3.39 |
| DYRK1A | 1 | 3' | -17 | 38 | 47 | N.D. | GAAGATAAGTGAGGTTTAAA | AGG | 5.30 ± 1.98 | AACCTCACTTATCTTCTTGT | AGG | 24.18 ± 3.22 |
| DYRK1A | 21 | 5' | -13 | 39 | 33 | 10.54 ± 0.63 | GTATCATTTGACATATCTAA | TGG | 26.90 ± 1.17 | TGTCAAATGATACAAACATT | AGG | 29.69 ± 0.86 |
| DYRK1A | 25 | 5' | -9 | 40 | 49 | 2.33 ± 0.11 | CAGCATGGAATGAAATGAC | CGG | 3.33 ± 0.56 | CCATGCTGCTGGCCTTCAGA | TGG | 20.43 ± 2.40 |
| DYRK1A | 29 | 5' | -5 | 41 | 50 | 27.76 ± 0.84 | GCAGCATGGAATGAATGA | CGG | 17.84 ± 5.46 | GCTGCTGGCCTTCAGATGGC | TGG | 21.92 ± 3.46 |
| DYRK1A | 33 | 5' | -1 | 34 | 51 | 10.42 ± 0.90 | ATCTGGTCAGAATATGATAA | AGG | 9.13 ± 2.32 | TCAGCAAACCTCACTAACC | AGG | 24.14 ± 2.95 |
| DYRK1A | 35 | 5' | 1 | 42 | 52 | 7.63 ± 0.51 | GTGCAAGCCGAACAGATGAA | AGG | 6.65 ± 2.19 | TCATTTTCATTCCATGCTGC | TGG | 20.61 ± 3.64 |
| DYRK1A | 36 | 5' | 2 | 28 | 29 | 38.46 ± 0.74 | GGAGTATCAGAAATGACTAT | TGG | 20.88 ± 9.09 | GGAGTATCAGAAATGACTAT | TGG | 30.3 ± 0.7 |
| DYRK1A | 41 | 5' | 7 | 30 | 31 | 34.41 ± 0.87 | GGTCACTGTACTGATGTGAA | TGG | 25.68 ± 5.95 | GCCAAACATAAGTGACCAAC | AGG | 33.1 ± 0.4 |
| DYRK1A | 42 | 5' | 8 | 43 | 31 | 38.36 ± 0.32 | TCACTGTACTGATGTGAATG | GGG | 24.68 ± 4.58 | GCCAAACATAAGTGACCAAC | AGG | 29.46 ± 3.30 |
| DYRK1A | 43 | 5' | 9 | 32 | 33 | 28.97 ± 0.32 | GTTCCTTAAATAAGAACTTT | AGG | 23.60 ± 2.56 | TGTCAAATGATACAAACATT | AGG | 22.4 ± 1.6 |
| DYRK1A | 46 | 5' | 12 | 44 | 53 | 11.90 ± 1.65 | TCCTACAAGAAGATAAGTGA | TGG | 6.57 ± 1.36 | CATGCAAACCTTCATCTGTT | AGG | 30.42 ± 1.14 |
| DYRK1A | 77 | 5' | 43 | 36 | 31 | 6.63 ± 0.27 | CATCTGAAGGCCAGCAGCAT | TGG | 10.02 ± 1.17 | GCCAAACATAAGTGACCAAC | AGG | 22.92 ± 5.16 |
| DYRK1A | 86 | 5' | 52 | 38 | 52 | N.D. | GAAGATAAGTGAGGTTTAAA | AGG | 2.90 ± 0.82 | TCATTTTCATTCCATGCTGC | TGG | 17.30 ± 1.62 |
| DYRK1A | 97 | 5' | 63 | 38 | 49 | N.D. | GAAGATAAGTGAGGTTTAAA | AGG | 2.16 ± 0.48 | CCATGCTGCTGGCCTTCAGA | TGG | 24.75 ± 2.50 |
| DYRK1A | 131 | 5' | 97 | 45 | 52 | N.D. | TATCATTTGACATATCTAAT | TGG | 8.21 ± 2.83 | TCATTTTCATTCCATGCTGC | TGG | 14.61 ± 4.10 |
| DYRK1A | 155 | 5' | 121 | 44 | 31 | N.D. | TCCTACAAGAAGATAAGTGA | AGG | 9.99 ± 4.12 | GCCAAACATAAGTGACCAAC | AGG | 19.74 ± 2.91 |

TABLE D-continued

List of sgRNA pairs to identify optimal spacing.

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| DYRK1A | 191 | 5' | 157 | 46 | 52 | N.D. | AACTTTTCTAACTACAAACA | AGG | 5.74 ± 2.24 | TCATTTTCATTCCATGCTGC | TGG | 21.37 |
| GRIN2B | 165 | 3' | -199 | 70 | 82 | N.D. | CCAACACCAACCAGAACTTG | GGG | 2.95 ± 0.21 | CTGGTAGATGGAGTTGGGTT | TGG | 17.25 ± 1.30 |
| GRIN2B | 67 | 3' | 101 | 71 | 83 | N.D. | ACAGCAATGCCAATGCTGGG | GGG | 18.00 ± 2.31 | AGTGCTGTTCTCCCAAGTTC | TGG | 28.64 ± 0.69 |
| GRIN2B | 42 | 3' | -76 | 72 | 84 | N.D. | GTGGAAATCATCTTTCTCGT | TGG | 14.56 ± 7.84 | GGCATTGCTGTCATCCTCGT | GGG | 21.26 ± 2.68 |
| GRIN2B | 16 | 3' | -50 | 73 | 85 | N.D. | TCTGCTGCCTGACACGGCCA | AGG | 4.24 ± 0.79 | TCCCAAGTTCTGGTTGGTGT | TGG | 19.64 ± 0.23 |
| GRIN2B | 2 | 3' | -36 | 74 | 86 | N.D. | CGAGCTCTGCTGCCTGACAC | CGG | 2.99 ± 0.31 | TTGGCCGTCCTGGCCGTGTC | AGG | 4.74 ± 0.15 |
| GRIN2B | 9 | 5' | -25 | 75 | 87 | 1.04 ± 0.53 | TCCTTGATGGCCACCTCGTC | CGG | 2.25 ± 1.08 | TTCCGACGAGGTGGCCATCA | AGG | 17.13 ± 2.90 |
| GRIN2B | 18 | 5' | -16 | 76 | 88 | 5.93 ± 1.25 | ATGACAGCAATGCCAATGCT | TGG | 16.46 ± 2.28 | TGGCATTGCTGTCATCCTCG | TGG | 16.35 ± 1.25 |
| GRIN2B | 23 | 5' | -11 | 77 | 88 | 2.28 ± 0.34 | AGCAATGCCAATGCTGGGGG | GGG | 3.19 ± 0.51 | TGGCATTGCTGTCATCCTCG | TGG | 15.17 ± 2.02 |
| GRIN2B | 28 | 5' | -6 | 78 | 86 | 1.45 ± 0.12 | GCCAACACCAACCAGAACTT | TGG | 17.80 ± 2.30 | TTGGCCGTCCTGGCCGTGTC | AGG | 4.46 ± 1.35 |
| GRIN2B | 30 | 5' | -4 | 69 | 85 | 11.80 ± 0.29 | GGAGAACAGCACTCCGCTCT | TGG | 21.80 ± 1.40 | TCCCAAGTTCTGGTTGGTGT | TGG | 21.33 ± 0.63 |
| GRIN2B | 33 | 5' | -1 | 76 | 65 | 24.24 ± 0.23 | ATGACAGCAATGCCAATGCT | TGG | 19.48 ± 1.88 | CCTCGTGGGCACTTCCGACG | AGG | 21.19 ± 3.42 |
| GRIN2B | 34 | 5' | 0 | 79 | 65 | 20.83 ± 0.95 | TGACAGCAATGCCAATGCTG | GGG | 21.44 ± 3.02 | CCTCGTGGGCACTTCCGACG | AGG | 24.11 ± 0.14 |
| GRIN2B | 36 | 5' | 2 | 58 | 59 | 31.76 ± 1.00 | CCGGCCAAGACCTTGAAGCC | AGG | 32.50 ± 0.50 | CTGGTTGTAGGATTTGAGTT | AGG | 26.7 ± 2.9 |
| GRIN2B | 38 | 5' | 4 | 54 | 55 | 34.45 ± 0.45 | TATTACAGAATGAGAGACTG | TGG | 30.90 ± 1.40 | TTATTTCTGAAGAGATATTAA | AGG | 27.6 ± 2.5 |

TABLE D-continued

List of sgRNA pairs to identify optimal spacing.

| Gene | Overhang Length (bp) | Overhang Type | Offset Length (bp) | Left sgRNA ID | Right sgRNA ID | Cas9n with left and right sgRNA indel (%) | left sgRNA target site guide sequence (5' to 3') | PAM | left sgRNA with wildtype Cas9 indel (%) | right sgRNA target site guide sequence (5' to 3') | PAM | right sgRNA with wildtype Cas9 indel (%) |
|---|---|---|---|---|---|---|---|---|---|---|---|---|
| GRIN2B | 38 | 5' | 4 | 56 | 57 | 44.22 ± 0.55 | AAAAGACCTAAACAAAAGAA | TGG | 23.20 ± 2.10 | TGTGTGAGGATAAAAGAGTT | GGG | 29.4 ± 2.7 |
| GRIN2B | 38 | 5' | 4 | 77 | 65 | 9.60 ± 0.25 | AGCAATGCCAATGCTGGGGG | GGG | 4.19 ± 0.58 | CCTCGTGGGCACTTCCGACG | AGG | 21.78 ± 1.70 |
| GRIN2B | 40 | 5' | 6 | 60 | 61 | 42.54 ± 1.39 | TCAGAGCTTCCTGACACCCA | TGG | 14.20 ± 1.50 | AATACCTAGTTACAGGCATT | TGG | 24.8 ± 1.0 |
| GRIN2B | 45 | 5' | 11 | 76 | 87 | 18.96 ± 0.93 | ATGACAGCAATGCCAATGCT | TGG | 20.45 ± 0.98 | TTCCGACGAGGTGGCCATCA | AGG | 13.21 ± 0.74 |
| GRIN2B | 50 | 5' | 16 | 77 | 87 | 5.33 ± 0.57 | AGCAATGCCAATGCTGGGGG | GGG | 4.93 ± 2.06 | TTCCGACGAGGTGGCCATCA | AGG | 12.51 ± 1.21 |
| GRIN2B | 89 | 5' | 55 | 80 | 89 | 7.31 ± 0.83 | GAGAACAGCACTCCGCTCTG | GGG | 3.09 ± 0.54 | CAGAGAGCCCCCCAGCAT | TGG | 25.02 ± 1.86 |
| GRIN2B | 105 | 5' | 71 | 78 | 90 | 10.56 ± 1.21 | GCCAACACCAACCAGAACTT | TGG | 25.29 ± 1.65 | CGTGGGCACTTCCGACGAGG | TGG | 23.32 ± 0.78 |
| GRIN2B | 132 | 5' | 98 | 81 | 67 | 2.66 ± 0.89 | CTGCCTGACACGGGCCAGGAC | CGG | 4.34 ± 0.62 | TGATTTCCACCATCTCTCCG | TGG | 20.95 ± 0.79 |
| GRIN2B | 175 | 5' | 141 | 80 | 67 | N.D. | GAGAACAGCACTCCGCTCTG | GGG | 2.96 ± 0.93 | TGATTTCCACCATCTCTCCG | TGG | 19.77 ± 2.20 |
| GRIN2B | 231 | 5' | 197 | 81 | 91 | N.D. | CTGCCTGACACGGGCCAGGAC | CGG | 6.17 ± 2.09 | TGACCGGAAGATCCAGGGGG | TGG | 23.36 ± 2.34 |

N.D.: Not detected.

TABLE E

List of sgRNAs used in this study

| gene | sgRNA ID | sequence (5' to 3') | PAM | strand | species |
|---|---|---|---|---|---|
| EMX1 | 1 | GAGTCCGAGCAGAAGAAGAA | GGG | + | H. sapiens |
| EMX1 | 2 | GGAAGGGCCTGAGTCCGAGCAGAAGAAGA | GGG | + | H. sapiens |
| EMX1 | 3 | GGCCTCCAAGGAGTCCGAGCAGAAGAAGAA | GGG | + | H. sapiens |
| EMX1 | 4 | AGGCCCCAGTGGCTGCTCTG | GGG | + | H. sapiens |
| EMX1 | 5 | GGGGCACAGATGAGAAACTC | AGG | − | H. sapiens |
| EMX1 | 6 | TCACCTGGGCCAGGGAGGGA | GGG | − | H. sapiens |
| EMX1 | 7 | TGAAGGTGTGGTTCCAGAAC | CGG | + | H. sapiens |
| EMX1 | 8 | AGGTGTGGTTCCAGAACCGG | AGG | + | H. sapiens |
| EMX1 | 9 | GCCGTTTGTACTTTGTCCTC | CGG | − | H. sapiens |
| EMX1 | 10 | CAAACGGCAGAAGCTGGAGG | AGG | + | H. sapiens |
| EMX1 | 11 | CGGCAGAAGCTGGAGGAGGA | AGG | + | H. sapiens |
| EMX1 | 12 | TGAGTCCGAGCAGAAGAAGA | AGG | + | H. sapiens |
| EMX1 | 13 | GGAGCCCTTCTTCTTCTGCT | CGG | − | H. sapiens |
| EMX1 | 14 | AGGGCTCCCATCACATCAAC | CGG | + | H. sapiens |
| EMX1 | 15 | TGCGCCACCGGTTGATGTGA | TGG | − | H. sapiens |
| EMX1 | 16 | TTGCCACGAAGCAGGCCAAT | GGG | − | H. sapiens |
| EMX1 | 17 | CACGAAGCAGGCCAATGGGG | AGG | + | H. sapiens |
| EMX1 | 18 | TCACCTCCAATGACTAGGGT | GGG | + | H. sapiens |
| EMX1 | 19 | GGCAGAGTGCTGCTTGCTGC | TGG | − | H. sapiens |
| EMX1 | 20 | GACATCGATGTCCTCCCCAT | TGG | − | H. sapiens |
| EMX1 | 21 | GTCACCTCCAATGACTAGGG | TGG | + | H. sapiens |
| EMX1 | 22 | GGGCAACCACAAACCCACGA | GGG | + | H. sapiens |
| EMX1 | 23 | ACTCTGCCCTCGTGGGTTTG | TGG | − | H. sapiens |
| EMX1 | 24 | CAAGCAGCACTCTGCCCTCG | TGG | − | H. sapiens |
| EMX1 | 25 | TTCTTCTTCTGCTCGGACTC | AGG | − | H. sapiens |
| EMX1 | 26 | CTCCCCATTGGCCTGCTTCG | AGG | − | H. sapiens |
| EMX1 | 27 | GTCACCTCCAATGACTAGGG | TGG | + | H. sapiens |
| DYRK1A | 28 | GAACTTACCTGGTTAGTTAG | AGG | − | H. sapiens |
| DYRK1A | 29 | GGAGTATCAGAAATGACTAT | TGG | + | H. sapiens |
| DYRK1A | 30 | GGTCACTGTACTGATGTGAA | TGG | − | H. sapiens |
| DYRK1A | 31 | GCCAAACATAAGTGACCAAC | AGG | + | H. sapiens |
| DYRK1A | 32 | GTTCCTTAAATAAGAACTTT | AGG | − | H. sapiens |
| DYRK1A | 33 | TGTCAAATGATACAAACATT | AGG | + | H. sapiens |
| DYRK1A | 34 | ATCTGGTCAGAATATGATAA | AGG | − | H. sapiens |
| DYRK1A | 35 | GTCACTGTACTGATGTGAAT | TGG | − | H. sapiens |
| DYRK1A | 36 | CATCTGAAGGCCAGCAGCAT | TGG | − | H. sapiens |
| DYRK1A | 37 | TGATAAGGCAGAAACCTGTT | TGG | − | H. sapiens |
| DYRK1A | 38 | GAAGATAAGTGAGGTTTAAA | AGG | − | H. sapiens |
| DYRK1A | 39 | GTATCATTTGACATATCTAA | TGG | − | H. sapiens |
| DYRK1A | 40 | CAGCATGGAATGAAAATGAC | CGG | − | H. sapiens |
| DYRK1A | 41 | GCAGCATGGAATGAAAATGA | CGG | − | H. sapiens |
| DYRK1A | 42 | GTGCAAGCCGAACAGATGAA | AGG | − | H. sapiens |
| DYRK1A | 43 | TCACTGTACTGATGTGAATG | GGG | − | H. sapiens |
| DYRK1A | 44 | TCCTACAAGAAGATAAGTGA | AGG | − | H. sapiens |
| DYRK1A | 45 | TATCATTTGACATATCTAAT | TGG | − | H. sapiens |
| DYRK1A | 46 | AACTTTTCTAACTACAAACA | AGG | − | H. sapiens |
| DYRK1A | 47 | AACCTCACTTATCTTCTTGT | AGG | + | H. sapiens |
| DYRK1A | 48 | CTCACTTATCTTCTTGTAGG | AGG | + | H. sapiens |
| DYRK1A | 49 | CCATGCTGCTGGCCTTCAGA | TGG | + | H. sapiens |
| DYRK1A | 50 | GCTGCTGGCCTTCAGATGGC | TGG | + | H. sapiens |
| DYRK1A | 51 | TCAGCAACCTCTAACTAACC | AGG | + | H. sapiens |
| DYRK1A | 52 | TCATTTTCATTCCATGCTGC | TGG | + | H. sapiens |
| DYRK1A | 53 | CATGCAAACCTTCATCTGTT | CGG | + | H. sapiens |
| DYRK1A | 54 | TATTACAGAATGAGAGACTG | TGG | − | H. sapiens |
| DYRK1A | 55 | TTATTTCTGAAGAATATTAA | AGG | + | H. sapiens |
| DYRK1A | 56 | AAAAGACCTAAACAAAAGAA | TGG | − | H. sapiens |
| DYRK1A | 57 | TGTGTGAGGATAAAAGAGTT | GGG | + | H. sapiens |
| DYRK1A | 58 | CCGGCCAAGACCTTGAAGCC | AGG | − | H. sapiens |
| DYRK1A | 59 | CTGGTTGTAGGATTTGAGTT | AGG | + | H. sapiens |
| DYRK1A | 60 | TCAGAGCTTCCTGACACCCA | TGG | − | H. sapiens |
| DYRK1A | 61 | AATACCTAGTTACAGGCATT | TGG | + | H. sapiens |
| GRIN2B | 62 | GGTGATGATGCTCTTTGGGT | CGG | − | H. sapiens |
| GRIN2B | 63 | TCTGTGATCTCATGTCTGAC | CGG | + | H. sapiens |
| GRIN2B | 64 | CAGCAATGCCAATGCTGGGG | GGG | − | H. sapiens |
| GRIN2B | 65 | CCTCGTGGGCACTTCCGACG | AGG | + | H. sapiens |
| GRIN2B | 66 | TTTCTCGTGGGCATCCTTGA | TGG | − | H. sapiens |
| GRIN2B | 67 | TGATTTCCACCATCTCTCCG | TGG | + | H. sapiens |
| GRIN2B | 68 | GGAGAACAGCACTCCGCTCT | GGG | − | H. sapiens |
| GRIN2B | 69 | CTGGTTGGTGTTGGCCGTCC | TGG | + | H. sapiens |
| GRIN2B | 70 | CCAACACCAACCAGAACTTG | GGG | − | H. sapiens |
| GRIN2B | 71 | ACAGCAATGCCAATGCTGGG | GGG | − | H. sapiens |
| GRIN2B | 72 | GTGGAAATCATCTTTCTCGT | TGG | − | H. sapiens |
| GRIN2B | 73 | TCTGCTGCCTGACACGGCCA | AGG | − | H. sapiens |
| GRIN2B | 74 | CGAGCTCTGCTGCCTGACAC | CGG | − | H. sapiens |
| GRIN2B | 75 | TCCTTGATGGCCACCTCGTC | CGG | − | H. sapiens |
| GRIN2B | 76 | ATGACAGCAATGCCAATGCT | TGG | − | H. sapiens |

TABLE E-continued

List of sgRNAs used in this study

| gene | sgRNA ID | sequence (5' to 3') | PAM | strand | species |
|---|---|---|---|---|---|
| GRIN2B | 77 | AGCAATGCCAATGCTGGGGG | GGG | − | H. sapiens |
| GRIN2B | 78 | GCCAACACCAACCAGAACTT | TGG | − | H. sapiens |
| GRIN2B | 79 | TGACAGCAATGCCAATGCTG | GGG | − | H. sapiens |
| GRIN2B | 80 | GAGAACAGCACTCCGCTCTG | GGG | − | H. sapiens |
| GRIN2B | 81 | CTGCCTGACACGGCCAGGAC | CGG | − | H. sapiens |
| GRIN2B | 82 | CTGGTAGATGGAGTTGGGTT | TGG | + | H. sapiens |
| GRIN2B | 83 | AGTGCTGTTCTCCCAAGTTC | TGG | + | H. sapiens |
| GRIN2B | 84 | GGCATTGCTGTCATCCTCGT | GGG | + | H. sapiens |
| GRIN2B | 85 | TCCCAAGTTCTGGTTGGTGT | TGG | + | H. sapiens |
| GRIN2B | 86 | TTGGCCGTCCTGGCCGTGTC | AGG | + | H. sapiens |
| GRIN2B | 87 | TTCCGACGAGGTGGCCATCA | AGG | + | H. sapiens |
| GRIN2B | 88 | TGGCATTGCTGTCATCCTCG | TGG | + | H. sapiens |
| GRIN2B | 89 | CAGAAGAGCCCCCCCAGCAT | TGG | + | H. sapiens |
| GRIN2B | 90 | CGTGGGCACTTCCGACGAGG | TGG | + | H. sapiens |
| GRIN2B | 91 | TGACCGGAAGATCCAGGGGG | TGG | + | H. sapiens |

TABLE F

List of sgRNA scaffolds used in this study

| sgRNA Scaffold | Length | Sequence |
|---|---|---|
| Wild-type sp85 | 81 | gttttagagctaGAAAtagcaagttaaaataaggctagtccgttatcaacttGAAAaagtggcaccgAGTcggtgcTTTTT |
| Replace bulge with G-C pair | 79 | gttttagCgctaGAAAtagcGttaaaataaggctagtccgttatcaacttGAAAaagtggcaccgAGTcggtgcTTTTT |
| Replace PDR with CCGG trace, remove bulge | 79 | gCCGGCgCgctaGAAAtagcGtGCCGGtaaggctagtccgttatcaacttGAAAaagtggcaccgAGTcggtgcTTTTT |
| Replace PDR with CCGG tract, keep bulge | 71 | gCCGCCgCGAAAgtGCCGGtaaggctagtccgttatcaacttGAAAaagtggcaccgAGTcggtgcTTTTT |
| Shorten PDR, remove bulge | 81 | gCCGGCgagctaGAAAtagcaagtGCCGGtaaggctagtccgttatcaacttGAAAaagtggcaccgAGTcggtgcTTTTT |
| Replace PDR with CCCC tract | 80 | gccccagagctagaaatagcaagttggggtaaggctagtccgttatcaacttgaaaaagtggcaccgagtcggtgcttttt |
| Bulge randomization | 81 | gttttagagctaGAAAtagcNNNNtaaaataaggctagtccgttatcaacttGAAAaagtggcaccgAGTcggtgcTTTTT |
| Linker truncation, first half | 72 | gttttagagctaGAAAtagcaagttaaaataaggctagtacttGAAAaagtggcaccgAGTcggtgcTTTTT |
| Linder truncation, second half | 63 | gttttagagctaGAAAtagcaagttaaaatacttGAAAaagtggcaccgAGTcggtgcTTTTT |
| Linker scramble | 81 | gttttagagctaGAAAtagcaagttaaaatagatcgtatacatcattaacttGAAAaagtggcaccgAGTcggtgcTTTTT |
| Linker randomization | 81 | gttttagagctaGAAAtagcaagttaaaatNNNNNNNNNNNNNNNNNNNNacttGAAAaagtggcaccgAGTcggtgcTTTTT |
| Replace Stem 2 with G-C track | 81 | gttttagagctaGAAAtagcaagttaaaataaggctagtccgttatcaCGCCGAAAGGCGggcaccgAGTcggtgcTTTTT |
| Extend Stem 2 by 2 bp | 85 | gttttagagctaGAAAtagcaagttaaaataaggctagtccgttatcaacttgaGAAAtcaagtggcaccgAGTcggtgcTTTTT |
| Replace Stem 3 with G-C track | 80 | gttttagagctagaaatagcaagttaaaataaggctagtccgttatcaacttgaaaaagtggcccgcggcggggctttt |

TABLE F-continued

List of sgRNA scaffolds used in this study

| sgRNA Scaffold | Length | Sequence |
| --- | --- | --- |
| Lengthen Stem 3 (add 3 bp) | 84 | gttttagagctagaaatagcaagttaaaataaggctagtccgttatcaacttgaaaaagtggcaccgaaagtttcggtgctttt |
| 4558 | 82 | gttttagagctaGAAAtagcaagttaaaataaggctagtccgttatcaCGCCGAAAGGCGggcaccgAGTcggtgccTTTTT |
| 4561 | 92 | gttttagagctaGAAAtagcaagttaaaataaggctagtccgttatcaccttgggccGAAAggcccaaggggcgccgAGTcggcgccTTTTT |
| 4638 | 82 | gttttagagccgGAAAcggcaagttaaaataaggctagtccgttatcaCGCCGAAAGGCGggcaccgAGTcggtgccTTTTT |
| Opt1CCCC | 81 | gccccagCgctaGAAAtagcaagttggggtaaggctagtccgttatcaCGCCGAAAGGCGggcaccgAGTcggtgcTTTTT |
| Opt1CTTC | 81 | gcttcagCgctaGAAAtagcaagttgaagtaaggctagtccgttatcaCGCCGAAAGGCGggcaccgAGTcggtgcTTTTT |
| Scrmbl1 | 92 | gttttagatgcaattatgcaaagttaaaataaggctagtccgttatcaacttataccaataagtcatcgtcgagAAGctcgacgatgTTTTT |
| Scrmbl2 | 92 | gttttagaactcattagagtaagttaaaataaggctagtccgttatcaacatgcaccagcatgttcaggattcaAAGtgaatcctgaTTTTT |
| ShScrmbl1 PolyC | 82 | gccccagatgcaattatgcaaagttggggtaaggcaagtccgttatcaaccgaccacggtcacgtcgAAGcgacgtgTTTTT |
| ShScrmbl1 CTTC | 82 | gcttcagatgcaattatgcaaagttgaagtaaggcaagtccgttatcacctgaccacagggtgtcgtAAGacgacacTTTTT |
| Shorter Scrmbl1 PolyC | 77 | gccccagaccattggaagttggggtaaggcaagtccgttatcaaccgaccacggtcacgtcgAAGcgacgtgTTTTT |
| Shorter Scrmbl1 CTTC | 77 | gcttcagaggattccaagttgaagtaaggcaagtccgttatcacctgaccacagggtgtcgtAAGacgacacTTTTT |

TABLE G

Primers used for SURVEYOR assays

| Primer Name | Genomic Target | Sequence |
| --- | --- | --- |
| SUV901 | EMX1 | CCATCCCCTTCTGTGAATGT |
| SUV902 | EMX1 | GGAGATTGGAGACACGGAGA |
| DYRK1A-F | DYRK1A | GGAGCTGGTCTGTTGGAGAA |
| DYRK1A-R | DYRK1A | TCCCAATCCATAATCCCACGTT |
| GRIN2B-F | GRIN2B | CAGGAGGGCCAGGAGATTTG |
| GRIN2B-R | GRIN2B | TGAAATCGAGGATCTGGGCG |

TABLE H

Primers used to generate amplicons for NGS

| Primer Name | Sequence |
| --- | --- |
| EMX1-F | GGAGGACAAAGTACAAACGGC |
| EMX1-R | ATCGATGTCCTCCCCATTGG |
| EMX1-HR-F | CCATCCCCTTCTGTGAATGT |
| EMX1-HR-R | GGAGATTGGAGACACGGAGA |
| EMX1-OT1.1-F | TGGGAGAGAGACCCCTTCTT |
| EMX1-OT1.1-R | TCCTGCTCTCACTTAGACTTTCTC |
| EMX1-OT1.2-F | GACATTCCTCCTGAGGGAAAA |
| EMX1-OT1.2-R | GATAAAATGTATTCCTTCTCACCATTC |
| EMX1-OT1.3-F | CCAGACTCAGTAAAGCCTGGA |
| EMX1-OT1.3-R | TGGCCCCAGTCTCTCTTCTA |
| EMX1-OT1.4-F | CACGGCCTTTGCAAATAGAG |
| EMX1-OT1.4-R | CATGACTTGGCCTTTGTAGGA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

REFERENCES

1. Ding, Q. et al. A TALEN genome-editing system for generating human stem cell-based disease models. Cell Stem Cell 12, 238-251 (2013).

2. Soldner, F. et al. Generation of isogenic pluripotent stem cells differing exclusively at two early onset Parkinson point mutations. Cell 146, 318-331 (2011).
3. Carlson, D. F. et al. Efficient TALEN-mediated gene knockout in livestock. Proc Natl Acad Sci USA 109, 17382-17387 (2012).
4. Geurts, A. M. et al. Knockout Rats via Embryo Microinjection of Zinc-Finger Nucleases. Science 325, 433-433 (2009).
5. Takasu, Y. et al. Targeted mutagenesis in the silkworm *Bombyx mori* using zinc finger nuclease mRNA injection. Insect Biochem Molec 40, 759-765 (2010).
6. Watanabe, T. et al. Non-transgenic genome modifications in a hemimetabolous insect using zinc-finger and TAL effector nucleases. Nat Commun 3 (2012).
7. Porteus, M. H. & Baltimore, D. Chimeric nucleases stimulate gene targeting in human cells. Science 300, 763 (2003).
8. Miller, J. C. et al. An improved zinc-finger nuclease architecture for highly specific genome editing. Nat Biotechnol 25, 778-785 (2007).
9. Sander, J. D. et al. Selection-free zinc-finger-nuclease engineering by context-dependent assembly (CoDA). Nat Methods 8, 67-69 (2011).
10. Wood, A. J. et al. Targeted genome editing across species using ZFNs and TALENs. Science 333, 307 (2011).
11. Christian, M. et al. Targeting DNA double-strand breaks with TAL effector nucleases. Genetics 186, 757-761 (2010).
12. Zhang, F. et al. Efficient construction of sequence-specific TAL effectors for modulating mammalian transcription. Nat Biotechnol 29, 149-153 (2011).
13. Miller, J. C. et al. A TALE nuclease architecture for efficient genome editing. Nat Biotechnol 29, 143-148 (2011).
14. Reyon, D. et al. FLASH assembly of TALENs for high-throughput genome editing. Nat Biotechnol 30, 460-465 (2012).
15. Boch, J. et al. Breaking the code of DNA binding specificity of TAL-type III effectors. Science 326, 1509-1512 (2009).
16. Moscou, M. J. & Bogdanove, A. J. A simple cipher governs DNA recognition by TAL effectors. Science 326, 1501 (2009).
17. Sanjana, N. E. et al. A transcription activator-like effector toolbox for genome engineering. Nat Protoc 7, 171-192 (2012).
18. Deveau, H., Garneau, J. E. & Moineau, S. CRISPR-Cas system and its role in phage-bacteria interactions. Annu Rev Microbiol 64, 475-493 (2010).
19. Horvath, P. & Barrangou, R. CRISPR-Cas, the immune system of bacteria and archaea. Science 327, 167-170 (2010).
20. Makarova, K. S. et al. Evolution and classification of the CRISPR-Cas systems. Nat Rev Microbiol 9, 467-477 (2011).
21. Bhaya, D., Davison, M. & Barrangou, R. CRISPR-Cas systems in bacteria and archaea: versatile small RNAs for adaptive defense and regulation. Annu Rev Genet 45, 273-297 (2011).
22. Cong, L. et al. Multiplex genome engineering using CRISPR-Cas systems. Science 339, 819-823 (2013).
23. Mali, P. et al. RNA-guided human genome engineering via Cas9. Science 339, 823-826 (2013).
24. Jinek, M. et al. RNA-programmed genome editing in human cells. eLife 2, e00471 (2013).
25. Cho, S. W., Kim, S., Kim, J. M. & Kim, J. S. Targeted genome engineering in human cells with the Cas9 RNA-guided endonuclease. Nat Biotechnol 31, 230-232 (2013).
26. Garneau, J. E. et al. The CRISPR-Cas bacterial immune system cleaves bacteriophage and plasmid DNA. Nature 468, 67-71 (2010).
27. Jinek, M. et al. A programmable dual-RNA-guided DNA endonuclease in adaptive bacterial immunity. Science 337, 816-821 (2012).
28. Gasiunas, G., Barrangou, R., Horvath, P. & Siksnys, V. Cas9-crRNA ribonucleoprotein complex mediates specific DNA cleavage for adaptive immunity in bacteria. Proc Natl Acad Sci USA 109, E2579-2586 (2012).
29. Urnov, F. D., Rebar, E. J., Holmes, M. C., Zhang, H. S. & Gregory, P. D. Genome editing with engineered zinc finger nucleases. Nat Rev Genet 11, 636-646 (2010).
30. Hsu, P. D. & Zhang, F. Dissecting neural function using targeted genome engineering technologies. ACS Chem Neurosci 3, 603-610 (2012).
31. Perez, E. E. et al. Establishment of HIV-1 resistance in CD4(+) T cells by genome editing using zinc-finger nucleases. Nat Biotechnol 26, 808-816 (2008).
32. Cong, L. et al. Multiplex Genome Engineering Using CRISPR-Cas Systems. Science 339, 819-823 (2013).
33. Chen, F. Q. et al. High-frequency genome editing using ssDNA oligonucleotides with zinc-finger nucleases. Nat Methods 8, 753-U796 (2011).
34. Bedell, V. M. et al. In vivo genome editing using a high-efficiency TALEN system. Nature 491, 114-U133 (2012).
35. Saleh-Gohari, N. & Helleday, T. Conservative homologous recombination preferentially repairs DNA double-strand breaks in the S phase of the cell cycle in human cells. Nucleic Acids Res 32, 3683-3688 (2004).
36. Deltcheva, E. et al. CRISPR RNA maturation by trans-encoded small RNA and host factor RNase III. Nature 471, 602-607 (2011).
37. Sapranauskas, R. et al. The *Streptococcus thermophilus* CRISPR-Cas system provides immunity in *Escherichia coli*. Nucleic Acids Res 39, 9275-9282 (2011).
38. Hwang, W. Y. et al. Efficient genome editing in zebrafish using a CRISPR-Cas system. Nat Biotechnol 31, 227-229 (2013).
39. Wang, H. et al. One-Step Generation of Mice Carrying Mutations in Multiple Genes by CRISPR-Cas-Mediated Genome Engineering. Cell 153, 910-918 (2013).
40. Shen, B. et al. Generation of gene-modified mice via Cas9/RNA-mediated gene targeting. Cell Res 23, 720-723 (2013).
41. Qi, L. S. et al. Repurposing CRISPR as an RNA-guided platform for sequence-specific control of gene expression. Cell 152, 1173-1183 (2013).
42. Tuschl, T. Expanding small RNA interference. Nat Biotechnol 20, 446-448 (2002).
43. Smithies, O., Gregg, R. G., Boggs, S. S., Koralewski, M. A. & Kucherlapati, R. S. Insertion of DNA sequences into the human chromosomal beta-globin locus by homologous recombination. Nature 317, 230-234 (1985).
44. Thomas, K. R., Folger, K. R. & Capecchi, M. R. High frequency targeting of genes to specific sites in the mammalian genome. Cell 44, 419-428 (1986).
45. Hasty, P., Rivera-Perez, J. & Bradley, A. The length of homology required for gene targeting in embryonic stem cells. Mol Cell Biol 11, 5586-5591 (1991).
46. Wu, S., Ying, G. X., Wu, Q. & Capecchi, M. R. A protocol for constructing gene targeting vectors: generating knockout mice for the cadherin family and beyond. Nat Protoc 3, 1056-1076 (2008).
47. Guschin, D. Y. et al. A rapid and general assay for monitoring endogenous gene modification. Methods Mol Biol 649, 247-256 (2010).
48. Oliveira, T. Y. et al. Translocation capture sequencing: a method for high throughput mapping of chromosomal rearrangements. J Immunol Methods 375, 176-181 (2012).
49. Deltcheva, E. et al. CRISPR RNA maturation by trans-encoded small RNA and host factor RNase III. Nature 471, 602-607 (2011).
50. Bogenhagen, D. F. & Brown, D. D. Nucleotide sequences in *Xenopus* 5S DNA required for transcription termination. Cell 24, 261-270 (1981).
51. Bultmann, S. et al. Targeted transcriptional activation of silent oct4 pluripotency gene by combining designer TALEs and inhibition of epigenetic modifiers. Nucleic Acids Res 40, 5368-5377 (2012).
52. Valton, J. et al. Overcoming transcription activator-like effector (TALE) DNA binding domain sensitivity to cytosine methylation. J Biol Chem 287, 38427-38432 (2012).
53. Christian, M. et al. Targeting DNA double-strand breaks with TAL effector nucleases. Genetics 186, 757-761 (2010).
54. Mussolino, C. et al. A novel TALE nuclease scaffold enables high genome editing activity in combination with low toxicity. Nucleic acids research 39, 9283-9293 (2011).
55. Bobis-Wozowicz, S., Osiak, A., Rahman, S. H. & Cathomen, T. Targeted genome editing in pluripotent stem cells using zinc-finger nucleases. Methods 53, 339-346 (2011).
56. Jiang, W., Bikard, D., Cox, D., Zhang, F. & Marraffini, L. A. RNA-guided editing of bacterial genomes using CRISPR-Cas systems. Nat Biotechnol 31, 233-239 (2013).
57. Michaelis, L. M., Maud "Die kinetik der invertinwirkung.". Biochem. z (1913).
58. Mahfouz, M. M. et al. De novo-engineered transcription activator-like effector (TALE) hybrid nuclease with novel DNA binding specificity creates double-strand breaks. Proc Natl Acad Sci USA 108, 2623-2628 (2011).
59. Wilson, E. B. Probable inference, the law of succession, and statistical inference. J Am Stat Assoc 22, 209-212 (1927).
60. Tangri S, et al., Rationally engineered therapeutic proteins with reduced immunogenicity, J Immunol. 2005 Mar. 15; 174(6):3187-96.
61. REMINGTON'S PHARMACEUTICAL SCIENCES (Mack Pub. Co., N.J. 1991)
62. Lopes, V. S., etc al., Retinal gene therapy with a large MYO7A cDNA using adeno-associated virus. Gene Ther, 2013 Jan. 24. doi: 10.1038/gt 2013.3.[Epub ahead of print]
63. Kaplitt, M. G., et al., Safety and tolerability of gene therapy with an adeno-associated virus (AAV) borne GAD gene for Parkinson's disease: an open label, phase I trial. Lancet. 2007 Jun. 23; 369(9579):2097-105.
64. Nathwani, A. C., et al., Adenovirus-associated virus vector-mediated gene transfer in hemophilia B. N Engl J Med. 2011 Dec. 22; 365(25):2357-65. doi: 10.1056/NEJMoa1108046. Epub 2011 Dec. 10.
65. Gray S J, Foti S B, Schwartz J W, Bachaboina L, Taylor-Blake B, Coleman J, Ehlers M D, Zylka M J, McCown T J, Samulski R J. Optimizing promoters for recombinant adeno-associated virus-mediated gene expression in the peripheral and central nervous system using self-complementary vectors. Hum Gene Ther. 2011 September; 22(9):1143-53. doi: 10.1089/hum.2010.245.
66. Liu D, Fischer I. Two alternative promoters direct neuron-specific expression of the rat microtubule-associated protein 1B gene. J Neurosci. 1996 Aug. 15; 16(16): 5026-36.
67. Levitt N. Briggs D. Gil A. Proudfoot N.J. Definition of an efficient synthetic poly(A) site. Genes Dev. 1989; 3:1019-1025.
68. McClure C, Cole K L, Wulff P, Klugmann M, Murray A J. Production and titering of recombinant adeno-associated viral vectors. J Vis Exp. 2011 Nov. 27; (57):e3348. doi: 10.3791/3348.
69. Banker G, Goslin K. Developments in neuronal cell culture. Nature. 1988 Nov. 10; 336(6195):185-6.
70. Capecchi, M. R. Gene targeting in mice: functional analysis of the mammalian genome for the twenty-first century. Nat Rev Genet 6, 507-512 (2005).
71. Bradley, A., Evans, M., Kaufman, M. H. & Robertson, E. Formation of germ-line chimaeras from embryo-derived teratocarcinoma cell lines. Nature 309, 255-256 (1984).
72. Smithies, R. O. & Koralewski, M. A. Insertion of DNA sequences into the human chromosomal B-globin locus by homologous recombination. Nature (1985).
73. Rudin, N., Sugarman, E. & Haber, J. E. Genetic and physical analysis of double-strand break repair and recombination in *Saccharomyces cerevisiae*. Genetics (1989).
74. Rouet, P., Smih, F. & Jasin, M. Introduction of double-strand breaks into the genome of mouse cells by expression of a rare-cutting endonuclease. Mol Cell Biol (1994).
75. Choulika, A., Perrin, A. & Dujon, B. Induction of homologous recombination in mammalian chromosomes by using the I-SceI system of *Saccharomyces cerevisiae*. Molecular and cellular (1995).
76. Wyman, C. & Kanaar, R. DNA double-strand break repair: all's well that ends well. Annu. Rev. Genet. (2006).
77. Li, L., Wu, L. P. & Chandrasegaran, S. Functional domains in Fok I restriction endonuclease. in (1992).
78. Kim, Y. G. & Chandrasegaran, S. Chimeric restriction endonuclease. in (1994).
79. Miller, J., McLachlan, A. D. & Klug, A. Repetitive zinc-binding domains in the protein transcription factor IIIA from *Xenopus* oocytes. EMBO J (1985).
80. Pavletich, N. P. & Pabo, C. O. Zinc finger-DNA recognition: crystal structure of a Zif268-DNA complex at 2.1 A. Science (1991).
81. Klug, A. The Discovery of Zinc Fingers and Their Applications in Gene Regulation and Genome Manipulation. Annu. Rev. Biochem. 79, 213-231 (2010).
82. Beerli, R. R. & Barbas, C. F. Engineering polydactyl zinc-finger transcription factors. Nat Biotech (2002).
83. Maeder, M. L., Thibodeau-Beganny, S., Osiak, A. & Wright, D. A. Rapid 'open-source' engineering of customized zinc-finger nucleases for highly efficient gene modification. Molecular Cell (2008).
84. Boch, J., Scholze, H., Schornack, S., Landgraf, A. & Hahn, S. Breaking the code of DNA binding specificity of TAL-type III effectors. Science (2009).
85. Gaj, T., Gersbach, C. A. & Barbas, C. F., III. ZFN, TALEN, and CRISPR/Cas-based methods for genome engineering. Trends in Biotechnology 1-9 (2013). doi: 10.1016/j.tibtech.2013.04.004

86. Ding, Q. et al. A TALEN Genome-Editing System for Generating Human Stem Cell-Based Disease Models. Stem Cell 12, 238-251 (2013).
87. McManus, M. T. & Sharp, P. A. Gene silencing in mammals by small interfering RNAs. Nat Rev Genet 3, 737-747 (2002).
88. Montgomery, M. K., Kostas, S. A., Driver, S. E. & Mello, C. C. Potent and specific genetic interference by double-stranded RNA in *Caenorhabditis elegans*. Nature (1998).
89. Vert, J.-P., Foveau, N., Lajaunie, C. & Vandenbrouck, Y. An accurate and interpretable model for siRNA efficacy prediction. BMC Bioinformatics 7, 520 (2006).
90. Bernstein, E., Caudy, A. A., Hammond, S. M. & Hannon, G. J. Role for a bidentate ribonuclease in the initiation step of RNA interference. Nature (2001).
91. Song, J., Giang, A., Lu, Y., Pang, S. & Chiu, R. Multiple shRNA expressing vector enhances efficiency of gene silencing. BMB Rep (2008).
92. van Parijs, L., Chen, J. & Sharp, P. A. Small interfering RNA-mediated gene silencing in T lymphocytes. The Journal of . . . (2002).
93. Grimm, D. & Kay, M. A. Combinatorial RNAi: A Winning Strategy for the Race Against Evolving Targets & quest. Mol Ther (2007).
94. Silva, J. M., Marran, K., Parker, J. S., Silva, J. & Golding, M. Profiling essential genes in human mammary cells by multiplex RNAi screening. Science (2008).
95. Stockwell, B. R., Hacohen, N., Hahn, W. C. & Lander, E. S. A lentiviral RNAi library for human and mouse genes applied to an arrayed viral high-content screen. Cell (2006).
96. Ishino, Y., Shinagawa, H., Makino, K., Amemura, M. & Nakata, A. Nucleotide sequence of the iap gene, responsible for alkaline phosphatase isozyme conversion in *Escherichia coli*, and identification of the gene product. Journal of Bacteriology 169, 5429-5433 (1987).
97. Spilman, M., Cocozaki, A., Hale, C., Shao, Y. & Ramia, N. Structure of an RNA silencing complex of the CRISPR-Cas immune system. Molecular Cell (2013).
98. Wiedenheft, B., Sternberg, S. H. & Doudna, J. A. RNA-guided genetic silencing systems in bacteria and archaea. Nature 482, 331-338 (2012).
99. Mojica, F. J. M., Diez-Villaseñor, C., Garcia-Martinez, J. & Almendros, C. Short motif sequences determine the targets of the prokaryotic CRISPR defense system. Microbiology (Reading, Engl.) 155, 733-740 (2009).
100. Mali, P. et al. RNA-guided human genome engineering via Cas9. Science (2013).
101. Gilbert, L. A. et al. CRISPR-Mediated Modular RNA-Guided Regulation of Transcription in Eukaryotes. Cell 154, 442-451 (2013).
102. Konermann, S. et al. NOT FINAL PROOF. Nature 1-17 (2013). doi:10.1038/nature12466
103. Maeder, M. L. et al. nbt.2726. Nat Biotech 1-9 (2013). doi:10.1038/nbt.2726
104. Perez-Pinera, P. et al. RNA-guided gene activation by CRISPR-Cas9-based transcription factors. Nat Meth 10, 973-976 (2013).
105. Hsu, P. D., Scott, D. A., Weinstein, J. A. & Ran, F. A. DNA targeting specificity of RNA-guided Cas9 nucleases. Nature (2013).
106. Fu, Y. et al. High-frequency off-target mutagenesis induced by CrIsPr-Cas nucleases in human cells. Nat Biotech 1-6 (2013). doi:10.1038/nbt.2623.
107. Dianov, G. L. & Hübscher, U. Mammalian Base Excision Repair: the Forgotten Archangel. Nucleic Acids Res (2013).
108. Ran, F. A. et al. Genome engineering using the CRISPR-Cas9 system. Nature Protocols 8, 2281-2308 (2013).
109. Ran, F. A. et al. Double Nicking by RNA-Guided CRISPR Cas9 for Enhanced Genome Editing Specificity. Cell 1-10 (2013). doi:10.1016/j.cell.2013.08.021
110. O'Roak, B. J., Deriziotis, P., Lee, C., Vives, L. & Schwartz, J. J. Exome sequencing in sporadic autism spectrum disorders identifies severe de novo mutations. Nature (2011).
111. Ng, S. B., Turner, E. H., Robertson, P. D. & Flygare, S. D. Targeted capture and massively parallel sequencing of 12 human exomes. Nature (2009).
112. Hsu, P. D. & Zhang, F. Dissecting Neural Function Using Targeted Genome Engineering Technologies. ACS Chemical Neuroscience (2012).
113. Hofacker, I. L., Fontana, W. & Stadler, P. F. Fast folding and comparison of RNA secondary structures. Monatshefte für Chemie/ . . . (1994).
114. Niu, Y. et al. Generation of Gene-Modified Cynomolgus Monkey via Cas9/RNA-MediatedGene Targeting in One-Cell Embryos. Cell 1-8 (2014). doi:10.1016/j.cell.2014.01.027
115. Grieger, J. C. & Samulski, R. J. Packaging capacity of adeno-associated virus serotypes: impact of larger genomes on infectivity and postentry steps. J Virol (2005).
116. Gabriel, R., Lombardo, A., Arens, A. & Miller, J. C. An unbiased genome-wide analysis of zinc-finger nuclease specificity. Nature (2011).
117. Tesson, L., Usal, C., Menoret, S., Leung, E. & Niles, B. J. Knockout rats generated by embryo microinjection of TALENs. Nature (2011).
118. Fu, Y., Sander, J. D., Reyon, D., Cascio, V. M. & Joung, J. K. Improving CRISPR-Cas nuclease specificity using truncated guide RNAs. Nat Biotech (2014). doi:10.1038/nbt.2808
119. Zhang, Y. et al. Processing-Independent CRISPR RNAs Limit Natural Transformation in *Neisseria meningitidis*. Molecular Cell 50, 488-503 (2013).
120. Zoephel, J. & Randau, L. RNA-Seq analyses reveal CRISPR RNA processing and regulation patterns. Biochem. Soc. Trans. 41, 1459-1463 (2013).
121. Shalem, O. et al. Genome-Scale CRISPR-Cas9 Knockout Screening in Human Cells. Science 343, 84-87 (2014).
122. Wang, T., Wei, J. J., Sabatini, D. M. & Lander, E. S. Genetic screens in human cells using the CRISPR-Cas9 system. Science (2014).
123. Pattanayak, V., Lin, S., Guilinger, J. P. & Ma, E. High-throughput profiling of off-target DNA cleavage reveals RNA-programmed Cas9 nuclease specificity. Nature (2013).

What is claimed is:

1. A polynucleotide comprising, from upstream to downstream, a single promoter operably linked to a nucleotide sequence encoding a tandem guide RNA, which tandem guide RNA comprises:
   (a) a first guide sequence capable of hybridizing to a first target sequence in a eukaryotic cell,
   (b) a first tracr mate sequence capable of hybridizing to a first tracr sequence,
   (c) a first tracr sequence,
   (d) a second guide sequence capable of hybridizing to a second target sequence in a eukaryotic cell,
   (e) a second tracr mate sequence capable of hybridizing to a second tracr sequence, and
   (f) a second tracr sequence,
   wherein (a), (b), (c), (d), (e) and (f) are arranged in a 5' to 3' orientation, and (c) and (d) are linked by a nucleotide linker, wherein the nucleotide linker is transcribed from a sequence selected from the group consisting of ATTA, AATTATTA, AATTATTAATTA (SEQ ID NO: 462), AATTATTAATTATAAT (SEQ ID NO: 463), GTTT-TAGAGCTATGCT (SEQ ID NO: 464), and GTTTT-GAATGGTCCCAAAAC (SEQ ID NO: 465).

2. A composition comprising the polynucleotide of claim 1 for modifying an organism or a non-human organism by manipulation of a first and a second target sequence on opposite strands of a DNA duplex in a genomic locus of interest in a eukaryotic cell,
   which composition further comprises a polynucleotide sequence encoding a Cas9 protein comprising at least one or more nuclear localization sequences
   wherein the first guide sequence is capable of directing cleavage of one strand of the DNA duplex near the first target sequence in the eukaryotic cell and the second guide sequence is capable of directing cleavage of the other strand near the second target sequence in the eukaryotic cell inducing a double strand break to modify the organism or the non-human organism.

3. The composition of claim 2, wherein the nucleotide linker is ATTA or AATTATTA.

4. The composition of claim 2, wherein the nucleotide linker is AATTATTAATTA (SEQ ID NO: 462).

5. The composition of claim 2, wherein the nucleotide linker is AATTATTAATTATAAT (SEQ ID NO: 463).

6. The composition of claim 2, wherein the nucleotide linker is GTTTTAGAGCTATGCT (SEQ ID NO: 464) or GTTTTGAATGGTCCCAAAAC (SEQ ID NO: 465).

7. The composition of claim 2, wherein the first or second guide sequence, the first or second tracr sequence, and/or the first or second tracr mate sequence are modified.

8. The composition of claim 7, wherein the modification comprises optimized first or second tracr sequence and/or optimized first or second guide sequence and/or co-fold structure of first or second tracr sequence and/or first or second tracr mate sequence(s) respectively and/or stabilizing secondary structures of first or second tracr sequence and/or first or second tracr sequence with a reduced region of base-pairing and/or first or second tracr sequence fused RNA elements.

9. The composition of claim 2, wherein any or all of the polynucleotide sequences encoding the Cas9 protein, the first and the second guide sequence, the first and the second tracr mate sequence or the first and the second tracr sequence, is/are RNA.

10. The composition of claim 2, wherein the polynucleotides encoding the sequence encoding the Cas9 protein, the first and the second guide sequence, the first and the second tracr mate sequence or the first and the second tracr sequence, is/are RNA and are delivered via nanoparticles, exosomes, microvesicles, or a gene-gun.

11. The composition of claim 2, wherein the first and second tracr mate sequence share 100% identity.

12. The composition of claim 2, wherein the first and second tracr sequence share 100% identity.

13. The composition of claim 2, wherein the Cas9 protein is a nuclease or a nickase.

14. The composition of claim 13, wherein the Cas9 protein is *Streptococcus pyogenes* Cas9 (SpCas9).

15. A composition comprising the polynucleotide of claim 1 for modifying an organism or a non-human organism by manipulation of a first and a second target sequence on opposite strands of a DNA duplex in a genomic locus of interest in a eukaryotic cell,
which composition further comprises a polynucleotide sequence encoding a Cas9 protein comprising at least one or more nuclear localization sequences and comprising one or more mutations,
wherein the first guide sequence is capable of directing cleavage of one strand of the DNA duplex near the first target sequence in the eukaryotic cell and the second guide sequence is capable of directing cleavage of the other strand near the second target sequence in the eukaryotic cell inducing a double strand break to modify the organism or the non-human organism.

16. The composition of claim 15, wherein the first guide sequence capable of directing cleavage of one strand of the DNA duplex near the first target sequence and the second guide sequence capable of directing cleavage of the other strand near the second target sequence are configured to generate a 5' overhang.

17. The composition of claim 16, wherein the 5' overhang is at most 200 base pairs.

18. The composition of claim 16, wherein the 5' overhang is at most 100 base pairs.

19. The composition of claim 16, wherein the 5' overhang is at most 50 base pairs.

20. The composition of claim 16, wherein the 5' overhang is at least 26 base pairs.

21. The composition of claim 16, wherein the 5' overhang is at least 30 base pairs.

22. The composition of claim 16, wherein the 5' overhang is 34-50 base pairs.

23. The composition of claim 15, wherein any or all of the polynucleotide sequences encoding the Cas9 protein, the first and the second guide sequence, the first and the second tracr mate sequence or the first and the second tracr sequence, is/are RNA.

24. The composition of claim 15, wherein the first and second tracr mate sequence share 100% identity.

25. The composition of claim 15, wherein the first and second tracr sequence share 100% identity.

26. The composition of claim 15, wherein the Cas9 protein is *Streptococcus pyogenes* Cas9 (SpCas9).

27. The composition of claim 26, wherein the Cas9 protein comprises one or more mutations in a catalytic domain.

28. The composition of claim 27, wherein the Cas9 protein comprises one or more mutations selected from the group consisting of D10A, E762A, H840A, N854A, N863A and D986A.

29. The composition of claim 28, wherein the Cas9 protein has the D10A mutation.

30. The composition of claim 15, wherein the modification comprises optimized first or second tracr sequence and/or optimized first or second guide sequence and/or co-fold structure of first or second tracr sequence and/or first or second tracr mate sequence(s) respectively and/or stabilizing secondary structures of first or second tracr sequence and/or first or second tracr sequence with a reduced region of base-pairing and/or first or second tracr sequence fused RNA elements.

31. The composition of claim 15, wherein the nucleotide linker is ATTA or AATTATTA.

32. The composition of claim 15, wherein the nucleotide linker is AATTATTAATTA (SEQ ID NO: 462).

33. The composition of claim 15, wherein the nucleotide linker is AATTATTAATTATAAT (SEQ ID NO: 463).

34. The composition of claim 15, wherein the nucleotide linker is GTTTTAGAGCTATGCT (SEQ ID NO: 464) or GTTTTGAATGGTCCCAAAAC (SEQ ID NO: 465).

35. The polynucleotide of claim 1, wherein the first target sequence is on a first strand of a DNA duplex and the second target sequence is on the opposite strand of the DNA duplex, and when the first and second guide sequences are hybridized to said target sequences in the duplex, the 5' ends of the first guide sequence and the second guide sequence are offset relative to each other by at least one base pair of the duplex.

36. A tandem guide RNA comprising:
(a) a first guide sequence capable of hybridizing to a first target sequence in a eukaryotic cell,
(b) a first tracr mate sequence capable of hybridizing to a first tracr sequence,
(c) a first tracr sequence,
(d) a second guide sequence capable of hybridizing to a second target sequence in a eukaryotic cell,
(e) a second tracr mate sequence capable of hybridizing to a second tracr sequence, and
(f) a second tracr sequence,
wherein (a), (b), (c), (d), (e) and (f) are arranged in a 5' to 3' orientation, and (c) and (d) are linked by a nucleotide linker, wherein the nucleotide linker is transcribed from a sequence selected from the group consisting of ATTA, AATTATTA, AATTATTAATTA (SEQ ID NO: 462), AATTATTAATTATAAT (SEQ ID NO: 463), GTTT-TAGAGCTATGCT (SEQ ID NO: 464), and GTTTT-GAATGGTCCCAAAAC (SEQ ID NO: 465).

37. A composition comprising (I) the polynucleotide of claim 1, and (II) a polynucleotide encoding a Cas9 protein comprising one or more nuclear localization sequences.

38. An isolated mammalian cell comprising the composition of claim 37.

39. A composition comprising:
(I) a polynucleotide encoding a tandem guide RNA, which tandem guide RNA comprises:
(a) a first guide sequence capable of hybridizing to a first target sequence in a eukaryotic cell,
(b) a first tracr mate sequence capable of hybridizing to a first tracr sequence,
(c) a first tracr sequence,
(d) a second guide sequence capable of hybridizing to a second target sequence in a eukaryotic cell,
(e) a second tracr mate sequence capable of hybridizing to a second tracr sequence, and
(f) a second tracr sequence,
wherein (a), (b), (c), (d), (e) and (f) are arranged in a 5' to 3' orientation, wherein (c) and (d) are linked by a nucleotide linker, wherein the nucleotide linker is transcribed from a sequence selected from the group consisting of ATTA, AATTATTA, AATTATTAATTA (SEQ ID NO: 462), AATTATTAATTATAAT (SEQ ID NO: 463), GTTTTAGAGCTATGCT (SEQ ID NO: 464), and GTTTTGAATGGTCCCAAAAC (SEQ ID NO: 465);
and
(II) a polynucleotide comprising a sequence encoding a Cas9 protein and one or more nuclear localization sequences, wherein the first target sequence is on a first strand of a DNA duplex and the second target sequence is on the opposite strand of the DNA duplex, and when the first and second guide sequences are hybridized to said target sequences in the duplex, the 5' ends of the first guide sequence and the second guide sequence are offset relative to each other by at least one base pair of the duplex;

and optionally wherein each of I and II is provided in the same or a different vector.

40. The composition according to claim 39, wherein the composition is capable of modifying a DNA duplex at a locus of interest in a eukaryotic cell.

41. The composition according to claim 40, wherein the composition is capable of prevention or treatment of a disease caused by a defect in said locus of interest.

42. An isolated mammalian cell comprising the composition of claim 39.

43. The composition of claim 39, wherein the Cas9 protein is *Streptococcus pyogenes* Cas9 (SpCas9).

44. The tandem guide RNA of claim 36, wherein the first target sequence is on a first strand of a DNA duplex and the second target sequence is on the opposite strand of the DNA duplex, and when the first and second guide sequences are hybridized to said target sequences in the duplex, the 5' ends of the first guide sequence and the second guide sequence are offset relative to each other by at least one base pair of the duplex.

45. A composition comprising (I) the tandem guide RNA of claim 36, and (II) a Cas9 protein comprising one or more nuclear localization sequences.

46. An isolated mammalian cell comprising the composition of claim 45.

\* \* \* \* \*